United States Patent
Hadida Ruah et al.

(10) Patent No.: US 7,671,221 B2
(45) Date of Patent: Mar. 2, 2010

(54) MODULATORS OF ATP-BINDING CASSETTE TRANSPORTERS

(75) Inventors: Sara S. Hadida Ruah, La Jolla, CA (US); Mark T. Miller, San Diego, CA (US); Brian Bear, Oceanside, CA (US); Jason McCartney, Cardiff by the Sea, CA (US); Peter D. J. Grootenhuis, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 76 days.

(21) Appl. No.: 11/824,606

(22) Filed: Jun. 29, 2007

(65) Prior Publication Data

US 2008/0009524 A1    Jan. 10, 2008

Related U.S. Application Data

(63) Continuation-in-part of application No. 11/647,092, filed on Dec. 28, 2006.

(60) Provisional application No. 60/754,558, filed on Dec. 28, 2005, provisional application No. 60/802,580, filed on May 22, 2006.

(51) Int. Cl.
C07D 317/06 (2006.01)
C07D 417/12 (2006.01)
C07D 405/12 (2006.01)

(52) U.S. Cl. ............... 549/434; 548/209; 546/283.7

(58) Field of Classification Search ............. 549/434; 548/209; 546/283.7
See application file for complete search history.

(56) References Cited

U.S. PATENT DOCUMENTS

| | | | |
|---|---|---|---|
| 5,430,060 A | 7/1995 | Brittain et al. |
| 5,723,606 A | 3/1998 | Tanaka et al. |
| 5,856,564 A | 1/1999 | Tanaka et al. |
| 6,071,920 A | 6/2000 | Leonardi et al. |
| 6,271,390 B1 | 8/2001 | Sircar et al. |
| 6,291,453 B1 | 9/2001 | Ashwell et al. |
| 6,319,939 B1 | 11/2001 | Mabire et al. |
| 6,329,395 B1 | 12/2001 | Dugar et al. |
| 6,369,091 B1 | 4/2002 | Sircar et al. |
| 6,399,614 B1 | 6/2002 | Leonardi et al. |
| 6,444,849 B1 | 9/2002 | Ando et al. |
| 6,472,394 B1 | 10/2002 | McKittrick et al. |
| 6,531,491 B1 | 3/2003 | Kania et al. |
| 6,635,641 B2 | 10/2003 | Bender et al. |
| 6,887,889 B2 | 5/2005 | Hobbs et al. |
| 2002/0035104 A1 | 3/2002 | Artis et al. |
| 2003/0100582 A1 | 5/2003 | Sircar et al. |
| 2003/0149083 A1 | 8/2003 | Tanaka et al. |
| 2003/0171588 A1 | 9/2003 | Kahl et al. |
| 2004/0110793 A1 | 6/2004 | Lloyd et al. |
| 2004/0110832 A1 | 6/2004 | Mjalli et al. |
| 2004/0110947 A1 | 6/2004 | Chandrakumar et al. |
| 2004/0180881 A1 | 9/2004 | Berta et al. |
| 2004/0209878 A1 | 10/2004 | Guzi et al. |
| 2004/0220191 A1 | 11/2004 | Schwink et al. |
| 2004/0229889 A1 | 11/2004 | Urano et al. |
| 2004/0254159 A1 | 12/2004 | Hasvold et al. |
| 2005/0004142 A1 | 1/2005 | Adams et al. |
| 2005/0107399 A1 | 5/2005 | Boman et al. |
| 2005/0119489 A1 | 6/2005 | Ladouceur et al. |
| 2005/0197375 A1 | 9/2005 | Sircar et al. |
| 2006/0020003 A1 | 1/2006 | Commons |
| 2006/0052358 A1 | 3/2006 | Ruah et al. |
| 2007/0037824 A1 | 2/2007 | Guzi et al. |
| 2007/0078120 A1 | 4/2007 | Ban et al. |
| 2007/0244159 A1 | 10/2007 | Ruah et al. |
| 2008/0019915 A1* | 1/2008 | Hadida-Ruah et al. ....... 424/9.2 |
| 2008/0044355 A1 | 2/2008 | Ruah et al. |
| 2008/0113985 A1 | 5/2008 | Ruah et al. |
| 2008/0176899 A1 | 7/2008 | Ruah et al. |
| 2008/0286204 A1 | 11/2008 | Ruah et al. |
| 2008/0306062 A1 | 12/2008 | Ruah et al. |
| 2009/0131492 A1 | 5/2009 | Ruah et al. |
| 2009/0143381 A1 | 6/2009 | Ruah et al. |

FOREIGN PATENT DOCUMENTS

| | | |
|---|---|---|
| WO | WO 9732863 | 9/1997 |
| WO | WO 9906434 | 2/1999 |
| WO | WO 9920606 | 4/1999 |
| WO | WO 9964394 | 12/1999 |
| WO | WO 0104107 | 1/2001 |
| WO | WO 0121596 | 3/2001 |
| WO | WO 0164652 | 9/2001 |
| WO | WO 03002519 | 1/2003 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL;http://www.cnn.com/2003/HEALTH/conditions/09/24/alzheimers.drug.ap/indexhtml>.*
Areces, Pilar, et al; Synthesis of dihydrothiophenes by an amino-directed thioisomuenchnone-alkene cycloaddition reaction; *European Journal of Organic Chemistry* (2001) , (11) , 2135-2144 CODEN: EJOCFK; ISSN: 1434-193X; Wiley-VCH Verlag GmbH.

(Continued)

*Primary Examiner*—Rebecca L Anderson
*Assistant Examiner*—Shawquia Young
(74) *Attorney, Agent, or Firm*—Michael J. DiVerdi

(57) ABSTRACT

Compounds of the present invention and pharmaceutically acceptable compositions thereof, are useful as modulators of ATP-Binding Cassette ("ABC") transporters or fragments thereof, including Cystic Fibrosis Transmembrane Conductance Regulator ("CFTR"). The present invention also relates to methods of treating ABC transporter mediated diseases using compounds of the present invention.

6 Claims, No Drawings

OTHER PUBLICATIONS

Avalos, Martin, et al; Cycloaddition Chemistry of 1,3-Thiazolium-4-olate Systems. Reaction with Nitroalkenes and Interpretation of Results Using PM3 Calculations; *Journal of Organic Chemistry* (1996), 61 (11), 3738-3748 CODEN: JOCEAH; ISSN: 0022-3263; American Chemical Society.

Lai, J. T.; Totally hindered phenols. 2,6-Di-tert-butyl-4-(1,1-dialkyl-1-acetamide) phenols and their persistent phenoxy radicals *Tetrahedron Letters* (2001), 42 (4), 557-560 CODEN: TELEAY; ISSN: 0040-4039; Elsevier Science Ltd.

Lewis, Richard J., et al; Structure-activity studies on amides inhibiting photosystem II; *Journal of the Chemical Society*, Perkin Transactions 2: Physical Organic Chemistry (1972-1999) (1991), (10), 1625-30 CODEN: JCPKBH; ISSN: 0300-9580.

* cited by examiner

MODULATORS OF ATP-BINDING CASSETTE TRANSPORTERS

CROSS-REFERENCE

This application is a continuation-in-part of U.S. patent application Ser. No. 11/647,092 filed on Dec. 28, 2006, which claims the benefit of U.S. provisional patent application Ser. Nos. 60/754,558, filed on Dec. 28, 2005, and 60/802,580, filed on May 22, 2006, each of which is hereby incorporated herein by reference.

TECHNICAL FIELD OF THE INVENTION

The present invention relates to modulators of ATP-Binding Cassette ("ABC") transporters or fragments thereof, including Cystic Fibrosis Transmembrane Conductance Regulator ("CFTR"), compositions thereof and methods therewith. The present invention also relates to methods of treating ABC transporter mediated diseases using such modulators.

BACKGROUND OF THE INVENTION

ABC transporters are a family of membrane transporter proteins that regulate the transport of a wide variety of pharmacological agents, potentially toxic drugs, and xenobiotics, as well as anions. ABC transporters are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. To date, 48 ABC Transporters have been identified and grouped into 7 families based on their sequence identity and function.

ABC transporters regulate a variety of important physiological roles within the body and provide defense against harmful environmental compounds. Because of this, they represent important potential drug targets for the treatment of diseases associated with defects in the transporter, prevention of drug transport out of the target cell, and intervention in other diseases in which modulation of ABC transporter activity may be beneficial.

One member of the ABC transporter family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in Cystic Fibrosis ("CF"), the most common fatal genetic disease in humans. Cystic Fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as $\Delta$F508-CFTR. This mutation occurs in approximately 70% of the cases of cystic fibrosis and is associated with a severe disease.

The deletion of residue 508 in $\Delta$F508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of $\Delta$F508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to $\Delta$F508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl— channels expressed on the basolateral surface of the cell. Secondary active transport of chloride from the luminal side leads to the accumulation of intracellular chloride, which can then passively leave the cell via Cl⁻ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to Cystic Fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as Cystic Fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002) ; Morello, J P et al., TIPS, 21, pp. 466-469 (2000); Bross P., et al., Human Mut., 14, pp. 186-198 (1999)]. The diseases associated with the first class of ER malfunction are Cystic fibrosis (due to misfolded ΔF508-CFTR as discussed above), Hereditary emphysema (due to a1-antitrypsin; non Piz variants), Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses (due to Lysosomal processing enzymes), Sandhof/Tay-Sachs (due to β-Hexosaminidase), Crigler-Najjar type II (due to UDP-glucuronyl-sialyc-transferase), Polyendocrinopathy/Hyperinsulemia, Diabetes mellitus (due to Insulin receptor), Laron dwarfism (due to Growth hormone receptor), Myleoperoxidase deficiency, Primary hypoparathyroidism (due to Preproparathyroid hormone), Melanoma (due to Tyrosinase). The diseases associated with the latter class of ER malfunction are Glycanosis CDG type 1, Hereditary emphysema (due to α1-Antitrypsin (PiZ variant), Congenital hyperthyroidism, Osteogenesis imperfecta (due to Type I, II, IV procollagen), Hereditary hypofibrinogenemia (due to Fibrinogen), ACT deficiency (due to α1-Antichymotrypsin), Diabetes insipidus (DI), Neurophyseal DI (due to Vasopvessin hormone/V2-receptor), Neprogenic DI (due to Aquaporin II), Charcot-Marie Tooth syndrome (due to Peripheral myelin protein 22), Perlizaeus-Merzbacher disease, neurodegenerative diseases such as Alzheimer's disease (due to βAPP and presenilins), Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease (due to lysosomal α-galactosidase A) and Straussler-Scheinker syndrome (due to Prp processing defect).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrhea causing bacteria is enterotoxogenic *E-coli* (ETEC) having the K99 pilus antigen. Common viral causes of diarrhea include rotavirus and coronavirus. Other infectious agents include cryptosporidium, *giardia lamblia*, and *salmonella*, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for modulators of an ABC transporter activity, and compositions thereof, that can be used to modulate the activity of the ABC transporter in the cell membrane of a mammal.

There is a need for methods of treating ABC transporter mediated diseases using such modulators of ABC transporter activity.

There is a need for methods of modulating an ABC transporter activity in an ex vivo cell membrane of a mammal.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of ABC transporter activity. These compounds have the general formula I:

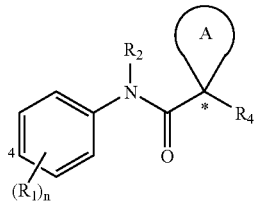

I or a pharmaceutically acceptable salt thereof, wherein $R_1$, $R_2$, $R_4$, ring A, and n are described herein.

These compounds and pharmaceutically acceptable compositions are useful for treating or lessening the severity of a variety of diseases, disorders, or conditions, including, but not limited to, Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

DETAILED DESCRIPTION OF THE INVENTION

Definitions

As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

The term "modulating" as used herein means increasing or decreasing, e.g. activity, by a measurable amount. Compounds that modulate ABC Transporter activity, such as CFTR activity, by increasing the activity of the ABC Transporter, e.g., a CFTR anion channel, are called agonists. Compounds that modulate ABC Transporter activity, such as CFTR activity, by decreasing the activity of the ABC Transporter, e.g., CFTR anion channel, are called antagonists. An agonist interacts with an ABC Transporter, such as CFTR anion channel, to increase the ability of the receptor to transduce an intracellular signal in response to endogenous ligand binding. An antagonist interacts with an ABC Transporter, such as CFTR, and competes with the endogenous ligand(s) or substrate(s) for binding site(s) on the receptor to decrease the ability of the receptor to transduce an intracellular signal in response to endogenous ligand binding.

The phrase "treating or reducing the severity of an ABC Transporter mediated disease" refers both to treatments for diseases that are directly caused by ABC Transporter and/or CFTR activities and alleviation of symptoms of diseases not directly caused by ABC Transporter and/or CFTR anion channel activities. Examples of diseases whose symptoms may be affected by ABC Transporter and/or CFTR activity include, but are not limited to, Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type I chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot- Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B. and March, J., John Wiley & Sons, New York: 2001, the entire contents of which are hereby incorporated by reference.

As used herein the term "aliphatic' encompasses the terms alkyl, alkenyl, alkynyl, each of which being optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino], amino [e.g., aliphaticamino, cycloaliphaticamino, or heterocycloaliphaticamino], sulfonyl [e.g., aliphaticsulfonyl], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, hydroxyalkyl, aralkyl, (alkoxyaryl)alkyl, (sulfonylamino)alkyl (such as (alkylsulfonylamino)alkyl), aminoalkyl, amidoalkyl, (cycloaliphatic)alkyl, cyanoalkyl, or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, cycloaliphatic, heterocycloaliphatic, aryl, heteroaryl, alkoxy, aroyl, heteroaroyl, acyl [e.g., (cycloaliphatic)carbonyl, or (heterocycloaliphatic)carbonyl], nitro, cyano, acyl [e.g., aliphaticcarbonyl, cycloaliphaticcarbonyl, arylcarbonyl, heterocycloaliphaticcarbonyl or heteroarylcarbonyl], amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, or aliphaticsulfonylamino], sulfonyl [e.g., alkylsulfonyl, cycloaliphaticsulfonyl, or arylsulfonyl], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphaticsulfonyl, aliphaticaminosulfonyl, or cycloaliphaticsulfonyl], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refers to an amido group such as $N(R^X)_2$—C(O)— or $R^YC(O)$—$N(R^X)$— when used terminally and —C(O)—$N(R^X)$— or —$N(R^X)$—C(O)— when used internally, wherein $R^X$ and $R^Y$ are defined below. Examples of amido groups include alkylamido (such as alkylcarbonylamino or alkylcarbonylamino), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, alkyl, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not a terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl or cycloaliphaticsulfinyl]; sulfanyl [e.g., aliphaticsulfanyl]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-dienyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkylsulfonyl and arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

As used herein, "cyclic moiety" includes cycloaliphatic, heterocycloaliphatic, aryl, or heteroaryl, each of which has been defined previously.

As used herein, the term "heterocyclic" encompasses a heterocycloaliphatic group and a heteroaryl group.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicyclic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety such as tetrahydroisoquinoline.

A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S). Monocyclic and bicyclicheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 3-8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pyranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, benzo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl)heteroaryl]; (hydroxyalkyl)heteroaryl; (alkoxyalkyl) heteroaryl; (hydroxy)heteroaryl; ((carboxy)alkyl)heteroaryl; [((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic" (such as a heteroalkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" includes cycloalkyl, heterocycloalkyl, cycloalkenyl, heterocycloalkenyl, aryl, or heteroaryl, each of which has been defined previously.

As used herein, an "acyl" group refers to a formyl group or $R^X$—C(O)— (such as -alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$ wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, a "haloaliphatic" group refers to an aliphatic group substituted with 1, 2, or 3 halogen atoms. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include alkylsulfanyl.

As used herein a "sulfinyl" group refers to —S(O)—R$^X$ when used terminally and —S(O)— when used internally, wherein R$^X$ has been defined above.

As used herein, a "sulfonyl" group refers to —S(O)$_2$—R$^X$ when used terminally and —S(O)$_2$-when used internally, wherein R$^X$ has been defined above.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, an "aminoalkyl" refers to the structure R$^X$R$^Y$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidino" group refers to the structure —N=C(N(R$^X$R$^Y$))N(R$^X$R$^Y$) wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, "cyclic group" includes mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-6. A branched aliphatic chain is a straight aliphatic chain that is substituted with one or more aliphatic groups. A branched aliphatic chain has the structure —[CQQ]$_v$- where Q is hydrogen or an aliphatic group; however, at least one Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables R$_1$, R$_2$, R$_3$, and R$_4$, and other variables contained therein formulae I encompass specific groups, such as alkyl and aryl. Unless otherwise noted, each of the specific groups for the variables R$_1$, R$_2$, R$_3$, and R$_4$, and other variables contained therein can be optionally substituted with one or more substituents described herein. Each substituent of a specific group is further optionally substituted with one to three of halo, cyano, oxoalkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxoalkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent independently selected from a specified group, the substituent can be either the same or different at every position. A ring substituent, such as a heterocycloalkyl, can be bound to another ring, such as a cycloalkyl, to form a spirobicyclic ring system, e.g., both rings share one common atom. As one of ordinary skill in the art will recognize, combinations of substituents envisioned by this invention are those combinations that result in the formation of stable or chemically feasible compounds.

The phrase "up to" as used herein, refers to zero or any integer number that is equal or less than the number following the phrase. For example, "up to 3" means any one of 0, 1, 2, and 3.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

Compounds

Compounds of the present invention are useful modulators of ABC transporters and are useful in the treatment of ABC transporter mediated diseases.

Generic Compounds

The present invention includes a compound of formula I:

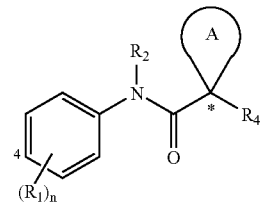

I or a pharmaceutically acceptable salt thereof.

A method of modulating the number of functional ABC transporters in a membrane of a cell comprising the step of contacting said cell with a compound of formula I:

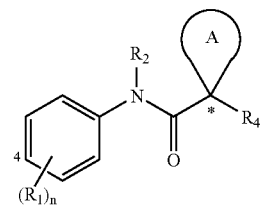

I or a pharmaceutically acceptable salt thereof, wherein:

Each $R_1$ is an optionally substituted $C_{1-6}$ aliphatic, an optionally substituted aryl, an optionally substituted heteroaryl, an optionally substituted $C_{3-10}$ cycloaliphatic, or an optionally substituted 4 to 10 membered heterocycloaliphatic, carboxy [e.g., hydroxycarbonyl or alkoxycarbonyl], alkoxy, amido [e.g., aminocarbonyl], amino, halo, cyano, alkylsulfanyl, or hydroxy;

provided that at least one $R_1$ is an optionally substituted aryl or an optionally substituted heteroaryl and said $R_1$ is attached to the 3- or 4-position of the phenyl ring;

Each $R_2$ is hydrogen, an optionally substituted $C_{1-6}$ aliphatic, an optionally substituted $C_{3-6}$ cycloaliphatic, an optionally substituted phenyl, or an optionally substituted heteroaryl;

Each $R_4$ is an optionally substituted aryl or an optionally substituted heteroaryl; Each n is 1, 2, 3, 4 or 5; and Ring A is an optionally substituted cycloaliphatic or an optionally substituted heterocycloaliphatic where the atoms of ring A adjacent to C* are carbon atoms, and each of which is optionally substituted with 1, 2, or 3 substituents.

SPECIFIC EMBODIMENTS

Substituent $R_1$

Each $R_1$ is an optionally substituted $C_{1-6}$ aliphatic, an optionally substituted aryl, an optionally substituted heteroaryl, an optionally substituted $C_{3-10}$ cycloaliphatic, an optionally substituted 4 to 10 membered heterocycloaliphatic, carboxy [e.g., hydroxycarbonyl or alkoxycarbonyl], amido [e.g., aminocarbonyl], amino, halo, alkoxy, or hydroxy.

In some embodiments, one $R_1$ is an optionally substituted $C_{1-6}$ aliphatic. In several examples, one $R_1$ is an optionally substituted $C_{1-6}$ alkyl, an optionally substituted $C_{2-6}$ alkenyl, or an optionally substituted $C_{2-6}$ alkynyl. In several examples, one $R_1$ is $C_{1-6}$ alkyl, $C_{2-6}$ alkenyl, or $C_{2-6}$ alkynyl.

In several embodiments, one $R_1$ is an aryl or heteroaryl with 1, 2, or 3 substituents. In several examples, one $R_1$ is a monocyclic aryl or heteroaryl. In several embodiments, $R_1$ is an aryl or heteroaryl with 1, 2, or 3 substituents. In several examples, $R_1$ is a monocyclic aryl or heteroaryl.

In several embodiments, at least one $R_1$ is an optionally substituted aryl or an optionally substituted heteroaryl and $R_1$ is bonded to the core structure at the 4-position on the phenyl ring.

In several embodiments, at least one $R_1$ is an optionally substituted aryl or an optionally substituted heteroaryl and $R_1$ is bonded to the core structure at the 3-position on the phenyl ring.

In several embodiments, one $R_1$ is phenyl with up to 3 substituents. In several embodiments, $R_1$ is phenyl with up to 2 substituents.

In several embodiments, one $R_1$ is a heteroaryl ring with up to 3 substituents. In certain embodiments, one $R_1$ is a monocyclic heteroaryl ring with up to 3 substituents. In other embodiments, one $R_1$ is a bicyclic heteroaryl ring with up to 3 substituents. In several embodiments, $R_1$ is a heteroaryl ring with up to 3 substituents.

In some embodiments, one $R_1$ is an optionally substituted $C_{3-10}$ cycloaliphatic or an optionally substituted 3-8 membered heterocycloaliphatic. In several examples, one $R_1$ is a monocyclic cycloaliphatic substituted with up to 3 substituents. In several examples, one $R_1$ is a monocyclic heterocycloaliphatic substituted with up to 3 substituents. In one embodiment, one $R_1$ is a 4 membered heterocycloaliphatic having one ring member selected from oxygen, nitrogen (including NH and $NR^X$), or sulfur (including S, SO, and $SO_2$); wherein said heterocycloaliphatic is substituted with up to 3 substitutents. In one example, one $R_1$ is 3-methyloxetan-3-yl.

In several embodiments, one $R_1$ is carboxy [e.g., hydroxycarbonyl or alkoxycarbonyl]. Or, one $R_1$ is amido [e.g., aminocarbonyl]. Or, one $R_1$ is amino. Or, is halo. Or, is cyano. Or, hydroxy.

In some embodiments, $R_1$ is hydrogen, methyl, ethyl, iso-propyl, tert-butyl, cyclopropyl, cyclobutyl, cyclopentyl, cyclohexyl, allyl, F, Cl, methoxy, ethoxy, iso-propoxy, tert-butoxy, $CF_3$, $OCF_3$, $SCH_3$, $SCH_2CH_3$, CN, hydroxy, or amino. In several examples, $R_1$ is hydrogen, methyl, ethyl, iso-propyl, tert-butyl, methoxy, ethoxy, $SCH_3$, $SCH_2CH_3$, F, Cl, $CF_3$, or $OCF_3$. In several examples, $R_1$ can be hydrogen. Or, $R_1$ can be methyl. Or, $R_1$ can be ethyl. Or, $R_1$ can be iso-propyl. Or, $R_1$ can be tert-butyl. Or, $R_1$ can be F. Or, $R_1$ can be Cl. Or, $R_1$ can be OH. Or, $R_1$ can be $OCF_3$. Or, $R_1$ can be $CF_3$. Or, $R_1$ can be methoxy. Or, $R_1$ can be ethoxy. Or, $R_1$ can be $SCH_3$.

In several embodiments, $R_1$ is substituted with no more than three substituents independently selected from halo, oxo, or optionally substituted aliphatic, cycloaliphatic, heterocycloaliphatic, amino [e.g., (aliphatic)amino], amido [e.g., aminocarbonyl, ((aliphatic)amino)carbonyl, and ((aliphatic)$_2$amino)carbonyl], carboxy [e.g., alkoxycarbonyl and hydroxycarbonyl], sulfamoyl [e.g., aminosulfonyl, ((aliphatic)$_2$amino)sulfonyl, ((cycloaliphatic)aliphatic)aminosulfonyl, and ((cycloaliphatic)amino)sulfonyl], cyano, alkoxy, aryl, heteroaryl [e.g., monocyclic heteroaryl and bicycloheteroaryl], sulfonyl [e.g., aliphaticsulfonyl or (heterocycloaliphatic)sulfonyl], sulfinyl [e.g., aliphaticsulfinyl], aroyl, heteroaroyl, or heterocycloaliphaticcarbonyl.

In several embodiments, $R_1$ is substituted with halo. Examples of $R_1$ substituents include F, Cl, and Br. In several examples, $R_1$ is substituted with F.

In several embodiments, $R_1$ is substituted with an optionally substituted aliphatic. Examples of $R_1$ substituents include optionally substituted alkoxyaliphatic, heterocycloaliphatic, aminoalkyl, hydroxyalkyl, (heterocycloalkyl)aliphatic, alkylsulfonylaliphatic, alkylsulfonylaminoaliphatic, alkylcarbonylaminoaliphatic, alkylaminoaliphatic, or alkylcarbonylaliphatic.

In several embodiments, $R_1$ is substituted with an optionally substituted amino. Examples of $R_1$ substituents include aliphaticcarbonylamino, aliphaticamino, arylamino, or aliphaticsulfonylamino.

In several embodiments, $R_1$ is substituted with a sulfonyl. Examples of $R_1$ include heterocycloaliphatic sulfonyl, aliphatic sulfonyl, aliphaticaminosulfonyl, aminosulfonyl, aliphaticcarbonylaminosulfonyl, alkoxyalkylheterocycloalkylsulfonyl, alkylheterocycloalkylsulfonyl, alkylaminosulfonyl, cycloalkylaminosulfonyl, (heterocycloalkyl)alkylaminosulfonyl, and heterocycloalkylsulfonyl.

In several embodiments, $R_1$ is substituted with carboxy. Examples of $R_1$ substituents include alkoxycarbonyl and hydroxycarbonyl.

In several embodiments $R_1$ is substituted with amido. Examples of $R_1$ substituents include alkylaminocarbonyl, aminocarbonyl, ((aliphatic)$_2$amino)carbonyl, and [((aliphatic)aminoaliphatic)amino]carbonyl.

In several embodiments, $R_1$ is substituted with carbonyl. Examples of $R_1$ substituents include arylcarbonyl, cycloaliphaticcarbonyl, heterocycloaliphaticcarbonyl, and heteroarylcarbonyl.

In several embodiments, each $R_1$ is a hydroxycarbonyl, hydroxy, or halo.

In some embodiments, $R_1$ is hydrogen. In some embodiments, $R_1$ is -$Z^E R_9$, wherein each $Z^E$ is independently a bond or an optionally substituted branched or straight $C_{1-6}$ aliphatic chain wherein up to two carbon units of $Z^E$ are optionally and independently replaced by —CO—, —CS—, —$CONR^E$—, —$CONR^E NR^E$—, —$CO_2$—, —OCO—, —$NR^E CO_2$—, —O—, —$NR^E CONR^E$—, —$OCONR^E$—, —$NR^E NR^E$—, —$NR^E CO$—, —S—, —SO—, —$SO_2$—, —$NR^E$—, —$SO_2 NR^E$—, —$NR^E SO_2$—, or —$NR^E SO_2 NR^E$—. Each $R_9$ is hydrogen, $R^E$, halo, —OH, —$NH_2$, —$NO_2$, —CN, —$CF_3$, or —$OCF_3$. Each $R^E$ is independently a $C_{1-8}$ aliphatic group, a cycloaliphatic, a heterocycloaliphatic, an aryl, or a heteroaryl, each of which is optionally substituted with 1, 2, or 3 of $R^A$. Each $R^A$ is -$Z^A R_5$, wherein each $Z^A$ is independently a bond or an optionally substituted branched or straight $C_{1-6}$ aliphatic chain wherein up to two carbon units of $Z^A$ are optionally and independently replaced by —CO—, —CS—, —$CONR^B$—, —$CONR^B NR^B$—, —$CO_2$—, —OCO—, —$NR^B CO_2$—, —O—, —$NR^B CONR^B$—, —$OCONR^B$—, —$NR^B NR^B$—, —$NR^B CO$—, —S—, —SO—, —$SO_2$—, —$NR^B$—, —$SO_2 NR^B$—, —$NR^B SO_2$—, or —$NR^B SO_2 NR^B$—. Each $R_5$ is independently $R^B$, halo, —$B(OH)_2$, —OH, —$NH_2$, —$NO_2$, —CN, —$CF_3$, or —OCF$_3$. Each R$^B$ is independently hydrogen, an optionally substituted C$_{1-6}$ aliphatic group, an optionally substituted cycloaliphatic, an optionally substituted heterocycloaliphatic, an optionally substituted aryl, or an optionally substituted heteroaryl.

In several embodiments, R$_1$ is -Z$^E$R$_9$, wherein each Z$^E$ is independently a bond or an optionally substituted branched or straight C$_{1-6}$ aliphatic chain wherein up to two carbon units of Z$^E$ are optionally and independently replaced by —CO—, —CONR$^E$—, —CO$_2$—, —O—, —S—, —SO—, —SO$_2$—, —NR$^E$—, or —SO$_2$NR$^B$E. Each R$_9$ is hydrogen, R$^E$, halo, —OH, —NH$_2$, —CN, —CF$_3$, or —OCF$_3$. Each R$^E$ is independently an optionally substituted group selected from C$_{1-8}$ aliphatic group, cycloaliphatic, heterocycloaliphatic, aryl, and heteroaryl. In one embodiment, Z$^E$ is a bond. In one embodiment, Z$^E$ is a straight C$_{1-6}$ aliphatic chain, wherein one carbon unit of Z$^E$ is optionally replaced by —CO—, —CONR$^E$—, —CO$_2$—, —O—, or —NR$^B$—. In one embodiment, Z$^E$ is a C$_{1-6}$ alkyl chain. In one embodiment, Z$^E$ is —CH$_2$—. In one embodiment, Z$^E$ is —CO—. In one embodiment, Z$^E$ is —CO$_2$—. In one embodiment, Z$^E$ is —CONR$^E$—.

In some embodiments, R$_9$ is H, —NH$_2$, hydroxy, —CN, or an optionally substituted group selected from C$_{1-8}$ aliphatic, C$_{3-8}$ cycloaliphatic, 3-8 membered heterocycloaliphatic, C$_{6-10}$ aryl, and 5-10 membered heteroaryl. In one embodiment, R$_9$ is H. In one embodiment, R$_9$ is hydroxy. Or, R$_9$ is —NH$_2$. Or, R$_9$ is —CN. In some embodiments, R$_9$ is an optionally substituted 3-8 membered heterocycloaliphatic, having 1, 2, or 3 ring members independently selected from nitrogen (including NH and NR$^X$), oxygen, and sulfur (including S, SO, and SO$_2$). In one embodiment, R$_9$ is an optionally substituted five membered heterocycloaliphatic with one nitrogen (including NH and NR$^X$) ring member. In one embodiment, R$_9$ is an optionally substituted pyrrolidin-1-yl. Examples of said optionally substituted pyrrolidin-1-yl include pyrrolidin-1-yl and 3-hydroxy-pyrrolidin-1-yl. In one embodiment, R$_9$ is an optionally substituted six membered heterocycloaliphatic with two heteroatoms independently selected from nitrogen (including NH and NR$^X$) and oxygen. In one embodiment, R$_9$ is morpholin-4-yl. In some embodiments, R$_9$ is an optionally substituted 5-10 membered heteroaryl. In one embodiment, R$_9$ is an optionally substituted 5 membered heteroaryl, having 1, 2, 3, or 4 ring members independently selected from nitrogen (including NH and NR$^X$), oxygen, and sulfur (including S, SO, and SO$_2$). In one embodiment, R$_9$ is 1H-tetrazol-5-yl.

In one embodiment, one R$_1$ is Z$^E$R$_9$; wherein Z$^E$ is CH$_2$ and R$_9$ is 1H-tetrazol-5-yl. In one embodiment, one R$_1$ is Z$^E$R$_9$; wherein Z$^E$ is CH$_2$ and R$_9$ is morpholin-4-yl. In one embodiment, one R$_1$ is Z$^E$R$_9$; wherein Z$^E$ is CH$_2$ and R$_9$ is pyrrolidin-1-yl. In one embodiment, one R$_1$ is Z$^E$R$_9$; wherein Z$^E$ is CH$_2$ and R$_9$ is 3-hydroxy-pyrrolidin-1-yl. In one embodiment, one R$_1$ is Z$^E$R$_9$; wherein Z$^E$ is CO and R$_9$ is 3-hydroxy-pyrrolidin-1-yl.

In some embodiments, R$_1$ is selected from CH$_2$OH, COOH, CH$_2$OCH$_3$, COOCH$_3$, CH$_2$NH$_2$, CH$_2$NHCH$_3$, CH$_2$CN, CONHCH$_3$, CH$_2$CONH$_2$, CH$_2$OCH$_2$CH$_3$, CH$_2$N(CH$_3$)$_2$, CON(CH$_3$)$_2$, CH$_2$NHCH$_2$CH$_2$OH, CH$_2$NHCH$_2$CH$_2$COOH, CH$_2$OCH(CH$_3$)$_2$, CONHCH(CH$_3$)CH$_2$OH, or CONHCH(tert-butyl)CH$_2$OH.

In several embodiments, R$_1$ is halo, or R$_1$ is C$_{1-6}$ aliphatic, aryl, heteroaryl, alkoxy, cycloaliphatic, heterocycloaliphatic, each of which is optionally substituted with 1, 2, or 3 of R$^A$; or R$_1$ is halo; wherein each R$^A$ is -Z$^A$R$_5$, each Z$^A$ is independently a bond or an optionally substituted branched or straight C$_{1-6}$ aliphatic chain wherein up to two carbon units of Z$^A$ are optionally and independently replaced by —CO—, —CS—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—; each R$_5$ is independently R$^B$, halo, —B(OH)$_2$, —OH, —NH$_2$, —NO$_2$, —CN, —CF$_3$, or —OCF$_3$; and each R$^B$ is hydrogen, optionally substituted C$_{1-4}$ aliphatic, optionally substituted C$_{3-6}$ cycloaliphatic, optionally substituted heterocycloaliphatic, optionally substituted phenyl, or optionally substituted heteroaryl.

In some embodiments, Z$^A$ is independently a bond or an optionally substituted branched or straight C$_{1-6}$ aliphatic chain wherein up to two carbon units of Z$^A$ are optionally and independently replaced by —CO—, —CS—, —CONR$^B$—, —CONR$^B$NR$^B$—, —CO$_2$—, —OCO—, —NR$^B$,CO$_2$—, —O—, —NR$^B$CONR$^B$—, —OCONR$^B$—, —NR$^B$NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—. In one embodiment, Z$^A$ is a bond. In some embodiments, Z$^A$ is an optionally substituted straight or branched C$_{1-6}$ aliphatic chain wherein up to two carbon unites of Z$^A$ are optionally and independently replaced by —CO—, —CS—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—. In one embodiment, Z$^A$ is an optionally substituted straight or branched C$_{1-6}$ alkyl chain wherein up to two carbon units of Z$^A$ is optionally replaced by —O—, —NHC(O)—, —C(O)NR$^B$—, —SO$_2$—, —NHSO$_2$—, —NHC(O)—, —SO—, NR$^B$SO$_2$—, —SO$_2$NH—, —SO$_2$NR$^B$—, —NH—, or —C(O)O—. In one embodiment, Z$^A$ is an optionally substituted straight or branched C$_{1-6}$ alkyl chain wherein one carbon unit of Z$^A$ is optionally replaced by —O—, —NHC(O)—, —C(O)NR$^B$—, —SO$_2$—, —NHSO$_2$—, —NHC(O)—, —SO—, —NR$^B$SO$_2$—, —SO$_2$NH—, —SO$_2$NR$^B$—, —NH—, or —C(O)O—. In one embodiment, Z$^A$ is an optionally substituted straight or branched C$_{1-6}$ alkyl chain wherein one carbon unit of Z$^A$ is optionally replaced by —CO—, —CONR$^B$—, —CO$_2$—, —O—, —NR$^B$CO—, —SO$_2$—, —NR$^B$—, —SO$_2$NR$^B$—, or —NR$^B$SO$_2$—. In one embodiment, Z$^A$ is an optionally substituted straight or branched C$_{1-6}$ alkyl chain wherein one carbon unit of Z$^A$ is optionally replaced by —SO$_2$—, —CONR$^B$—, or —SO$_2$NR$^B$—. In one embodiment, Z$^A$ is —CH$_2$— or —CH$_2$CH$_2$—. In one embodiment, Z$^A$ is an optionally substituted straight or branched C$_{1-6}$ alkyl chain wherein one carbon unit of Z$^A$ is optionally replaced by —CO—, —CONR$^B$—, —CO$_2$—, —O—, —NHCO—, —SO—, —SO$_2$—, —NR$^B$—, —SO$_2$NR$^B$—, or —NR$^B$SO$_2$—. In some embodiments, Z$^A$ is —CO$_2$—, —CH$_2$CO$_2$—, —CH$_2$CH$_2$CO$_2$—, —CH(NH$_2$)CH$_2$CO$_2$—, or —CH(CH$_3$)CH$_2$CO$_2$—. In some embodiments, Z$^A$ is —CONH—, —NHCO—, or —CON(CH$_3$)—. In some embodiments, Z$^A$ is —O—. Or, Z$^A$ is —SO—, —SO$_2$—, —SO$_2$NH—, or —SO$_2$N(CH$_3$). In one embodiment, Z$^A$ is an optionally substituted branched or straight C$_{1-6}$ aliphatic chain wherein one carbon unit of Z$^A$ is optionally replaced by —SO$_2$—.

In some embodiments, R$_5$ is H, F, Cl, —B(OH)$_2$, —OH, —NH$_2$, —CF$_3$, —OCF$_3$, or —CN. In one embodiment, R$_5$ is H. Or, R$_5$ is F. Or, R$_5$ is Cl. Or, R$_5$ is —B(OH)$_2$. Or, R$_5$ is —OH. Or, R$_5$ is —NH$_2$. Or, R$_5$ is —CF$_3$. Or, R$_5$ is —OCF$_3$. Or, R$_5$ is —CN.

In some embodiments, R$_5$ is an optionally substituted C$_{1-4}$ aliphatic. In one embodiment, R$_5$ is an optionally substituted $C_{1-4}$ alkyl. In one embodiment, $R_5$ is methyl, ethyl, iso-propyl, or tert-butyl. In one embodiment, $R_5$ is an optionally substituted aryl. In one embodiment, $R_5$ is an optionally substituted phenyl. In some embodiments, $R_5$ is an optionally substituted heteroaryl or an optionally substituted heterocycloaliphatic. In some embodiments, $R_5$ is an optionally substituted heteroaryl. In one embodiment, $R_5$ is an optionally substituted monocyclic heteroaryl, having 1, 2, 3, or 4 ring members optionally and independently replaced with nitrogen (including NH and $NR^X$), oxygen or sulfur (including S, SO, and $SO_2$). In one embodiment, $R_5$ is an optionally substituted 5 membered heteroaryl. In one embodiment, $R_5$ is 1H-tetrazol-5-yl. In one embodiment, $R_5$ is an optionally substituted bicyclic heteroaryl. In one embodiment, $R_5$ is a 1,3-dioxoisoindolin-2-yl. In some embodiments, $R_5$ is an optionally substituted heterocycloaliphatic having 1 or 2 nitrogen (including NH and $NR^X$) atoms and $R_5$ attaches directly to —$SO_2$— via one ring nitrogen.

In some embodiments, two occurrences of $R^A$, taken together with carbon atoms to which they are attached, form an optionally substituted 3-8 membered saturated, partially unsaturated, or aromatic ring, having up to 4 ring members optionally and independently replaced with nitrogen (including NH and $NR^X$), oxygen, or sulfur (including S, SO, and $SO_2$). In some embodiments, two occurrences of $R^A$, taken together with carbon atoms to which they are attached, form $C_{4-8}$ cycloaliphatic ring optionally substituted with 1, 2, or 3 substituents independently selected from oxo, =$NR^B$, =N—N($R^B$)$_2$, halo, —CN, —$CO_2$, —$CF_3$, —$OCF_3$, —OH, —$SR^B$, —S(O)$R^B$, —$SO_2R^B$, —$NH_2$, —$NHR^B$, —N($R^B$)$_2$, —COOH, —COO$R^B$, —O$R^B$, or $R^B$. In one embodiment, said cycloaliphatic ring is substituted with oxo. In one embodiment, said cycloaliphatic ring is

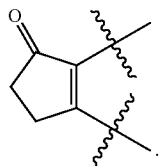

In some embodiments, two occurrences of $R^A$, taken together with carbon atoms to which they are attached, form an optionally substituted 5-8 membered heterocycloaliphatic ring, having up to 4 ring members optionally and independently replaced with nitrogen (including NH and $NR^X$), oxygen, or sulfur (including S, SO, and $SO_2$). In some embodiments, two occurrences of $R^A$, taken together with carbon atoms to which they are attached, form a 5 or 6 membered heterocycloaliphatic ring, optionally substituted with 1, 2, or 3 substituents independently selected from oxo, =$NR^B$, =N—N($R^B$)$_2$, halo, CN, $CO_2$, $CF_3$, $OCF_3$, OH, $SR^B$, S(O)$R^B$, $SO_2R^B$, $NH_2$, $NHR^B$, N($R^B$)$_2$, COOH, COO$R^B$, O$R^B$, or $R^B$. In some embodiments, said heterocycloaliphatic ring is selected from:

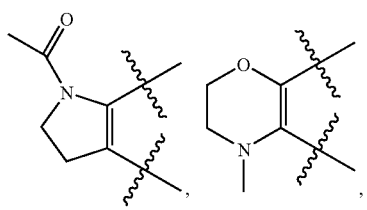

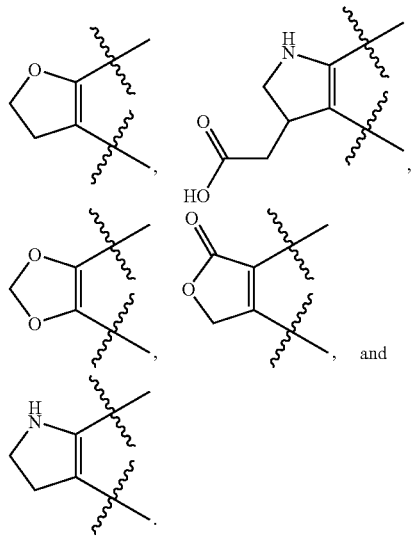

In some embodiments, two occurrences of $R^A$, taken together with carbon atoms to which they are attached, form an optionally substituted $C_{6-10}$ aryl. In some embodiments, two occurrences of $R^A$, taken together with carbon atoms to which they are attached, form a 6 membered aryl, optionally substituted with 1, 2, or 3 substituents independently selected from halo, —CN, —$CO_2$, —$CF_3$, —$OCF_3$, —OH, —$SR^B$, —S(O)$R^B$, —$SO_2R^B$, —$NH_2$, —$NHR^B$, —N($R^B$)$_2$, —COOH, —COO$R^B$, —O$R^B$, or $R^B$. In some embodiments, said aryl is

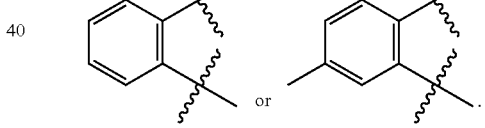

In some embodiments, two occurrences of $R^A$, taken together with carbon atoms to which they are attached, form an optionally substituted 5-8 membered heteroaryl, having up to 4 ring members optionally and independently replaced with nitrogen (including NH and $NR^X$), oxygen, or sulfur (including S, SO, and $SO_2$). In some embodiments, two occurrences of $R^A$, taken together with carbon atoms to which they are attached, form a 5 or 6 membered heteroaryl, optionally substituted with 1, 2, or 3 substituents independently selected from halo, CN, $CO_2$, $CF_3$, $OCF_3$, OH, $SR^B$, S(O)$R^B$, $SO_2R^B$, $NH_2$, $NHR^B$, N($R^B$)$_2$, COOH, COO$R^B$, O$R^B$, or $R^B$. In some embodiments, said heteroaryl is selected from:

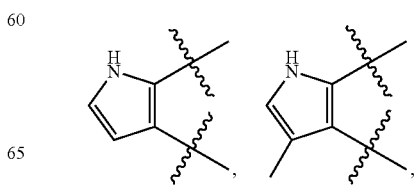

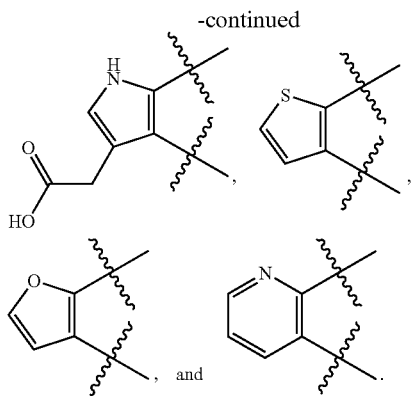

In some embodiments, one $R_1$ is aryl or heteroaryl, each optionally substituted with 1, 2, or 3 of $R^A$, wherein $R^A$ is defined above.

In several embodiments, one $R_1$ is carboxy [e.g., hydroxycarbonyl or alkoxycarbonyl], amido [e.g., aminocarbonyl], amino, halo, cyano, or hydroxy.

In several embodiments, $R_1$ is:

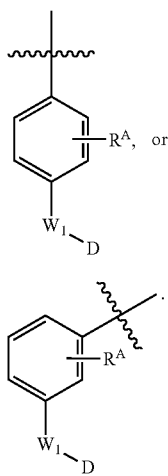

(Z-1)

(Z-2)

wherein $W_1$ is —C(O)—, —SO$_2$—, —NHC(O)—, or —CH$_2$—;

D is H, hydroxy, or an optionally substituted group selected from aliphatic, cycloaliphatic, alkoxy, and amino; and $R^A$ is defined above.

In several embodiments, $W_1$ is —C(O)—. Or, $W_1$ is —SO$_2$—. Or, $W_1$ is —NHC(O)—. Or, $W_1$ is —CH$_2$—.

In several embodiments, D is OH. Or, D is an optionally substituted $C_{1-6}$ aliphatic or an optionally substituted $C_3$-$C_8$ cycloaliphatic. Or, D is an optionally substituted alkoxy. Or, D is an optionally substituted amino.

In several examples, D is

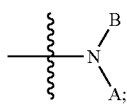

wherein each of A and B is independently H, an optionally substituted $C_{1-6}$ aliphatic, an optionally substituted $C_3$-$C_8$ cycloaliphatic, an optionally substituted 3-8 membered heterocycloaliphatic, acyl, sulfonyl, alkoxy or A and B, taken together, form an optionally substituted 3-7 membered heterocycloaliphatic ring.

In some embodiments, A is H. In some embodiments, A is an optionally substituted $C_{1-6}$ aliphatic. In several examples, A is an optionally substituted $C_{1-6}$ alkyl. In one example, A is methyl. Or, A is ethyl. Or, A is n-propyl. Or, A is iso-propyl. Or, A is 2-hydroxyethyl. Or, A is 2-methoxyethyl.

In several embodiments, B is $C_{1-6}$ straight or branched alkyl, optionally substituted with 1, 2, or 3 substituents each independently selected from halo, oxo, CN, hydroxy, or an optionally substituted group selected from alkyl, alkenyl, hydroxyalkyl, alkoxy, alkoxyalkyl, cycloaliphatic, amino, heterocycloaliphatic, aryl, and heteroaryl. In several embodiments, B is substituted with 1, 2, or 3 substituents each independently selected from halo, oxo, CN, $C_{1-6}$ alkyl, $C_{2-6}$ alkenyl, hydroxy, hydroxy-($C_{1-6}$)alkyl, ($C_{1-6}$)alkoxy, ($C_{1-6}$) alkoxy($C_{1-6}$)alkyl, NH$_2$, NH($C_{1-6}$ alkyl), N($C_{1-6}$ alkyl)$_2$, $C_{3-8}$ cycloaliphatic, NH($C_{3-8}$ cycloaliphatic), N($C_{1-6}$ alkyl)($C_{3-8}$ cycloaliphatic), N($C_{3-8}$ cycloaliphatic)$_2$, 3-8 membered heterocycloaliphatic, phenyl, and 5-10 membered heteroaryl. In one example, said substituent is oxo. Or, said substituent is optionally substituted ($C_{1-6}$) alkoxy. Or, is hydroxy. Or, is NH$_2$. Or, is NHCH$_3$. Or, is NH(cyclopropyl). Or, is NH(cyclobutyl). Or, is N(CH$_3$)$_2$. Or, is CN. In one example, said substituent is optionally substituted phenyl. In some embodiments, B is substituted with 1, 2, or 3 substituents each independently selected from an optionally substituted $C_{3-8}$ cycloaliphatic or 3-8 membered heterocycloaliphatic. In one example, said substituent is an optionally substituted group selected from cyclopropyl, cyclobutyl, cyclopentyl, cyclohexyl, cycloheptyl, cyclohexenyl, morpholin-4-yl, pyrrolidin-1-yl, pyrrolidin-2-yl, 1,3-dioxolan-2-yl, and tetrahydrofuran-2-yl. In some embodiments, B is substituted with 1, 2, or 3 substituents each independently selected from an optionally substituted 5-8 membered heteroaryl. In one example, said substituent is an optionally substituted group selected from pyridyl, pyrazyl, 1H-imidazol-1-yl, and 1H-imidazol-5-yl.

In some embodiments, B is $C_3$-$C_8$ cycloaliphatic optionally substituted with 1, 2, or 3 substituents independently selected from halo, oxo, alkyl, hydroxy, hydroxyalkyl, alkoxy, alkoxyalkyl, dialkyamino, or an optionally substituted group selected from cycloaliphatic, heterocycloaliphatic, aryl, and heteroaryl. In several examples, B is an optionally substituted $C_{3-8}$ cycloalkyl. In one embodiment, B is cyclopropyl. Or, B is cyclobutyl. Or, B is cyclopentyl. Or, B is cyclohexyl. Or, B is cycloheptyl.

In some embodiments, B is 3-8 membered heterocycloaliphatic optionally substituted with 1, 2, or 3 substituents independently selected from oxo, alkyl, hydroxy, hydroxyalkyl, alkoxy, alkoxyalkyl, dialkyamino, or an optionally substituted group selected from cycloaliphatic, heterocycloaliphatic, aryl, and heteroaryl. In one example, B is 3-oxo-isoxazolid-4-yl.

In several embodiments, A is H and B is an optionally substituted $C_{1-6}$ aliphatic. In several embodiments, B is substituted with 1, 2, or 3 substituents. Or, both, A and B, are H. Exemplary substituents on B include halo, oxo, alkyl, hydroxy, hydroxyalkyl, alkoxy, alkoxyalkyl, dialkyamino, or an optionally substituted group selected from cycloaliphatic, heterocycloaliphatic, aryl, and heteroaryl.

In several embodiments, A is H and B is an optionally substituted $C_{1-6}$ aliphatic. Exemplary substituents include oxo, alkyl, hydroxy, hydroxyalkyl, alkoxy, alkoxyalkyl, and an optionally substituted heterocycloaliphatic.

In several embodiments, A and B, taken together, form an optionally substituted 3-7 membered heterocycloaliphatic ring. In several examples, the heterocycloaliphatic ring is optionally substituted with 1, 2, or 3 substituents. Exemplary such rings include pyrrolidinyl, piperidinyl, morpholinyl, piperazinyl, oxazolidin-3-yl, and 1,4-diazepan-1-yl. Exemplary said substituents on such rings include halo, oxo, alkyl, aryl, heteroaryl, hydroxy, hydroxyalkyl, alkoxy, alkoxyalkyl, acyl (e.g., alkylcarbonyl), amino, amido, and carboxy. In some embodiments, each of said substituents is independently halo, oxo, alkyl, aryl, heteroaryl, hydroxy, hydroxyalkyl, alkoxy, alkoxyalkyl, amino, amido, or carboxy. In one embodiment, the substituent is oxo, F, Cl, methyl, ethyl, iso-propyl, 2-methoxyethyl, hydroxymethyl, methoxymethyl, aminocarbonyl, —COOH, hydroxy, acetyl, or pyridyl.

In several embodiments, $R_1$ is:

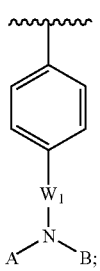

(Z)

wherein:

$W_1$ is —C(O)—, —SO$_2$—, —NHC(O)—, or —CH$_2$—;

Each of A and B is independently H, an optionally substituted $C_{1-6}$ aliphatic, an optionally substituted $C_3$-$C_8$ cycloaliphatic; or A and B, taken together, form an optionally substituted 4-7 membered heterocycloaliphatic ring.

In several examples, $R_1$ is selected from any one of the exemplary compounds in Table 1.

Substituent $R_2$

Each $R_2$ is hydrogen, or optionally substituted $C_{1-6}$ aliphatic, $C_{3-6}$ cycloaliphatic, phenyl, or heteroaryl.

In several embodiments, $R_2$ is a $C_{1-6}$ aliphatic that is optionally substituted with 1, 2, or 3 halo, $C_{1-2}$ aliphatic, or alkoxy. In several examples, $R_2$ is substituted or unsubstituted methyl, ethyl, propyl, or butyl.

In several embodiments, $R_2$ is hydrogen.

Ring A

Ring A is an optionally substituted cycloaliphatic or an optionally substituted heterocycloaliphatic where the atoms of ring A adjacent to C* are carbon atoms. In several embodiments, ring A is $C_{3-7}$ cycloaliphatic or 3-8 membered heterocycloaliphatic, each of which is optionally substituted with 1, 2, or 3 substituents.

In several embodiments, ring A is optionally substituted with 1, 2, or 3 of -$Z^B R_7$, wherein each $Z^B$ is independently a bond, or an optionally substituted branched or straight $C_{1-4}$ aliphatic chain wherein up to two carbon units of $Z^B$ are optionally and independently replaced by —CO—, —CS—, —CONR$^B$, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—; each $R_7$ is independently $R^B$, halo, —OH, —NH$_2$, —NO$_2$, —CN, or —OCF$_3$; and each $R^B$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In several embodiments, ring A is a $C_{3-7}$ cycloaliphatic or a 3-8 membered heterocycloaliphatic, each of which is optionally substituted with 1, 2, or 3 substituents.

In several embodiments, ring A is a 3, 4, 5, or 6 membered cycloaliphatic that is optionally substituted with 1, 2, or 3 substituents. In several examples, ring A is an optionally substituted cyclopropyl group. In several alternative examples, ring A is an optionally substituted cyclobutyl group. In several other examples, ring A is an optionally substituted cyclopentyl group. In other examples, ring A is an optionally substituted cyclohexyl group. In more examples, ring A is an unsubstituted cyclopropyl.

In several embodiments, ring A is a 5, 6, or 7 membered optionally substitute heterocycloaliphatic. For example, ring A is an optionally substituted tetrahydropyranyl group.

Substituent $R_4$

Each $R_4$ is independently an optionally substituted aryl or heteroaryl.

In several embodiments, $R_4$ is an aryl having 6 to 10 members (e.g., 7 to 10 members) optionally substituted with 1, 2, or 3 substituents. Examples of $R_4$ are optionally substituted benzene, naphthalene, or indene. Or, examples of $R_4$ can be optionally substituted phenyl, optionally substituted naphthyl, or optionally substituted indenyl.

In several embodiments, $R_4$ is an optionally substituted heteroaryl. Examples of $R_4$ include monocyclic and bicyclic heteroaryl, such a benzofused ring system in which the phenyl s fused with one or two $C_{4-8}$ heterocycloaliphatic groups.

In some embodiments, $R_4$ is an aryl or heteroaryl, each optionally substituted with 1, 2, or 3 of -$Z^C R_8$. Each $Z^C$ is independently a bond or an optionally substituted branched or straight $C_{1-6}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —SO—, —SO$_2$—, —NR$^C$—, —SO$_2$NR$^C$—, —NR$^C$SO$_2$—, or —NR$^C$SO$_2$NR$^C$—. Each $R_8$ is independently $R^C$, halo, —OH, —NH$_2$, —NO$_2$, —CN, or —OCF$_3$. Each $R^C$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl. In one embodiment, $R_4$ is an aryl optionally substituted with 1, 2, or 3 of $Z^C R_8$. In one embodiment, $R_4$ is an optionally substituted phenyl.

In several embodiments, $R_4$ is a heteroaryl optionally substituted with 1, 2, or 3 substituents. Examples of $R_4$ include optionally substituted benzo[d][1,3]dioxole or 2,2-difluorobenzo[d][1,3]dioxole.

In some embodiments, two occurrences of -$Z^C R_8$, taken together with carbons to which they are attached, form a 4-8 membered saturated, partially saturated, or aromatic ring with up to 3 ring atoms independently selected from the group consisting of O, NH, NR$^C$, and S (including S, SO, and SO$_2$); wherein R$^C$ is defined herein.

In several embodiments, $R_4$ is one selected from

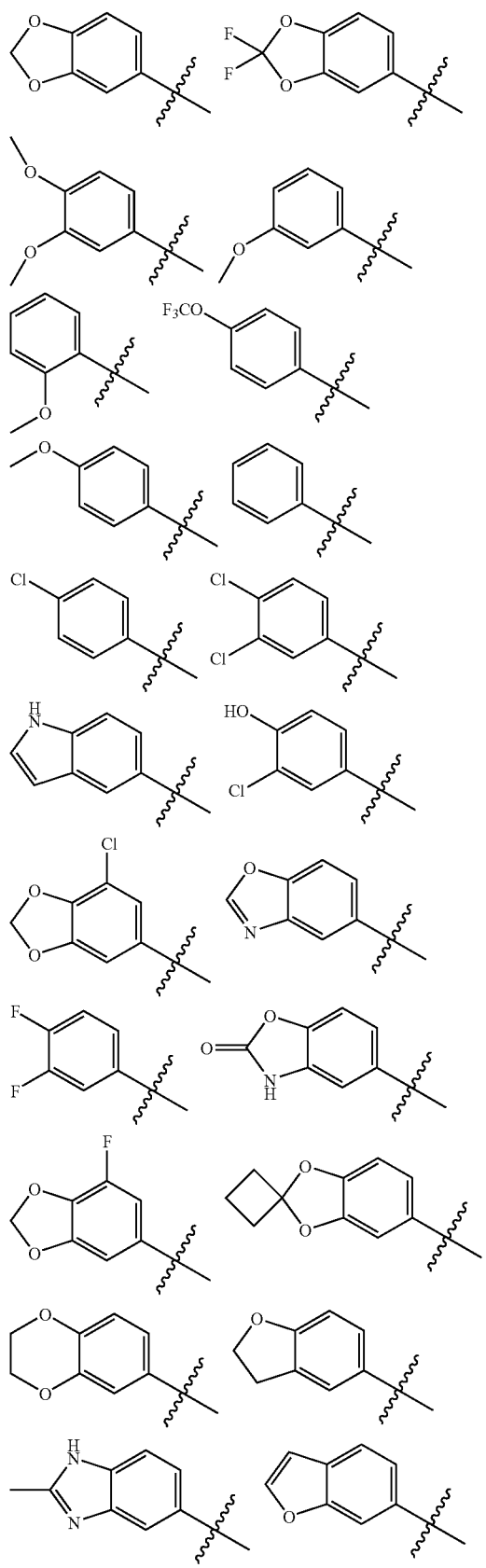
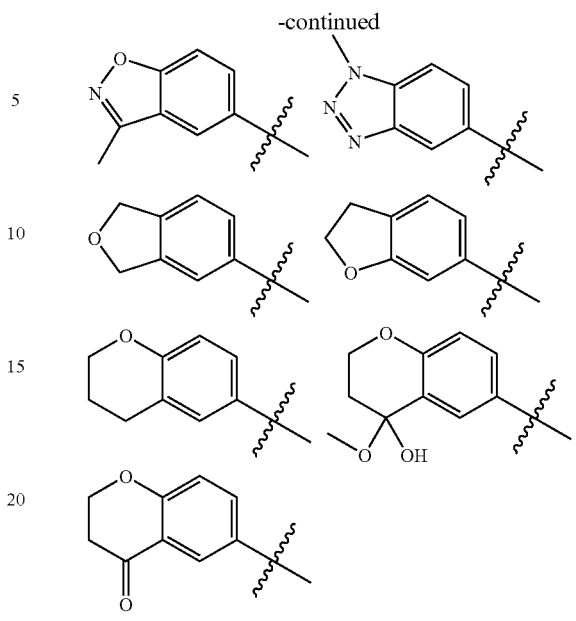

Sub-Generic Compounds

Another aspect of the present invention includes compounds of formula Ia:

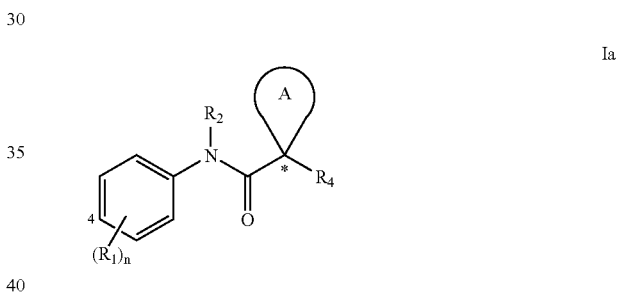

Ia or a pharmaceutically acceptable salt thereof, wherein $R_2$, $R_4$, and n have been defined in formula I.

Each $R_1$ is independently aryl, monocyclic heteroaryl or indolizinyl, indolyl, isoindolyl, 3H-indolyl, indolinyl, benzo[b]furanyl, benzo[b]thiophenyl, 1H-indazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, imidazo[1,2-a]pyridinyl, or benzo[d]oxazolyl, each of which is optionally substituted with 1, 2, or 3 of $R^A$; or $R_1$ is independently methyl, trifluoromethyl, or halo. In one embodiment, $R_1$ is an optionally substituted imidazo[1,2-a]pyridine-2-yl. In one embodiment, $R_1$ is an optionally substituted oxazolo[4,5-b]pyridine-2-yl. In one embodiment, $R_1$ is an optionally substituted 1H-pyrrolo[2,3-b]pyrid-6-yl. In one embodiment, $R_1$ is an optionally substituted benzo[d]oxazol-2-yl. In one embodiment, $R_1$ is an optionally substituted benzo[d]thiazol-2-yl.

In some embodiments, $R_1$ is a monocyclic aryl or a monocyclic heteroaryl, each is optionally substituted with 1, 2, or 3 of $R^A$. In some embodiments, $R_1$ is substituted or unsubstituted phenyl. In one embodiment, $R_1$ is substituted or unsubstituted pyrid-2-yl. In some embodiments, $R_1$ is pyrid-3-yl, pyrid-4-yl, thiophen-2-yl, thiophen-3-yl, 1H-pyrrol-2-yl, 1H-pyrrol-3-yl, 1H-imidazol-5-yl, 1H-pyrrol-4-yl, 1H-pyrazol-3-yl, thiazol-4-yl, furan-3-yl, furan-2-yl, or pyrimidin-5-yl, each of which is optionally substituted. In some embodiments, $R_1$ is phenyl, pyrid-2-yl, pyrid-3-yl, pyrid-4-yl, thiophen-2-yl, thiophen-3-yl, 1H-pyrrol-2-yl, 1H-pyrrol-3-yl, 1H-imidazol-5-yl, 1H-pyrazol-4-yl, 1H-pyrazol-3-yl, thiazol-4-yl, furan-3-yl, furan-2-yl, or pyrimidin-5-yl, each of which is optionally substituted with 1, 2, or 3 substituents independently selected from CN, or a group chosen from $C_{1-6}$ alkyl, carboxy, alkoxy, halo, amido, acetoamino, and aryl, each of which is further optionally substituted.

Each $R^A$ is -$Z^A R_5$, wherein each $Z^A$ is independently a bond or an optionally substituted branched or straight $C_{1-6}$ aliphatic chain wherein up to two carbon units of $Z^A$ are optionally and independently replaced by —CS—, —CONR$^B$—, —CONR$^B$NR$^B$—, —CO$_2$—, —NR$^B$CO$_2$—, —NR$^B$-CONR$^B$—, —NR$^B$NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—.

Each $R_5$ is independently $R^B$, halo, —OH, —NH$_2$, —NO$_2$, —CN, or —OCF$_3$.

Each $R^B$ is hydrogen, an optionally substituted $C_{1-4}$ aliphatic, an optionally substituted $C_{3-6}$ cycloaliphatic, an optionally substituted heterocycloaliphatic, an optionally substituted phenyl, or an optionally substituted heteroaryl.

Ring A is an optionally substituted cycloaliphatic, an optionally substituted 5 membered heterocycloaliphatic having 1, 2, or 3 heteroatoms independently selected from nitrogen (including NH and NR$^X$), oxygen, or sulfur (including S, SO, and SO$_2$); an optionally substituted 6 membered heterocycloaliphatic having 1 heteroatom selected from O and S (including S, SO, and SO$_2$); a piperidinyl optionally substituted with halo, aliphatic, aminocarbonyl, aminocarbonylaliphatic, aliphatic carbonyl, aliphaticsulfonyl, aryl, or combinations thereof; or an optionally substituted 7-8 membered heterocycloaliphatic having 1, 2, or 3 heteroatoms independently selected from nitrogen (including NH and NR$^X$), oxygen, or sulfur (including S, SO, and SO$_2$).

In some embodiments, one $R_1$ attached to the 3- or 4-position of the phenyl ring is an aryl or heteroaryl optionally substituted with 1, 2, or 3 of $R^A$, wherein $R^A$ is -$Z^A R_5$; in which each $Z^A$ is independently a bond or an optionally substituted branched or straight $C_{1-6}$ aliphatic chain wherein up to two carbon units of $Z^A$ are optionally and independently replaced by —CO—, —CS—, —CONR$^B$—, —CONR$^B$-NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—; each $R_5$ is independently $R^B$, halo, —OH, —NH$_2$, —NO$_2$, —CN, or —OCF$_3$; and each $R^B$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In some embodiments, one $R_1$ attached to the 3- or 4-position of the phenyl ring is a phenyl optionally substituted with 1, 2, or 3 of $R^A$.

In some embodiments, one $R_1$ attached to the 3- or 4-position of the phenyl ring is a phenyl substituted with one of $R^A$, wherein $R^A$ is -$Z^A R_5$; each $Z^A$ is independently a bond or an optionally substituted branched or straight $C_{1-6}$ aliphatic chain wherein up to two carbon units of $Z^A$ are optionally and independently replaced by —O—, —NHC(O)—, —C(O)NR$^B$—, —SO$_2$—, —NHSO$_2$—, —NHC(O)—, —SO—, —NR$^B$SO$_2$—, —SO$_2$NH—, —SO$_2$NR$^B$—, —NH—, or —C(O)O—. In one embodiment, one carbon unit of $Z^A$ is replaced by —O—, —NHC(O)—, —C(O)NR$^B$—, —SO$_2$—, —NHSO$_2$—, —NHC(O)—, —SO—, —NR$^B$SO$_2$—, —SO$_2$NH—, —SO$_2$NR$^B$—, —NH—, or —C(O)O—. In some embodiments, $R_5$ is independently an optionally substituted aliphatic, an optionally substituted cycloaliphatic, an optionally substituted heterocycloaliphatic, an optionally substituted aryl, an optionally substituted heteroaryl, hydrogen, or halo.

In some embodiments, one $R_1$ attached to the 3- or 4-position of the phenyl ring is heteroaryl optionally substituted with 1, 2, or 3 of $R^A$. In several examples, one $R_1$ attached to the 3- or 4-position of the phenyl ring is a 5 or 6 membered heteroaryl having 1, 2, or 3 heteroatoms independently selected from nitrogen (including NH and NR$^X$), oxygen or sulfur (including S, SO, and SO$_2$), wherein the heteroaryl is substituted with one of $R^A$, wherein $R^A$ is -$Z^A R_5$; wherein each $Z^A$ is independently a bond or an optionally substituted branched or straight $C_{1-6}$ aliphatic chain wherein up to two carbon units of $Z^A$ are optionally and independently replaced by —O—, —NHC(O)—, —C(O)NR$^B$—, —SO$_2$—, —NHSO$_2$—, —NHC(O)—, —SO—, —NR$^B$SO$_2$—, —SO$_2$NH—, —SO$_2$NR$^B$—, —NH—, or —C(O)O—. In one embodiment, one carbon unit of $Z^A$ is replaced by —O—, —NHC(O)—, —C(O)NR$^B$—, —SO$_2$—, —NHSO$_2$—, —NHC(O)—, —SO—, —NR$^B$SO$_2$—, —SO$_2$NH—, —SO$_2$NR$^B$—, —NH—, or —C(O)O—. In one embodiment, $R_5$ is independently an optionally substituted aliphatic, an optionally substituted cycloaliphatic, an optionally substituted heterocycloaliphatic, an optionally substituted aryl, an optionally substituted heteroaryl, hydrogen, or halo.

Another aspect of the present invention includes compounds of formula Ib:

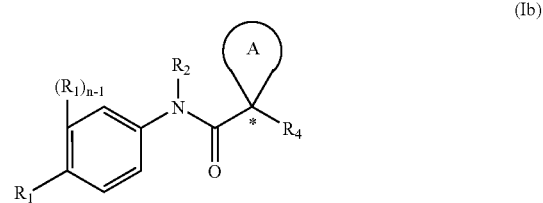

(Ib)

or a pharmaceutically acceptable salt thereof, wherein $R_2$, $R_4$ and ring A are defined in formula I.

The $R_1$ attached at the para position relative to the amide is an aryl or a heteroaryl optionally substituted with 1, 2, or 3 of $R^A$; wherein each $R^A$ is -$Z^A R_5$, each $Z^A$ is independently a bond or an optionally substituted branched or straight $C_{1-6}$ aliphatic chain wherein up to two carbon units of $Z^A$ are optionally and independently replaced by —CO—, —CS—, —CONR$^B$, —CONR$^B$NR$^B$—, —CO$_2$—, —OCO—, —NR$^B$CO$_2$—, —O—, —NR$^B$CONR$^B$—, —OCONR$^B$—, —NR$^B$-NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—; each $R_5$ is independently $R^B$, halo, —OH, —NH$_2$, —NO$_2$, —CN, or —OCF$_3$; each $R^B$ is hydrogen, an optionally substituted $C_{1-4}$ aliphatic, an optionally substituted $C_{3-6}$ cycloaliphatic, an optionally substituted heterocycloaliphatic, an optionally substituted phenyl, or optionally substituted heteroaryl.

The other $R_1$ are each independently hydrogen, halo, optionally substituted $C_{1-4}$ aliphatic, or optionally substituted $C_{1-4}$ alkoxy.

In several embodiments, the $R_1$ attached at the para position relative to the amide is a phenyl optionally substituted with 1, 2, or 3 of $R^A$ and the other $R_1$'s are each hydrogen. For example, the $R_1$ attached at the para position relative to the amide is phenyl optionally substituted with aliphatic, alkoxy, (amino)aliphatic, hydroxyaliphatic, aminosulfonyl, aminocarbonyl, alcoxycarbonyl, (aliphatic)aminocarbonyl, COOH, (aliphatic)aminosulfonyl, or combinations thereof, each of which is optionally substituted. In other embodiments, the $R_1$ attached at the para position relative to the amide is phenyl optionally substituted with halo. In several examples, the $R_1$ attached at the para position relative to the amide is phenyl optionally substituted with alkyl, alkoxy, (amino)alkyl, hydroxyalkyl, aminosulfonyl, (alkyl)aminocarbonyl, (alkyl)aminosulfonyl, or combinations thereof, each of which is optionally substituted; or the $R_1$ attached at the para position relative to the amide is phenyl optionally substituted with halo.

In several embodiments, the $R_1$ attached at the para position relative to the amide is an optionally substituted heteroaryl. In other embodiments, the $R_1$ attached at the para position relative to the amide is an optionally substituted monocyclic or optionally substituted bicyclic heteroaryl. For example, the $R_1$ attached at the para position relative to the amide is a benzo[d]oxazolyl, thiazolyl, benzo[d]thiazolyl, indolyl, or imidazo[1,2-a]pyridinyl, each of which is optionally substituted. In other examples, the $R_1$ attached at the para position relative to the amide is a benzo[d]oxazolyl, thiazolyl, benzo[d]thiazolyl, or imidazo[1,2-a]pyridinyl, each of which is optionally substituted with 1,2, or 3 of halo, hydroxy, aliphatic, alkoxy, or combinations thereof, each of which is optionally substituted.

In several embodiments, each $R_1$ not attached at the para position relative to the amide is hydrogen. In some examples, each $R_1$ not attached at the para position relative to the amide is methyl, ethyl, propyl, isopropyl, or tert-butyl, each of which is optionally substituted with 1, 2, or 3 of halo, hydroxy, cyano, or nitro. In other examples, each $R_1$ not attached at the para position relative to the amide is halo or optionally substituted methoxy, ethoxy, or propoxy. In several embodiments, each $R_1$ not attached at the para position relative to the amide is hydrogen, halo, —$CH_3$, —$OCH_3$, or —$CF_3$.

In several embodiments, compounds of formula Ib include compounds of formulae Ib1, Ib2, Ib3, or Ib4:

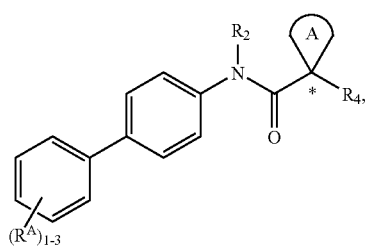

Ib1

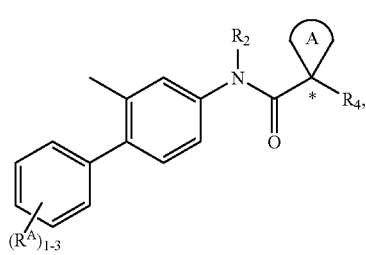

Ib2

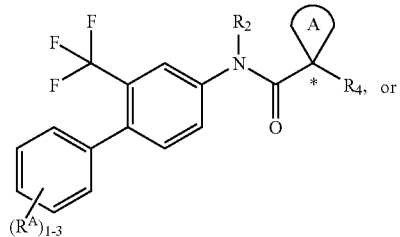

Ib3

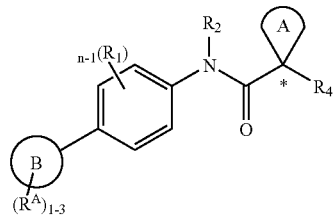

Ib4 where $R^A$, $R_1$, $R_2$, $R_4$, and ring A are defined above.

In formula Ib4, ring B is monocyclic or bicyclic heteroaryl that is substituted with 1, 2, or 3 $R^A$; and "n–1" is equal to 0, 1, or 2.

In several embodiments, the $R_1$ attached at the para position relative to the amide in formula Ib is an optionally substituted aryl. In several embodiments, the $R_1$ attached at the para position relative to the amide is a phenyl optionally substituted with 1, 2, or 3 of $R^A$. For example, the $R_1$ attached at the para position relative to the amide is phenyl optionally substituted with 1, 2, or 3 aliphatic, alkoxy, COOH, (amino)aliphatic, hydroxyaliphatic, aminosulfonyl, (aliphatic)aminocarbonyl, (aliphatic)aminosulfonyl, (((aliphatic)sulfonyl)amino)aliphatic, (heterocycloaliphatic)sulfonyl, heteroaryl, aliphaticsulfanyl, or combinations thereof, each of which is optionally substituted; or $R_1$ is optionally substituted with 1-3 of halo.

In several embodiments, the $R_1$ attached at the para position relative to the amide in formula Ib is an optionally substituted heteroaryl. In other embodiments $R_1$ is an optionally substituted monocyclic or an optionally substituted bicyclic heteroaryl. For example, $R_1$ is a pyridinyl, thiazolyl, benzo[d]oxazolyl, or oxazolo[4,5-b]pyridinyl, each of which is optionally substituted with 1, 2, or 3 of halo, aliphatic, alkoxy, or combinations thereof.

In several embodiments, one $R_1$ not attached at the para position relative to the amide is halo, optionally substituted $C_{1-4}$ aliphatic, $C_{1-4}$ alkoxy $C_{1-4}$ aliphatic, or optionally substituted $C_{1-4}$ alkoxy, such as For example, one $R_1$ not attached at the para position relative to the amide is halo, —$CH_3$, ethyl, propyl, isopropyl, tert-butyl, or —$OCF_3$.

In several embodiments, compounds of the invention include compounds of formulae Ic3, Ic4, Ic5, Ic6, Ic7, or Ic8:

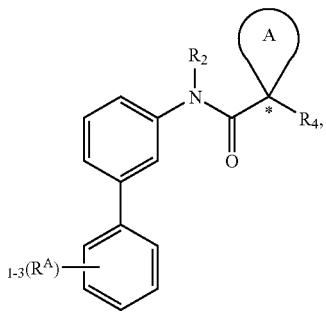

Ic1

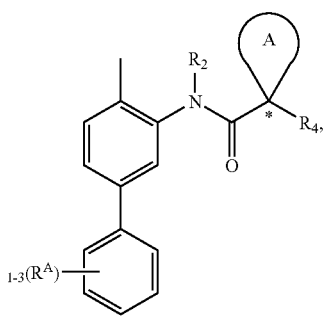

Ic2

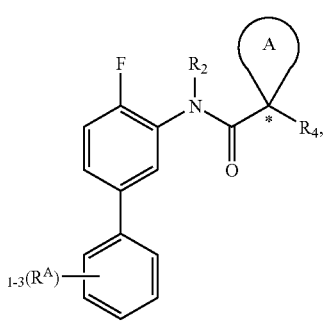

Ic3

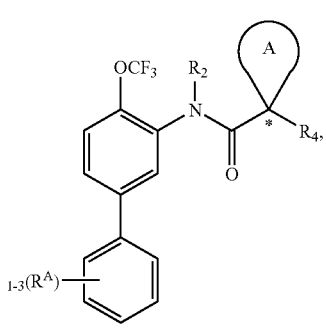

Ic4

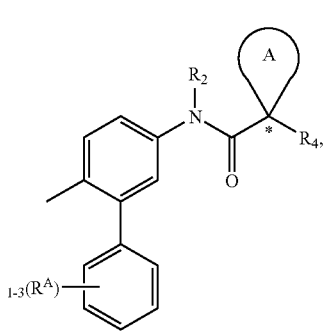

Ic5

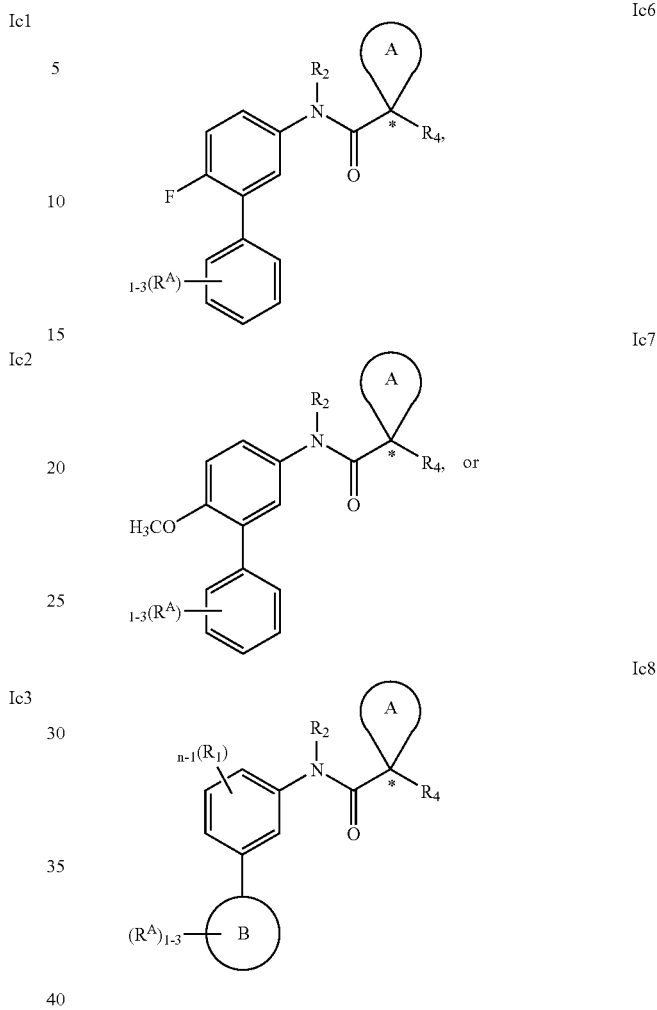

-continued

Ic6

Ic7

Ic8 or pharmaceutically acceptable salts, wherein $R^A$, $R_2$, $R_1$, $R_4$, and ring A are defined above.

In formula Ic8, ring B is monocyclic or bicyclic heteroaryl that is substituted with 1, 2, or 3 $R^A$; and "n−1" is equal to 0, 1, or 2.

Another aspect of the present invention provides compounds of formula Id:

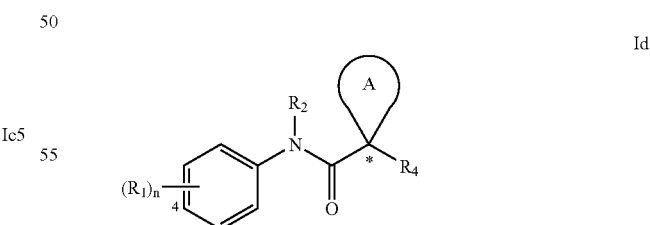

Id or a pharmaceutically acceptable salt thereof, wherein $R_1$, $R_2$, $R_4$, and n are defined in formula I.

Ring A is an optionally substituted cycloaliphatic.

In several embodiments, ring A is a cyclopropyl, cyclopentyl, or cyclohexyl, each of which is optionally substituted.

Another aspect of the present invention provides compounds of formula Ie:

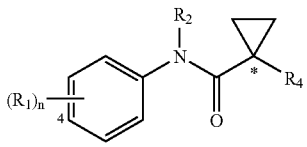

Ie or a pharmaceutically acceptable salt thereof, wherein $R_1$, $R_2$, and n are defined in formula I.

$R_4$ is an optionally substituted phenyl or an optionally substituted benzo[d][1,3]dioxolyl. In several embodiments, $R_4$ is optionally substituted with 1, 2, or 3 of hydrogen, halo, optionally substituted aliphatic, optionally substituted alkoxy, or combinations thereof. In several embodiments, $R_4$ is phenyl that is substituted at position 2, 3, 4, or combinations thereof with hydrogen, halo, optionally substituted aliphatic, optionally substituted alkoxy, or combinations thereof. For example, $R_4$ is phenyl that is optionally substituted at the 3 position with optionally substituted alkoxy. In another example, $R_4$ is phenyl that is optionally substituted at the 3 position with —$OCH_3$. In another example, $R_4$ is phenyl that is optionally substituted at the 4 position with halo or substituted alkoxy. A more specific example includes an $R_4$ that is phenyl optionally substituted with chloro, fluoro, —$OCH_3$, or —$OCF_3$. In other examples, $R_4$ is a phenyl that is substituted at the 2 position with an optionally substituted alkoxy. In more specific examples, $R_4$ is a phenyl optionally substituted at the 2 position with —$OCH_3$. In other examples, $R_4$ is an unsubstituted phenyl.

In several embodiments, $R_4$ is optionally substituted benzo[d][1,3]dioxolyl. In several examples, $R_4$ is benzo[d][1,3]dioxolyl that is optionally mono-, di-, or tri-substituted with 1, 2, or 3 halo. In more specific examples, $R_4$ is benzo[d][1,3]dioxolyl that is optionally di-substituted with halo.

Another aspect of the present invention provides compounds of formula If:

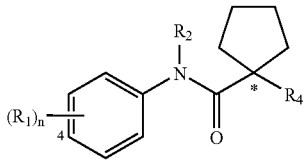

If or a pharmaceutically acceptable salt thereof, wherein $R_1$, $R_2$, $R_4$, and n are defined in formula I.

Another aspect of the present invention provides compounds of formula Ig:

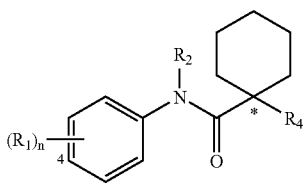

Ig or a pharmaceutically acceptable salt thereof, wherein $R^1$, $R_2$, $R_4$, and n are defined in formula I.

Another aspect of the present invention provides compounds of formula Ih:

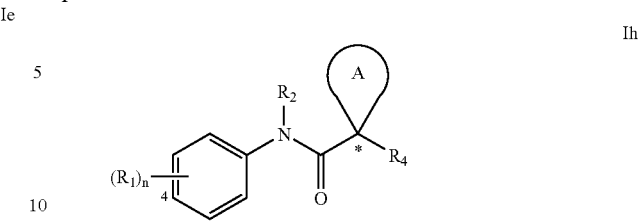

Ih or a pharmaceutically acceptable salt thereof, wherein $R_1$, $R_2$, $R_4$, and n are defined in formula I.

Ring A is an optionally substituted heterocycloaliphatic.

In several embodiments, compounds of formula Ih include compounds of formulae Ih1:

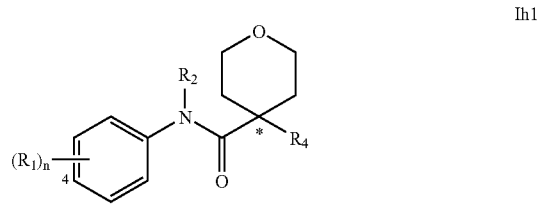

Ih1 or a pharmaceutically acceptable salt thereof, wherein $R_1$, $R_2$, $R_4$, and n are defined in formula I.

Another aspect of the present invention provides compounds of formula II:

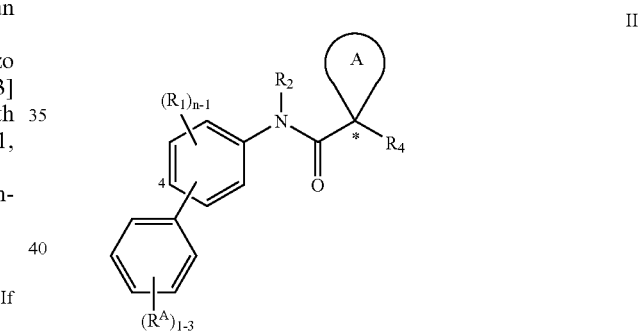

II or a pharmaceutically acceptable salt thereof, wherein
$R_1$, $R_2$, ring A, and $R_4$ are defined in formula I;
n is 1, 2, 3, or 4; and
Each $R^A$ is independently -$Z^A R_5$, wherein each $Z^A$ is independently a bond or an optionally substituted branched or straight $C_{1-6}$ aliphatic chain wherein up to two carbon units of $Z^A$ are optionally and independently replaced by —CO—, —CS—, —$CONR^B$—, —$CONR^B NR^B$—, —$CO_2$—, —OCO—, —$NR^B CO_2$—, —O—, —$NR^B CONR^B$—, —$OCONR^B$—, —$NR^B NR^B$—, —$NR^B CO$—, —S—, —SO—, —$SO_2$—, —$NR^B$—, —$SO_2 NR^B$—, —$NR^B SO_2$—, or —$NR^B SO_2 NR^B$—. Each $R_5$ is independently $R^B$, halo, —OH, —$NH_2$, —$NO_2$, —CN, or —$OCF_3$. Each $R^B$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In some embodiments, each $R_1$ is an optionally substituted $C_{1-6}$ aliphatic, an optionally substituted aryl, an optionally substituted heteroaryl, an optionally substituted 3 to 10 membered cycloaliphatic, or an optionally substituted 3 to 10 membered heterocycloaliphatic, each of which is optionally substituted with 1, 2, or 3 of $R^A$; wherein each $R^A$ is -$Z^A R_5$, wherein each $Z^A$ is independently a bond or an optionally substituted branched or straight $C_{1-6}$ aliphatic chain wherein up to two carbon units of $Z^A$ are optionally and independently replaced by —CO—, —CS—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—; and R$_5$ is independently R$^B$, halo, —OH, —NH$_2$, —NO$_2$, —CN, or —OCF$_3$; wherein each R$^B$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In some embodiments, R$_2$ is $C_{1-4}$ aliphatic, $C_{3-6}$ cycloaliphatic, phenyl, or heteroaryl, each of which is optionally substituted, or R$_2$ is hydrogen.

In some embodiments, ring A is an optionally substituted $C_{3-7}$ cycloaliphatic or an optionally substituted $C_{3-7}$ heterocycloaliphatic where the atoms of ring A adjacent to C* are carbon atoms, and said ring A is optionally substituted with 1, 2, or 3 of -$Z^B$R$_7$, wherein each $Z^B$ is independently a bond, or an optionally substituted branched or straight $C_{1-4}$ aliphatic chain wherein up to two carbon units of $Z^B$ are optionally and independently replaced by —CO—, —CS—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—; Each R$_7$ is independently R$^B$, halo, —OH, —NH$_2$, —NO$_2$, —CN, or —OCF$_3$.

In some embodiments, each R$_4$ is an aryl or heteroaryl, each of which is optionally substituted with 1, 2, or 3 of -$Z^C$R$_8$, wherein each $Z^C$ is independently a bond or an optionally substituted branched or straight $C_{1-6}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —SO—, —SO$_2$—, —NR$^C$—, —SO$_2$NR$^C$—, —NR$^C$SO$_2$—, or —NR$^C$SO$_2$NR$^C$—; wherein each R$_8$ is independently R$^C$, halo, —OH, —NH$_2$, —NO$_2$, —CN, or —OCF$_3$; wherein each R$^C$ is independently an optionally substituted $C_{1-8}$ aliphatic group, an optionally substituted cycloaliphatic, an optionally substituted heterocycloaliphatic, an optionally substituted aryl, or an optionally substituted heteroaryl.

Another aspect of the present invention provides compounds of formula IIa:

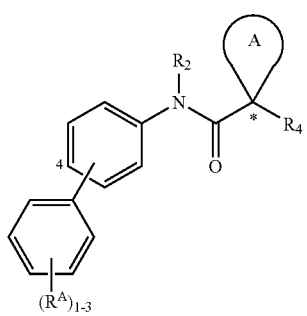

IIa or pharmaceutically acceptable salts thereof, wherein R$_2$, ring A and R$_4$ are defined in formula I, and R$^A$ is defined above.

Another aspect of the present invention provides compounds of formula IIb:

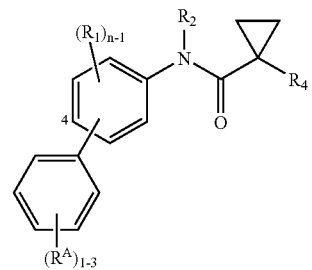

IIb or a pharmaceutically acceptable salt thereof, wherein R$_1$, R$_2$, R$_4$, and n are defined in formula I and R$^A$ is defined in formula II.

Another aspect of the present invention provides compounds of formula IIc:

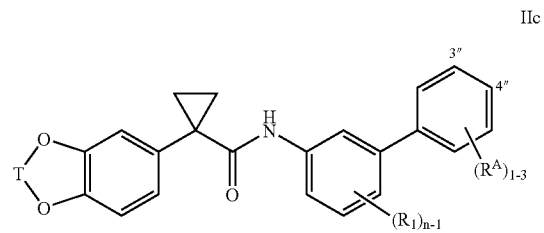

IIc or a pharmaceutically acceptable salt thereof, wherein:

T is an optionally substituted $C_{1-2}$ aliphatic chain, wherein each of the carbon units is optionally and independently replaced by —CO—, —CS—, —COCO—, —SO$_2$—, —B(OH)—, or —B(O(C$_{1-6}$ alkyl))-;

Each of R$_1$ is independently an optionally substituted $C_{1-6}$ aliphatic, an optionally substituted aryl, an optionally substituted heteroaryl, an optionally substituted 3 to 10 membered cycloaliphatic, an optionally substituted 3 to 10 membered heterocycloaliphatic, carboxy, amido, amino, halo, or hydroxy;

Each R$^A$ is independently -$Z^A$R$_5$, wherein each $Z^A$ is independently a bond or an optionally substituted branched or straight $C_{1-6}$ aliphatic chain wherein up to two carbon units of $Z^A$ are optionally and independently replaced by —CO—, —CS—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—;

Each R$_5$ is independently R$^B$, halo, —OH, —NH$_2$, —NO$_2$, —CN, —CF$_3$, or —OCF$_3$; or two R$^A$, taken together with atoms to which they are attached, form a 3-8 membered saturated, partially unsaturated, or aromatic ring with up to 3 ring members independently selected from the group consisting of O, NH, NR$^B$, and S, provided that one R$^A$ is attached to carbon 3" or 4".

Each R$^B$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

n is 2 or 3 provided that when n is 3, a first $R_1$ is attached ortho relative to the phenyl ring substituted with $R^A$ and that a second one $R_1$ is attached para relative to the phenyl ring substituted with $R^A$.

In some embodiments, T is an optionally substituted —$CH_2$—. In some other embodiments, T is an optionally substituted —CH2CH$_2$—.

In some embodiments, T is optionally substituted by -$Z^F R_{10}$; wherein each $Z^F$ is independently a bond or an optionally substituted branched or straight $C_{1-6}$ aliphatic chain wherein up to two carbon units of $Z^F$ are optionally and independently replaced by —CO—, —CS—, —CONR$^F$—, —CONR$^F$NR$^F$—, —CO$_2$—, —OCO—, —NR$^F$CO$_2$—, —O—, —NR$^F$CONR$^F$—, —OCONR$^F$—, —NR$^F$NR$^F$—, —NR$^F$CO—, —S—, —SO—, —SO$_2$—, —NR$^F$—, —SO$_2$NR$^F$—, —NR$^F$SO$_2$—, or —NR$^F$SO$_2$NR$^F$—; $R_{10}$ is independently $R^F$, halo, —OH, —NH$_2$, —NO$_2$, —CN, —CF$_3$, or —OCF$_3$; each $R^F$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl. In one example, $Z^F$ is —O—.

In some embodiments, $R_{10}$ is an optionally substituted $C_{1-6}$ alkyl, an optionally substituted $C_{2-6}$ alkenyl, an optionally substituted $C_{3-7}$ cycloaliphatic, or an optionally substituted $C_{6-10}$ aryl. In one embodiment, $R_{10}$ is methyl, ethyl, isopropyl, or tert-butyl.

In some embodiments, up to two carbon units of T are independently and optionally replaced with —CO—, —CS—, —B(OH)—, or —B(O(C$_{1-6}$ alkyl)-.

In some embodiments, T is selected from the group consisting of —CH$_2$—, —CH$_2$CH$_2$—, —CF$_2$—, —C(CH$_3$)$_2$—, —C(O)—,

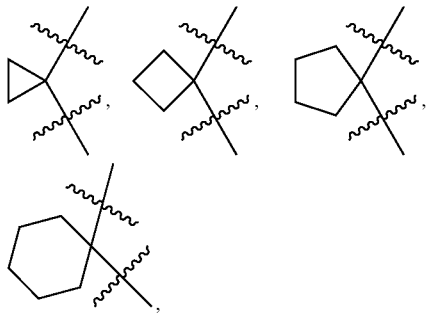

—C(phenyl)$_2$-, —B(OH)—, and —CH(OEt)-. In some embodiments, T is —CH$_2$—, —CF$_2$—, —C(CH$_3$)$_2$—,

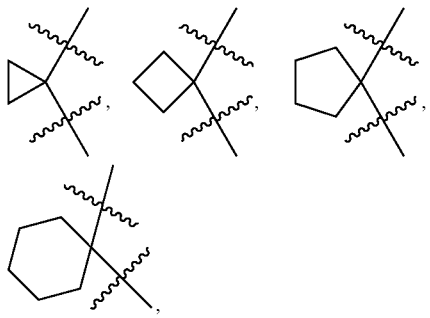

or —C(Phenyl)$_2$-. In other embodiments, T is —CH$_2$H$_2$—, —C(O)—, —B(OH)—, and —CH(OEt)-. In several embodiments, T is —CH$_2$—, —CF$_2$—, —C(CH$_3$)$_2$—,

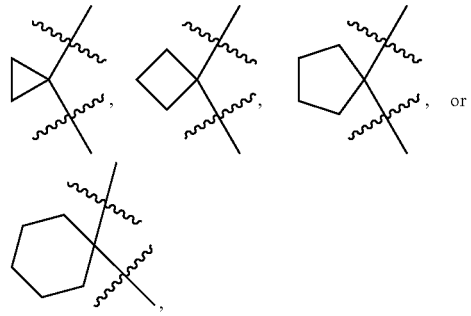

More preferably, T is —CH$_2$—, —CF$_2$—, or —C(CH$_3$)$_2$—. In several embodiments, T is —CH$_2$—. Or, T is —CF$_2$—. Or, T is —C(CH$_3$)$_2$—. Or, T is

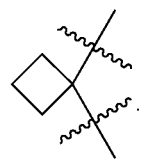

In some embodiments, each $R_1$ is hydrogen. In some embodiments, each of $R_1$ is independently -$Z^E R_9$, wherein each $Z^E$ is independently a bond or an optionally substituted branched or straight $C_{1-6}$ aliphatic chain wherein up to two carbon units of $Z^E$ are optionally and independently replaced by —CO—, —CS—, —CONR$^E$—, —CONR$^E$NR$^E$—, —CO$_2$—, —OCO—, —NR$^E$CO$_2$—, —O—, —NR$^E$CONR$^E$—, —OCONR$^E$—, —NR$^E$NR$^E$—, —NR$^E$CO—, —S—, —SO—, —SO$_2$—, —NR$^E$—, —SO$_2$NR$^E$—, —NR$^E$SO$_2$—, or —NR$^E$SO$_2$NR$^E$—. Each $R^9$ is independently H, $R^E$, halo, —OH, —NH$_2$, —NO$_2$, —CN, —CF$_3$, or —OCF$_3$. Each $R^E$ is independently an optionally substituted group selected from $C_{1-8}$ aliphatic group, cycloaliphatic, heterocycloaliphatic, aryl, and heteroaryl.

In several embodiments, a first $R_1$ is attached ortho relative to the phenyl ring substituted with $R^A$ is —H, —F, —Cl, —CF$_3$, —OCH$_3$, —OCF$_3$, methyl, ethyl, iso-propyl, or tert-butyl.

In several embodiments, a first $R_1$ is attached ortho relative to the phenyl ring substituted with $R^A$ is -$Z^E R_9$, wherein each $Z^E$ is independently a bond or an optionally substituted branched or straight $C_{1-6}$ aliphatic chain wherein up to two carbon units of $Z^E$ are optionally and independently replaced by —CO—, —CONR$^E$—, —CO$_2$—, —O—, —S—, —SO—, —SO$_2$—, —NR$^E$—, or —SO$_2$NR$^E$—. Each $R_9$ is hydrogen, $R^E$, halo, —OH, —NH$_2$, —CN, —CF$_3$, or —OCF$_3$. Each $R^E$ is independently an optionally substituted group selected from the group including $C_{1-8}$ aliphatic group, a cycloaliphatic, a heterocycloaliphatic, an aryl, and a heteroaryl. In one embodiment, $Z^E$ is a bond. In one embodiment, $Z^E$ is a straight $C_{1-6}$ aliphatic chain, wherein one carbon unit of $Z^E$ is optionally replaced by —CO—, —CONR$^E$—, —CO$_2$—, —O—, or —NR$^E$—. In one embodiment, $Z^E$ is a $C_{1-6}$ alkyl chain. In one embodiment, $Z^E$ is —CH$_2$—. In one embodiment, $Z^E$ is —CO—. In one embodiment, $Z^E$ is —$CO_2$—. In one embodiment, $Z^E$ is —$CONR^E$. In one embodiment, $Z^E$ is —CO—.

In some embodiments, $R_9$ is H, —$NH_2$, hydroxy, —CN, or an optionally substituted group selected from the group of $C_{1-8}$ aliphatic, $C_{3-8}$ cycloaliphatic, 3-8 membered heterocycloaliphatic, $C_{6-10}$ aryl, and 5-10 membered heteroaryl. In one embodiment, $R_9$ is H. In one embodiment, $R_9$ is hydroxy. Or, $R_9$ is —$NH_2$. Or, $R_9$ is —CN. In some embodiments, $R_9$ is an optionally substituted 3-8 membered heterocycloaliphatic, having 1, 2, or 3 ring members independently selected from nitrogen (including NH and $NR^X$), oxygen, and sulfur (including S, SO, and $SO_2$). In one embodiment, $R_9$ is an optionally substituted five membered heterocycloaliphatic with one nitrogen (including NH and $NR^X$) ring member. In one embodiment, $R_9$ is an optionally substituted pyrrolidin-1-yl. Examples of said optionally substituted pyrrolidin-1-yl include pyrrolidin-1-yl and 3-hydroxy-pyrrolidin-1-yl. In one embodiment, $R_9$ is an optionally substituted six membered heterocycloaliphatic with two heteroatoms independently selected from nitrogen (including NH and $NR^X$) and oxygen. In one embodiment, $R_9$ is morpholin-4-yl. In some embodiments, $R_9$ is an optionally substituted 5-10 membered heteroaryl. In one embodiment, $R_9$ is an optionally substituted 5 membered heteroaryl, having 1, 2, 3, or 4 ring members independently selected from nitrogen (including NH and $NR^X$), oxygen, and sulfur (including S, SO, and $SO_2$). In one embodiment, $R_9$ is I H-tetrazol-5-yl.

In one embodiment, a first $R_1$ is attached ortho relative to the phenyl ring substituted with $R^A$ is $Z^E R_9$; wherein $Z^E$ is $CH_2$ and $R_9$ is 1H-tetrazol-5-yl. In one embodiment, one $R_1'$ is $Z^E R^9$; wherein $Z^E$ is $CH_2$ and $R_9$ is morpholin-4-yl. In one embodiment, one $R_1'$ is $Z^E R_9$; wherein $Z^E$ is $CH_2$ and $R_9$ is pyrrolidin-1-yl. In one embodiment, one $R_1'$ is $Z^E R_9$; wherein $Z^E$ is $CH_2$ and $R_9$ is 3-hydroxy-pyrrolidin-1-yl. In one embodiment, one $R_1'$ is $Z^E R_9$; wherein $Z^E$ is CO and $R_9$ is 3-hydroxy-pyrrolidin-1-yl.

In some embodiments, a first $R_1$ is attached ortho relative to the phenyl ring substituted with $R^A$ is selected from $CH_2OH$, COOH, $CH_2OCH_3$, $COOCH_3$, $CH_2NH_2$, $CH_2NHCH_3$, $CH_2CN$, $CONHCH_3$, $CH_2CONH_2$, $CH_2OCH_2CH_3$, $CH_2N(CH_3)_2$, $CON(CH_3)_2$, $CH_2NHCH_2CH_2OH$, $CH_2NHCH_2CH_2COOH$, $CH_2OCH(CH_3)_2$, $CONHCH(CH_3)CH_2OH$, or $CONHCH(tert-butyl)CH_2OH$.

In some embodiments, a first $R_1$ is attached ortho relative to the phenyl ring substituted with $R^A$ is an optionally substituted $C_{3-10}$ cycloaliphatic or an optionally substituted 4-10 membered heterocycloaliphatic. In one embodiment, $R_1'$ is an optionally substituted 4, 5, or 6 membered heterocycloalkyl containing one oxygen atom. In one embodiment, $R_1'$ is 3-methyloxetan-3-yl.

In some embodiments, a second one $R_1$ is attached para relative to the phenyl ring substituted with $R^A$ is selected from the group consisting of H, halo, optionally substituted $C_{1-6}$ aliphatic, and optionally substituted —$O(C_{1-6}$ aliphatic). In some embodiments, a second one $R_1$ is attached para relative to the phenyl ring substituted with $R^A$ is selected from the group consisting of H, methyl, ethyl, iso-propyl, tert-butyl, F, Cl, $CF_3$, —$OCH_3$, —$OCH_2CH_3$, —O-(iso-propyl), —O-(tert-butyl), and —$OCF_3$. In one embodiment, a second one $R_1$ is attached para relative to the phenyl ring substituted with $R^A$ is H. In one embodiment, a second one $R_1$ is attached para relative to the phenyl ring substituted with $R^A$ is methyl. In one embodiment, a second one $R_1$ is attached para relative to the phenyl ring substituted with $R^A$ is F. In one embodiment, a second one $R_1$ is attached para relative to the phenyl ring substituted with $R^A$ is —$OCF_3$. In one embodiment, a second one $R_1$ is attached para relative to the phenyl ring substituted with $R^A$ is —$OCH_3$.

In some embodiments, one $R^A$ is attached to carbon 3" or 4" and is -$Z^A R_5$, wherein each $Z^A$ is independently a bond or an optionally substituted branched or straight $C_{1-6}$ aliphatic chain wherein up to two carbon units of $Z^A$ are optionally and independently replaced by —CO—, —CS—, —$CONR^B$—, —$CONR^B NR^B$—, —$CO_2$—, —OCO—, —$NR^B CO_2$—, —O—, —$NR^B CONR^B$—, —$OCONR^B$—, —$NR^B NR^B$—, —$NR^B CO$—, —S—, —SO—, —$SO_2$—, —$NR^B$—, —$SO_2 NR^B$—, —$NR^B SO_2$—, or —$NR^B SO_2 NR^B$—. In yet some embodiments, $Z^A$ is independently a bond or an optionally substituted branched or straight $C_{1-6}$ aliphatic chain wherein one carbon unit of $Z^A$ is optionally replaced by —CO—, —SO—, —$SO_2$—, —COO—, —OCO—, —$CONR^B$—, —$NR^B CO$—, —$NR^B CO_2$—, —O—, —$NR^B SO_2$—, or —$SO_2 NR^B$—. In some embodiments, one carbon unit of $Z^A$ is optionally replaced by —CO—. Or, by —SO—. Or, by —$SO_2$—. Or, by —COO—. Or, by —OCO—. Or, by-$CONR^B$. Or, by —$NR^B CO$—. Or, by —$NR^B CO_2$—. Or, by —O—. Or, by —$NR^B SO_2$—. Or, by —$SO_2 NR^B$—.

In several embodiments, $R_5$ is hydrogen, halo, —OH, —$NH_2$, —CN, —$CF_3$, —$OCF_3$, or an optionally substituted group selected from the group consisting of $C_{1-6}$ aliphatic, $C_{3-8}$ cycloaliphatic, 3-8 membered heterocycloaliphatic, $C_{6-10}$ aryl, and 5-10 membered heteroaryl. In several examples, $R_5$ is hydrogen, F, Cl, —OH, —CN, —$CF_3$, or —$OCF_3$. In some embodiments, $R_5$ is $C_{1-6}$ aliphatic, $C_{3-8}$ cycloaliphatic, 3-8 membered heterocycloaliphatic, $C_{6-10}$ aryl, and 5-10 membered heteroaryl, each of which is optionally substituted with 1 or 2 substituents independently selected from the group consisting of $R^B$, oxo, halo, —OH, —$NR^B R^B$, —$OR^B$, —$COOR^B$, and —$CONR^B R^B$. In several examples, $R_5$ is optionally substituted by 1 or 2 substituents independently selected from the group consisting of oxo, F, Cl, methyl, ethyl, iso-propyl, tert-butyl, —$CH_2OH$, —$CH_2CH_2OH$, —C(O)OH, —C(O)$NH_2$, —$CH_2O(C_{1-6}$ alkyl), —$CH_2CH_2O(C_{1-6}$ alkyl), and —C(O)($C_{1-6}$ alkyl).

In one embodiment, $R_5$ is hydrogen. In some embodiments, $R_5$ is selected from the group consisting of straight or branched $C_{1-6}$ alkyl or straight or branched $C_{2-6}$ alkenyl; wherein said alkyl or alkenyl is optionally substituted with 1 or 2 substituents independently selected from the group consisting of $R^B$, oxo, halo, —OH, —$NR^B R^B$, —$OR^B$, —$COOR^B$, and —$CONR^B R^B$.

In other embodiments, $R_5$ is $C_{3-8}$ cycloaliphatic optionally substituted with 1 or 2 substituents independently selected from the group consisting of $R^B$, oxo, halo, —OH, —$NR^B R^B$, —$OR^B$, —$COOR^B$, and —$CONR^B R^B$. Examples of cycloaliphatic include but are not limited to cyclopropyl, cyclobutyl, cyclopentyl, cyclohexyl, and cycloheptyl.

In yet other embodiments, $R_5$ is a 3-8 membered heterocyclic with 1 or 2 heteroatoms independently selected from the group consisting of nitrogen (including NH and $NR^X$), oxygen, and sulfur (including S, SO, and $SO_2$); wherein said heterocyclic is optionally substituted with 1 or 2 substituents independently selected from the group $R^B$, oxo, halo, —OH, —$NR^B R^B$, —$OR^B$, —$COOR^B$, and —$CONR^B R^B$. Examples of 3-8 membered heterocyclic include but are not limited to

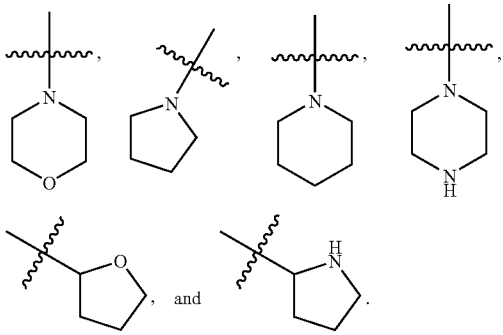

In yet some other embodiments, $R_5$ is an optionally substituted 5-8 membered heteroaryl with one or two ring atom independently selected from the group consisting of nitrogen (including NH and $NR^X$), oxygen, and sulfur (including S, SO, and $SO_2$). Examples of 5-8 membered heteroaryl include but are not limited to

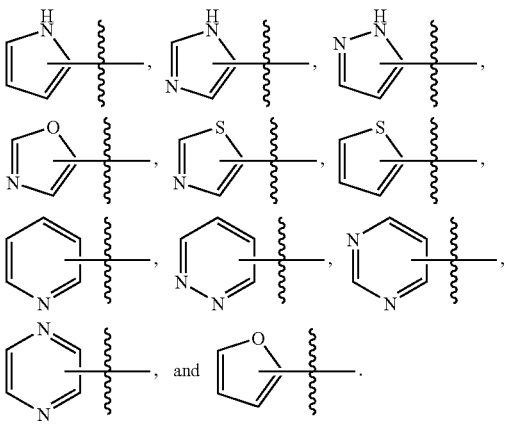

In some embodiments, two $R^4$s, taken together with carbons to which they are attached, form an optionally substituted 4-8 membered saturated, partially unsaturated, or aromatic ring with 0-2 ring atoms independently selected from the group consisting of nitrogen (including NH and $NR^X$), oxygen, and sulfur (including S, SO, and $SO_2$). Examples of two RAS, taken together with phenyl containing carbon atoms to which they are attached, include but are not limited to

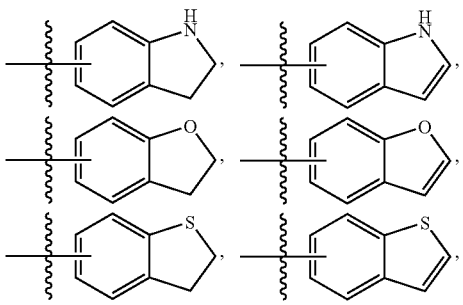

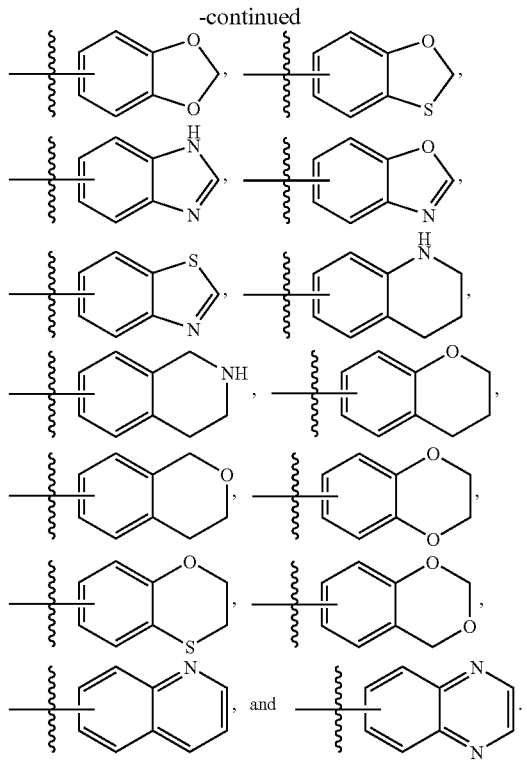

In some embodiments, one $R^A$ not attached top the carbon 3" or 4" is selected from the group consisting of H, $R^B$, halo, —OH, —$(CH_2)_r NR^B R^B$, —$(CH_2)_r$—$OR^B$, —$SO_2$—$R^B$, —$NR^B$—$SO_2$—$R^B$, —$SO_2 NR^B R^B$, —$C(O)R^B$, —$C(O)OR^B$, —$OC(O)OR^B$, —$NR^B C(O)OR^B$, and —$C(O)NR^B R^B$; wherein r is 0, 1, or 2; and each $R^B$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl. In other embodiments, one $R^A$ not attached top the carbon 3" or 4" is selected from the group consisting of H, $C_{1-6}$ aliphatic, halo, —CN, —$NH_2$, —NH ($C_{1-6}$ aliphatic), —$N(C_{1-6}$ aliphatic$)_2$, —$CH_2$—$N(C_{1-6}$ aliphatic$)_2$, —$CH_2$—$NH(C_{1-6}$ aliphatic), —$CH_2 NH_2$, —OH, —$O(C_{1-6}$ aliphatic), —$CH_2 OH$, —$CH_2$—$O(C_{1-6}$ aliphatic), —$SO_2$ ($C_{1-6}$ aliphatic), —$N(C_{1-6}$ aliphatic)-$SO_2$ ($C_{1-6}$ aliphatic), —NH—$SO_2(C_{1-6}$ aliphatic), —$SO_2 NH_2$, $SO_2 NH$ ($C_{1-6}$ aliphatic), —$SO_2 N(C_{1-6}$ aliphatic$)_2$, —$C(O)(C_{1-6}$ aliphatic), —$C(O)O(C_{1-6}$ aliphatic), —$C(O)OH$, —$OC(O)O$ ($C_{1-6}$ aliphatic), —$NHC(O)(C_{1-6}$ aliphatic), —$NHC(O)O$ ($C_{1-6}$ aliphatic), —$N(C_{1-6}$ aliphatic)$C(O)O(C_{1-6}$ aliphatic), —$C(O)NH_2$, and —$C(O)N(C_{1-6}$ aliphatic$)_2$. In several examples, $R^{A2}$ is selected from the group consisting of H, $C_{1-6}$ aliphatic, halo, —CN, —$NH_2$, —$CH_2 NH_2$, —OH, —$O(C_{1-6}$ aliphatic), —$CH_2 OH$, —$SO_2$ ($C_{1-6}$ aliphatic), —NH—$SO_2$ ($C_{1-6}$ aliphatic), —$C(O)O(C_{1-6}$ aliphatic), —$C(O)OH$, —$NHC(O)(C_{1-6}$ aliphatic), —$C(O)NH_2$, —$C(O)NH(C_{1-6}$ aliphatic), and —$C(O)N(C_{1-6}$ aliphatic$)_2$. For examples, one $R^A$ not attached top the carbon 3" or 4" is selected from the group consisting of H, methyl, ethyl, n-propyl, iso-propyl, tert-butyl, F, Cl, CN, —$NH_2$, —$CH_2 NH_2$, —OH, —$OCH_3$, —O-ethyl, —O-(iso-propyl), —O-(n-propyl), —$CH_2 OH$, —$SO_2 CH_3$, —NH—$SO_2 CH_3$, —$C(O)OCH_3$, —$C(O)OCH_2 CH_3$, —$C(O)OH$, —$NHC(O)CH_3$, —$C(O)NH_2$, and —$C(O)N(CH_3)_2$. In one embodiment, all $R^4$s not attached top the carbon 3" or 4" are hydrogen. In another embodiment, one $R^A$ not attached top the carbon 3" or 4" is methyl. Or, one $R^A$ not attached top the carbon 3" or 4" is ethyl. Or, one $R^A$ not attached top the carbon 3" or 4" is F. Or, one $R^A$ not attached top the carbon 3" or 4" is Cl. Or, one $R^A$ not attached top the carbon 3" or 4" is —$OCH_3$.

In one embodiment, the present invention provides compounds of formula IId or formula IIe:

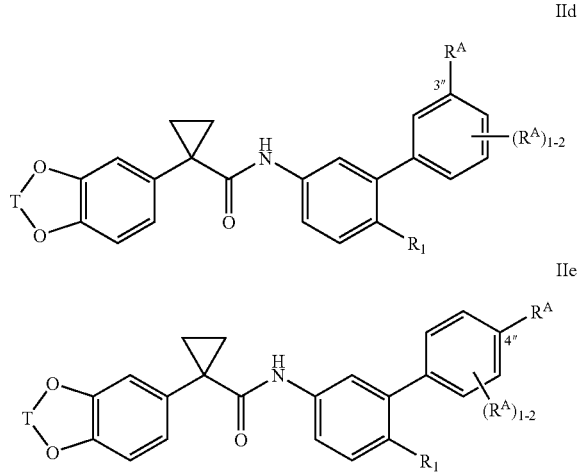

wherein T, each $R^A$, and $R_1$ are as defined above.

In one embodiment, T is —$CH_2$—, —$CF_2$—, —$C(CH_3)_2$—, or

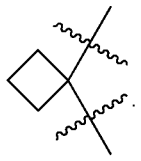

In one embodiment, T is —$CH_2$—. In one embodiment, T is —$CF_2$—. In one embodiment, T is —$C(CH_3)_2$—. In one embodiment, T is

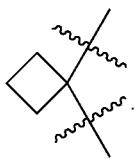

In one embodiment, $R_1$ is selected from the group consisting of H, halo, —$CF_3$, or an optionally substituted group selected from —$C_{1-6}$ aliphatic, —$O(C_{1-6}$ aliphatic), —$C_{3-5}$ cycloalkyl, 3-6 membered heterocycloalkyl containing one oxygen atom, carboxy, and aminocarbonyl. Said —$C_{1-6}$ aliphatic, —$O(C_{1-6}$ aliphatic), —$C_{3-5}$ cycloalkyl, 3-6 membered heterocycloalkyl containing one oxygen atom, carboxy, or aminocarbonyl is optionally substituted with halo, —CN, hydroxy, or a group selected from amino, branched or straight $C_{1-6}$ aliphatic, branched or straight alkoxy, aminocarbonyl, $C_{3-8}$ cycloaliphatic, 3-10 membered heterocyclicaliphatic having 1, 2, or 3 ring membered independently selected from nitrogen (including NH and $NR^X$), oxygen, or sulfur (including S, SO, and $SO_2$), $C_{6-10}$ aryl, and 5-10 membered heteroaryl, each of which is further optionally substituted with halo or hydroxy. Exemplary embodiments include H, methyl, ethyl, iso-propyl, tert-butyl, F, Cl, $CF_3$, $CHF_2$, —$OCF_3$, —$OCH_3$, —$OCH_2CH_3$, —O-(iso-propyl), —O-(tert-butyl), —COOH, —$COOCH_3$, —CONHCH(tert-butyl)$CH_2OH$, —CONHCH($CH_3$)$CH_2OH$, —CON($CH_3$)$_2$, —$CONHCH_3$, —$CH_2CONH_2$, pyrrolid-1-yl-methyl, 3-hydroxy-pyrrolid-1-yl-methyl, morpholin-4-yl-methyl, 3-hydroxy-pyrrolid-1-yl-formyl, tetrazol-5-yl-methyl, cyclopropyl, hydroxymethyl, methoxymethyl, ethoxymethyl, methylaminomethyl, dimethylaminomethyl, cyanomethyl, 2-hydroxyethylaminomethyl, iso-propoxymethyl, or 3-methyloxetan-3-yl. In still other embodiments, $R_1$ is H. Or, $R_1$ is methyl. Or, $R_1$ is ethyl. Or, $R_1$ is $CF_3$. Or, $R_1$ is oxetanyl.

In some embodiments, $R^A$ attached at the carbon 3" or 4" is H, halo, —OH, —$CF_3$, —$OCF_3$, —CN, —$SCH_3$, or an optionally substituted group selected from $C_{1-6}$ aliphatic, amino, alkoxy, or 3-8 membered heterocycloaliphatic having 1, 2, or 3 ring members each independently chosen from nitrogen (including NH and $NR^X$), oxygen, or sulfur (including S, SO, and $SO_2$). In some embodiments, $R^A$ attached at the carbon 3" or 4" is H, F, Cl, OH, $CF_3$, $OCF_3$, CN, or $SCH_3$. In some embodiments, $R^A$ attached at the carbon 3" or 4" is $C_{1-6}$ alkyl, amino, alkoxy, or 3-8 membered heterocycloalkyl having 1, 2, or 3 ring members each independently chosen from nitrogen (including NH and $NR^X$), oxygen, or sulfur (including S, SO, and $SO_2$); wherein said alkyl, amino, alkoxy, or heterocycloalkyl each is optionally substituted with 1, 2, or 3 groups independently selected from oxo, halo, hydroxy, or an optionally substituted group selected from $C_{1-6}$ aliphatic, cycloaliphatic, heterocycloaliphatic, aryl, heteroaryl, carbonyl, amino, and carboxy. In one embodiment, $R^A$ attached at the carbon carbon 3" or 4" is H, F, Cl, —OH, —$CF_3$, —$OCF_3$, —CN, —$SCH_3$, methyl, ethyl, iso-propyl, tert-butyl, 2-methylpropyl, cyanomethyl, aminomethyl, hydroxymethyl, 1-hydroxyethyl, methoxymethyl, methylaminomethyl, (2'-methylpropylamino)-methyl, 1-methyl-1-cyanoethyl, n-propylaminomethyl, dimethylaminomethyl, 2-(methylsulfonyl)-ethyl, $CH_2COOH$, CH(OH)COOH, diethylamino, piperid-1-yl, 3-methyloxetan-3-yl, 2,5-dioxopyrrolid-1-yl, morpholin-4-yl, 2-oxopyrrolid-1-yl, tetrazol-5-yl, methoxy, ethoxy, $OCH_2COOH$, amino, dimethylamino, $NHCH_2COOH$, or acetyl.

In one embodiment, $R^A$ attached at the carbon 3" or 4" is $Z^A R_5$, wherein $Z^A$ is selected from —CONH—, —CON($C_{1-6}$ alkyl)-, NHCO—, $SO_2NH$, $SO_2N(C_{1-6}$ alkyl)-, $NHSO_2$—, —$CH_2NHSO_2$—, $CH_2N(CH_3)SO_2$—, —$CH_2NHCO$—, —$CH_2N(CH_3)CO$—, —COO—, —$SO_2$—, —SO—, or —CO—.

In one embodiment, $R^A$ attached at the carbon 3" or 4" is $Z^A R_5$, wherein $Z^A$ is selected from —CONH—, —$SO_2NH$—, —$SO_2N(C_{1-6}$ alkyl)-, —$CH_2NHSO_2$—, —$CH_2N(CH_3)SO_2$—, —$CH_2NHCO$—, —COO—, —$SO_2$—, or —CO—.

In one embodiment, $Z^A$ is COO and $R_5$ is H. In one embodiment, $Z^A$ is COO and $R_5$ is an optionally substituted straight or branched $C_{1-6}$ aliphatic. In one embodiment, $Z^A$ is COO and $R_5$ is an optionally substituted straight or branched $C_{1-6}$ alkyl. In one embodiment, $Z^A$ is COO and $R_5$ is $C_{1-6}$ alkyl. In one embodiment, $Z^A$ is COO and $R_5$ is methyl.

In one embodiment, $Z^A$ is CONH and $R_5$ is H. In one embodiment, $Z^A$ is CONH and $R_5$ is an optionally substituted straight or branched $C_{1-6}$ aliphatic. In one embodiment, $Z^A$ is CONH and $R_5$ is $C_{1-6}$ straight or branched alkyl optionally substituted with one or more groups independently selected from —OH, halo, CN, optionally substituted $C_{1-6}$ alkyl, optionally substituted $C_{3-10}$ cycloaliphatic, optionally substituted 3-8 membered heterocycloaliphatic, optionally substituted $C_{6-10}$ aryl, optionally substituted 5-8 membered heteroaryl, optionally substituted alkoxy, optionally substituted amino, and optionally substituted aminocarbonyl. In one embodiment, $Z^A$ is CONH and $R_5$ is 2-(dimethylamino)ethyl, cyclopropylmethyl, cyclohexylmethyl, 2-(cyclohexen-1-yl)ethyl, 3-(morpholin-4-yl)propyl, 2-(morpholin-4-yl)ethyl, 2-(1H-imidazol-4-yl)ethyl, tetrahydrofuran-2-yl-methyl, 2-(pyrid-2-yl)ethyl, (1-ethyl-pyrrolidin-2-yl)methyl, 1-hydroxymethylpropyl, 1-hydroxymethylbutyl, 1-hydroxymethylpentyl, 1-hydroxymethyl-2-hydroxyethyl, 1-hydroxymethyl-2-methylpropyl, 1-hydroxymethyl-3-methylbutyl, 2,2-dimethyl-1-hydroxymethyl-propyl, 1,1-di(hydroxymethyl)ethyl, 1,1-di(hydroxymethyl)propyl, 3-ethoxypropyl, 2-acetoaminoethyl, 2-(2'-hydroxyethoxy)ethyl, 2-hydroxyethyl, 3-hydroxypropyl, 2-hydroxypropyl, 4-hydroxybutyl, 2,3-dihydroxypropyl, 2-hydroxy-1-methylethyl, 2-methoxyethyl, 3-methoxypropyl, 2-cyanoethyl, or aminoformylmethyl. In one embodiment, $Z^A$ is CONH and $R_5$ is straight or branched $C_{1-6}$ alkyl. In one embodiment, $Z^A$ is CONH and $R_5$ is methyl, ethyl, n-propyl, iso-propyl, 3-methylbutyl, 3,3-dimethylbutyl, 2-methylpropyl, or tert-butyl.

In one embodiment, $Z^A$ is CONH and $R_5$ is an optionally substituted $C_{3-10}$ cycloaliphatic. In one embodiment, $Z^A$ is CONH and $R_5$ is an optionally substituted $C_{3-10}$ cycloalkyl. In one embodiment, $Z^A$ is CONH and $R_5$ is cyclopropyl, cyclobutyl, cyclopentyl, or cyclohexyl.

In some embodiment, $Z^A$ is CONH and $R_5$ is an optionally substituted 3-8 membered heterocycloaliphatic. In several examples, $Z^A$ is CONH and $R_5$ is an optionally substituted 3-8 membered heterocycloalkyl, having 1, 2, or 3 ring members independently selected from nitrogen (including NH and $NR^X$), oxygen, or sulfur (including S, SO, and $SO_2$). In several examples, $Z^A$ is CONH and $R_5$ is 3-8 membered heterocycloalkyl optionally substituted with 1, 2, or 3 groups independently selected from oxo, halo, hydroxy, or an optionally substituted group selected from $C_{1-6}$ aliphatic, cycloaliphatic, heterocycloaliphatic, aryl, heteroaryl, carbonyl, amino, and carboxy. In one embodiment, $Z^A$ is CONH and $R_5$ is 3-oxo-isoxazolidin-4-yl.

In some embodiments, $Z^A$ is CON($C_{1-6}$ aliphatic) and $R_5$ is an optionally substituted $C_{1-6}$ aliphatic or an optionally substituted $C_{3-8}$ cycloaliphatic. In some embodiments, $Z^A$ is CON(branched or straight $C_{1-6}$ alkyl) and $R_5$ is branched or straight $C_{1-6}$ alkyl or $C_{3-8}$ cycloaliphatic, each optionally substituted with 1, 2, or 3 groups independently selected from CN, OH, and an optionally substituted group chosen from amino, branched or straight $C_{1-6}$ aliphatic, $C_{3-8}$ cycloaliphatic, 3-8 membered heterocycloaliphatic, $C_{6-10}$ aryl, and 5-10 membered heteroaryl. In one embodiment, $Z^A$ is CON($CH_3$) and $R_5$ is methyl, ethyl, n-propyl, butyl, 2-pyrid-2-ylethyl, dimethylaminomethyl, 2-dimethylaminoethyl, 1,3-dioxolan-2-ylmethyl, 2-cyanoethyl, cyanomethyl, or 2-hydroxyethyl. In one embodiment, $Z^A$ is CON($CH_2CH_3$) and $R_5$ is ethyl, propyl, iso-propyl, n-butyl, tert-butyl, cyclohexyl, 2-dimethylaminoethyl, or 2-hydroxyethyl. In one embodiment, $Z^A$ is CON($CH_2CH_2CH_3$) and $R_5$ is cyclopropylmethyl or 2-hydroxyethyl. In one embodiment, $Z^A$ is CON(iso-propyl) and $R_5$ is iso-propyl.

In some embodiments, $Z^A$ is $CH_2NHCO$ and $R_5$ is an optionally substituted straight or branched $C_{1-6}$ aliphatic, an optionally substituted $C_{3-8}$ cycloaliphatic, an optionally substituted alkoxy, or an optionally substituted heteroaryl. In some embodiments, $Z^A$ is $CH_2NHCO$ and $R_5$ is straight or branched $C_{1-6}$ alkyl, $C_{3-8}$ cycloalkyl, or alkoxy, each of which is optionally substituted with 1, 2, or 3 groups independently selected from halo, oxo, hydroxy, or an optionally substituted group selected from $C_{1-6}$ aliphatic, $C_{3-8}$ cycloaliphatic, 3-8 membered heterocycloaliphatic, $C_{6-10}$ aryl, 5-10 membered heteroaryl, alkoxy, amino, carboxyl, and carbonyl. In one embodiment, $Z^A$ is $CH_2NHCO$ and $R_5$ is methyl, ethyl, 1-ethylpropyl, 2-methylpropyl, 1-methylpropyl, 2,2-dimethylpropyl, n-propyl, iso-propyl, n-butyl, tert-butyl, cyclopentyl, dimethylaminomethyl, methoxymethyl, (2'-methoxyethoxy)methyl, (2'-methoxy)ethoxy, methoxy, ethoxy, iso-propoxy, or tert-butoxy. In one embodiment, $Z^A$ is $CH_2NHCO$ and $R_5$ is an optionally substituted heteroaryl. In one embodiment, $Z^A$ is $CH_2NHCO$ and $R_5$ is pyrazinyl.

In some embodiments, $Z^A$ is $CH_2N(CH_3)CO$ and $R_5$ is an optionally substituted straight or branched $C_{1-6}$ aliphatic, $C_{3-8}$ cycloaliphatic, or an optionally substituted heteroaryl. In some embodiments, $Z^A$ is $CH_2N(CH_3)CO$ and $R_5$ is straight or branched $C_{1-6}$ alkyl, or 5 or 6 membered heteroaryl, each of which is optionally substituted with 1, 2, or 3 groups independently selected from halo, oxo, hydroxy, or an optionally substituted group selected from $C_{1-6}$ aliphatic, $C_{3-8}$ cycloaliphatic, 3-8 membered heterocycloaliphatic, $C_{6-10}$ aryl, 5-10 membered heteroaryl, alkoxy, amino, carboxyl, and carbonyl. In one embodiment, $Z^A$ is $CH_2N(CH_3)CO$ and $R_5$ is methoxymethyl, (2'-methoxyethoxy)methyl, dimethylaminomethyl, or pyrazinyl. In some embodiments, Z A is $CH_2N(CH_3)CO$ and $R_5$ is branched or straight $C_{1-6}$ alkyl or $C_{3-8}$ cycloalkyl. In one embodiment, $Z^A$ is $CH_2N(CH_3)CO$ and $R_5$ is methyl, ethyl, iso-propyl, n-propyl, n-butyl, tert-butyl, 1-ethylpropyl, 2-methylpropyl, 2,2-dimethylpropyl, or cyclopentyl.

In one embodiment, $Z^A$ is $SO_2NH$ and $R_5$ is H. In some embodiments, $Z^A$ is $SO_2NH$ and $R_5$ is an optionally substituted straight or branched $C_{1-6}$ aliphatic. In some embodiments, $Z^A$ is $SO_2NH$ and $R_5$ is straight or branched $C_{1-6}$ alkyl optionally substituted with halo, oxo, hydroxy, or an optionally substituted group selected from $C_{1-6}$ aliphatic, $C_{3-8}$ cycloaliphatic, 3-8 membered heterocycloaliphatic, $C_{6-10}$ aryl, 5-10 membered heteroaryl, alkoxy, amino, amido, carboxyl, or carbonyl. In one embodiment, $Z^A$ is $SO_2NH$ and $R_5$ is methyl. In one embodiment, $Z^A$ is $SO_2NH$ and $R_5$ is ethyl. In one embodiment, $Z^A$ is $SO_2NH$ and $R_5$ is n-propyl. In one embodiment, $Z^A$ is $SO_2NH$ and $R_5$ is iso-propyl. In one embodiment, $Z^A$ is $SO_2NH$ and $R_5$ is tert-butyl. In one embodiment, $Z^A$ is $SO_2NH$ and $R_5$ is 3,3-dimethylbutyl. In one embodiment, $Z^A$ is $SO_2NH$ and $R_5$ is $CH_2CH_2OH$. In one embodiment, $Z^A$ is $SO_2NH$ and $R_5$ is $CH_2CH_2OCH_3$. In one embodiment, $Z^A$ is $SO_2NH$ and $R_5$ is $CH(CH_3)CH_2OH$. In one embodiment, $Z^A$ is $SO_2NH$ and $R_5$ is $CH_2CH(CH_3)OH$. In one embodiment, $Z^A$ is $SO_2NH$ and $R_5$ is $CH(CH_2OH)_2$. In one embodiment, $Z^A$ is $SO_2NH$ and $R_5$ is $CH_2CH(OH)CH_2OH$. In one embodiment, $Z^A$ is $SO_2NH$ and $R_5$ is $CH_2CH(OH)CH_2CH_3$. In one embodiment, $Z^A$ is $SO_2NH$ and $R_5$ is $C(CH_3)_2CH_2OH$. In one embodiment, $Z^A$ is $SO_2NH$ and $R_5$ is $CH(CH_2CH_3)CH_2OH$. In one embodiment, $Z^A$ is $SO_2NH$ and $R_5$ is $CH_2CH_2OCH_2CH_2OH$. In one embodiment, $Z^A$ is $SO_2NH$ and $R_5$ is $C(CH_3)(CH_2OH)_2$. In one embodiment, $Z^A$ is $SO_2NH$ and $R_5$ is $CH(CH_3)C(O)OH$. In one embodiment, $Z^A$ is $SO_2NH$ and $R_5$ is $CH(CH_2OH)C(O)OH$. In one embodiment, $Z^A$ is $SO_2NH$ and $R_5$ is $CH_2C(O)OH$. In one embodiment, $Z^A$ is $SO_2NH$ and $R_5$ is $CH_2CH_2C(O)OH$. In one embodiment, $Z^A$ is $SO_2NH$ and $R_5$ is $CH_2CH(OH)CH_2C(O)OH$. In one embodiment, $Z^A$ is $SO_2NH$ and $R_5$ is $CH_2CH_2N(CH_3)_2$. In one embodiment, $Z^A$ is $SO_2NH$ and $R_5$ is $CH_2CH_2NHC(O)CH_3$. In one embodiment, $Z^A$ is $SO_2NH$ and $R_5$ is $CH(CH(CH_3)_2)CH_2OH$. In one embodiment, $Z^A$ is $SO_2NH$ and $R_5$ is $CH(CH_2CH_2CH_3)CH_2OH$. In one embodiment, $Z^A$ is $SO_2NH$ and $R_5$ is tetrahydrofuran-2-ylmethyl. In one embodiment, $Z^A$ is $SO_2NH$ and $R_5$ is furylmethyl. In one embodiment, $Z^A$ is $SO_2NH$ and $R_5$ is (5-methylfuryl)-methyl.

In one embodiment, $Z^A$ is $SO_2NH$ and $R_5$ is 2-pyrrolidinyl-ethyl. In one embodiment, $Z^A$ is $SO_2NH$ and $R_5$ is 2-(1-methylpyrrolidinyl)-ethyl. In one embodiment, $Z^A$ is $SO_2NH$ and $R_5$ is 2-(morpholin-4-yl)-ethyl. In one embodiment, $Z^A$ is $SO_2NH$ and $R_5$ is 3-(morpholin-4-yl)-propyl. In one embodiment, $Z^A$ is $SO_2NH$ and $R_5$ is $C(CH_2CH_3)(CH_2OH)_2$. In one embodiment, $Z^A$ is $SO_2NH$ and $R_5$ is 2-(1H-imidazol-4-yl) ethyl. In one embodiment, $Z^A$ is $SO_2NH$ and $R_5$ is 3-(1H-imidazol-1-yl)-propyl. In one embodiment, $Z A$ is $SO_2NH$ and $R_5$ is 2-(pyridin-2-yl)-ethyl.

In some embodiment, $Z^A$ is $SO_2NH$ and $R_5$ is an optionally substituted $C_{3-8}$ cycloaliphatic. In several examples, $Z^A$ is $SO_2NH$ and $R_5$ is an optionally substituted $C_{3-8}$ cycloalkyl. In several examples, $Z^A$ is $SO_2NH$ and $R_5$ is $C_{3-8}$ cycloalkyl. In one embodiment, $Z^A$ is $SO_2NH$ and $R_5$ is cyclobutyl. In one embodiment, $Z^A$ is $SO_2NH$ and $R_5$ is cyclopentyl. In one embodiment, $Z^A$ is $SO_2NH$ and $R_5$ is cyclohexyl.

In some embodiment, $Z^A$ is $SO_2NH$ and $R_5$ is an optionally substituted 3-8 membered heterocycloaliphatic. In several examples, $Z^A$ is $SO_2NH$ and $R_5$ is an optionally substituted 3-8 membered heterocycloalkyl, having 1, 2, or 3 ring members independently selected from nitrogen (including NH and $NR^X$), oxygen, or sulfur (including S, SO, and $SO_2$). In several examples, $Z^A$ is $SO_2NH$ and $R_5$ is 3-8 membered heterocycloalkyl optionally substituted with 1, 2, or 3 groups independently selected from oxo, halo, hydroxy, or an optionally substituted group selected from $C_{1-6}$ aliphatic, aryl, heteroaryl, carbonyl, amino, and carboxy. In one embodiment, $Z^A$ is $SO_2NH$ and $R_5$ is 3-oxo-isoxazolidin-4-yl.

In some embodiments, $Z^A$ is $SO_2N(C_{1-6}$ alkyl) and $R_5$ is an optionally substituted straight or branched $C_{1-6}$ aliphatic or an optionally substituted cycloaliphatic. In some embodiments, $Z^A$ is $SO_2N(C_{1-6}$ alkyl) and $R_5$ is an optionally substituted straight or branched $C_{1-6}$ aliphatic. In some embodiments, $Z^A$ is $SO_2N(C_{1-6}$ alkyl) and $R_5$ is an optionally substituted straight or branched $C_{1-6}$ alkyl or an optionally substituted straight or branched $C_{2-6}$ alkenyl. In one embodiments, $Z^A$ is $SO_2N(CH_3)$ and $R_5$ is methyl. In one embodiments, $Z^A$ is $SO_2N(CH_3)$ and $R_5$ is n-propyl. In one embodiments, $Z^A$ is $SO_2N(CH_3)$ and $R_5$ is n-butyl. In one embodiments, $Z^A$ is $SO_2N(CH_3)$ and $R_5$ is cyclohexyl. In one embodiments, $Z^A$ is $SO_2N(CH_3)$ and $R_5$ is allyl. In one embodiments, $Z A$ is $SO_2N(CH_3)$ and $R_5$ is $CH_2CH_2OH$. In one embodiments, $Z^A$ is $SO_2N(CH_3)$ and $R_5$ is $CH_2CH(OH)CH_2OH$. In one embodiments, $Z^A$ is $SO_2N(ethyl)$ and $R_5$ is ethyl. In one embodiments, $Z^A$ is $SO_2N(CH_2CH_3)$ and $R_5$ is $CH_2CH_3OH$. In one embodiments, $Z A$ is $SO_2N(CH_2CH_2CH_3)$ and $R_5$ is cyclopropylmethyl. In one embodiments, $Z^A$ is $SO_2N(n$-propyl) and $R_5$ is n-propyl. In one embodiments, $Z^A$ is $SO_2N(iso$-propyl) and $R_5$ is iso-propyl.

In some embodiments, $Z^A$ is $CH_2NHSO_2$ and $R_5$ is an optionally substituted $C_{1-6}$ aliphatic. In some embodiments, $Z^A$ is $CH_2NHSO_2$ and $R_5$ is an optionally substituted straight or branched $C_{1-6}$ alkyl. In one embodiment, $Z^A$ is $CH_2NHSO_2$ and $R_5$ is methyl, ethyl, n-propyl, iso-propyl, or n-butyl. In some embodiments, $Z^A$ is $CH_2N(C_{1-6}$ aliphatic$)SO_2$ and $R_5$ is an optionally substituted $C_{1-6}$ aliphatic. In some embodiments, $Z^A$ is $CH_2N(C_{1-6}$ aliphatic$)SO_2$ and $R_5$ is an optionally substituted straight or branched $C_{1-6}$ alkyl. In one embodiment, $Z^A$ is $CH_2N(CH_3)SO_2$ and $R_5$ is methyl, ethyl, n-propyl, iso-propyl, or n-butyl.

In one embodiment, $Z^A$ is SO and $R_5$ is methyl. In one embodiment, $Z^A$ is $SO_2$ and $R_5$ is OH. In some embodiments, $Z^A$ is $SO_2$ and $R_5$ is an optionally substituted straight or branched $C_{1-6}$ aliphatic or an optionally substituted 3-8 membered heterocyclic, having 1, 2, or 3 ring members independently selected from the group consisting of nitrogen (including NH and $NR^X$), oxygen, or sulfur (including S, SO, and $SO_2$). In some embodiments, $Z^A$ is $SO_2$ and $R_5$ is straight or branched $C_{1-6}$ alkyl or 3-8 membered heterocycloaliphatic; each of which is optionally substituted with 1, 2, or 3 of oxo, halo, hydroxy, or an optionally substituted group selected from $C_{1-6}$ aliphatic, aryl, heteroaryl, carbonyl, amino, and carboxy. In one embodiment, $Z^A$ is $SO_2$ and $R_5$ is methyl, ethyl, or iso-propyl. In some embodiments, $Z^A$ is $SO_2$ and examples of $R_5$ include but are not limited to:

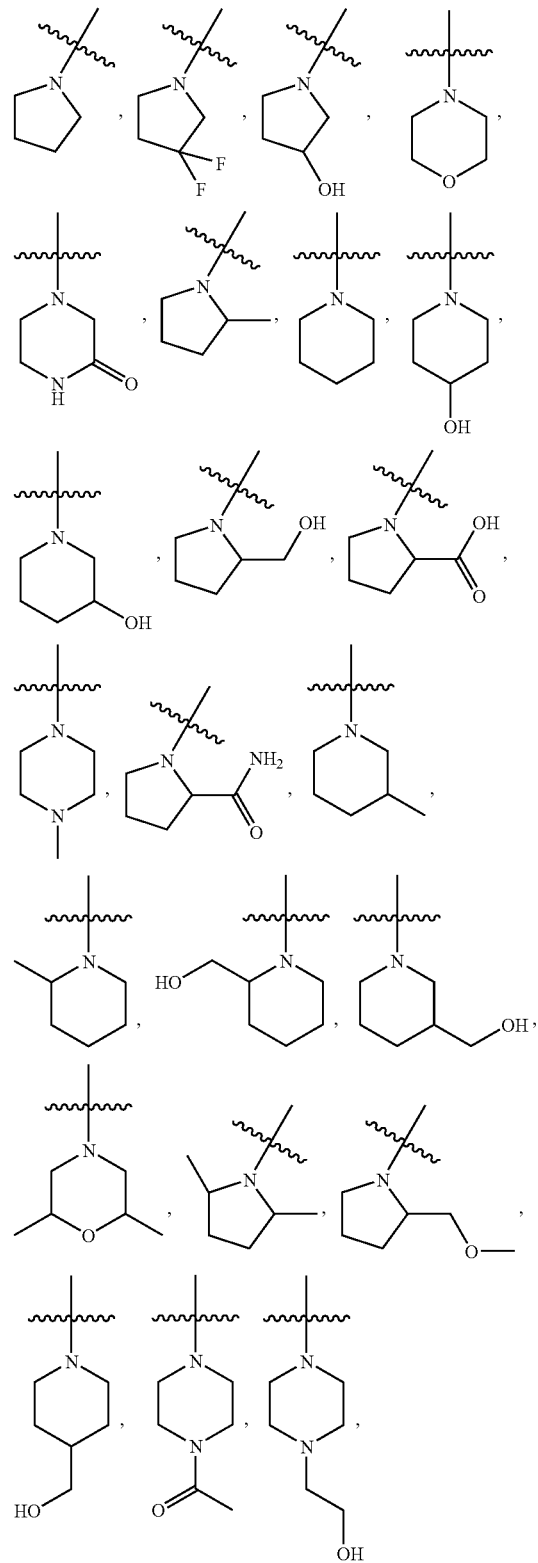

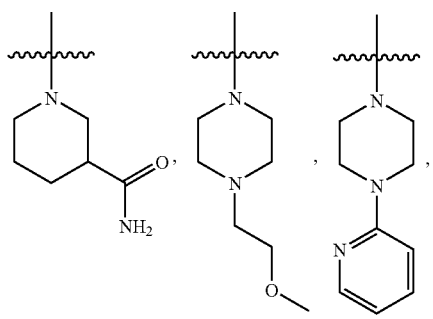

In one embodiment, $Z^A$ is CO and $R_5$ is an optionally substituted amino, an optionally substituted $C_{1-6}$ straight or branched aliphatic, or an optionally substituted 3-8 membered heterocyclic, having 1, 2, or 3 ring members independently selected from the group consisting of nitrogen (including NH and $NR^X$), oxygen, or sulfur (including S, SO, and $SO_2$). In one embodiment, $Z^A$ is CO and $R_5$ is di-(2-methoxyethyl)amino or di-(2-hydroxyethyl)amino. In some embodiments, $Z^A$ is CO and $R_5$ is straight or branched $C_{1-6}$ alkyl or 3-8 membered heterocycloaliphatic each of which is optionally substituted with 1, 2, or 3 of oxo, halo, hydroxy, or an optionally substituted group selected from $C_{1-6}$ aliphatic, aryl, heteroaryl, carbonyl, amino, and carboxy. In one embodiment, $Z^A$ is CO and $R_5$ is

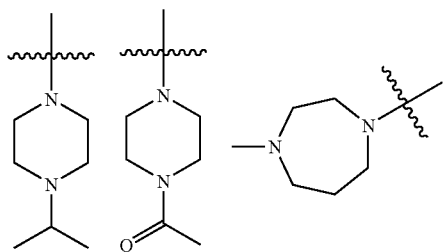

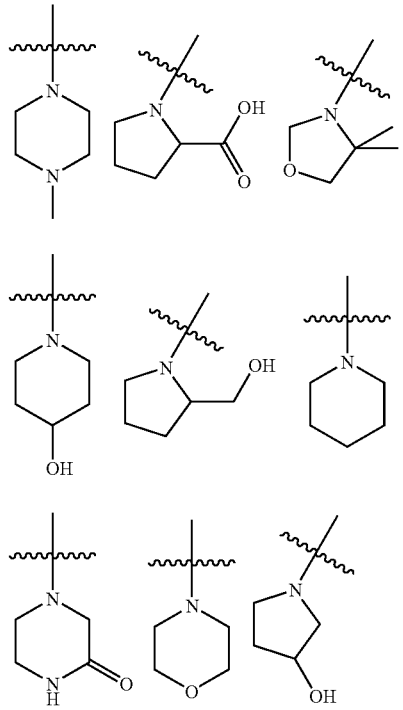

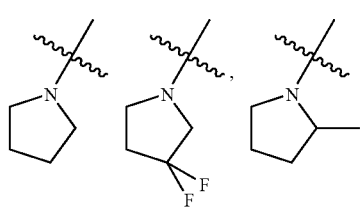

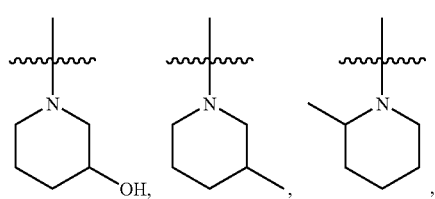

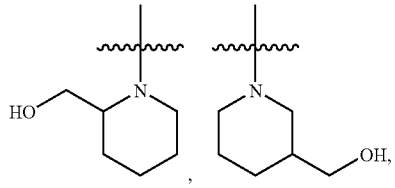

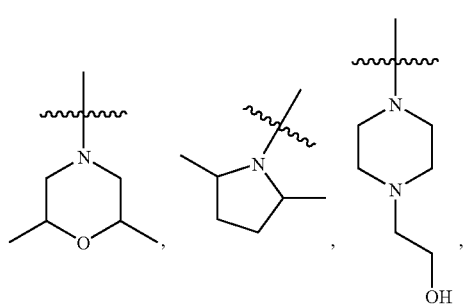

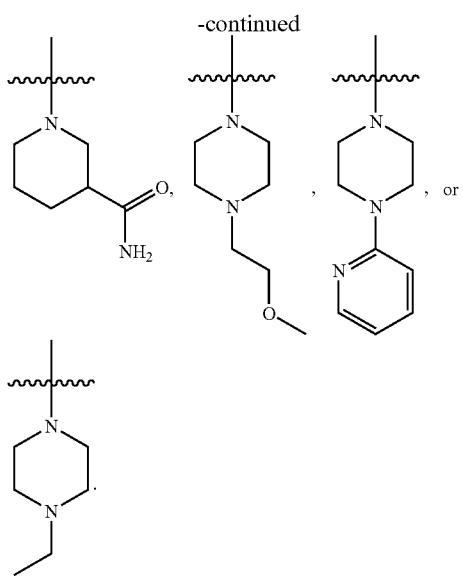

In some embodiments, $Z^A$ is NHCO and $R_5$ is an optionally substituted group selected from $C_{1-6}$ aliphatic, $C_{1-6}$ alkoxy, amino, and heterocycloaliphatic. In one embodiment, $Z^A$ is NHCO and $R_5$ is $C_{1-6}$ alkyl, $C_{1-6}$ alkoxy, amino, or 3-8 membered heterocycloalkyl having 1, 2, or 3 ring member independently selected from nitrogen (including NH and $NR^X$), oxygen, or sulfur (including S, SO, and $SO_2$); wherein said alkyl, alkoxy, amino or heterocycloalkyl each is optionally substituted with 1, 2, or 3 groups independently selected from oxo, halo, hydroxy, or an optionally substituted group selected from $C_{1-6}$ aliphatic, 3-8 membered heterocycloaliphatic, alkoxy, carbonyl, amino, and carboxy. In one embodiment, $Z^A$ is NHCO and $R_5$ is methyl, methoxymethyl, hydroxymethyl, (morpholin-4-yl)-methyl, $CH_2COOH$, ethoxy, dimethylamino, or morpholin-4-yl.

In some embodiments, one $R^A$ not attached at the carbon 3" or 4" is selected from the group consisting of H, $R^B$, halo, —OH, —$(CH_2)_rNR^BR^B$, —$(CH_2)_rOR^B$, —$SO_2$—$R^B$, —$NR^B$—$SO_2$—$R^B$, —$SO_2NR^BR^B$, —$C(O)R^B$, —$C(O)OR^B$, —$OC(O)OR^B$, —$NR^BC(O)OR^B$, and —$C(O)NR^BR^B$; wherein r is 0, 1, or 2; and each $R^B$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl. In other embodiments, one $R^A$ not attached at the carbon 3" or 4" is selected from the group consisting of H, $C_{1-6}$ aliphatic, $C_{3-8}$ cycloaliphatic, 3-8 membered heterocycloaliphatic, $C_{6-10}$ aryl, 5-8 membered heteroaryl, halo, —CN, —$NH_2$, —$NH(C_{1-6}$ aliphatic), —$N(C_{1-6}$ aliphatic$)_2$, —$CH_2$—$N(C_{1-6}$ aliphatic$)_2$, —$CH_2$— (heteroaryl), —$CH_2$—$NH(C_{1-6}$ aliphatic), —$CH_2NH_2$, —OH, —$O(C_{1-6}$ aliphatic), —$CH_2OH$, —$CH_2$—$O(C_{1-6}$ aliphatic), —$SO_2(C_{1-6}$ aliphatic), —$N(C_{1-6}$ aliphatic)-$SO_2(C_{1-6}$ aliphatic), —NH—$SO_2(C_{1-6}$ aliphatic), —$SO_2NH_2$, —$SO_2NH$ ($C_{1-6}$ aliphatic), —$SO_2N(C_{1-6}$ aliphatic$)_2$, —$C(O)(C_{1-6}$ aliphatic), —$C(O)O(C_{1-6}$ aliphatic), —$C(O)OH$, —$OC(O)O$ ($C_{1-6}$ aliphatic), —$NHC(O)(C_{1-6}$ aliphatic), —$NHC(O)O$ ($C_{1-6}$ aliphatic), —$N(C_{1-6}$ aliphatic$)C(O)O(C_{1-6}$ aliphatic), —$C(O)NH_2$, and —$C(O)N(C_{1-6}$ aliphatic$)_2$. In several examples, $R^{A2}$ is selected from the group consisting of H, $C_{1-6}$ aliphatic, 5-8 membered heteroaryl, halo, —CN, —$NH_2$, —$CH_2NH_2$, —OH, —$O(C_{1-6}$ aliphatic), —$CH_2OH$, —$CH_2$-(5-8 membered heteroaryl), —$SO_2(C_{1-6}$ aliphatic), —NH—$SO_2(C_{1-6}$ aliphatic), —$C(O)O(C_{1-6}$ aliphatic), —$C(O)OH$, —$NHC(O)(C_{1-6}$ aliphatic), —$C(O)NH_2$, —$C(O)NH(C_{1-6}$ aliphatic), and —$C(O)N(C_{1-6}$ aliphatic$)_2$. For examples, one $R^A$ not attached at the carbon 3" or 4" is selected from the group consisting of H, methyl, ethyl, n-propyl, iso-propyl, tert-butyl, tetrazol-5-yl, F, Cl, CN, —$NH_2$, —$CH_2NH_2$, —$CH_2CN$, —$CH_2COOH$, —$CH_2CH_2COOH$, 1,3-dioxoisoindolin-2-ylmethyl, —OH, —$OCH_3$, —$OCF_3$, ethoxy, iso-propoxy, n-propoxy, —$CH_2OH$, —$CH_2CH_2OH$, —$SO_2CH_3$, —NH—$SO_2CH_3$, —$C(O)OCH_3$, —$C(O)OCH_2CH_3$, —$C(O)OH$, —$NHC(O)CH_3$, —$C(O)NH_2$, and —$C(O)N(CH_3)_2$. In one embodiment, one $R^A$ not attached at the carbon 3" or 4" is hydrogen. In another embodiment, one $R^A$ not attached at the carbon 3" or 4" is methyl, ethyl, F, Cl, or —$OCH_3$.

In some embodiments, one $R^A$ not attached at the carbon 3" or 4" is H, hydroxy, halo, $C_{1-6}$ alkyl, $C_{1-6}$ alkoxy, $C_{3-6}$ cycloalkyl, or $NH_2$. In several examples, $R^{A2}$ is H, halo, $C_{1-4}$ alkyl, or $C_{1-4}$ alkoxy. Examples of one $R^A$ not attached at the carbon 3" or 4" include H, F, Cl, methyl, ethyl, and methoxy.

5. Exemplary Compounds

Exemplary compounds of the present invention include, but are not limited to, those illustrated in Table 1 below.

TABLE 1

Examples of compounds of the present invention.

1

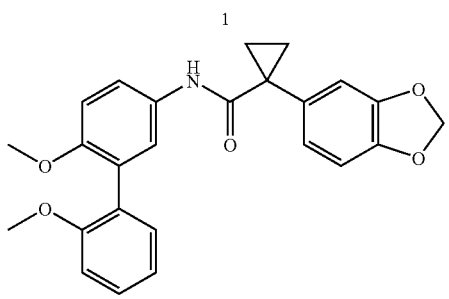

TABLE 1-continued
Examples of compounds of the present invention.
2
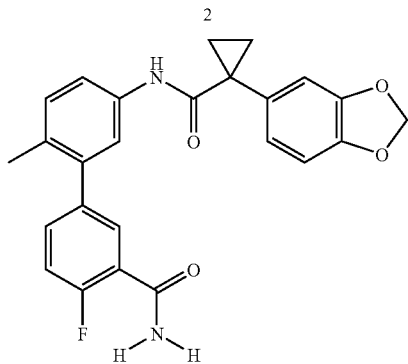
3
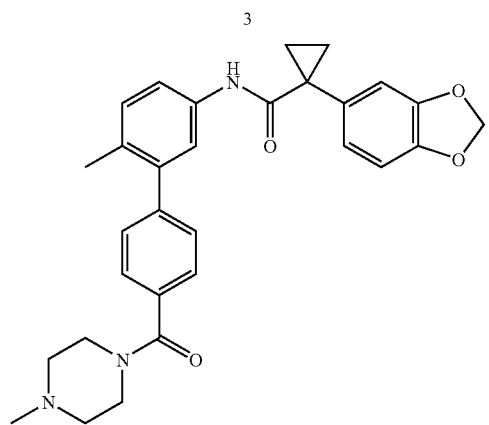
4
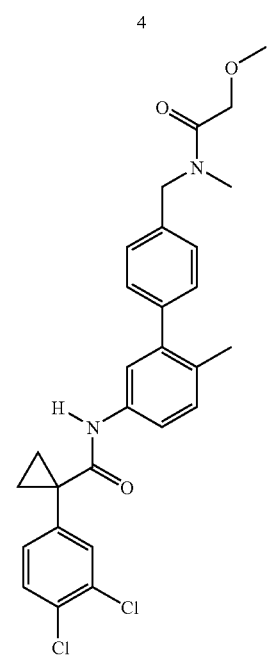

TABLE 1-continued
Examples of compounds of the present invention.
5
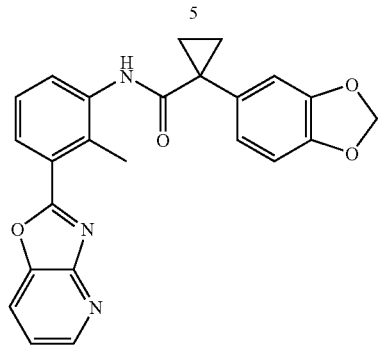
6
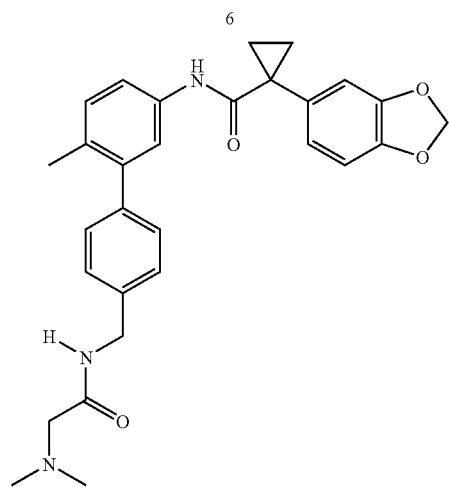
7
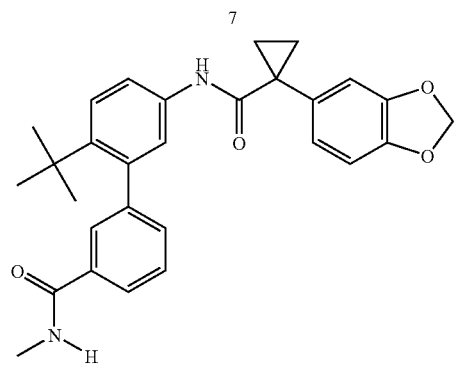
8
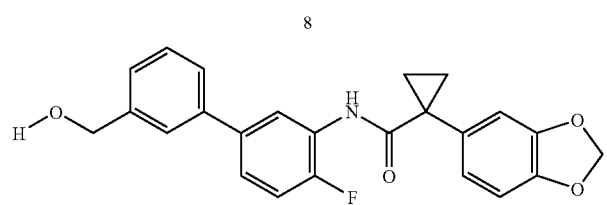

TABLE 1-continued
Examples of compounds of the present invention.
9
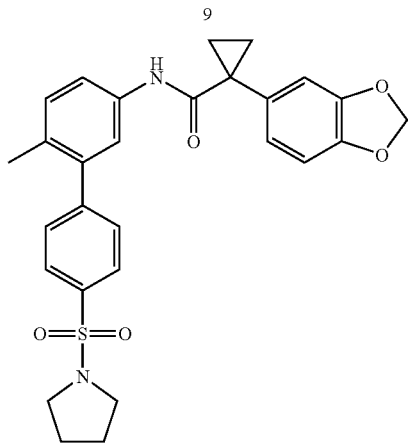
10
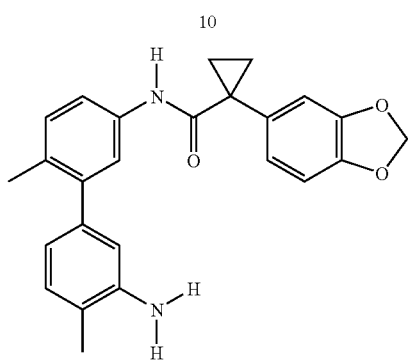
11
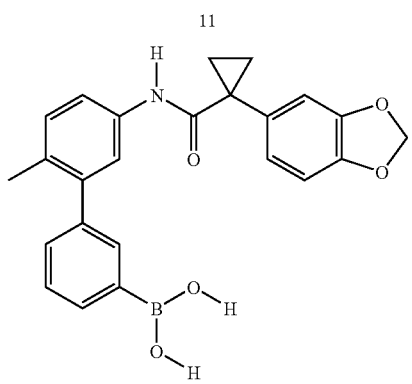
12
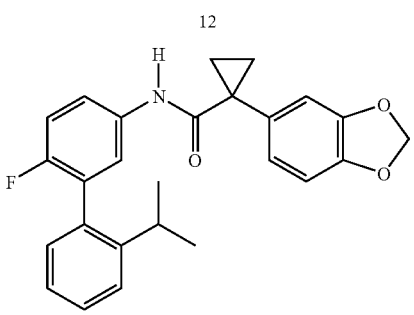

TABLE 1-continued
Examples of compounds of the present invention.
13
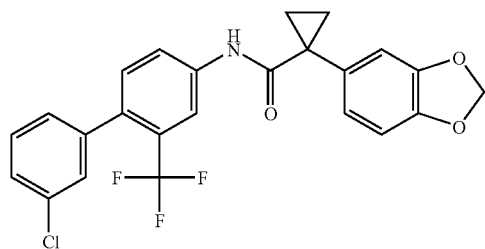
14
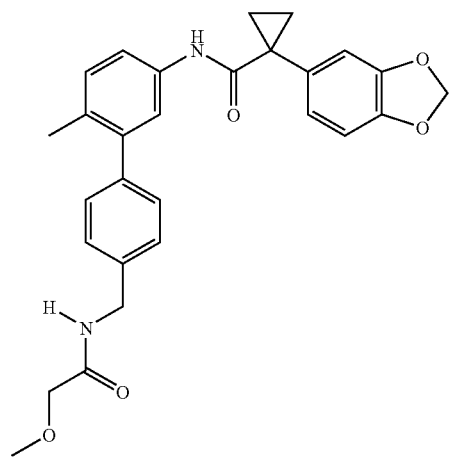
15
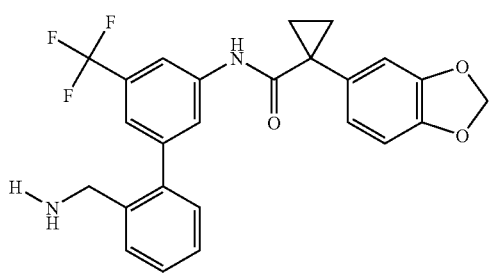
16
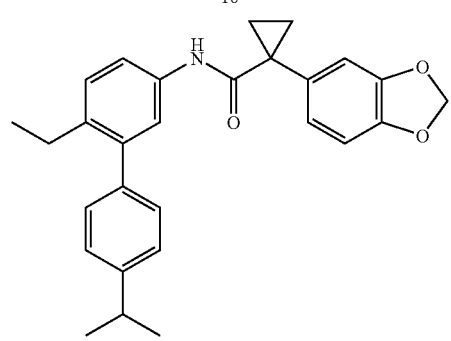

TABLE 1-continued
Examples of compounds of the present invention.
17
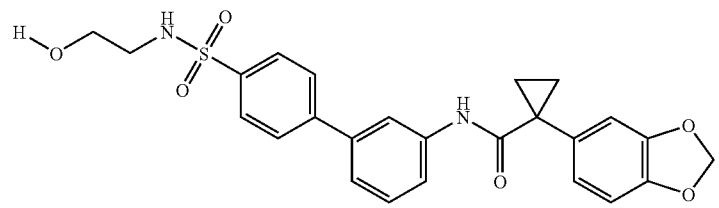
18
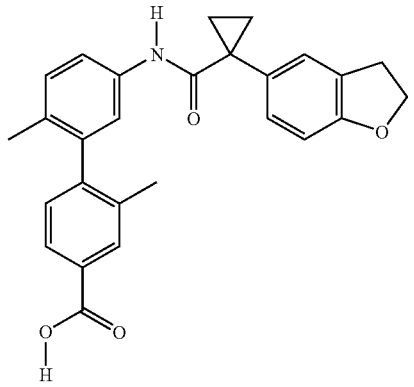
19
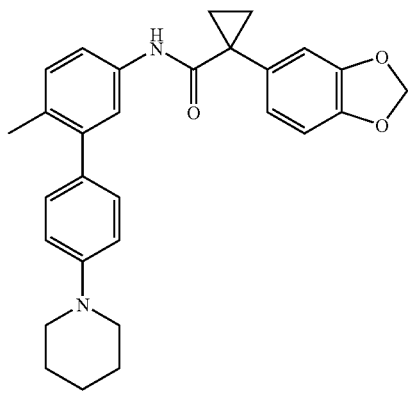
20
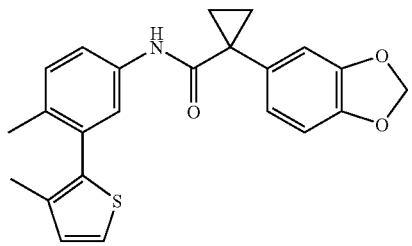

TABLE 1-continued
Examples of compounds of the present invention.
21
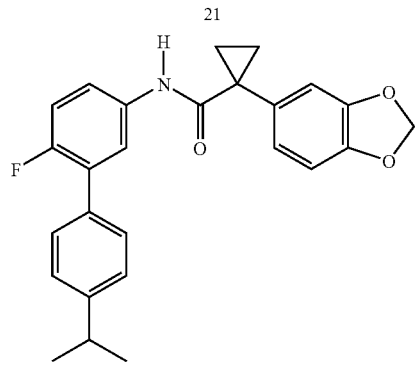
22
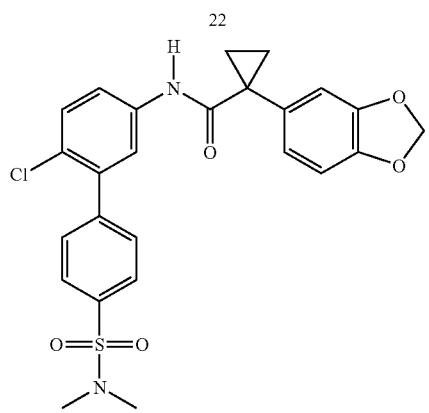
23
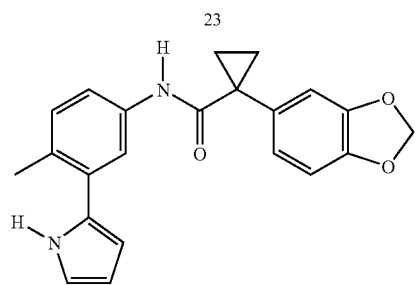
24
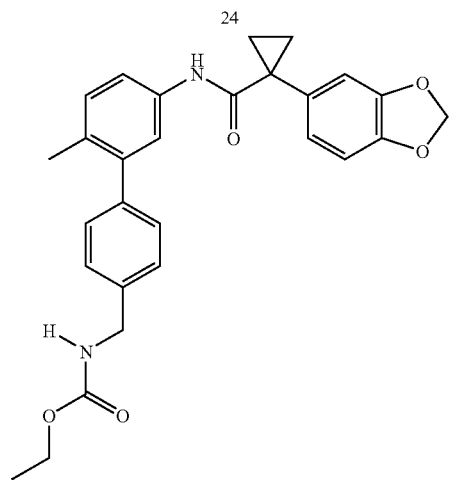

TABLE 1-continued
Examples of compounds of the present invention.
25
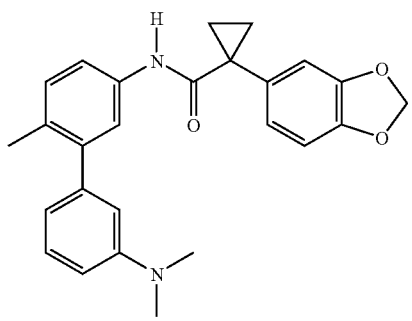
26
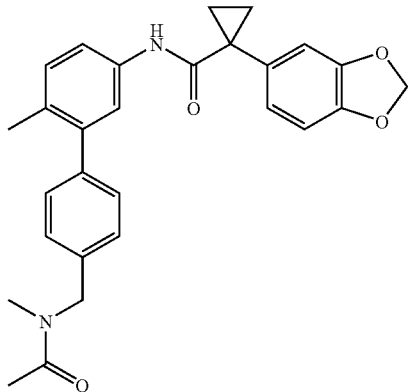
27
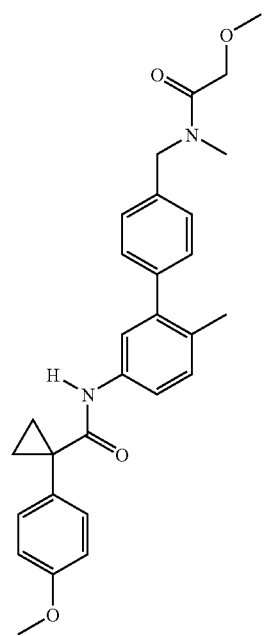

TABLE 1-continued
Examples of compounds of the present invention.
28
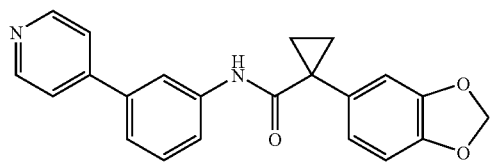
29
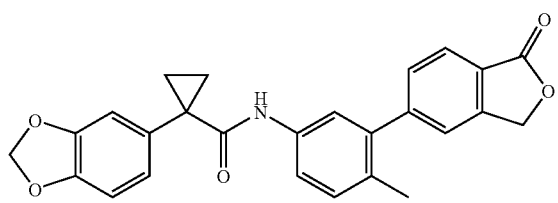
30
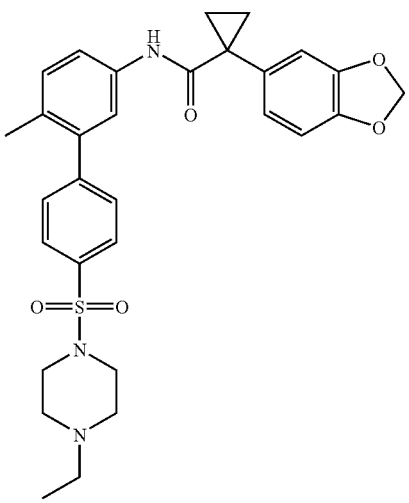
31
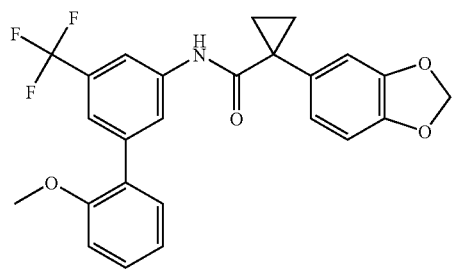

TABLE 1-continued
Examples of compounds of the present invention.
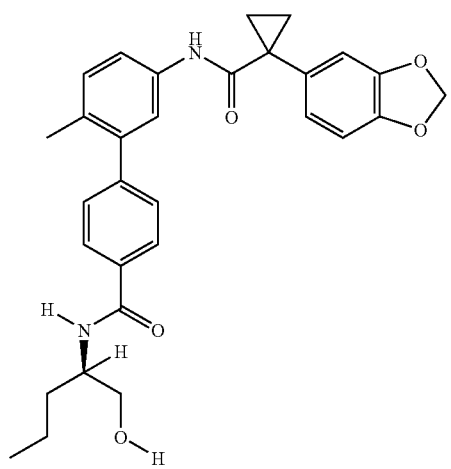
32
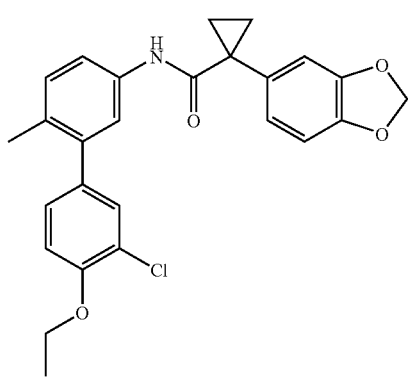
33
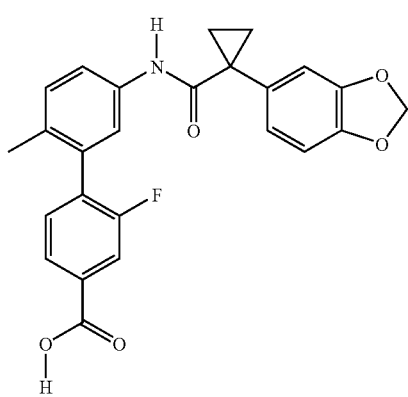
34

TABLE 1-continued
Examples of compounds of the present invention.
35
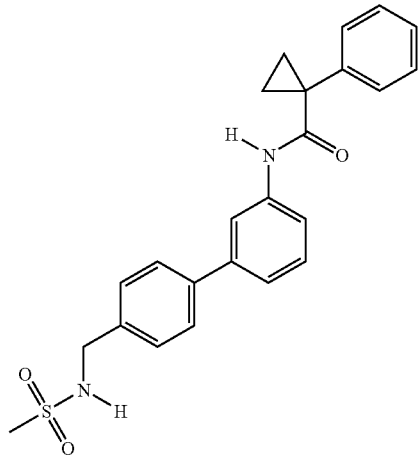
36
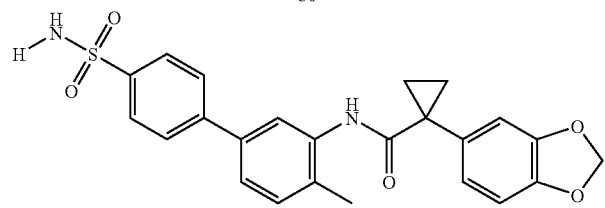
37
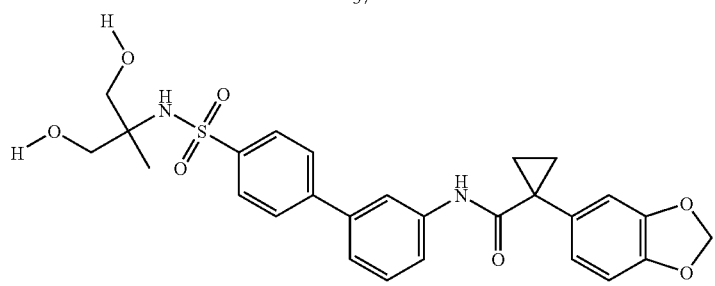
38
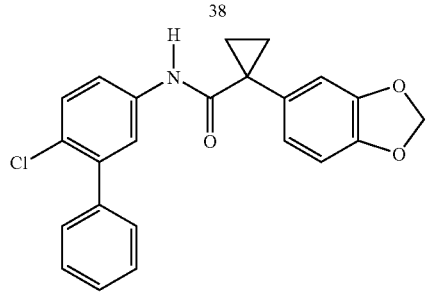

TABLE 1-continued
Examples of compounds of the present invention.
39
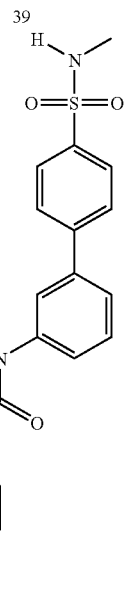
40
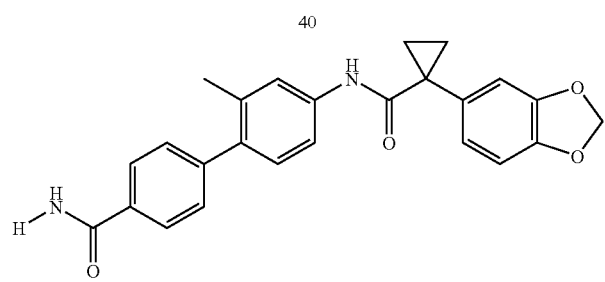
41
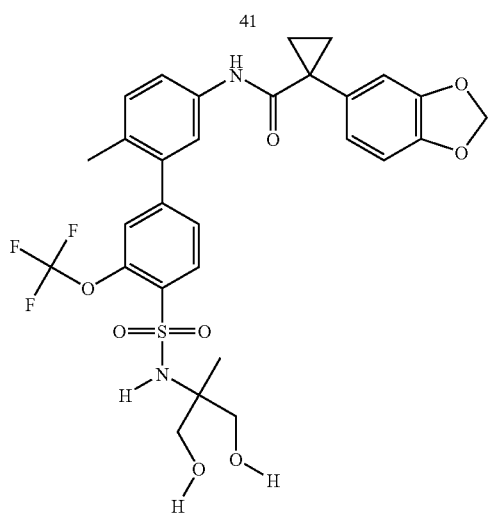

TABLE 1-continued
Examples of compounds of the present invention.
42
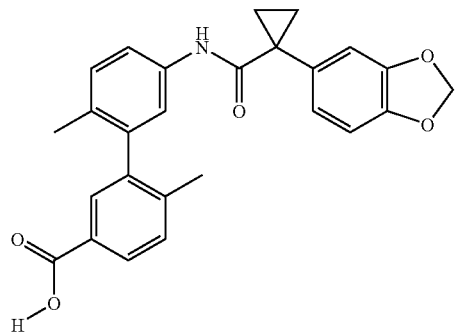
43
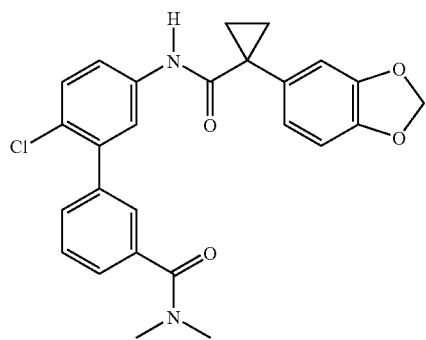
44
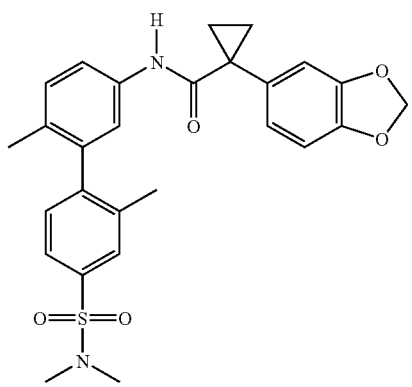
45
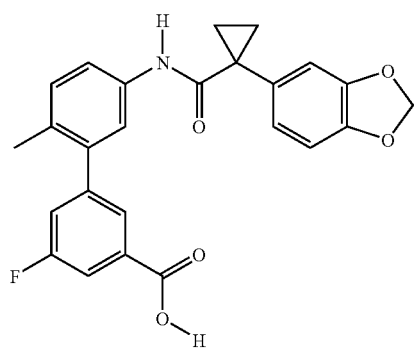

TABLE 1-continued
Examples of compounds of the present invention.
46
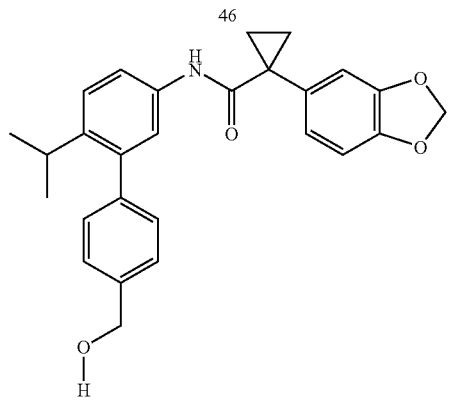
47
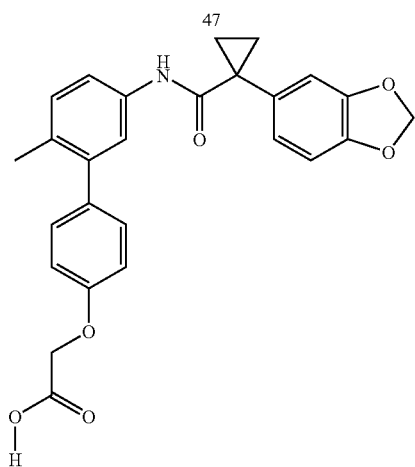
48
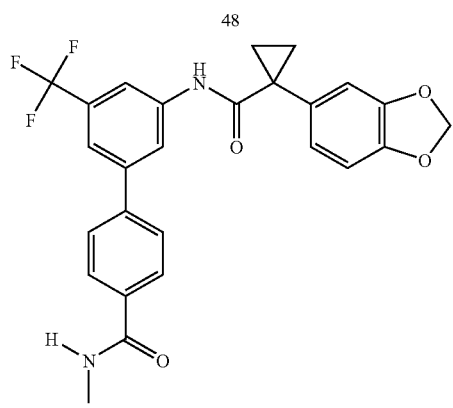
49
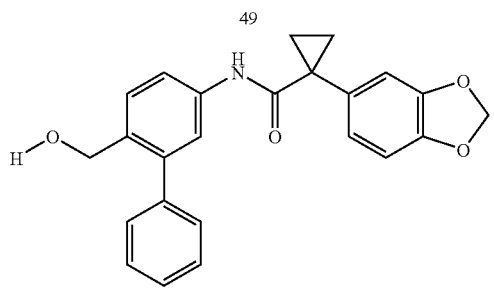

TABLE 1-continued
Examples of compounds of the present invention.
50
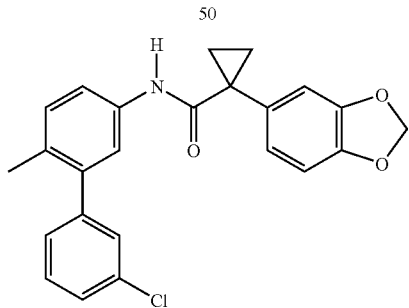
51
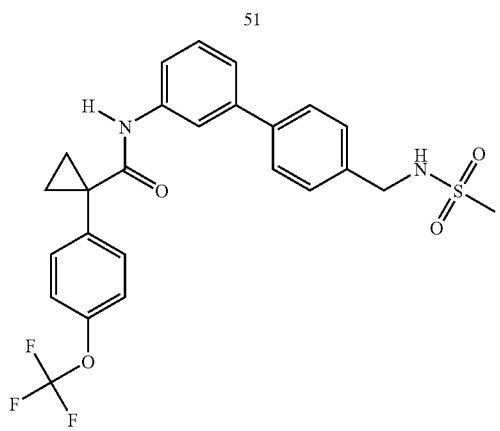
52
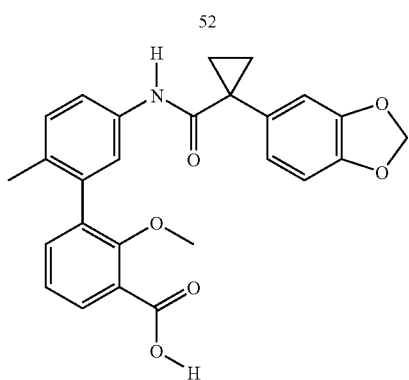
53
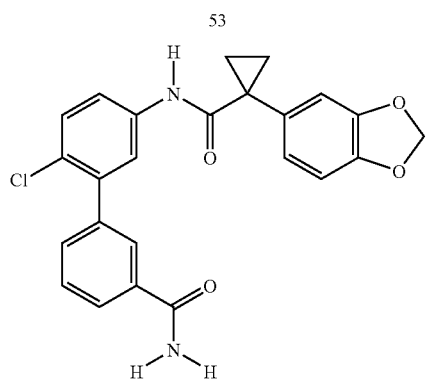

TABLE 1-continued
Examples of compounds of the present invention.
54
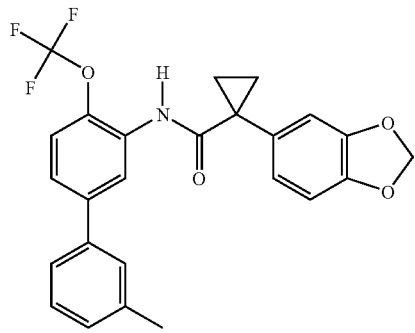
55
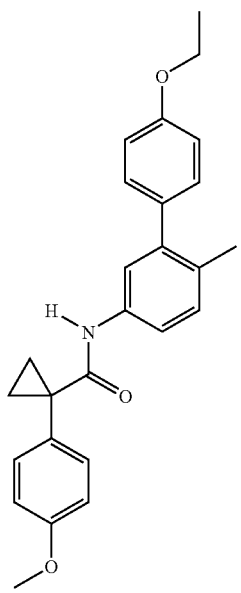
56
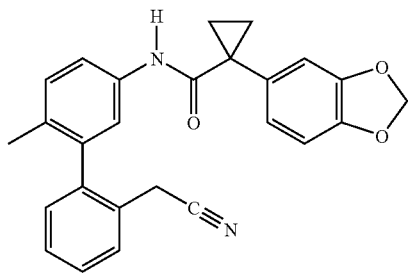
57
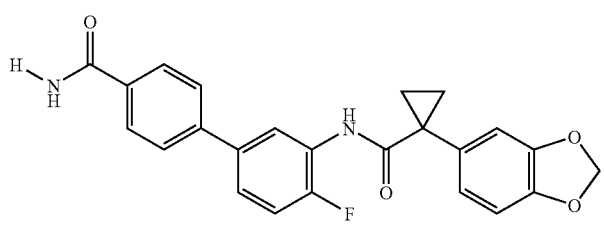

TABLE 1-continued
Examples of compounds of the present invention.
58
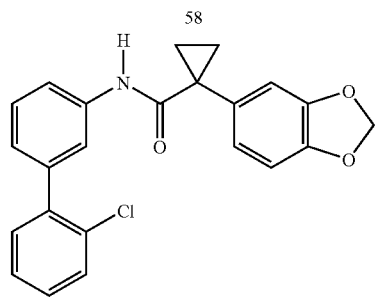
59
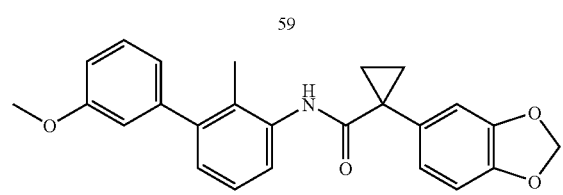
60
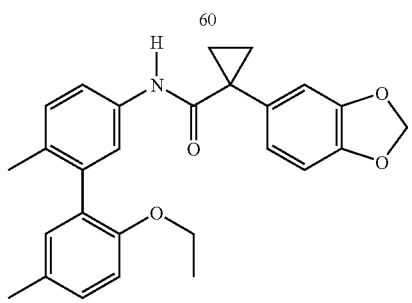
61
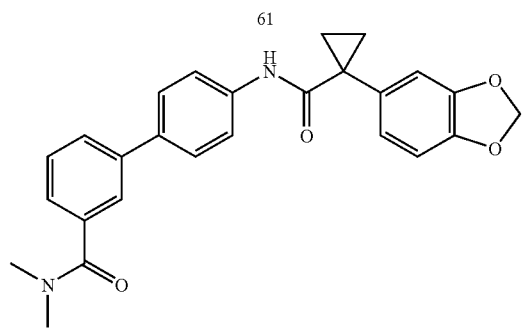
62
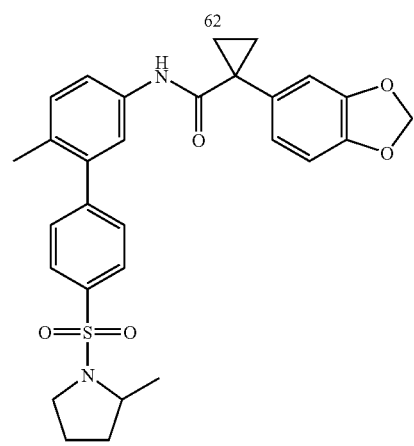

TABLE 1-continued
Examples of compounds of the present invention.
63
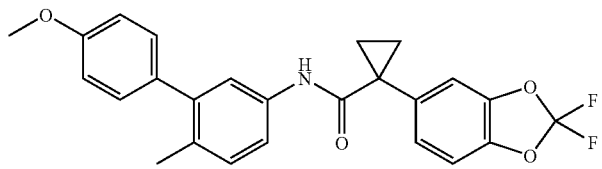
64
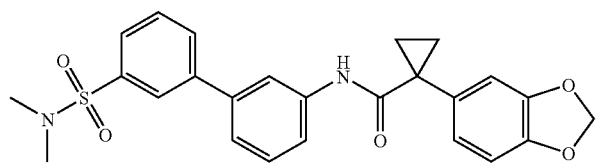
65
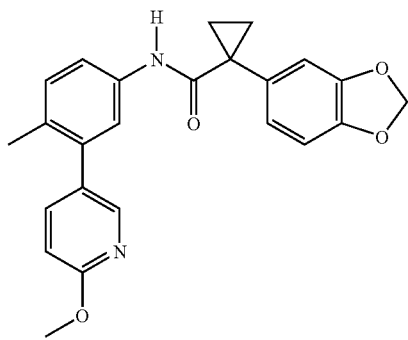
66
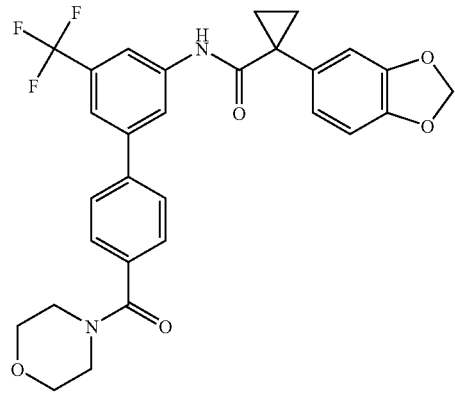
67
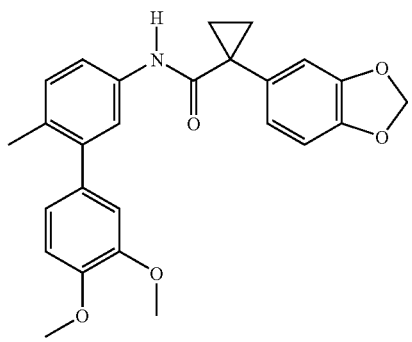

TABLE 1-continued
Examples of compounds of the present invention.
68
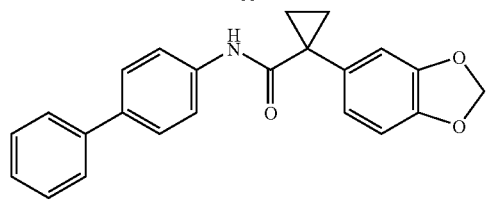
69
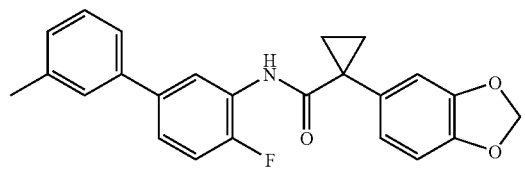
70
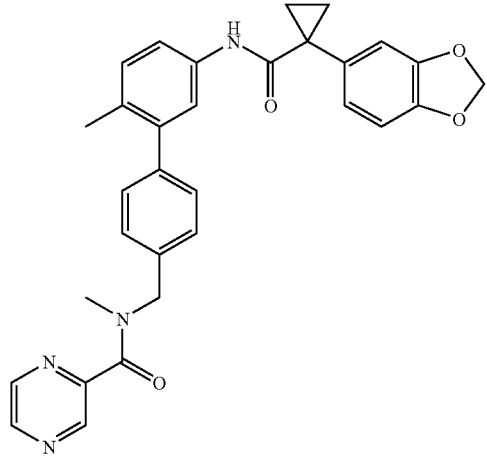
71
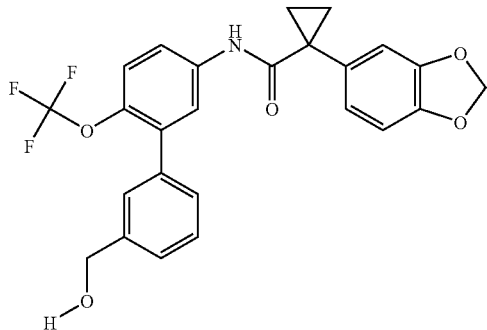
72
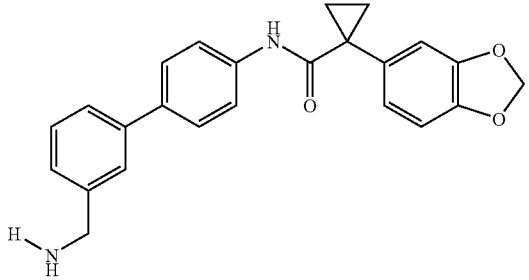

TABLE 1-continued
Examples of compounds of the present invention.
73
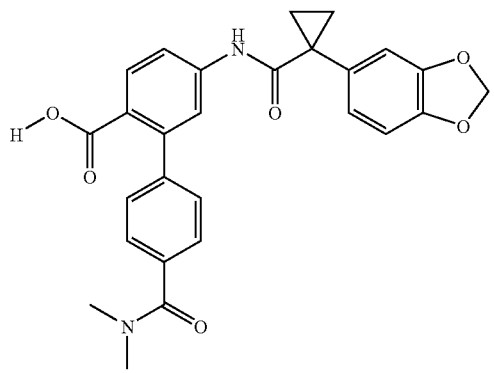
74
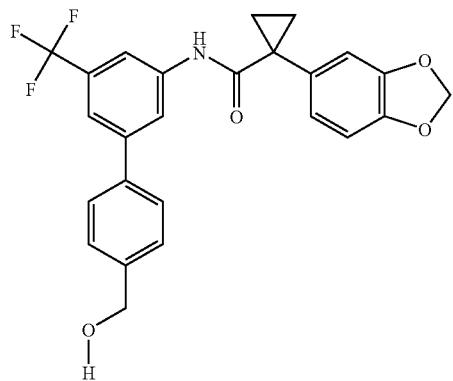
75
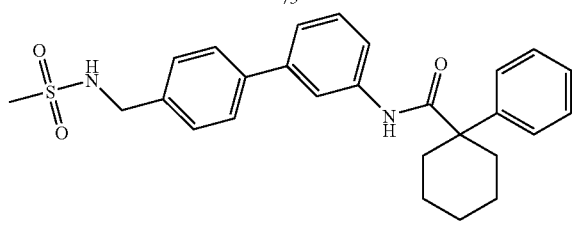
76
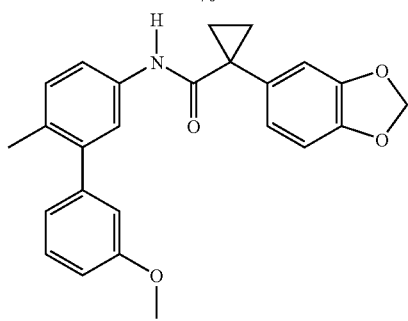

TABLE 1-continued
Examples of compounds of the present invention.
77
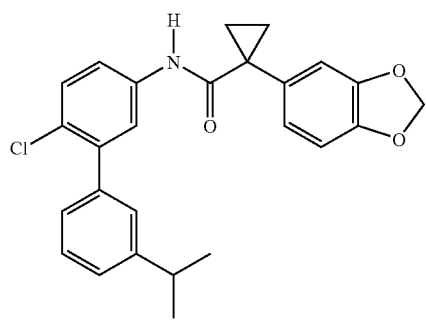
78
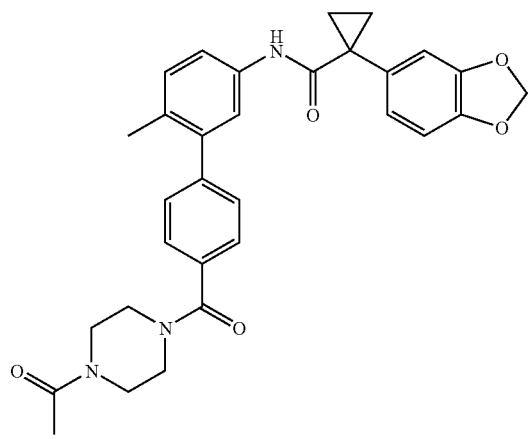
79
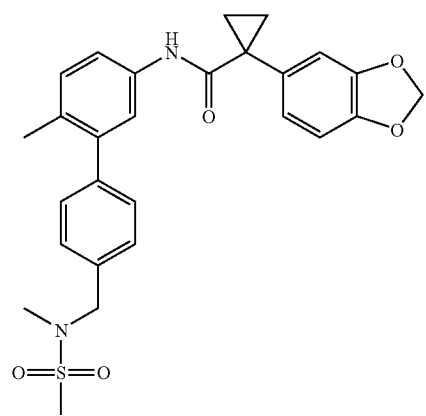

TABLE 1-continued
Examples of compounds of the present invention.
80
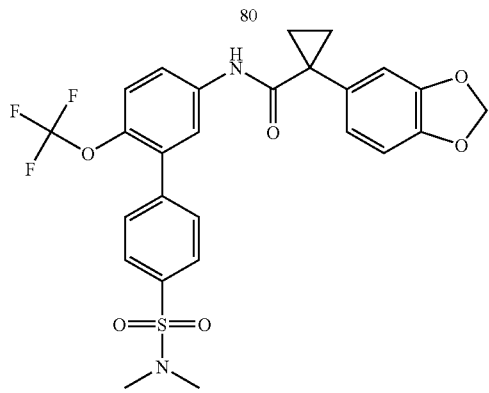
81
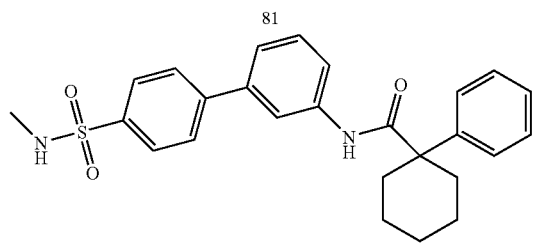
82
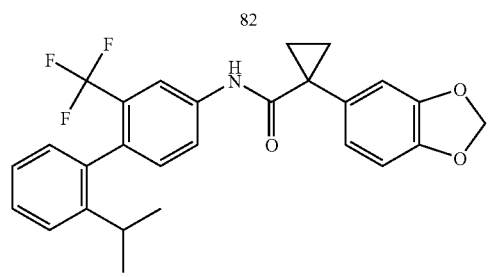
83
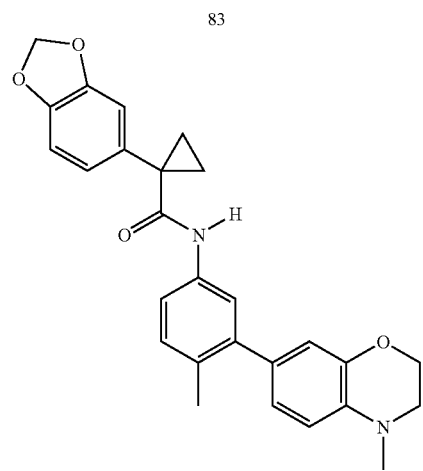

TABLE 1-continued
Examples of compounds of the present invention.
84
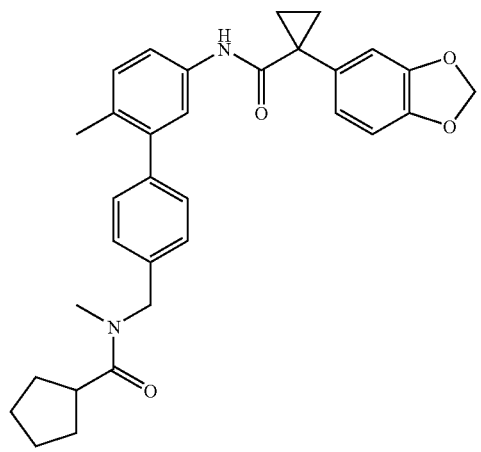
85
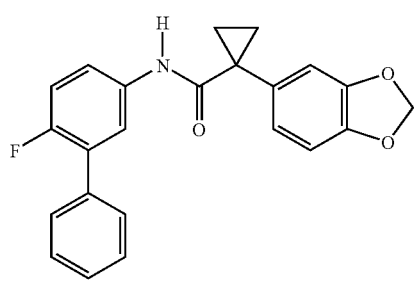
86
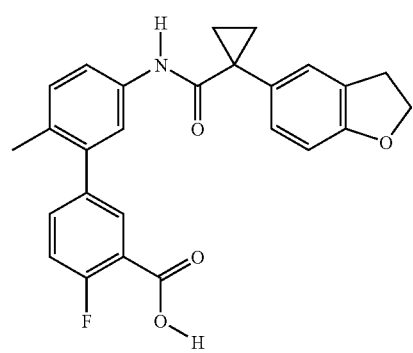
87
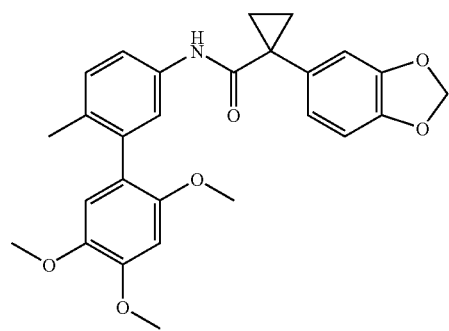

TABLE 1-continued
Examples of compounds of the present invention.
88
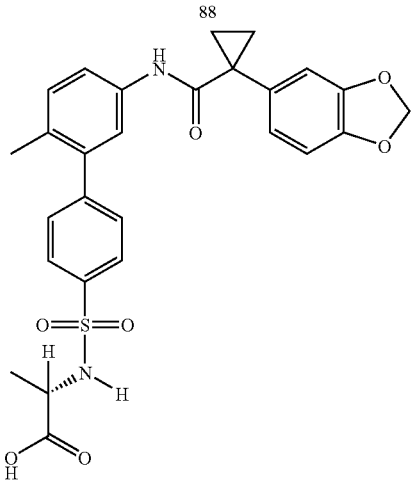
89
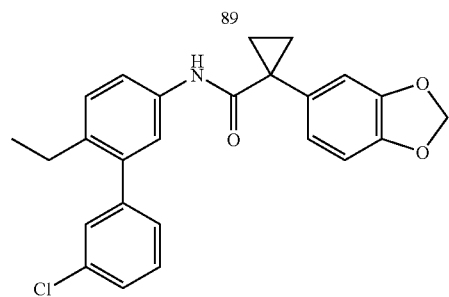
90
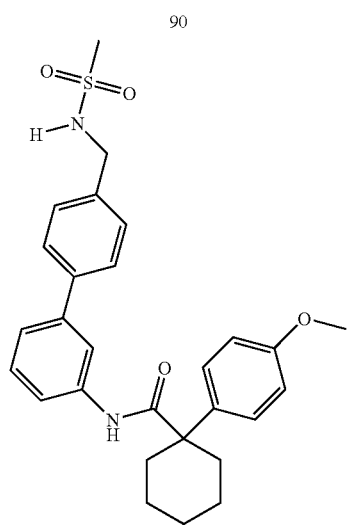

TABLE 1-continued
Examples of compounds of the present invention.
91
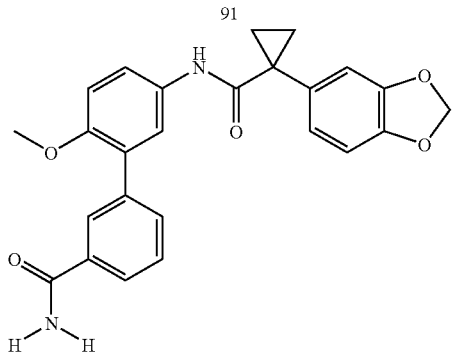
92
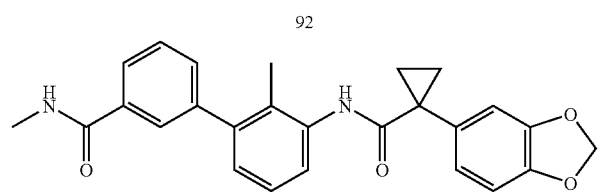
93
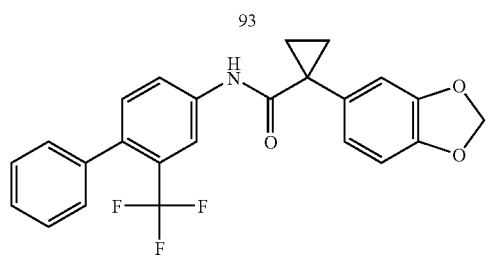
94
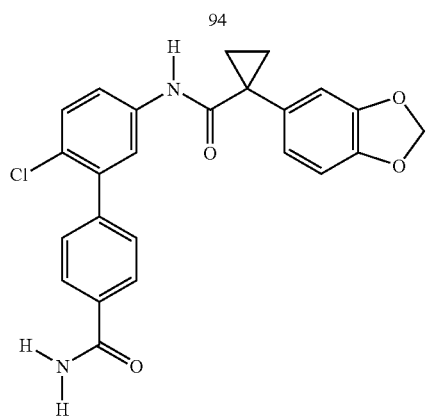
95
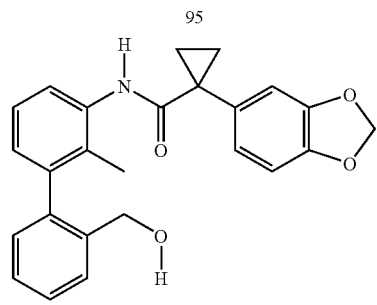

TABLE 1-continued
Examples of compounds of the present invention.
96
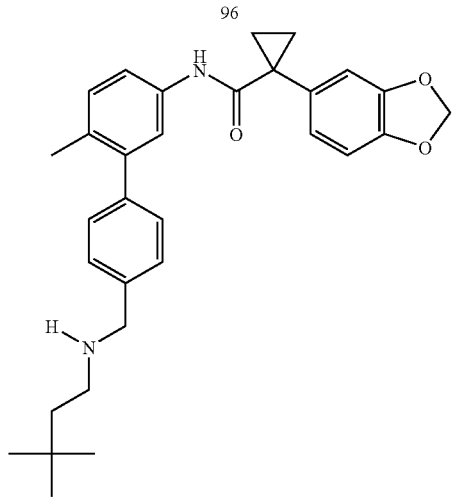
97
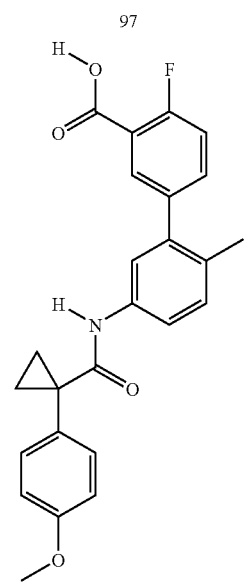
98
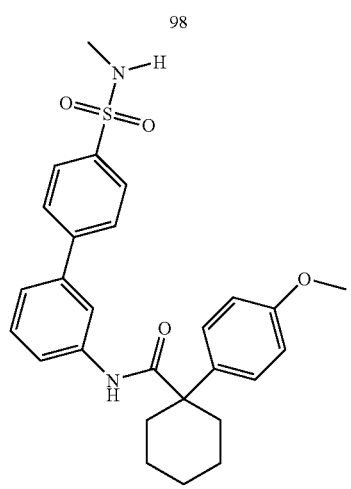

TABLE 1-continued
Examples of compounds of the present invention.
99
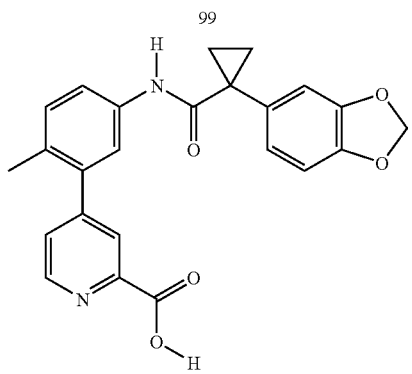
100
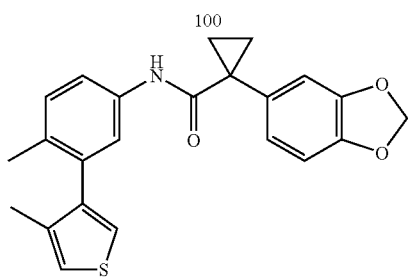
101
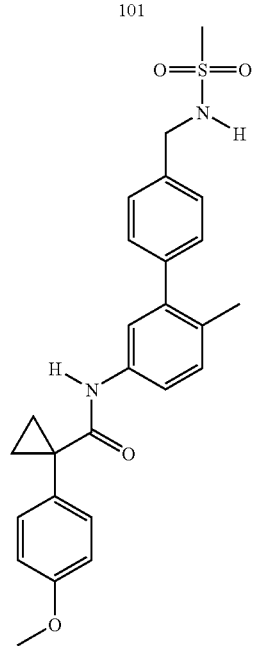
102
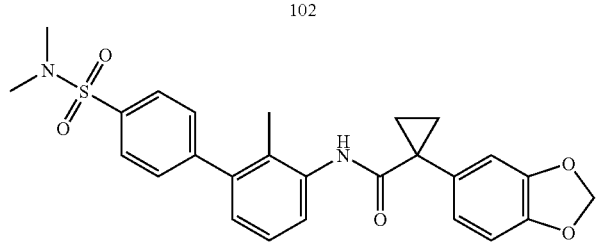

TABLE 1-continued
Examples of compounds of the present invention.
103
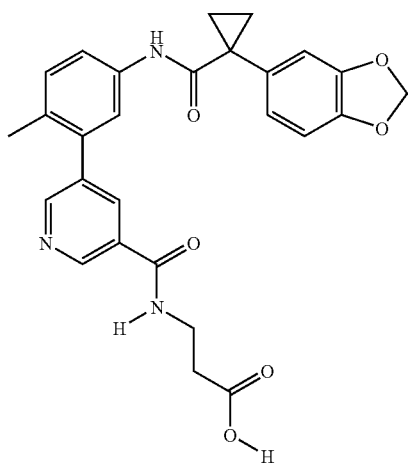
104
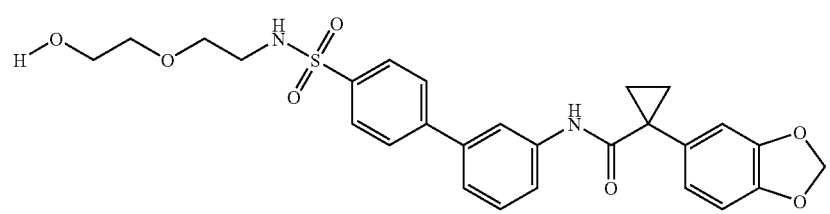
105
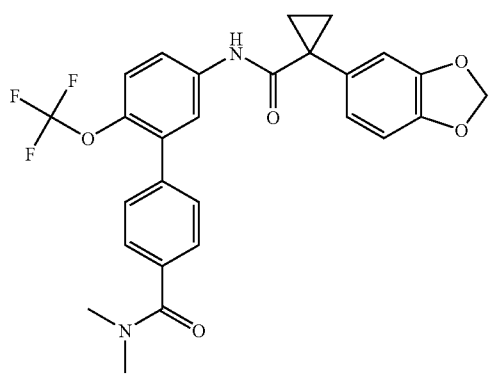
106
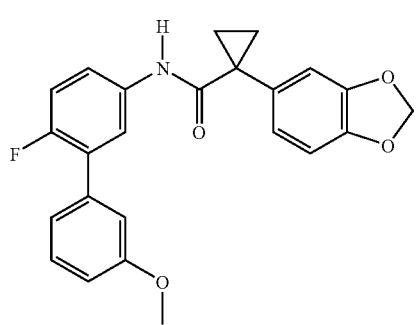

TABLE 1-continued
Examples of compounds of the present invention.
107
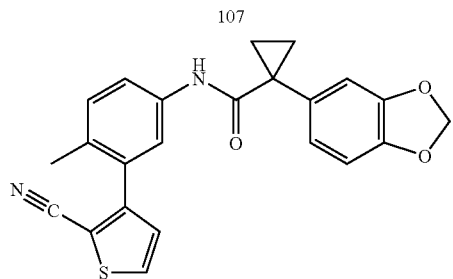
108
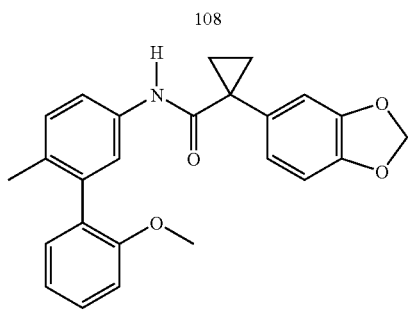
109
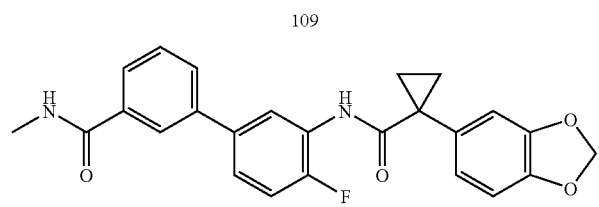
110
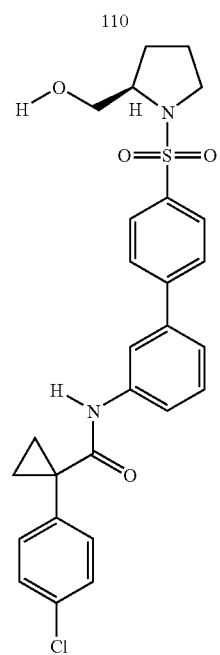

TABLE 1-continued
Examples of compounds of the present invention.
111
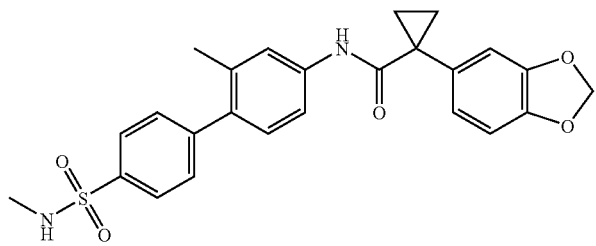
112
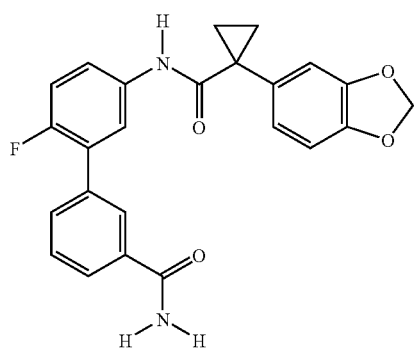
113
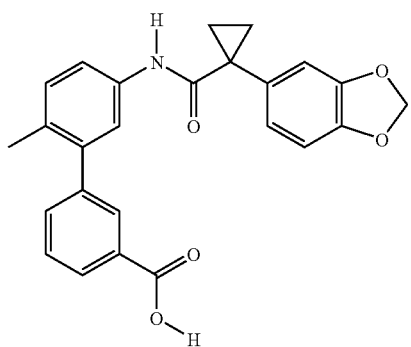
114
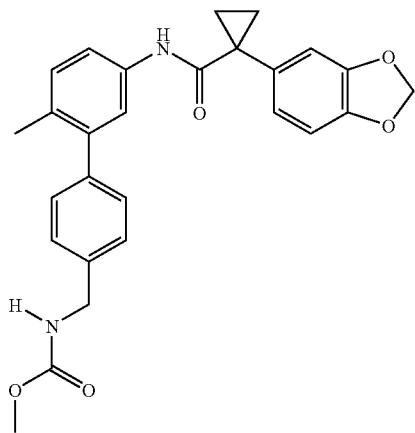

TABLE 1-continued
Examples of compounds of the present invention.
115
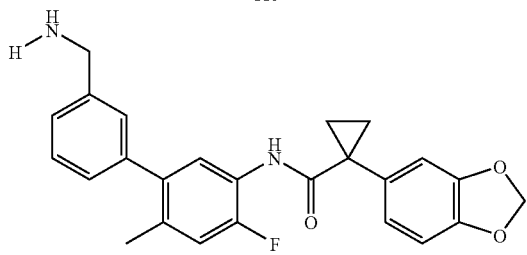
116
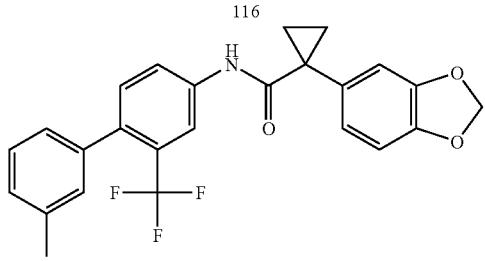
117
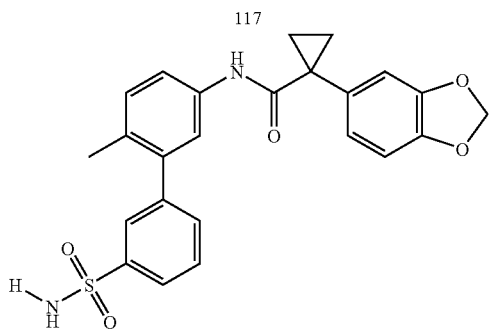
118
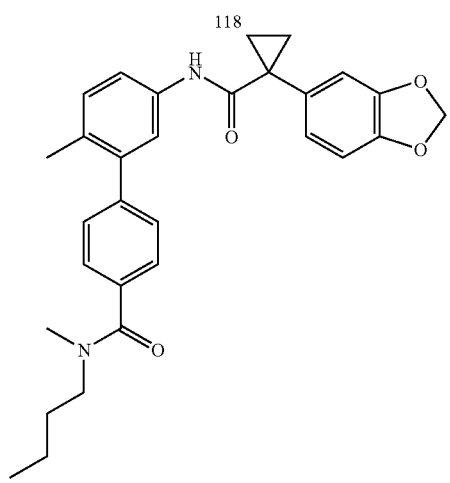

TABLE 1-continued
Examples of compounds of the present invention.
119
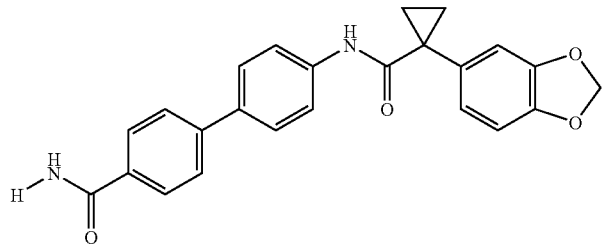
120
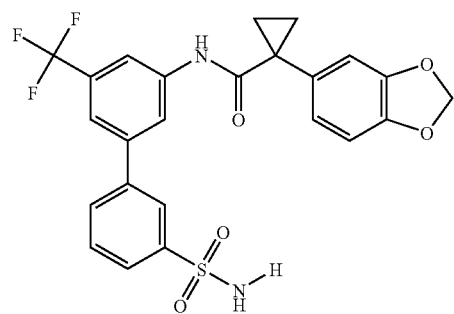
121
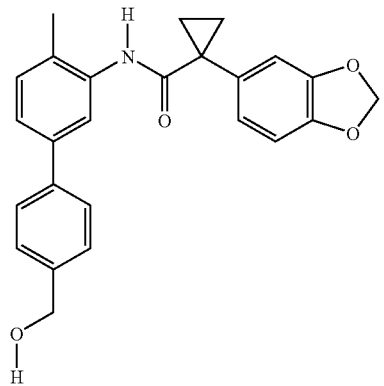
122
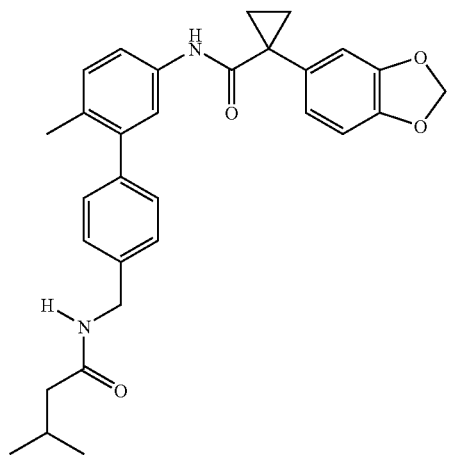

TABLE 1-continued
Examples of compounds of the present invention.
123
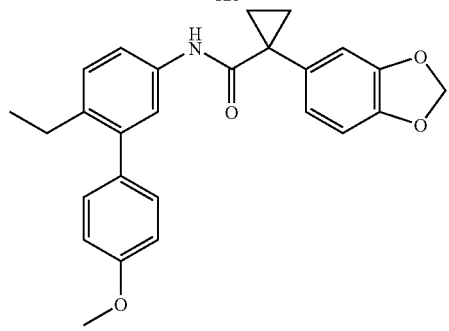
124
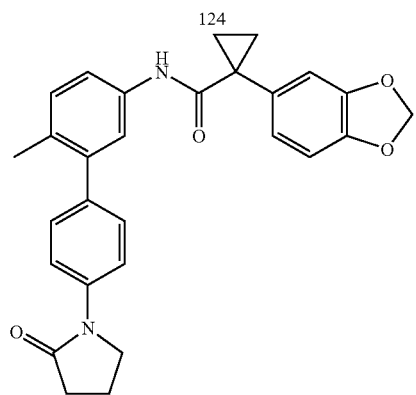
125
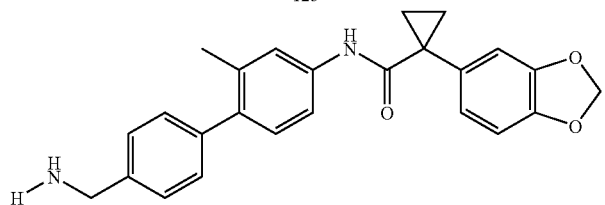
126
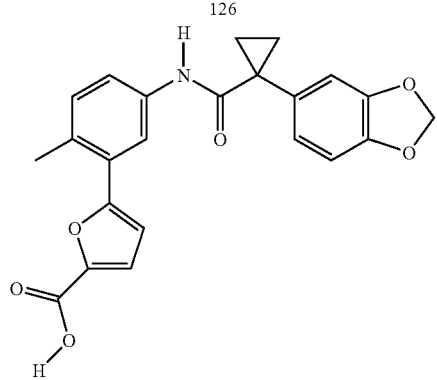

TABLE 1-continued
Examples of compounds of the present invention.
127
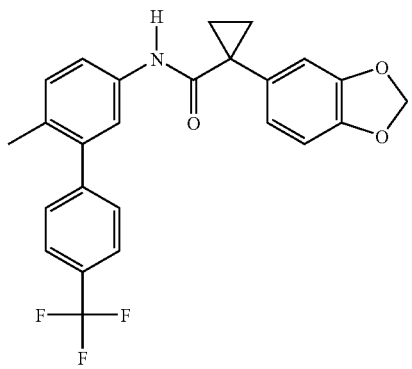
128
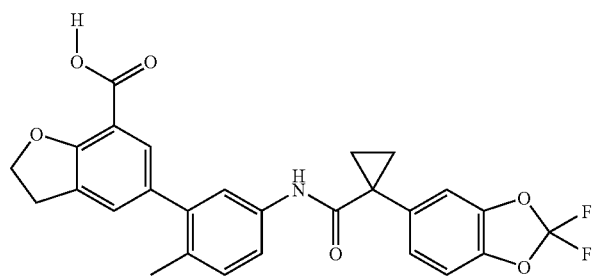
129
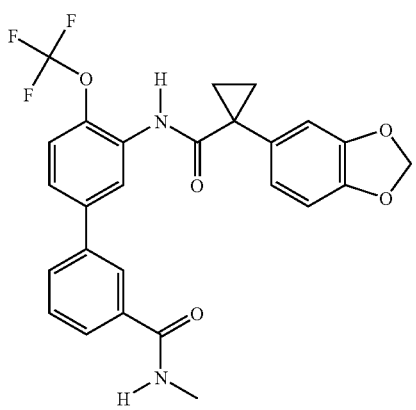
130
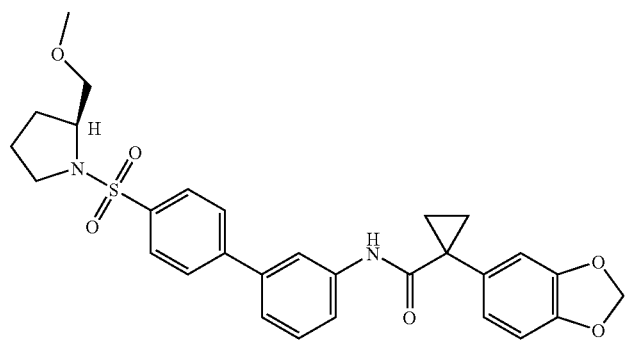

TABLE 1-continued
Examples of compounds of the present invention.
131
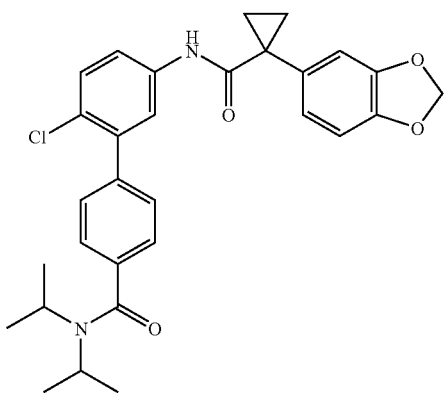
132
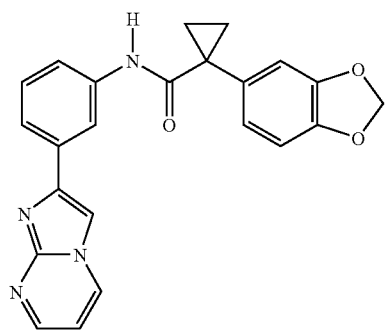
133
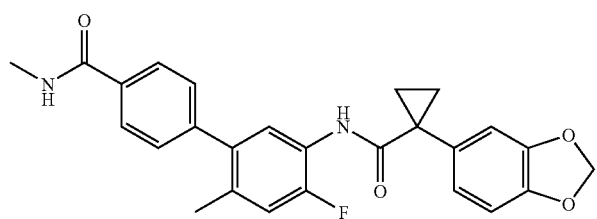
134
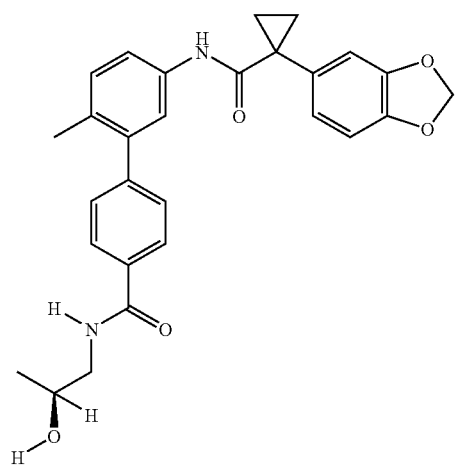

TABLE 1-continued
Examples of compounds of the present invention.
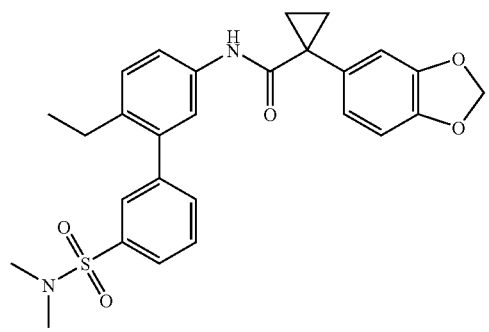
135
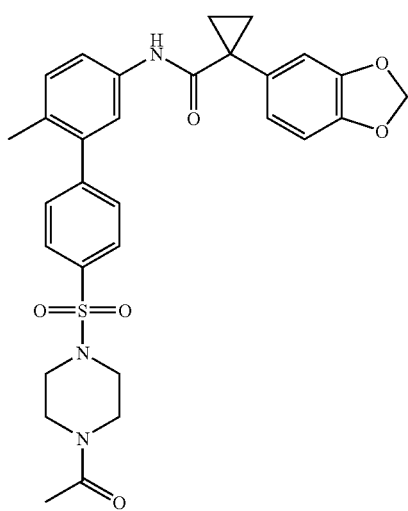
136
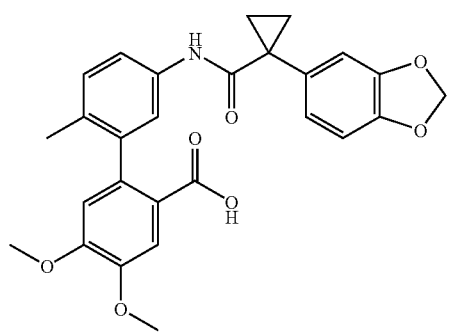
137

TABLE 1-continued
Examples of compounds of the present invention.
138
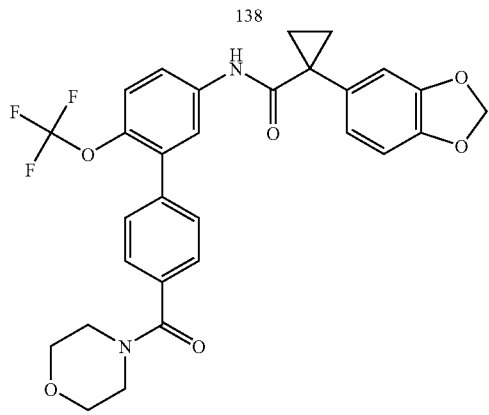
139
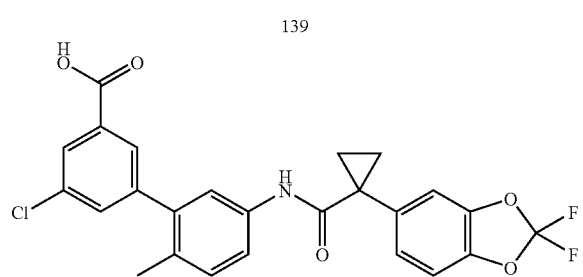
140
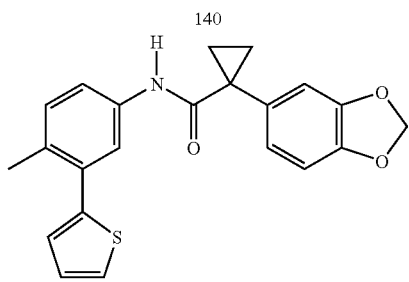
141
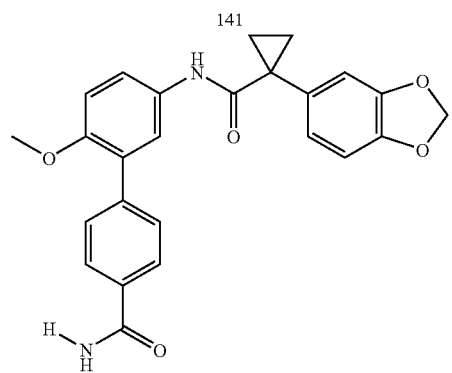

TABLE 1-continued
Examples of compounds of the present invention.
142
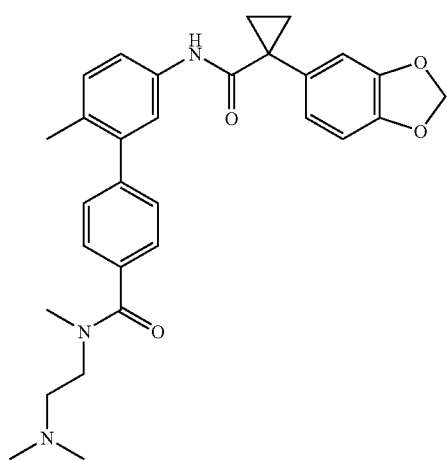
143
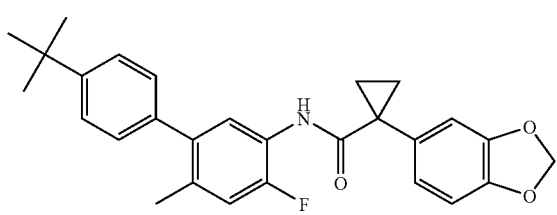
144
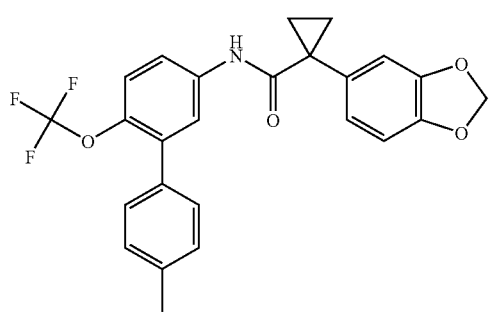
145
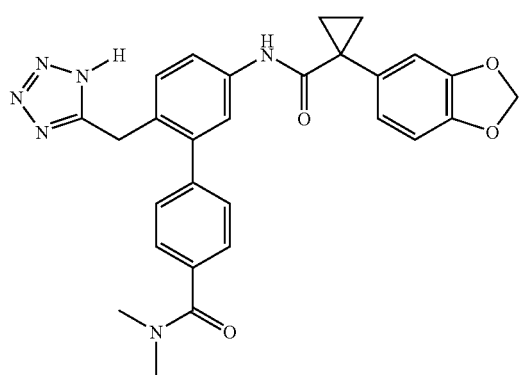

TABLE 1-continued
Examples of compounds of the present invention.
146
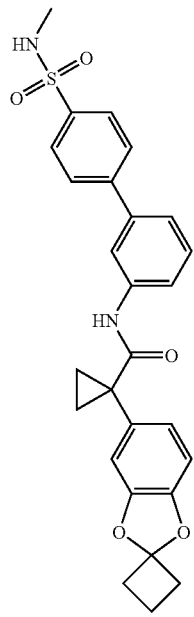
147
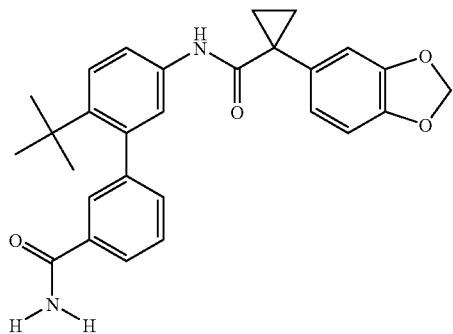
148
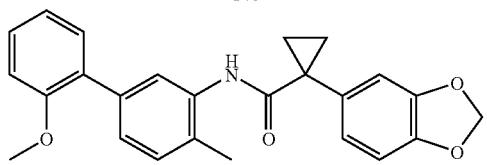
149
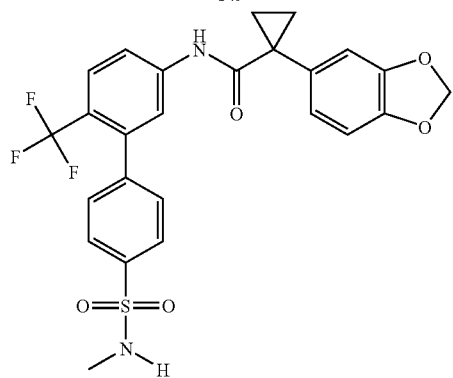

TABLE 1-continued
Examples of compounds of the present invention.
150
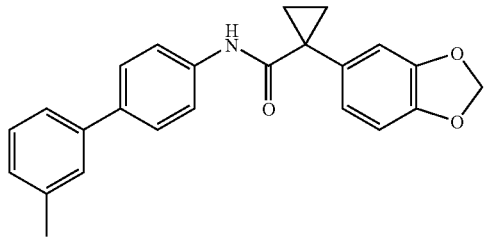
151
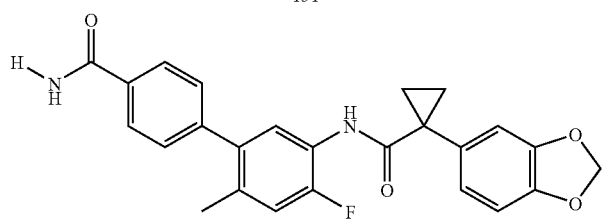
152
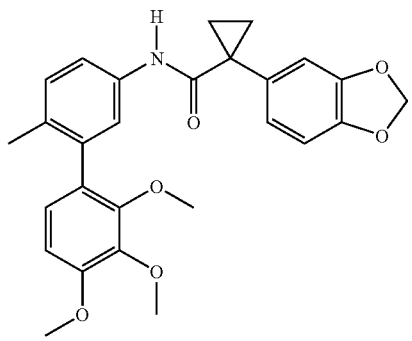
153
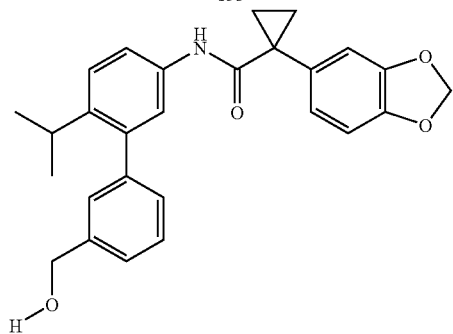

TABLE 1-continued
Examples of compounds of the present invention.
154
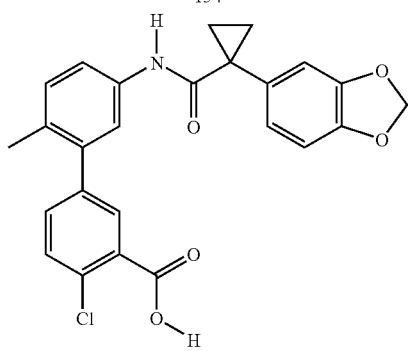
155
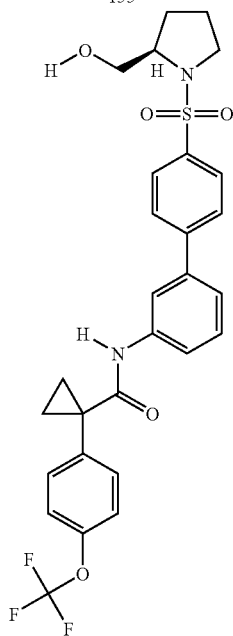
156
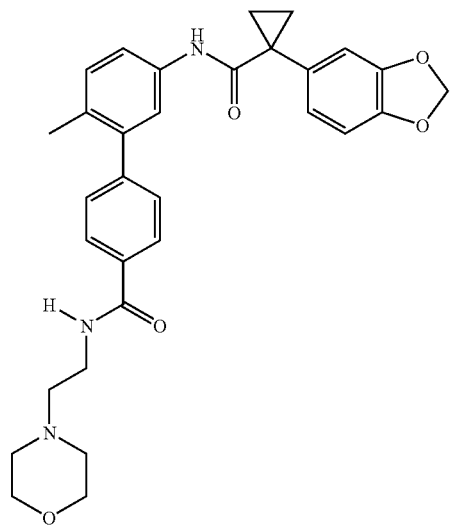

TABLE 1-continued
Examples of compounds of the present invention.
157
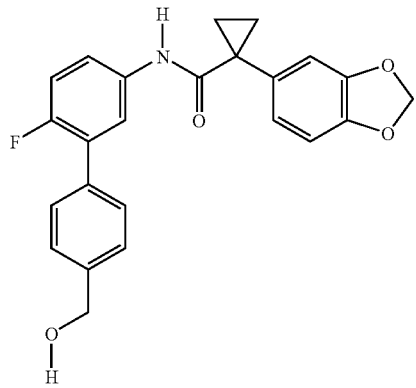
158
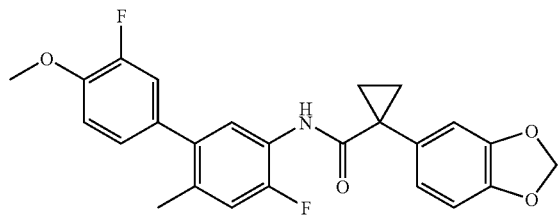
159
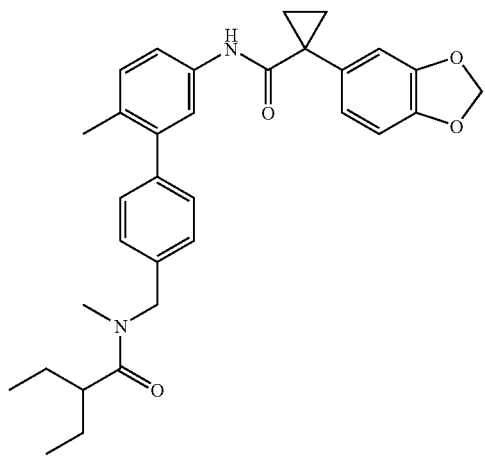
160
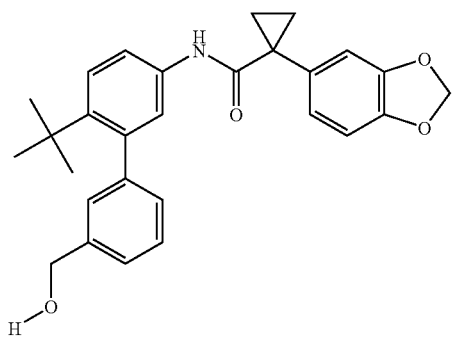

TABLE 1-continued
Examples of compounds of the present invention.
161
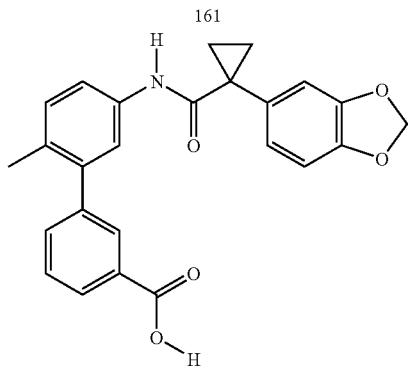
162
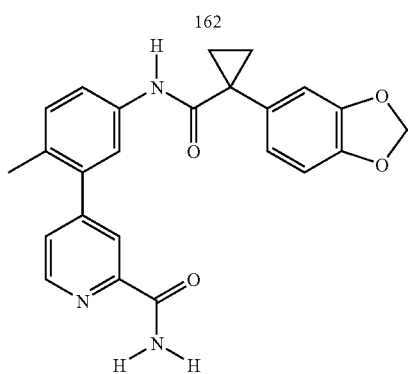
163
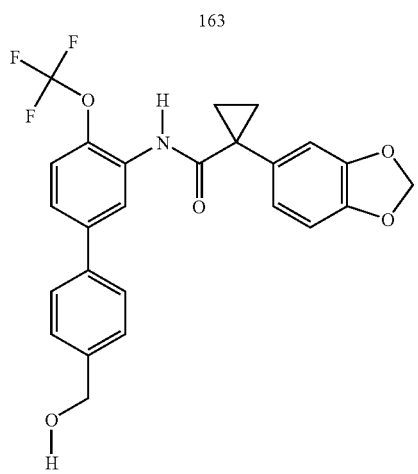
164
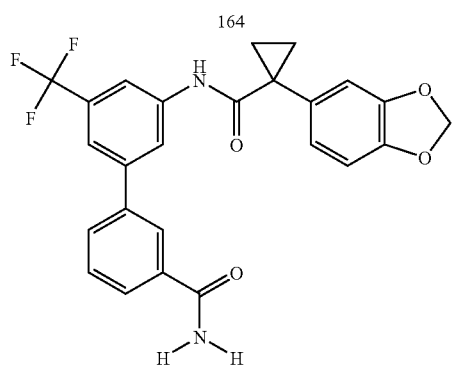

TABLE 1-continued
Examples of compounds of the present invention.
165
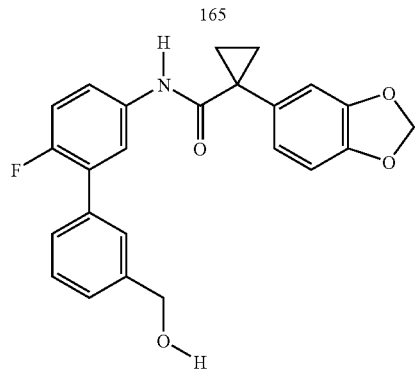
166
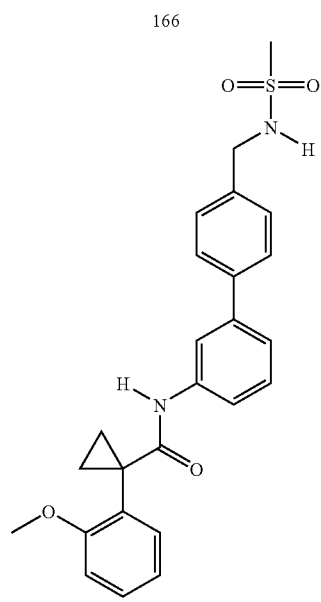
167
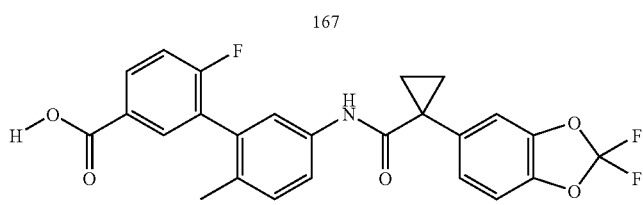
168
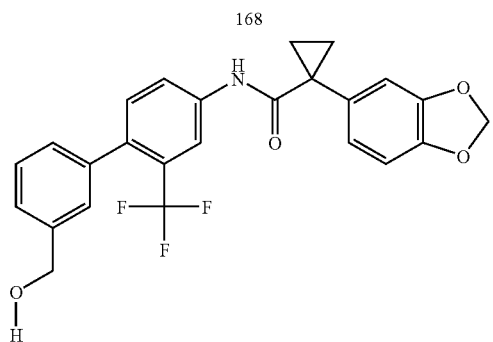

TABLE 1-continued
Examples of compounds of the present invention.
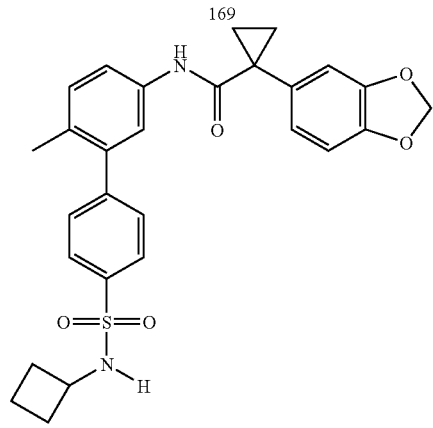
169
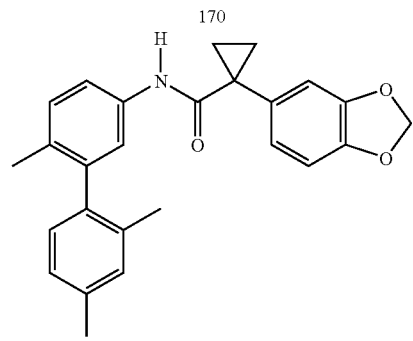
170
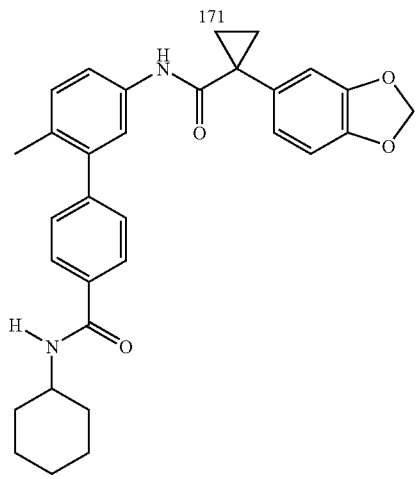
171
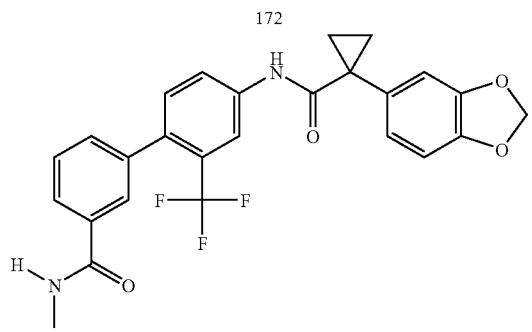
172

TABLE 1-continued
Examples of compounds of the present invention.
173
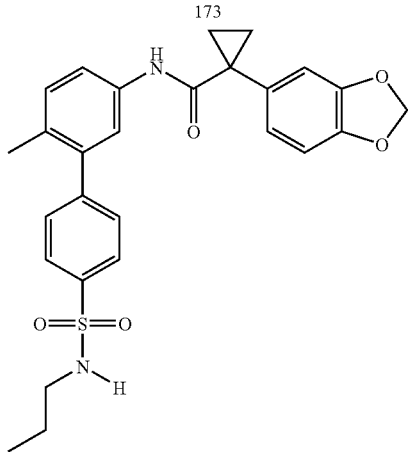
174
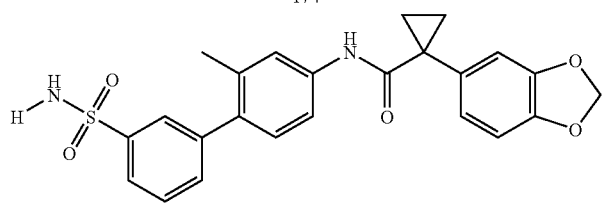
175
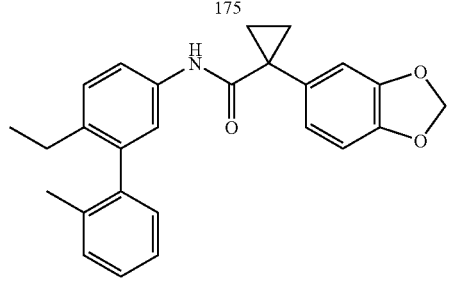
176
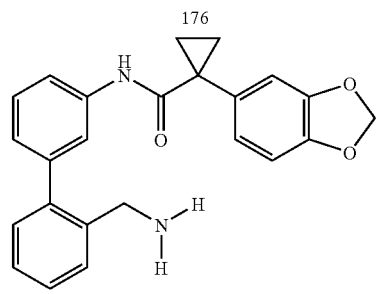

TABLE 1-continued
Examples of compounds of the present invention.
177
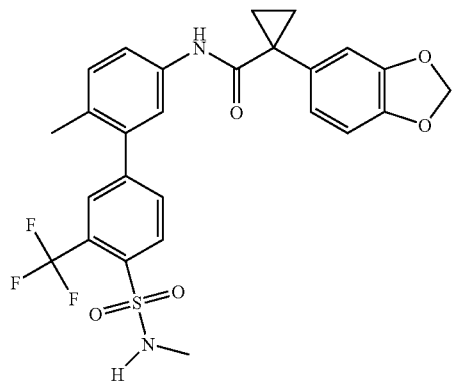
178
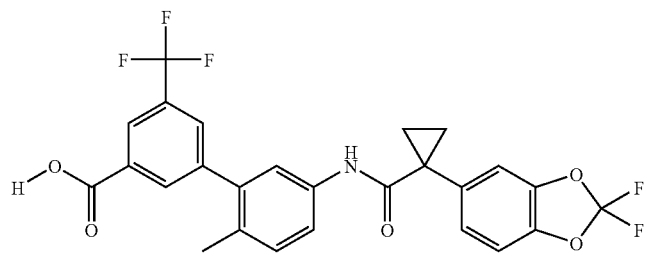
179
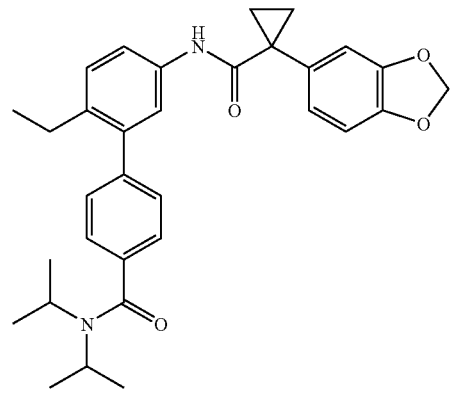
180
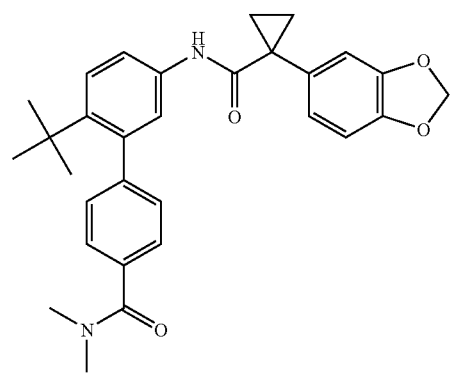

TABLE 1-continued
Examples of compounds of the present invention.
181
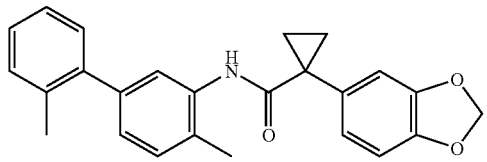
182
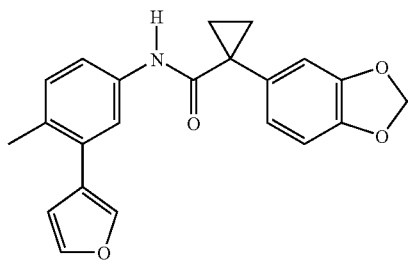
183
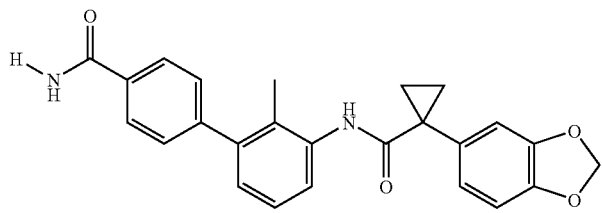
184
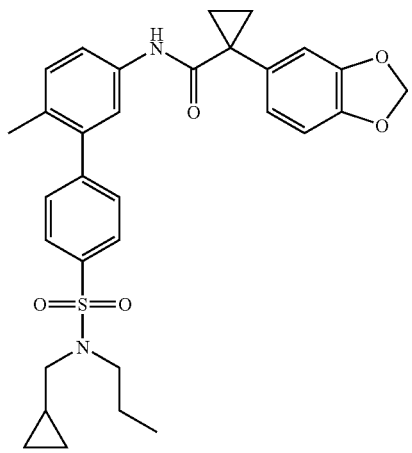
185
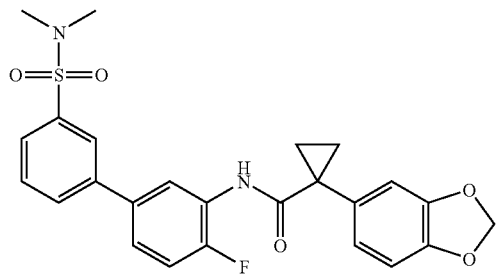

TABLE 1-continued
Examples of compounds of the present invention.
186
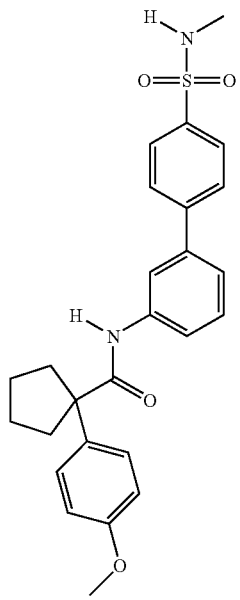
187
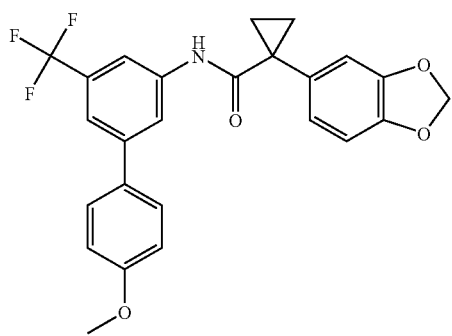
188
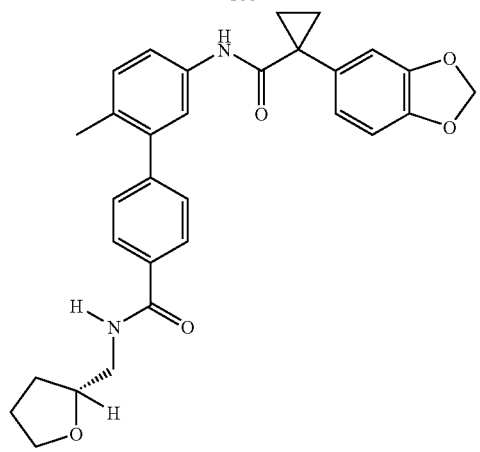

TABLE 1-continued
Examples of compounds of the present invention.
189
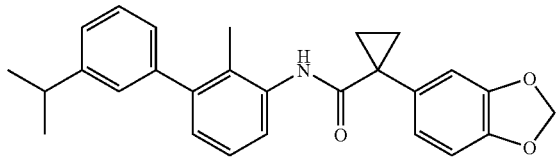
190
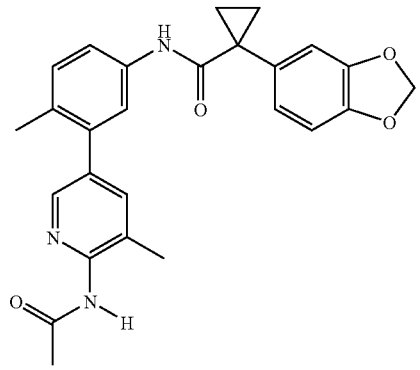
191
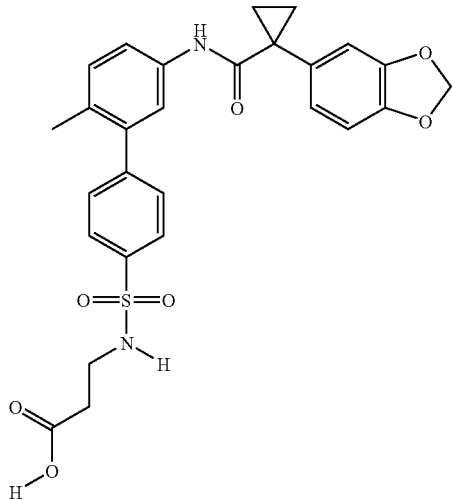
192
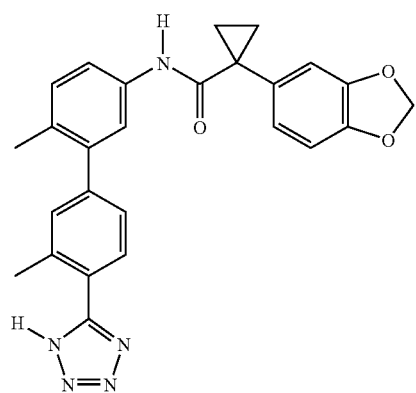

TABLE 1-continued
Examples of compounds of the present invention.
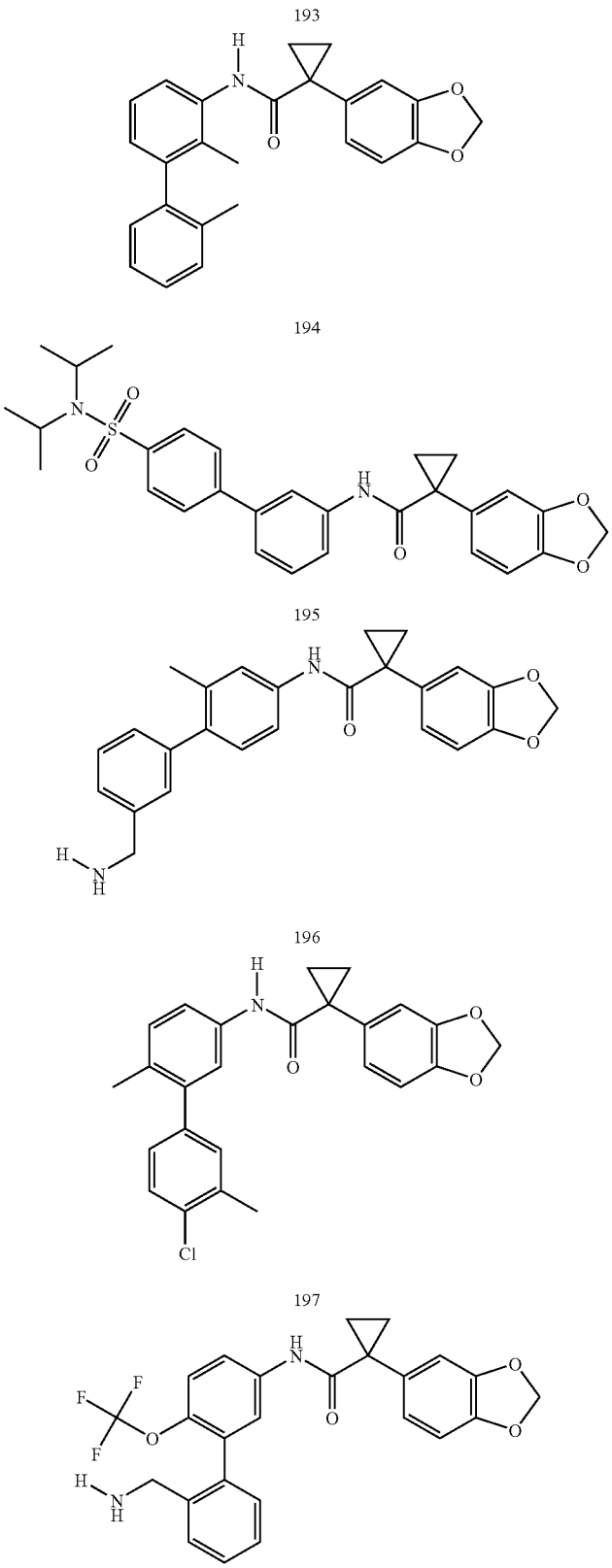

TABLE 1-continued
Examples of compounds of the present invention.
198
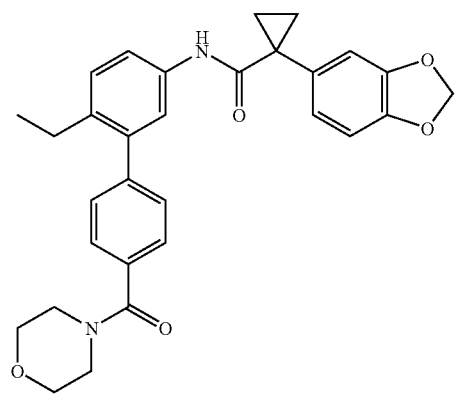
199
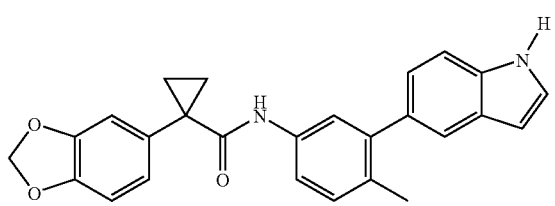
200
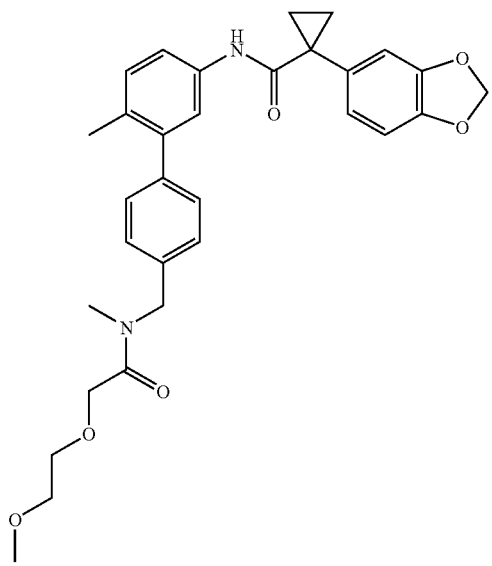

TABLE 1-continued
Examples of compounds of the present invention.
201
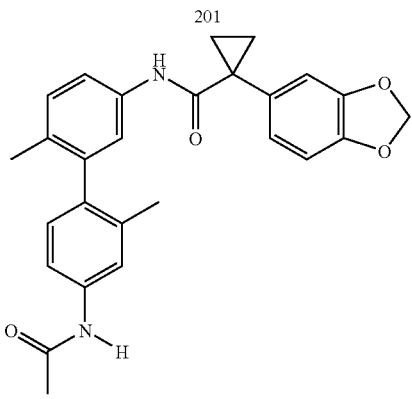
202
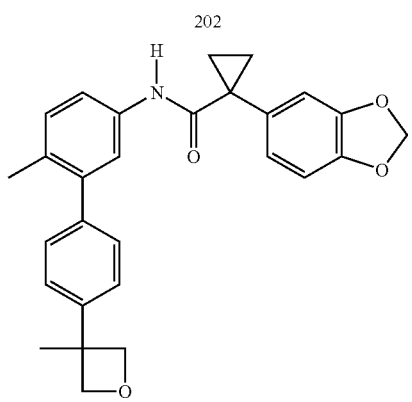
203
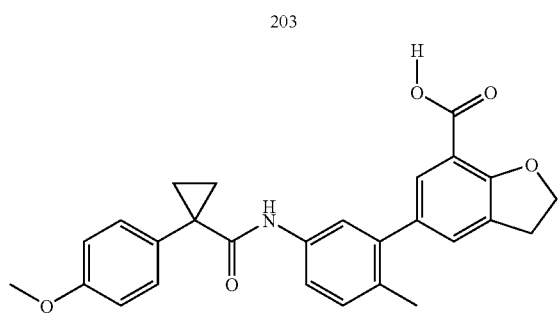
204
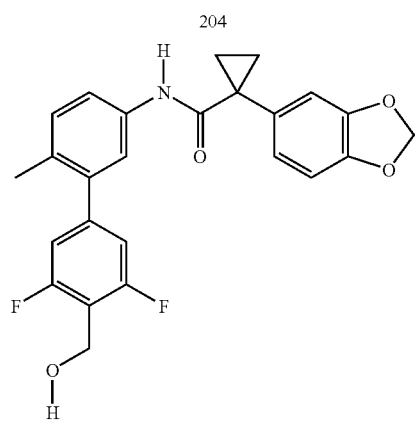

TABLE 1-continued
Examples of compounds of the present invention.
205
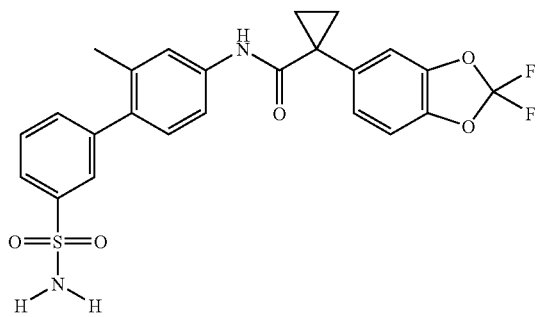
206
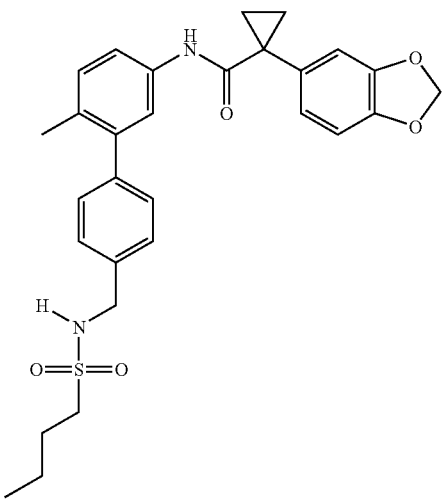
207
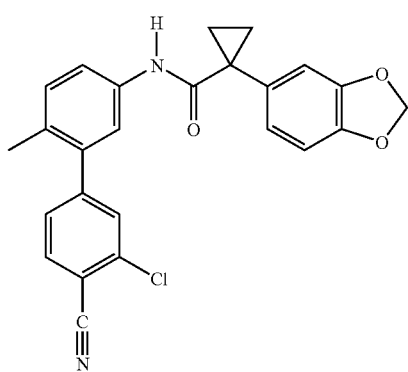
208
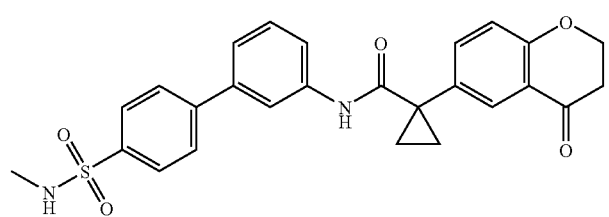

TABLE 1-continued
Examples of compounds of the present invention.
209
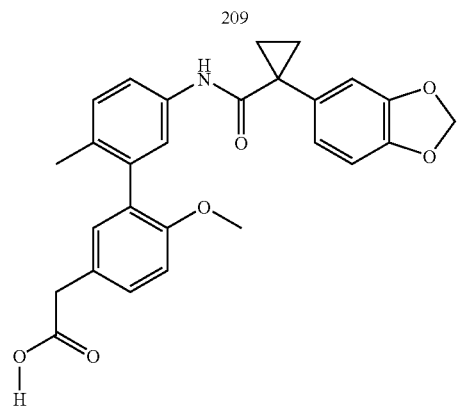
210
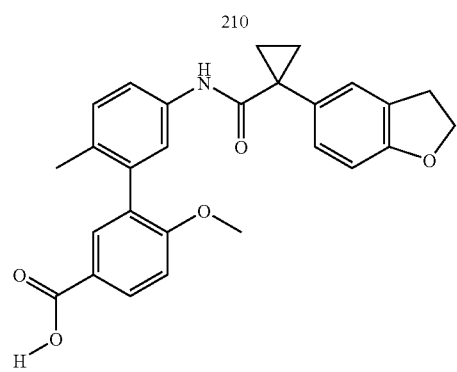
211
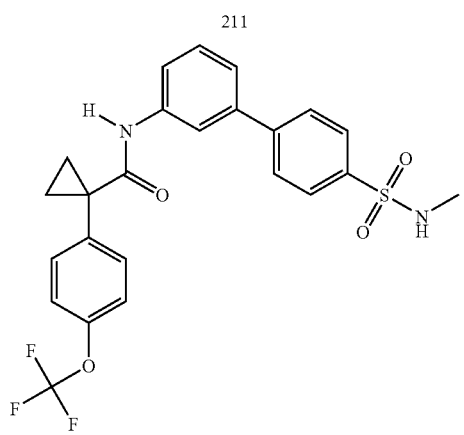
212
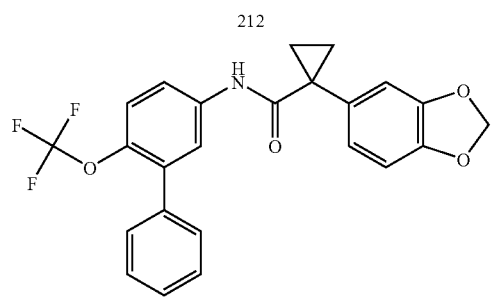

TABLE 1-continued
Examples of compounds of the present invention.
213
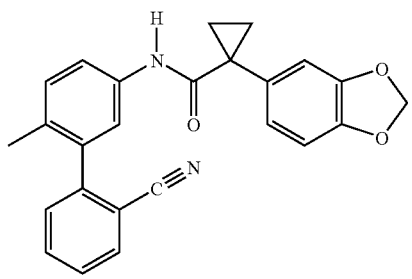
214
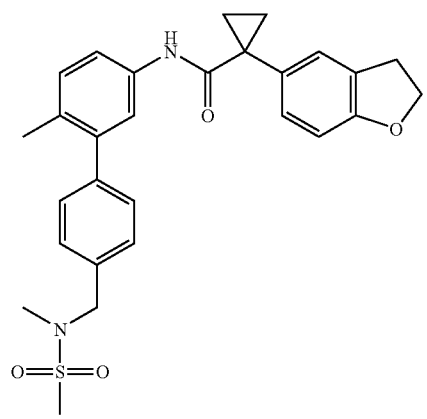
215
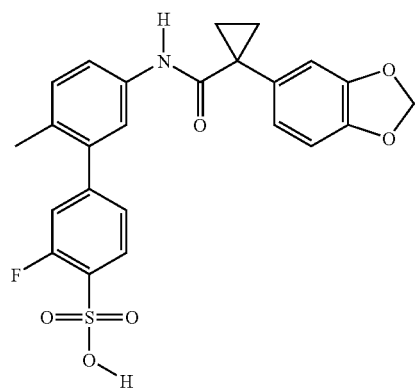

TABLE 1-continued
Examples of compounds of the present invention.
216
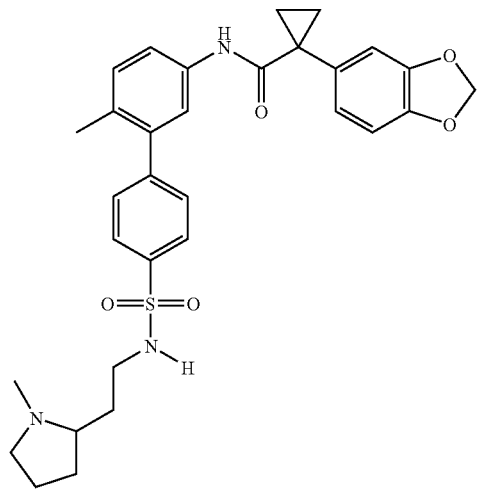
217
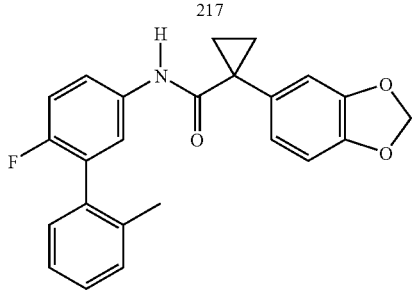
218
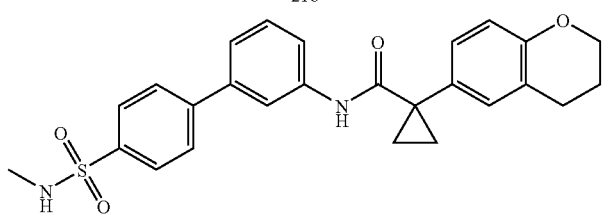
219
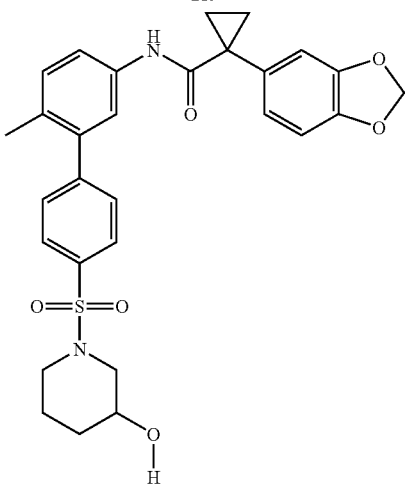

TABLE 1-continued
Examples of compounds of the present invention.
220
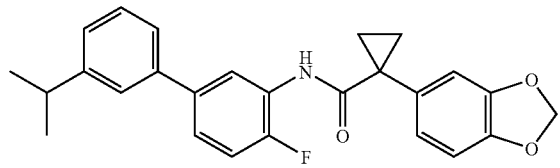
221
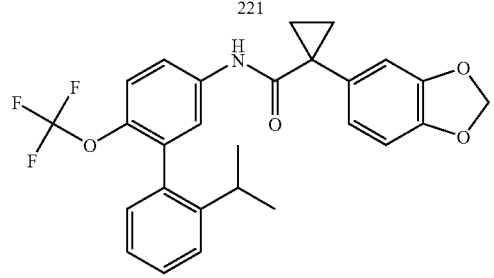
222
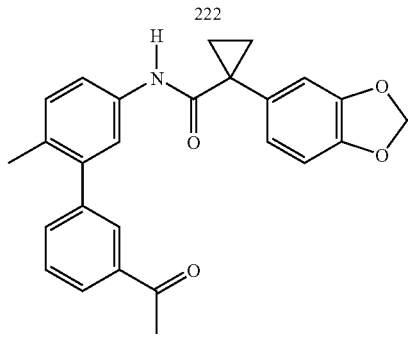
223
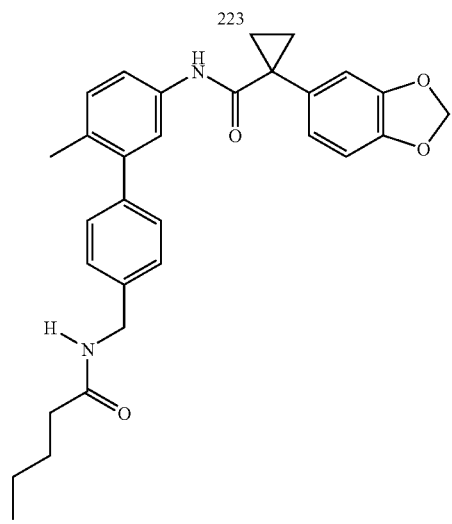

TABLE 1-continued
Examples of compounds of the present invention.
224
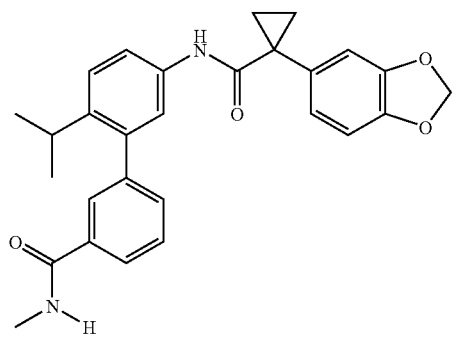
225
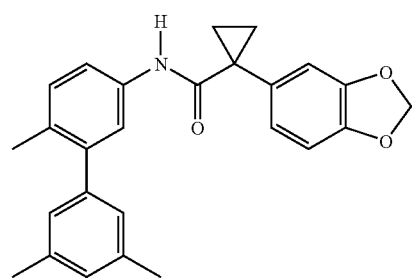
226
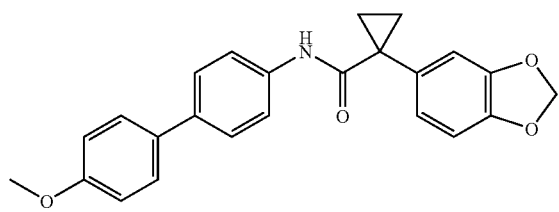
227
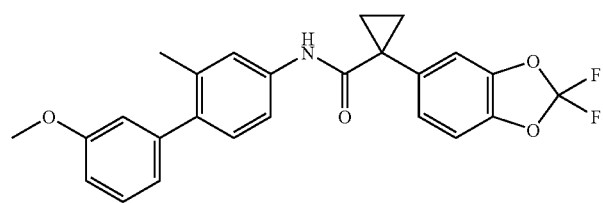
228
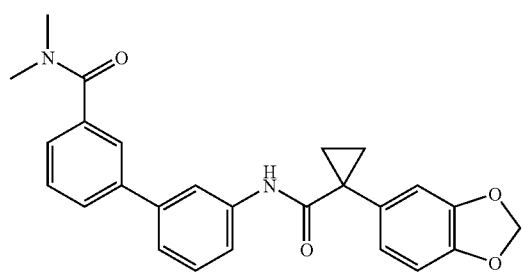

TABLE 1-continued
Examples of compounds of the present invention.
229
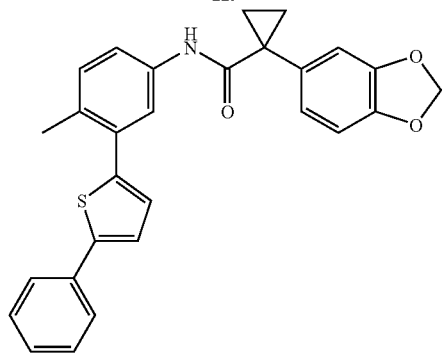
230
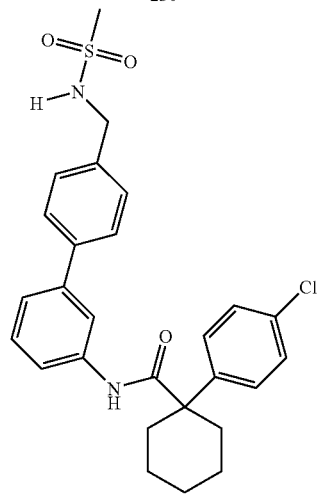
231
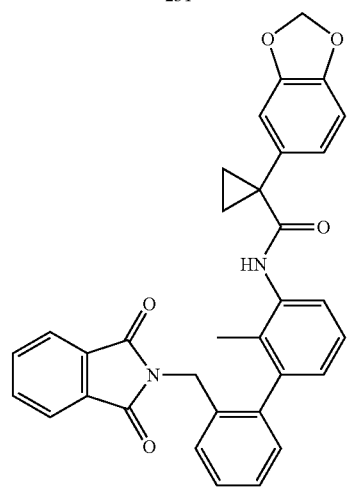

TABLE 1-continued
Examples of compounds of the present invention.
232
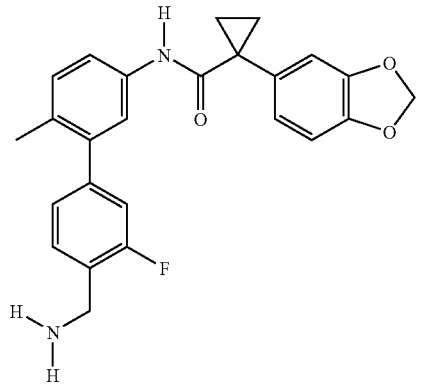
233
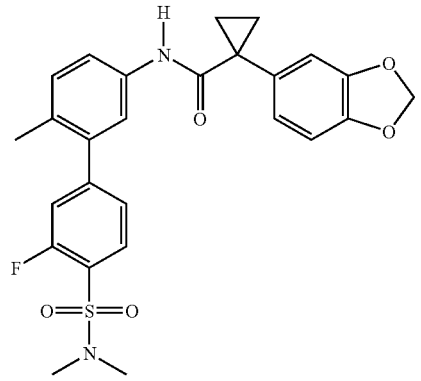
234
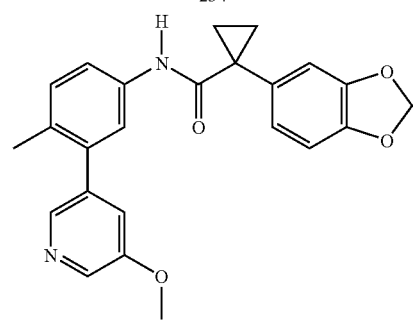
235
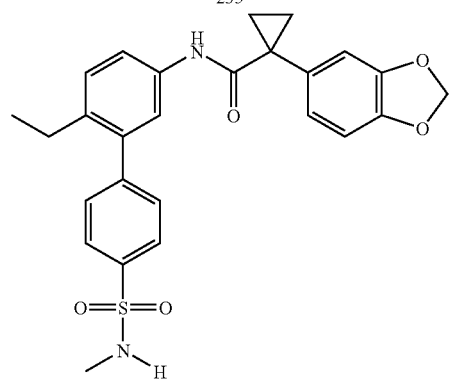

TABLE 1-continued
Examples of compounds of the present invention.
236
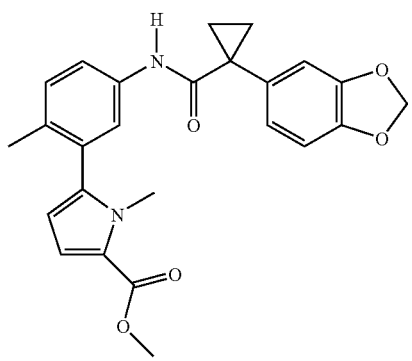
237
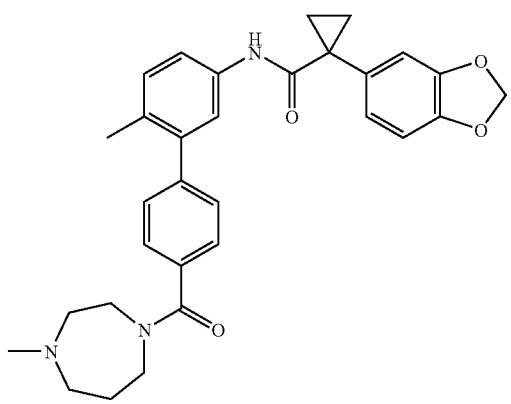
238
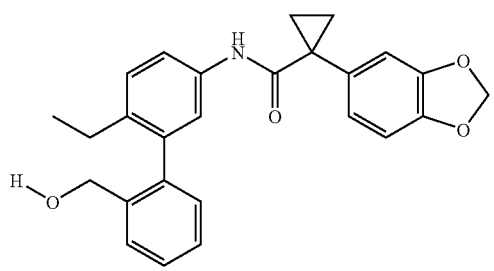

TABLE 1-continued
Examples of compounds of the present invention.
239
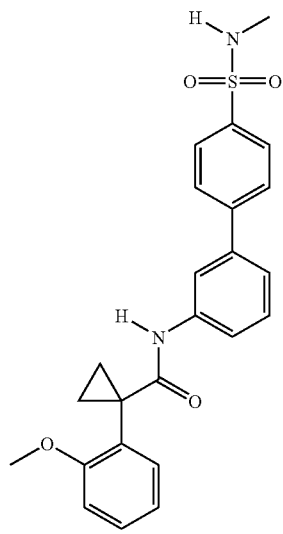
240
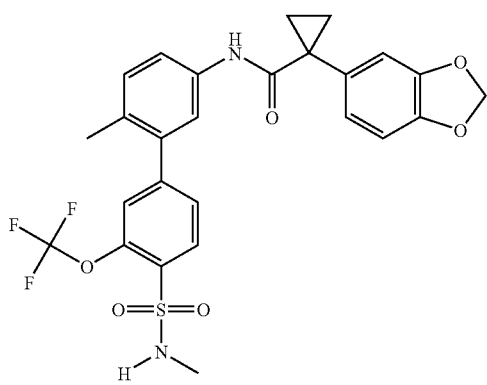
241
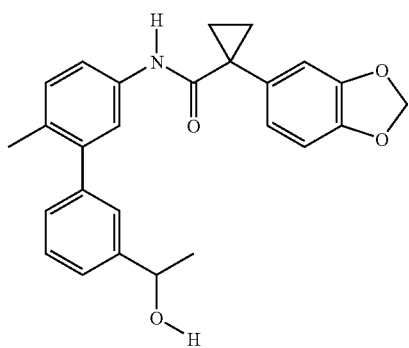

TABLE 1-continued
Examples of compounds of the present invention.
242
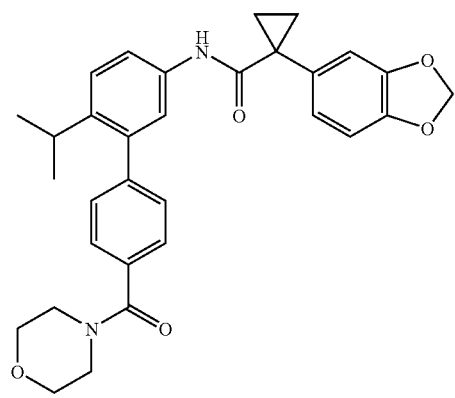
243
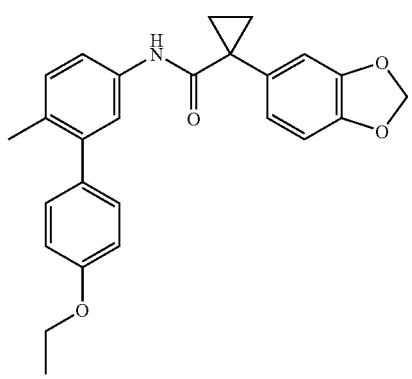
244
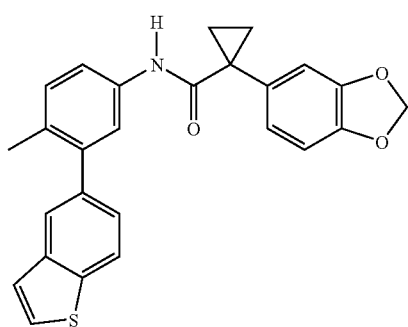

TABLE 1-continued
Examples of compounds of the present invention.
245
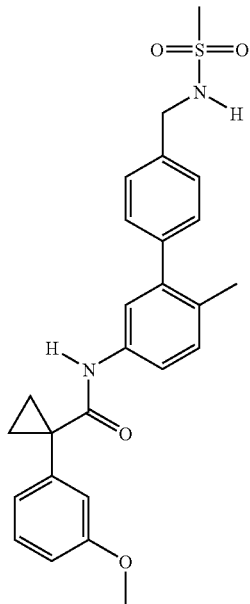
246
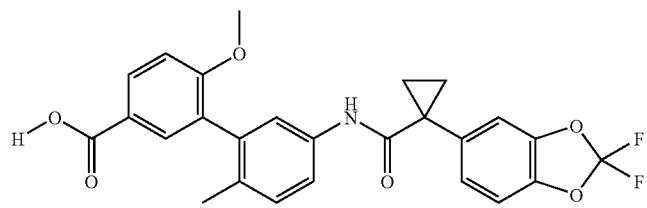
247
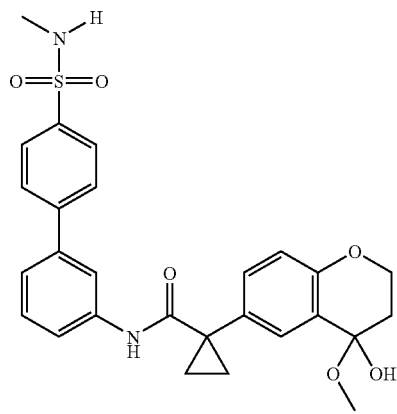

TABLE 1-continued
Examples of compounds of the present invention.
248
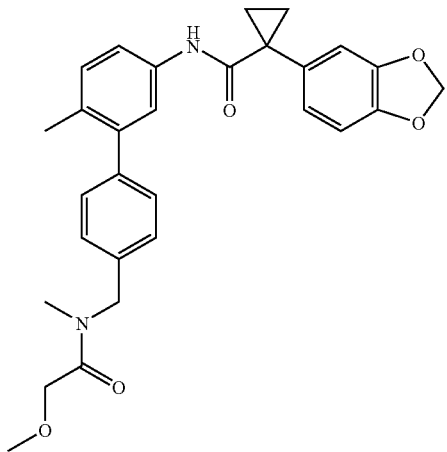
249
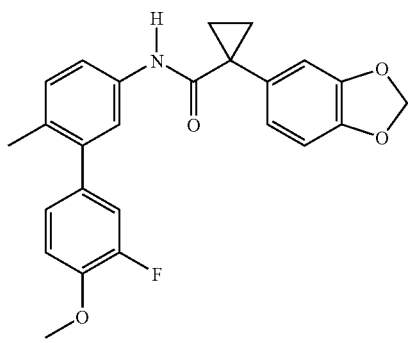
250
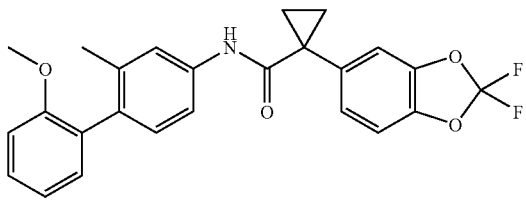
251
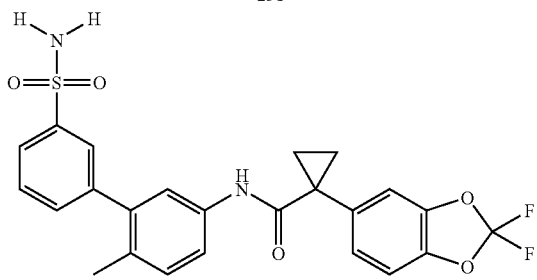

TABLE 1-continued
Examples of compounds of the present invention.
252
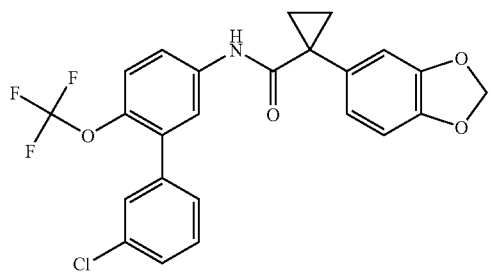
253
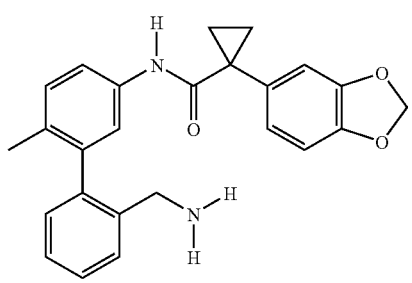
254
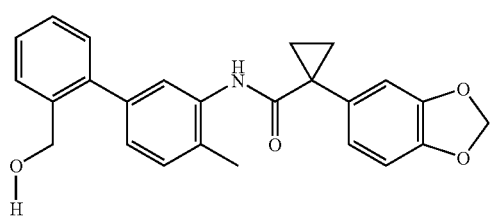
255
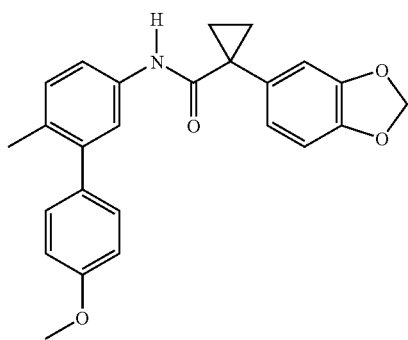
256
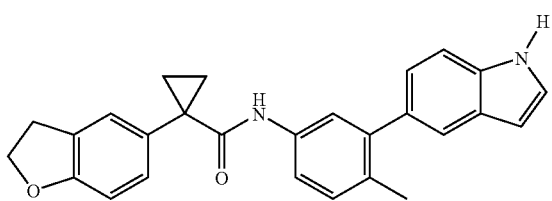

TABLE 1-continued
Examples of compounds of the present invention.
257
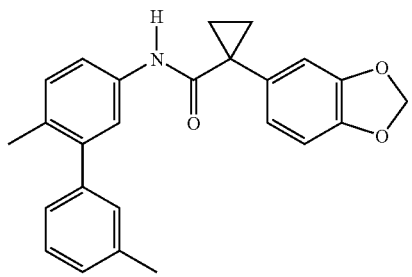
258
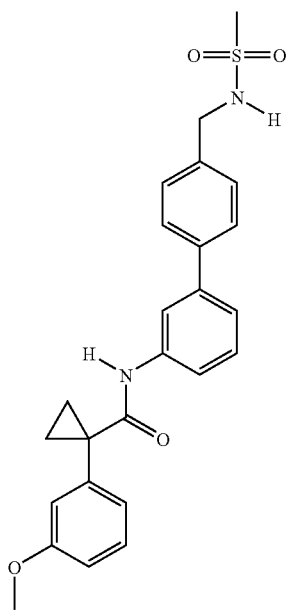
259
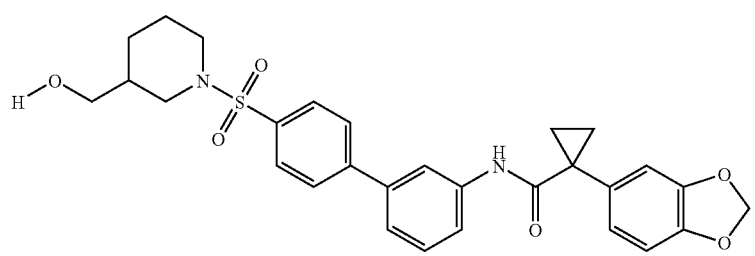
260
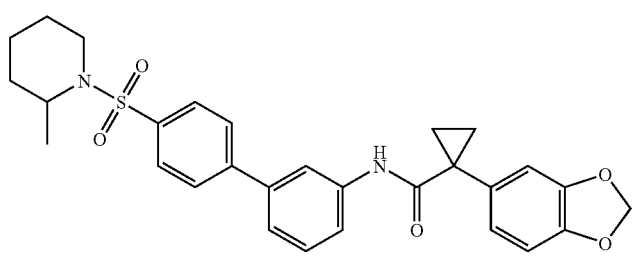

TABLE 1-continued
Examples of compounds of the present invention.
261
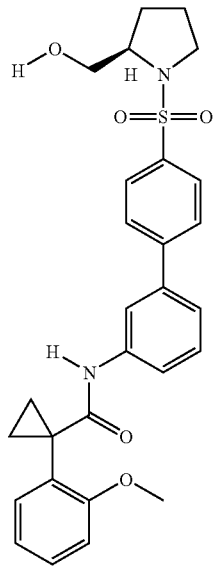
262
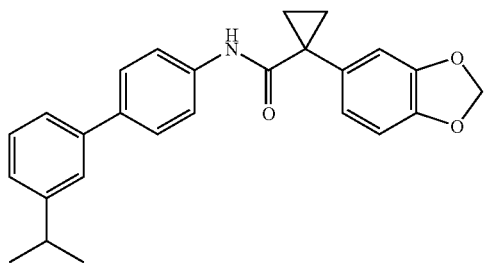
263
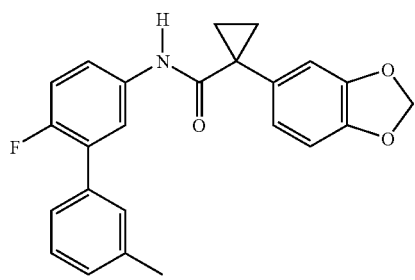

TABLE 1-continued
Examples of compounds of the present invention.
264
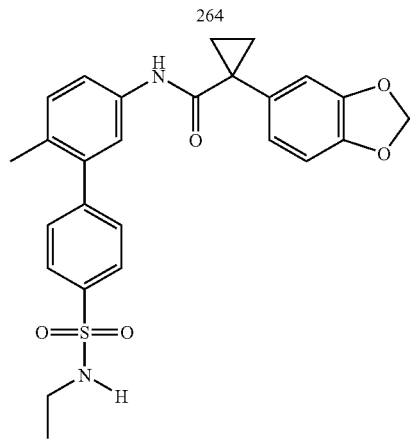
265
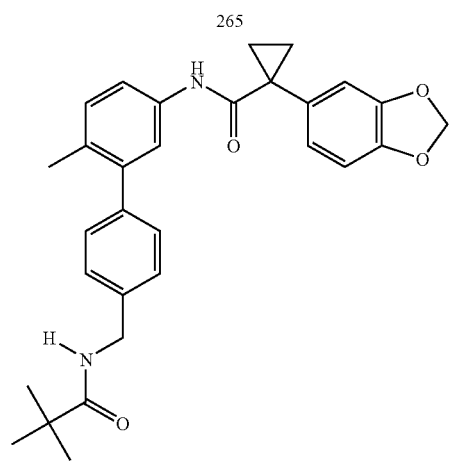
266
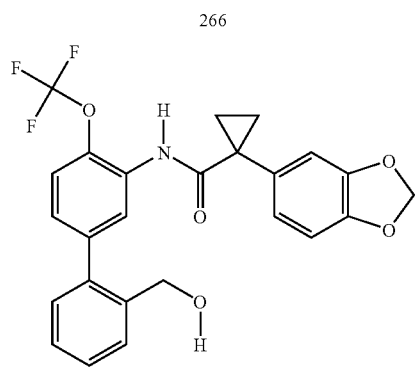

TABLE 1-continued
Examples of compounds of the present invention.
267
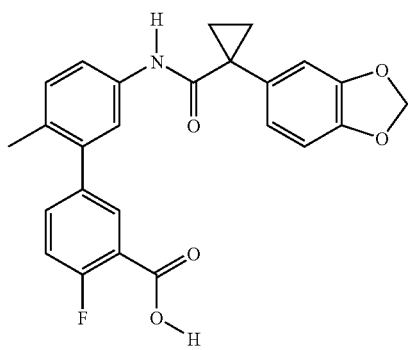
268
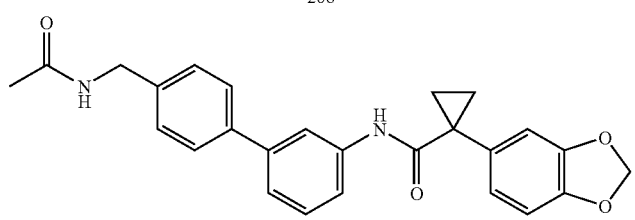
269
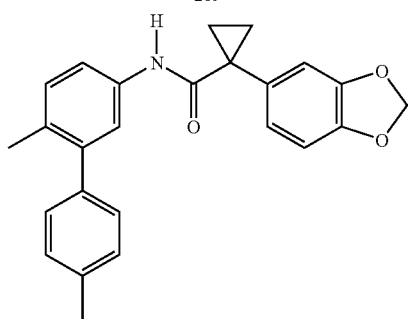
270
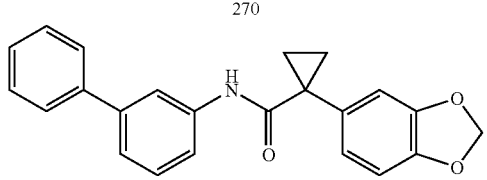
271
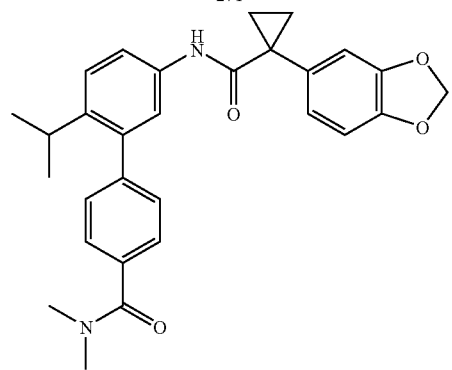

TABLE 1-continued
Examples of compounds of the present invention.
272
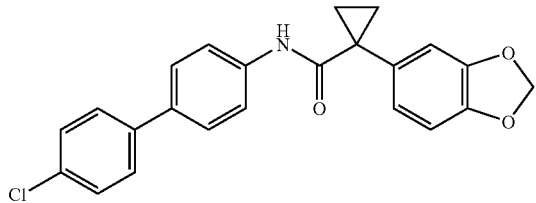
273
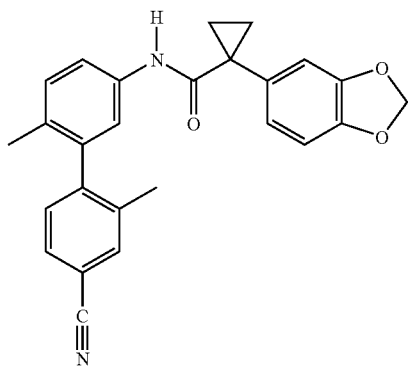
274
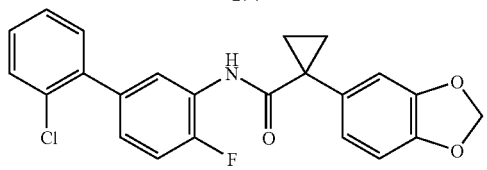
275
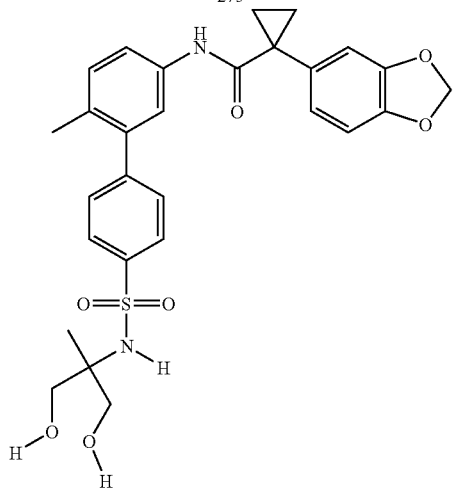

TABLE 1-continued
Examples of compounds of the present invention.
276
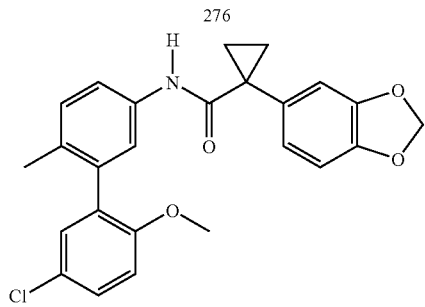
277
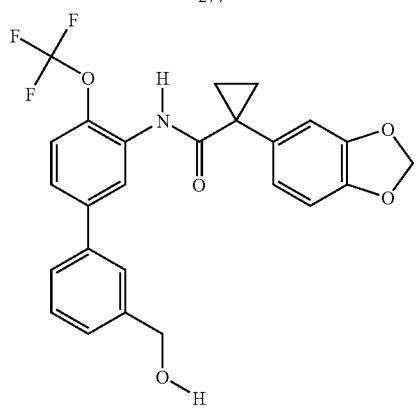
278
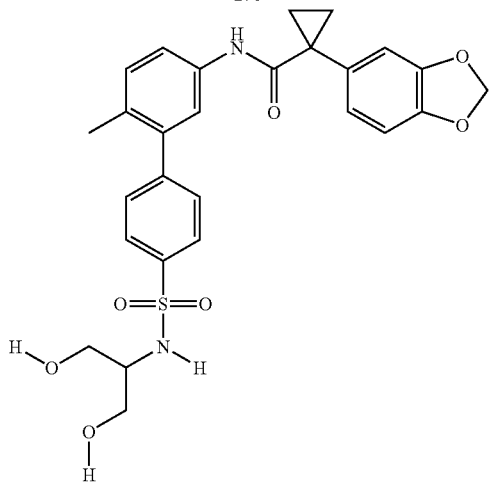
279
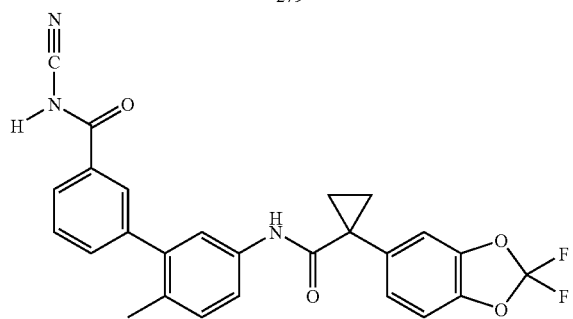

TABLE 1-continued
Examples of compounds of the present invention.
280
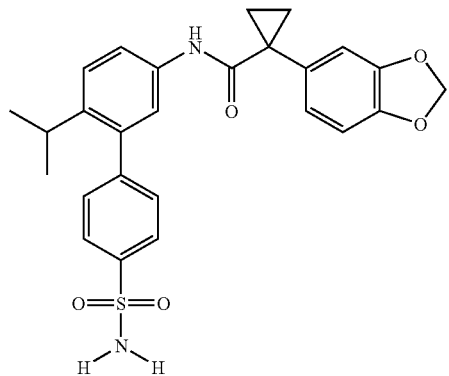
281
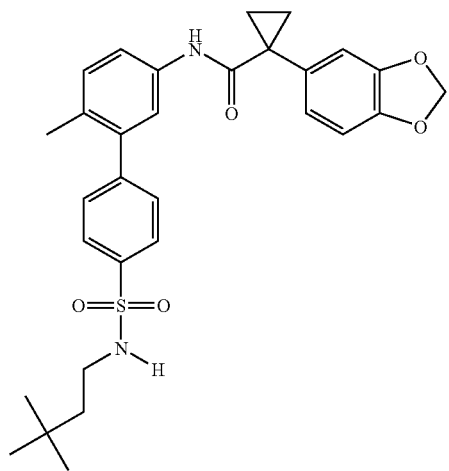
282
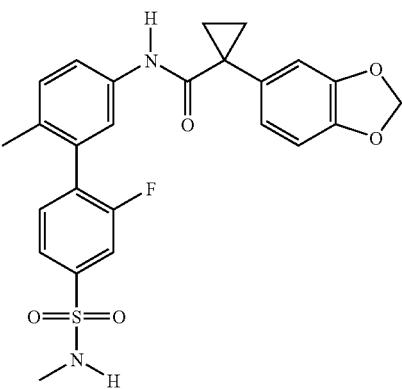

TABLE 1-continued
Examples of compounds of the present invention.
283
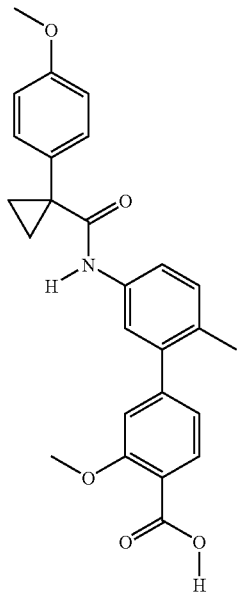
284
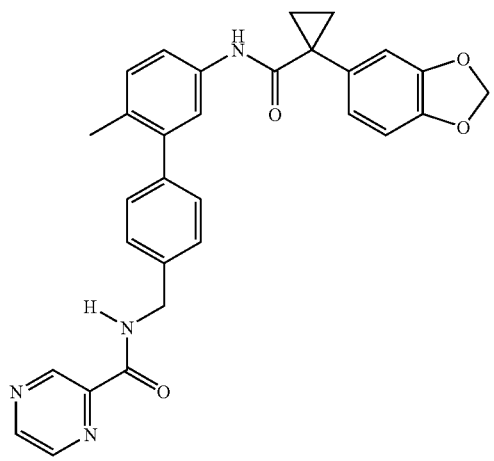
285
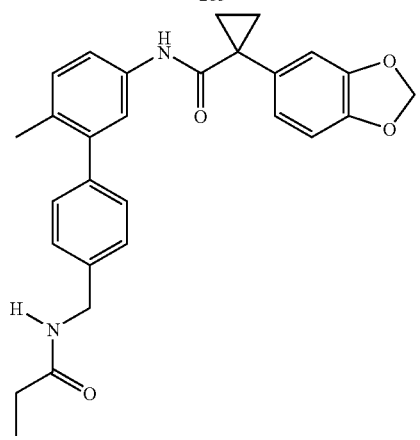

TABLE 1-continued
Examples of compounds of the present invention.
286
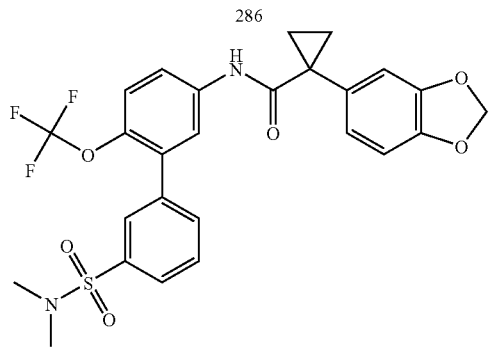
287
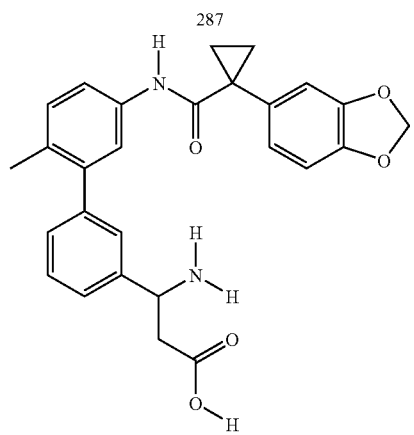
288
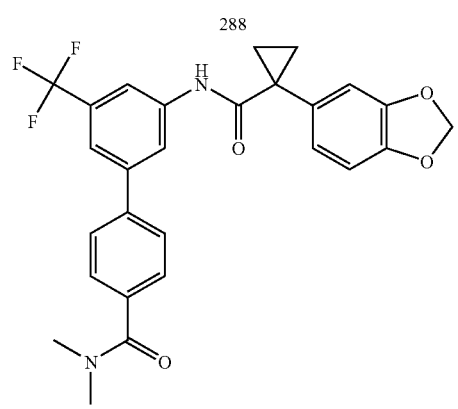
289
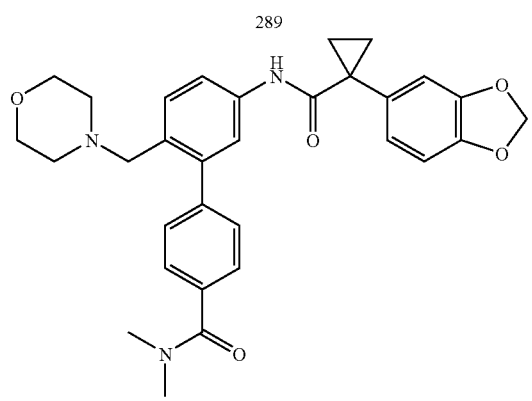

TABLE 1-continued
Examples of compounds of the present invention.
290
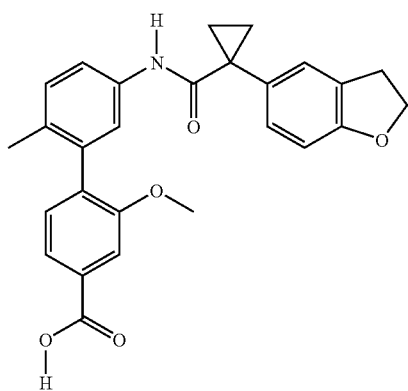
291
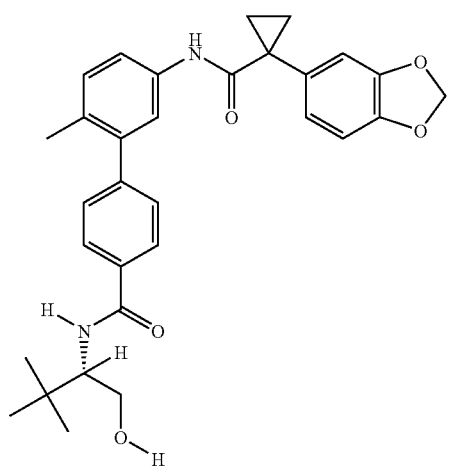
292
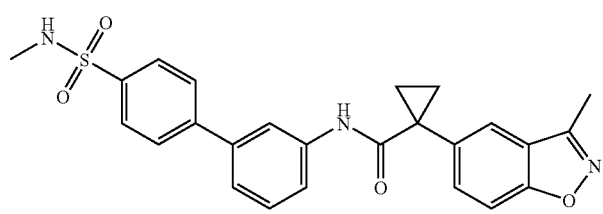
293
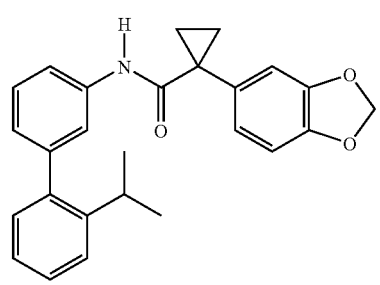

TABLE 1-continued
Examples of compounds of the present invention.
294
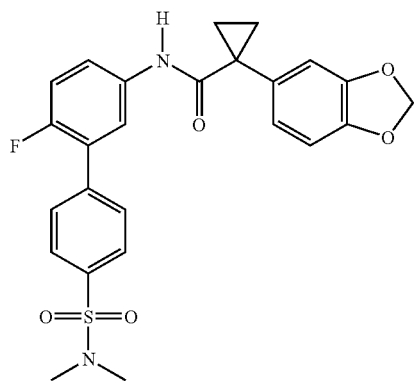
295
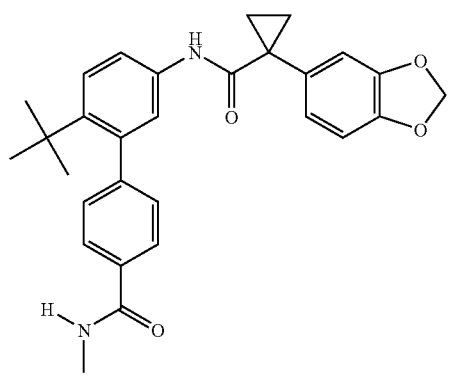
296
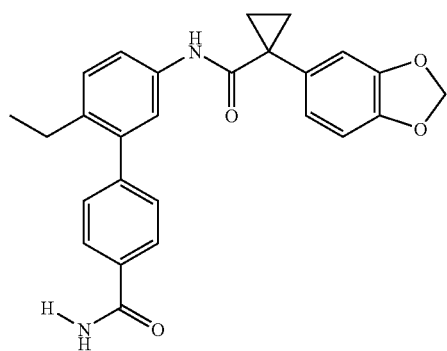

TABLE 1-continued
Examples of compounds of the present invention.
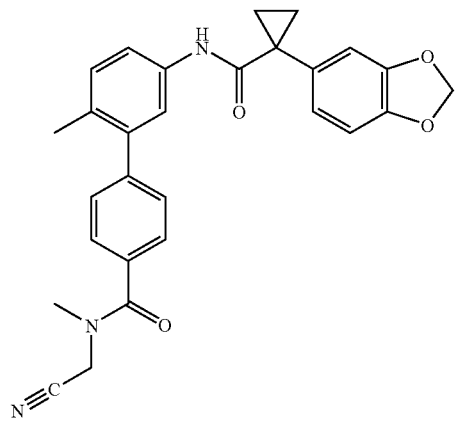
297
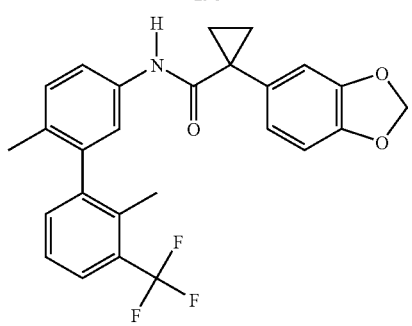
298
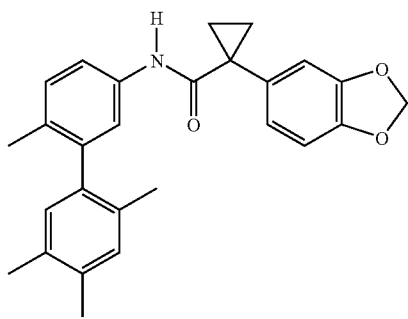
299
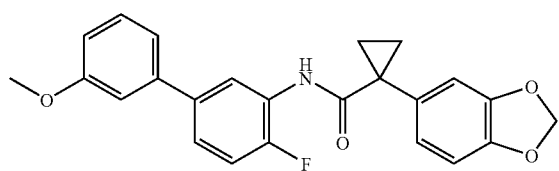
300

TABLE 1-continued
Examples of compounds of the present invention.
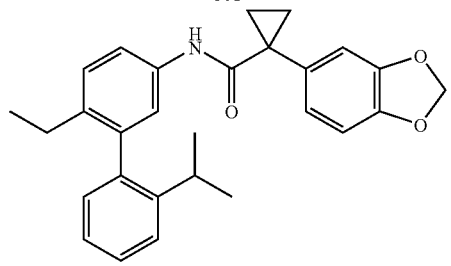
301
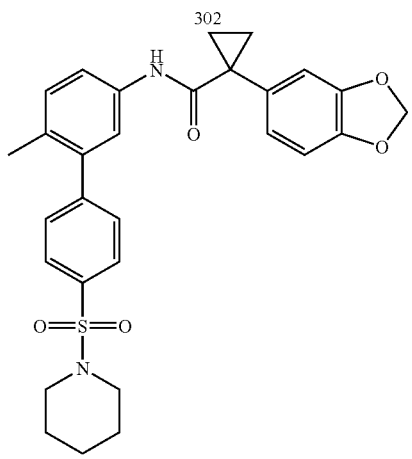
302
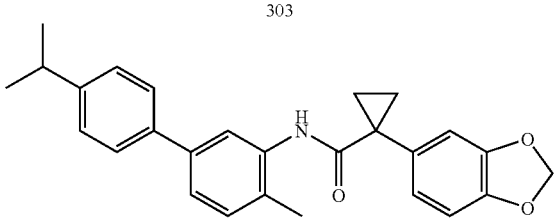
303
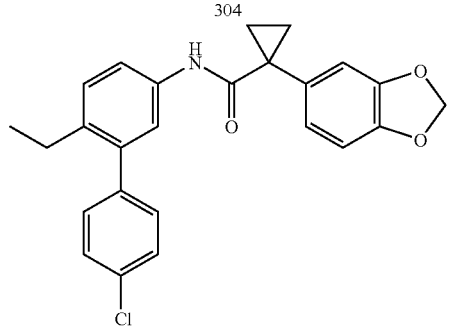
304

TABLE 1-continued
Examples of compounds of the present invention.
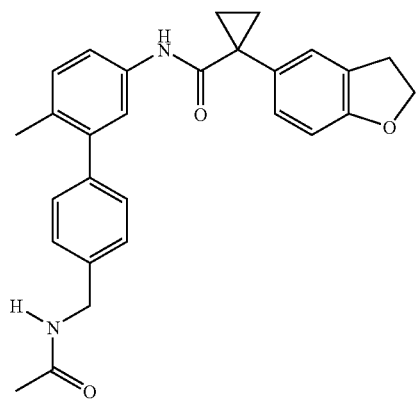
305
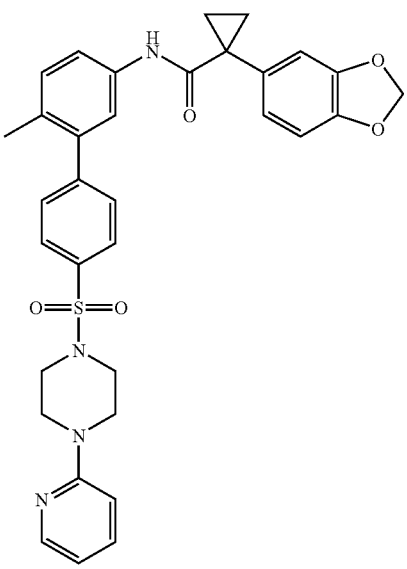
306
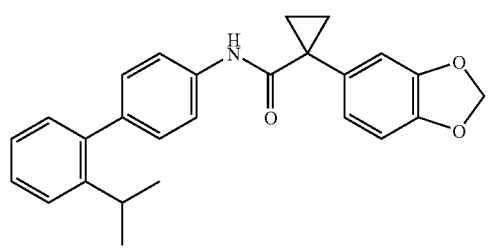
307

TABLE 1-continued
Examples of compounds of the present invention.
308
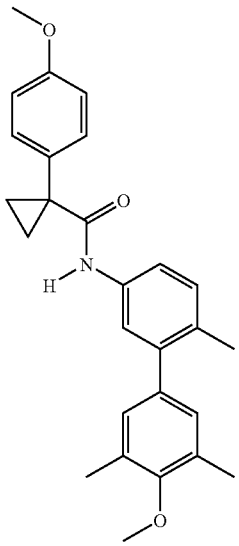
309
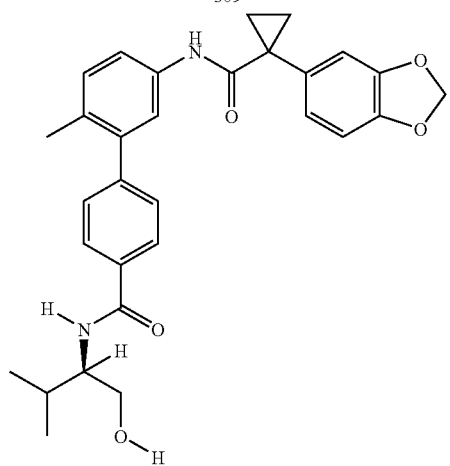
310
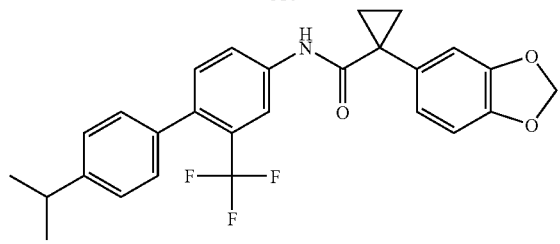

TABLE 1-continued
Examples of compounds of the present invention.
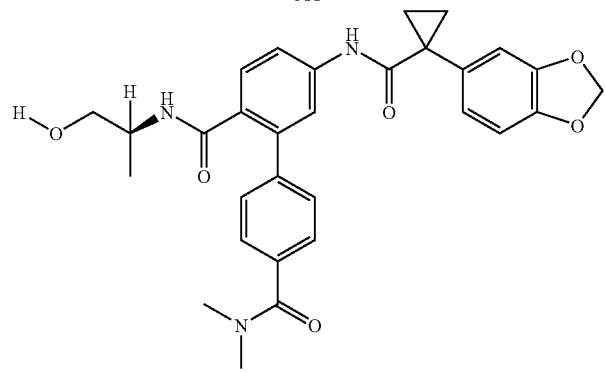
311
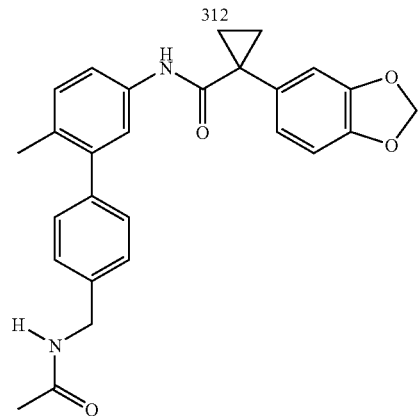
312
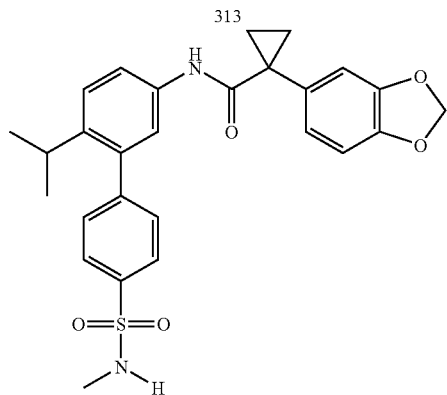
313
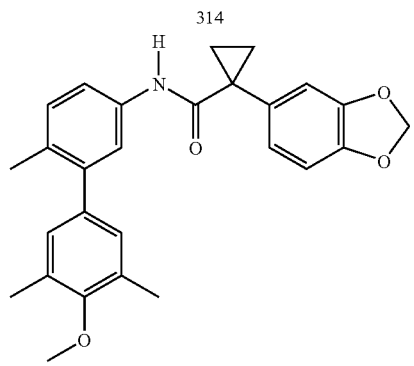
314

TABLE 1-continued
Examples of compounds of the present invention.
315
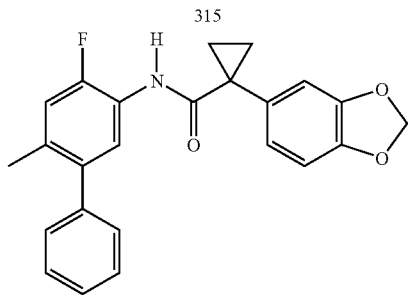
316
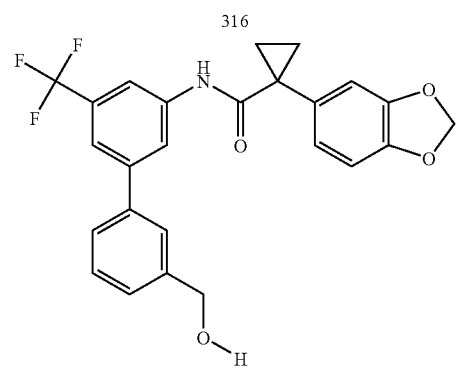
317
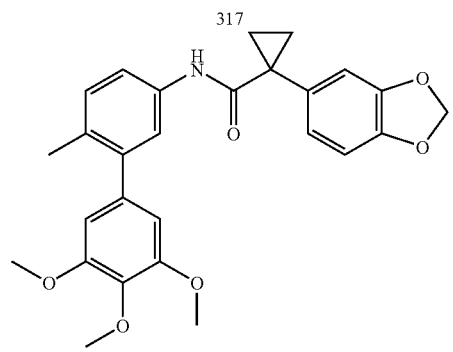
318
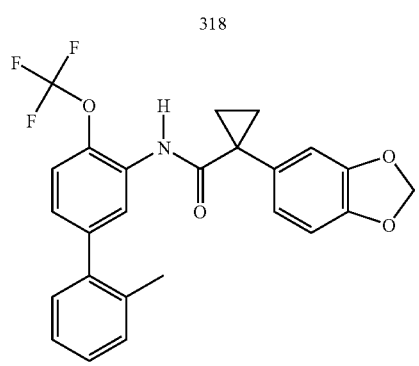

TABLE 1-continued
Examples of compounds of the present invention.
319
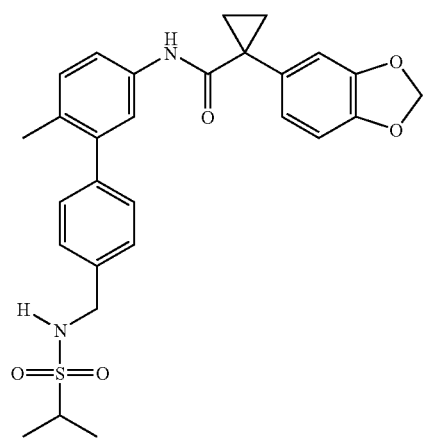
320
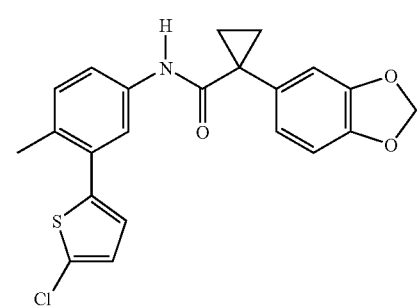
321
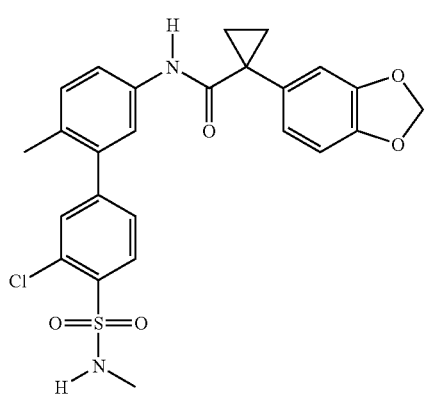

TABLE 1-continued
Examples of compounds of the present invention.
322
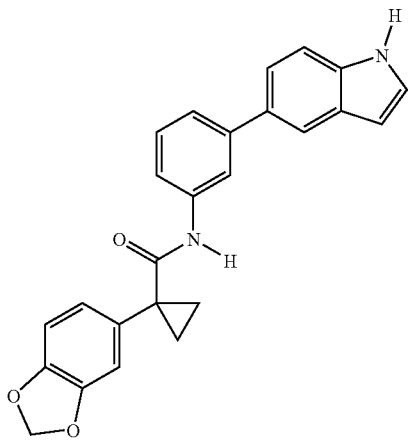
323
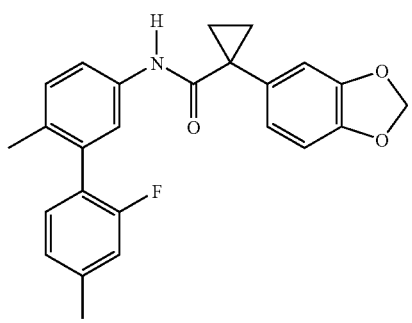
324
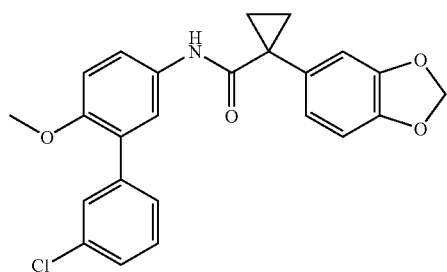
325
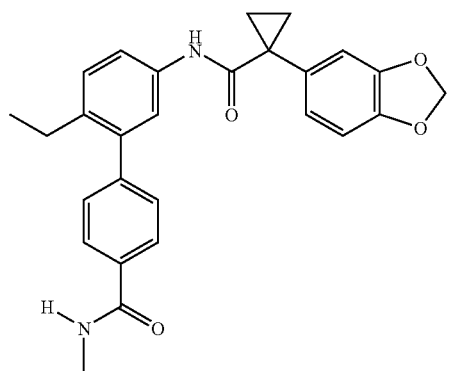

TABLE 1-continued
Examples of compounds of the present invention.
326
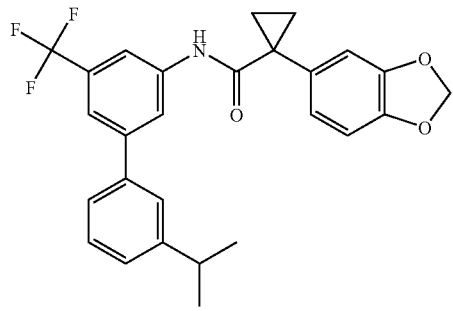
327
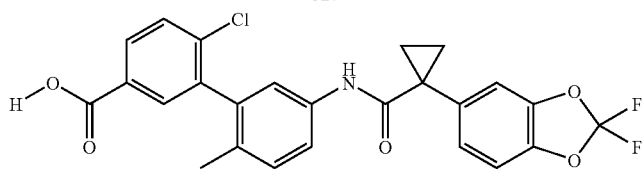
328
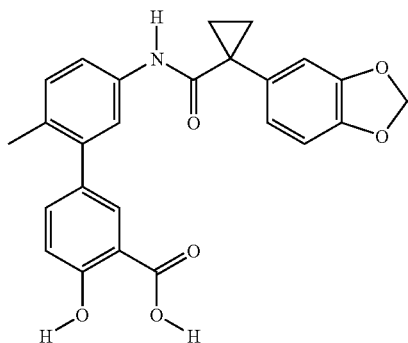
329
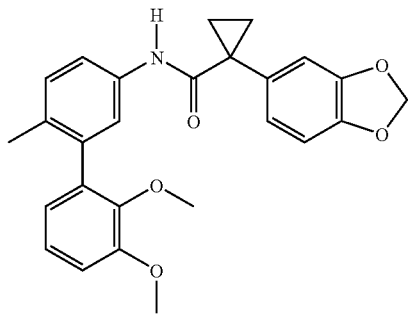
330
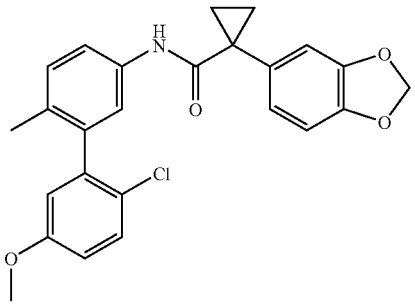

TABLE 1-continued
Examples of compounds of the present invention.
331
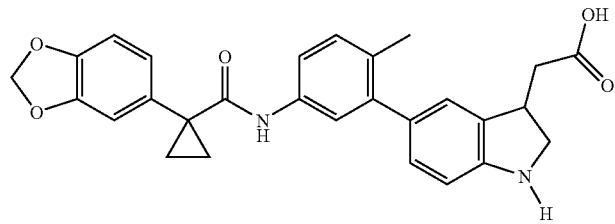
332
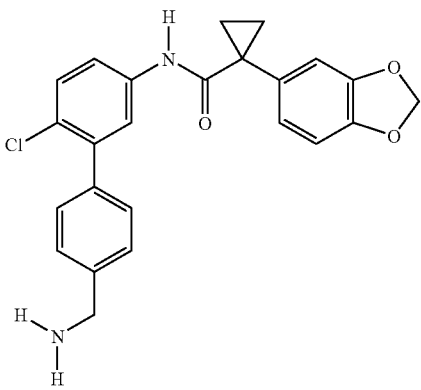
333
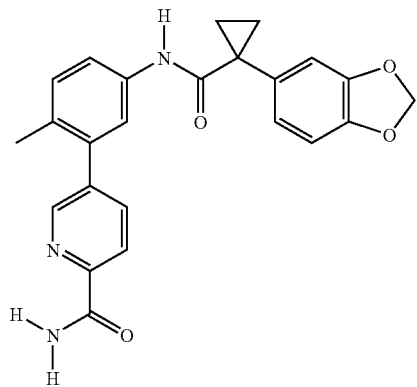
334
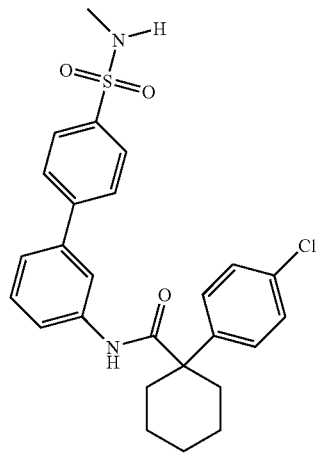

TABLE 1-continued
Examples of compounds of the present invention.
335
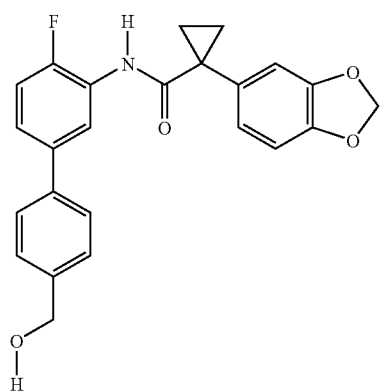
336
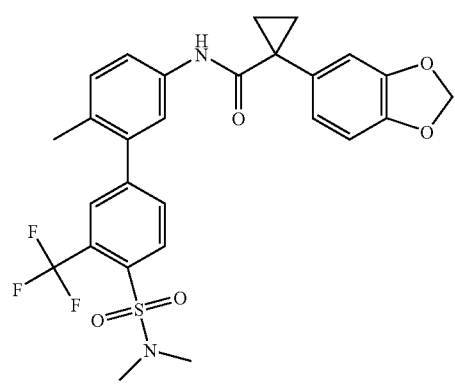
337
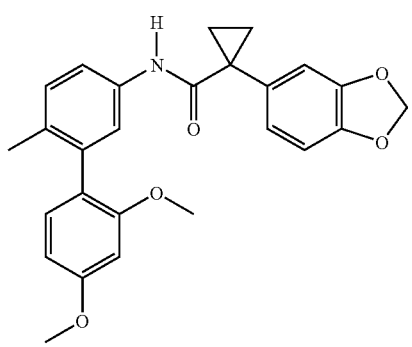

TABLE 1-continued
Examples of compounds of the present invention.
338
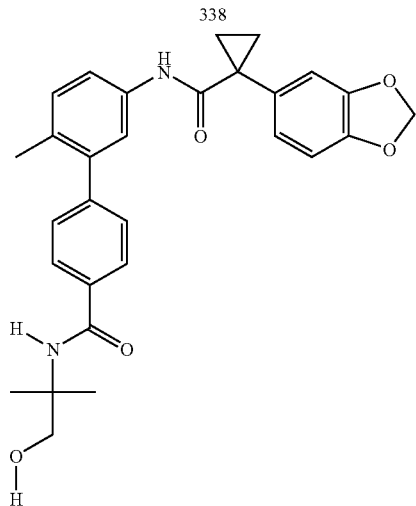
339
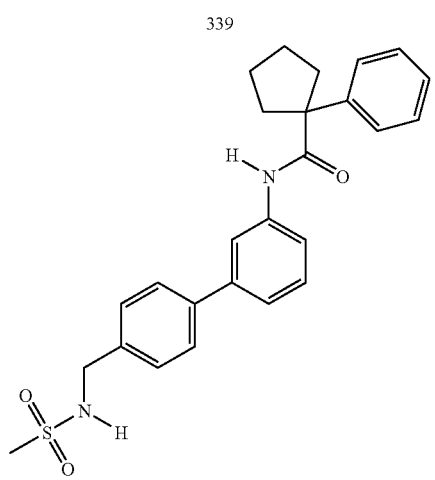
340
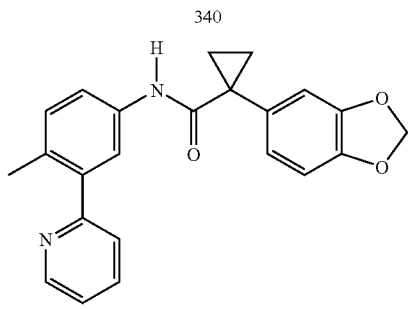

TABLE 1-continued
Examples of compounds of the present invention.
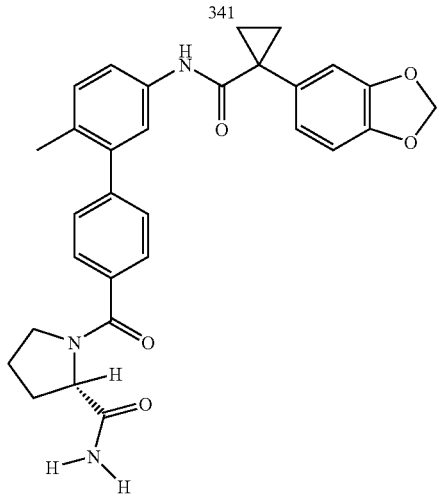
341
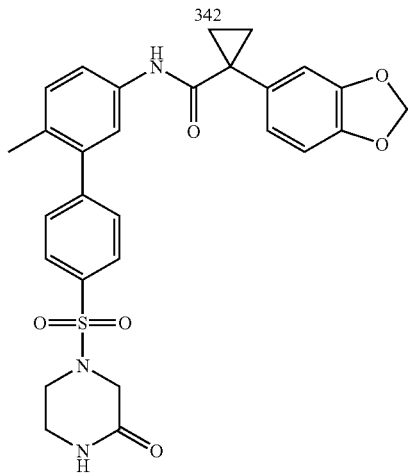
342
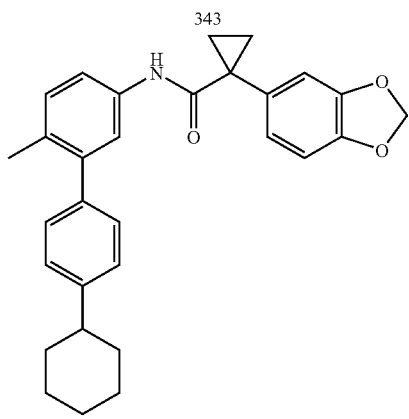
343

TABLE 1-continued
Examples of compounds of the present invention.
344
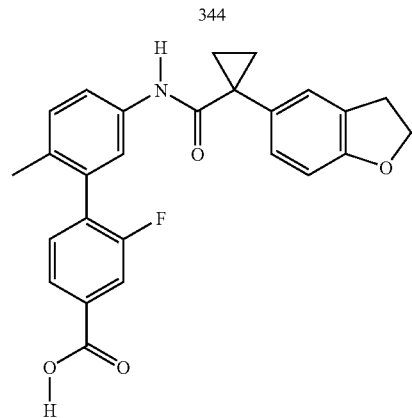
345
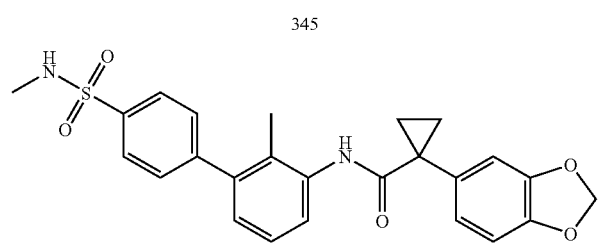
346
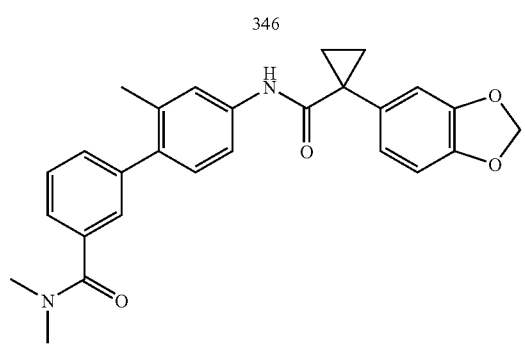
347
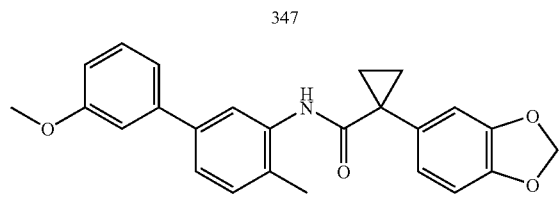

TABLE 1-continued
Examples of compounds of the present invention.
348
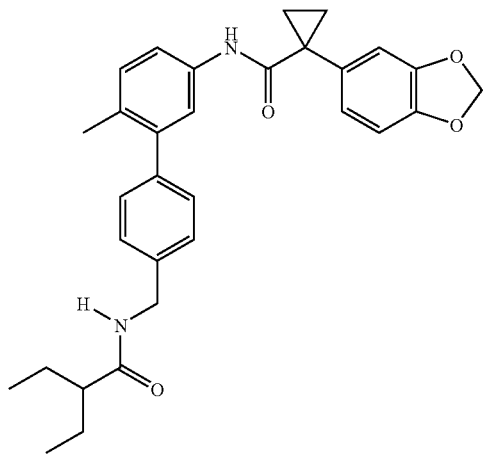
349
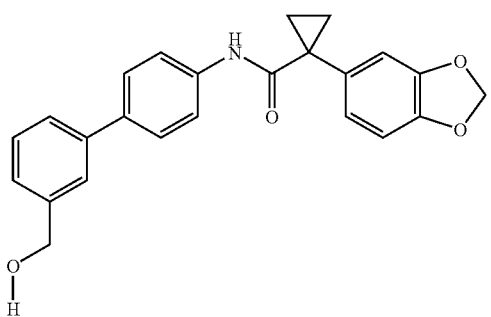
350
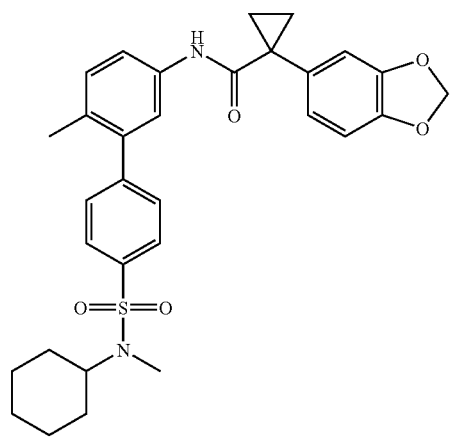

TABLE 1-continued
Examples of compounds of the present invention.
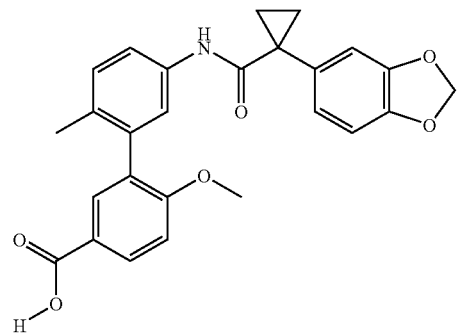
351
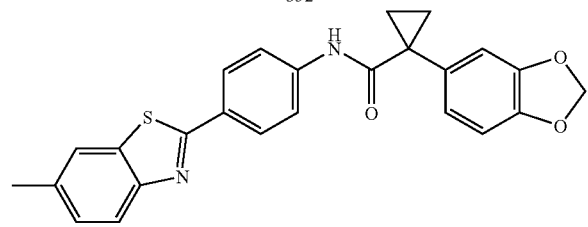
352
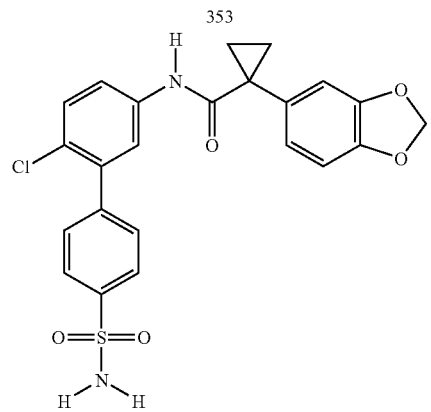
353
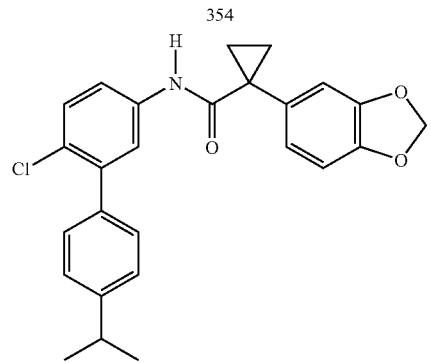
354

TABLE 1-continued
Examples of compounds of the present invention.
355
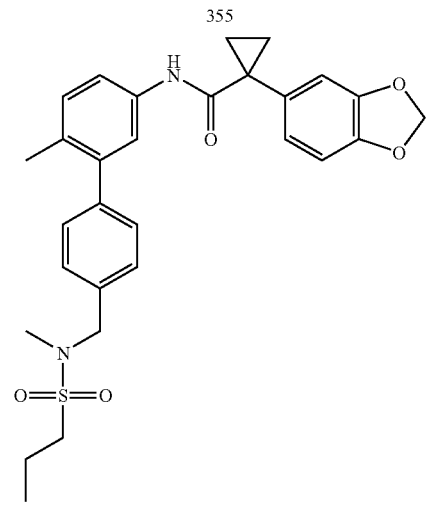
356
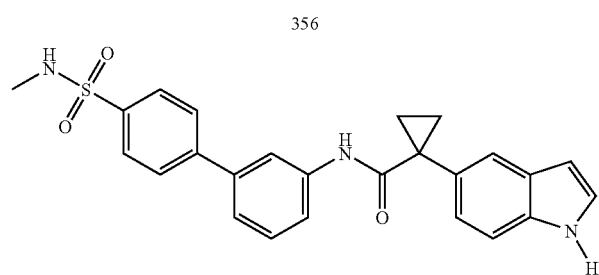
357
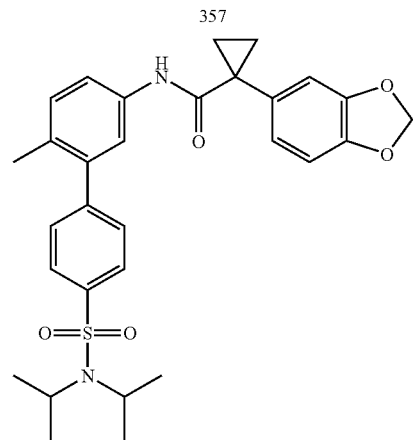

TABLE 1-continued
Examples of compounds of the present invention.
358
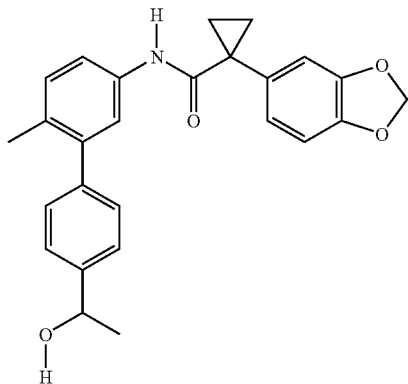
359
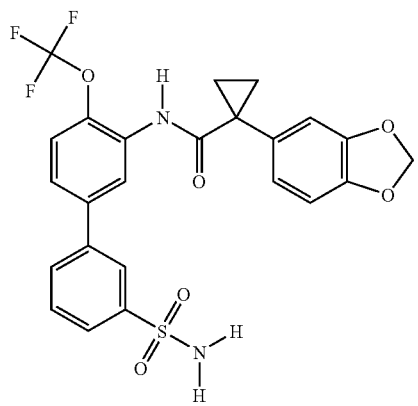
360
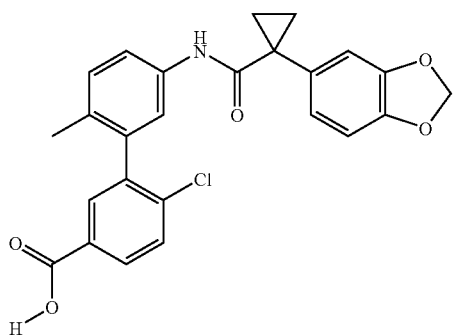
361
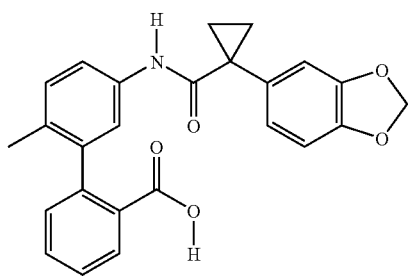

TABLE 1-continued
Examples of compounds of the present invention.
362
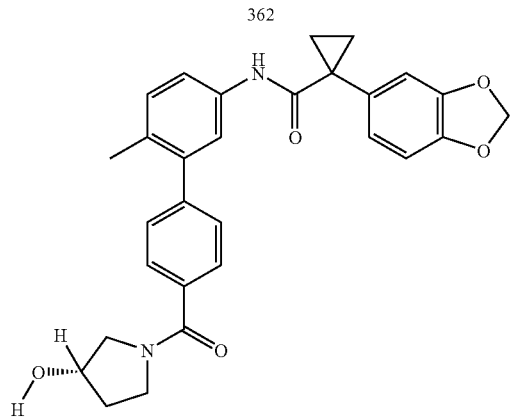
363
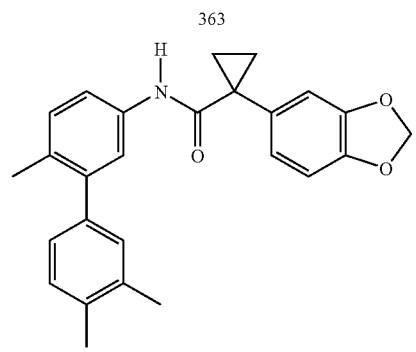
364
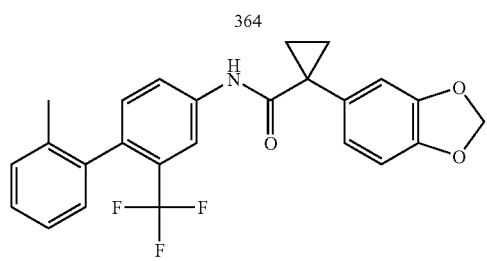
365
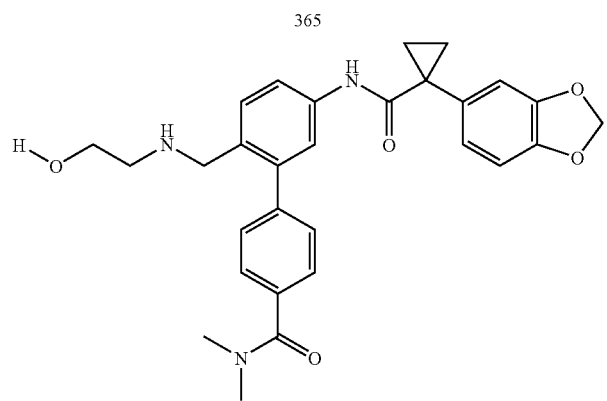

TABLE 1-continued
Examples of compounds of the present invention.
366
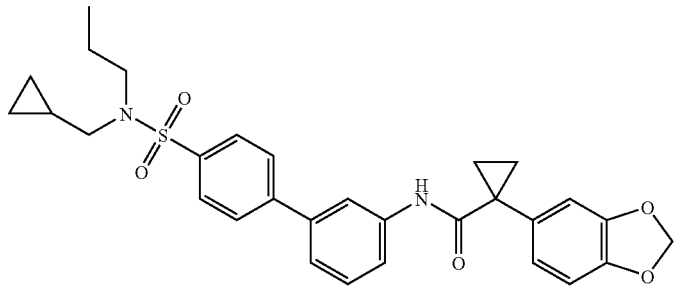
367
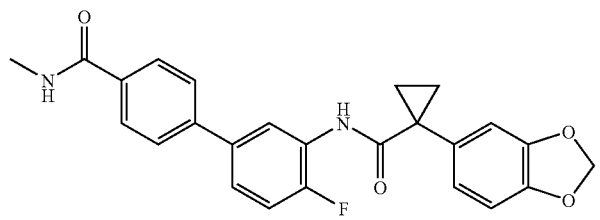
368
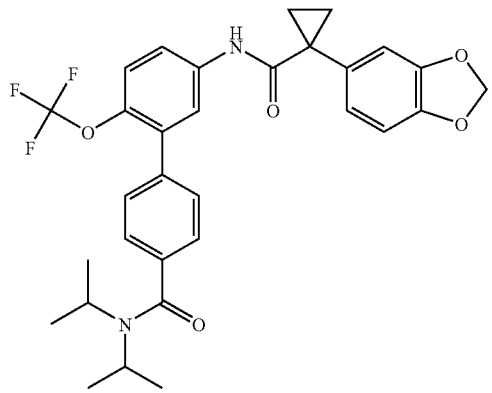
369
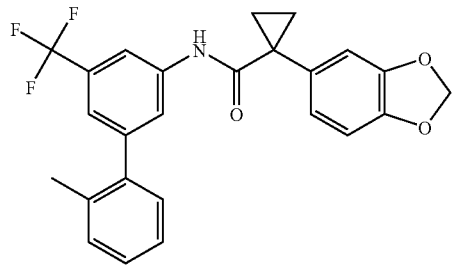

TABLE 1-continued
Examples of compounds of the present invention.
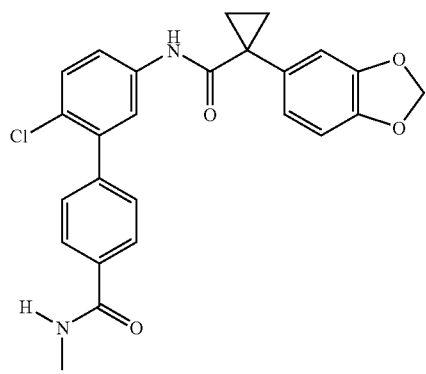
370
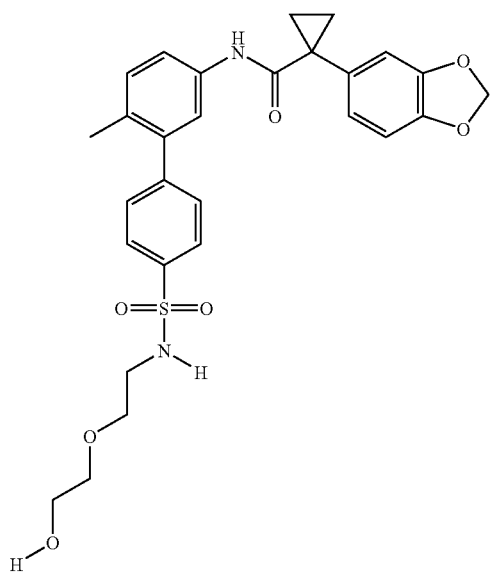
371
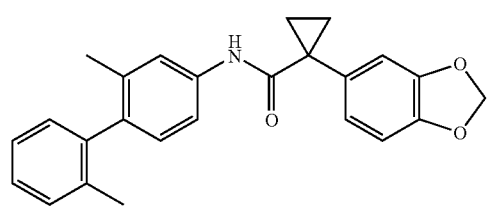
372

TABLE 1-continued
Examples of compounds of the present invention.
373
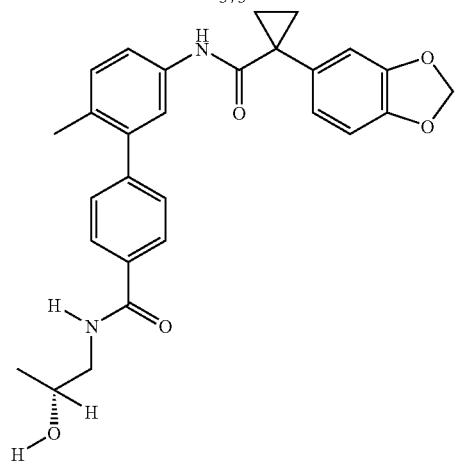
374
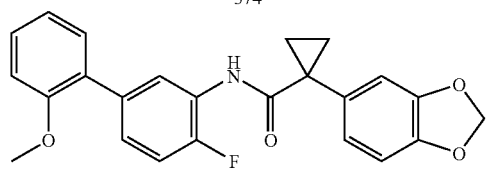
375
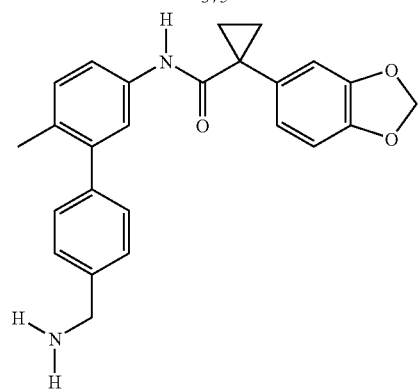
376
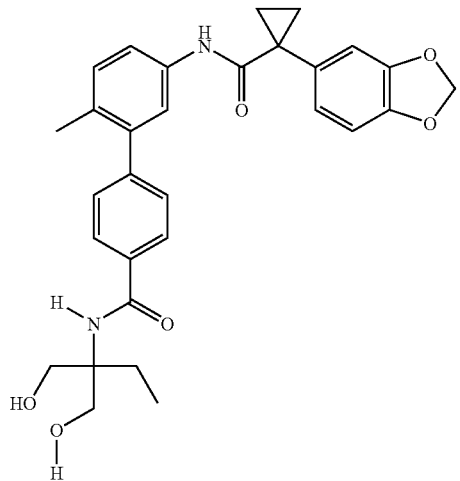

TABLE 1-continued
Examples of compounds of the present invention.
377
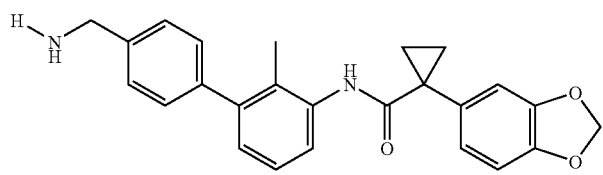
378
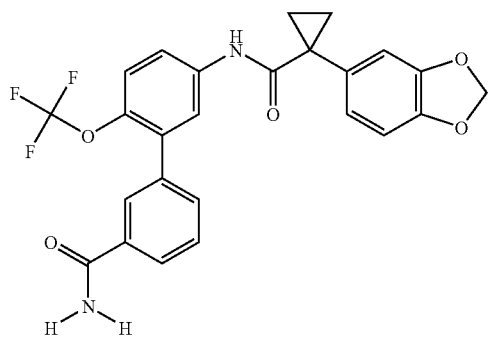
379
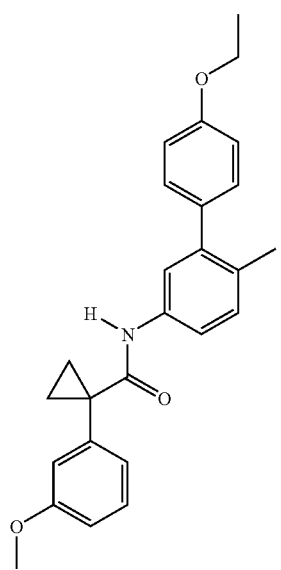

TABLE 1-continued
Examples of compounds of the present invention.
380
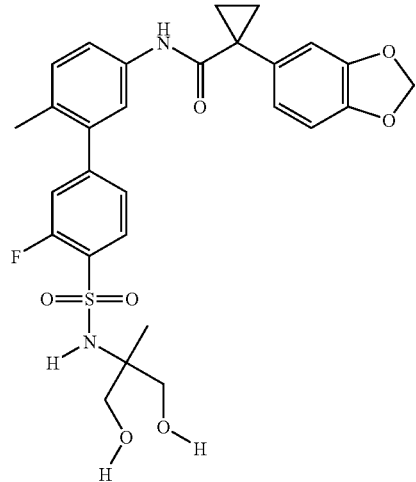
381
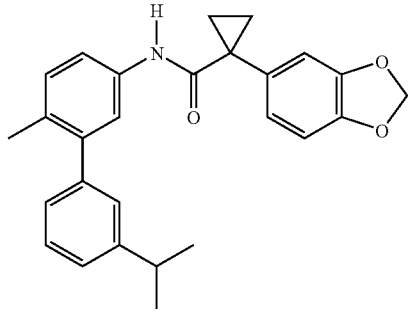
382
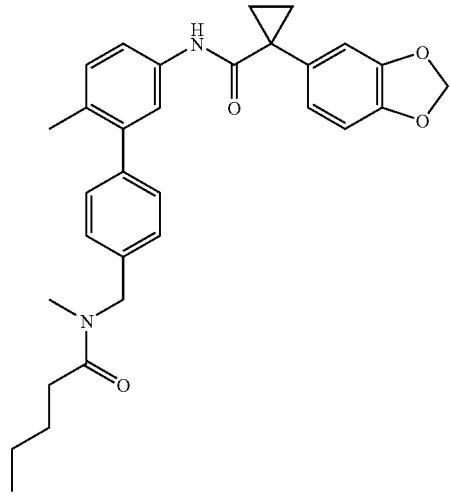

TABLE 1-continued
Examples of compounds of the present invention.
383
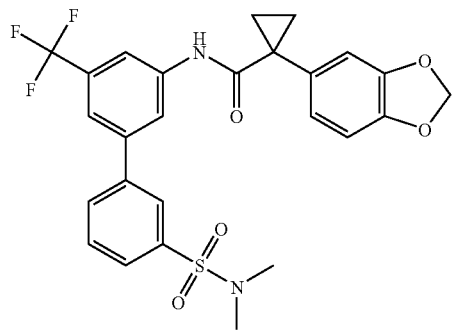
384
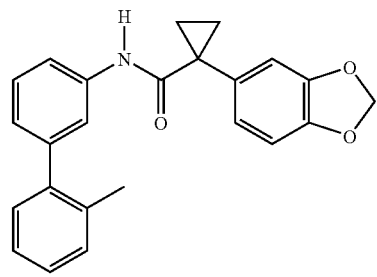
385
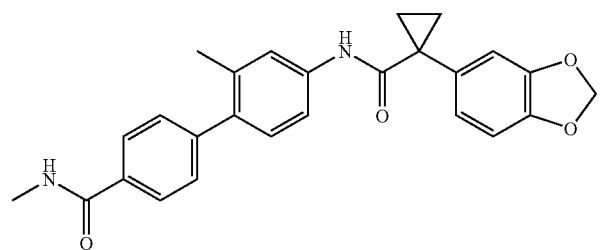
386
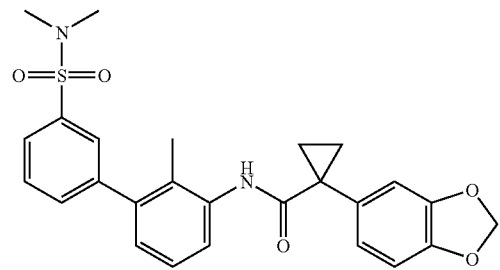

TABLE 1-continued
Examples of compounds of the present invention.
387
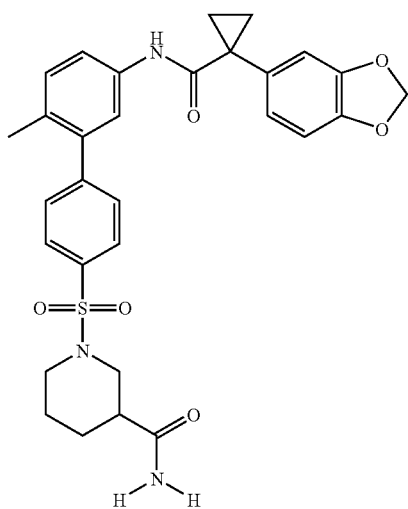
388
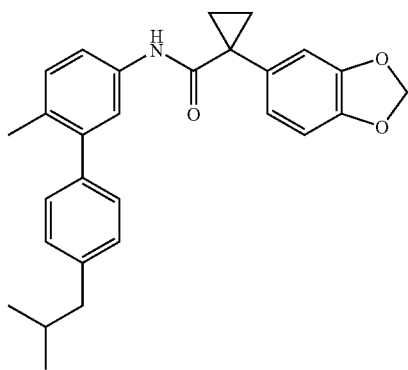
389
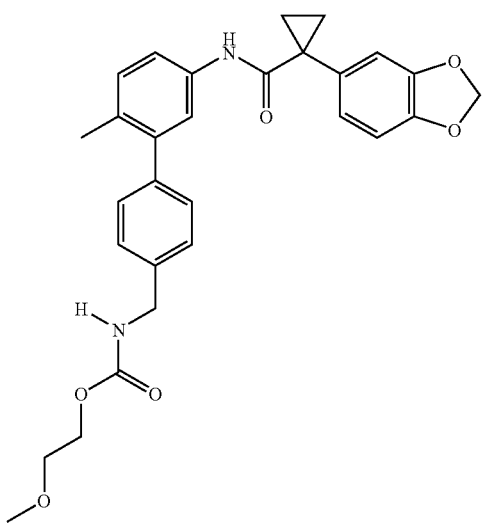

TABLE 1-continued
Examples of compounds of the present invention.
390
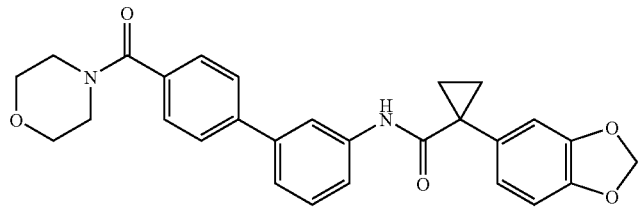
391
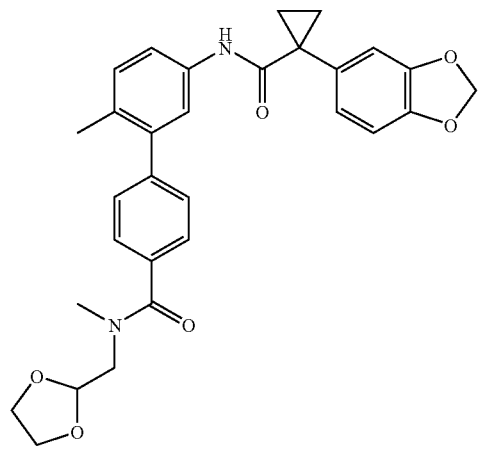
392
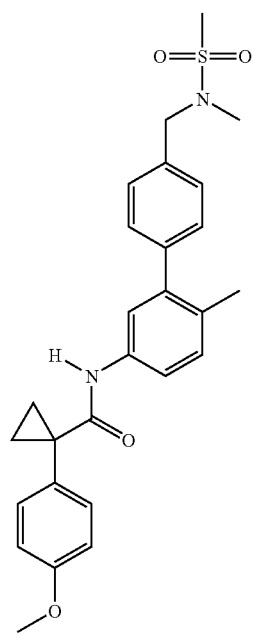

TABLE 1-continued
Examples of compounds of the present invention.
393
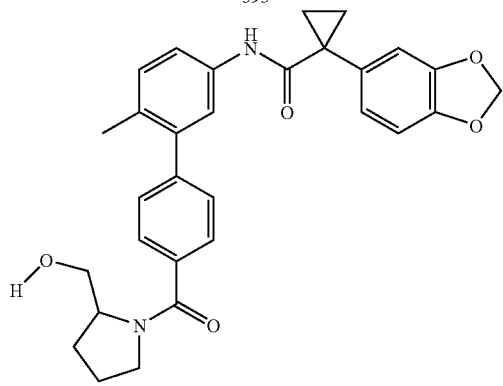
394
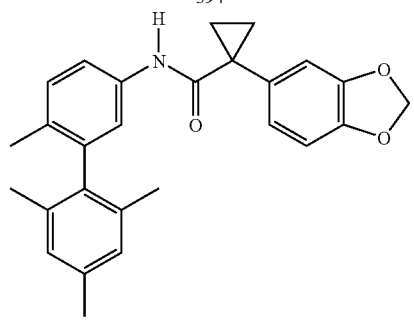
395
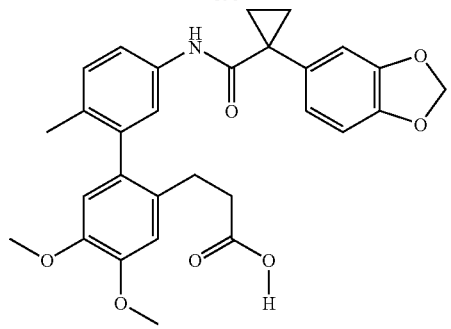
396
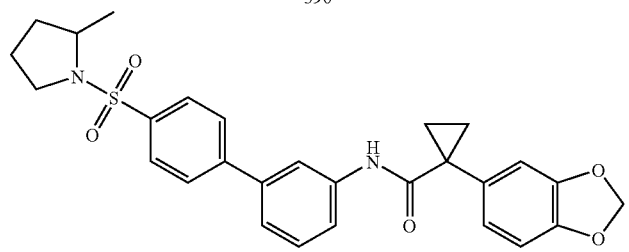
397
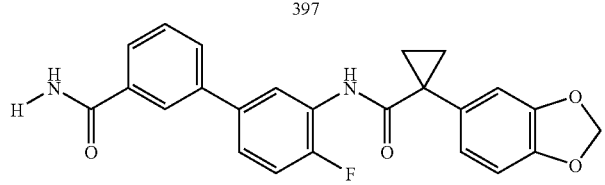

TABLE 1-continued
Examples of compounds of the present invention.
398
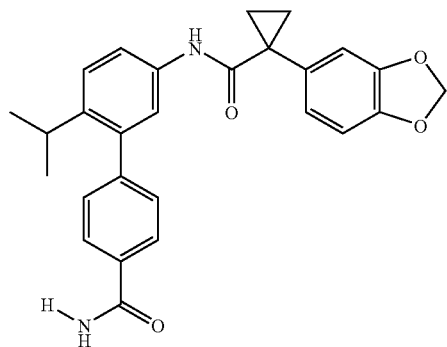
399
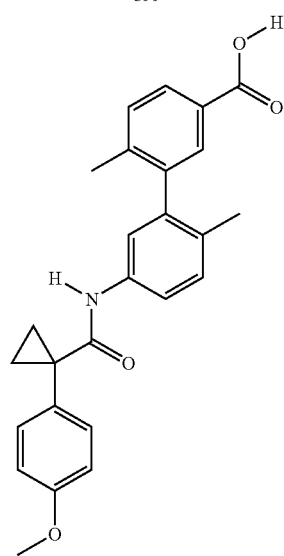
400
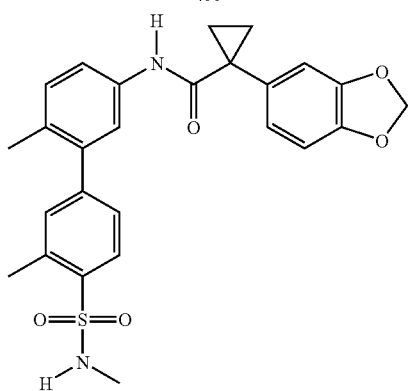

TABLE 1-continued
Examples of compounds of the present invention.
401
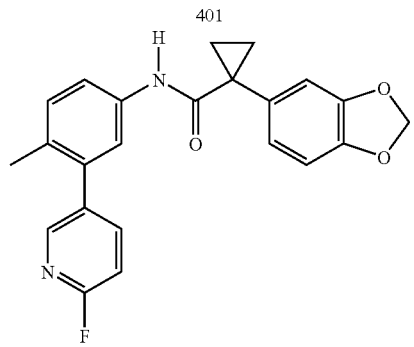
402
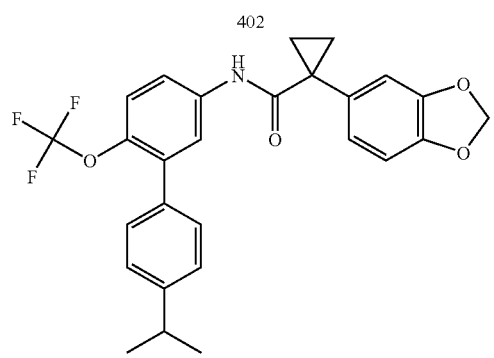
403
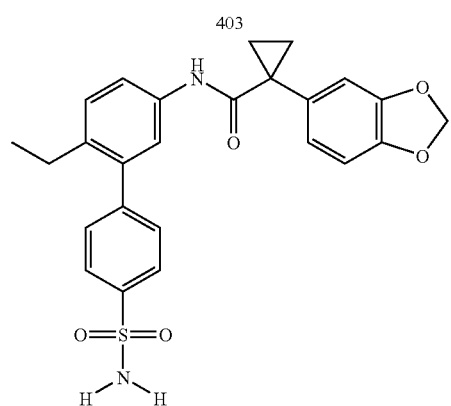
404
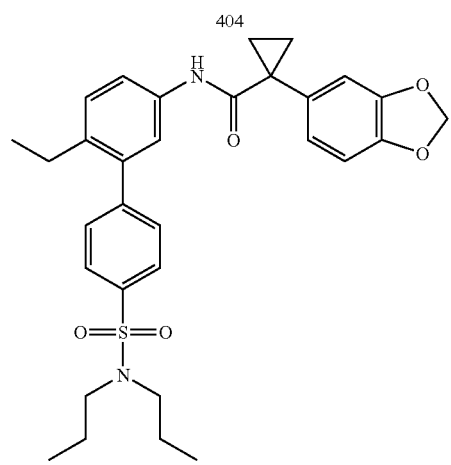

TABLE 1-continued
Examples of compounds of the present invention.
405
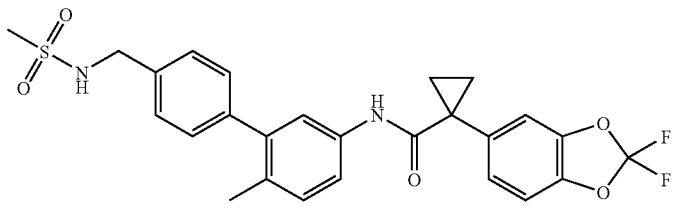
406
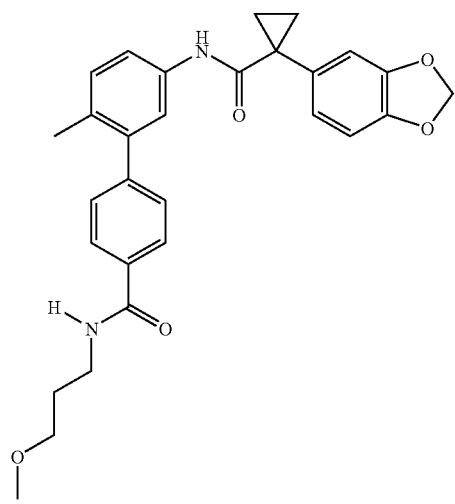
407
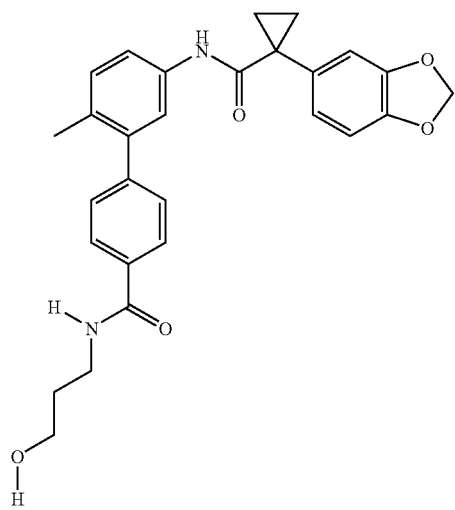

TABLE 1-continued
Examples of compounds of the present invention.
408
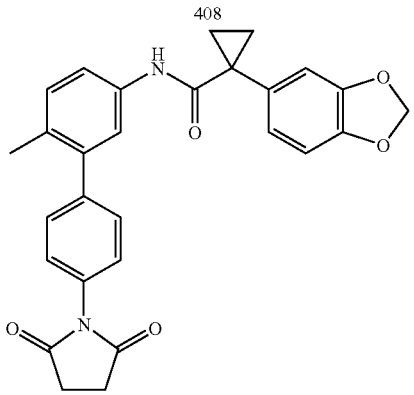
409
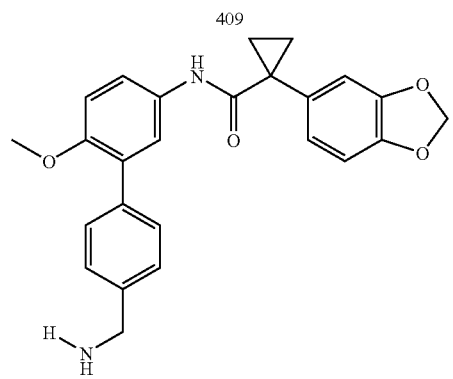
410
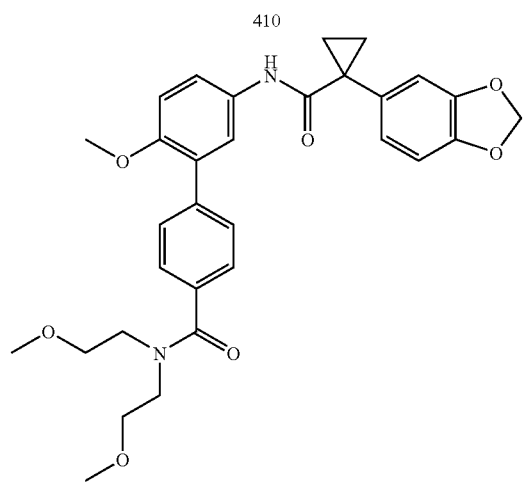

TABLE 1-continued
Examples of compounds of the present invention.
411
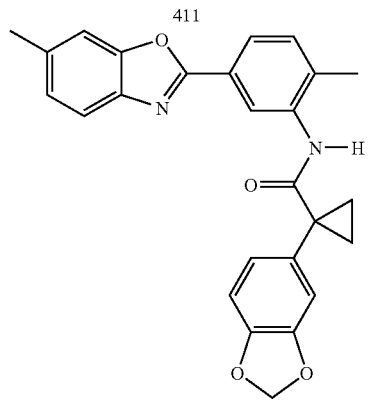
412
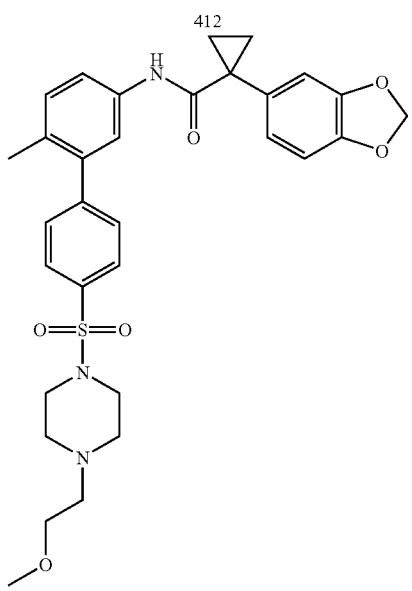
413
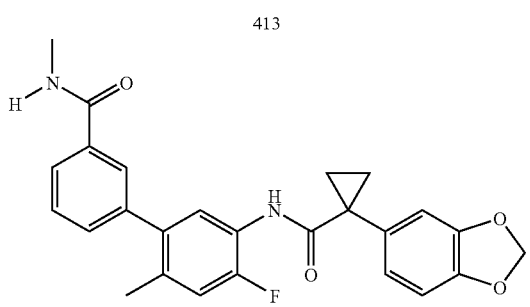
414
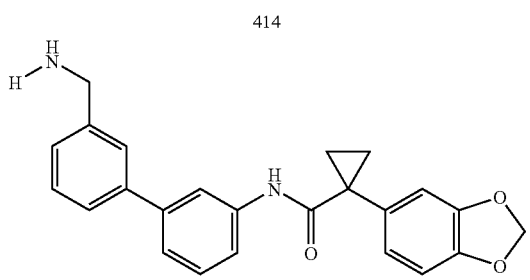

TABLE 1-continued
Examples of compounds of the present invention.
415
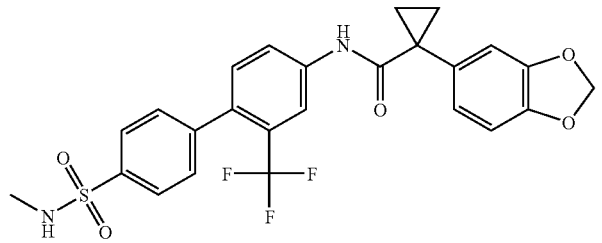
416
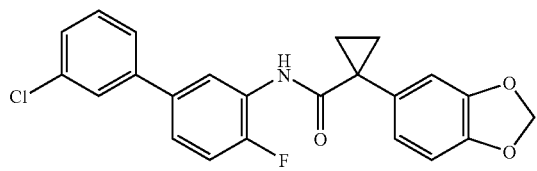
417
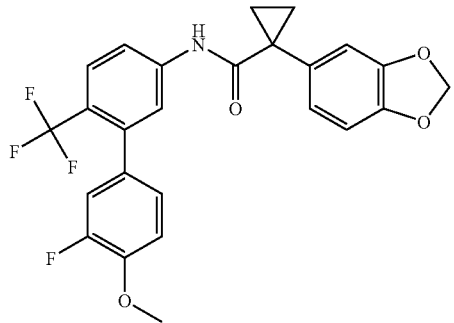
418
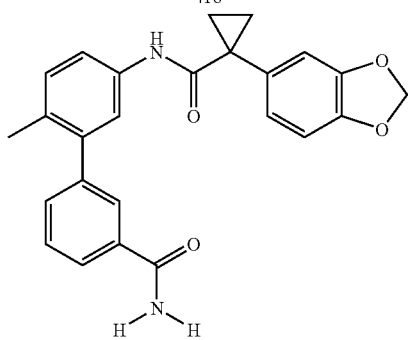
419
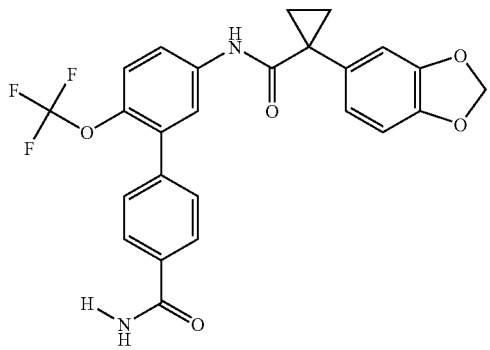

TABLE 1-continued
Examples of compounds of the present invention.
420
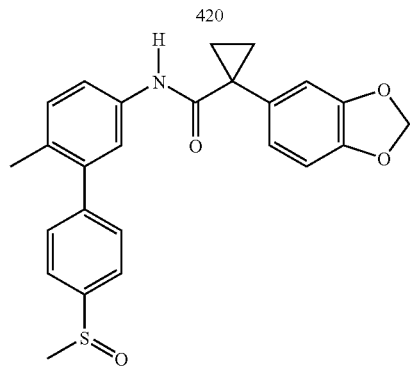
421
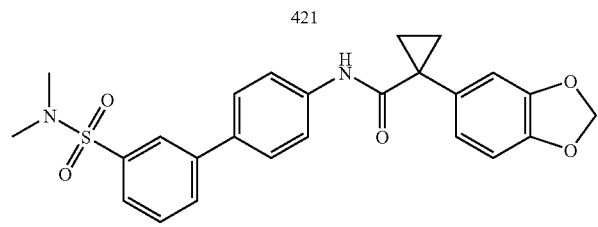
422
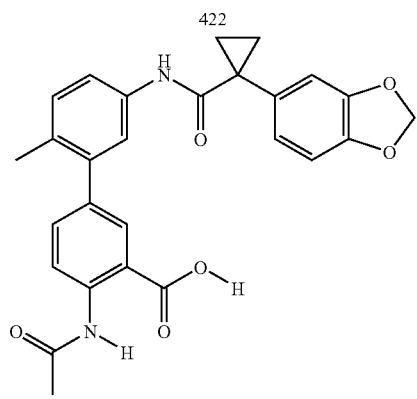
423
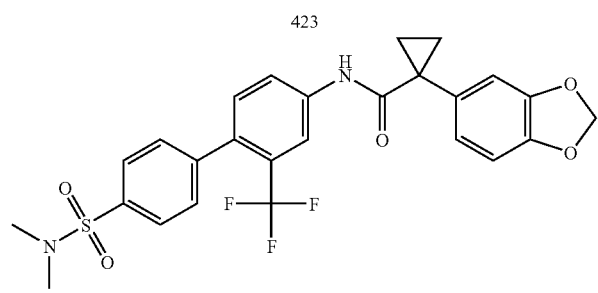

TABLE 1-continued
Examples of compounds of the present invention.
424
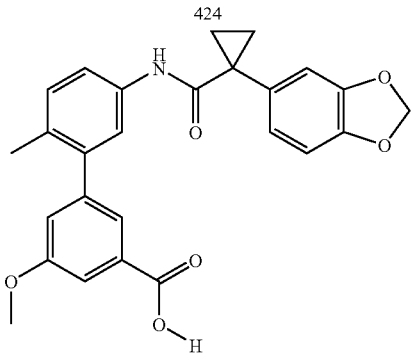
425
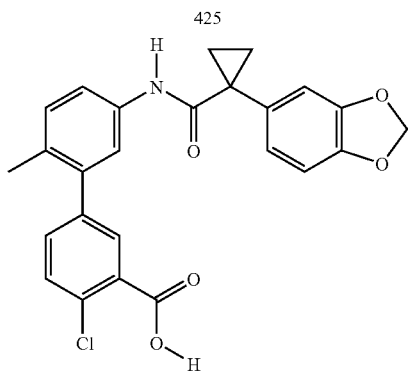
426
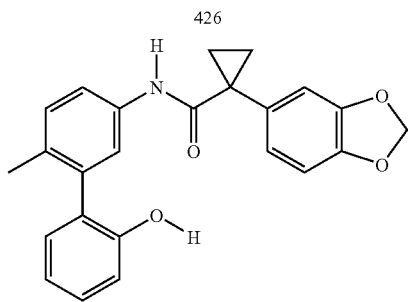
427
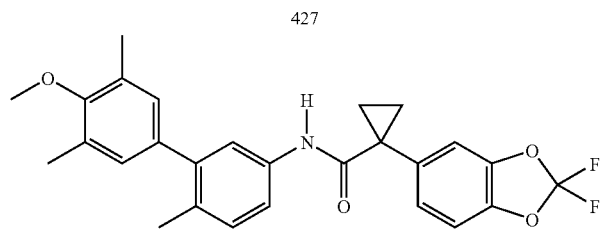

TABLE 1-continued
Examples of compounds of the present invention.
428
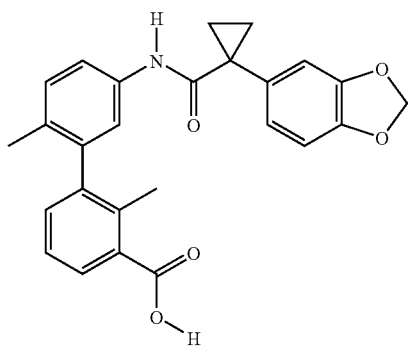
429
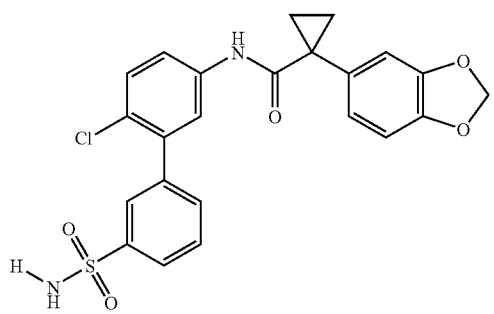
430
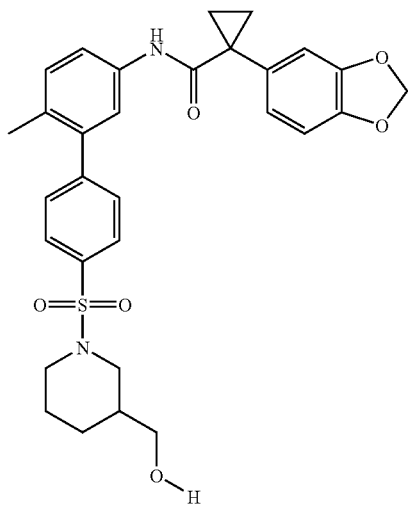

TABLE 1-continued
Examples of compounds of the present invention.
431
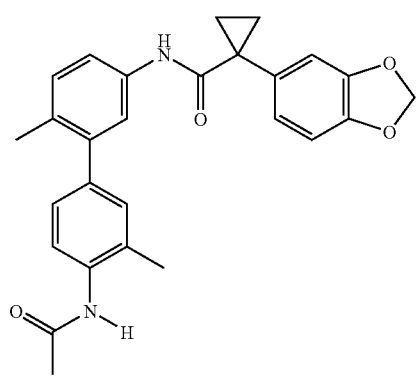
432
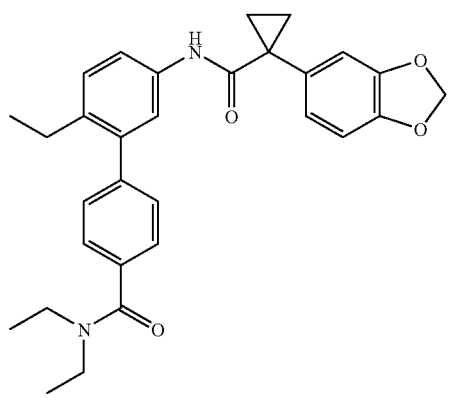
433
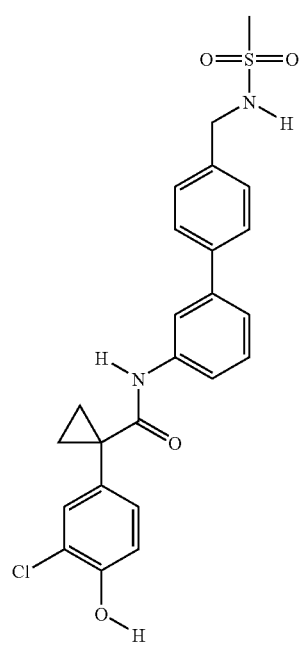

TABLE 1-continued
Examples of compounds of the present invention.
434
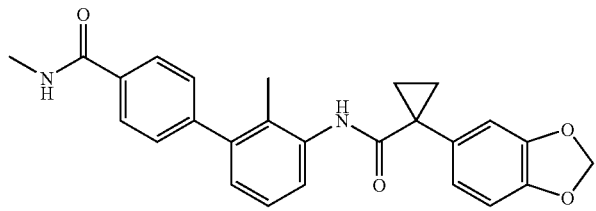
435
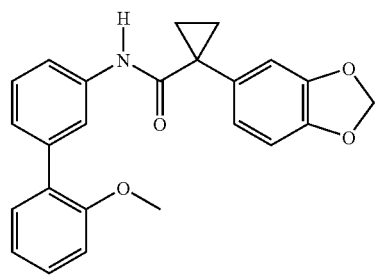
436
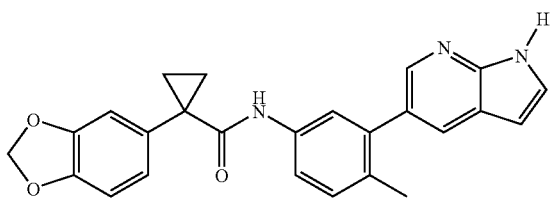
437
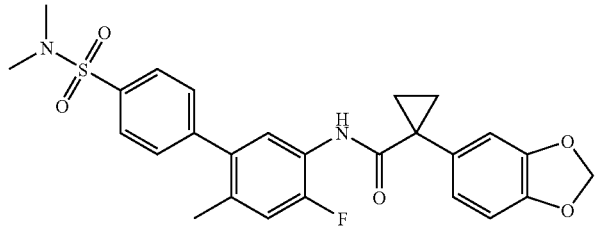
438
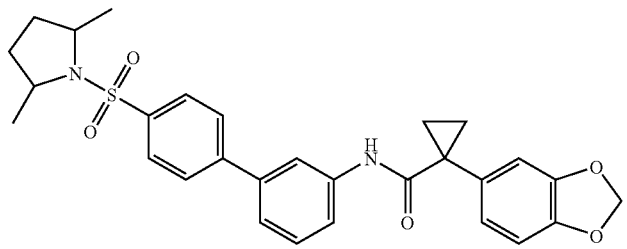

TABLE 1-continued
Examples of compounds of the present invention.
439
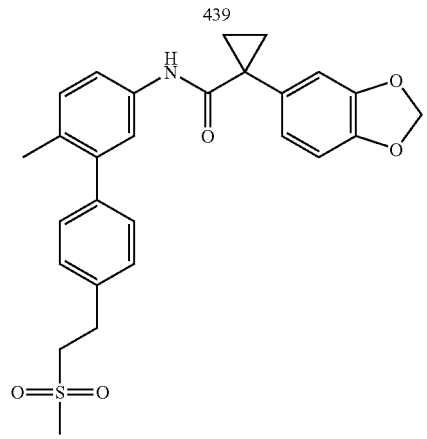
440
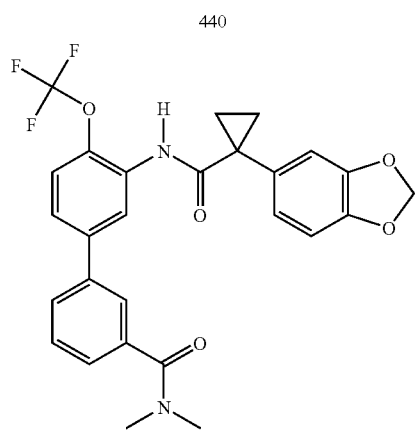
441
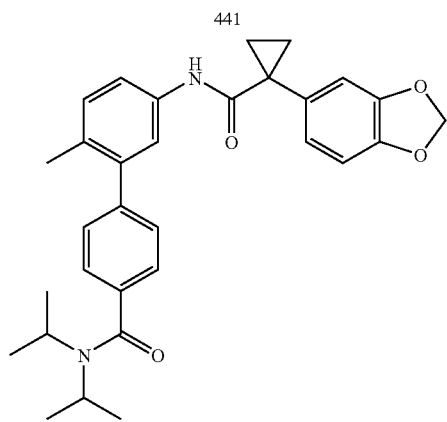

TABLE 1-continued
Examples of compounds of the present invention.
442
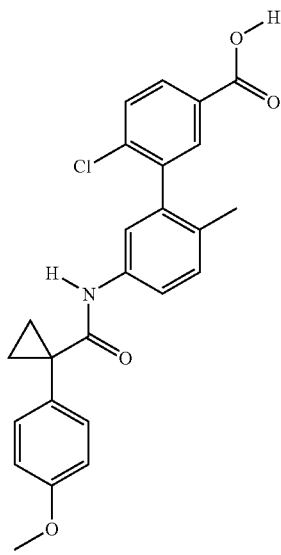
443
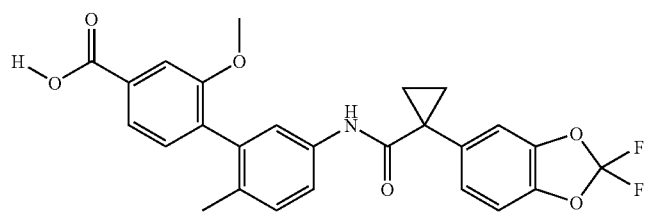
444
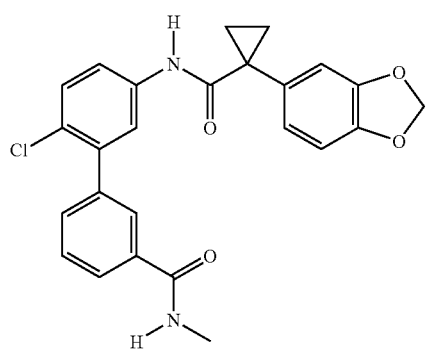
445
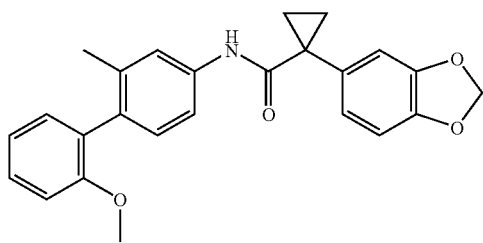

TABLE 1-continued
Examples of compounds of the present invention.
446
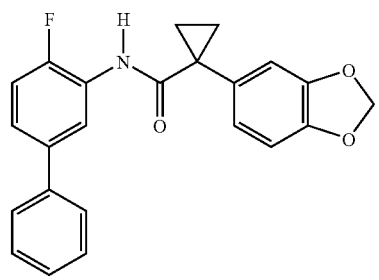
447
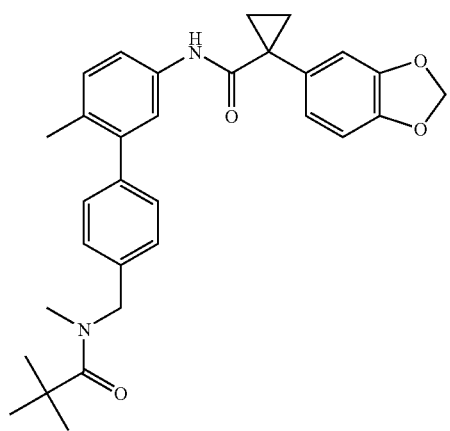
448
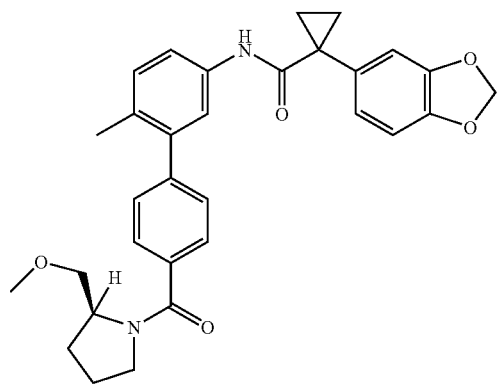

TABLE 1-continued
Examples of compounds of the present invention.
449
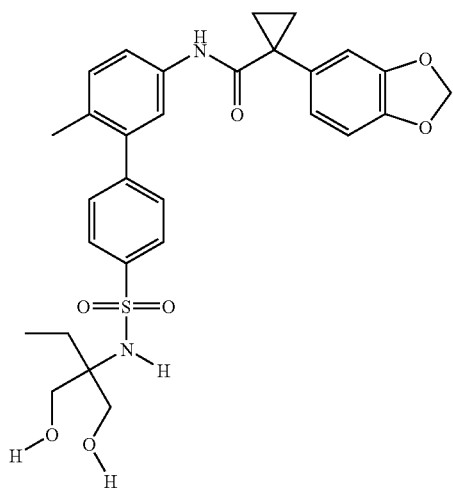
450
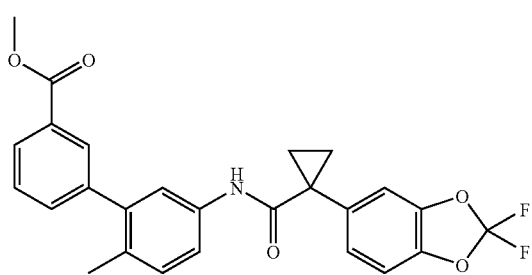
451
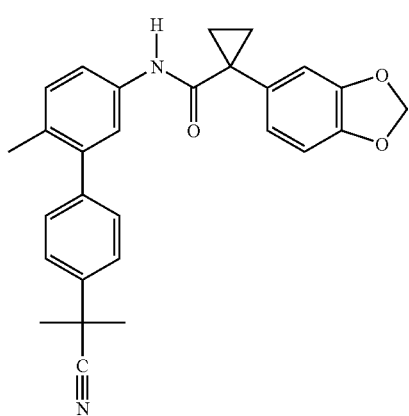

TABLE 1-continued
Examples of compounds of the present invention.
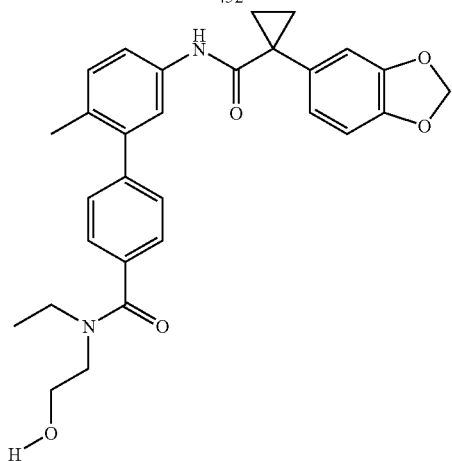
452
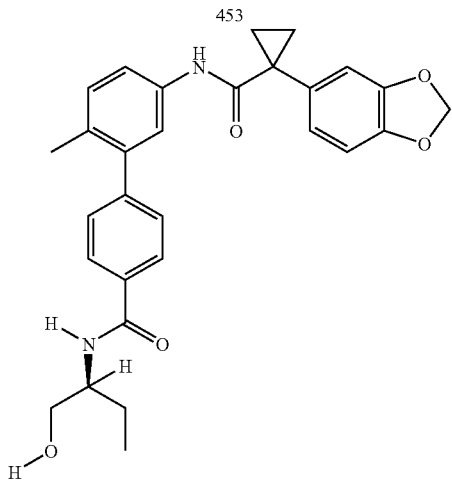
453
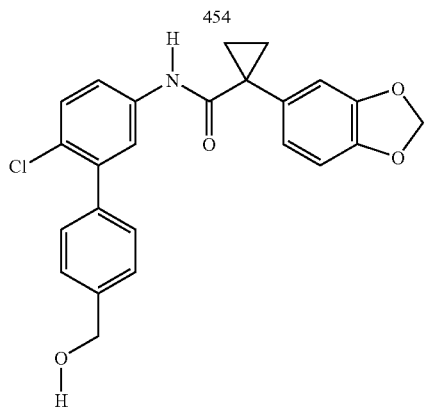
454

TABLE 1-continued
Examples of compounds of the present invention.
455
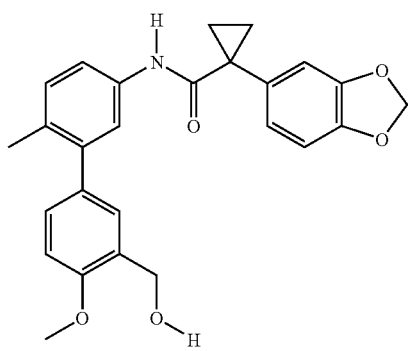
456
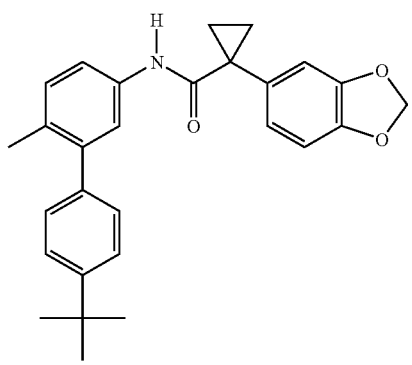
457
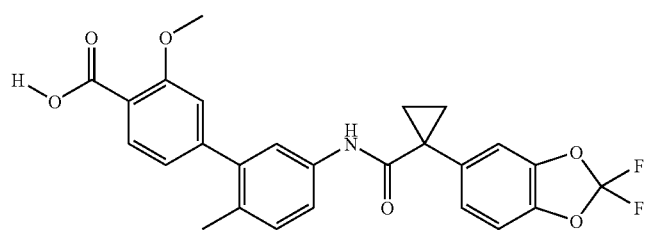
458
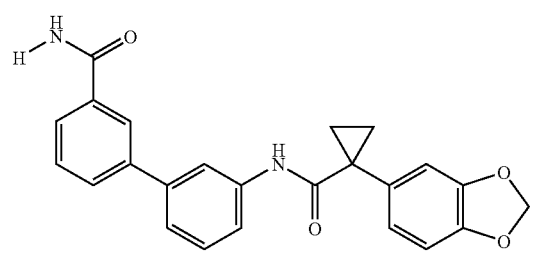

TABLE 1-continued
Examples of compounds of the present invention.
459
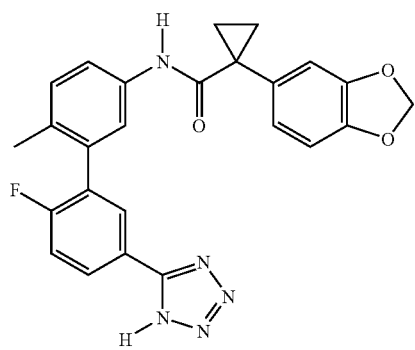
460
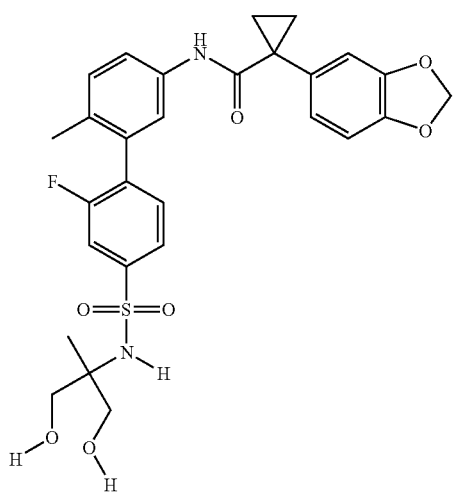
461
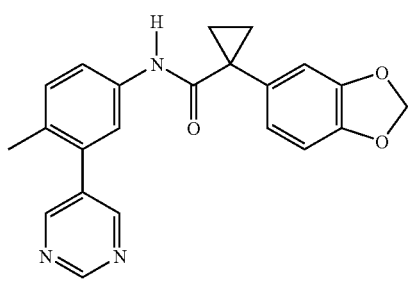
462
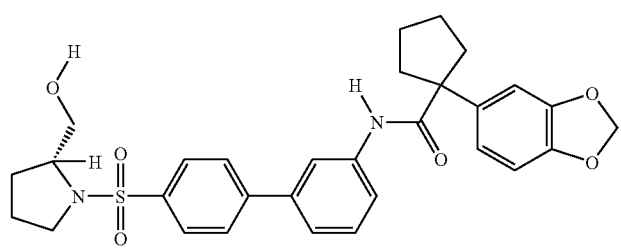

TABLE 1-continued
Examples of compounds of the present invention.
463
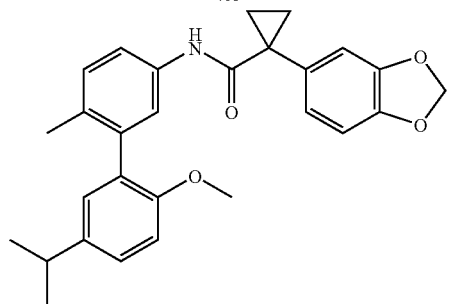
464
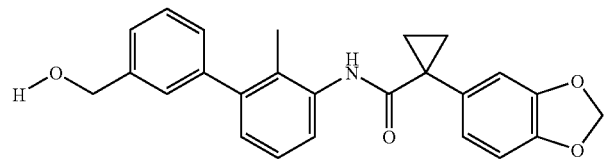
465
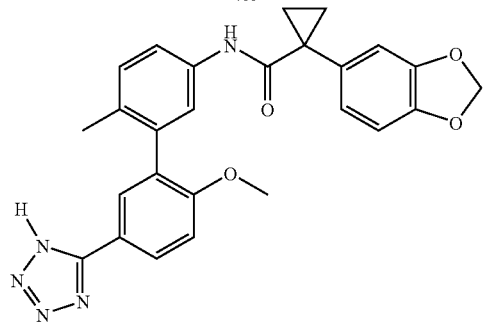
466
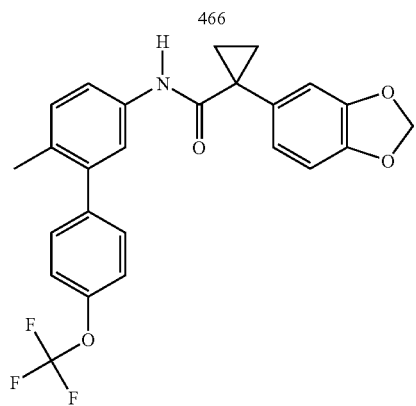

TABLE 1-continued
Examples of compounds of the present invention.
467
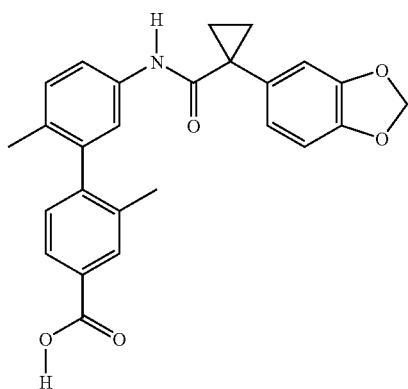
468
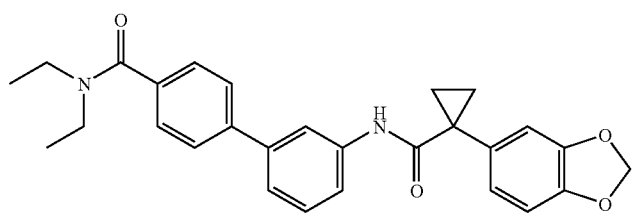
469
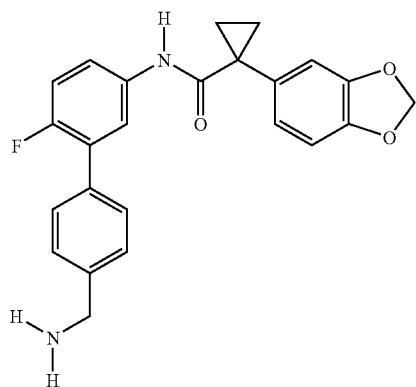
470
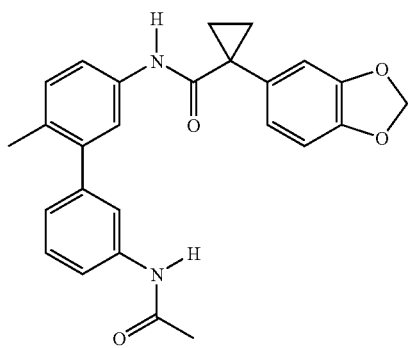

TABLE 1-continued
Examples of compounds of the present invention.
471
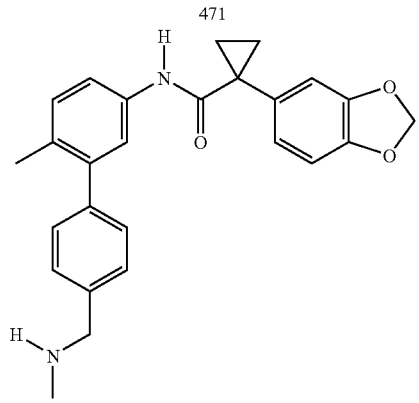
472
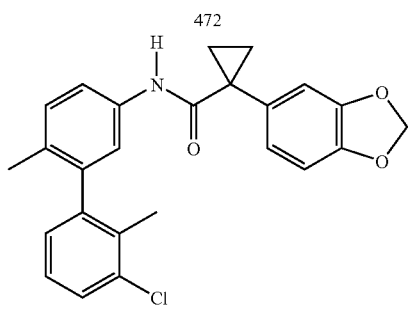
473
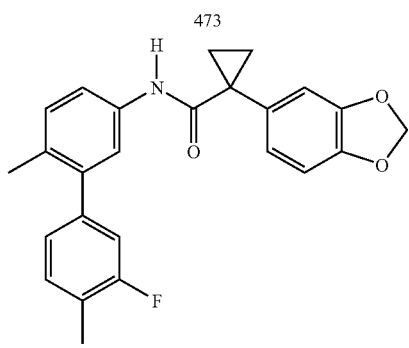
474
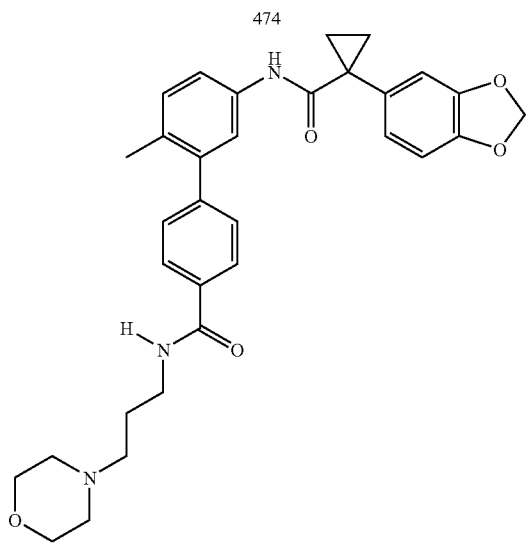

TABLE 1-continued
Examples of compounds of the present invention.
475
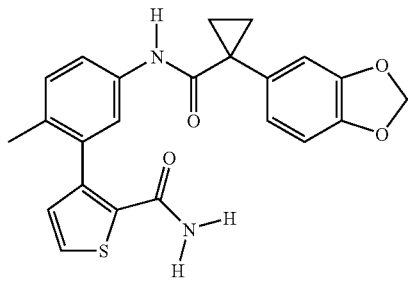
476
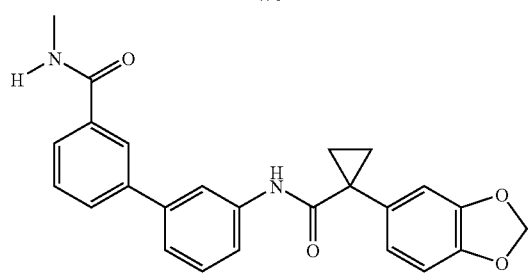
477
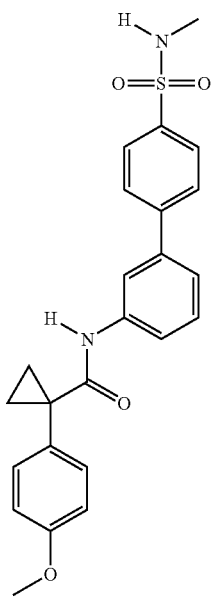
478
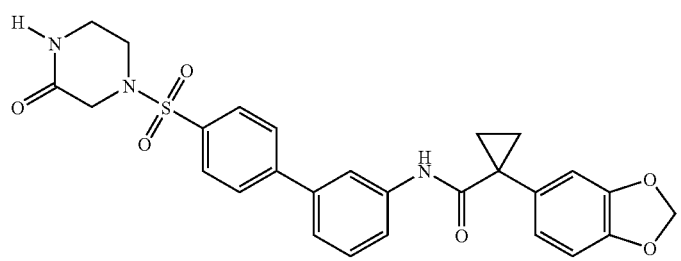

TABLE 1-continued
Examples of compounds of the present invention.
479
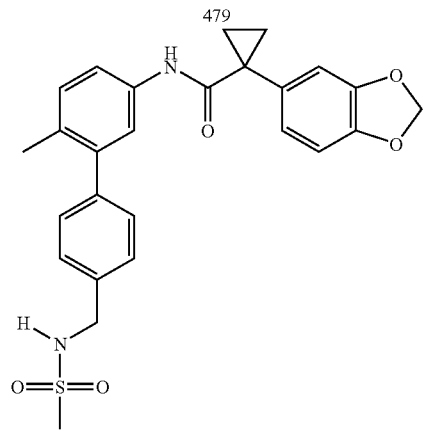
480
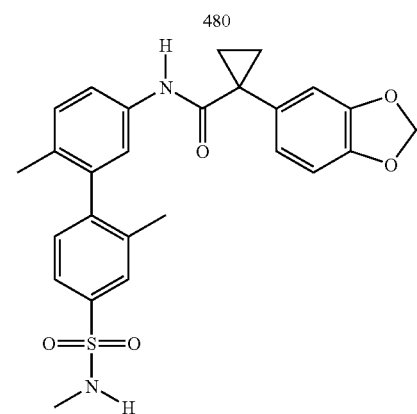
481
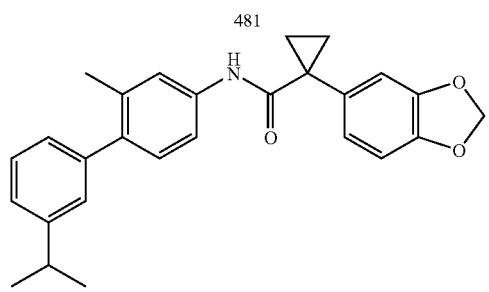
482
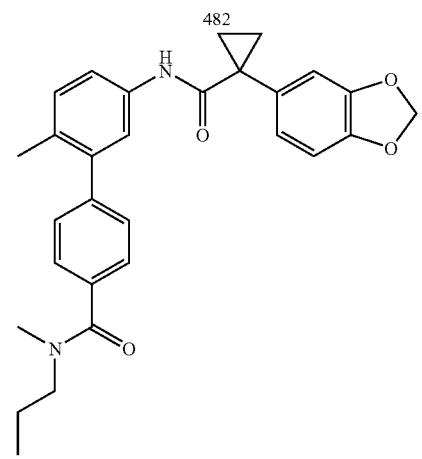

TABLE 1-continued
Examples of compounds of the present invention.
483
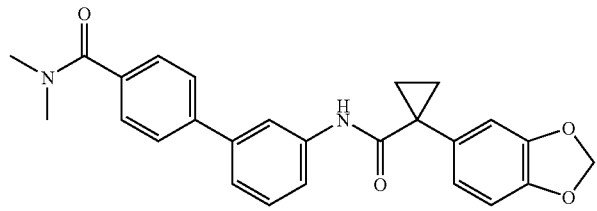
484
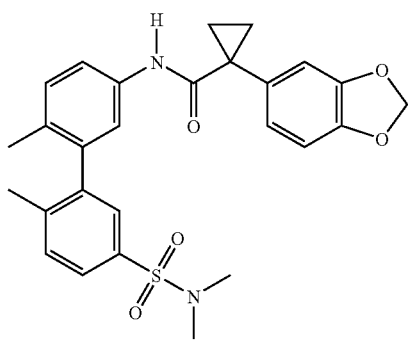
485
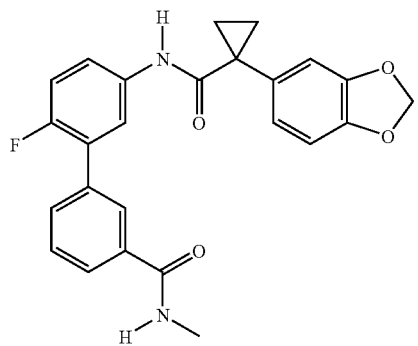
486
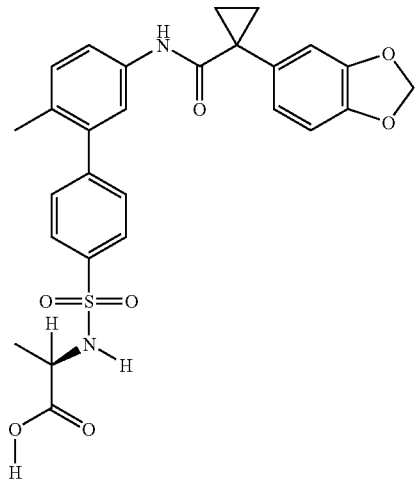

TABLE 1-continued
Examples of compounds of the present invention.
487
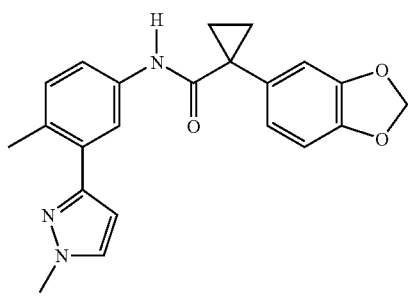
488
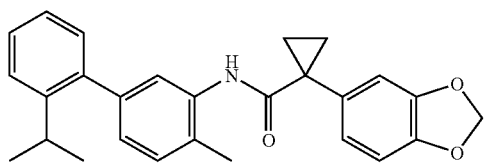
489
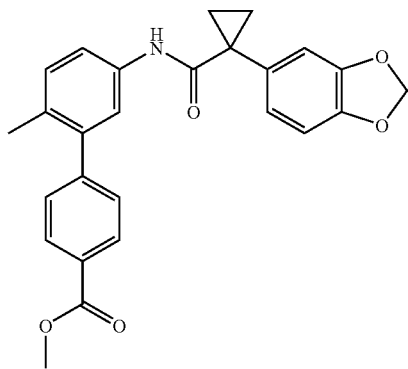
490
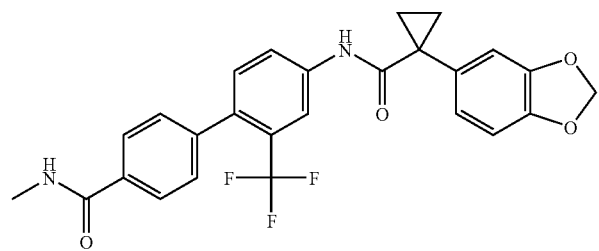

TABLE 1-continued
Examples of compounds of the present invention.
491
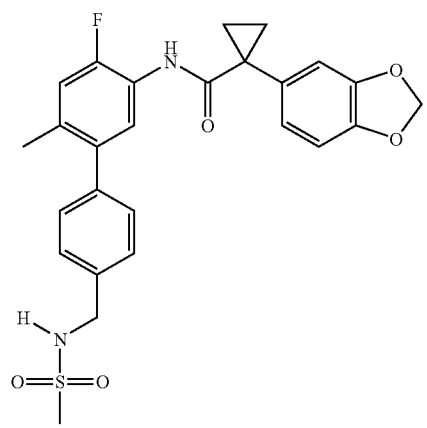
492
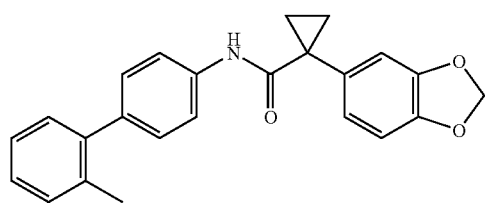
493
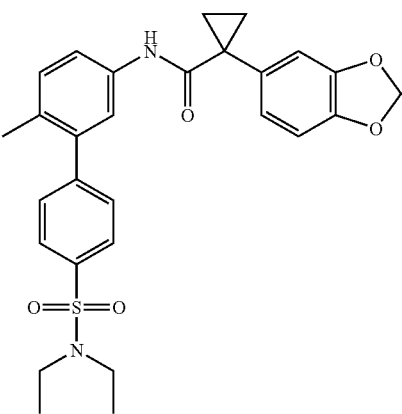

TABLE 1-continued
Examples of compounds of the present invention.
494
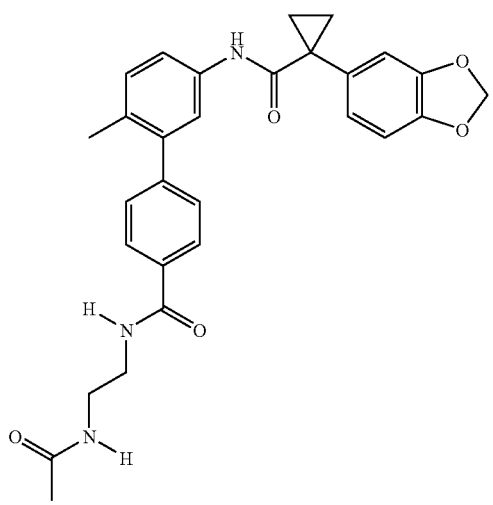
495
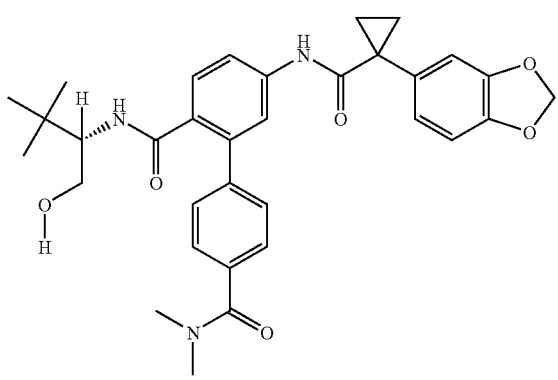
496
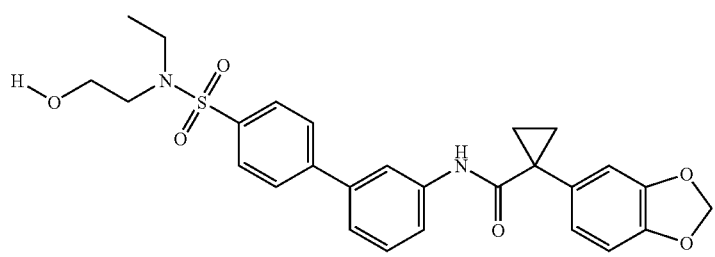

TABLE 1-continued
Examples of compounds of the present invention.
497
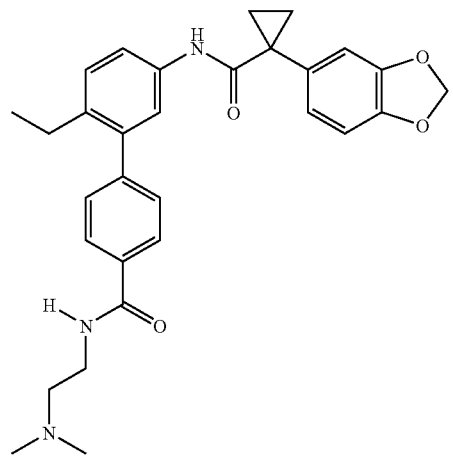
498
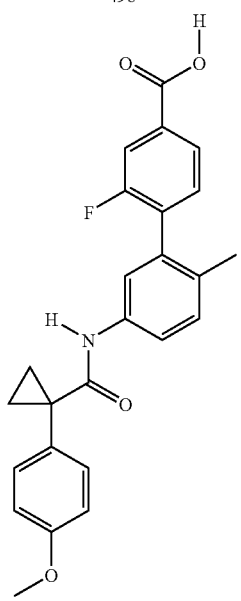
499
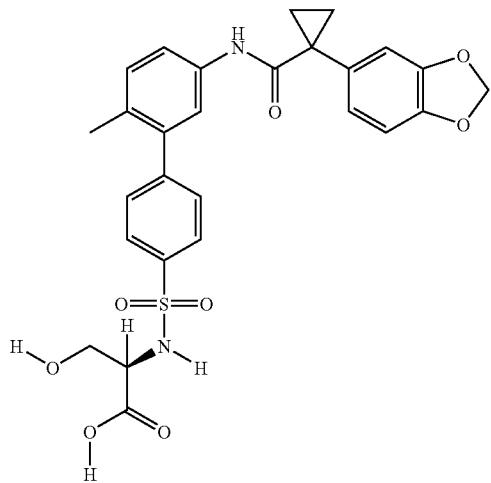

TABLE 1-continued
Examples of compounds of the present invention.
500
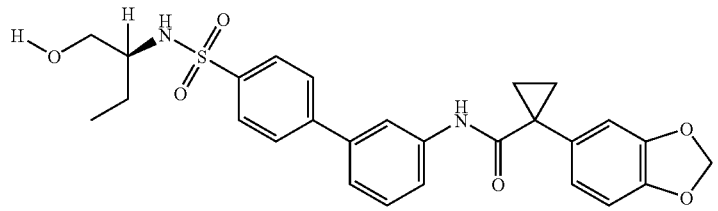
501
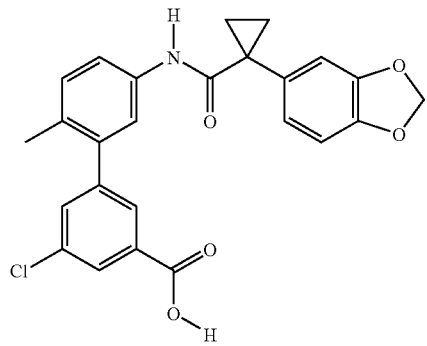
502
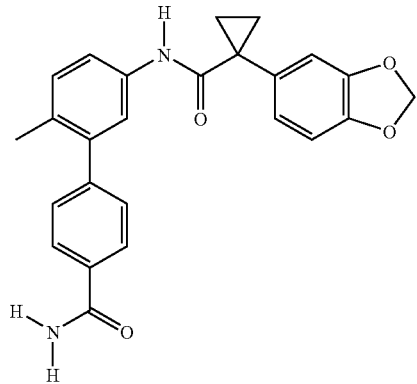
503
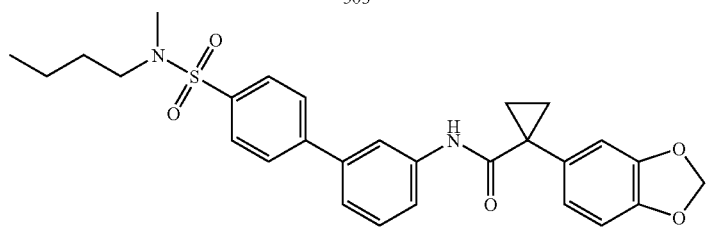

TABLE 1-continued
Examples of compounds of the present invention.
504
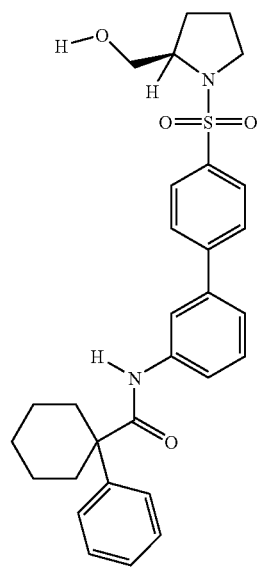
505
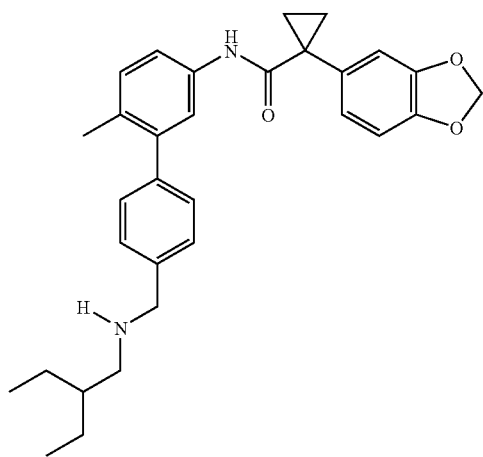
506
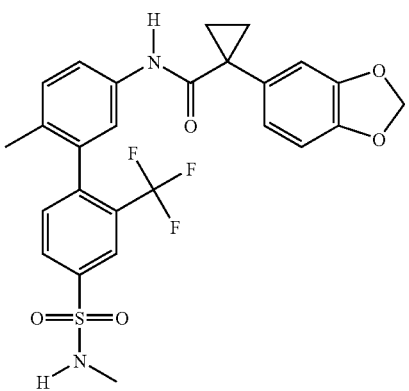

TABLE 1-continued
Examples of compounds of the present invention.
507
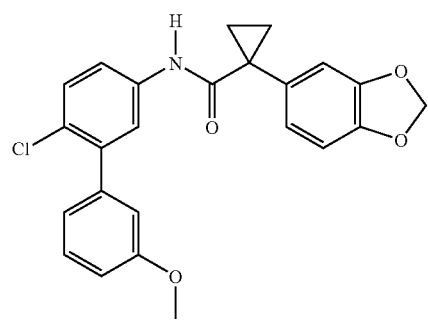
508
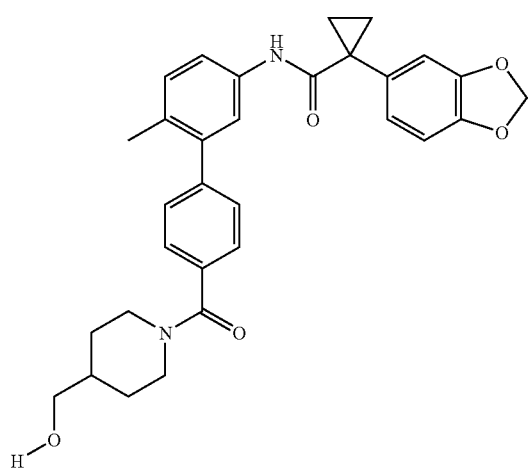
509
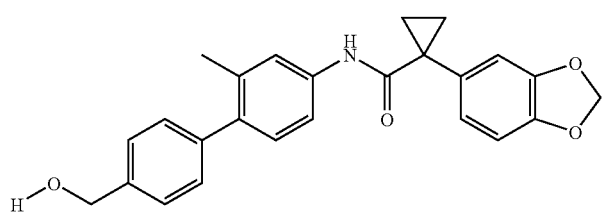
510
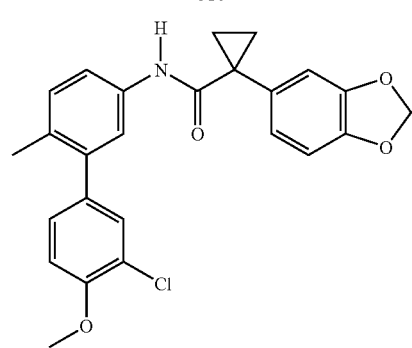

TABLE 1-continued
Examples of compounds of the present invention.
511
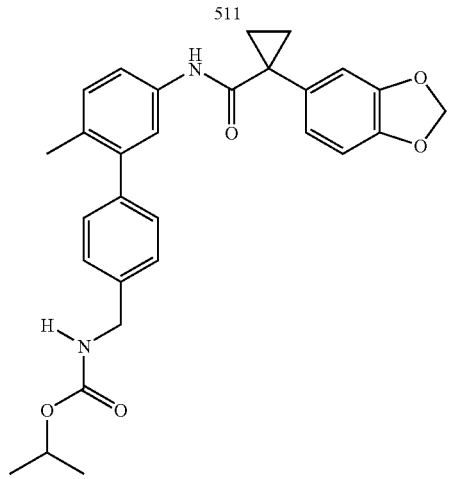
512
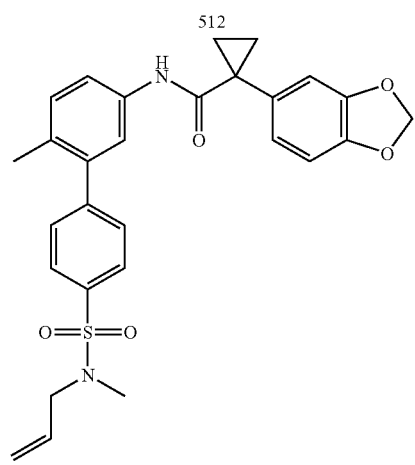
513
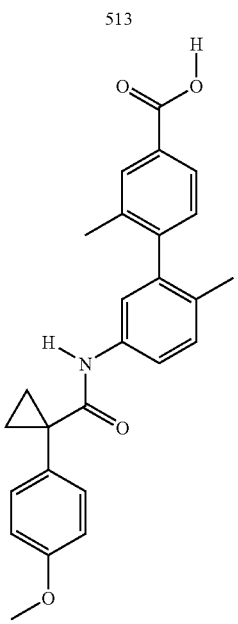

TABLE 1-continued
Examples of compounds of the present invention.
514
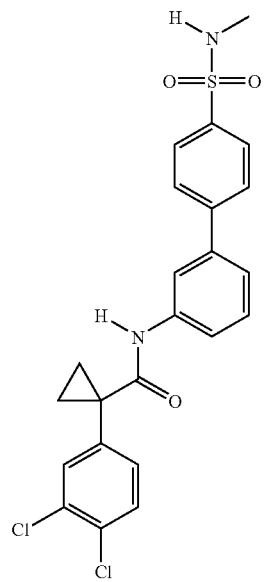
515
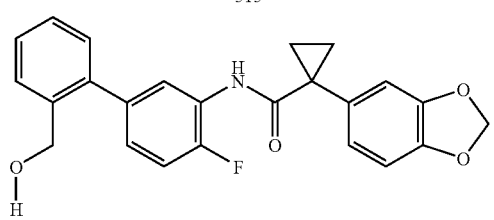
516
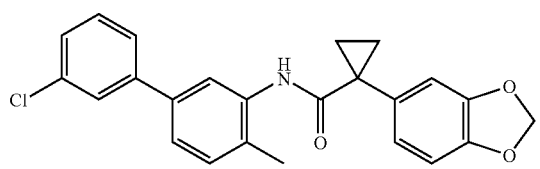
517
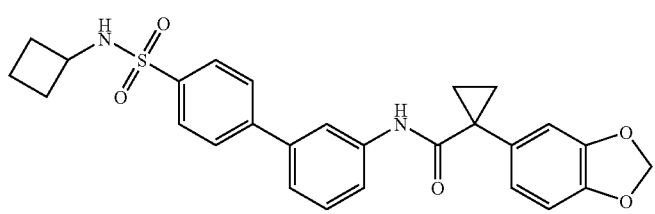

TABLE 1-continued
Examples of compounds of the present invention.
518
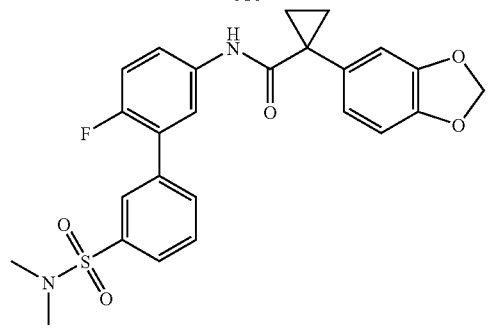
519
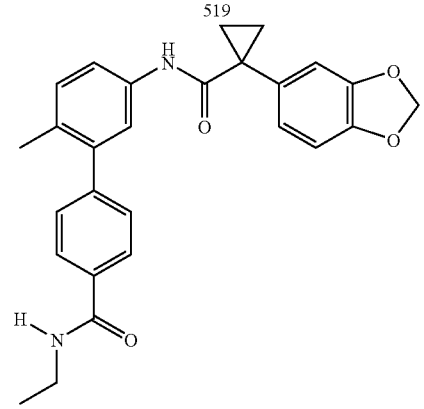
520
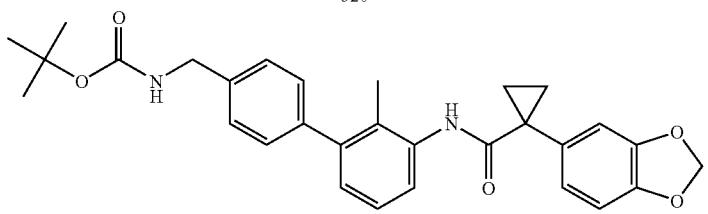
521
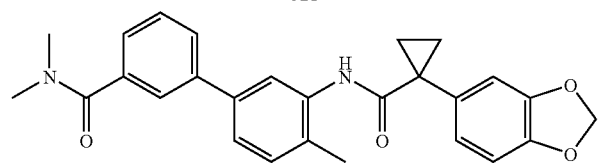
522
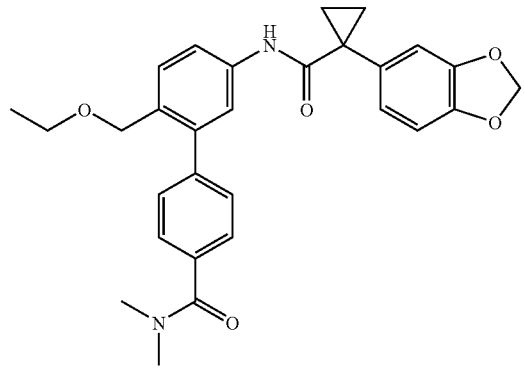

TABLE 1-continued
Examples of compounds of the present invention.
523
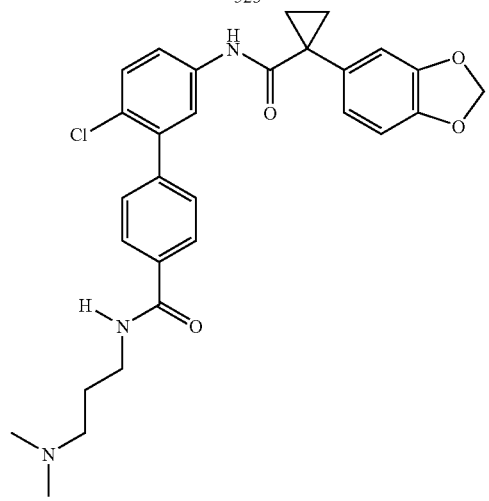
524
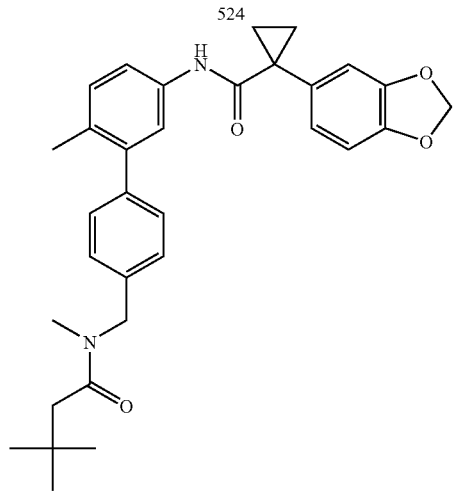
525
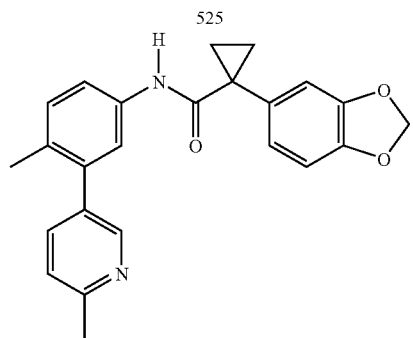

TABLE 1-continued
Examples of compounds of the present invention.
526
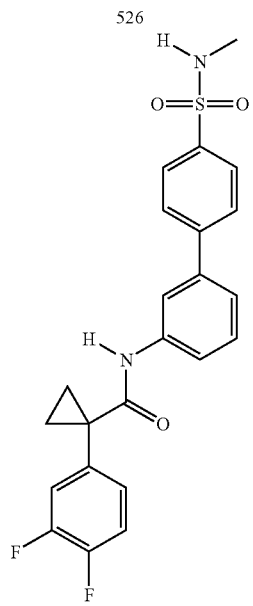
527
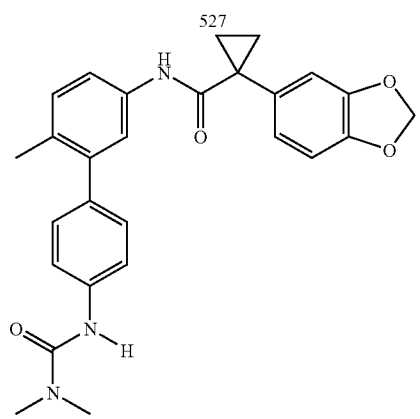
528
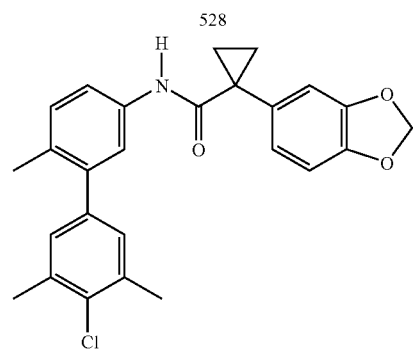

TABLE 1-continued
Examples of compounds of the present invention.
529
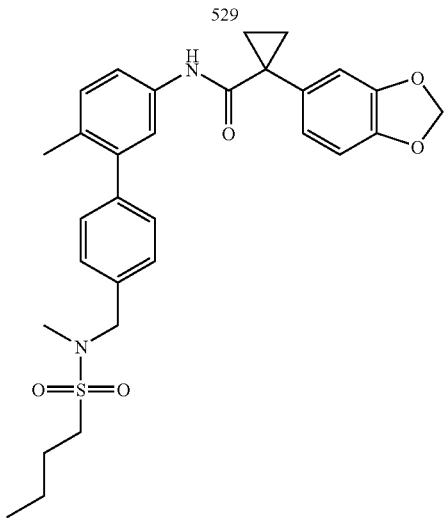
530
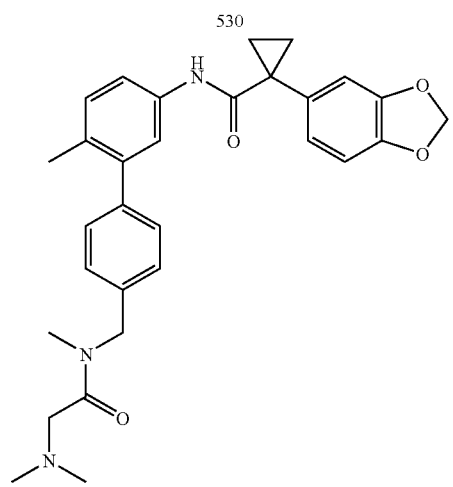
531
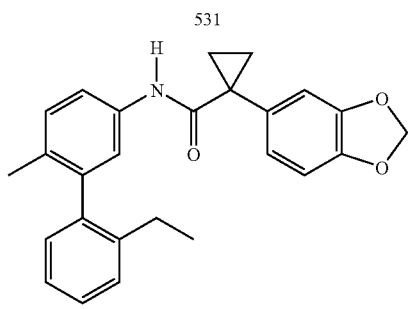

TABLE 1-continued
Examples of compounds of the present invention.
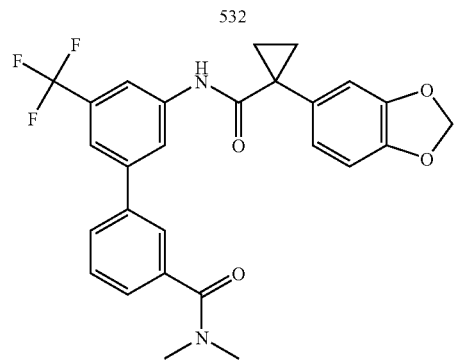
532
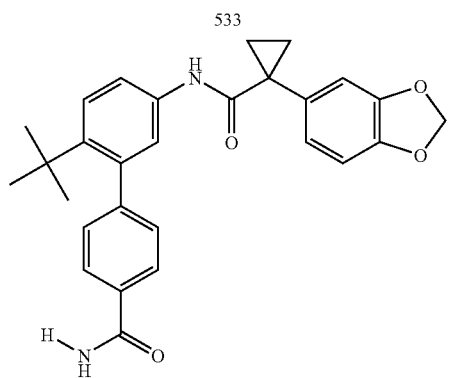
533
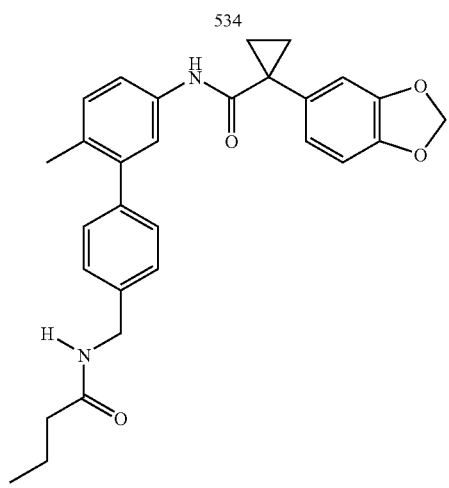
534
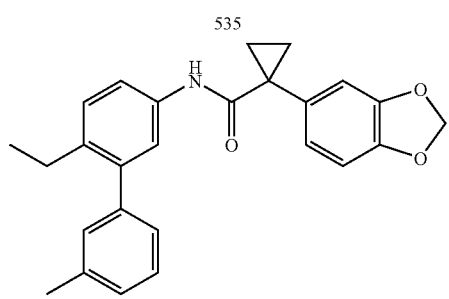
535

TABLE 1-continued
Examples of compounds of the present invention.
536
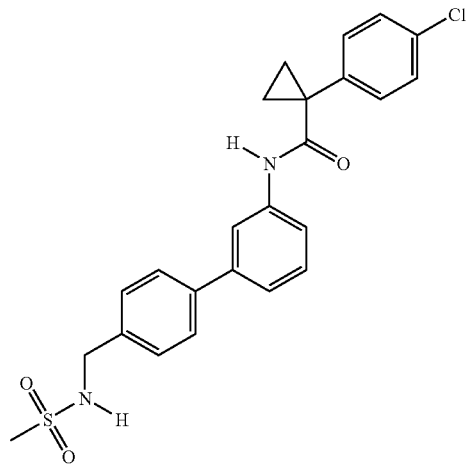
537
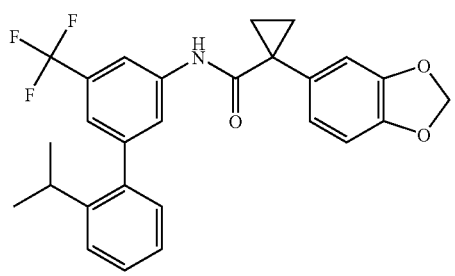
538
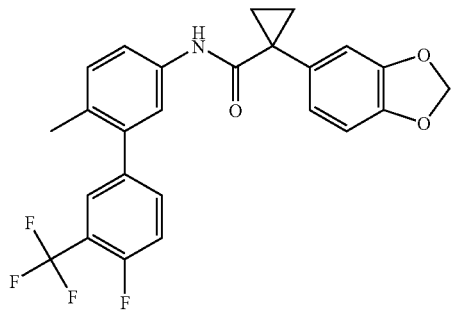
539
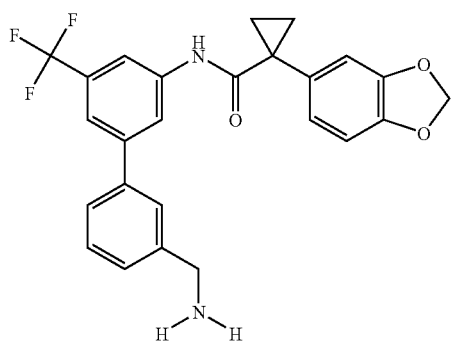

TABLE 1-continued
Examples of compounds of the present invention.
540
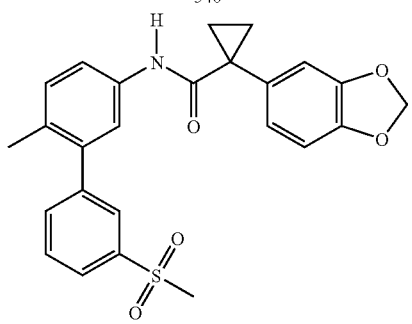
541
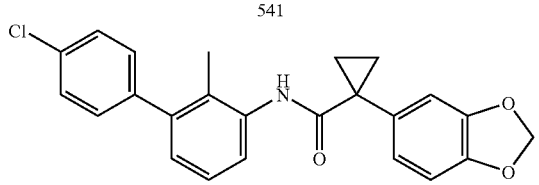
542
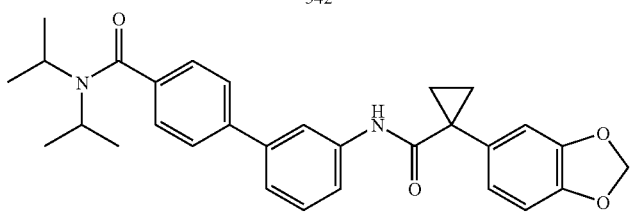
543
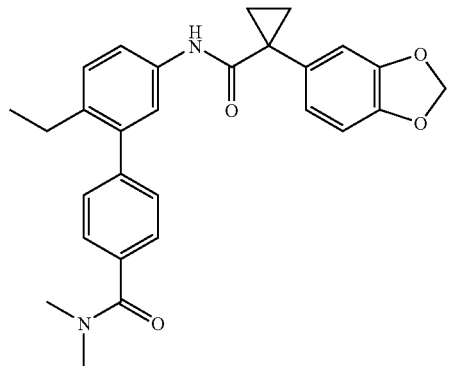
544
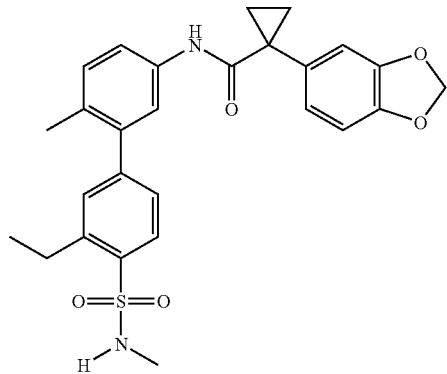

TABLE 1-continued
Examples of compounds of the present invention.
545
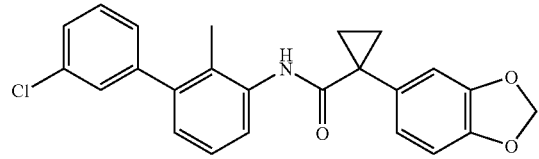
546
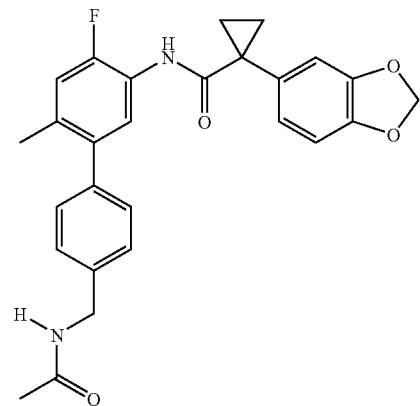
547
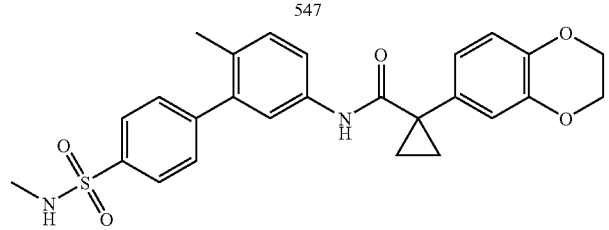
548
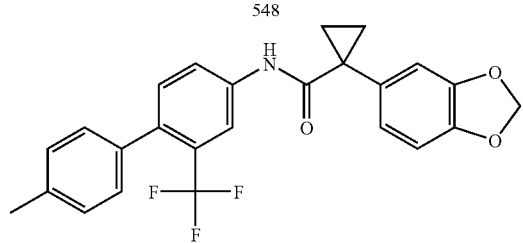

TABLE 1-continued
Examples of compounds of the present invention.
549
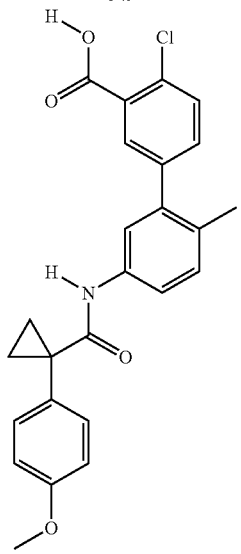
550
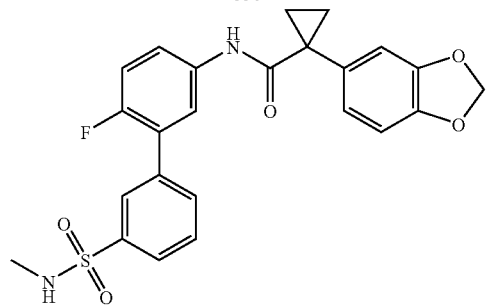
551
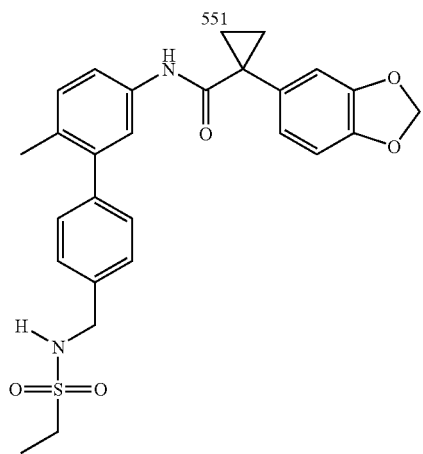

TABLE 1-continued
Examples of compounds of the present invention.
552
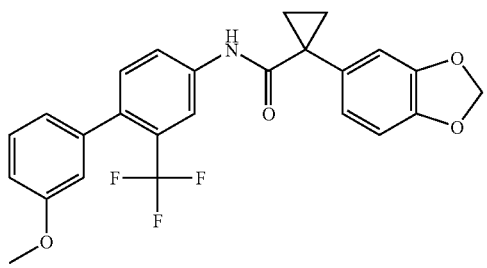
553
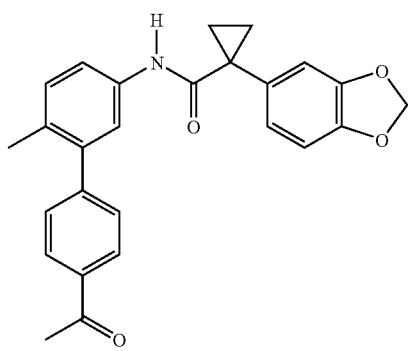
554
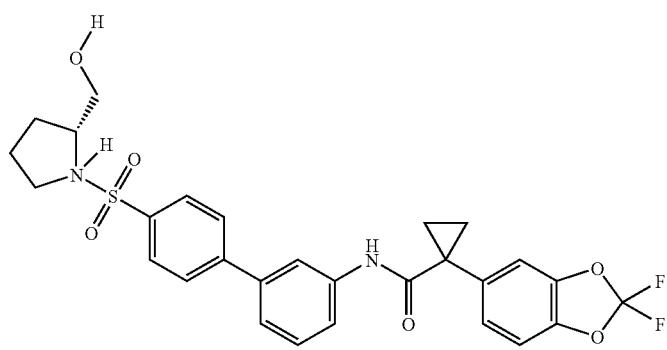
555
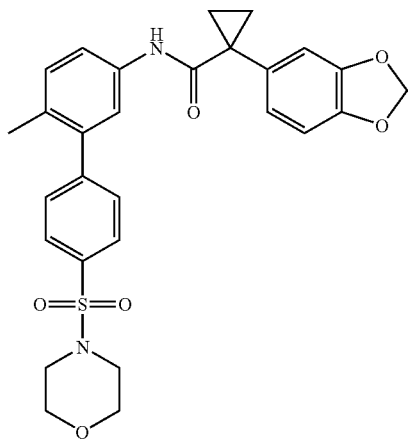

TABLE 1-continued
Examples of compounds of the present invention.
556
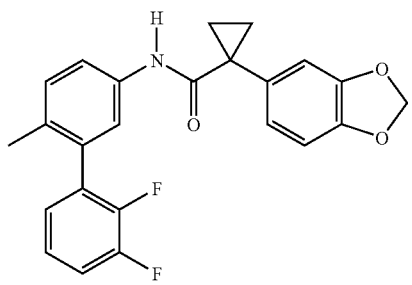
557
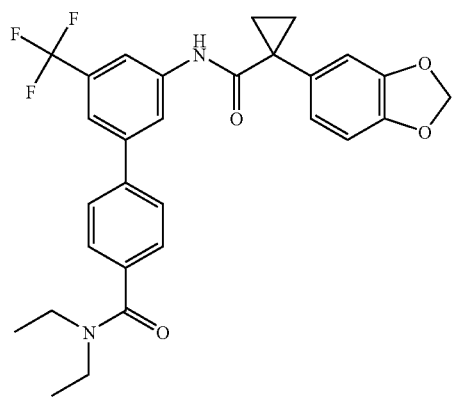
558
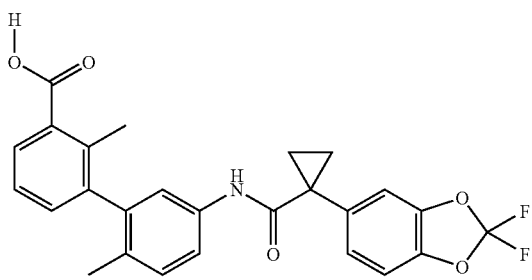
559
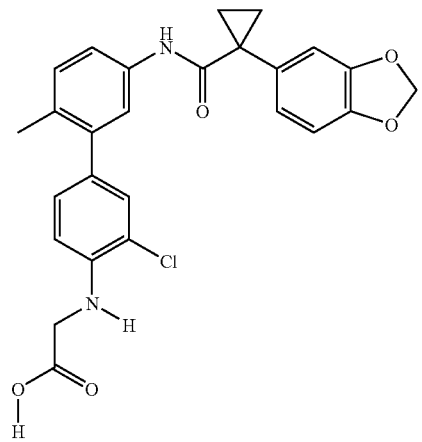

TABLE 1-continued
Examples of compounds of the present invention.
560
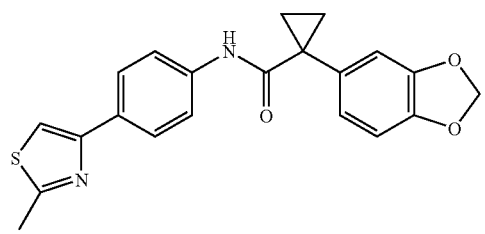
561
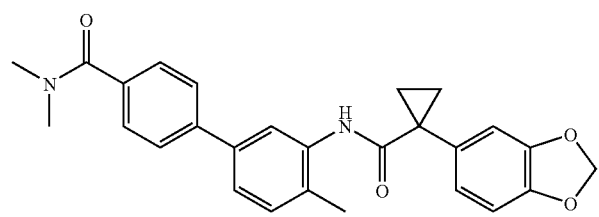
562
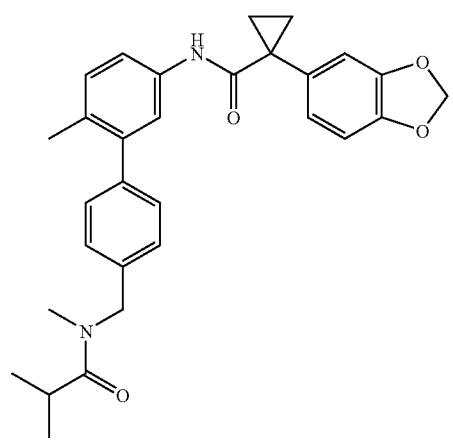
563
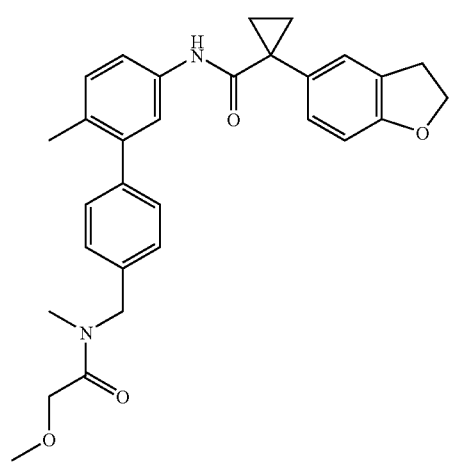

TABLE 1-continued
Examples of compounds of the present invention.
564
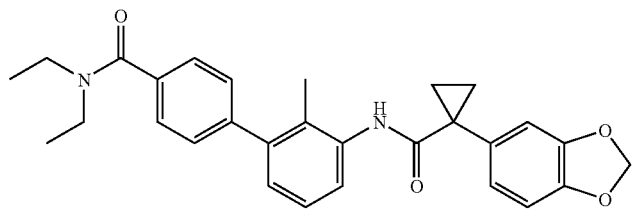
565
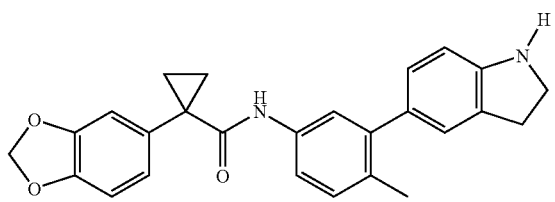
566
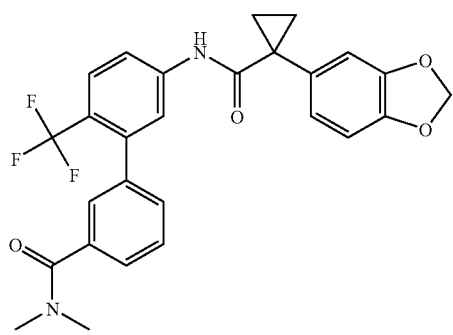
567
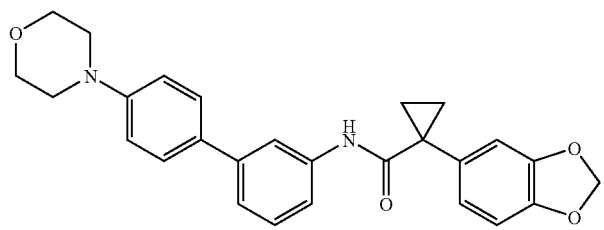
568
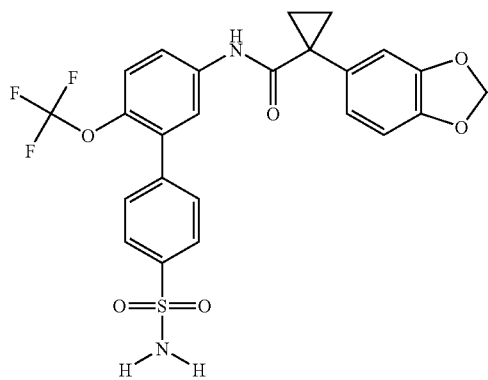

TABLE 1-continued
Examples of compounds of the present invention.
569
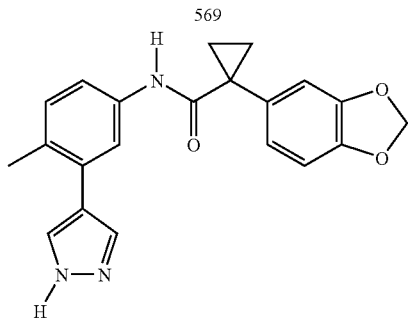
570
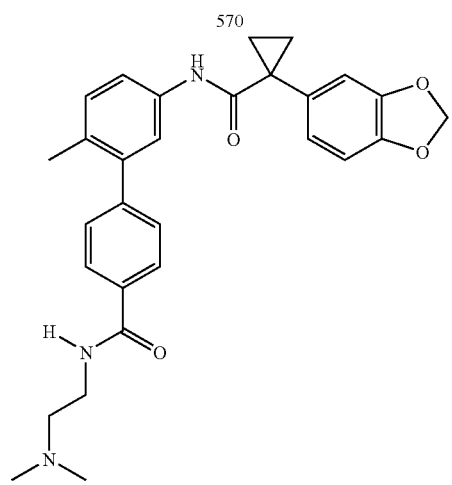
571
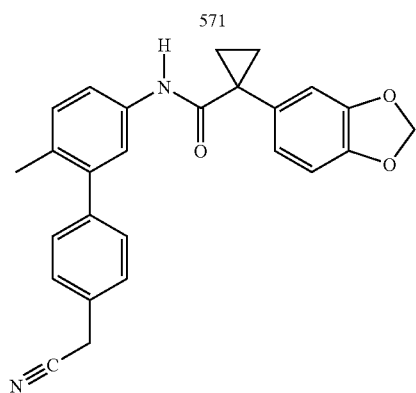
572
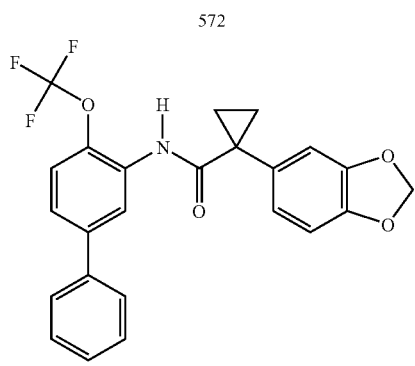

TABLE 1-continued
Examples of compounds of the present invention.
573
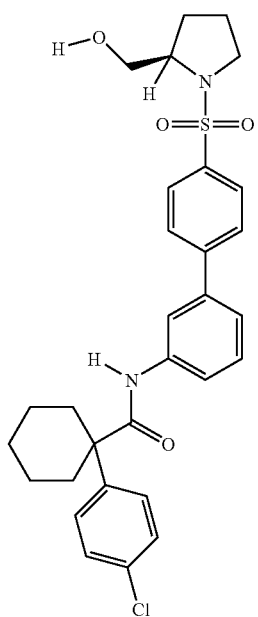
574
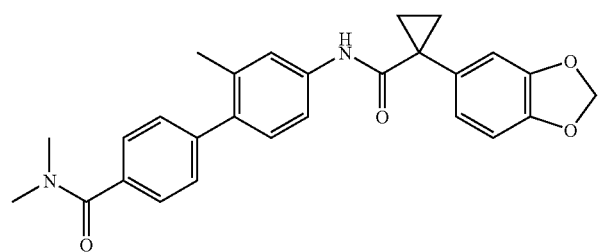
575
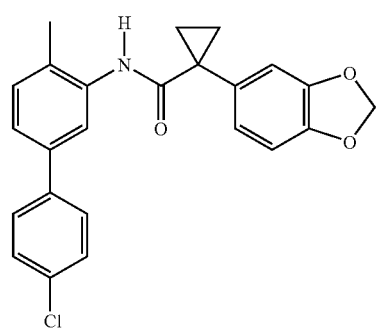
576
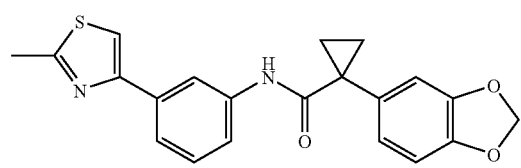

TABLE 1-continued
Examples of compounds of the present invention.
577
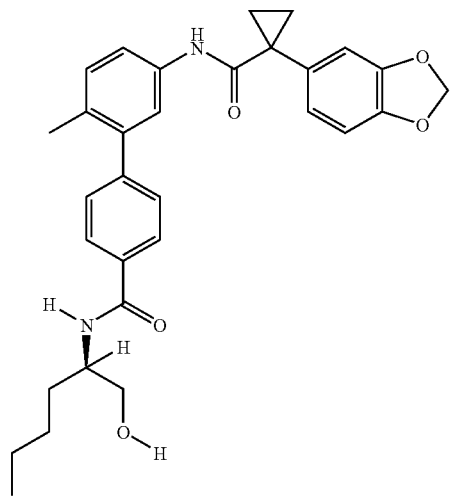
578
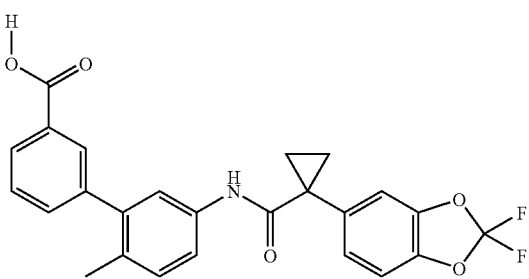
579
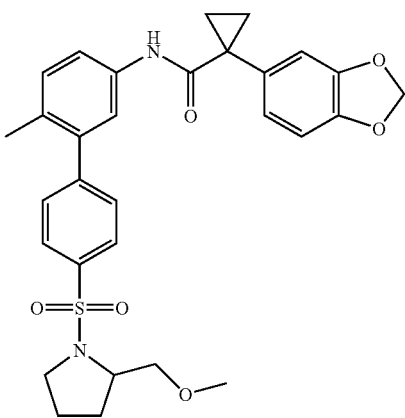

TABLE 1-continued
Examples of compounds of the present invention.
580
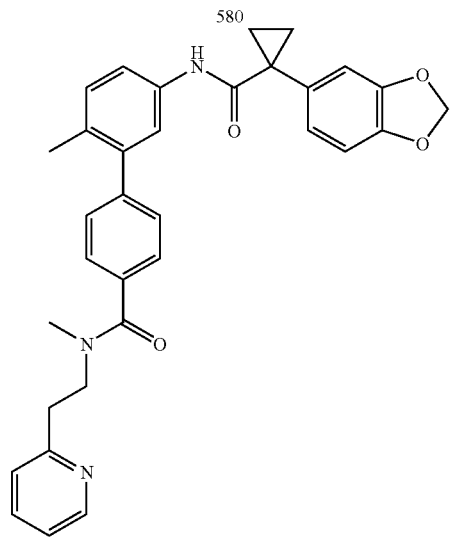
581
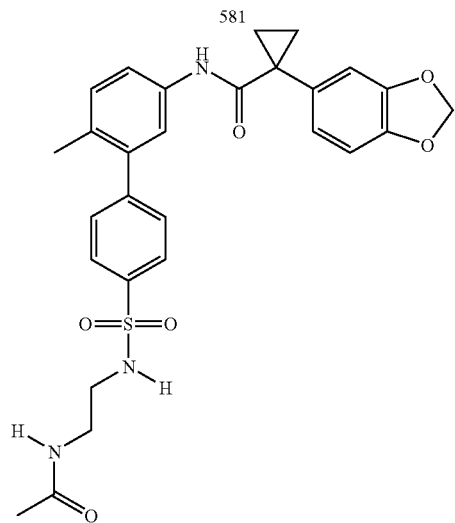
582
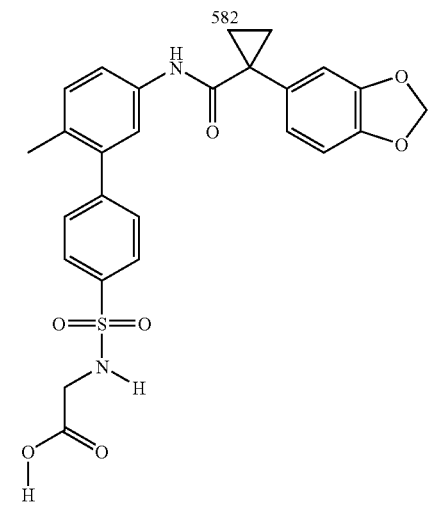

TABLE 1-continued
Examples of compounds of the present invention.
583
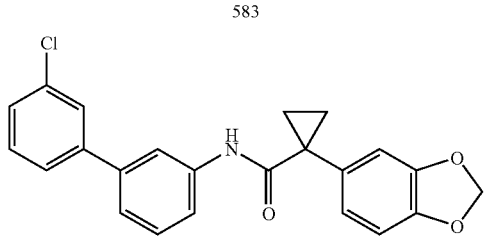
584
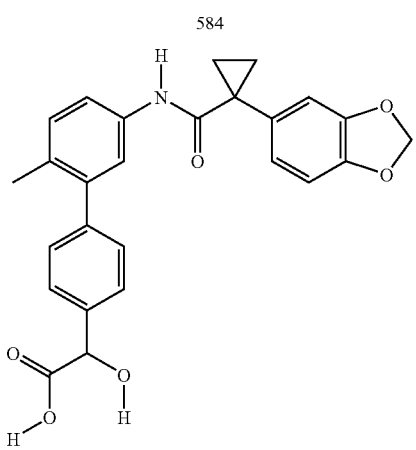
585
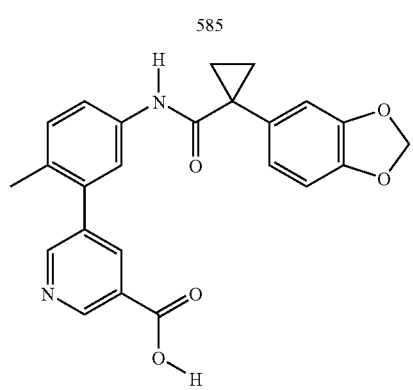
586
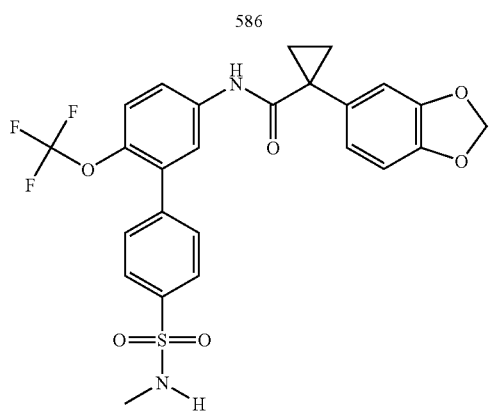

TABLE 1-continued
Examples of compounds of the present invention.
587
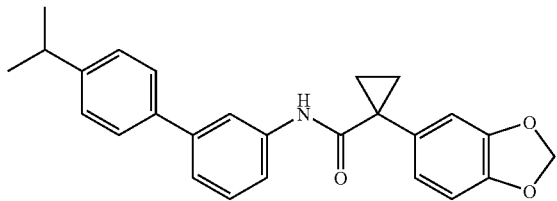
588
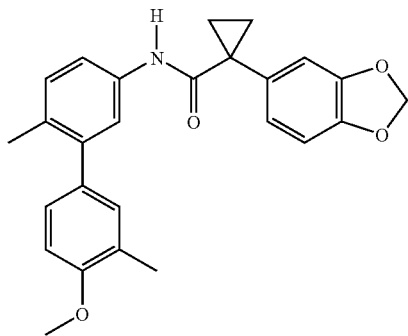
589
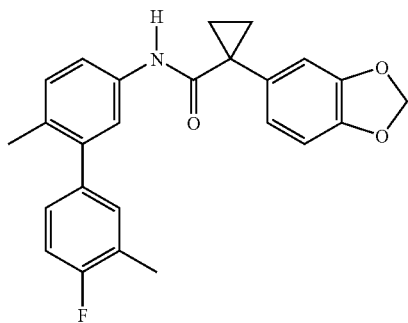
590
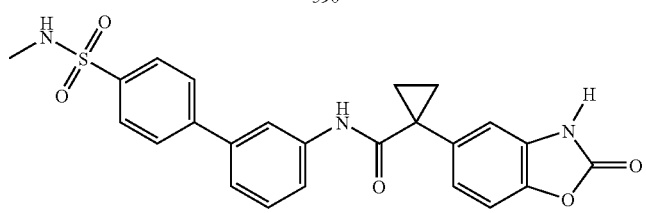

TABLE 1-continued
Examples of compounds of the present invention.
591
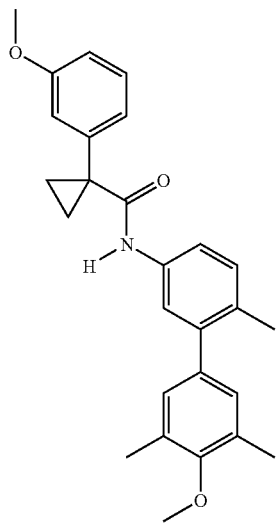
592
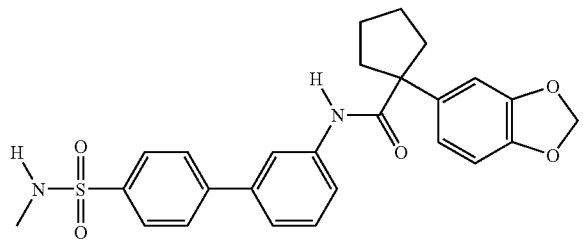
593
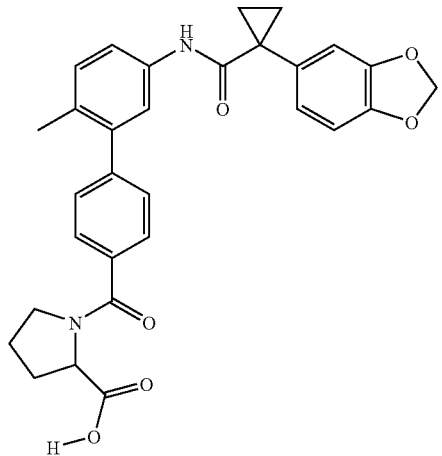

TABLE 1-continued
Examples of compounds of the present invention.
594
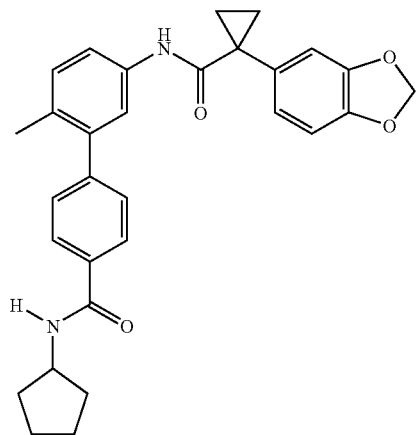
595
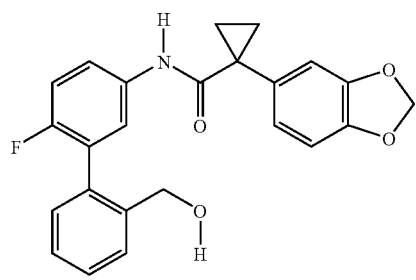
596
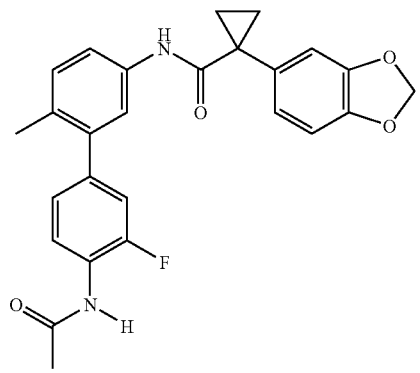
597
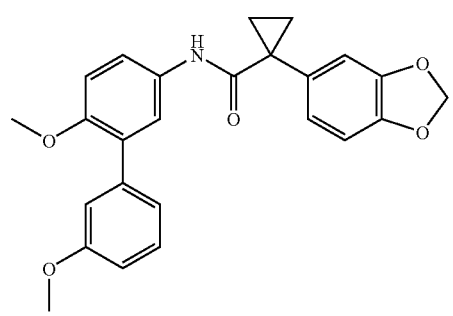

TABLE 1-continued
Examples of compounds of the present invention.
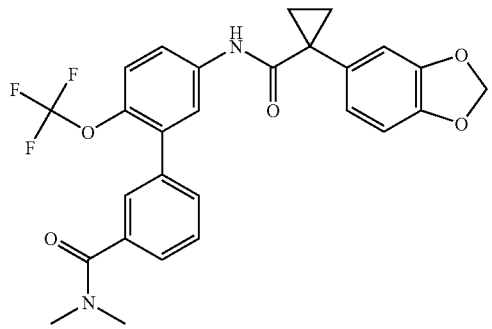
598
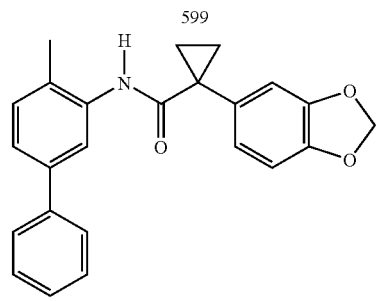
599
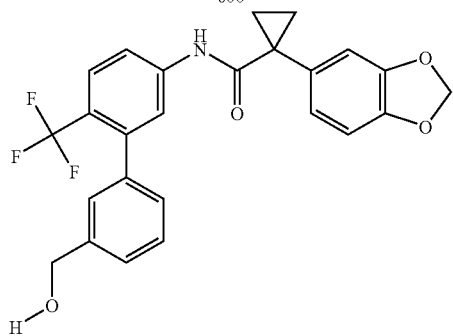
600
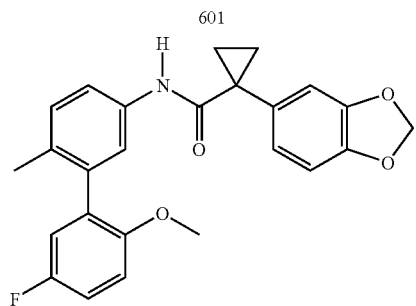
601

TABLE 1-continued
Examples of compounds of the present invention.
602
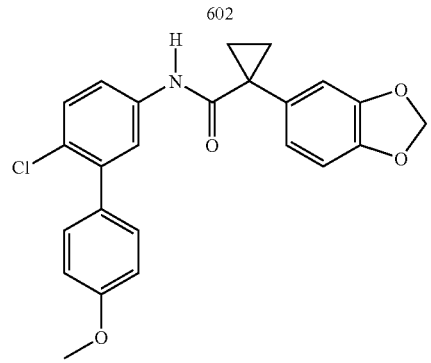
603
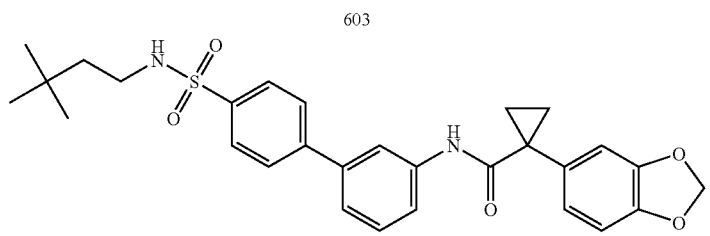
604
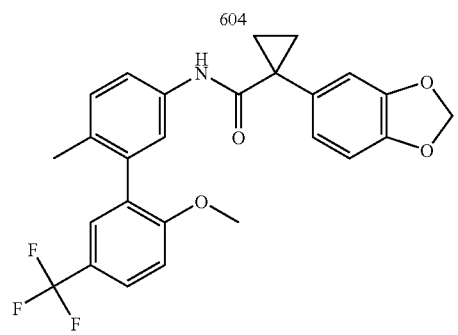
605
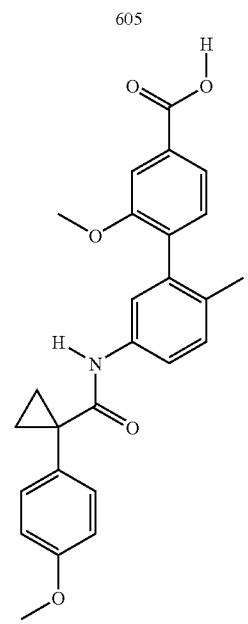

TABLE 1-continued
Examples of compounds of the present invention.
606
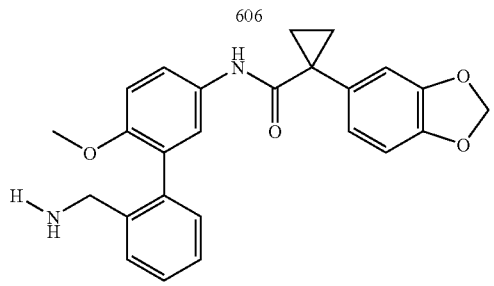
607
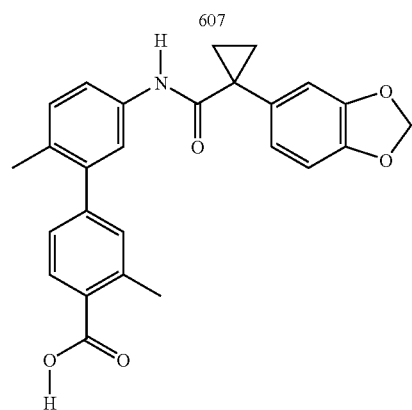
608
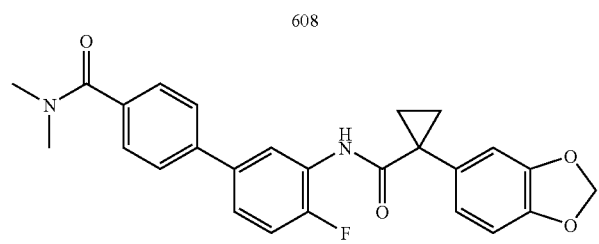
609
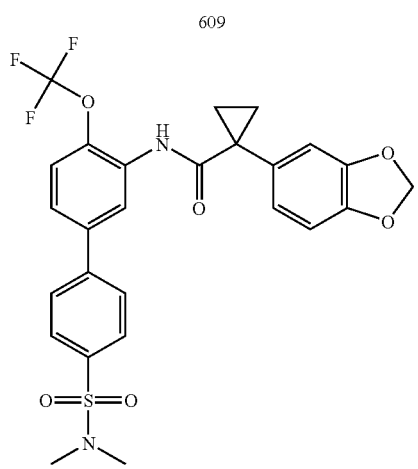

TABLE 1-continued
Examples of compounds of the present invention.
610
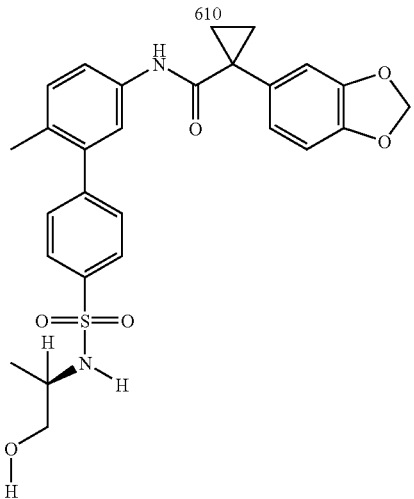
611
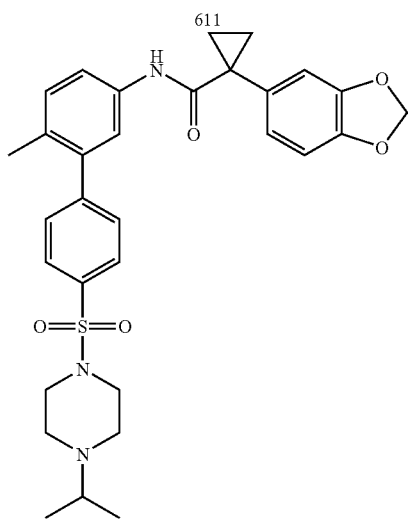
612
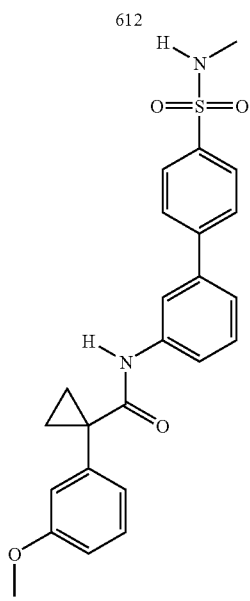

TABLE 1-continued
Examples of compounds of the present invention.
613
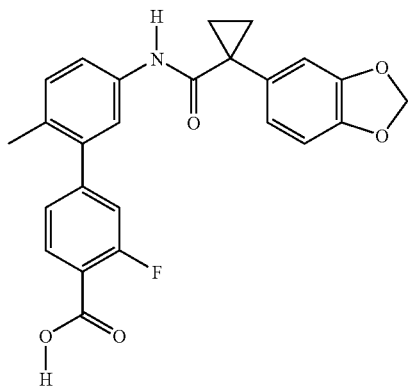
614
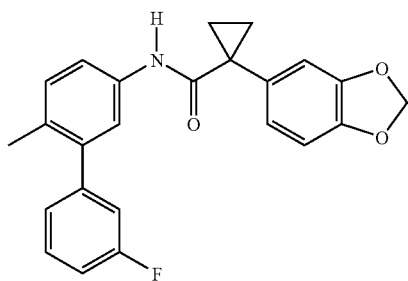
615
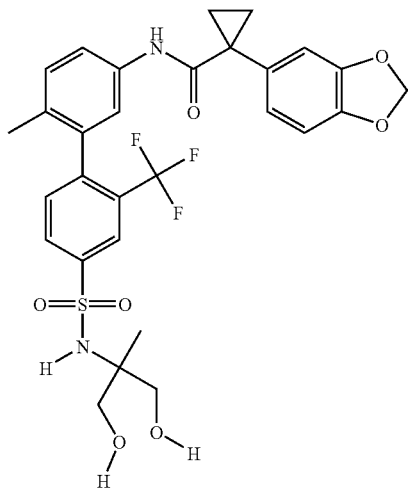
616
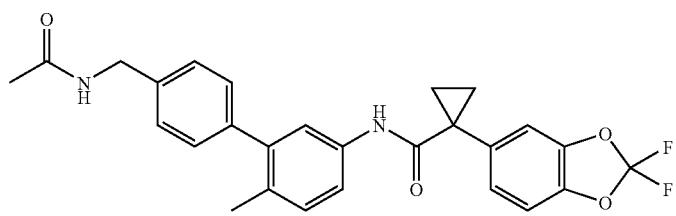

TABLE 1-continued
Examples of compounds of the present invention.
617
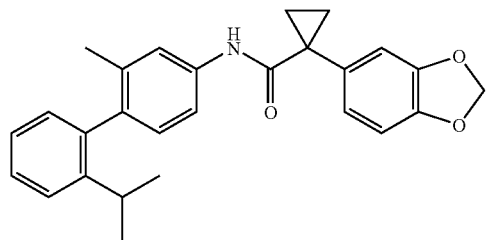
618
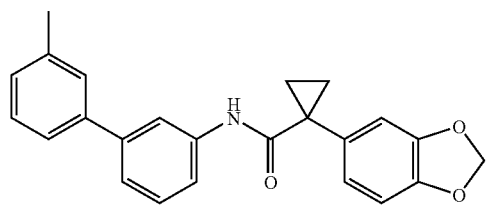
619
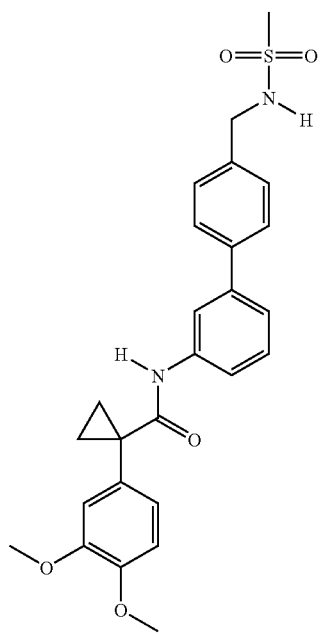
620
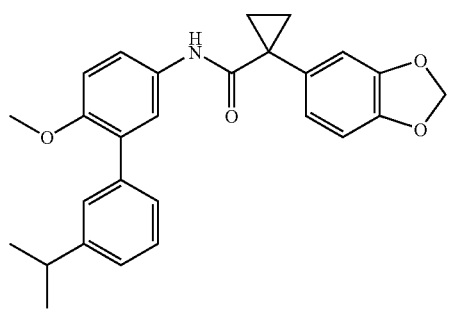

TABLE 1-continued
Examples of compounds of the present invention.
621
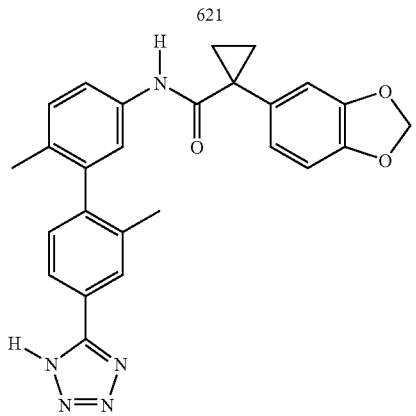
622
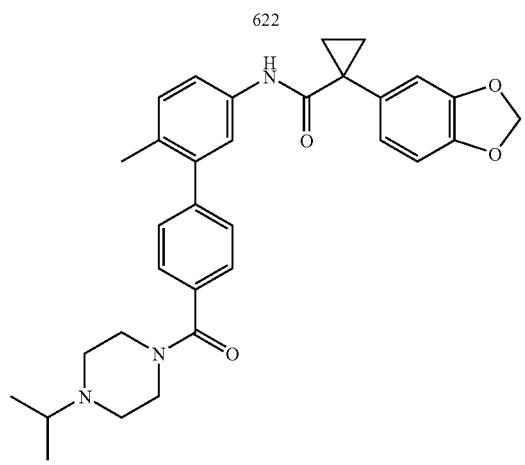
623
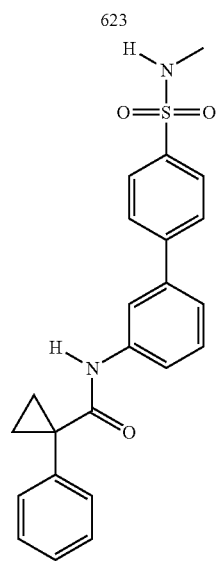

TABLE 1-continued
Examples of compounds of the present invention.
624
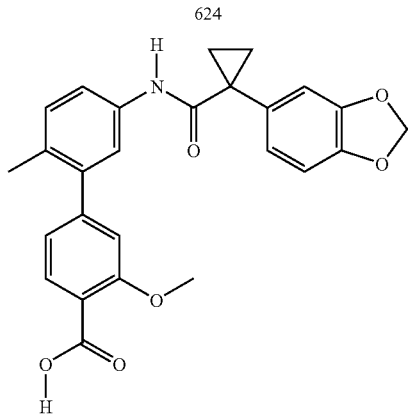
625
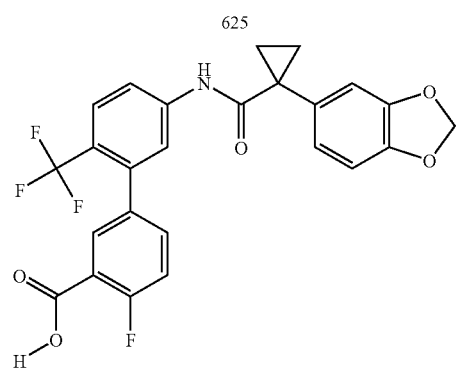
626
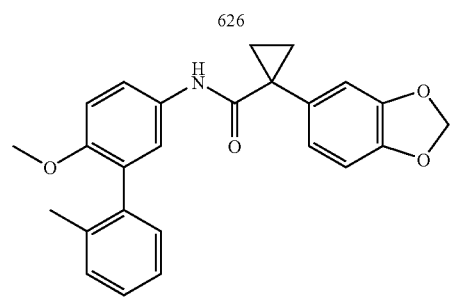

TABLE 1-continued
Examples of compounds of the present invention.
627
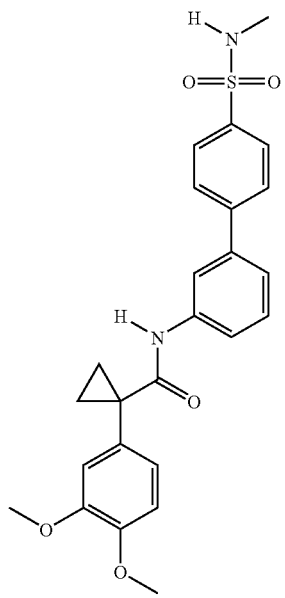
628
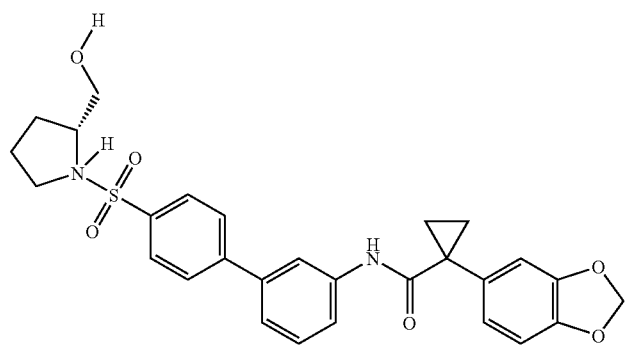
629
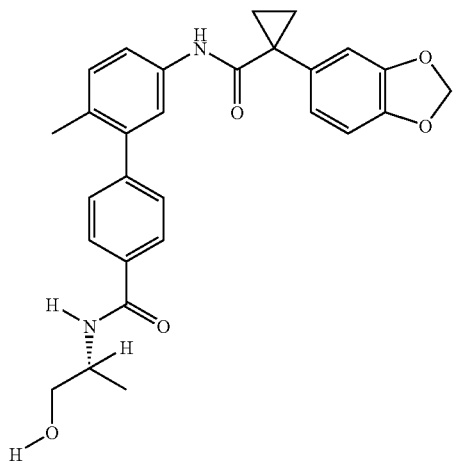

TABLE 1-continued
Examples of compounds of the present invention.
630
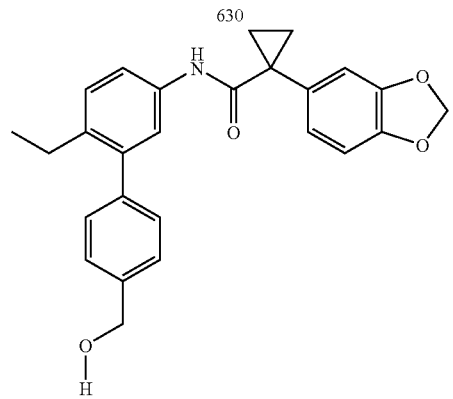
631
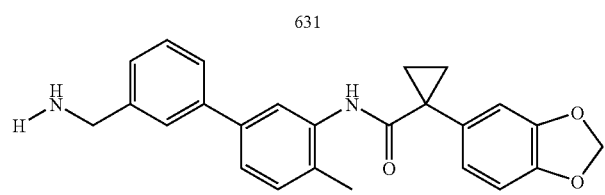
632
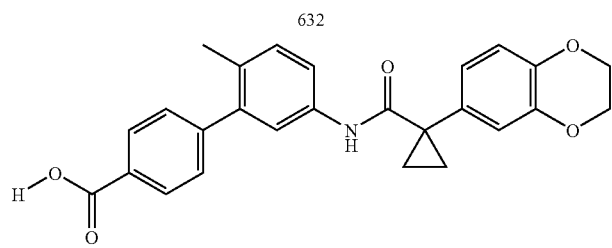
633
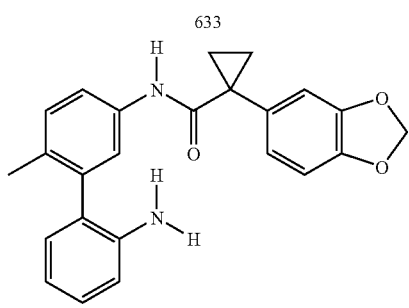
634
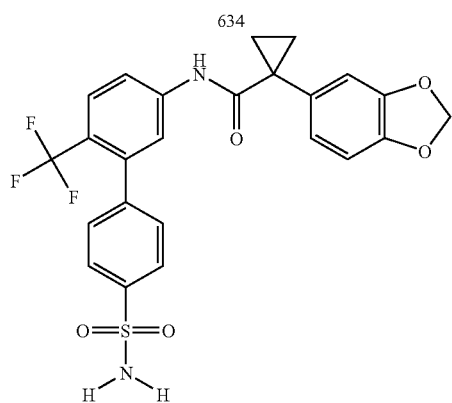

TABLE 1-continued
Examples of compounds of the present invention.
635
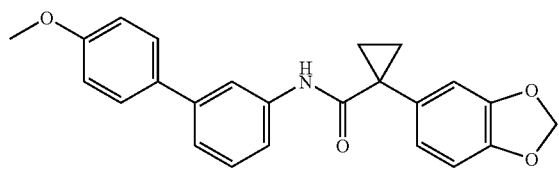
636
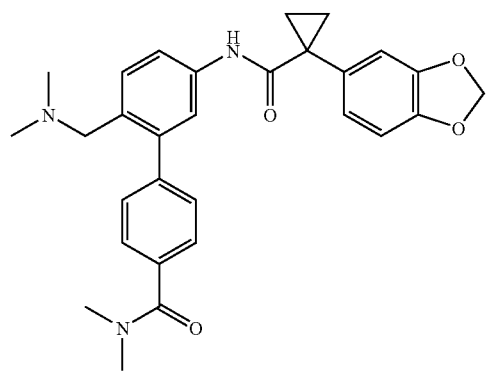
637
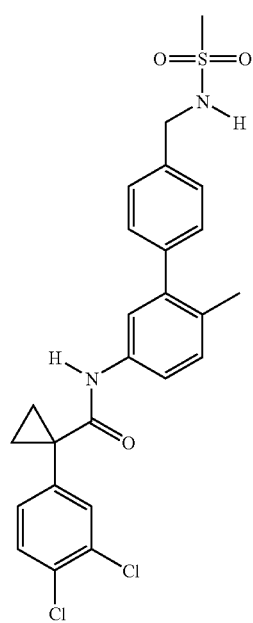

TABLE 1-continued
Examples of compounds of the present invention.
638
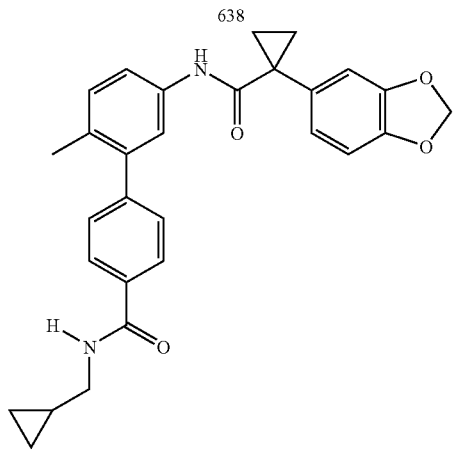
639
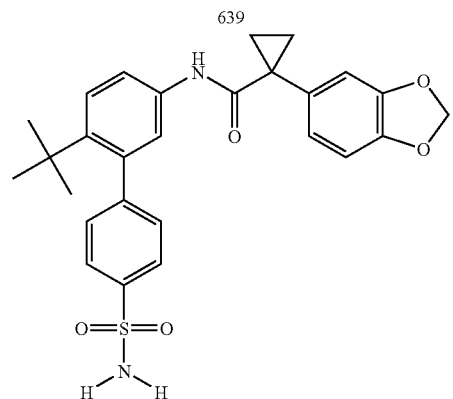
640
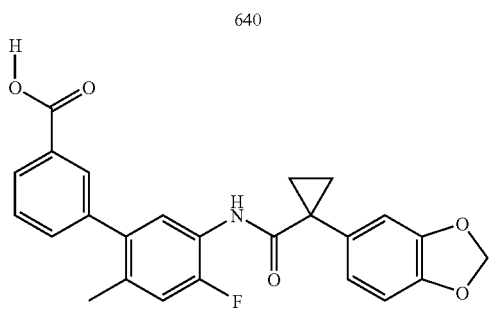
641
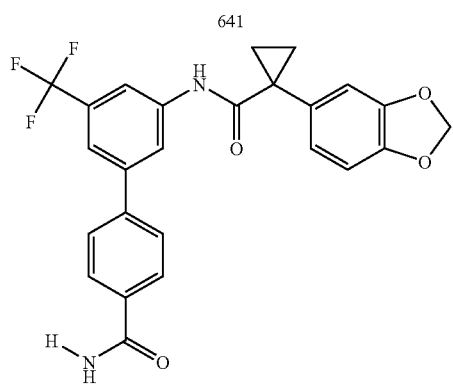

TABLE 1-continued
Examples of compounds of the present invention.
642
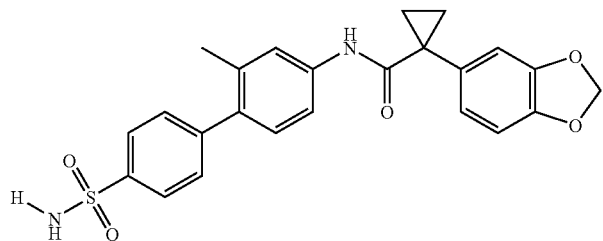
643
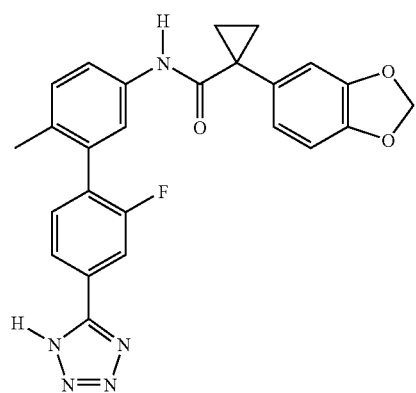
644
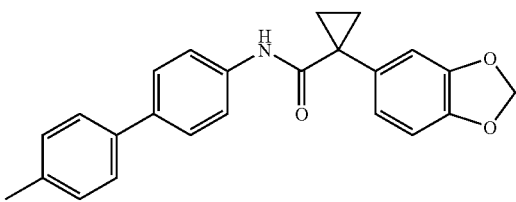
645
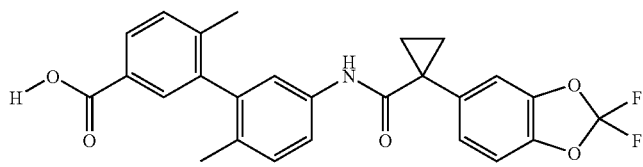
646
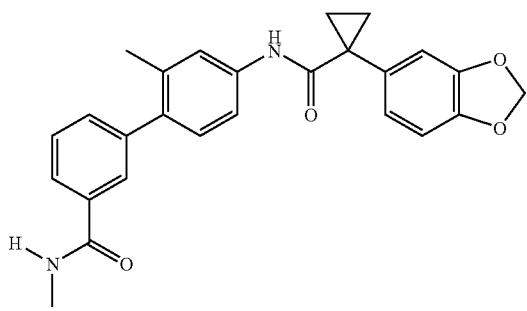

TABLE 1-continued
Examples of compounds of the present invention.
647
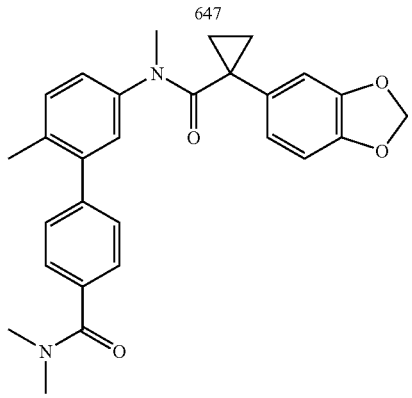
648
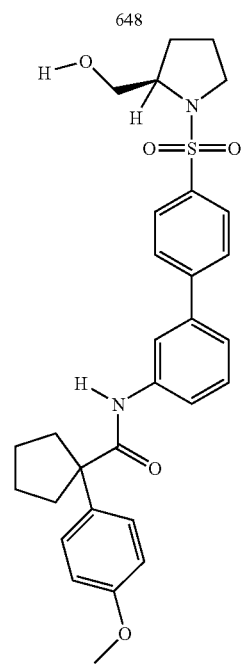
649
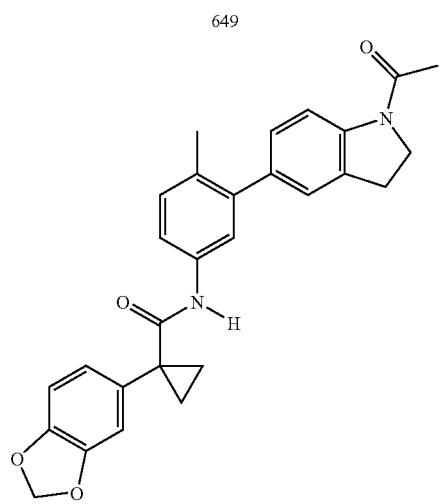

TABLE 1-continued
Examples of compounds of the present invention.
650
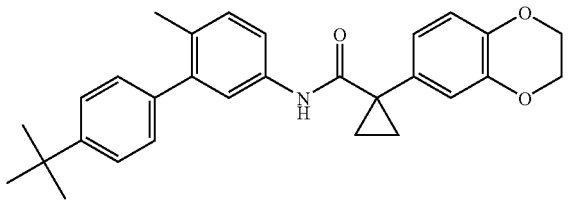
651
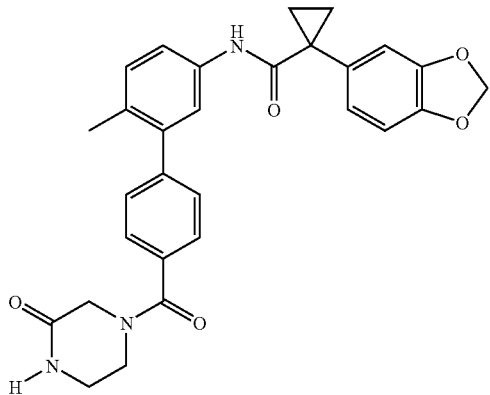
652
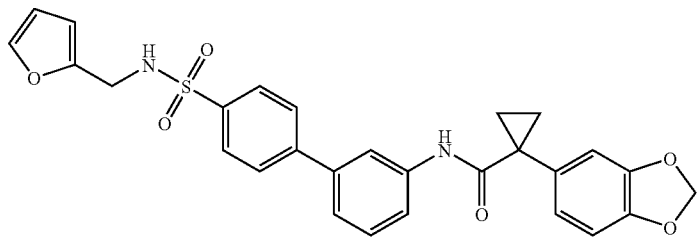
653
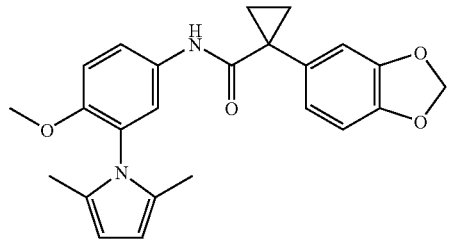
654
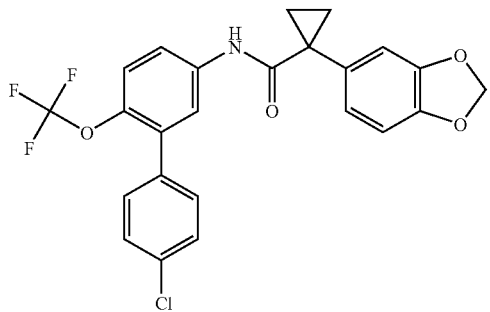

TABLE 1-continued
Examples of compounds of the present invention.
655
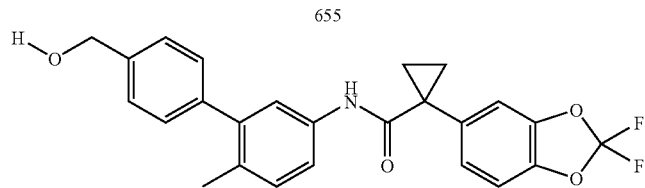
656
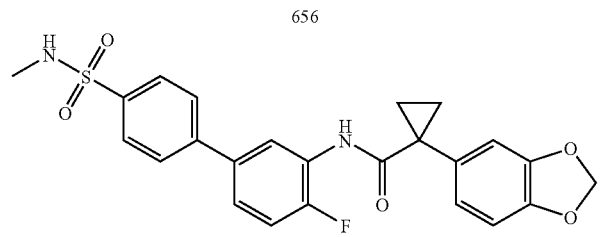
657
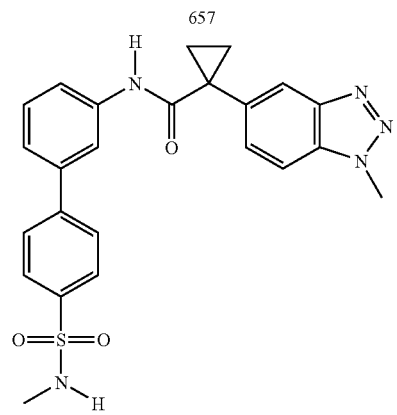
658
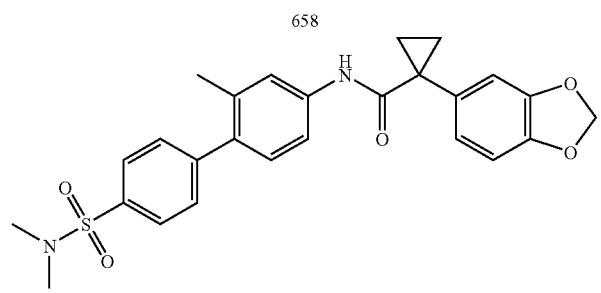
659
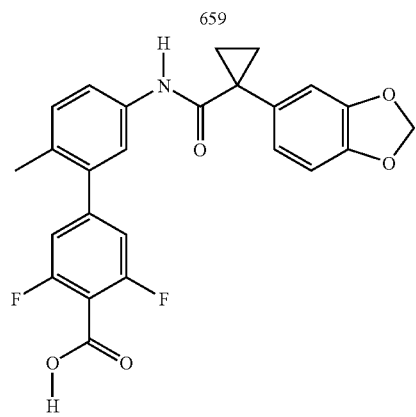

TABLE 1-continued
Examples of compounds of the present invention.
660
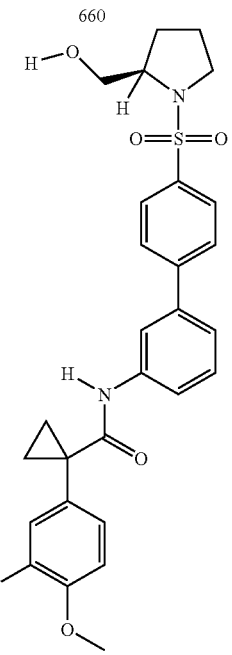
661
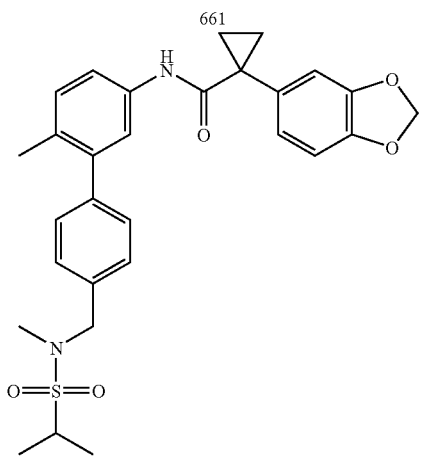
662
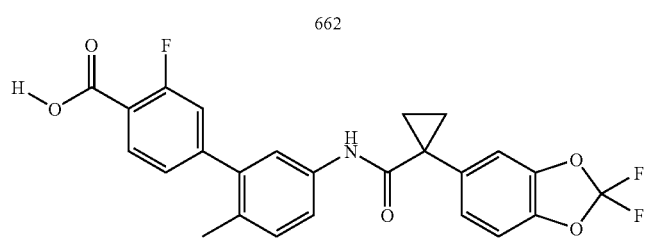

TABLE 1-continued
Examples of compounds of the present invention.
663
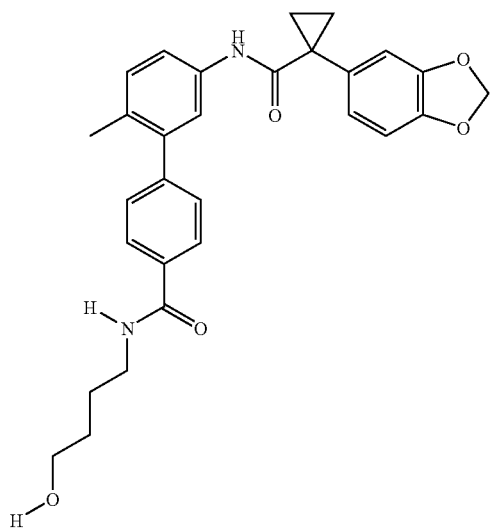
664
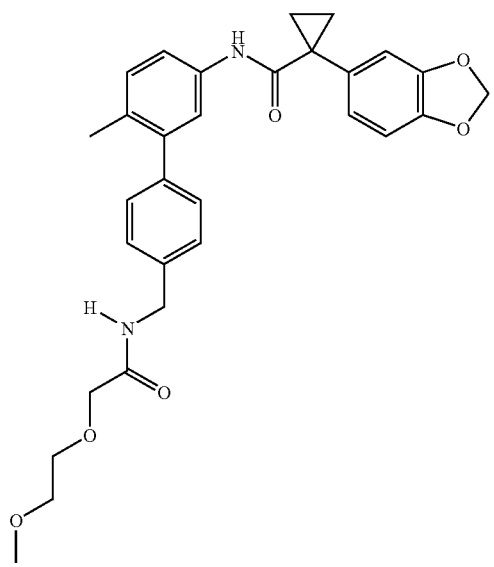
665
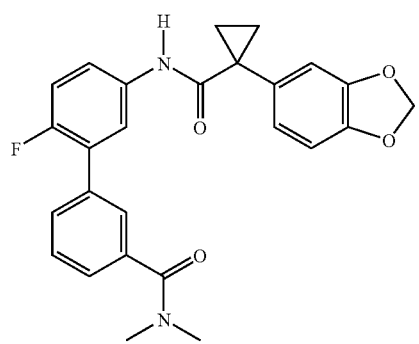

TABLE 1-continued
Examples of compounds of the present invention.
666
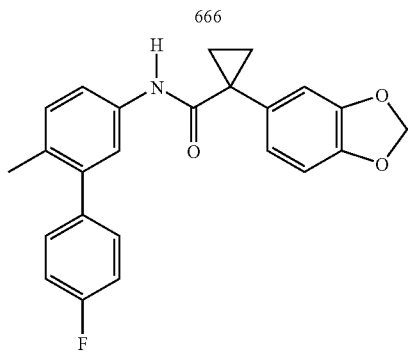
667
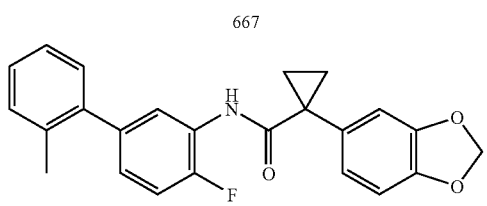
668
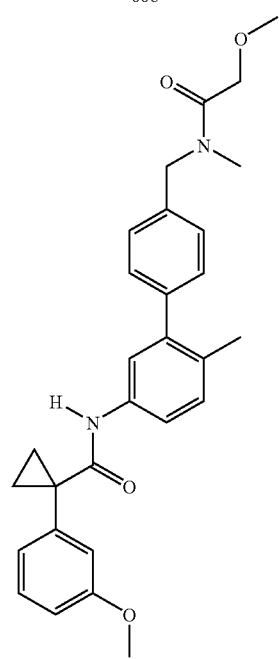

TABLE 1-continued
Examples of compounds of the present invention.
669
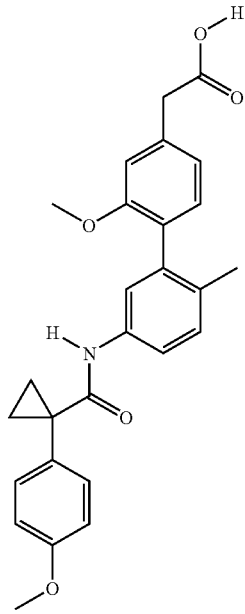
670
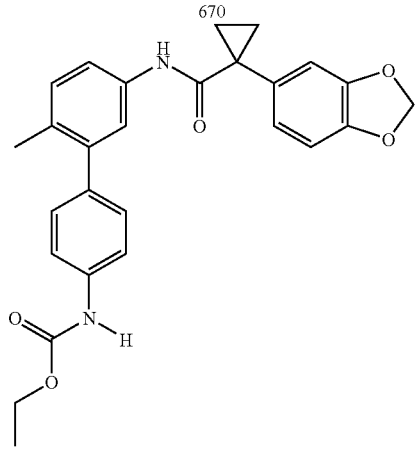
671
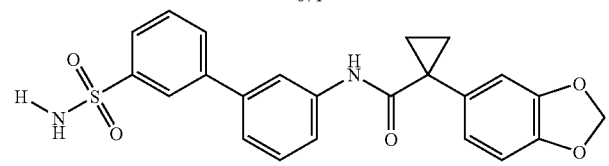

TABLE 1-continued
Examples of compounds of the present invention.
672
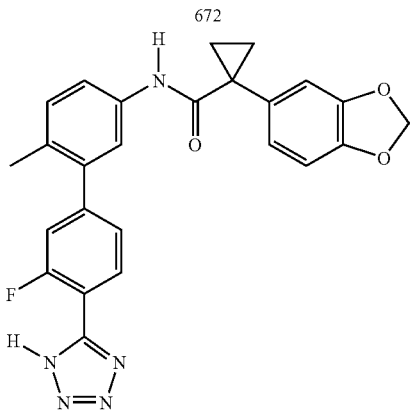
673
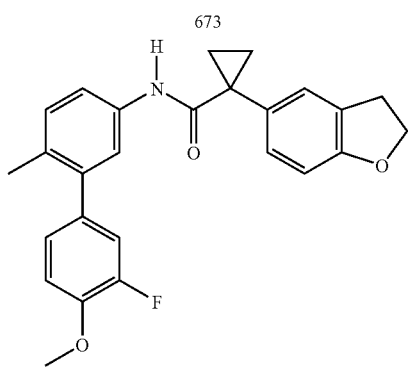
674
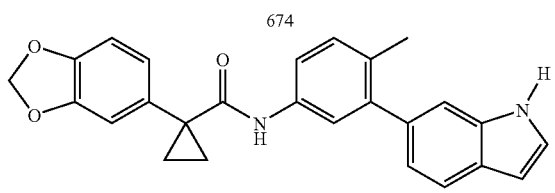
675
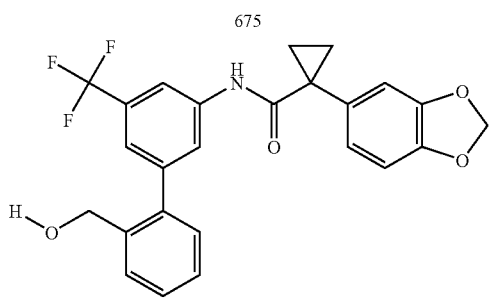
676
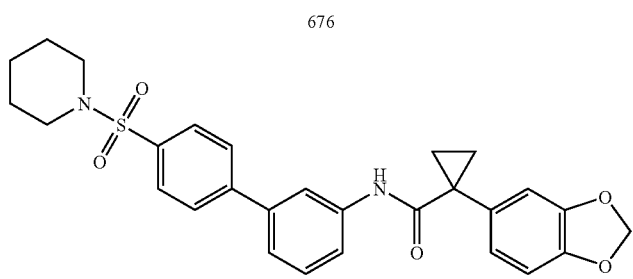

TABLE 1-continued
Examples of compounds of the present invention.
677
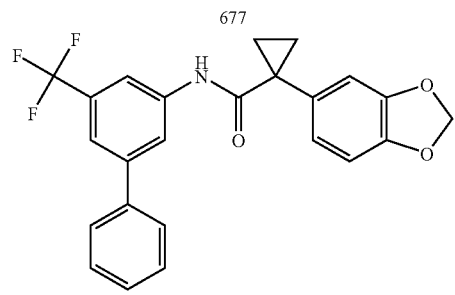
678
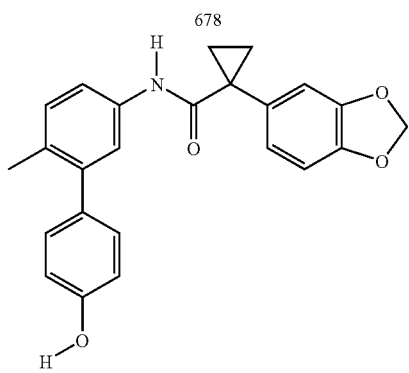
679
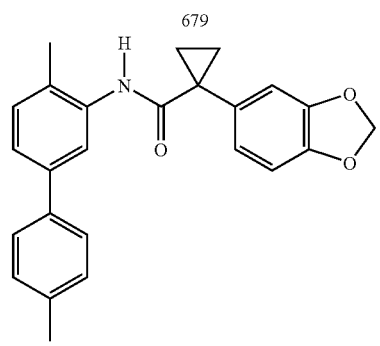
680
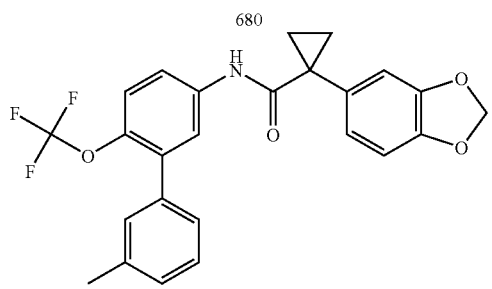

TABLE 1-continued
Examples of compounds of the present invention.
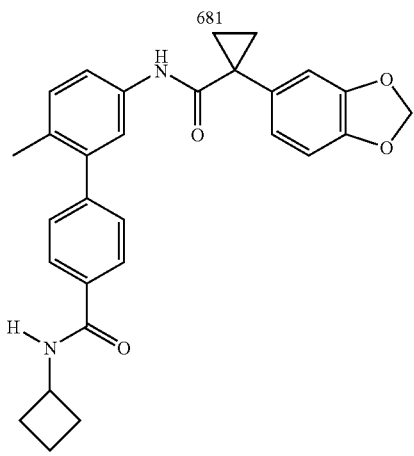
681
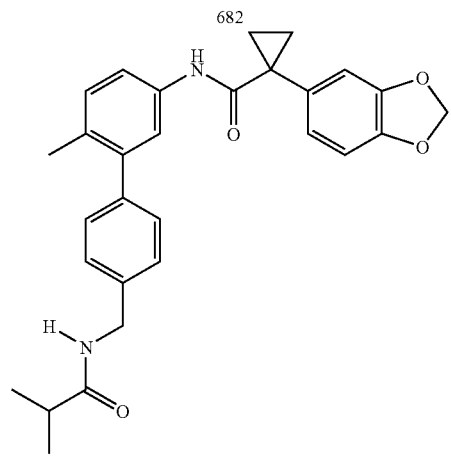
682
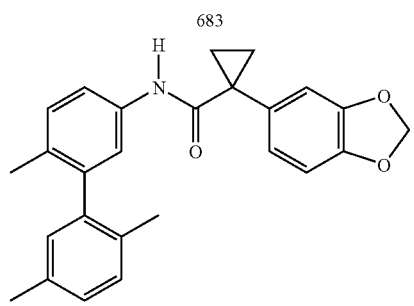
683
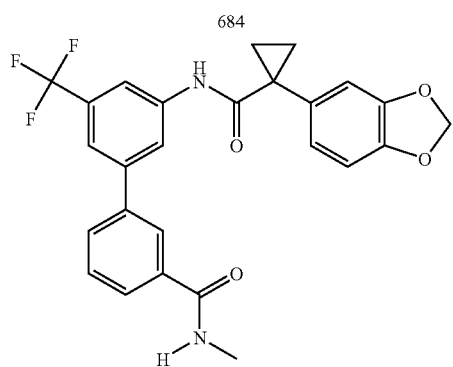
684

TABLE 1-continued
Examples of compounds of the present invention.
685
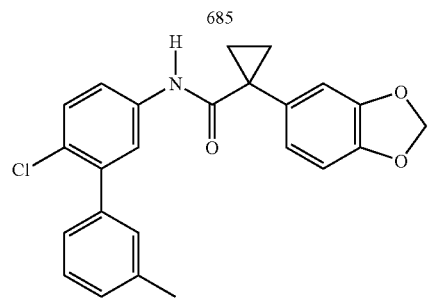
686
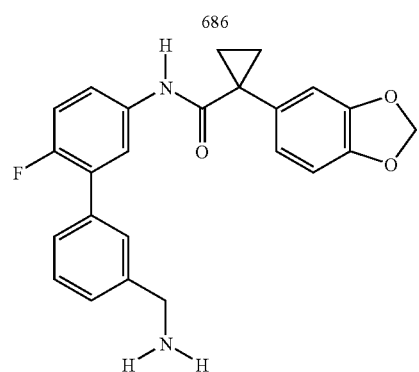
687
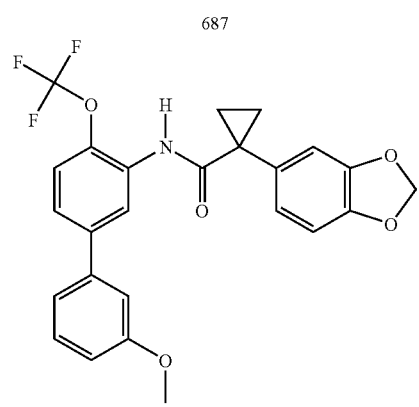
688
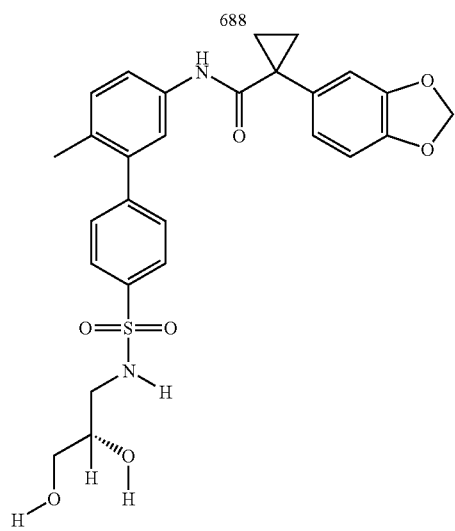

TABLE 1-continued
Examples of compounds of the present invention.
689
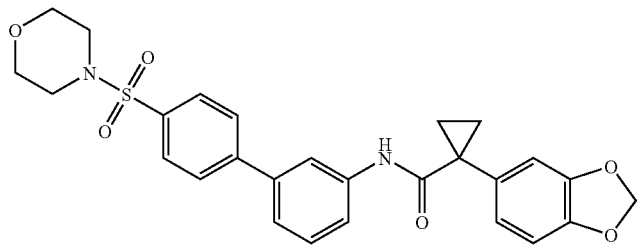
690
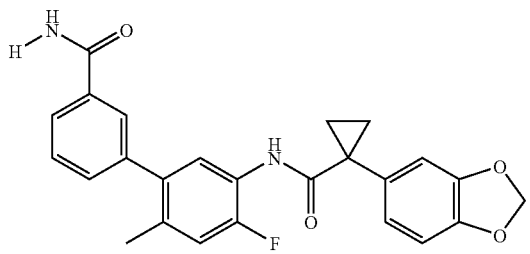
691
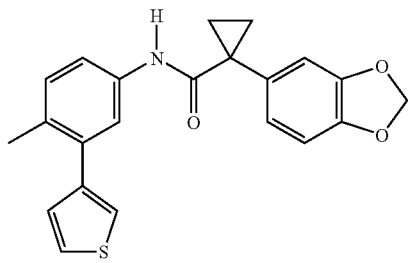
692
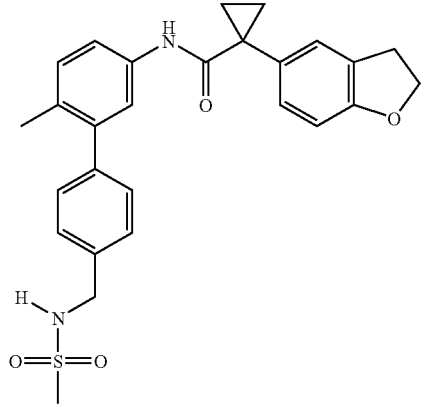
693
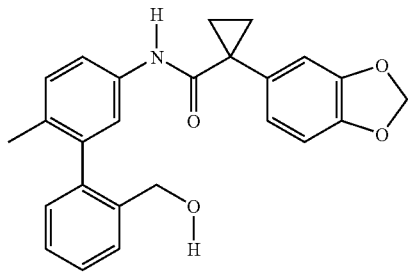

TABLE 1-continued
Examples of compounds of the present invention.
694
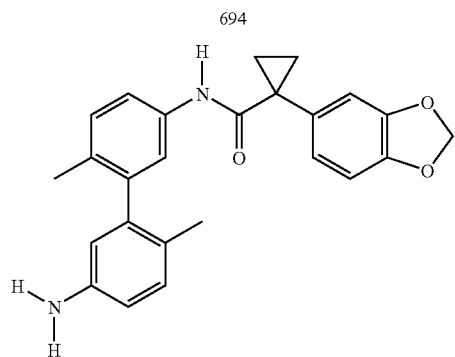
695
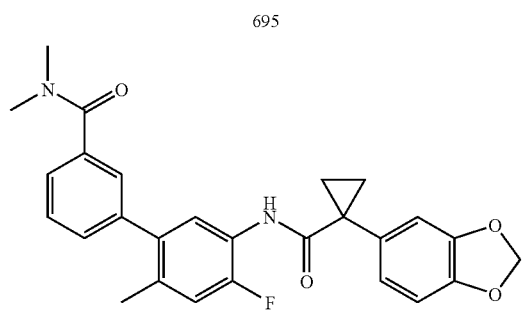
696
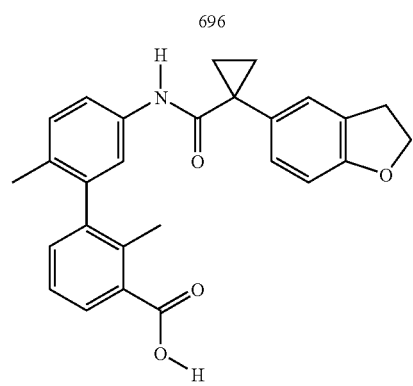
697
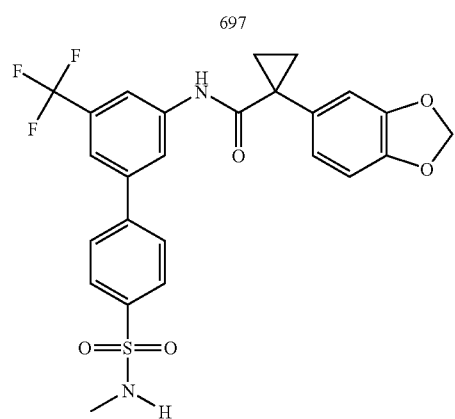

TABLE 1-continued
Examples of compounds of the present invention.
698
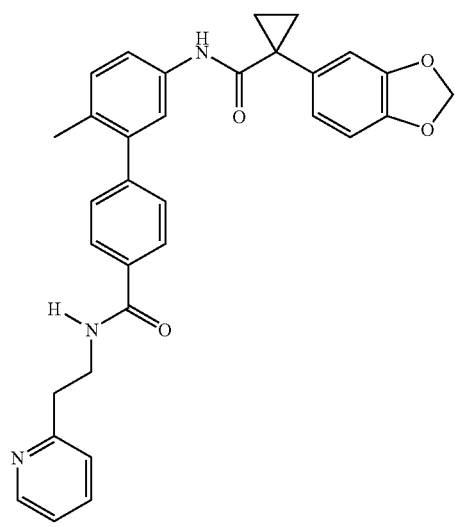
699
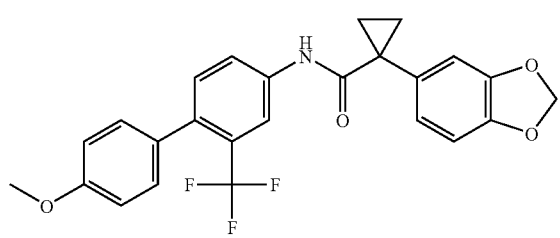
700
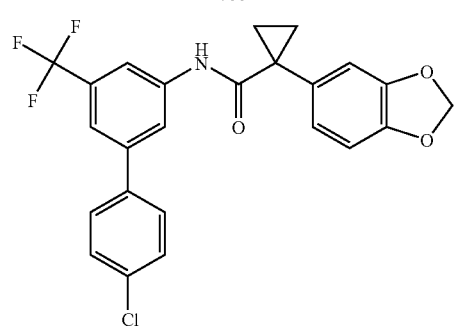

TABLE 1-continued
Examples of compounds of the present invention.
701
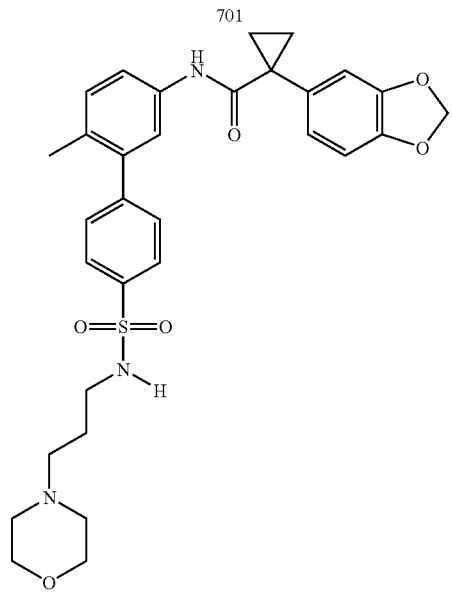
702
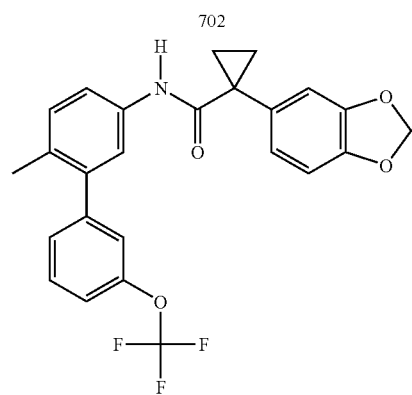
703
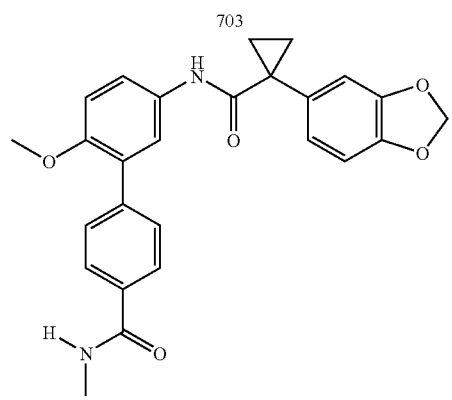

TABLE 1-continued
Examples of compounds of the present invention.
704
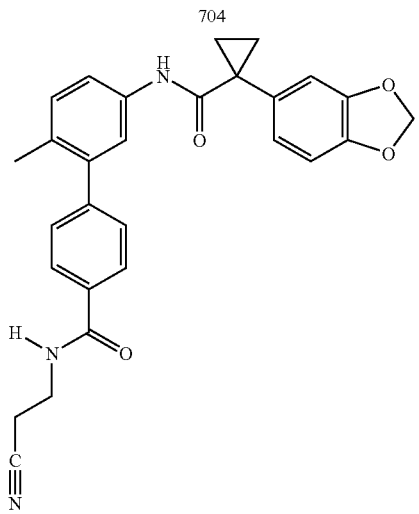
705
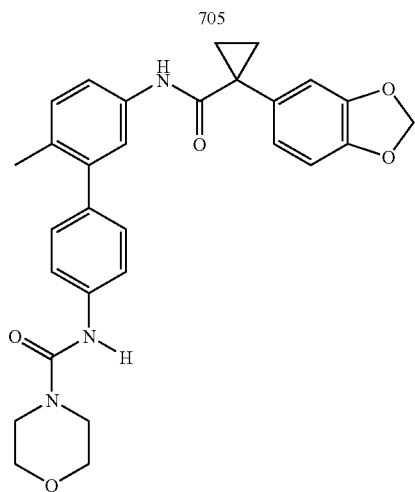
706
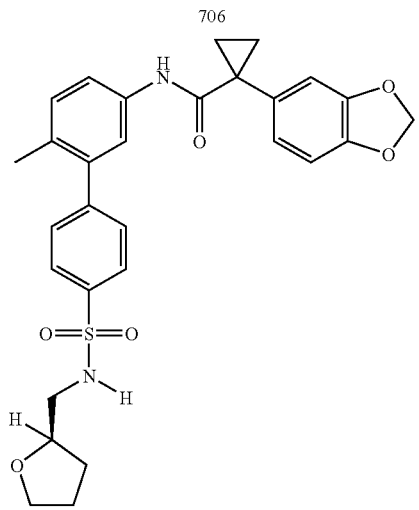

TABLE 1-continued
Examples of compounds of the present invention.
707
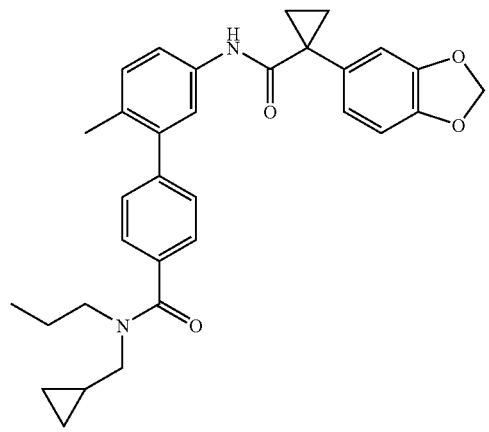
708
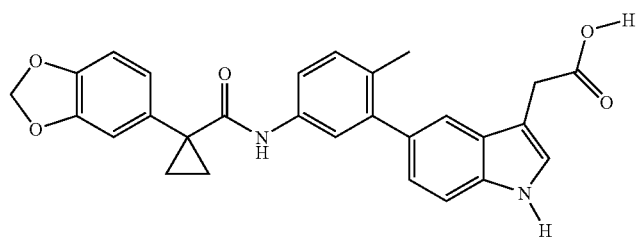
709
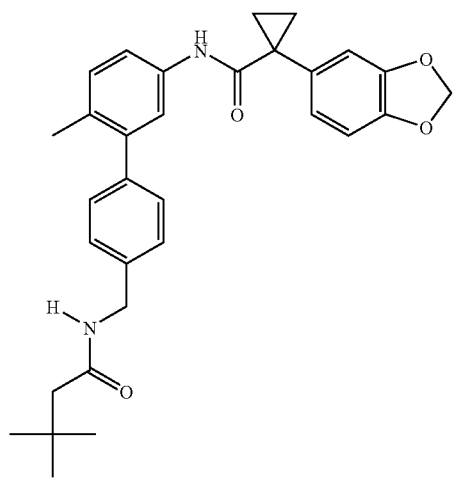

TABLE 1-continued
Examples of compounds of the present invention.
710
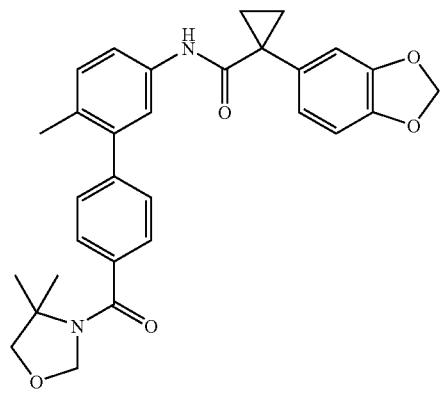
711
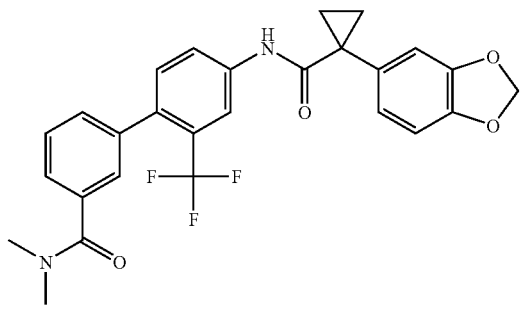
712
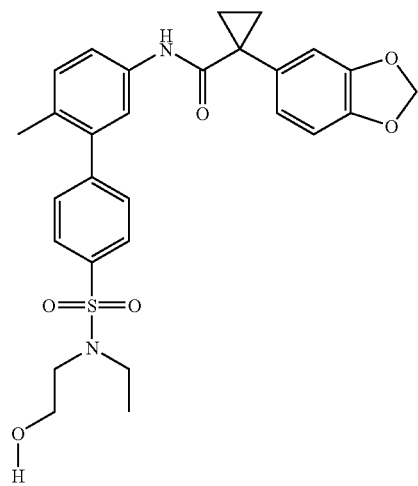
713
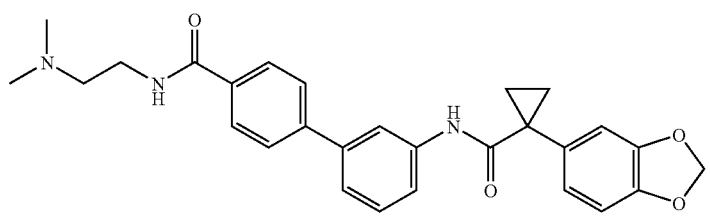

TABLE 1-continued
Examples of compounds of the present invention.
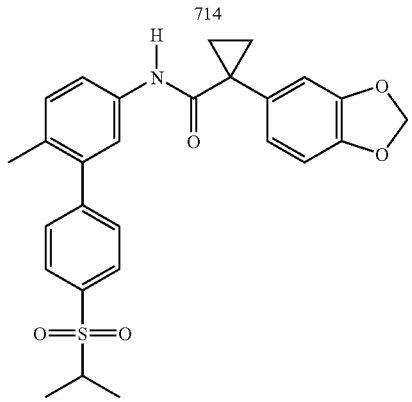
714
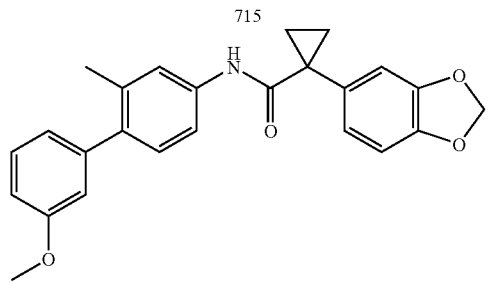
715
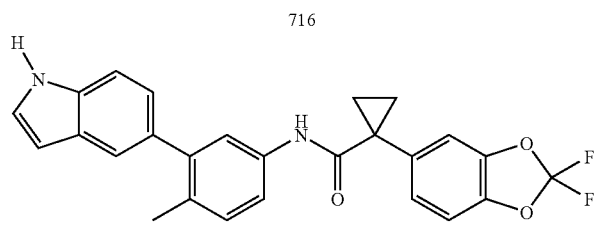
716
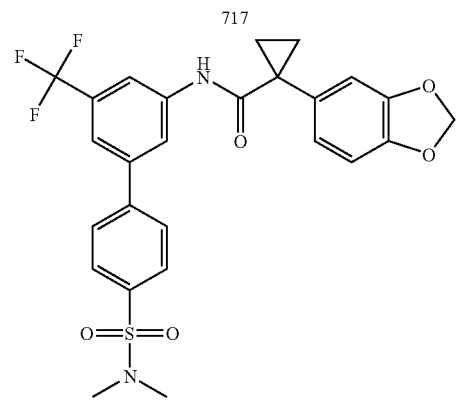
717

TABLE 1-continued
Examples of compounds of the present invention.
718
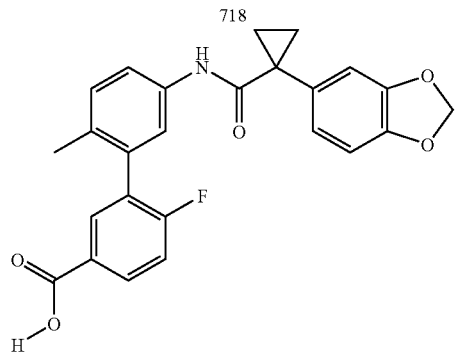
719
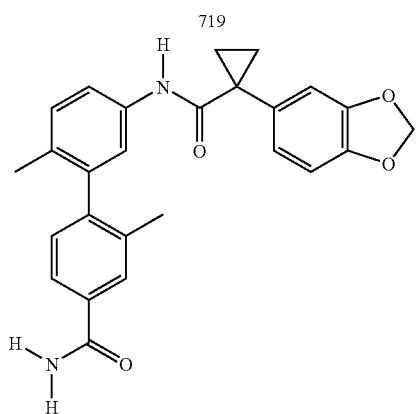
720
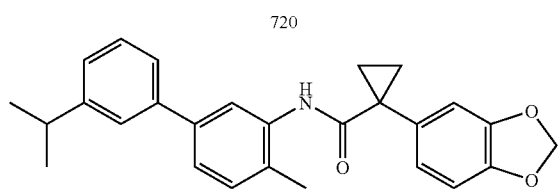
721
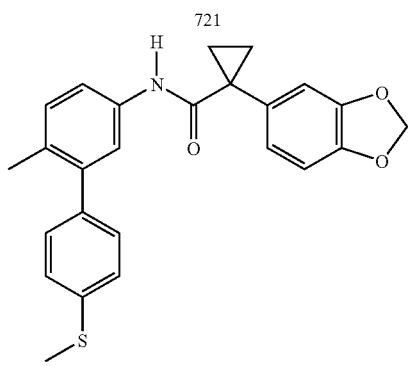
722
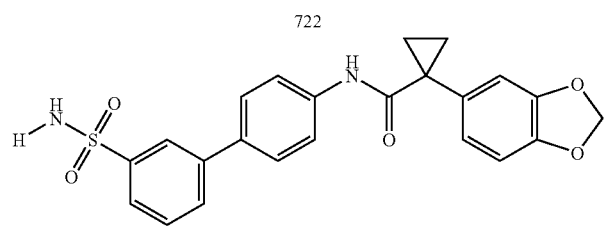

TABLE 1-continued
Examples of compounds of the present invention.
723
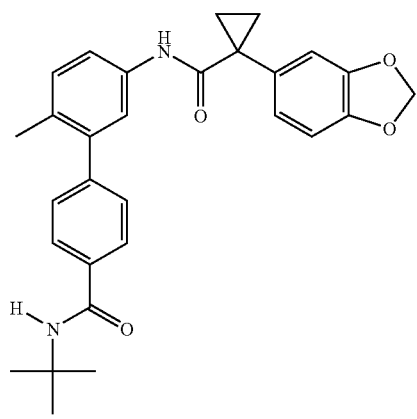
724
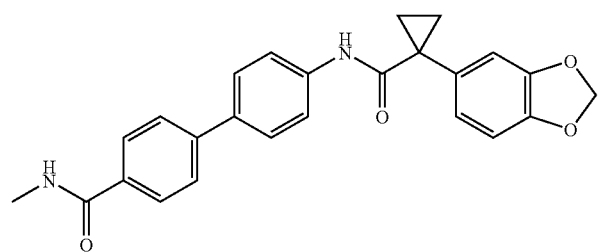
725
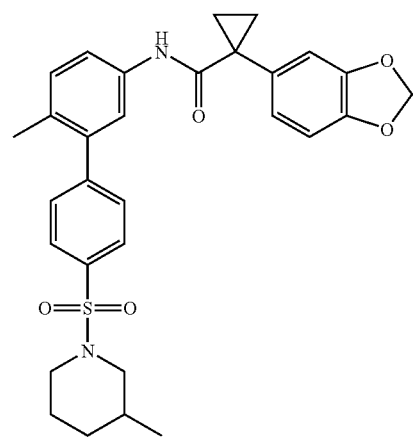
726
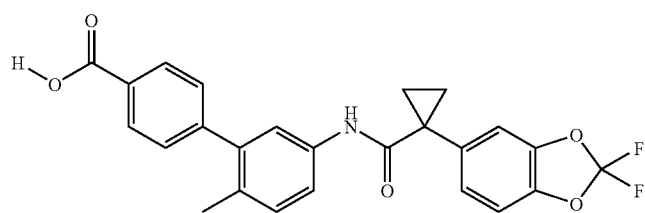

TABLE 1-continued
Examples of compounds of the present invention.
727
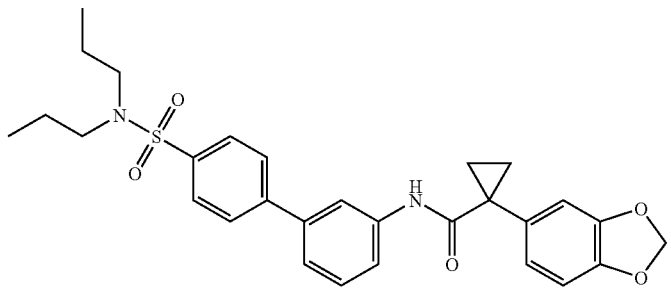
728
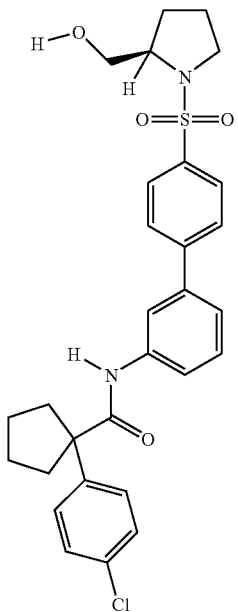
729
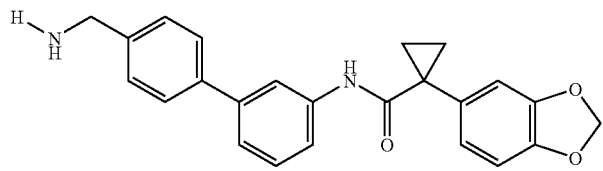
730
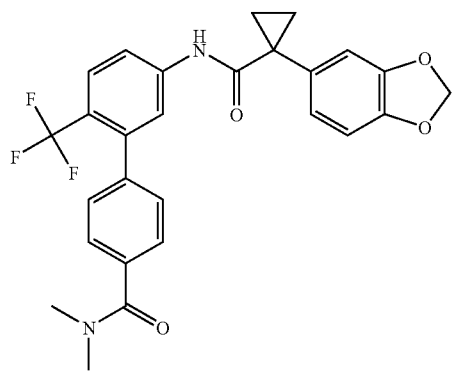

443 444
TABLE 1-continued
Examples of compounds of the present invention.
731
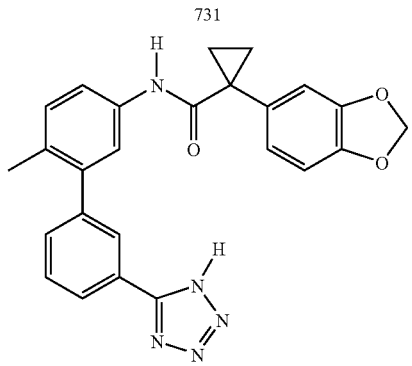
732
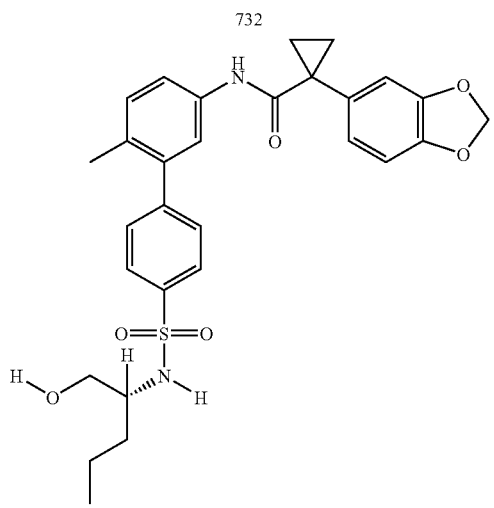
733
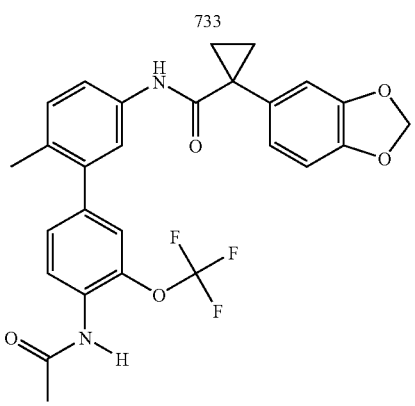
734
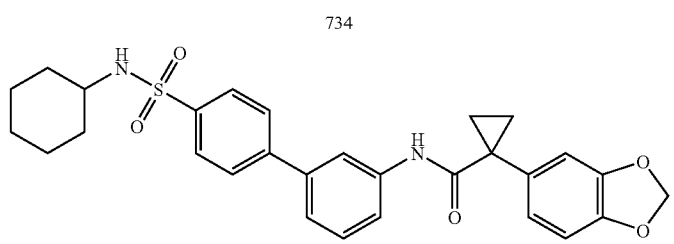

TABLE 1-continued
Examples of compounds of the present invention.
735
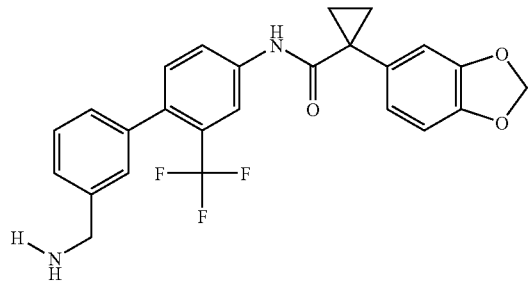
736
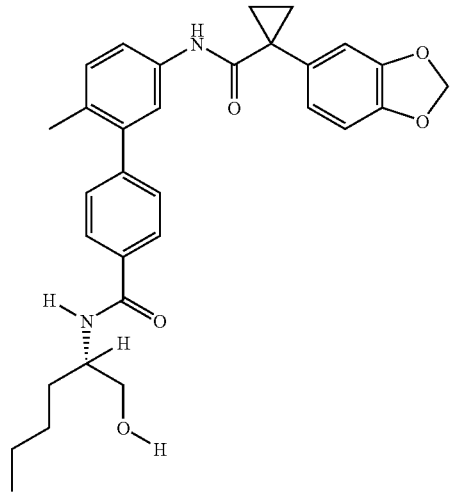
737
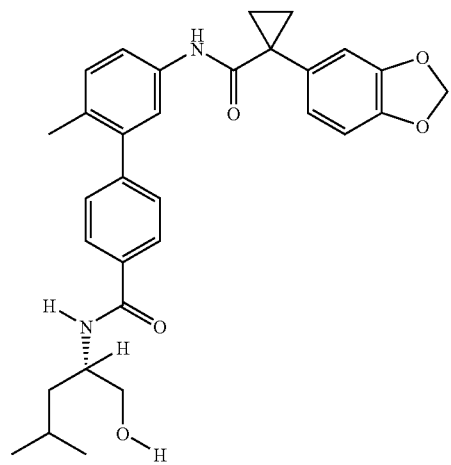

TABLE 1-continued
Examples of compounds of the present invention.
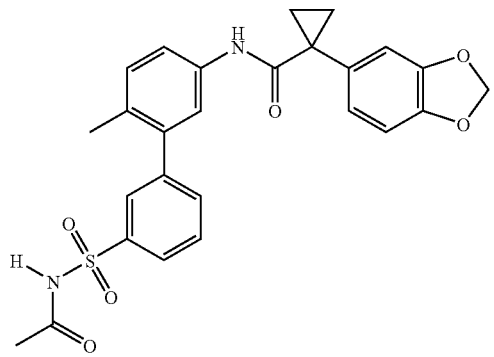
738
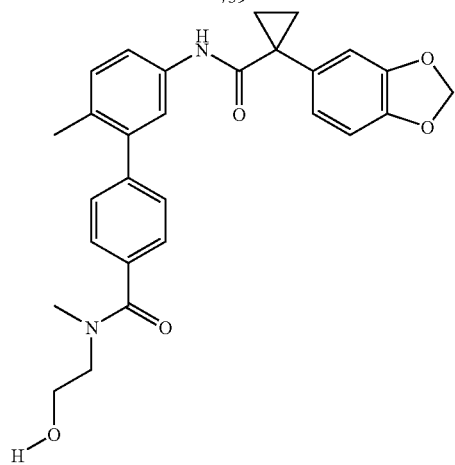
739
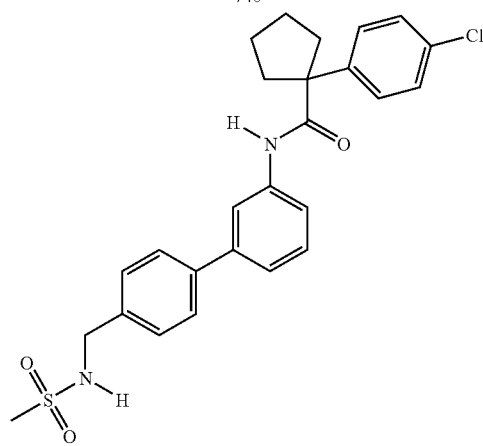
740

TABLE 1-continued
Examples of compounds of the present invention.
741
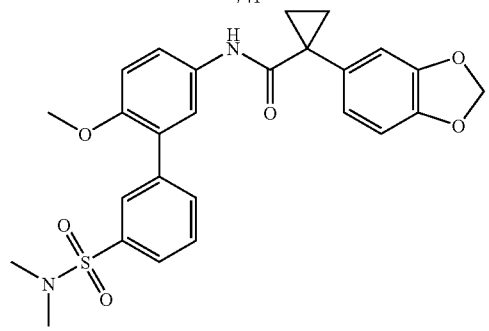
742
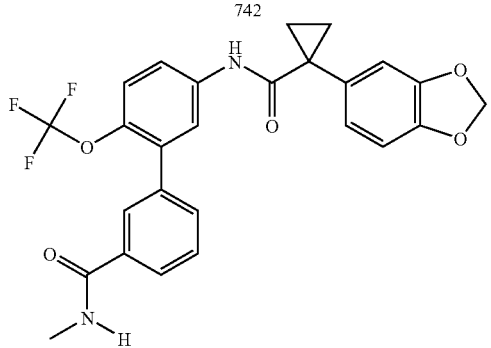
743
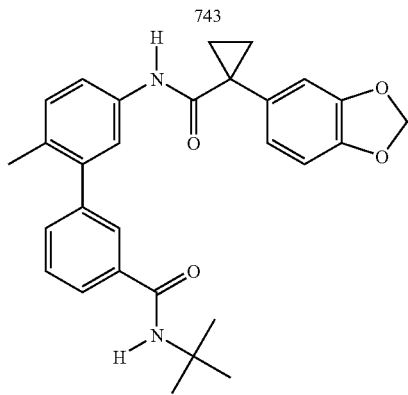
744
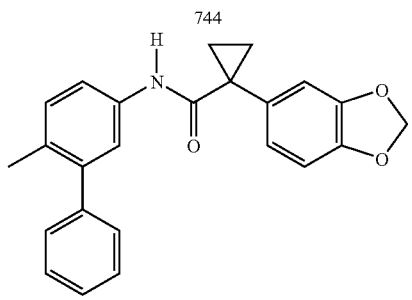

TABLE 1-continued
Examples of compounds of the present invention.
745
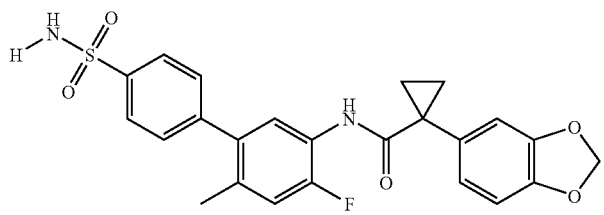
746
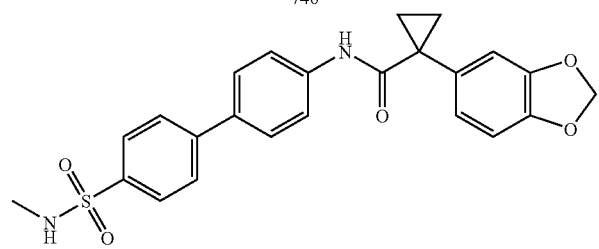
747
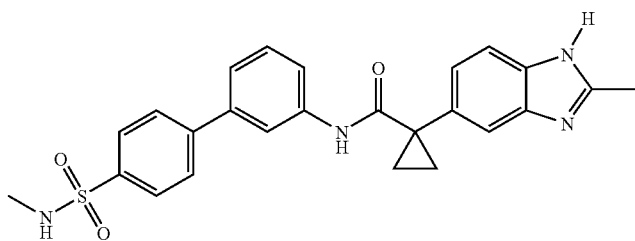
748
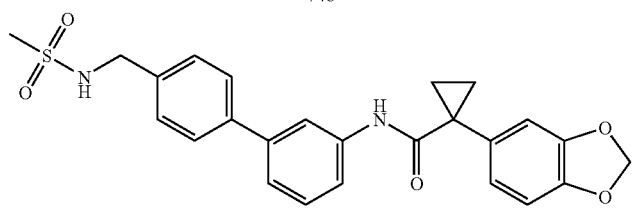
749
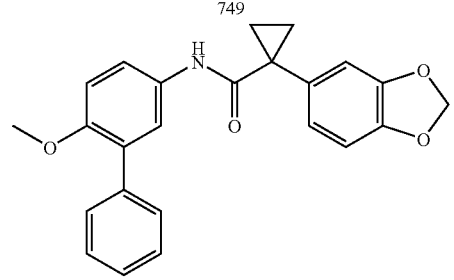

TABLE 1-continued
Examples of compounds of the present invention.
750
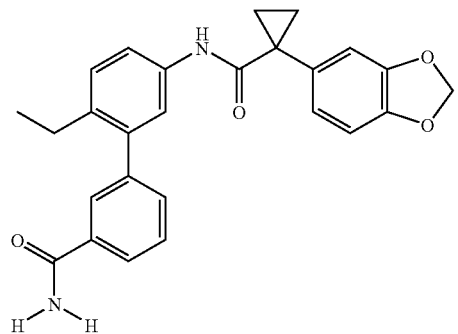
751
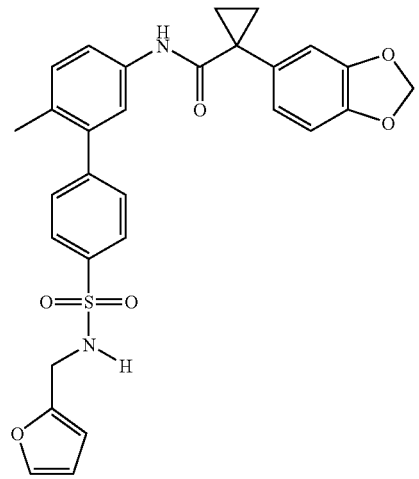
752
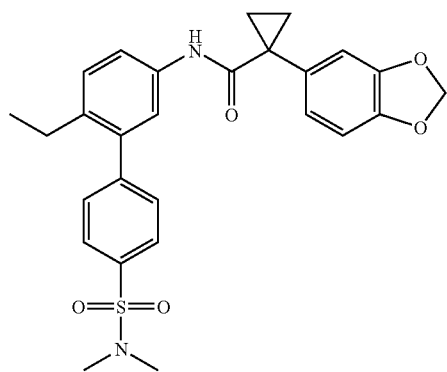
753
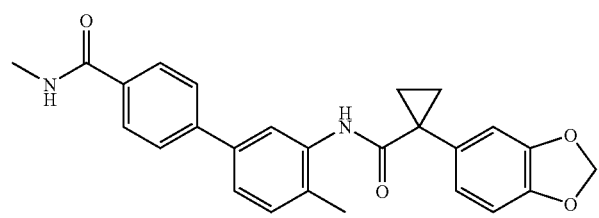

TABLE 1-continued
Examples of compounds of the present invention.
754
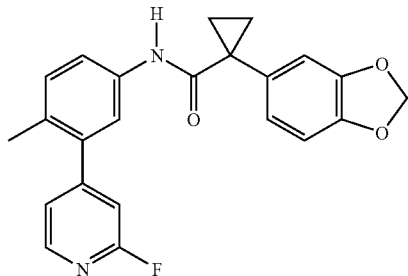
755
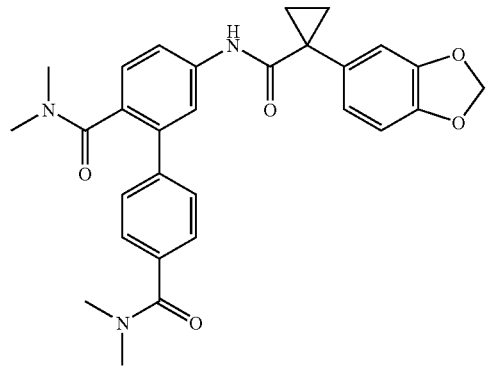
756
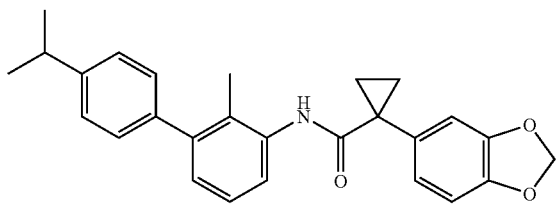
757
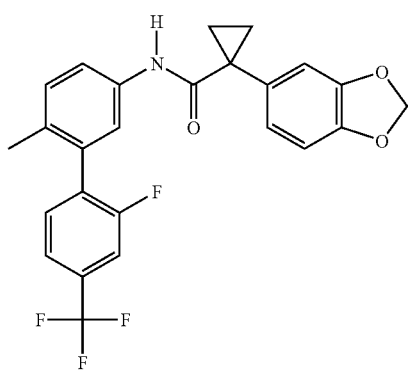

TABLE 1-continued
Examples of compounds of the present invention.
758
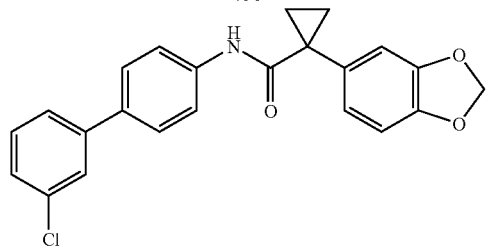
759
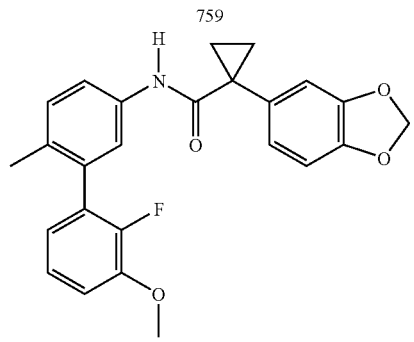
760
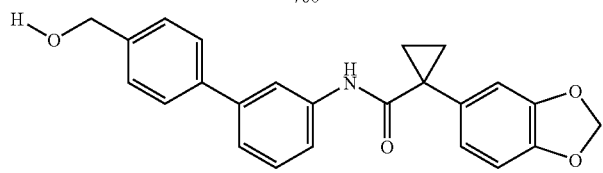
761
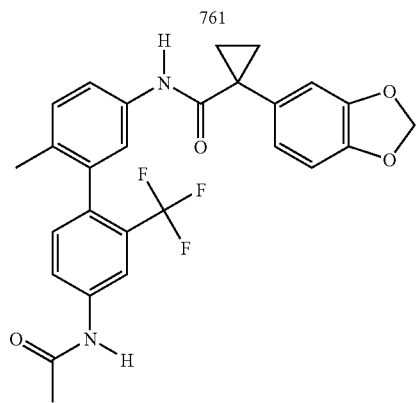

TABLE 1-continued
Examples of compounds of the present invention.
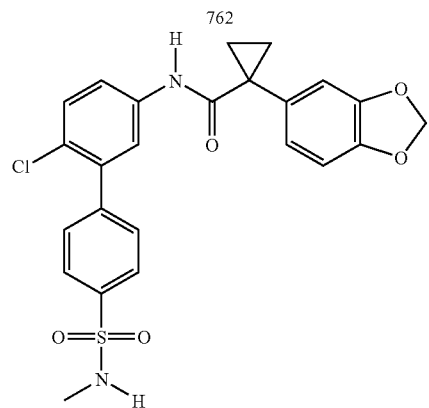
762
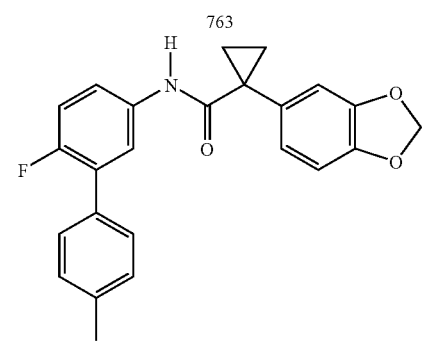
763
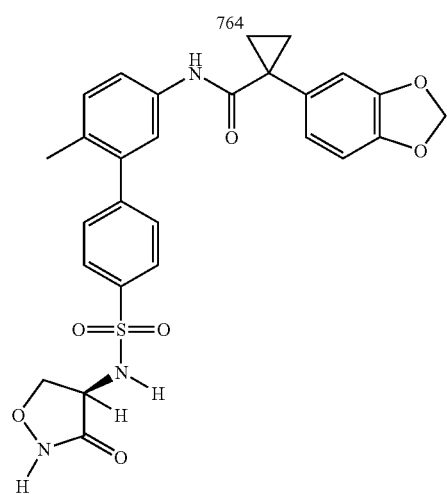
764
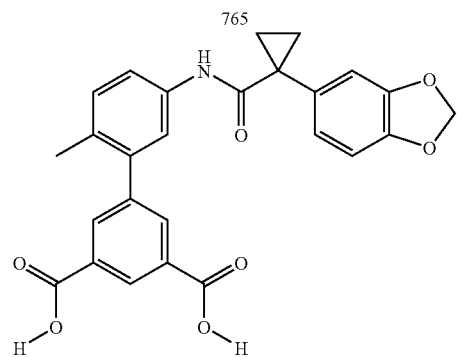
765

TABLE 1-continued
Examples of compounds of the present invention.
766
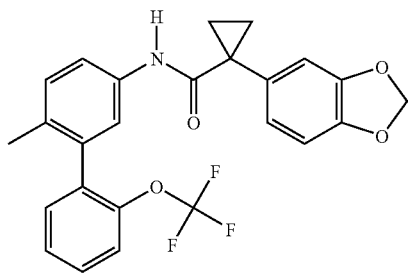
767
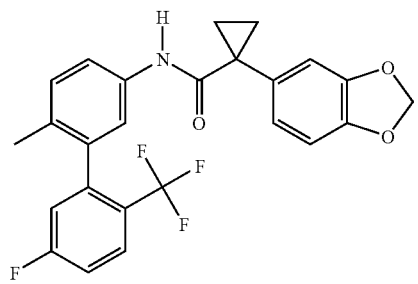
768
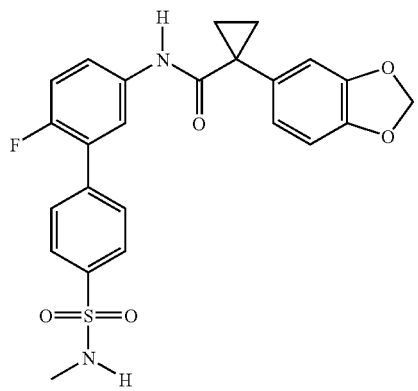
769
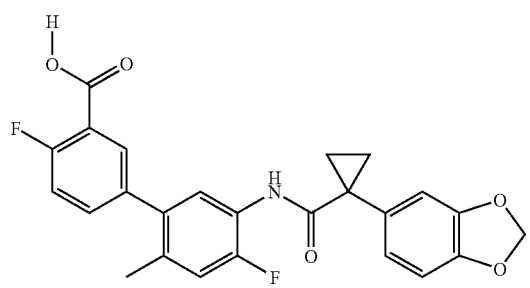

TABLE 1-continued
Examples of compounds of the present invention.
770
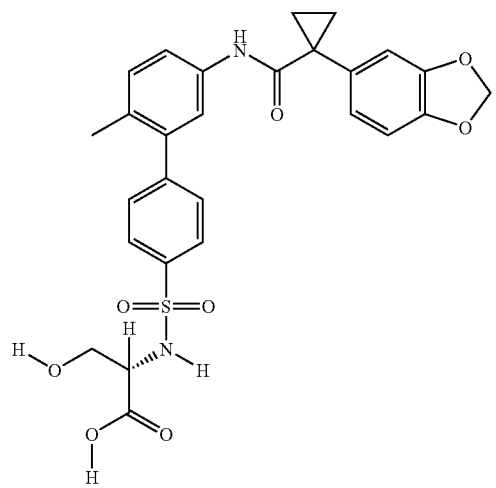
771
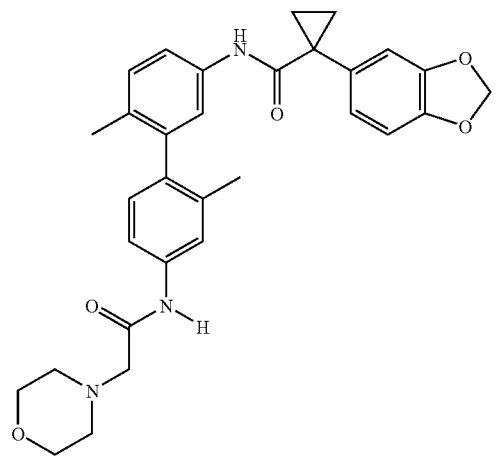
772
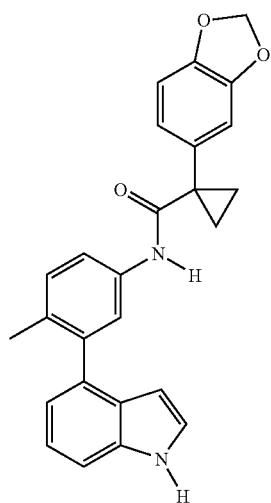

TABLE 1-continued
Examples of compounds of the present invention.
773
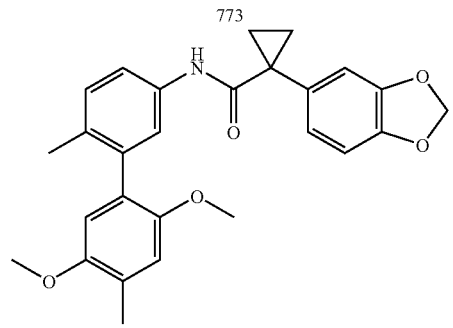
774
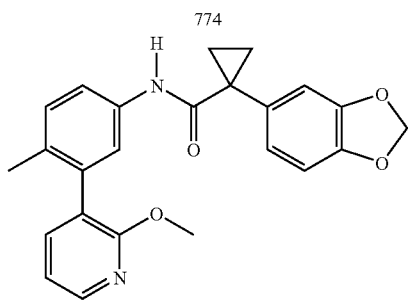
775
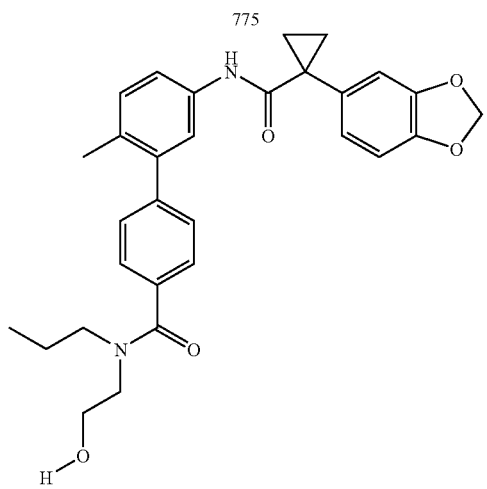
776
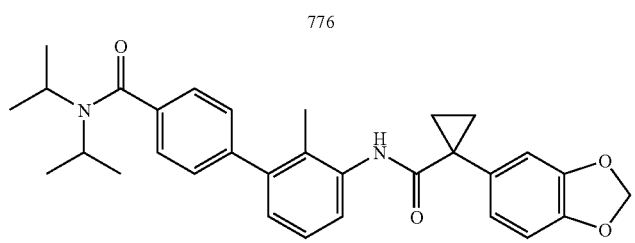
777
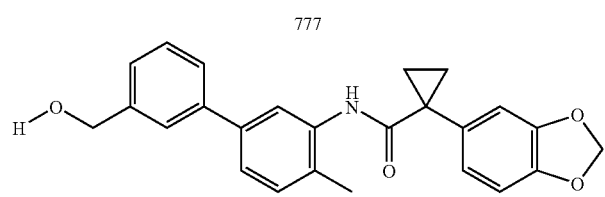

TABLE 1-continued
Examples of compounds of the present invention.
778
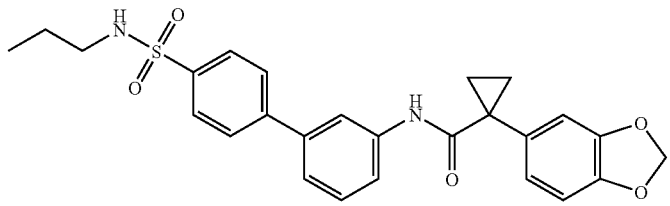
779
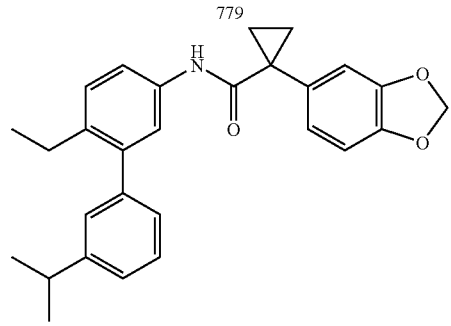
780
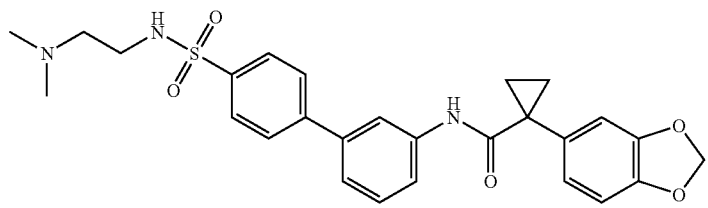
781
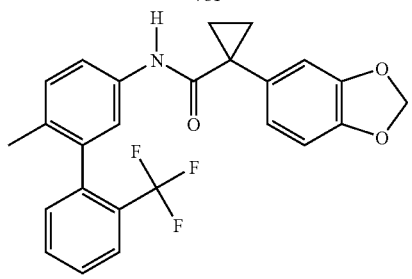
782
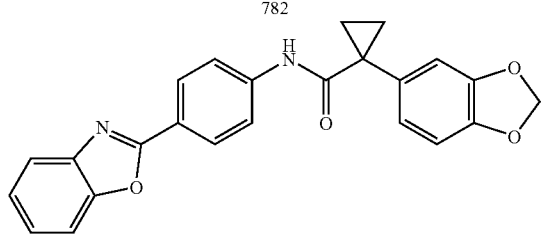

TABLE 1-continued
Examples of compounds of the present invention.
783
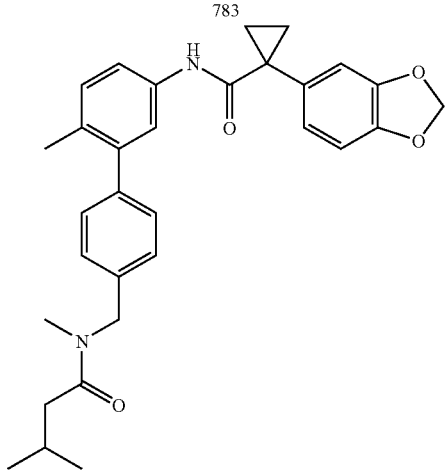
784
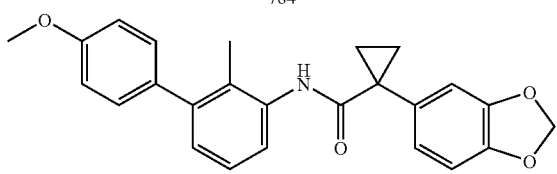
785
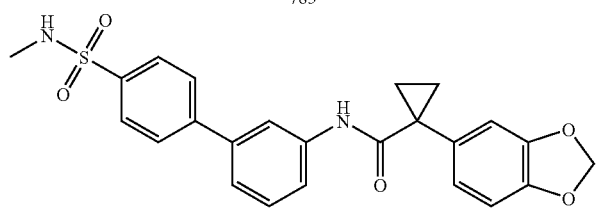
786
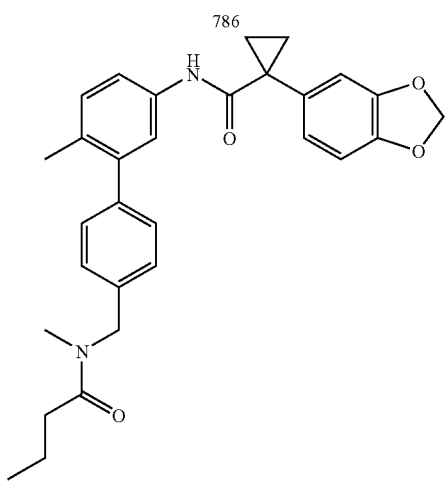

TABLE 1-continued
Examples of compounds of the present invention.
787
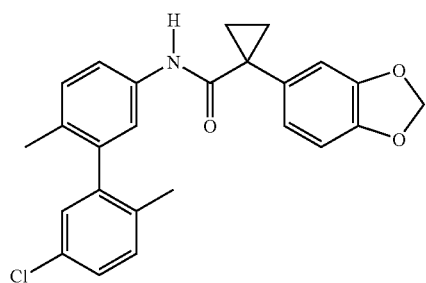
788
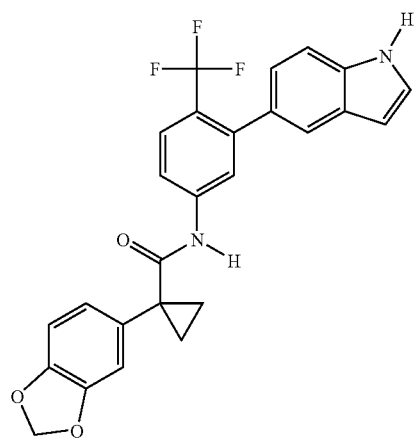
789
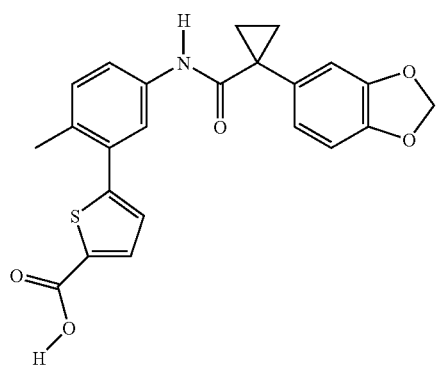

TABLE 1-continued
Examples of compounds of the present invention.
790
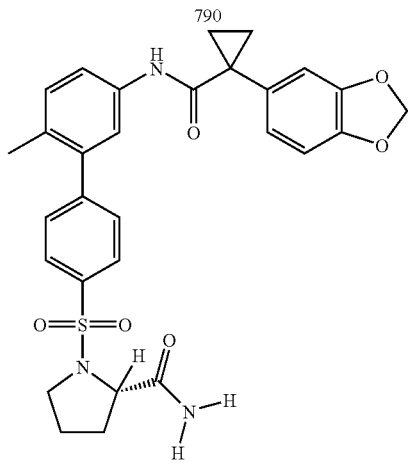
791
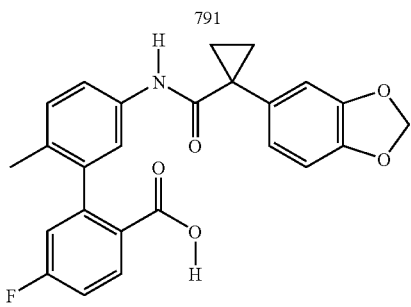
792
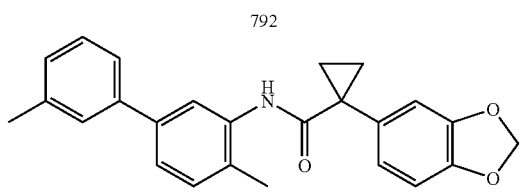
793
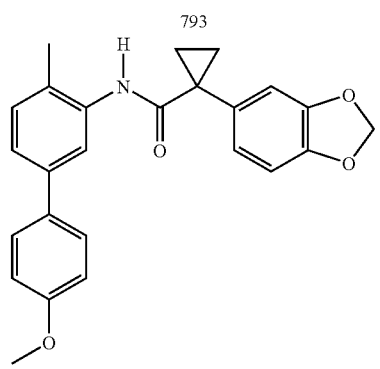
794
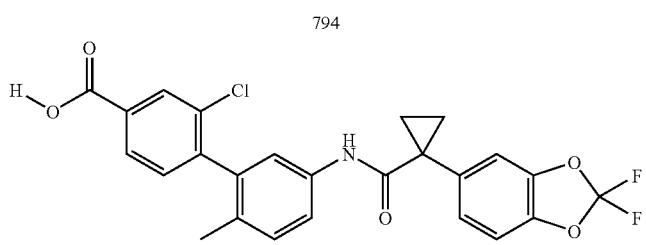

TABLE 1-continued
Examples of compounds of the present invention.
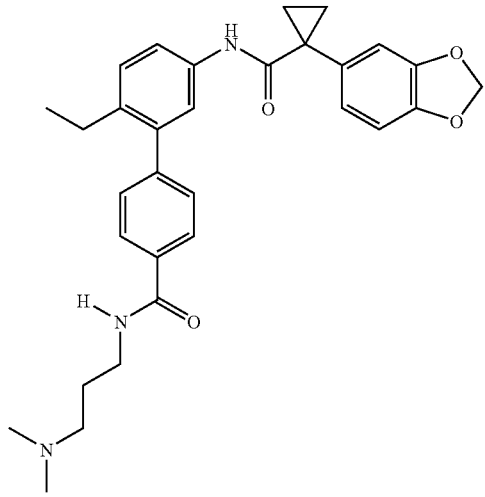
795
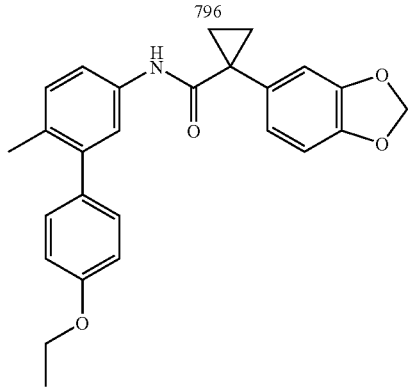
796
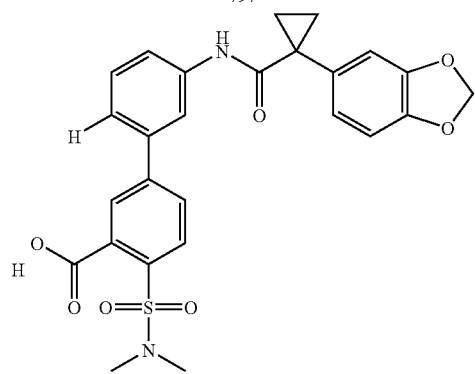
797

TABLE 1-continued
Examples of compounds of the present invention.
798
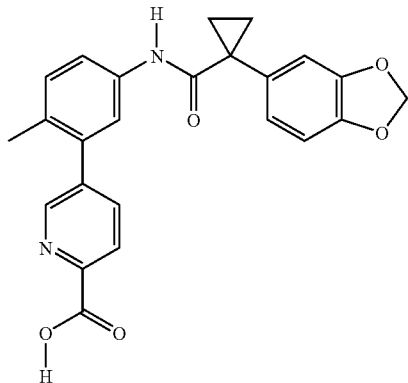
799
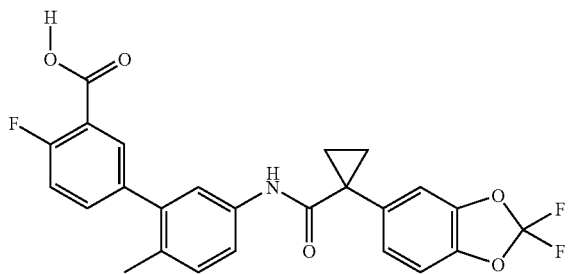
800
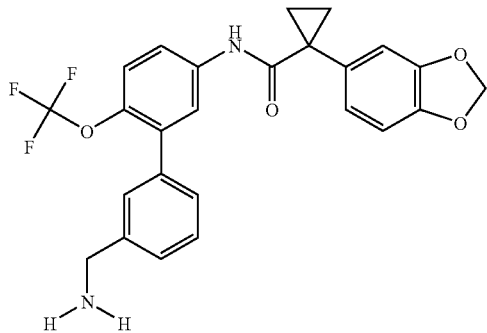
801
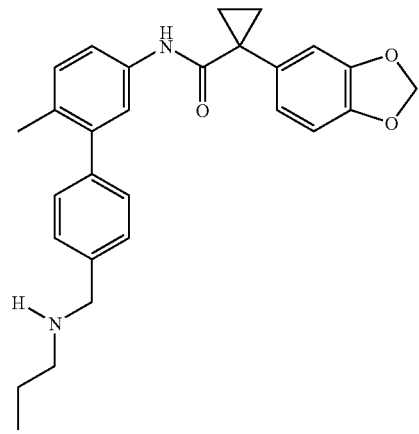

TABLE 1-continued
Examples of compounds of the present invention.
802
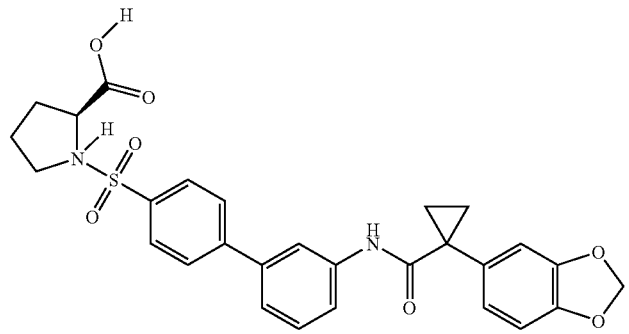
803
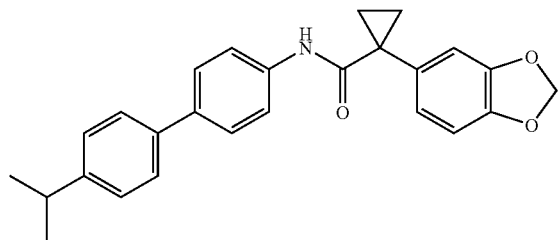
804
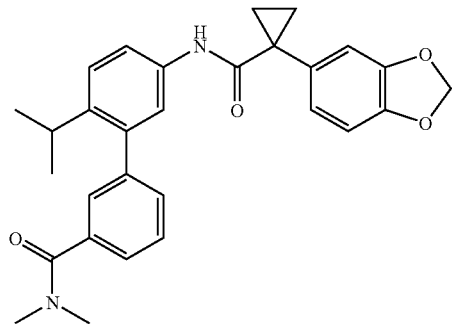
805
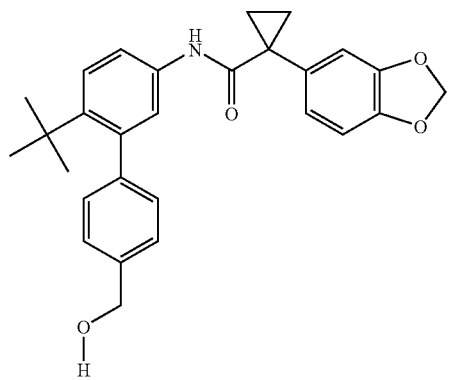

TABLE 1-continued
Examples of compounds of the present invention.
806
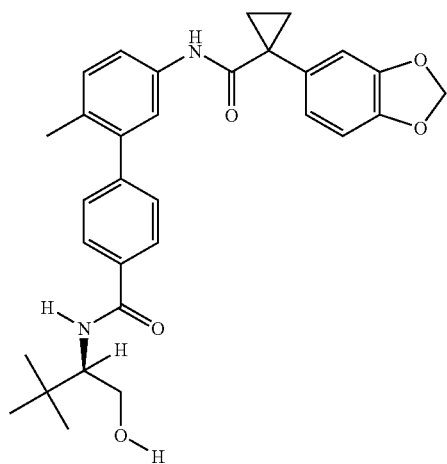
807
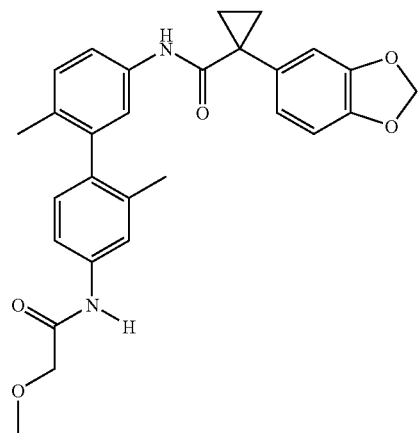
808
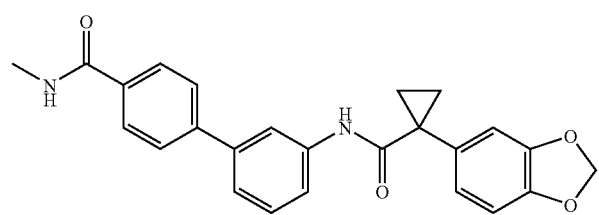

TABLE 1-continued
Examples of compounds of the present invention.
809
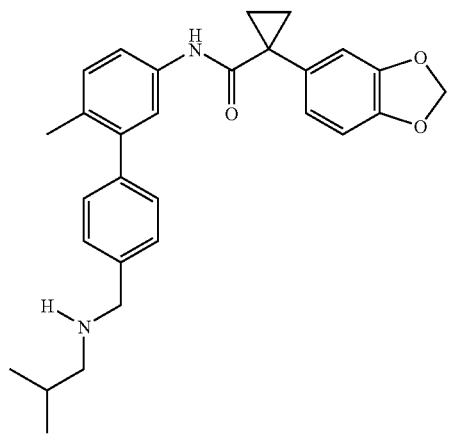
810
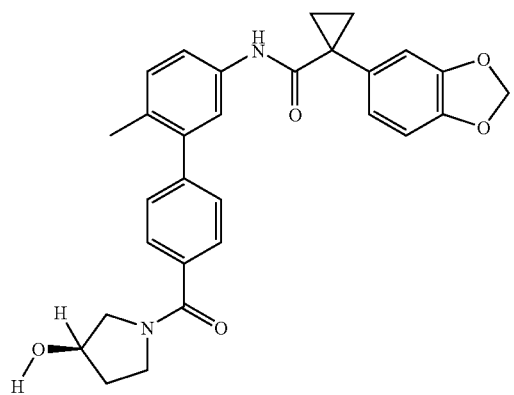
811
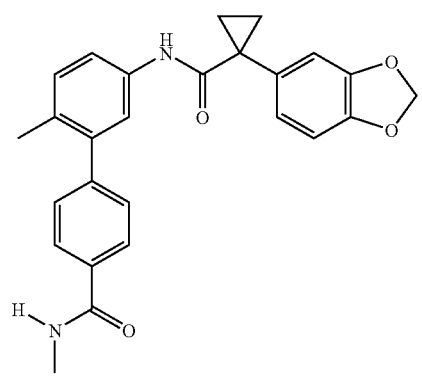

TABLE 1-continued
Examples of compounds of the present invention.
812
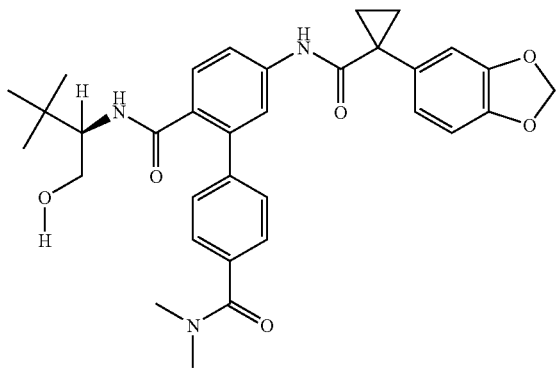
813
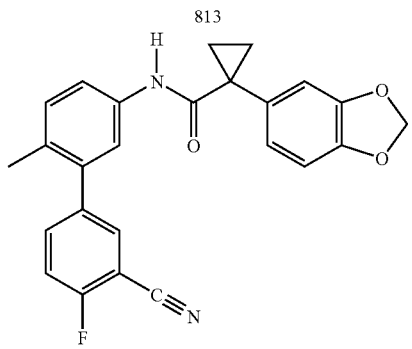
814
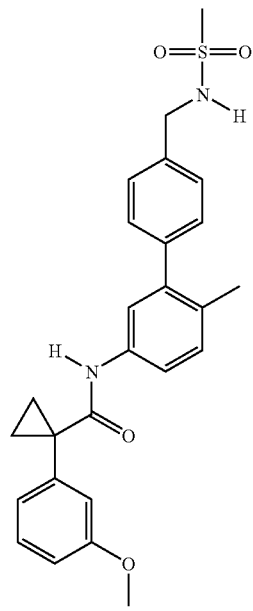
815
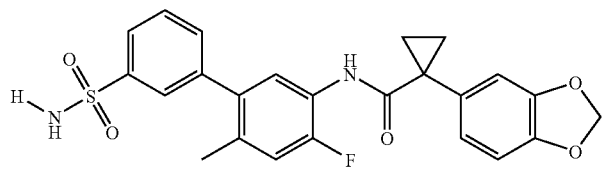

TABLE 1-continued
Examples of compounds of the present invention.
816
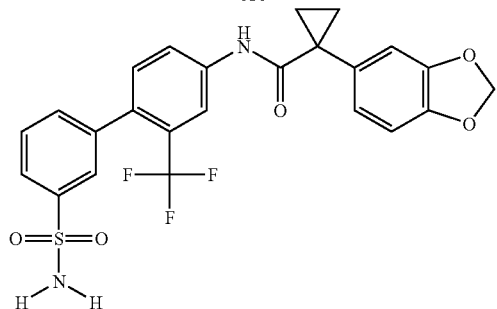
817
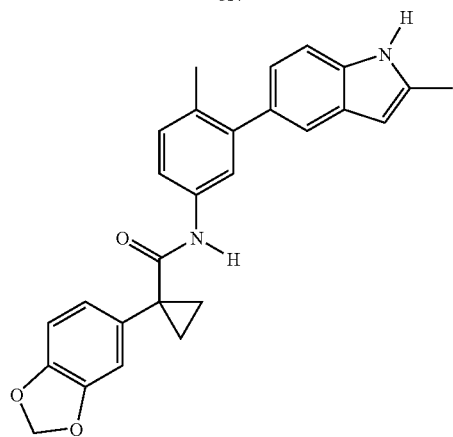
818
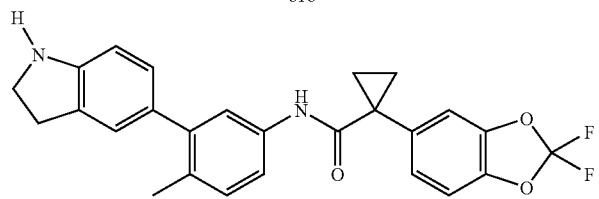
819
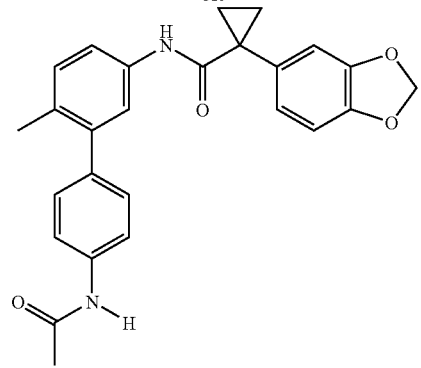

TABLE 1-continued
Examples of compounds of the present invention.
820
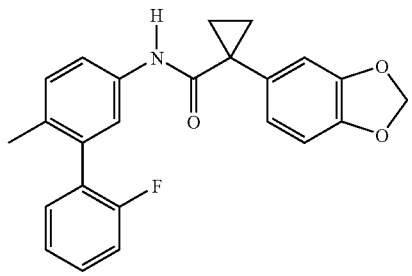
821
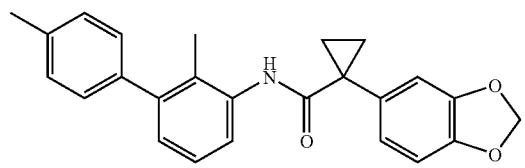
822
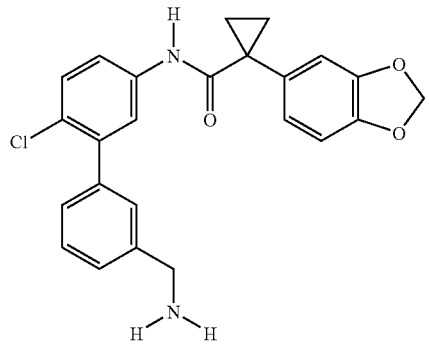
823
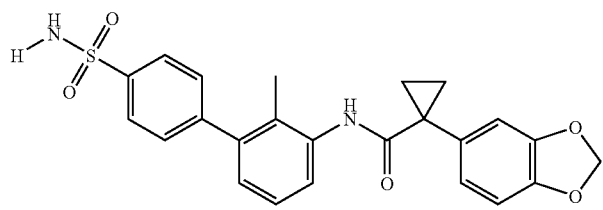
824
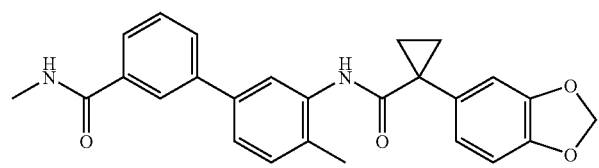

TABLE 1-continued
Examples of compounds of the present invention.
825
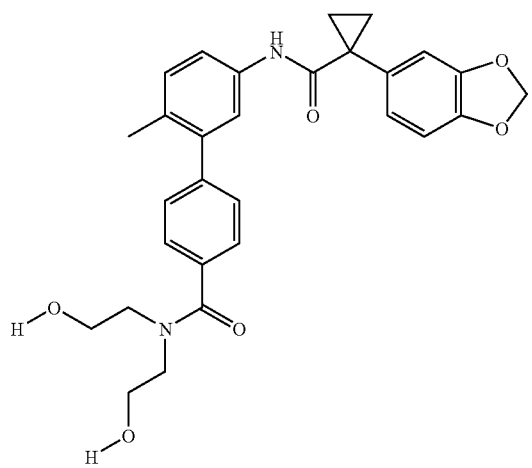
826
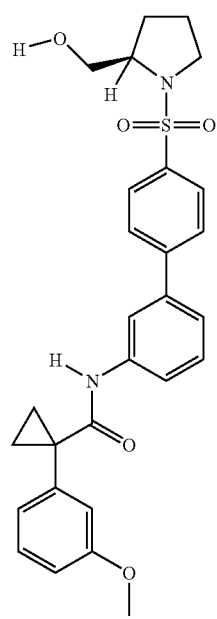

TABLE 1-continued
Examples of compounds of the present invention.
827
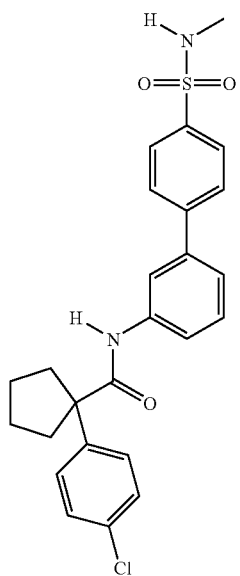
828
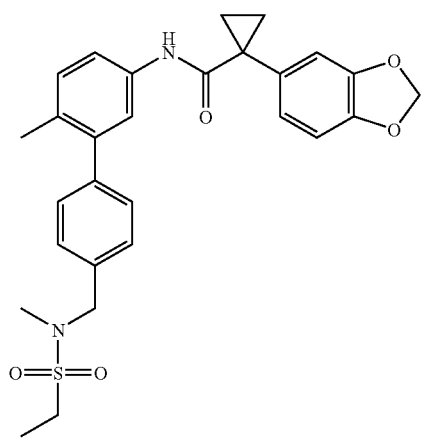
829
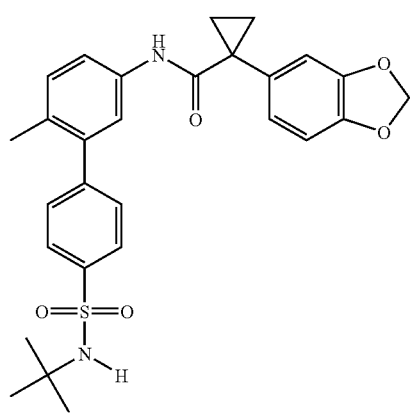

TABLE 1-continued
Examples of compounds of the present invention.
830
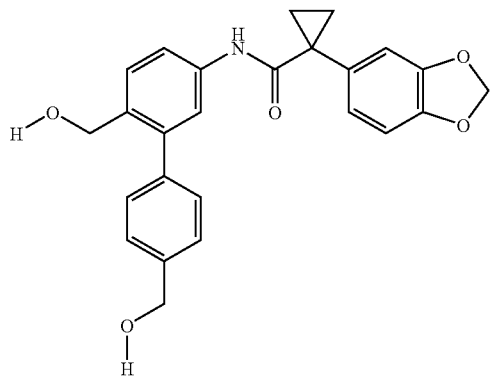
831
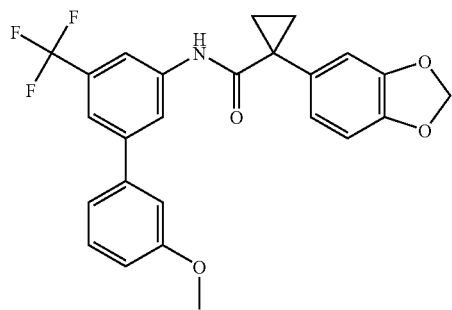
832
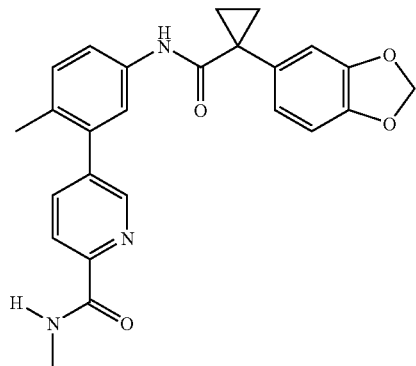
833
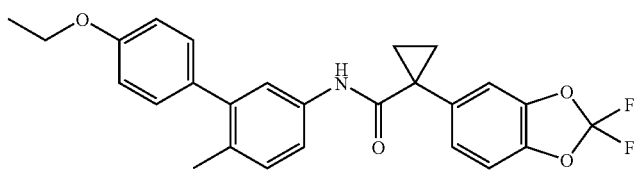

TABLE 1-continued
Examples of compounds of the present invention.
834
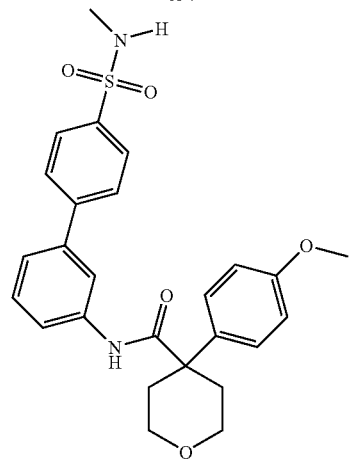
835
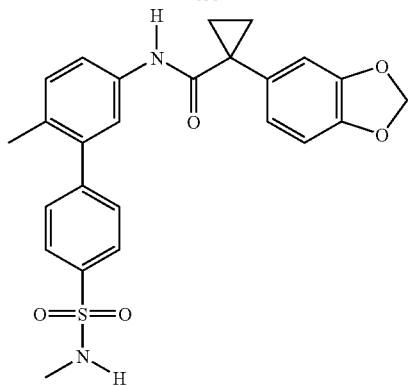
836
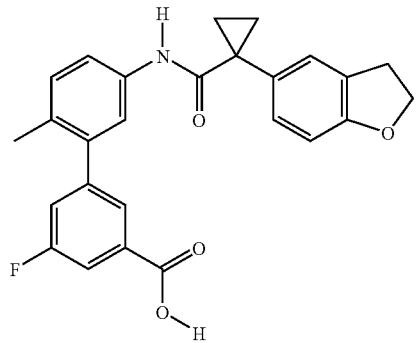
837
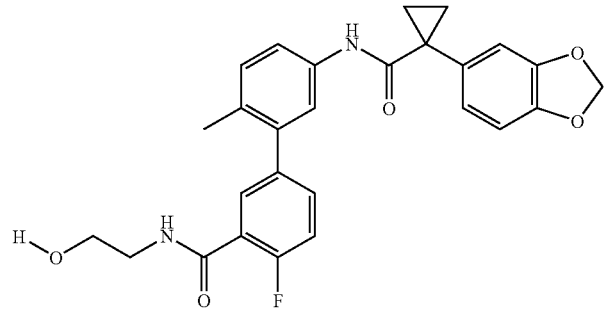

TABLE 1-continued
Examples of compounds of the present invention.
838
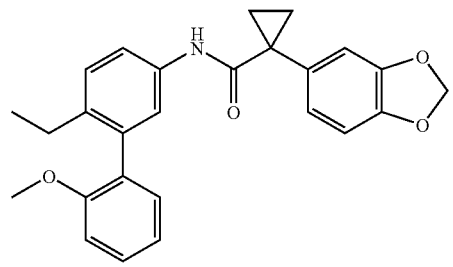
839
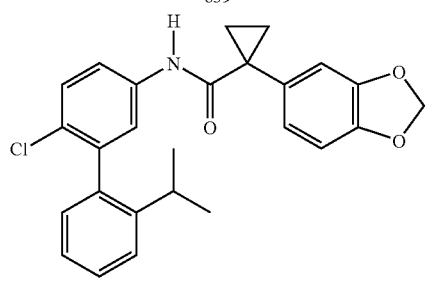
840
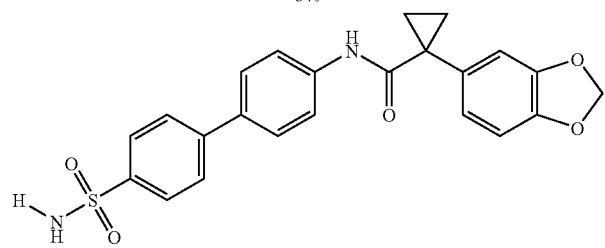
841
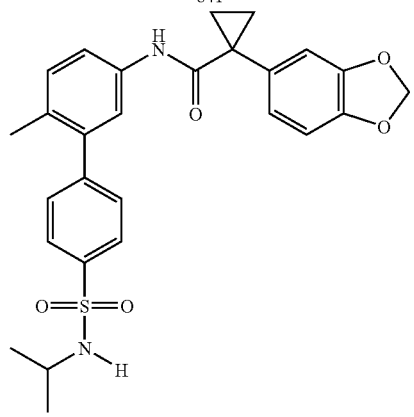
842
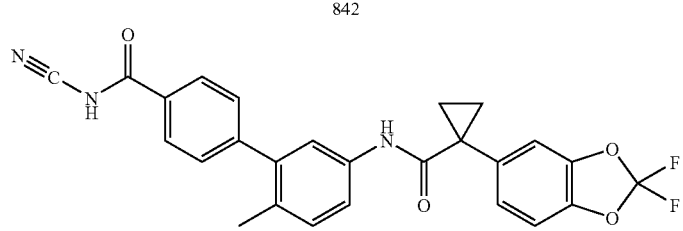

TABLE 1-continued
Examples of compounds of the present invention.
843
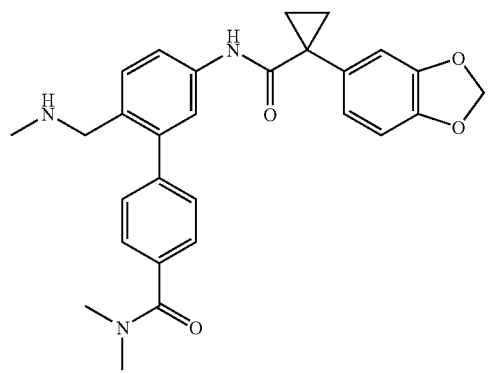
844
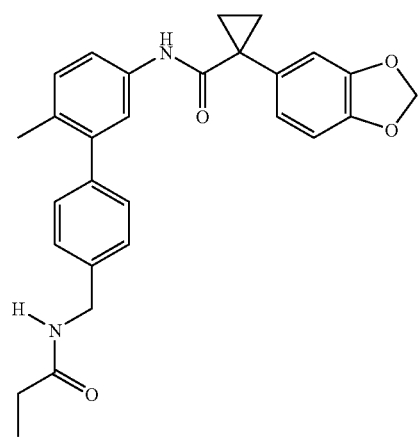
845
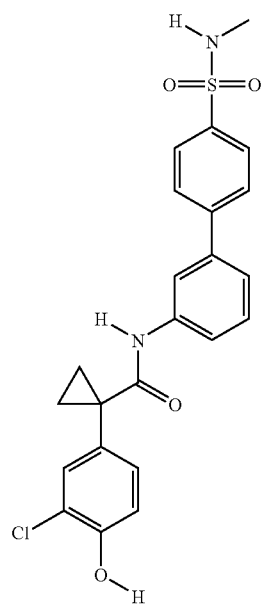

TABLE 1-continued
Examples of compounds of the present invention.
846
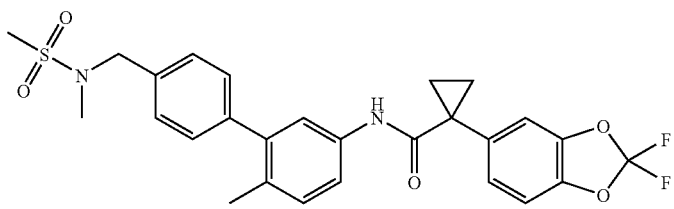
847
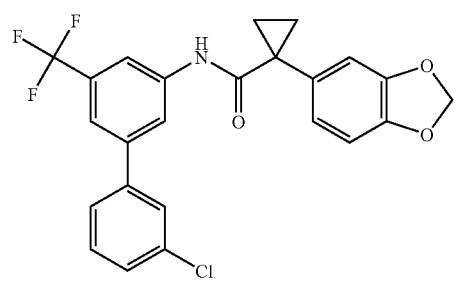
848
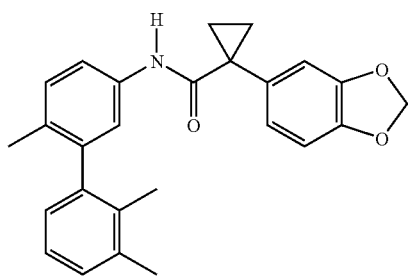
849
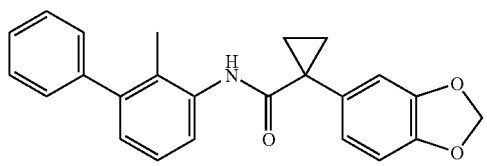
850
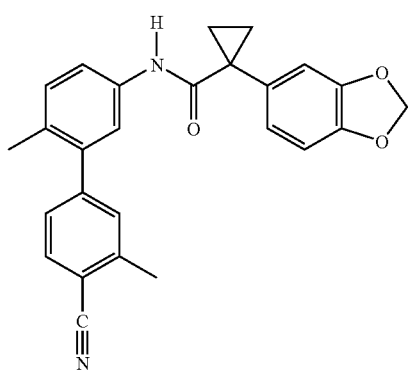

TABLE 1-continued
Examples of compounds of the present invention.
851
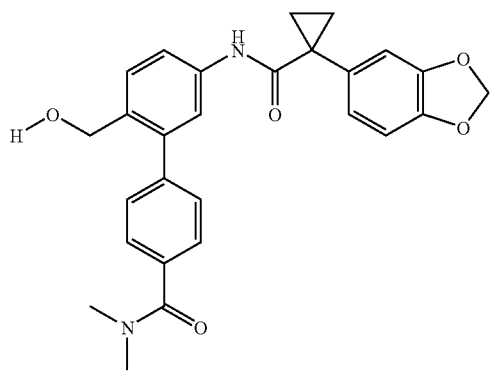
852
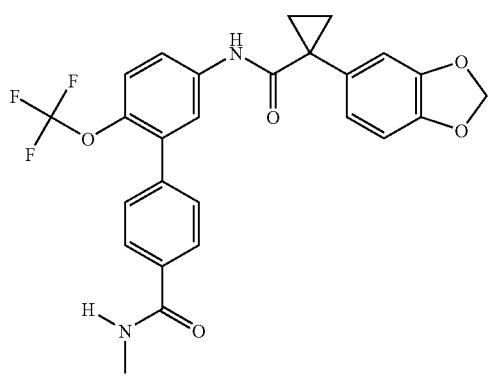
853
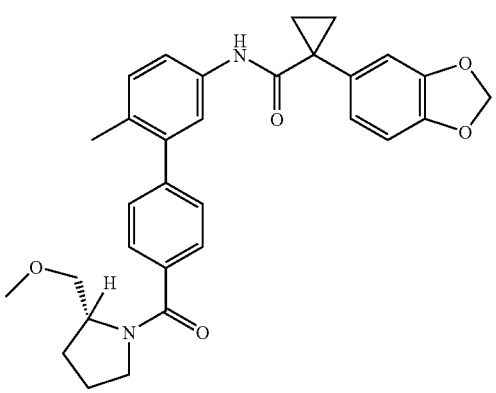
854
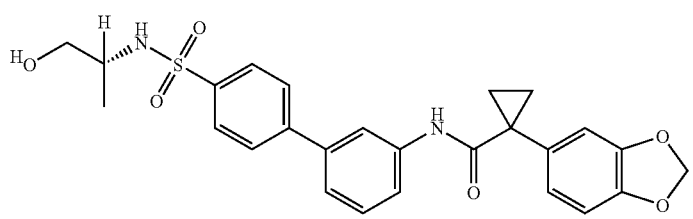

TABLE 1-continued
Examples of compounds of the present invention.
855
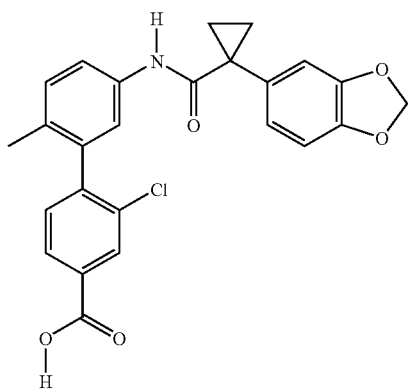
856
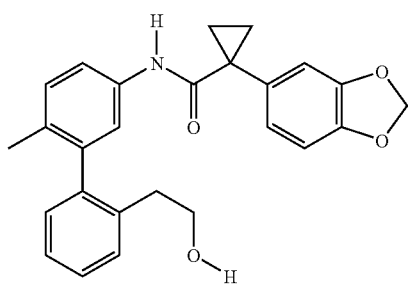
857
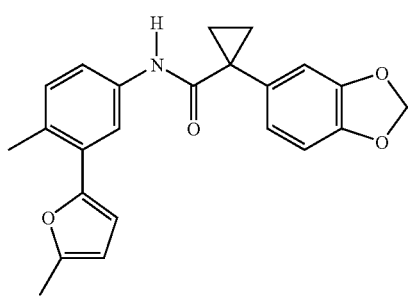
858
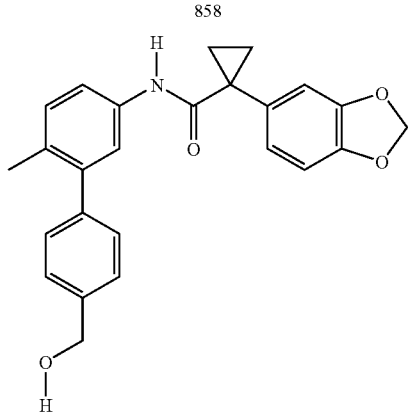

TABLE 1-continued
Examples of compounds of the present invention.
859
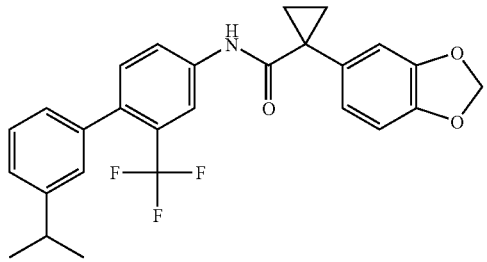
860
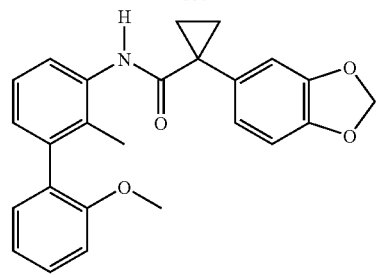
861
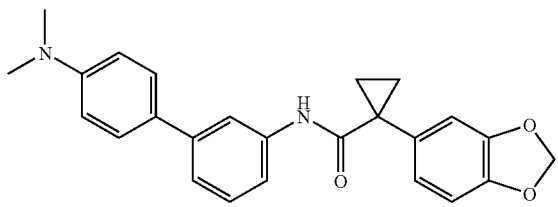
862
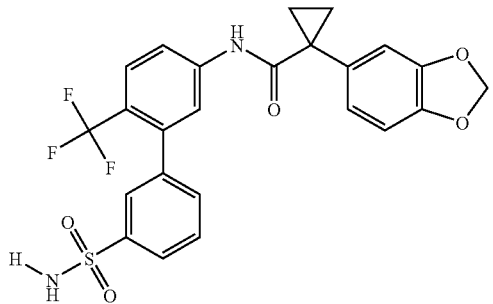
863
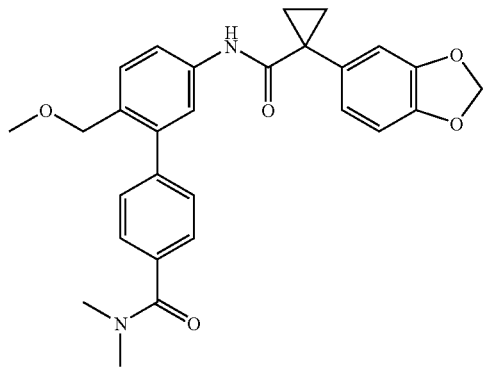

TABLE 1-continued
Examples of compounds of the present invention.
864
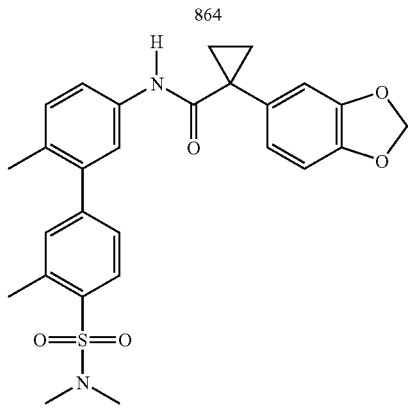
865
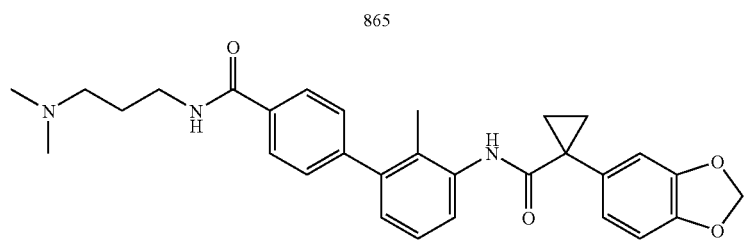
866
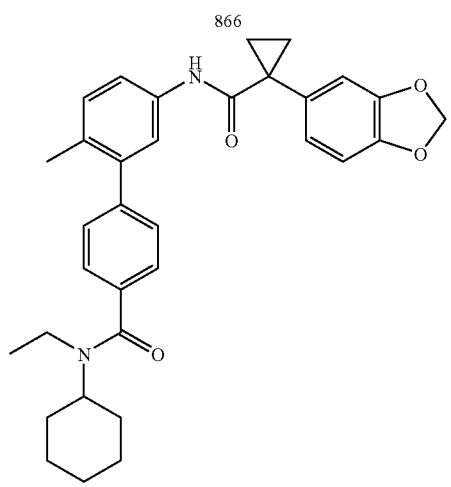
867
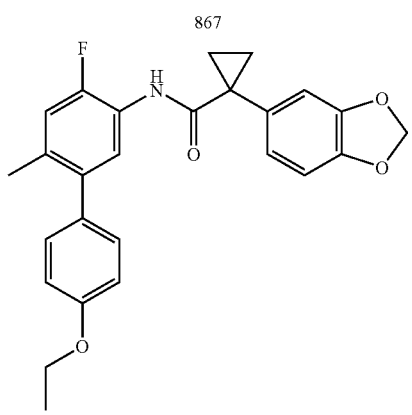

TABLE 1-continued
Examples of compounds of the present invention.
868
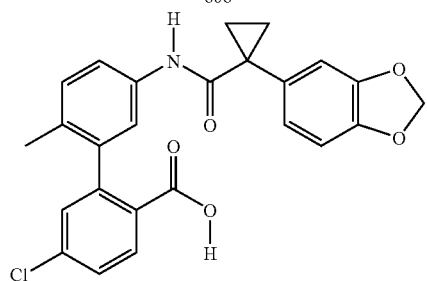
869
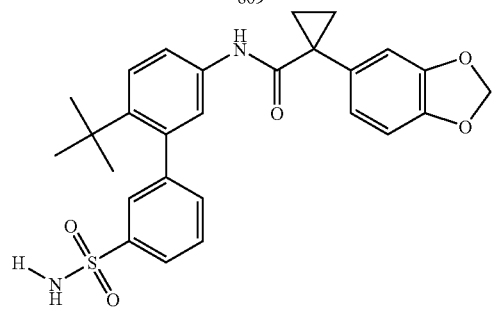
870
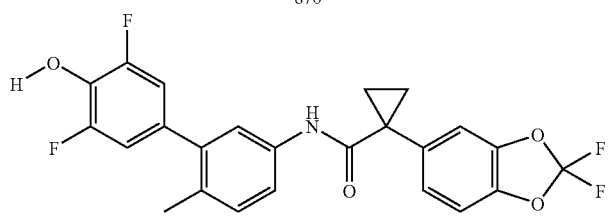
871
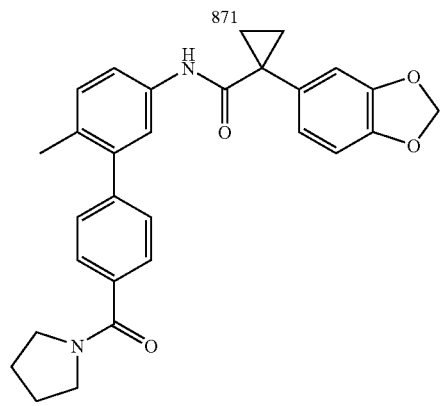
872
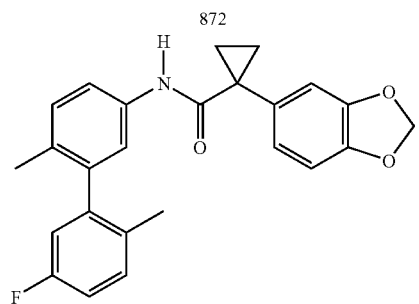

TABLE 1-continued
Examples of compounds of the present invention.
873
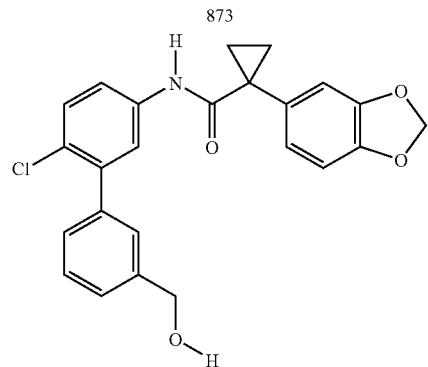
874
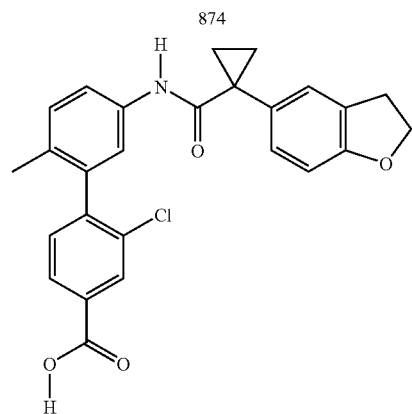
875
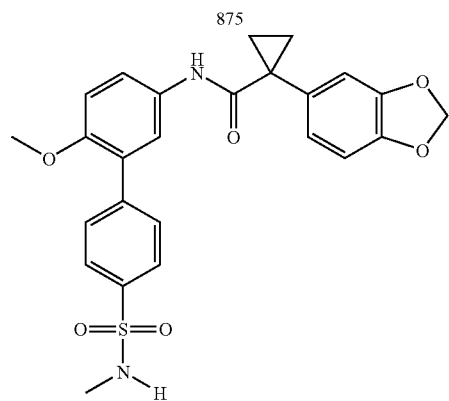
876
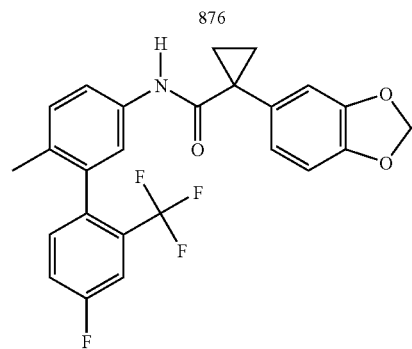

TABLE 1-continued
Examples of compounds of the present invention.
877
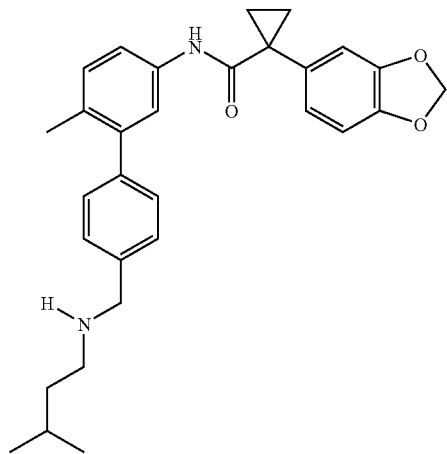
878
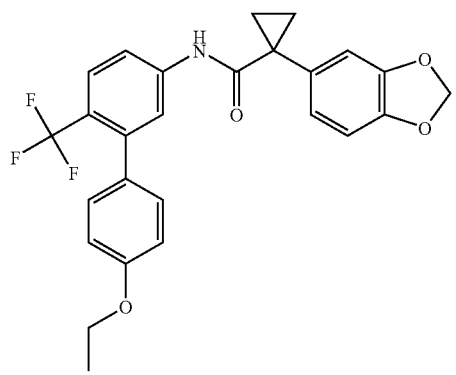
879
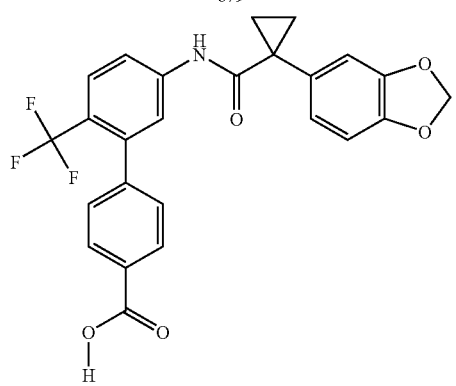

TABLE 1-continued
Examples of compounds of the present invention.
880
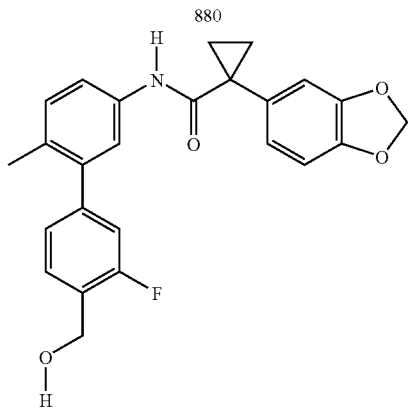
881
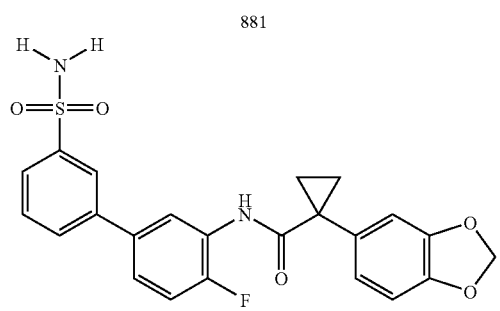
882
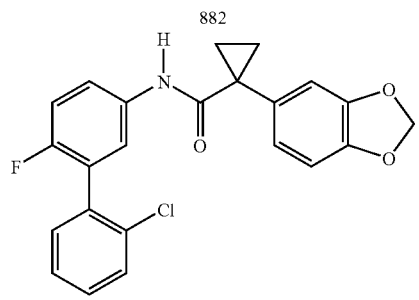
883
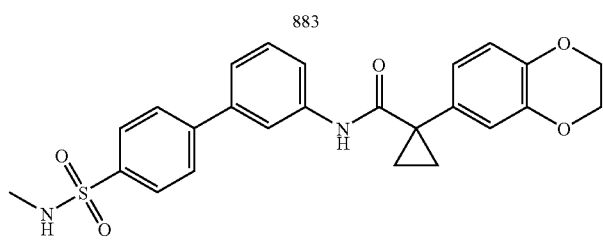
884
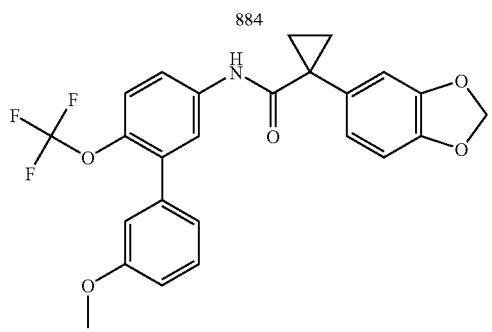

TABLE 1-continued
Examples of compounds of the present invention.
885
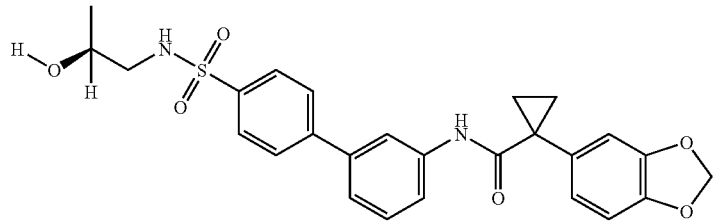
886
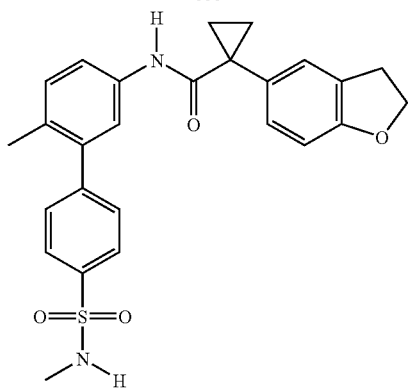
887
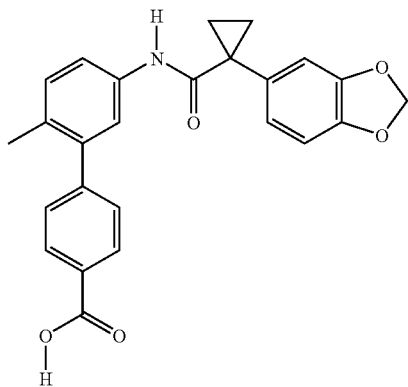
888
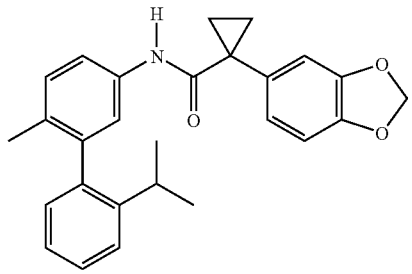

TABLE 1-continued
Examples of compounds of the present invention.
889
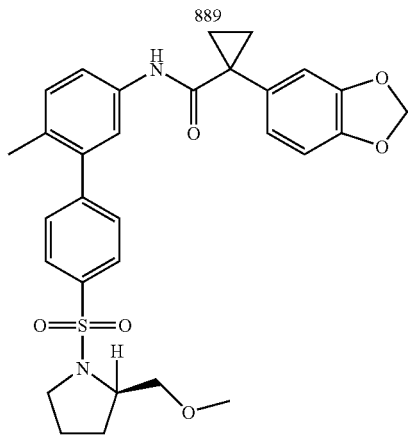
890
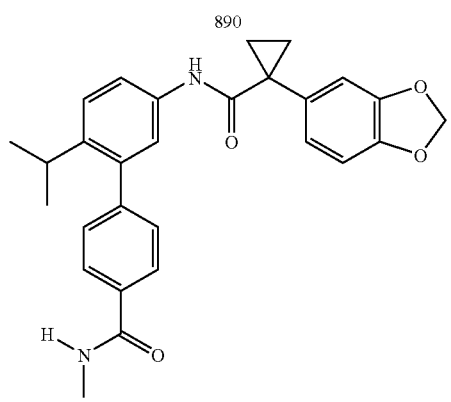
891
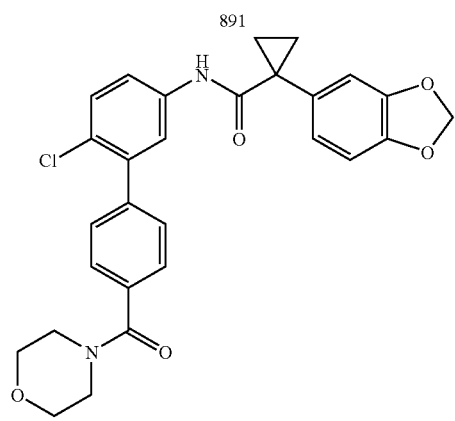

TABLE 1-continued
Examples of compounds of the present invention.
892
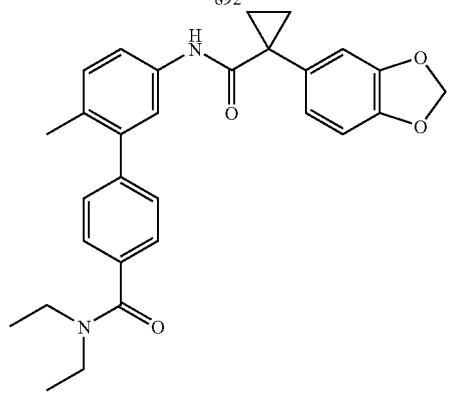
893
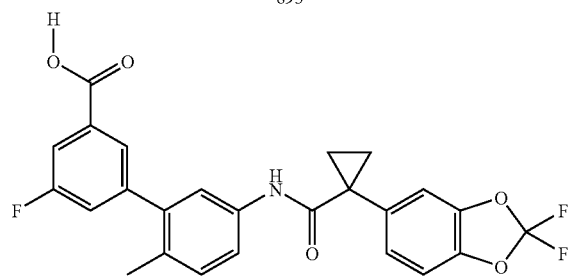
894
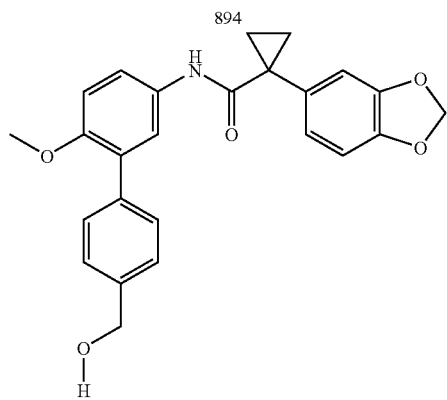
895
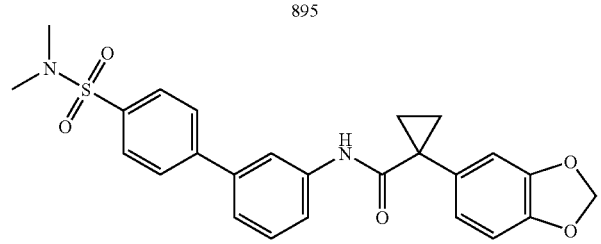

TABLE 1-continued
Examples of compounds of the present invention.
896
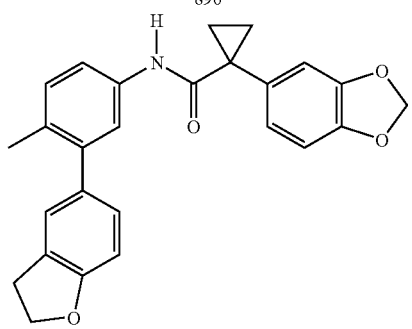
897
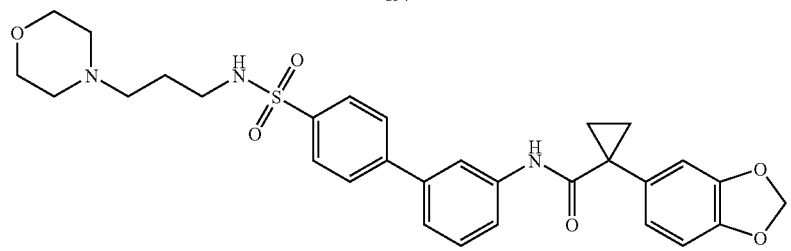
898
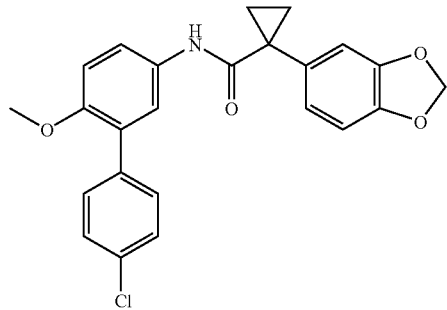
899
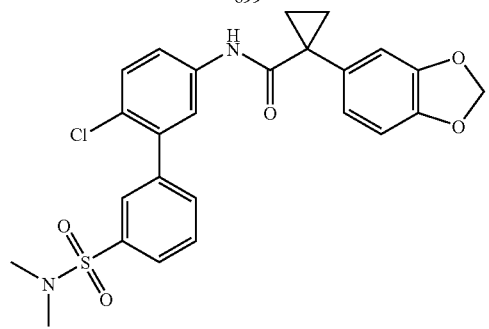

TABLE 1-continued
Examples of compounds of the present invention.
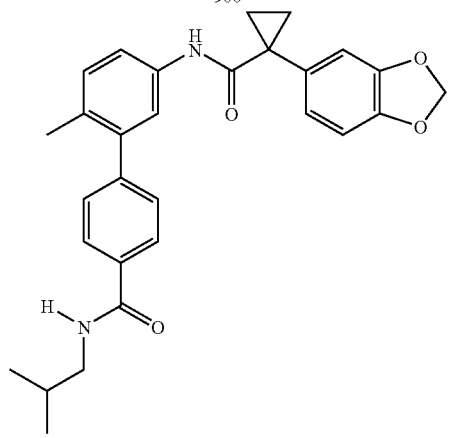
900
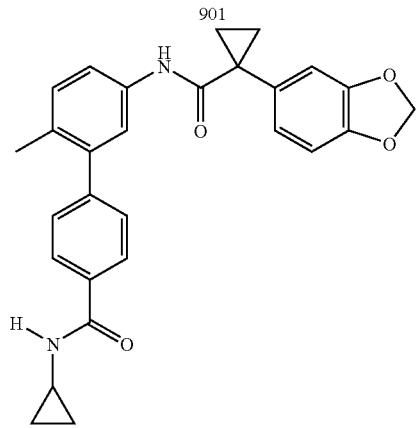
901
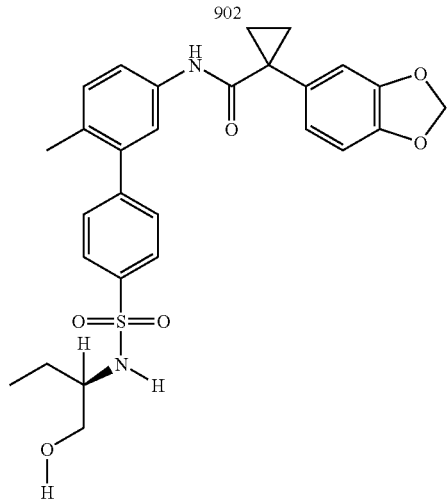
902

TABLE 1-continued
Examples of compounds of the present invention.
903
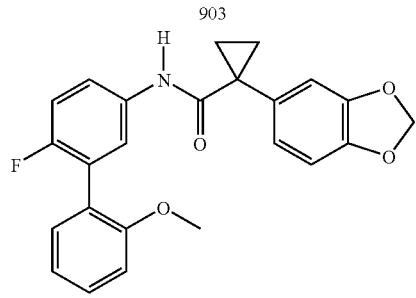
904
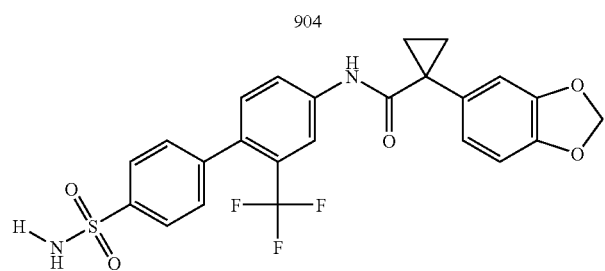
905
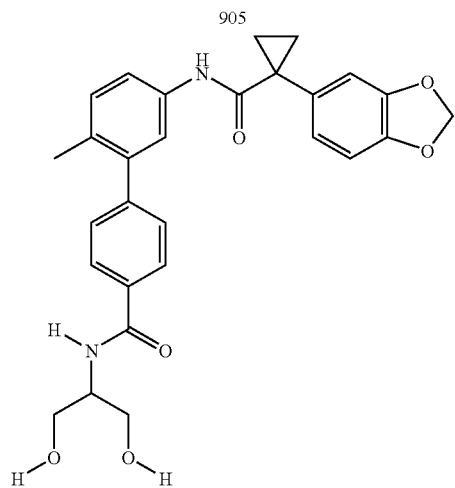
906
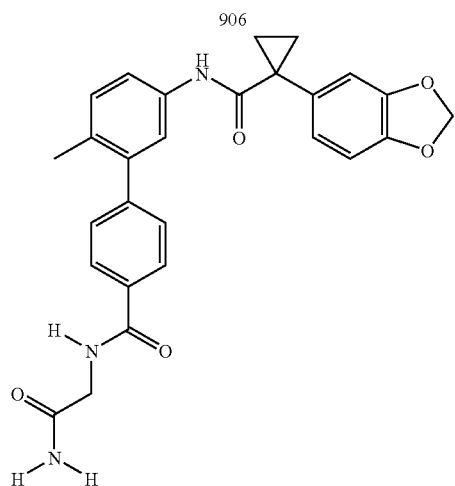

TABLE 1-continued
Examples of compounds of the present invention.
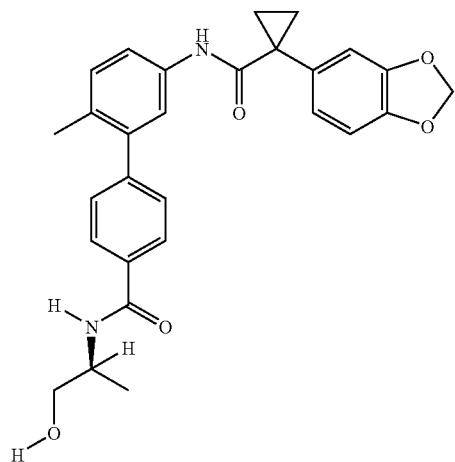
907
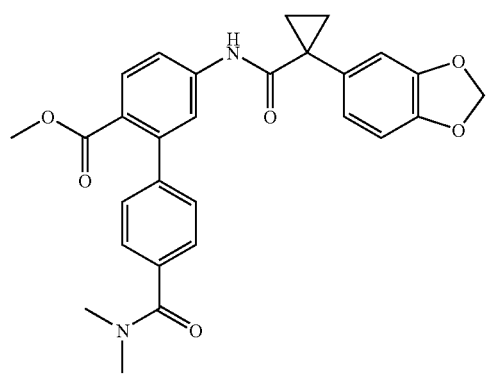
908
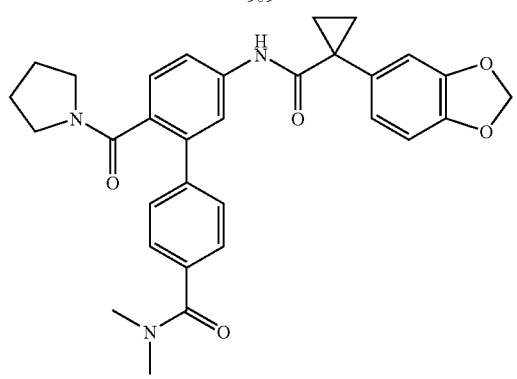
909

TABLE 1-continued
Examples of compounds of the present invention.
910
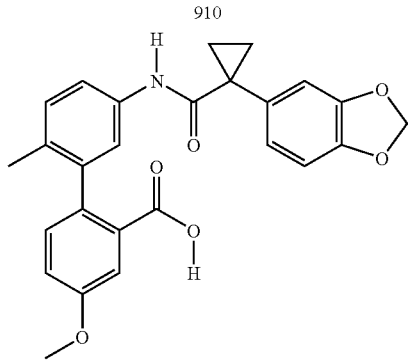
911
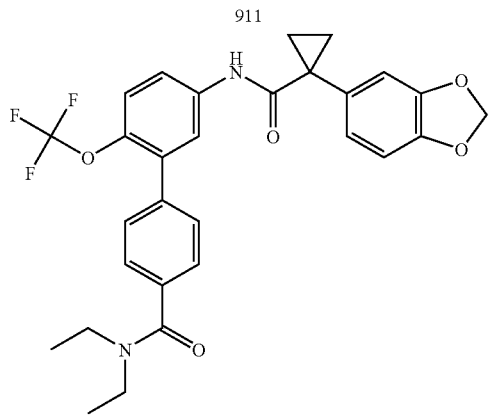
912
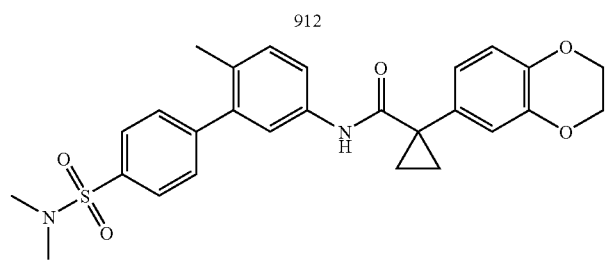
913
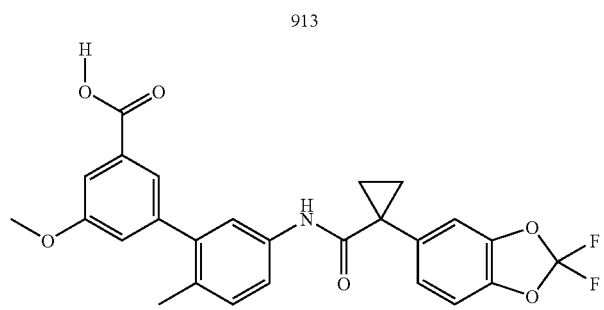

TABLE 1-continued
Examples of compounds of the present invention.
914
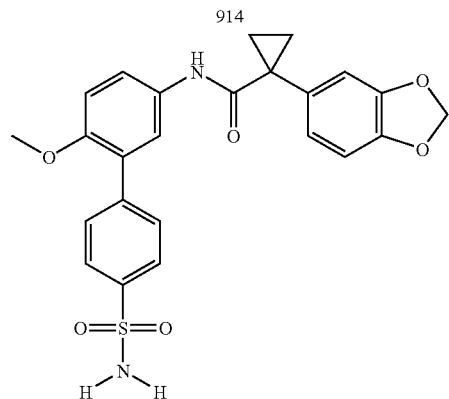
915
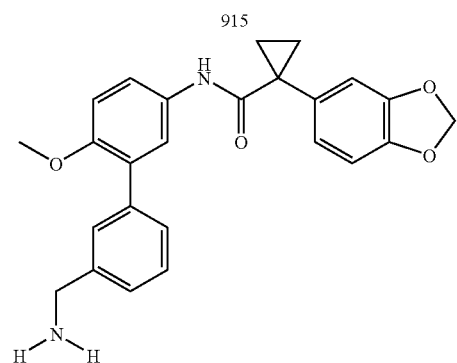
916
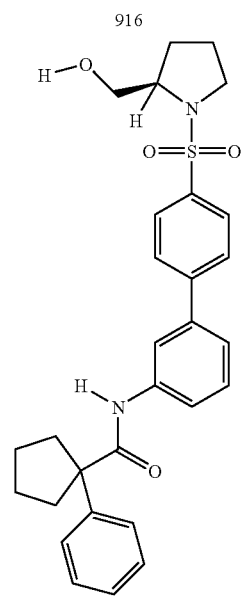

TABLE 1-continued
Examples of compounds of the present invention.
917
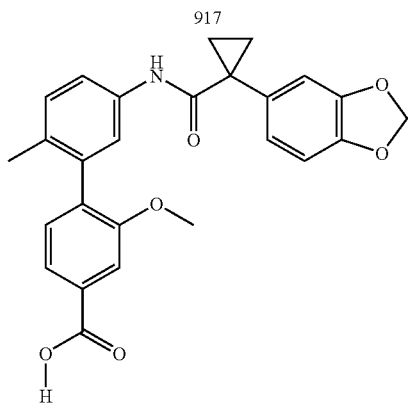
918
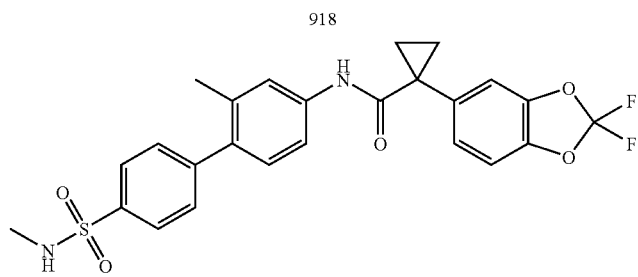
919
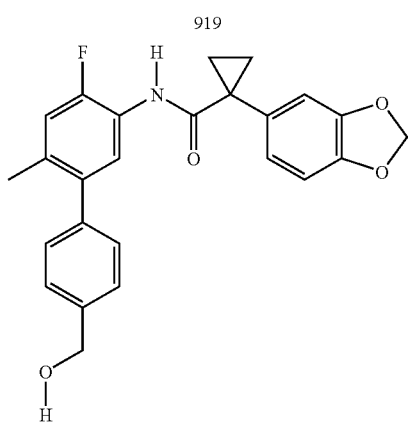
920
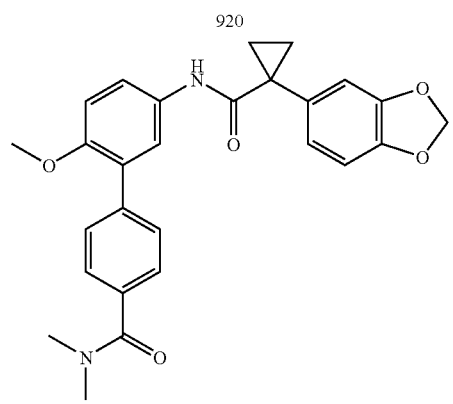

TABLE 1-continued
Examples of compounds of the present invention.
921
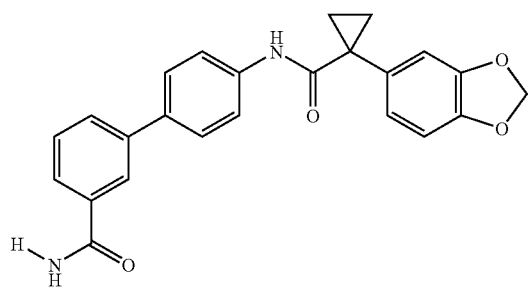
922
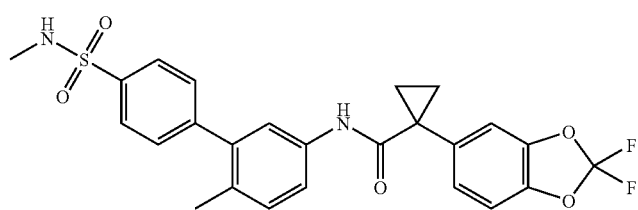
923
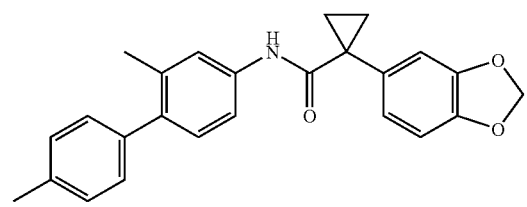
924
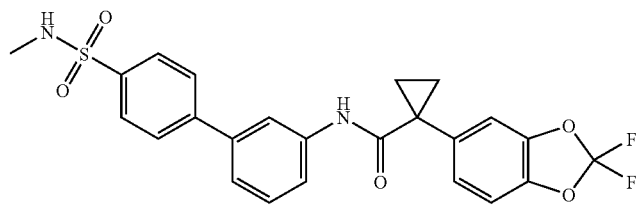
925
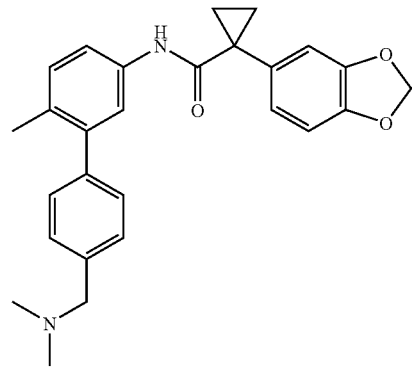

TABLE 1-continued
Examples of compounds of the present invention.
926
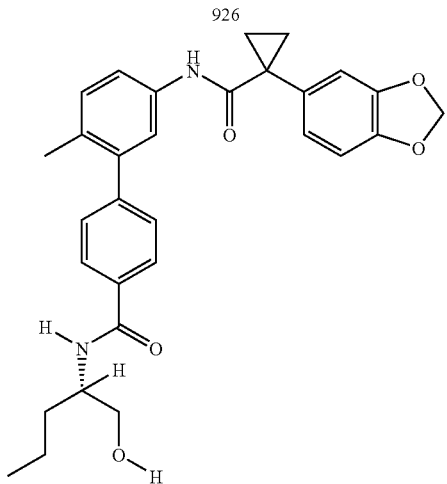
927
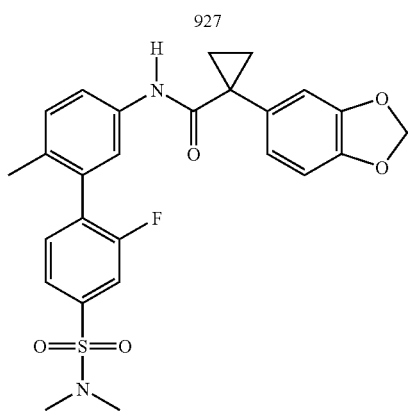
928
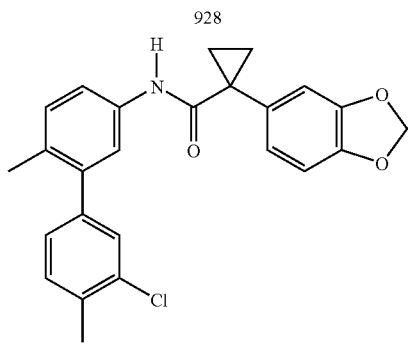

TABLE 1-continued
Examples of compounds of the present invention.
929
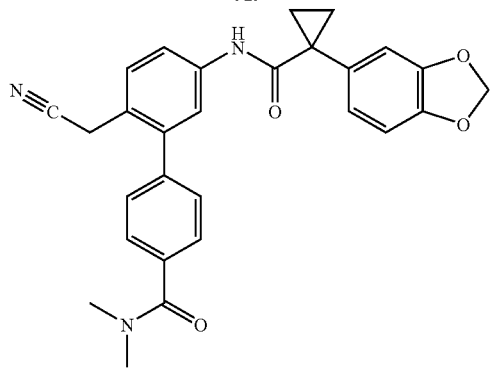
930
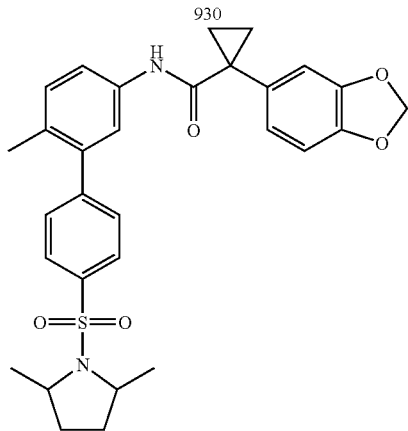
931
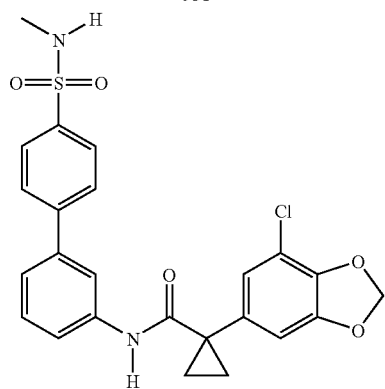
932
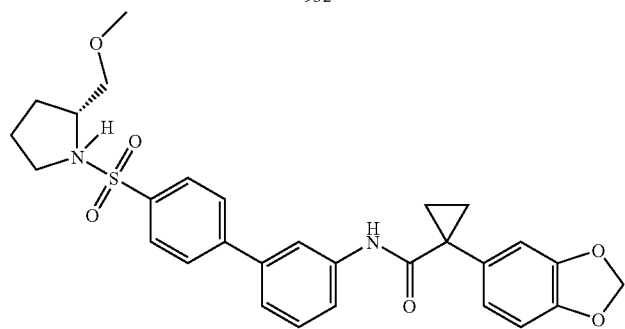

TABLE 1-continued
Examples of compounds of the present invention.
933
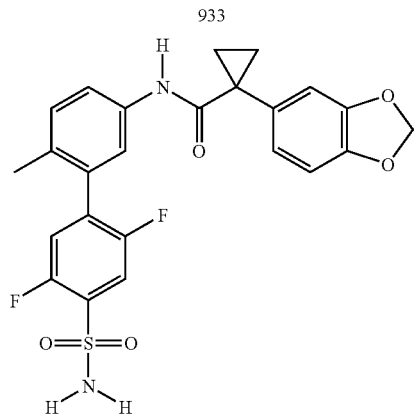
934
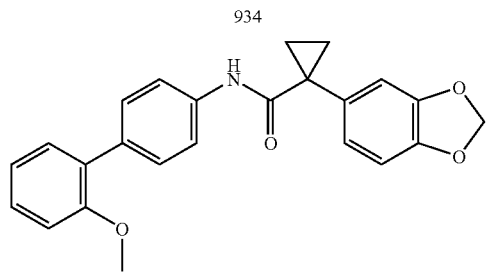
935
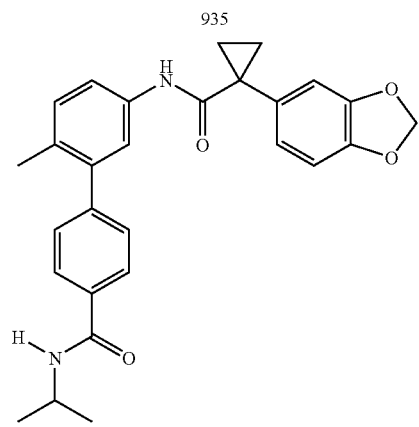
936
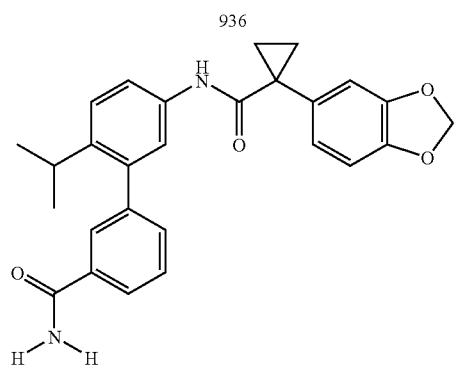

TABLE 1-continued
Examples of compounds of the present invention.
937
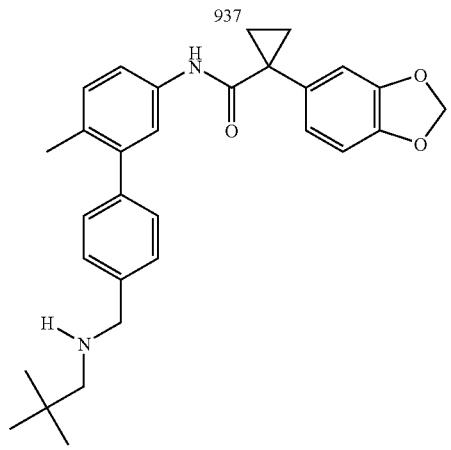
938
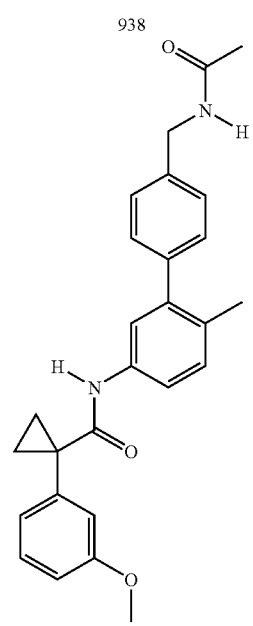
939
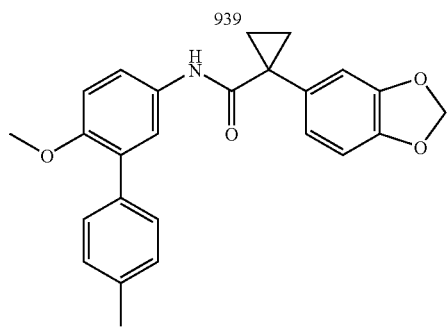

TABLE 1-continued
Examples of compounds of the present invention.
940
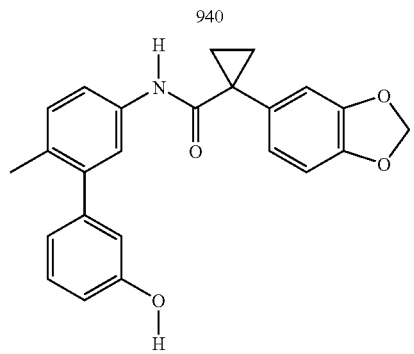
941
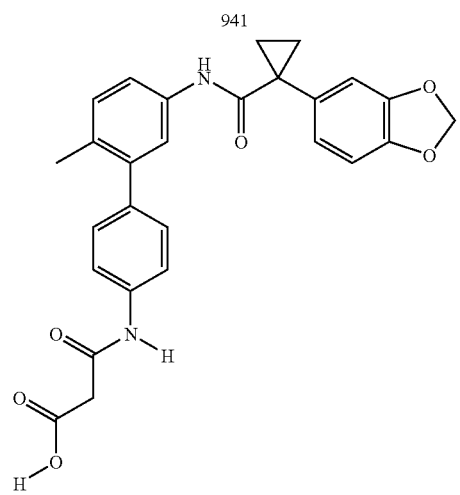
942
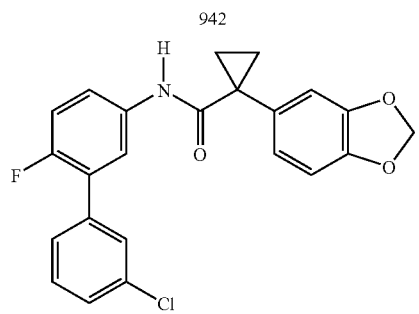
943
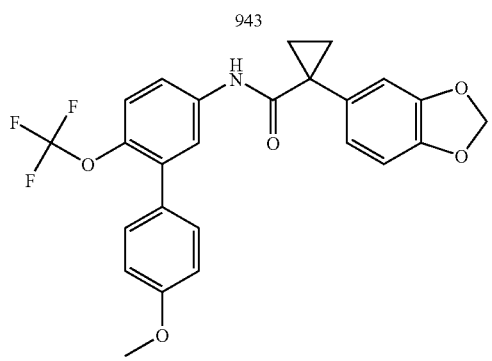

TABLE 1-continued
Examples of compounds of the present invention.
944
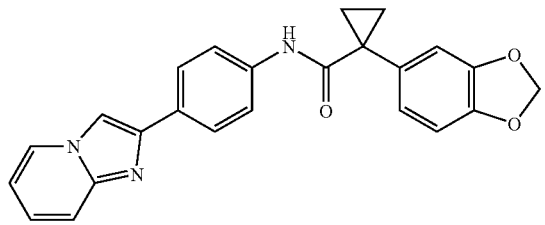
945
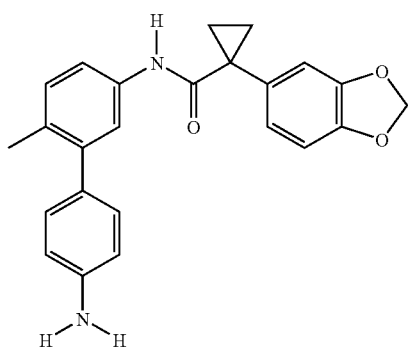
946
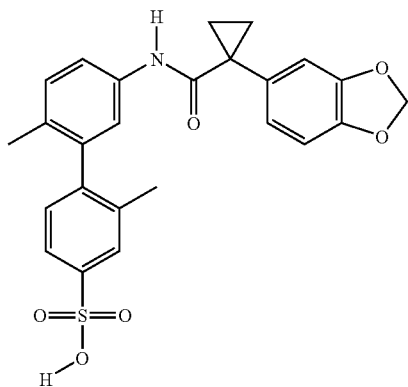
947
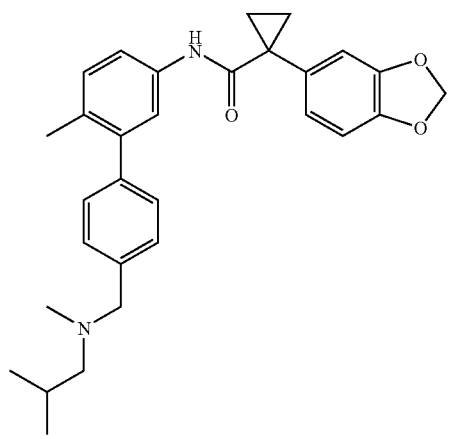

TABLE 1-continued
Examples of compounds of the present invention.
948
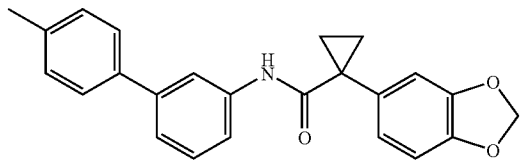
949
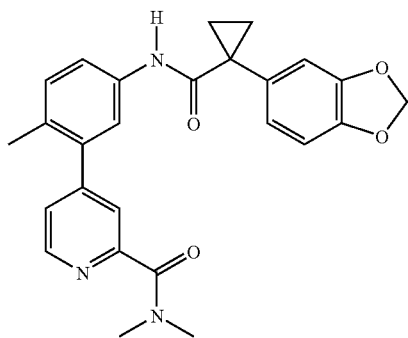
950
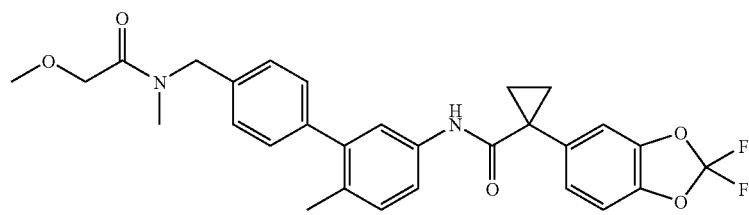
951
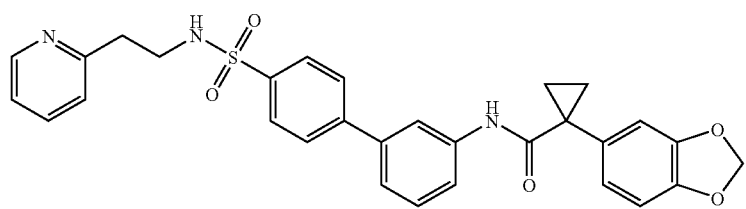
952
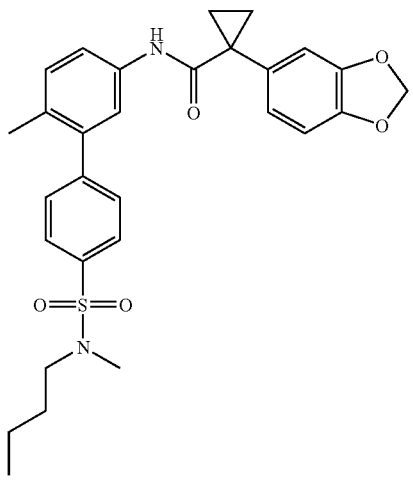

TABLE 1-continued
Examples of compounds of the present invention.
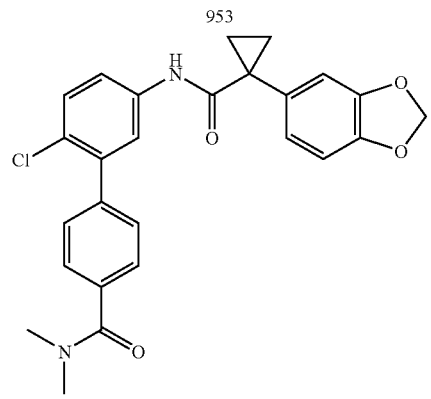
953
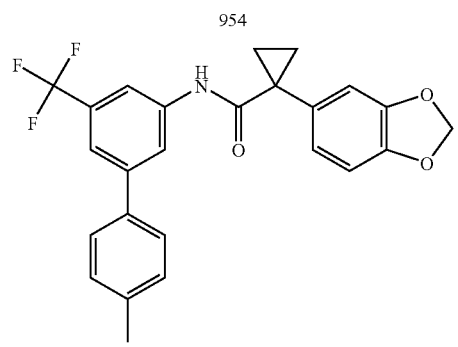
954
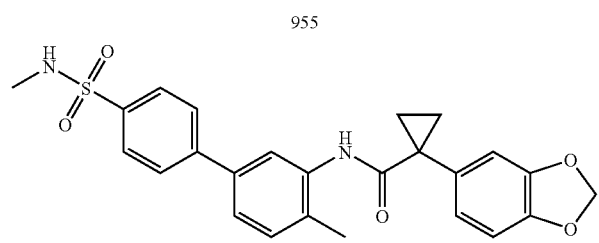
955
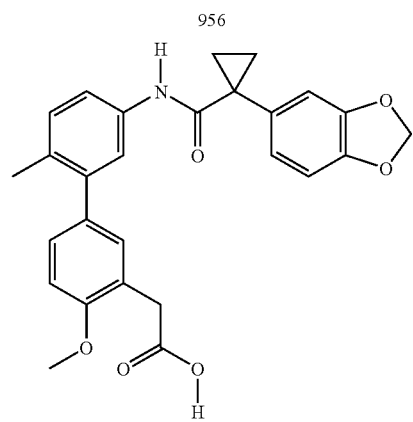
956

TABLE 1-continued
Examples of compounds of the present invention.
957
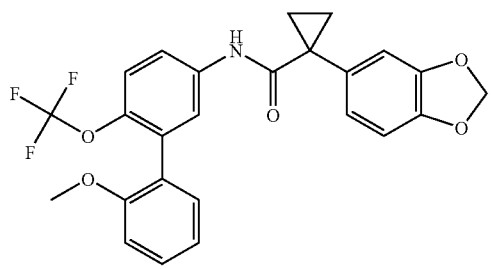
958
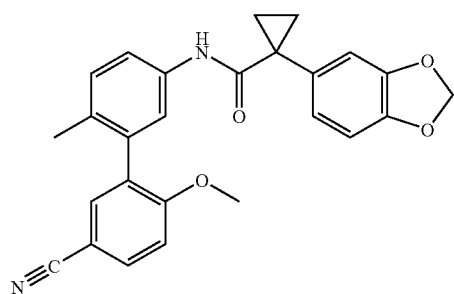
959
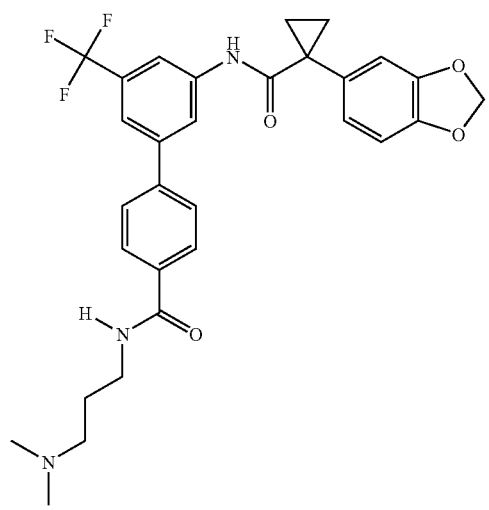
960
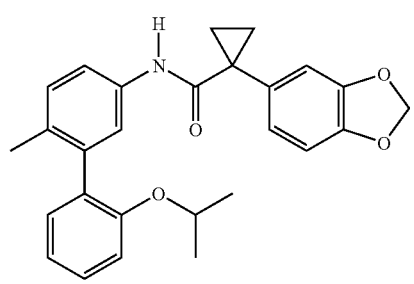

TABLE 1-continued
Examples of compounds of the present invention.
961
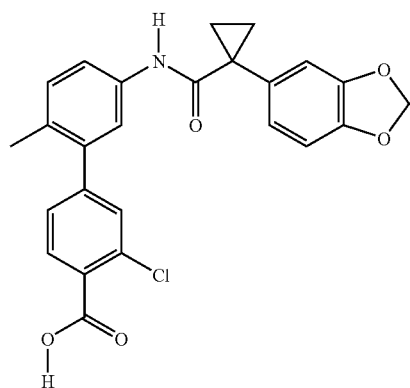
962
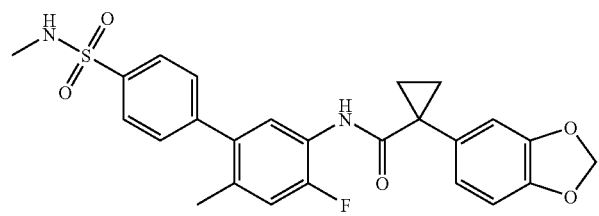
963
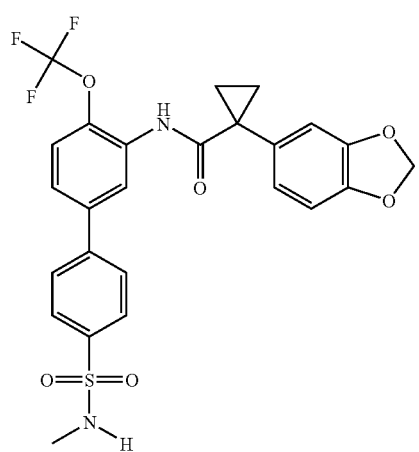
964
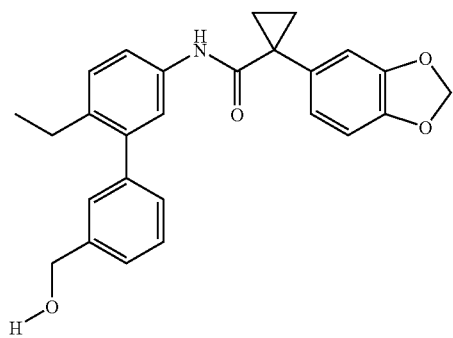

TABLE 1-continued
Examples of compounds of the present invention.
965
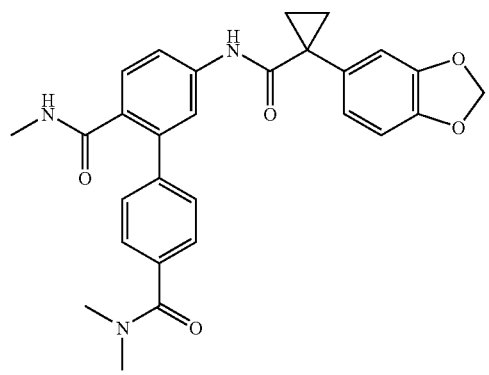
966
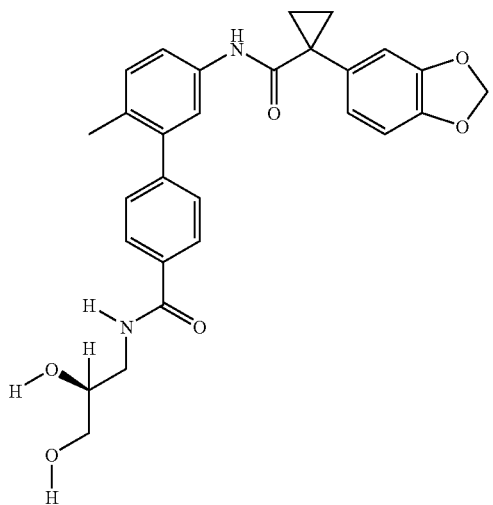
967
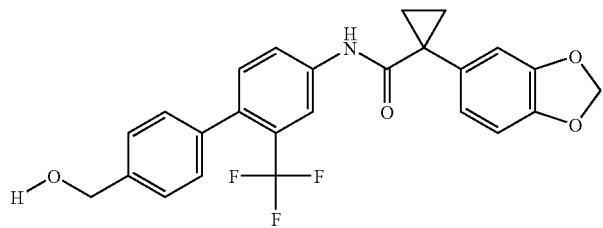
968
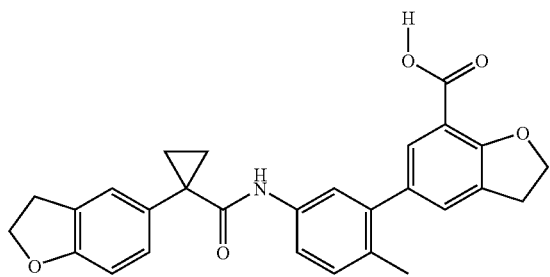

TABLE 1-continued
Examples of compounds of the present invention.
969
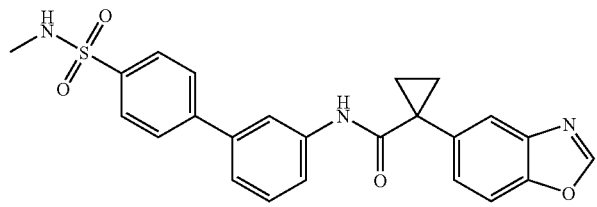
970
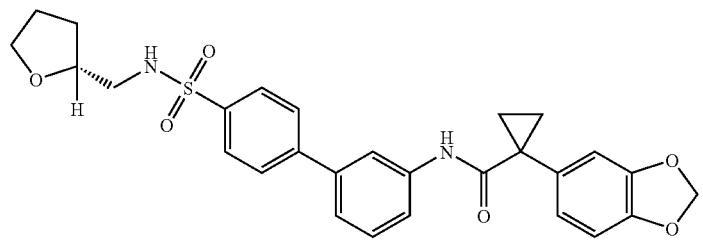
971
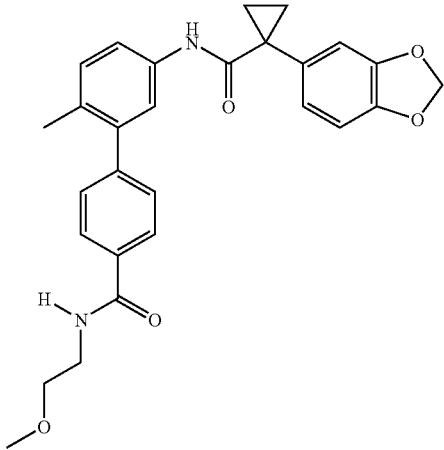
972
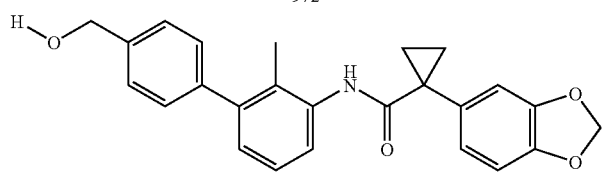

TABLE 1-continued
Examples of compounds of the present invention.
973
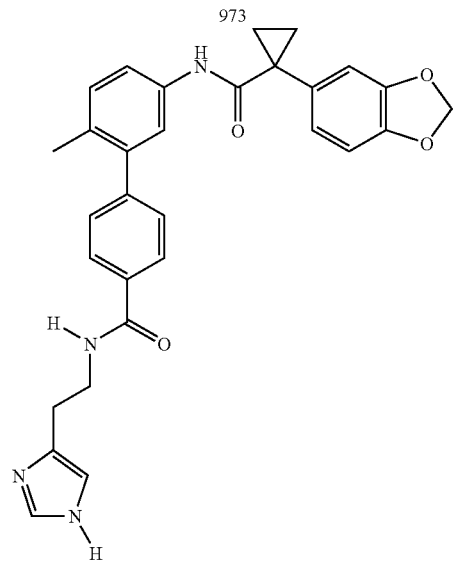
974
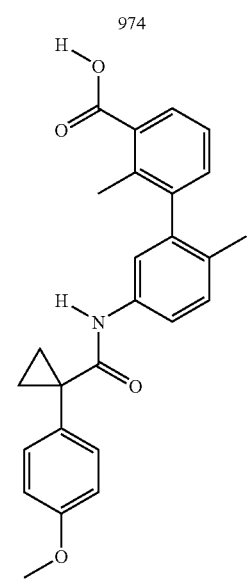
975
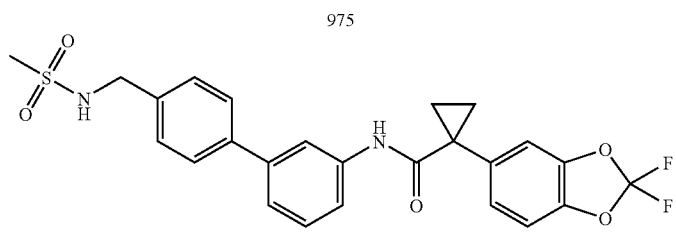

TABLE 1-continued
Examples of compounds of the present invention.
976
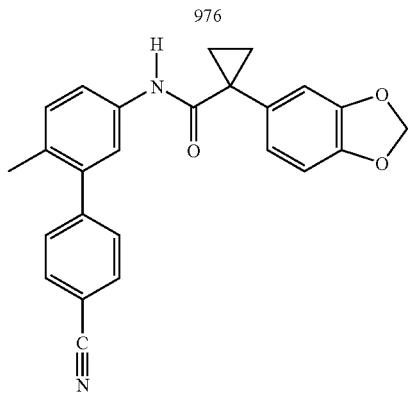
977
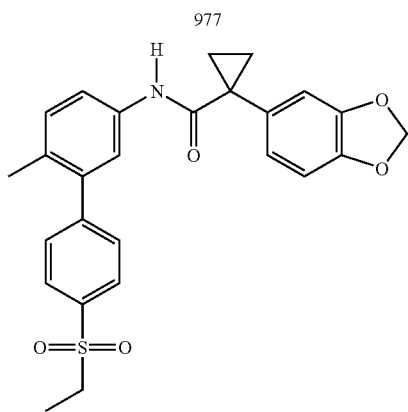
978
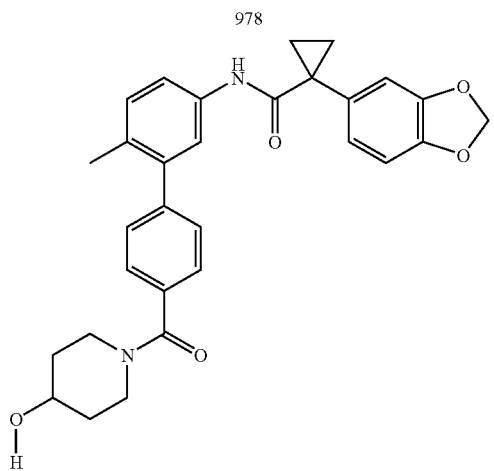

TABLE 1-continued
Examples of compounds of the present invention.
979
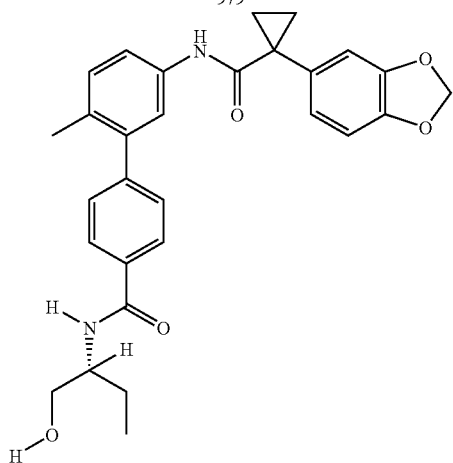
980
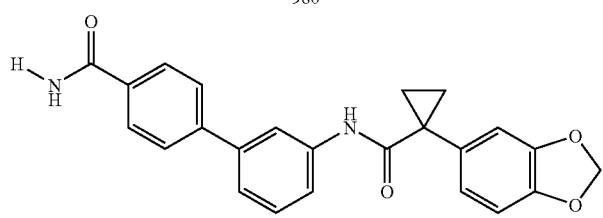
981
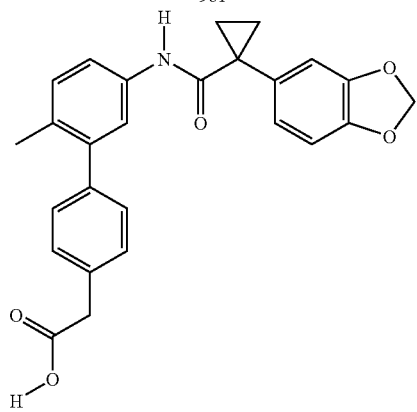
982
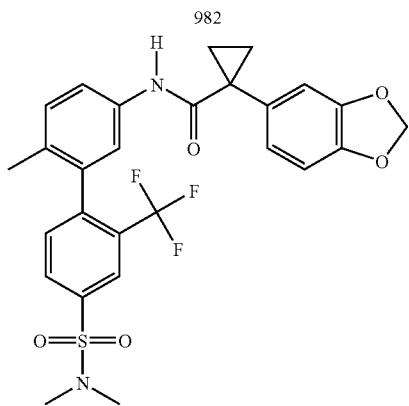

TABLE 1-continued
Examples of compounds of the present invention.
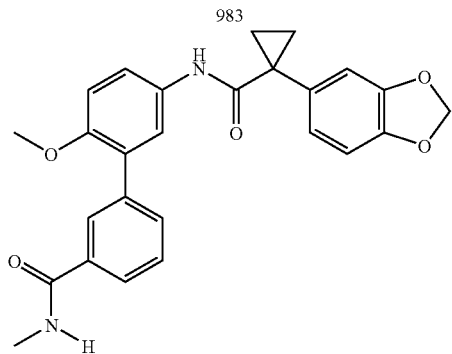
983
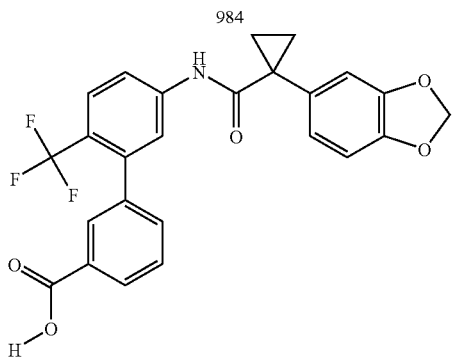
984
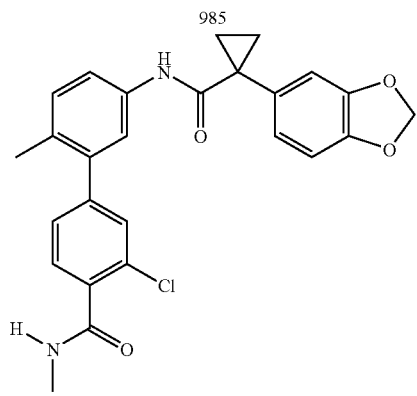
985
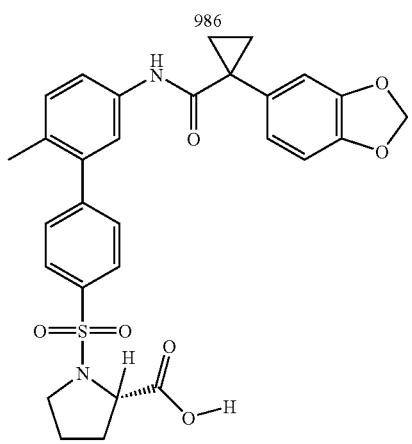
986

TABLE 1-continued
Examples of compounds of the present invention.
987
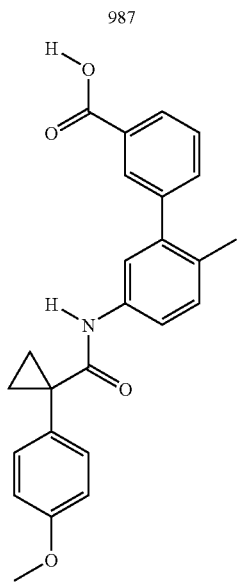
988
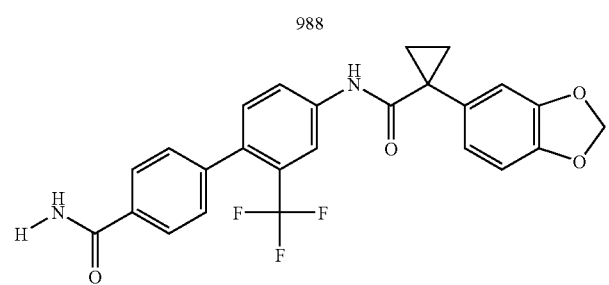
989
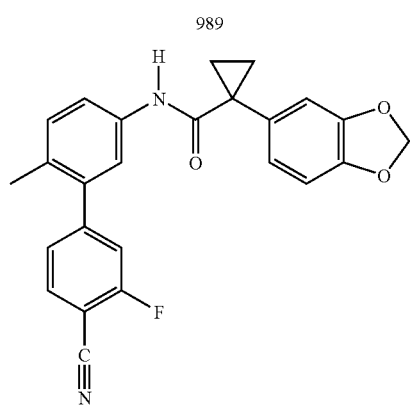

TABLE 1-continued
Examples of compounds of the present invention.
990
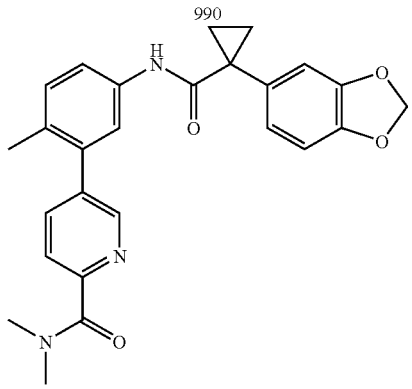
991
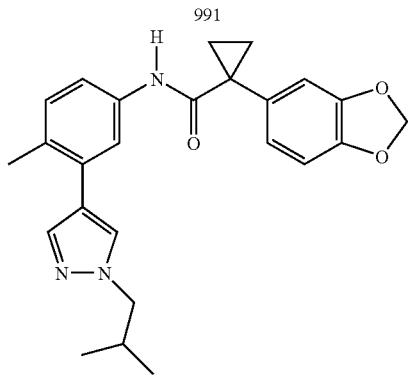
992
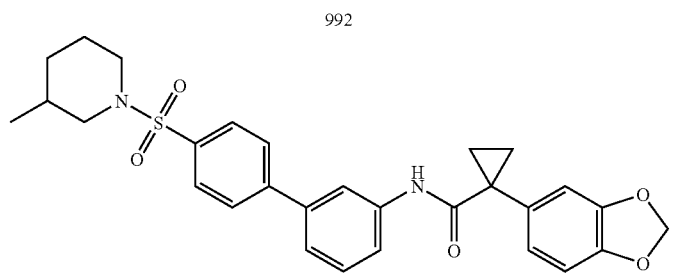
993
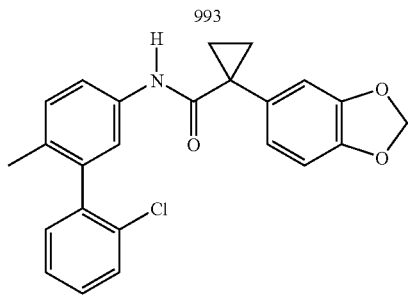
994
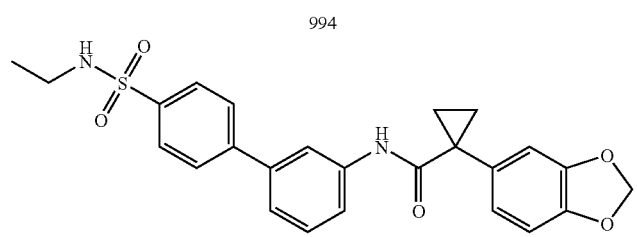

TABLE 1-continued
Examples of compounds of the present invention.
995
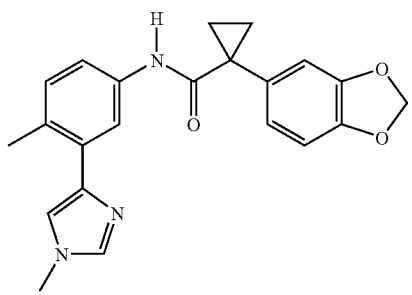
996
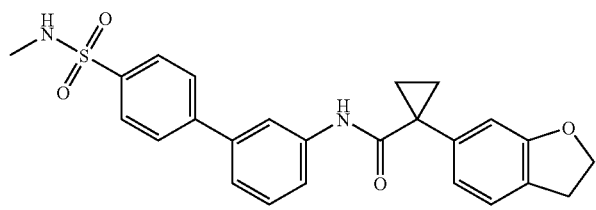
997
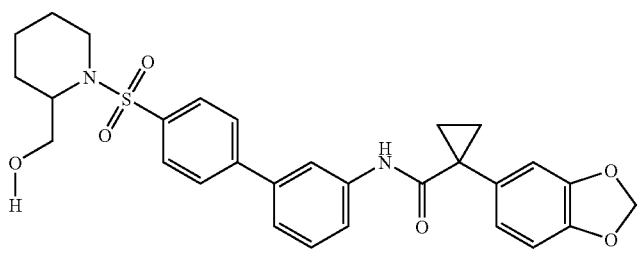
998
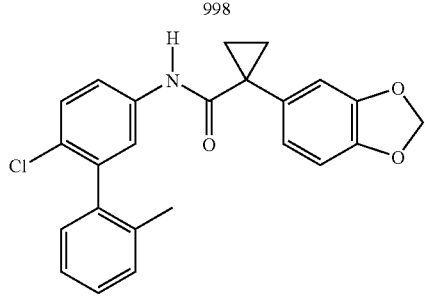
999
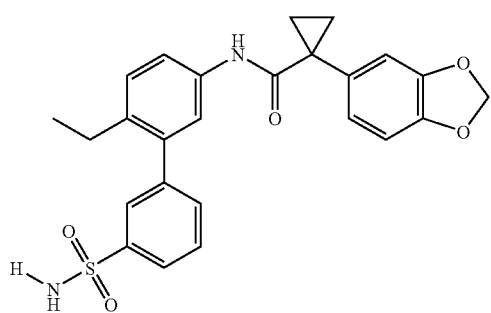

TABLE 1-continued
Examples of compounds of the present invention.
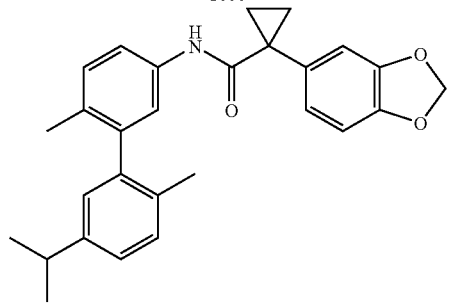
1000
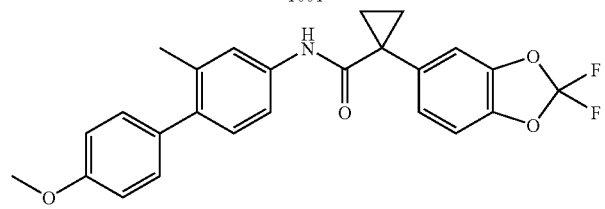
1001
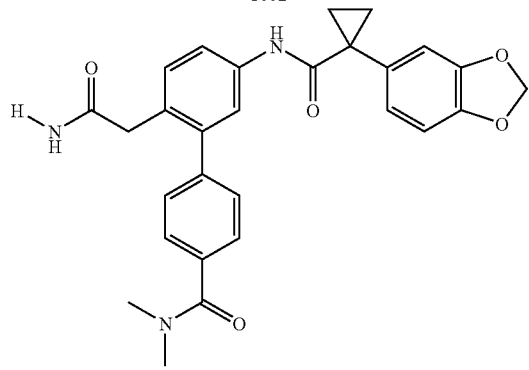
1002
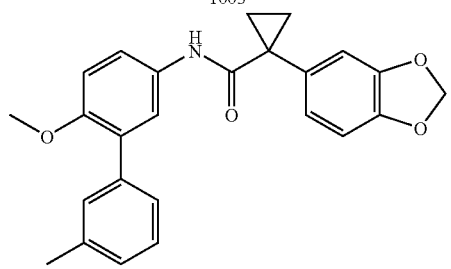
1003

TABLE 1-continued
Examples of compounds of the present invention.
1004
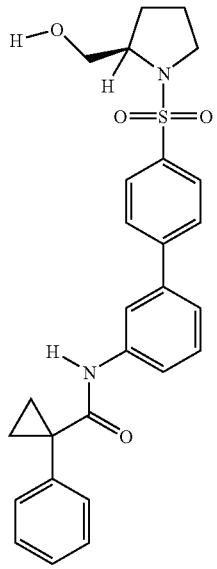
1005
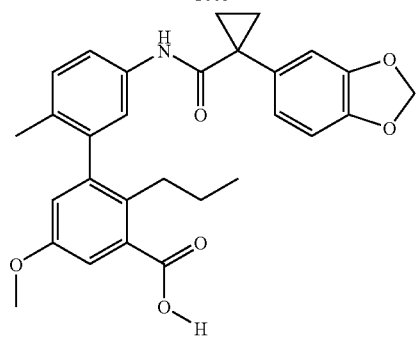
1006
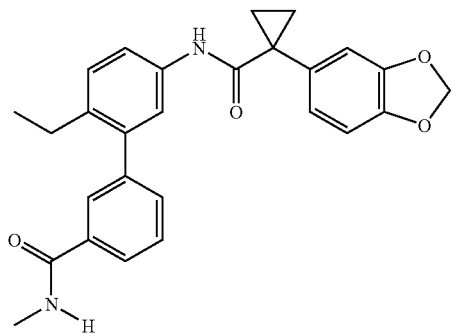

TABLE 1-continued
Examples of compounds of the present invention.
1007
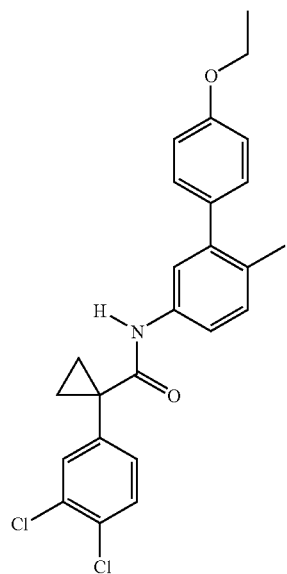
1008
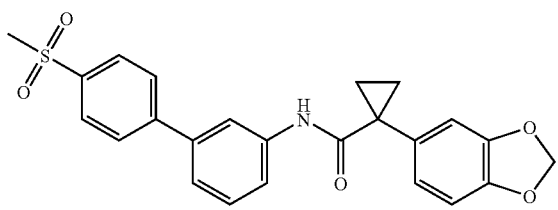
1009
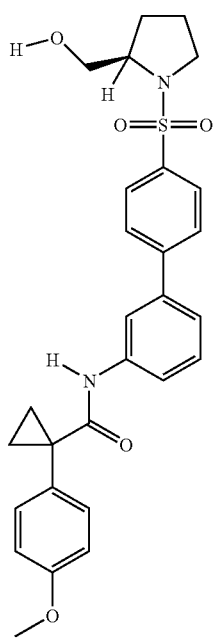

TABLE 1-continued
Examples of compounds of the present invention.
1010
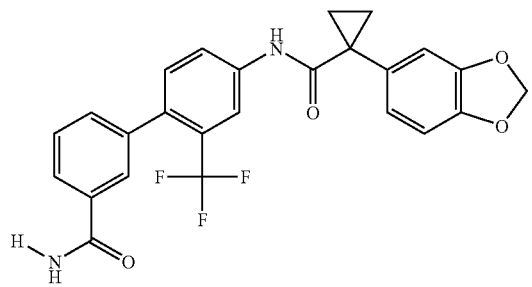
1011
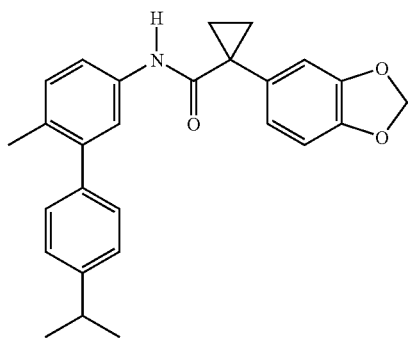
1012
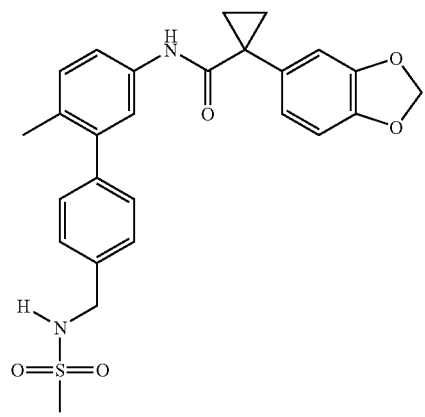
1013
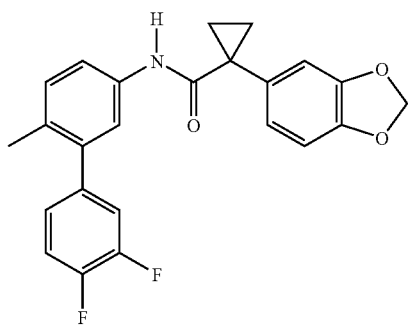

TABLE 1-continued
Examples of compounds of the present invention.
1014
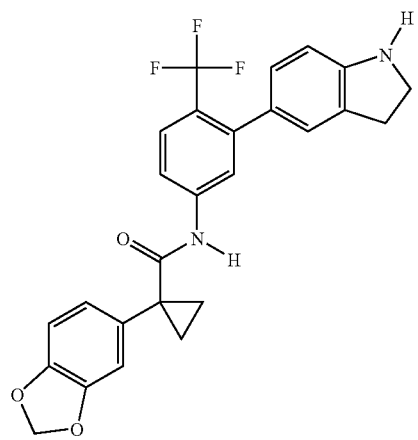
1015
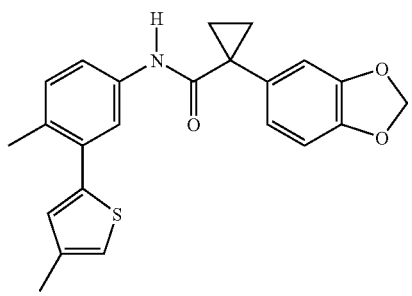
1016
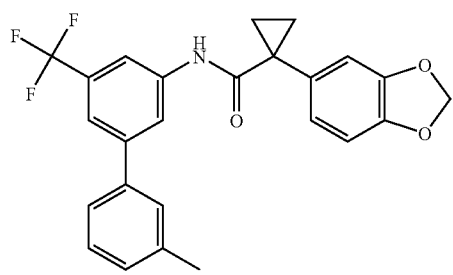
1017
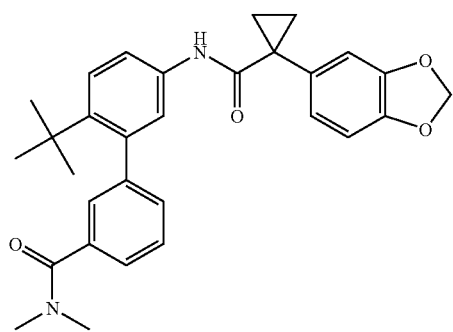

TABLE 1-continued
Examples of compounds of the present invention.
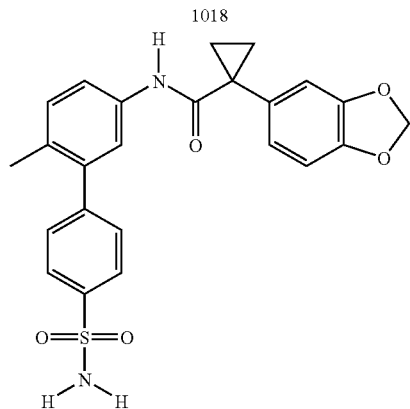
1018
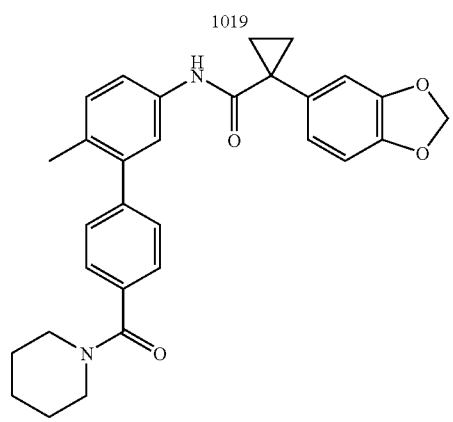
1019
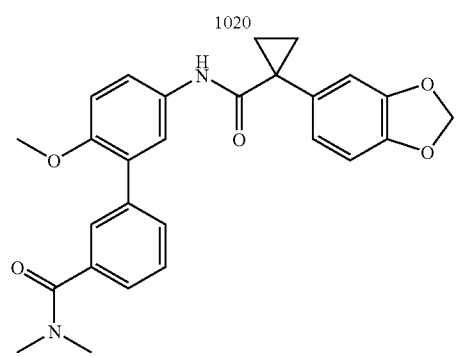
1020
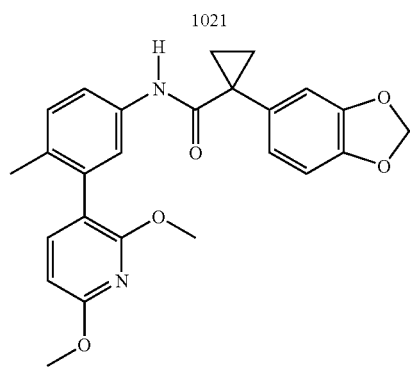
1021

TABLE 1-continued
Examples of compounds of the present invention.
1022
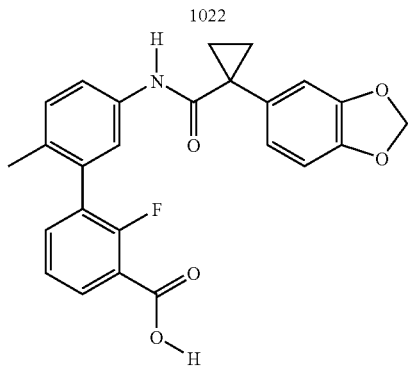
1023
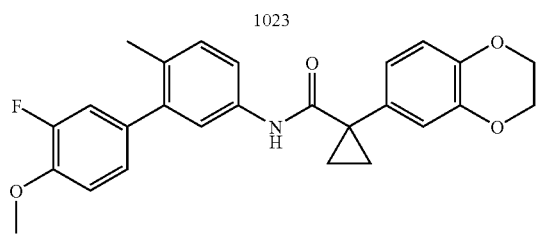
1024
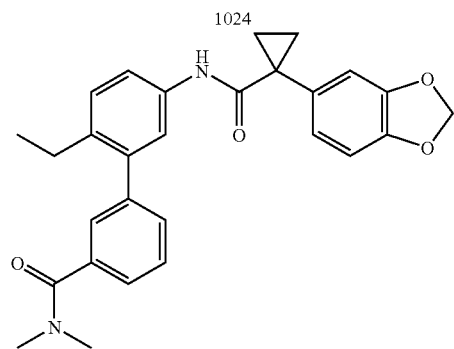
1025
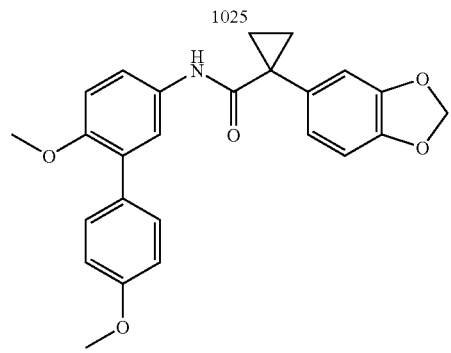
1026
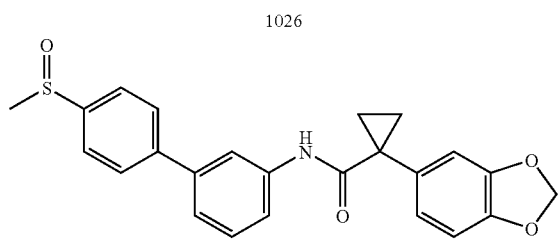

TABLE 1-continued
Examples of compounds of the present invention.
1027
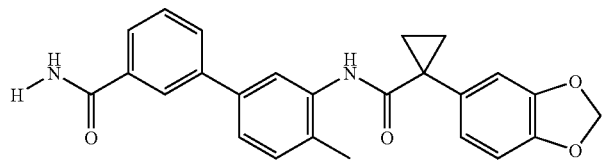
1028
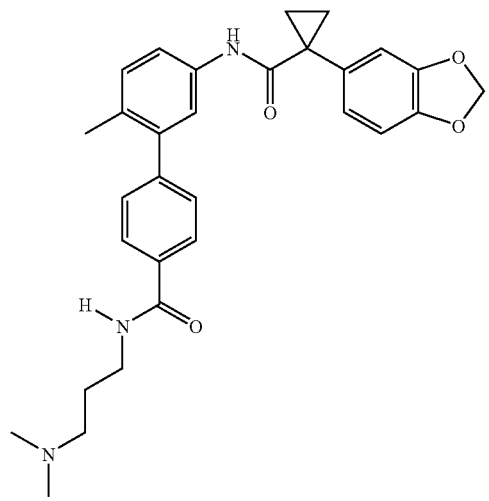
1029
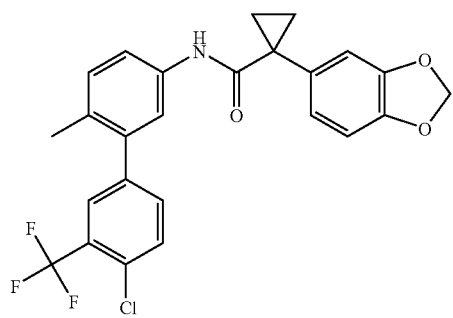
1030
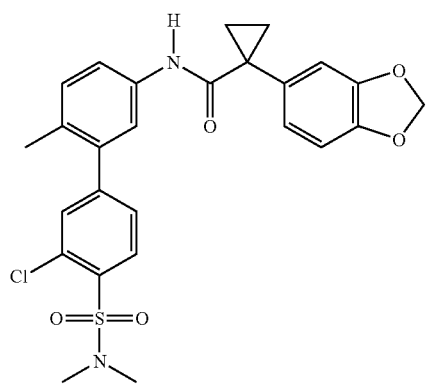

TABLE 1-continued
Examples of compounds of the present invention.
1031
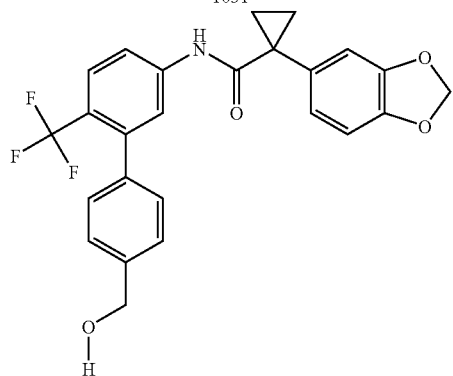
1032
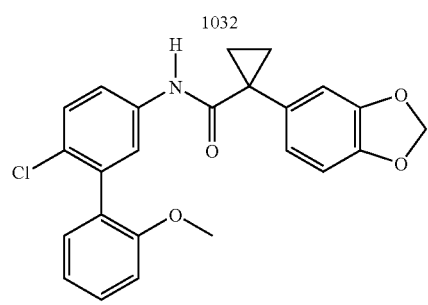
1033
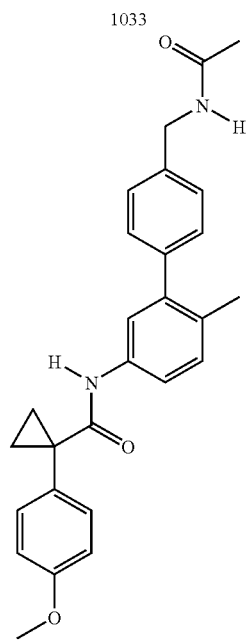

TABLE 1-continued
Examples of compounds of the present invention.
1034
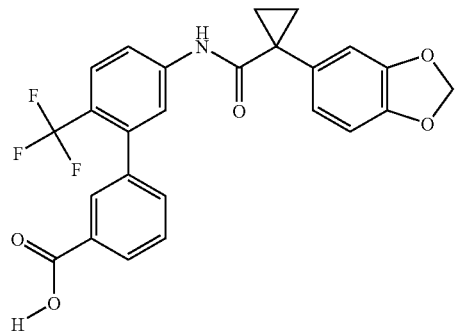
1035
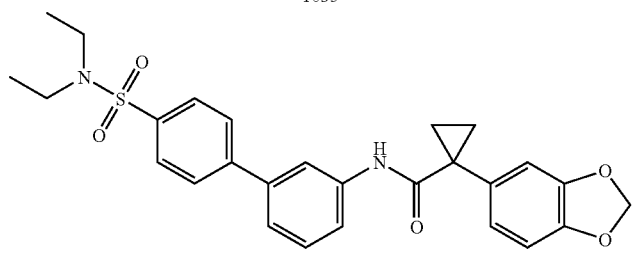
1036
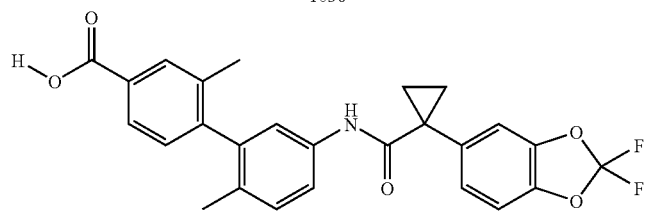
1037
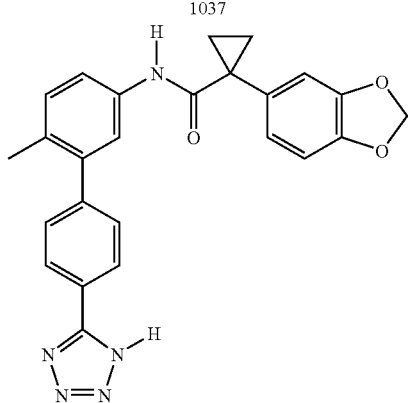

TABLE 1-continued
Examples of compounds of the present invention.
1038
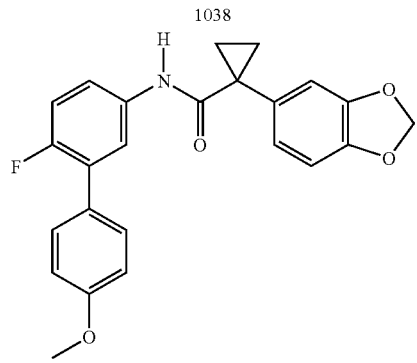
1039
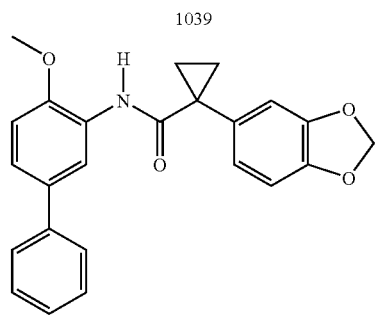
1040
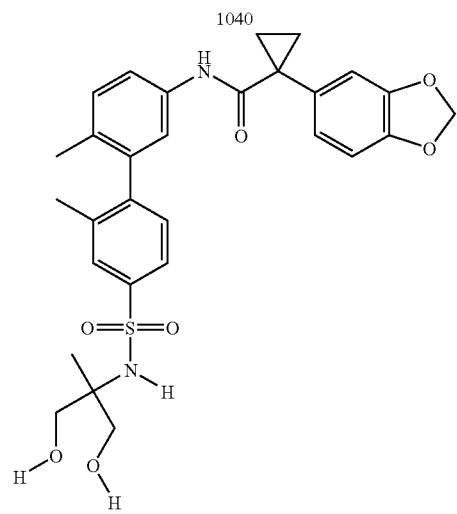
1041
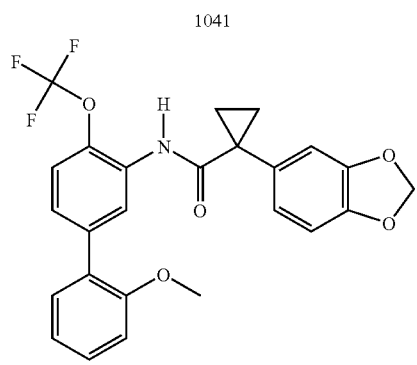

TABLE 1-continued
Examples of compounds of the present invention.
1042
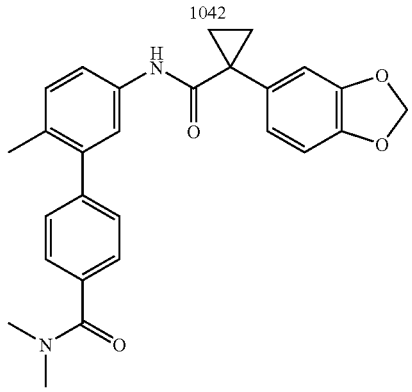
1043
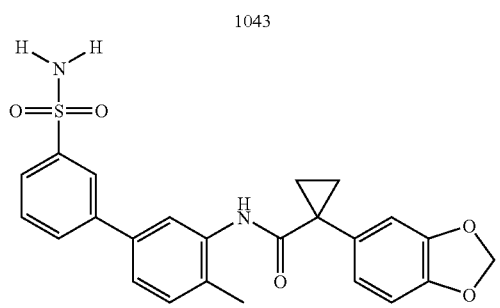
1044
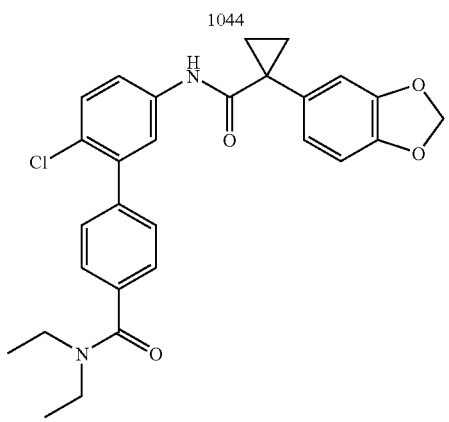
1045
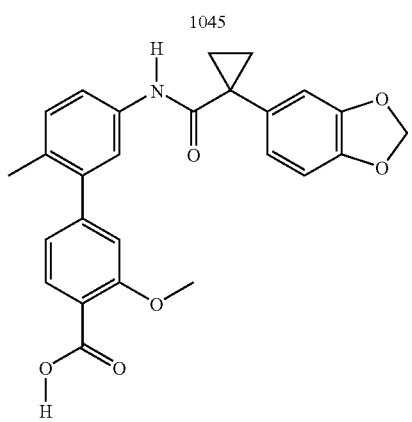

TABLE 1-continued
Examples of compounds of the present invention.
1046
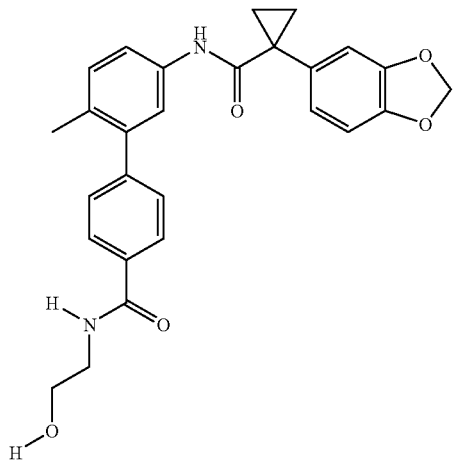
1047
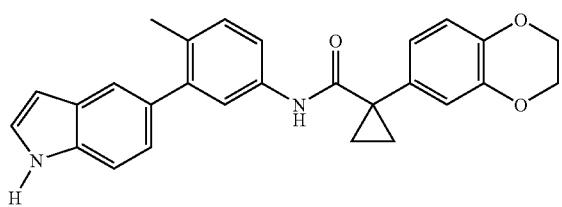
1048
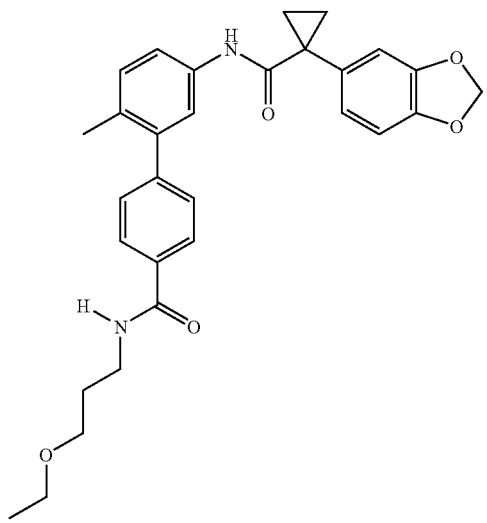

TABLE 1-continued
Examples of compounds of the present invention.
1049
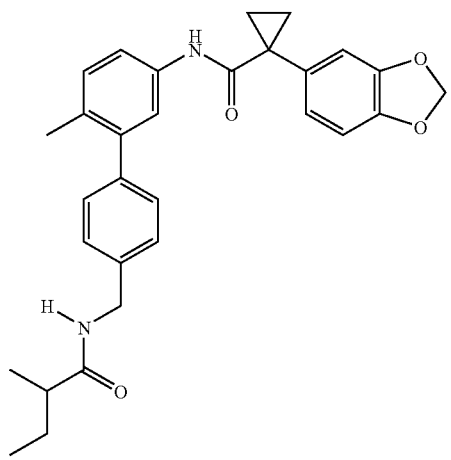
1050
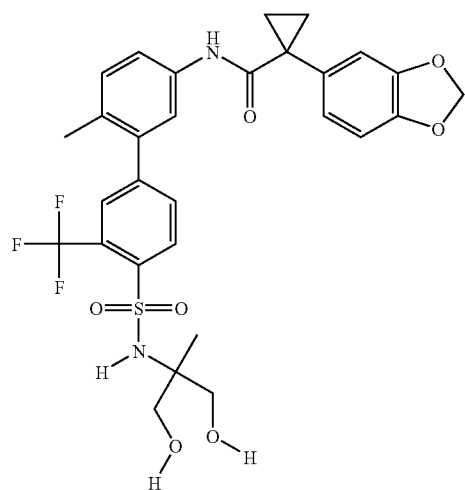
1051
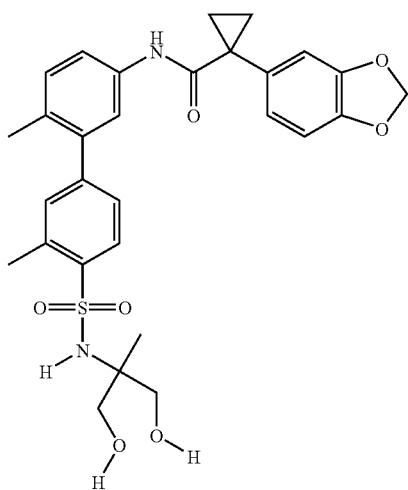

TABLE 1-continued
Examples of compounds of the present invention.
1052
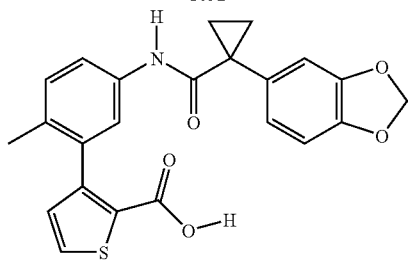
1053
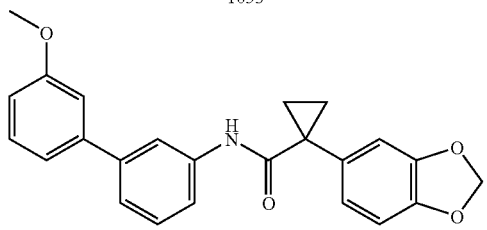
1054
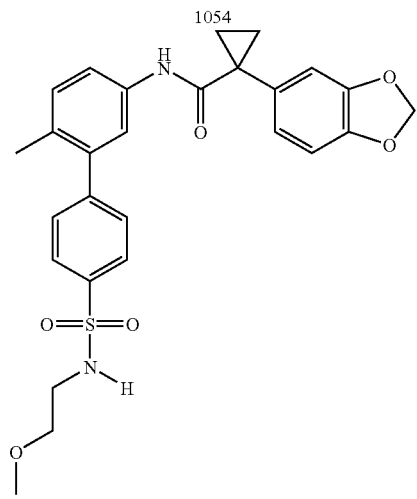
1055
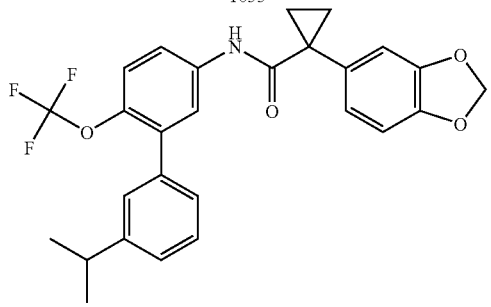

TABLE 1-continued
Examples of compounds of the present invention.
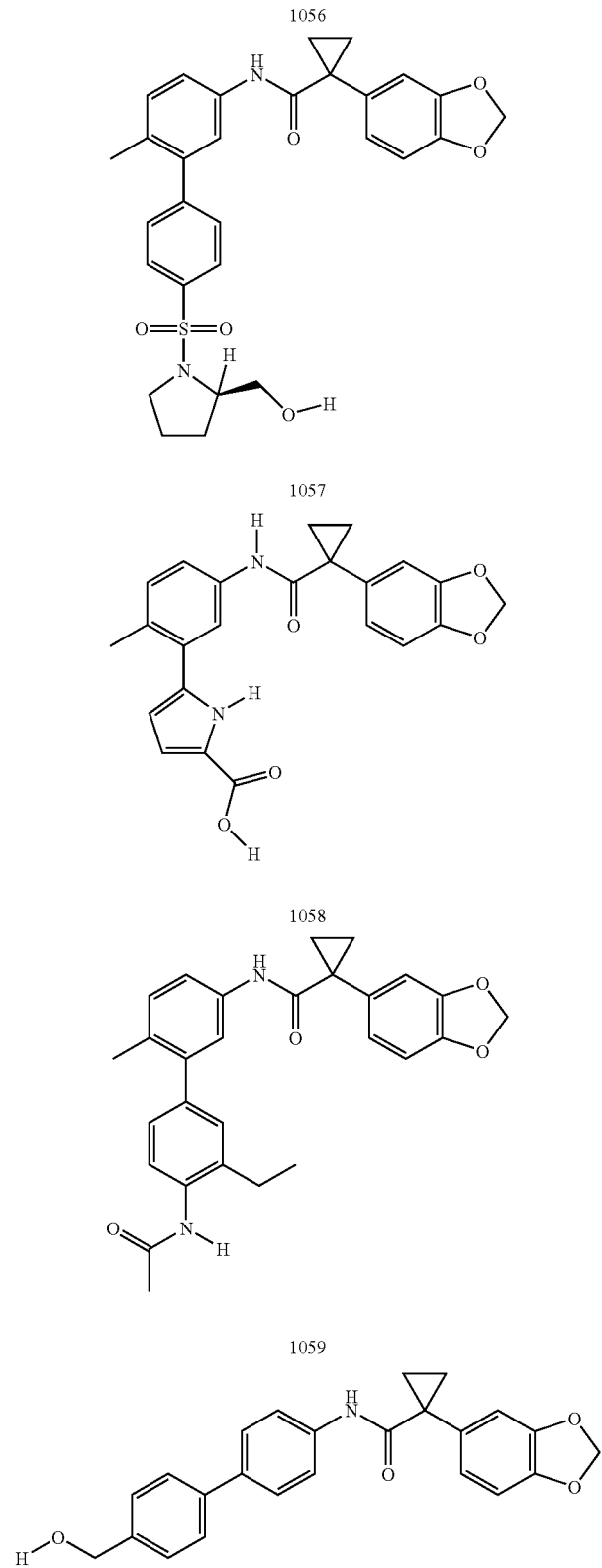

TABLE 1-continued
Examples of compounds of the present invention.
1060
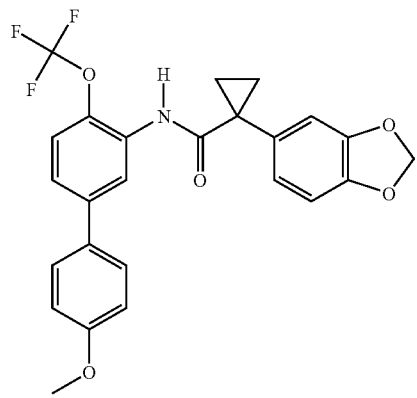
1061
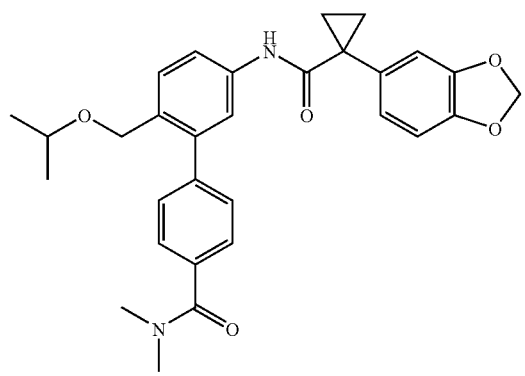
1062
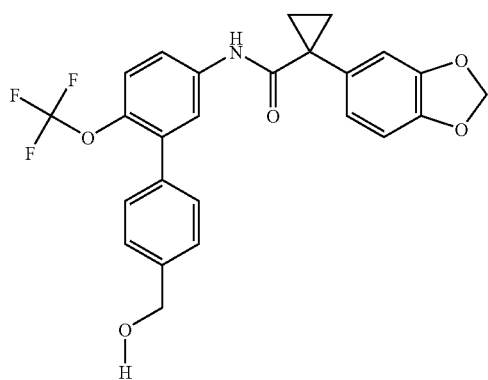

TABLE 1-continued
Examples of compounds of the present invention.
1063
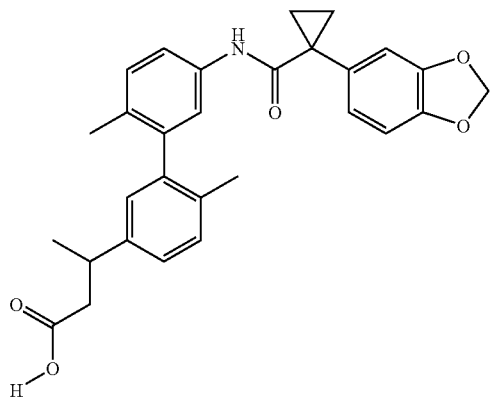
1064
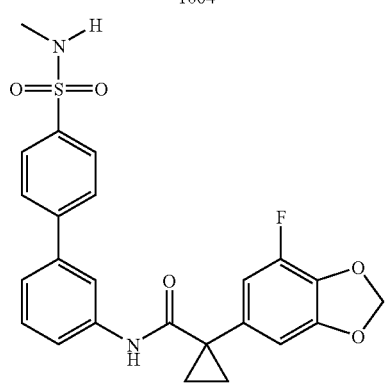
1065
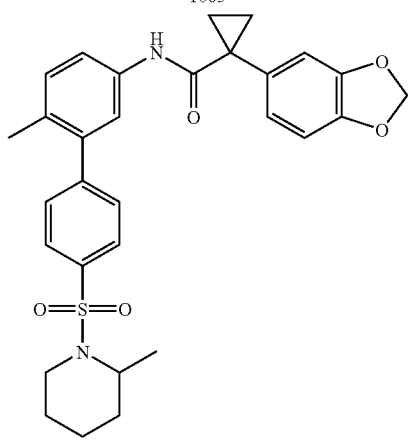

TABLE 1-continued
Examples of compounds of the present invention.
1066
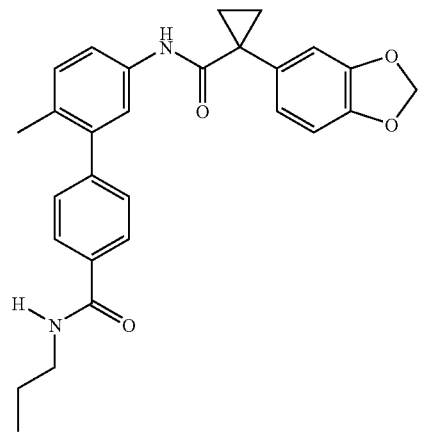
1067
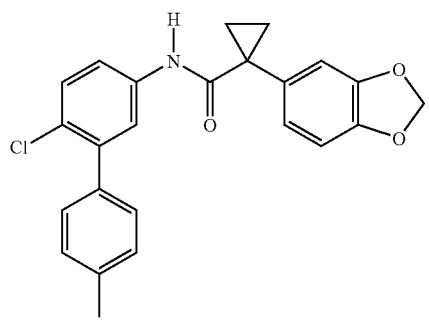
1068
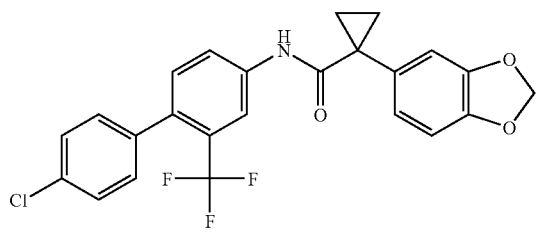
1069
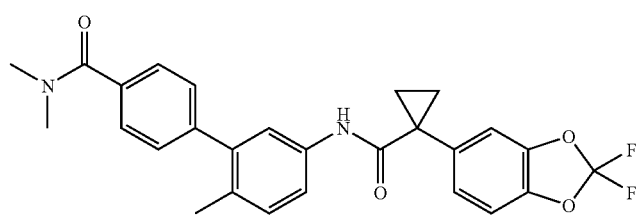

TABLE 1-continued
Examples of compounds of the present invention.
1070
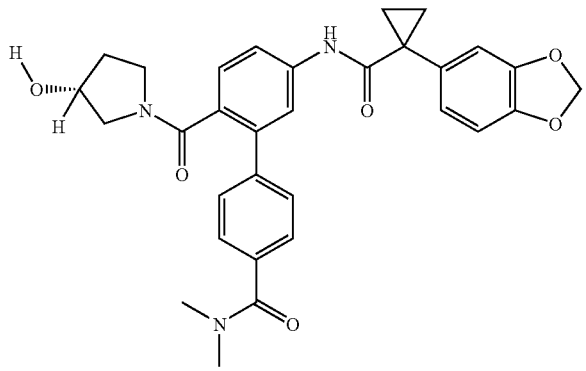
1071
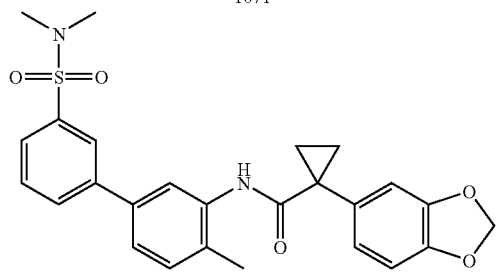
1072
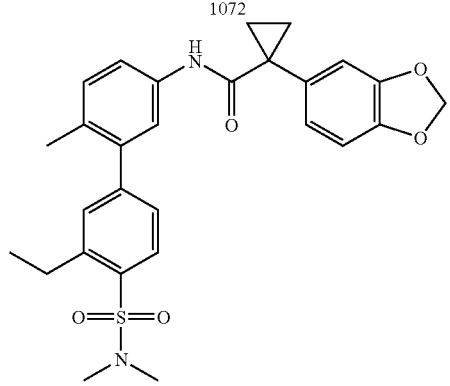
1073
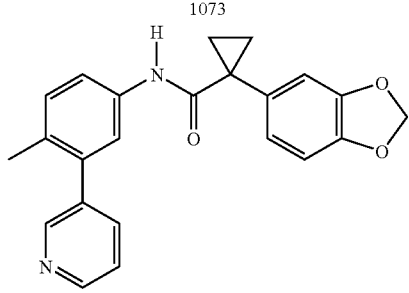

TABLE 1-continued
Examples of compounds of the present invention.
1074
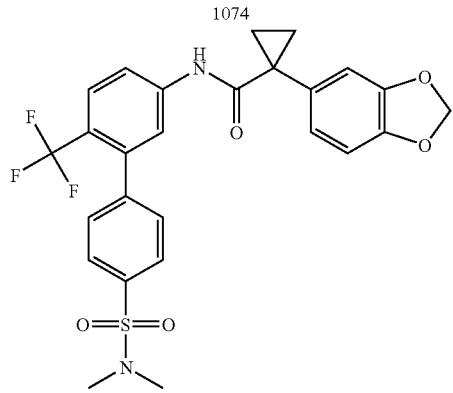
1075
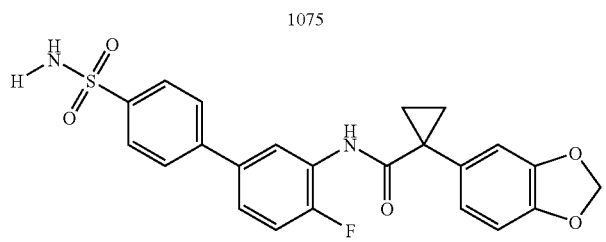
1076
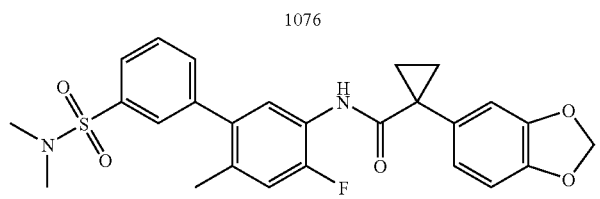
1077
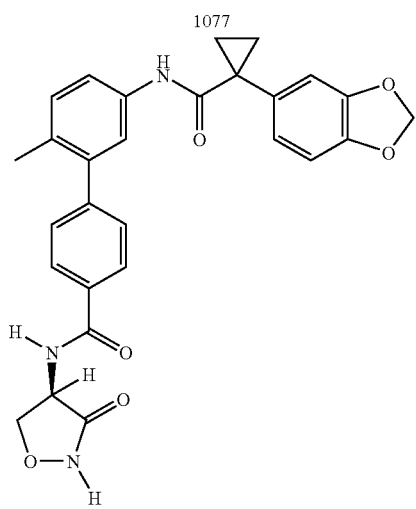
1078
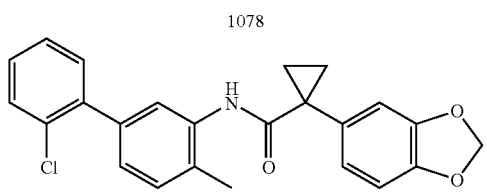

TABLE 1-continued
Examples of compounds of the present invention.
1079
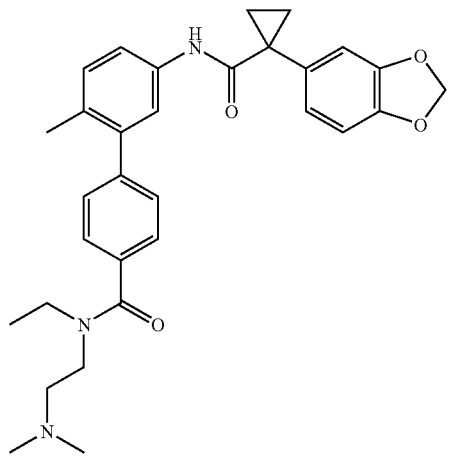
1080
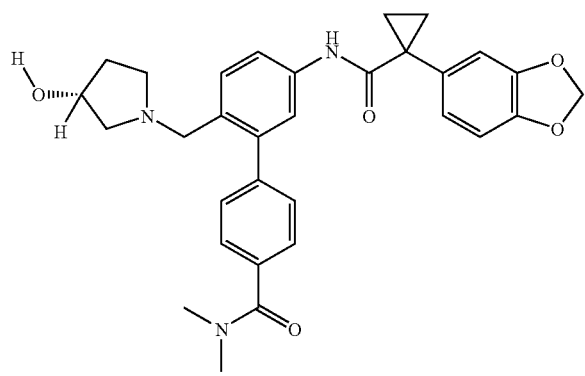
1081
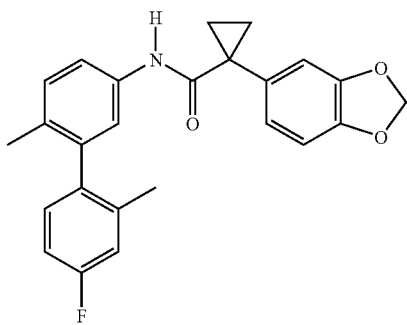
1082
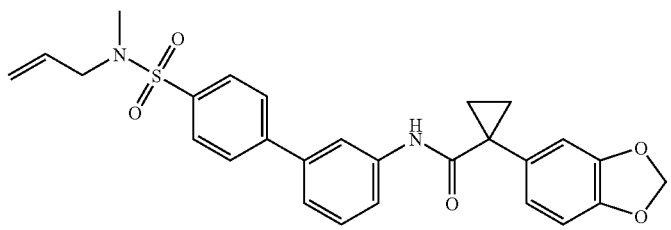

TABLE 1-continued
Examples of compounds of the present invention.
1083
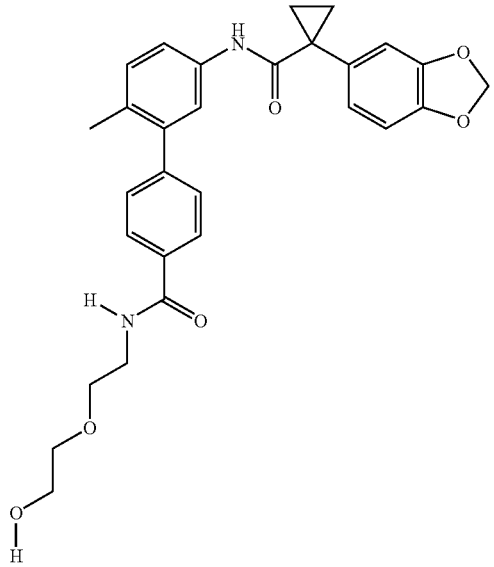
1084
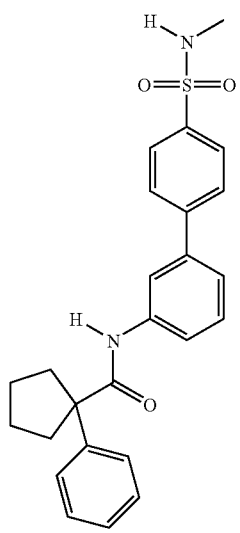
1085
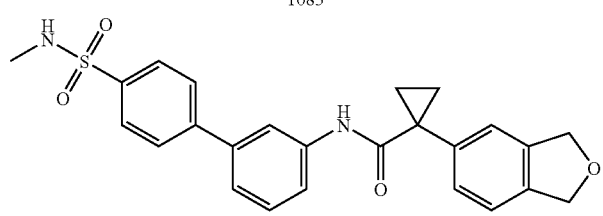

TABLE 1-continued
Examples of compounds of the present invention.
1086
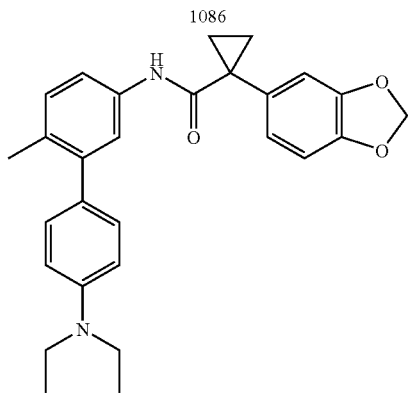
1087
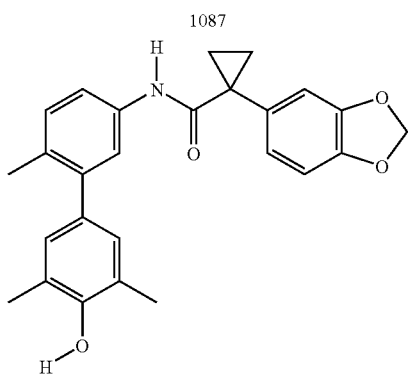
1088
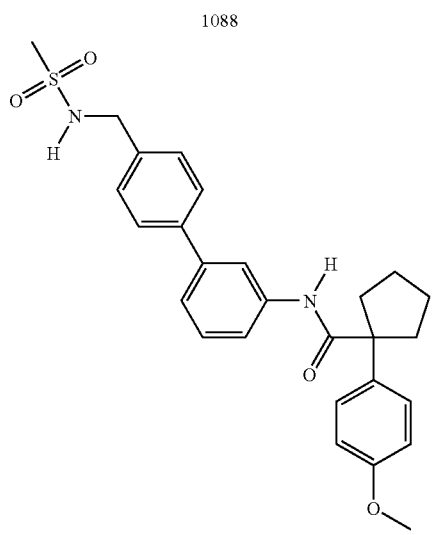

TABLE 1-continued
Examples of compounds of the present invention.
1089
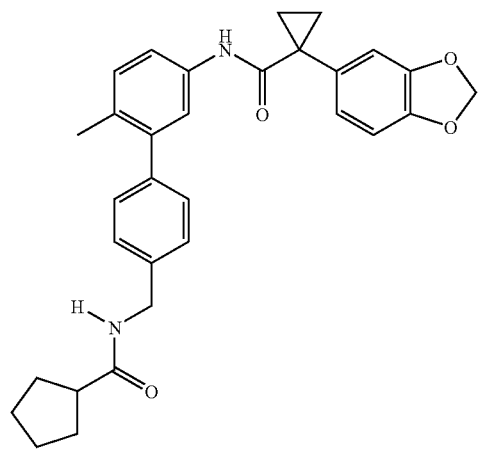
1090
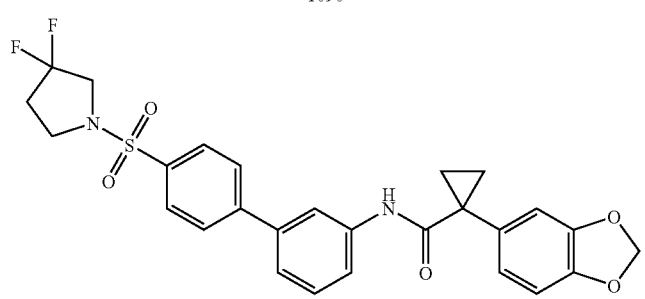
1091
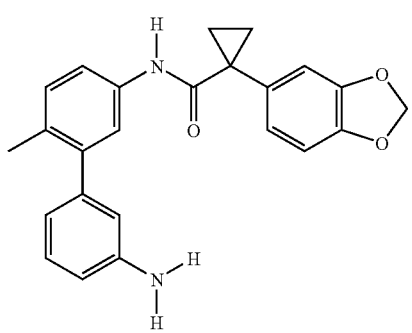
1092
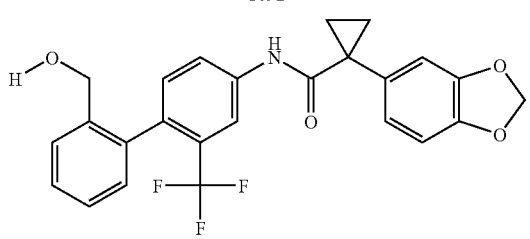

TABLE 1-continued
Examples of compounds of the present invention.
1093
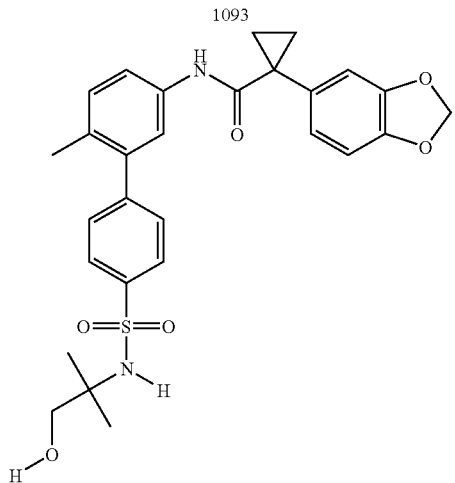
1094
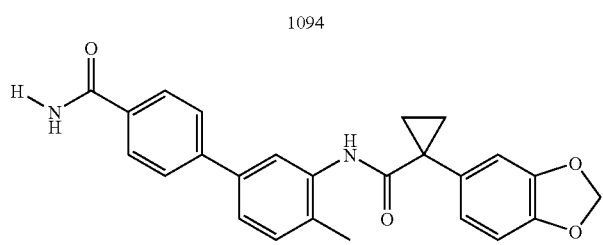
1095
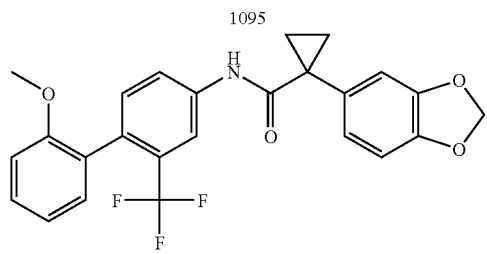
1096
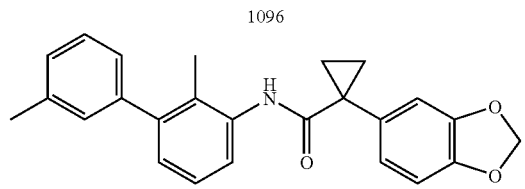

TABLE 1-continued
Examples of compounds of the present invention.
1097
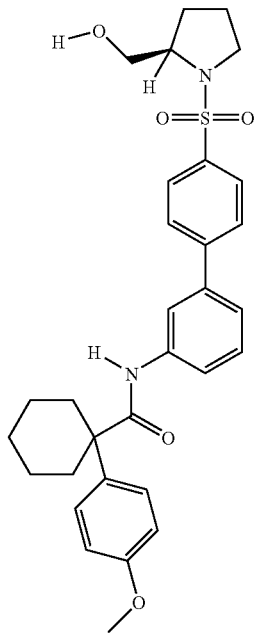
1098
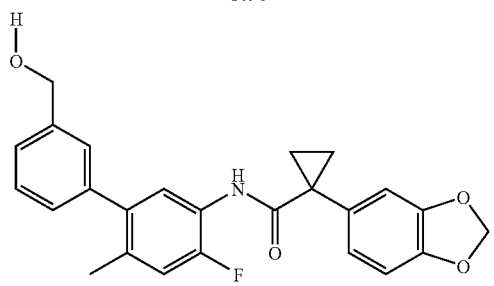
1099
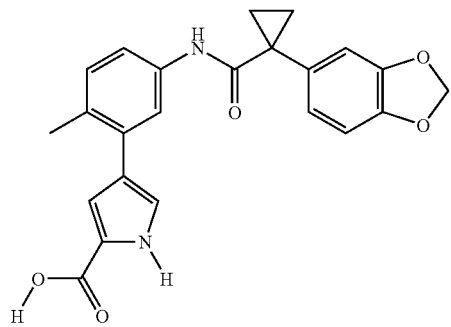

TABLE 1-continued
Examples of compounds of the present invention.
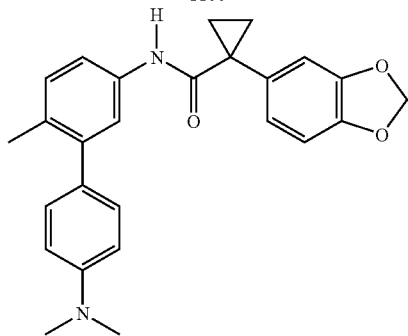
1100
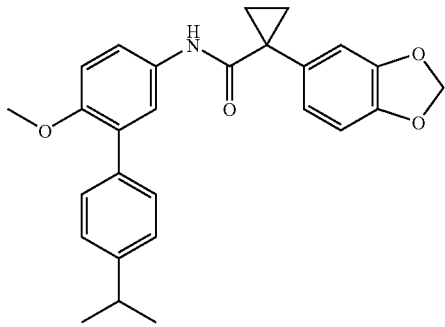
1101
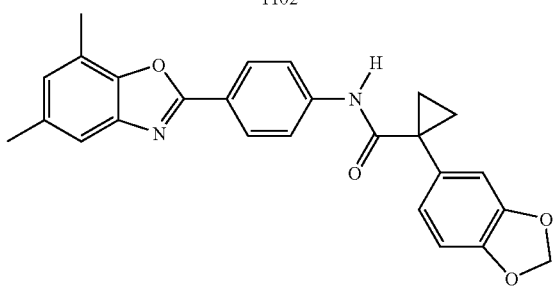
1102
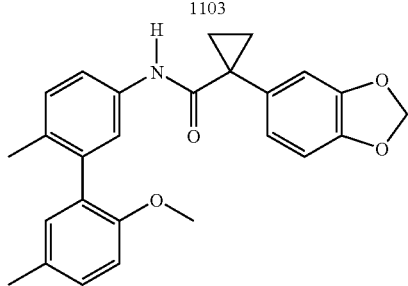
1103

TABLE 1-continued
Examples of compounds of the present invention.
1104
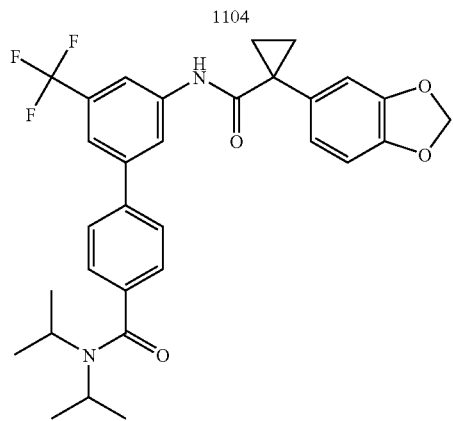
1105
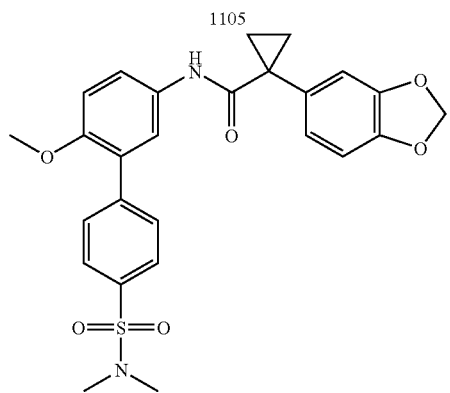
1106
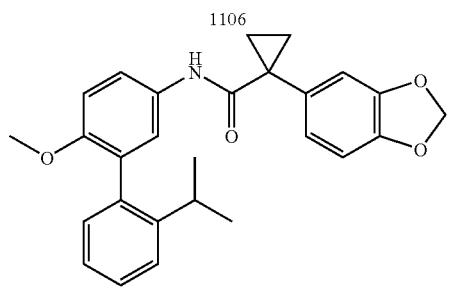
1107
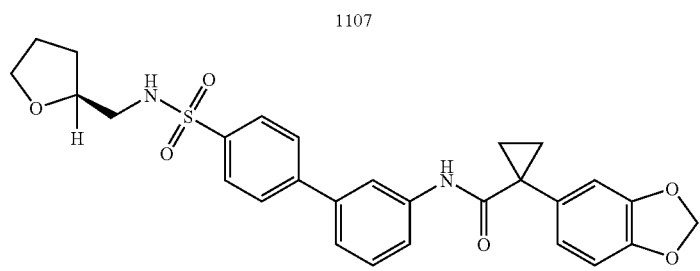

TABLE 1-continued
Examples of compounds of the present invention.
1108
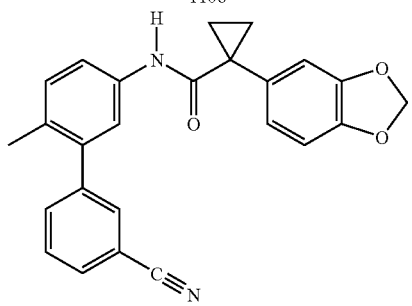
1109
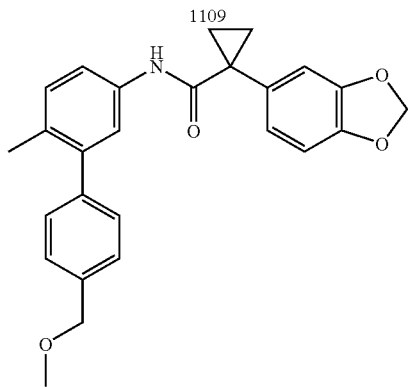
1110
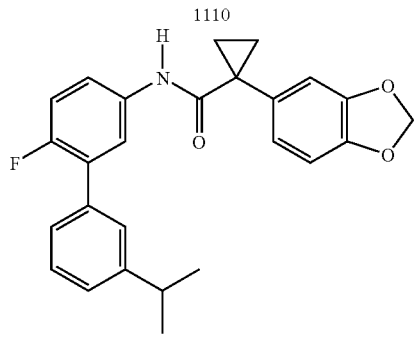
1111
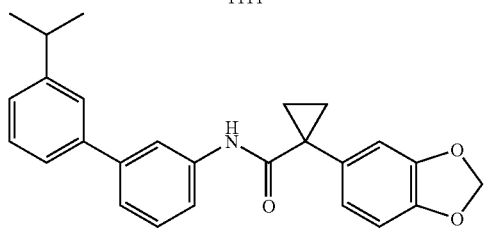

TABLE 1-continued
Examples of compounds of the present invention.
1112
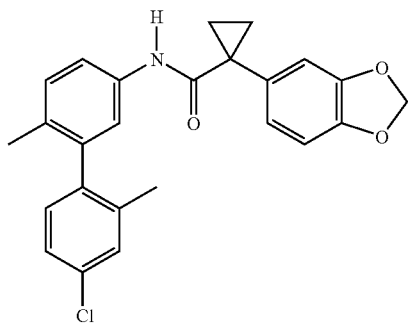
1113
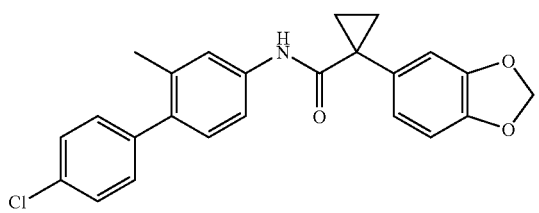
1114
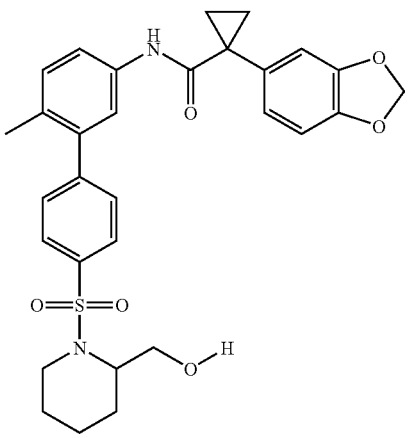
1115
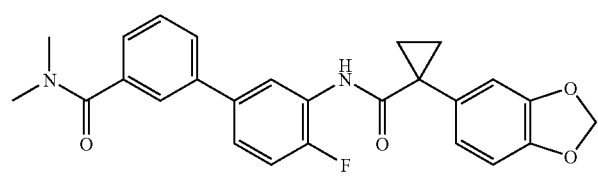
1116
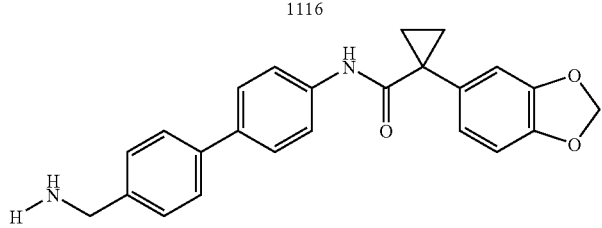

TABLE 1-continued
Examples of compounds of the present invention.
1117
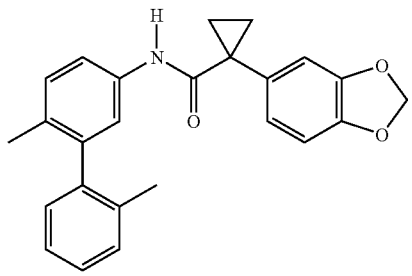
1118
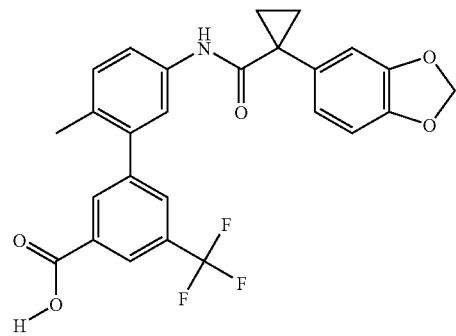
1119
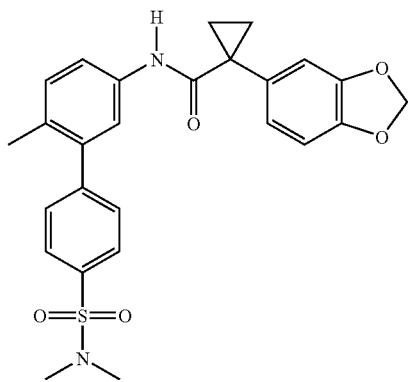
1120
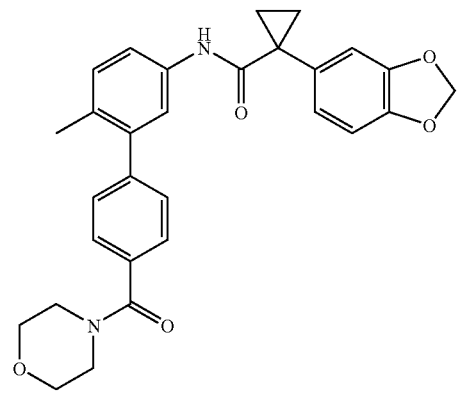

TABLE 1-continued
Examples of compounds of the present invention.
1121
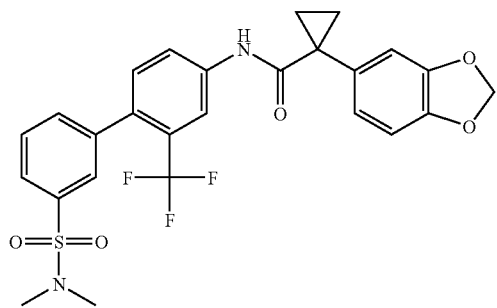
1122
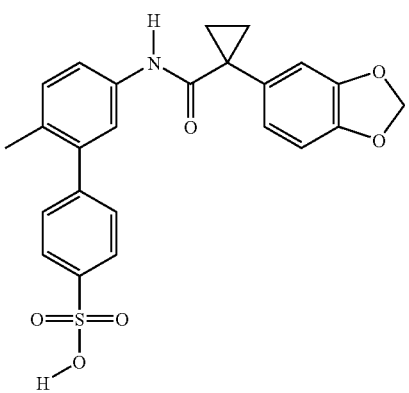
1123
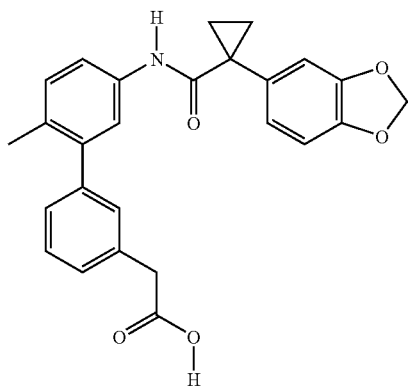

US 7,671,221 B2
647                                                                 648
TABLE 1-continued
Examples of compounds of the present invention.
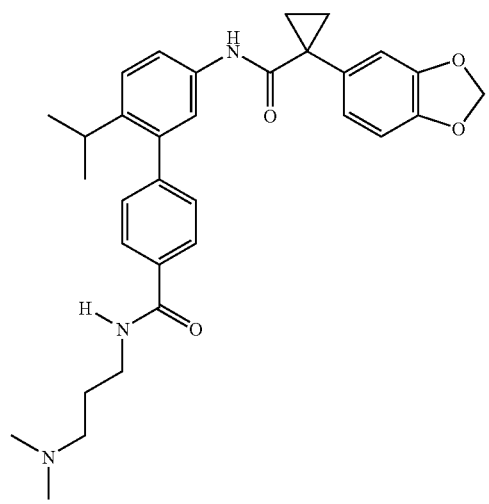
1124
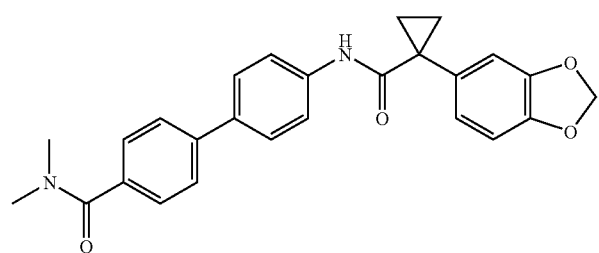
1125
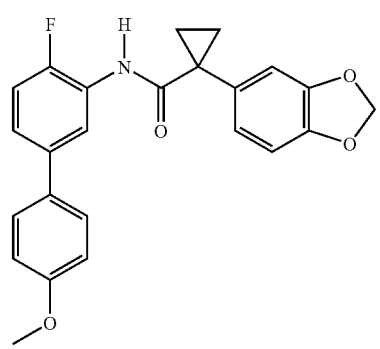
1126

TABLE 1-continued
Examples of compounds of the present invention.
1127
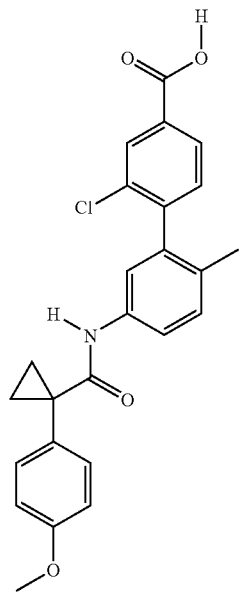
1128
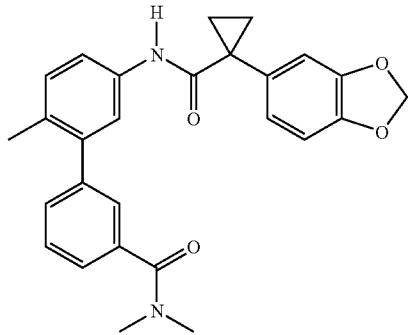
1129
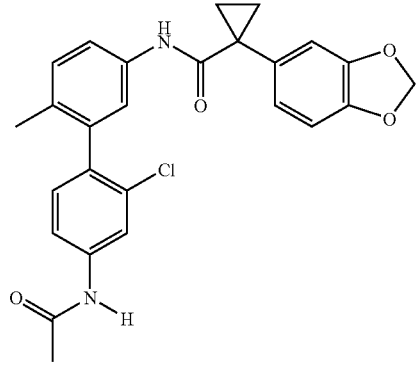

TABLE 1-continued
Examples of compounds of the present invention.
1130
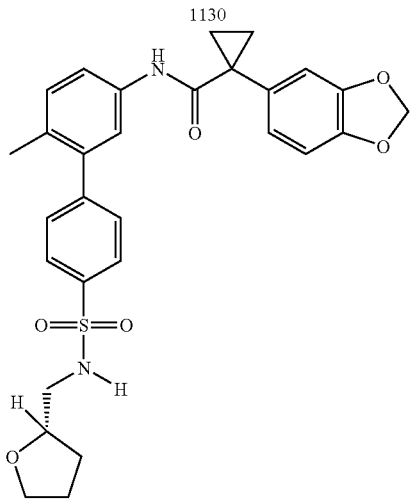
1131
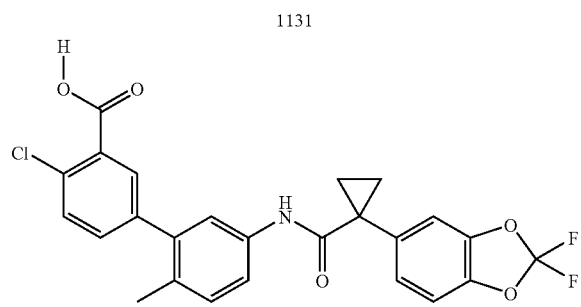
1132
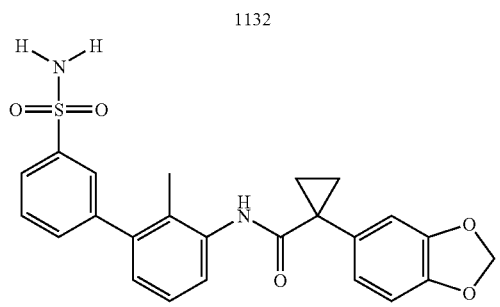
1133
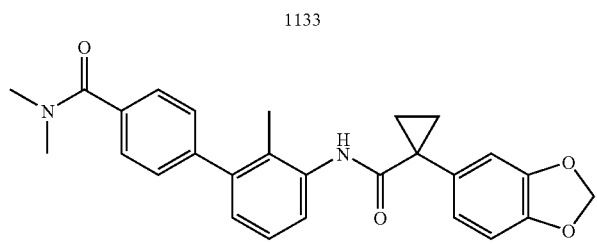

TABLE 1-continued
Examples of compounds of the present invention.
1134
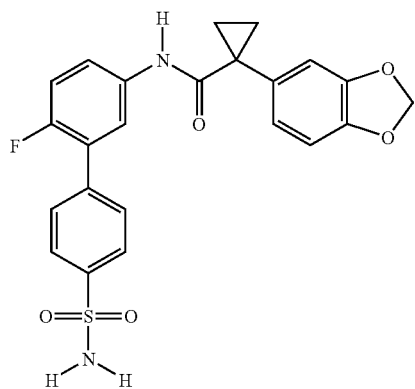
1135
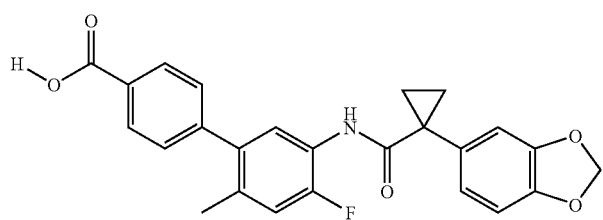
1136
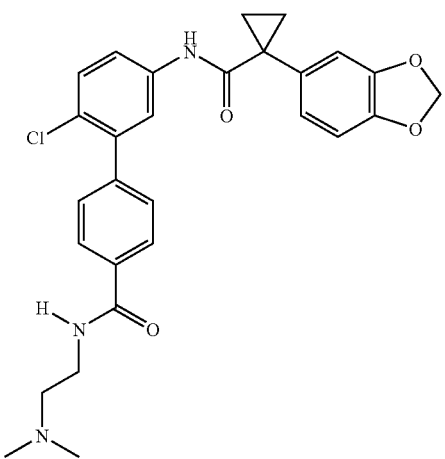
1137
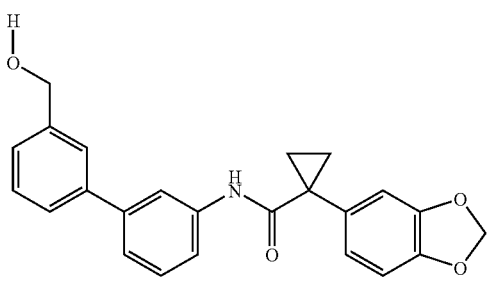

TABLE 1-continued
Examples of compounds of the present invention.
1138
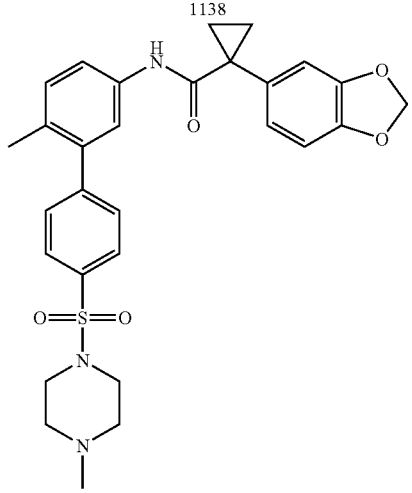
1139
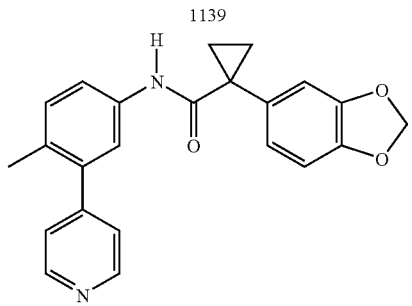
1140
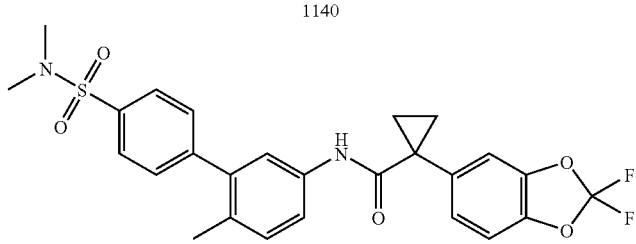
1141
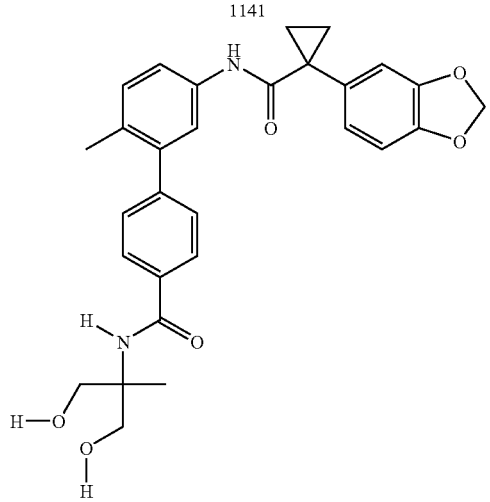

TABLE 1-continued
Examples of compounds of the present invention.
1142
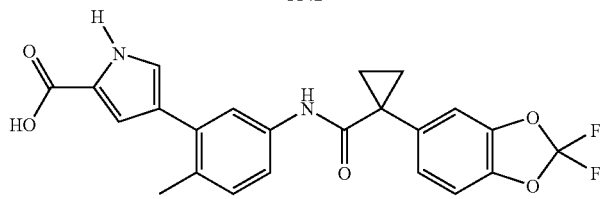
1143
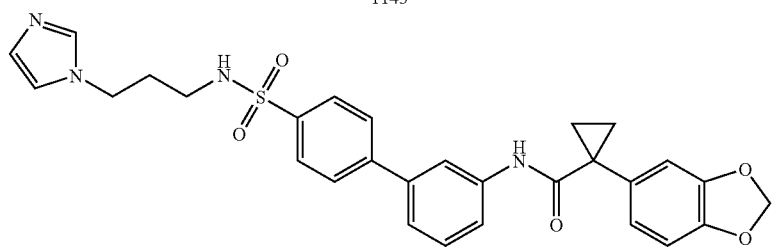
1144
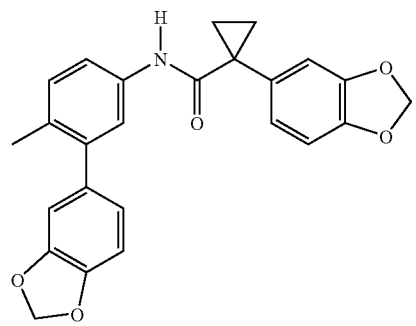
1145
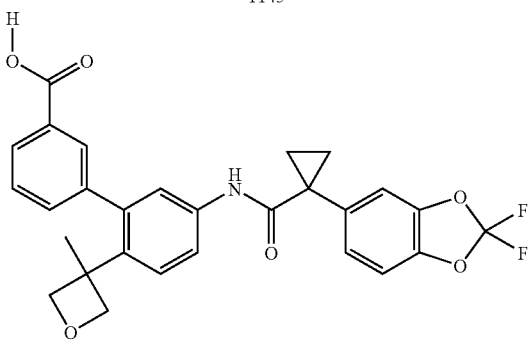
1146
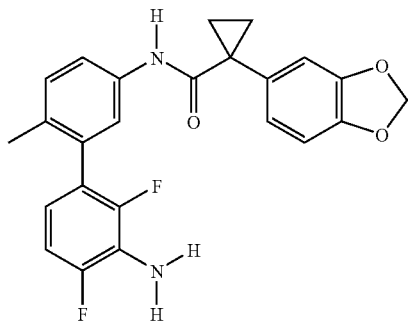

US 7,671,221 B2
TABLE 1-continued
Examples of compounds of the present invention.
1147
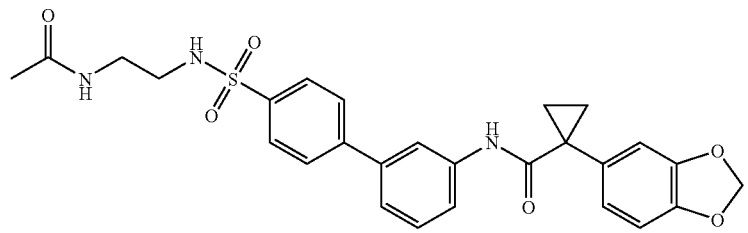
1148
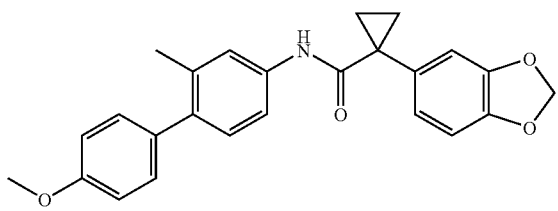
1149
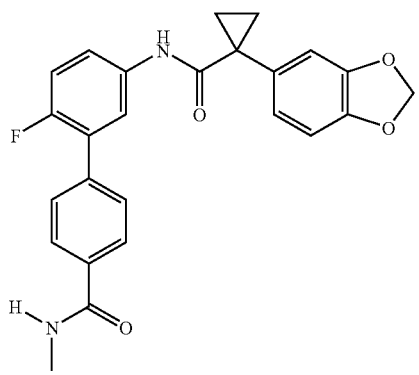
1150
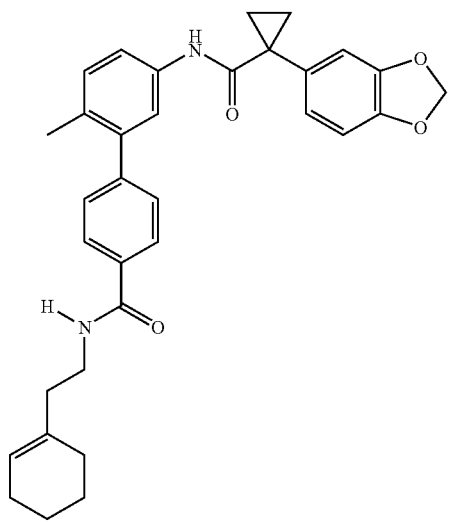

TABLE 1-continued
Examples of compounds of the present invention.
1151
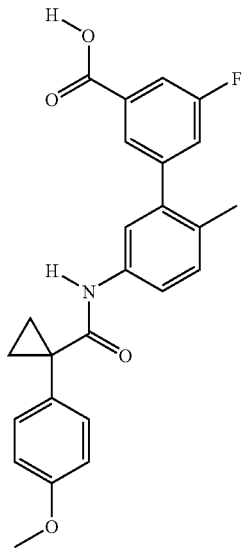
1152
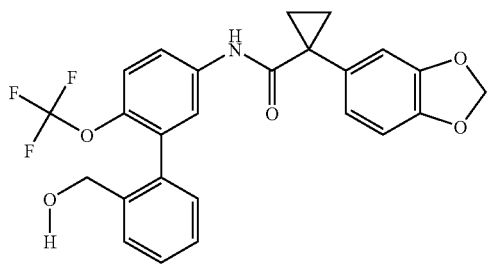
1153
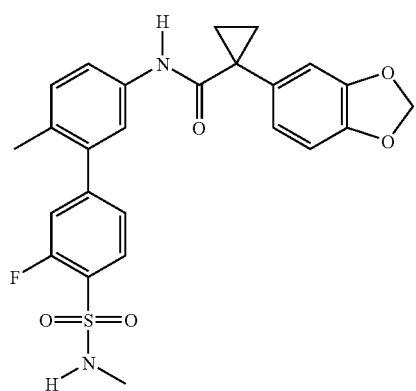

TABLE 1-continued
Examples of compounds of the present invention.
1154
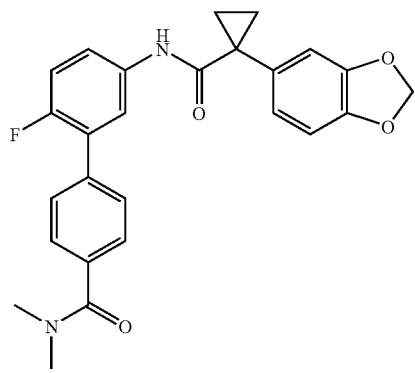
1155
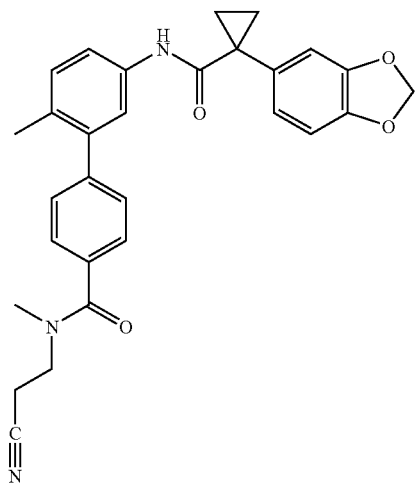
1156
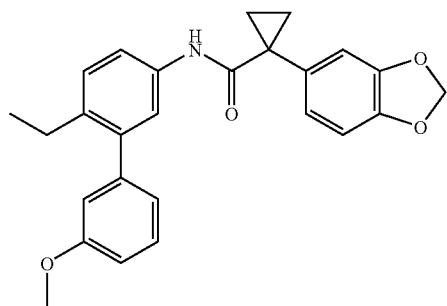
1157
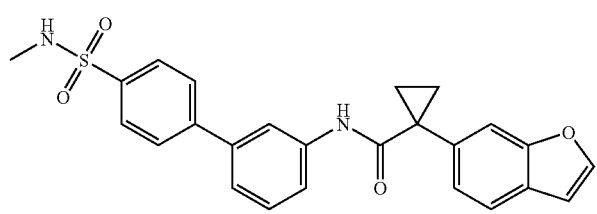

TABLE 1-continued
Examples of compounds of the present invention.
1158
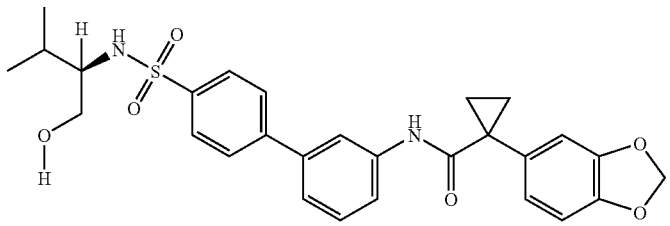
1159
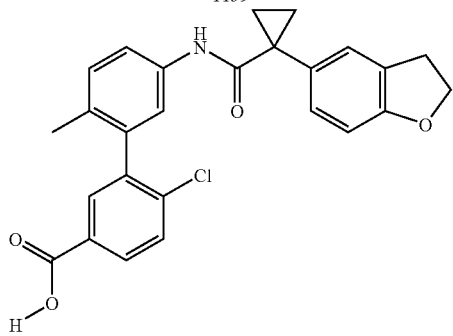
1160
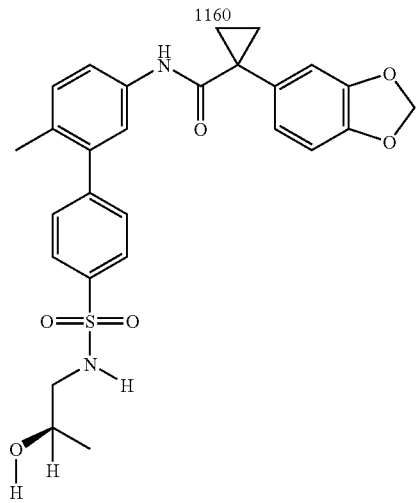
1161
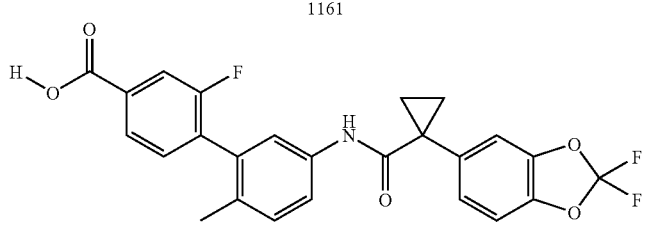

TABLE 1-continued
Examples of compounds of the present invention.
1162
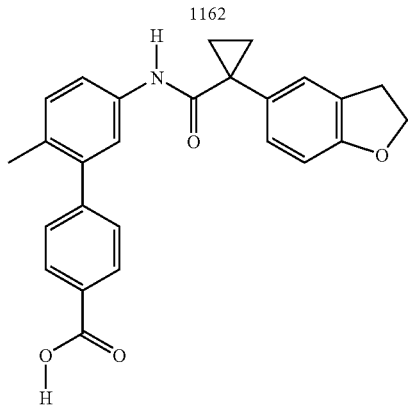
1163
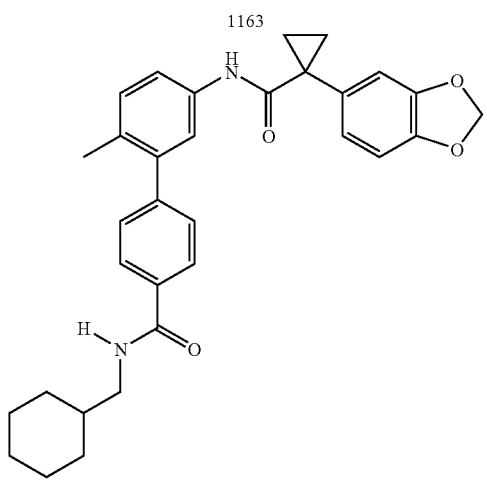
1164
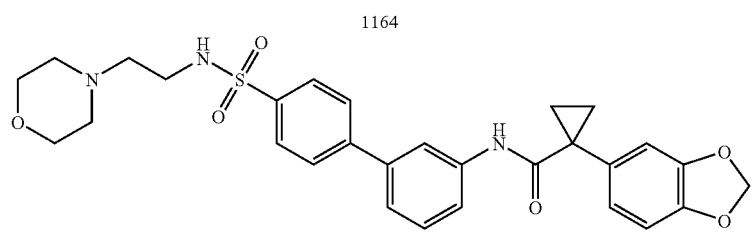
1165
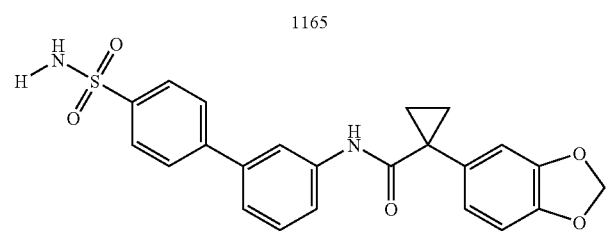

TABLE 1-continued
Examples of compounds of the present invention.
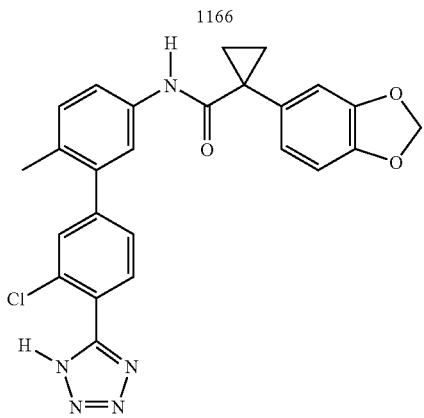
1166
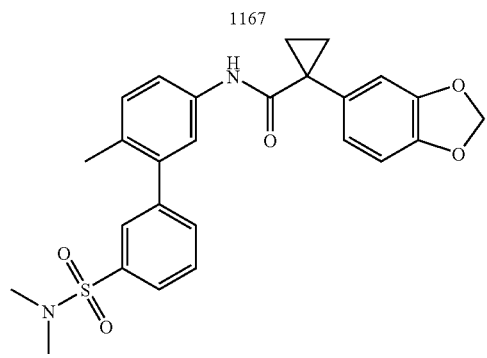
1167
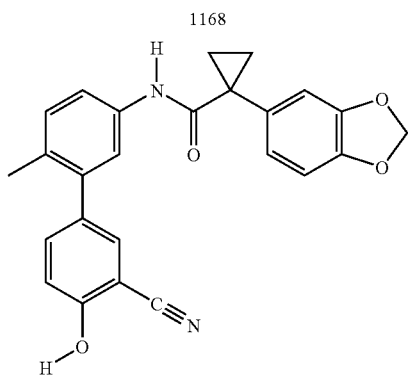
1168
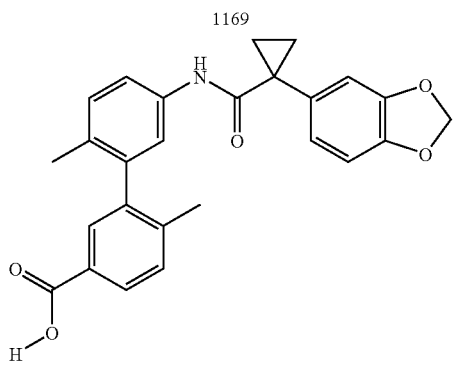
1169

TABLE 1-continued
Examples of compounds of the present invention.
1170
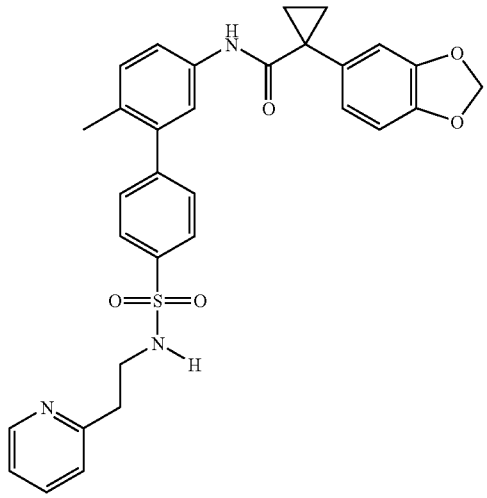
1171
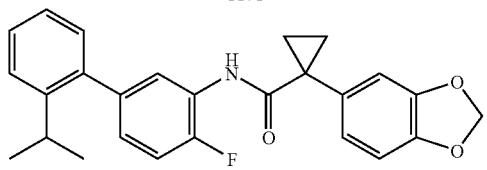
1172
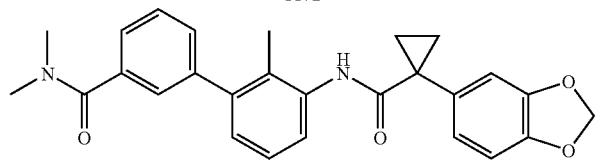
1173
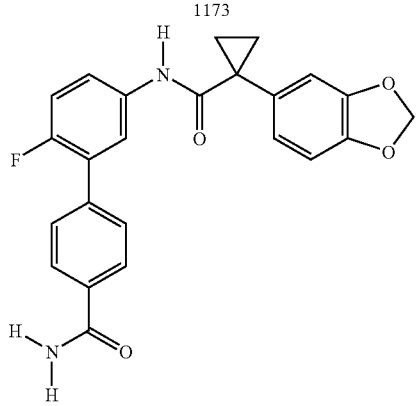
1174
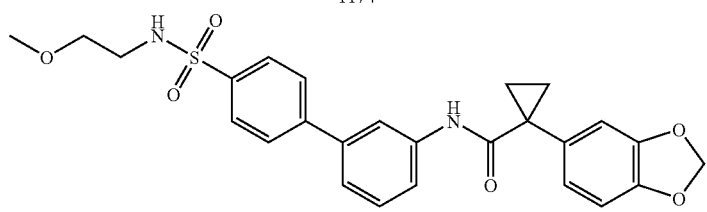

TABLE 1-continued
Examples of compounds of the present invention.
1175
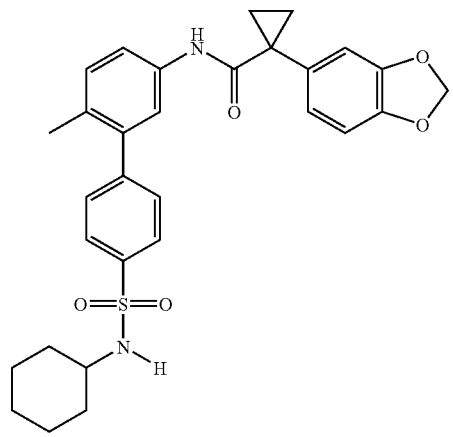
1176
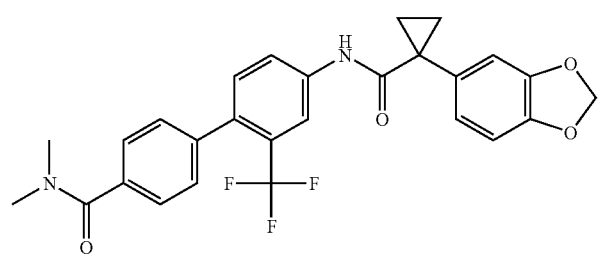
1177
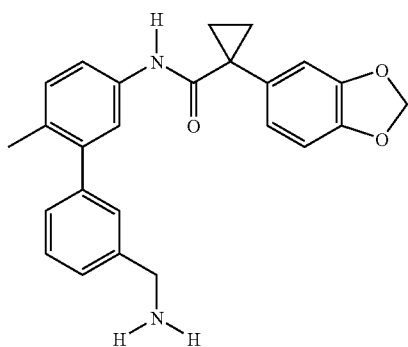
1178
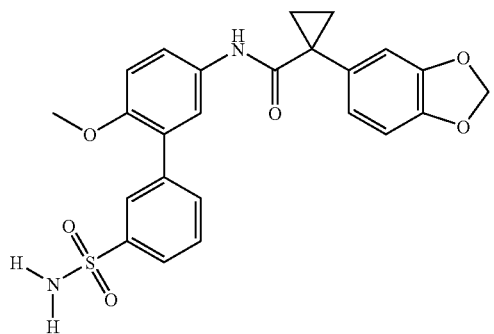

TABLE 1-continued
Examples of compounds of the present invention.
1179
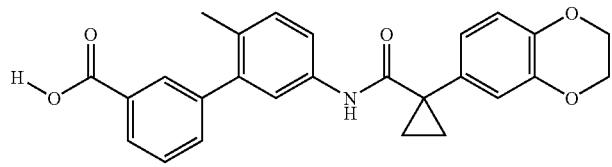
1180
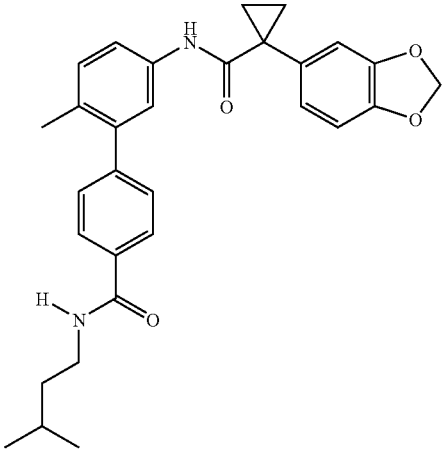
1181
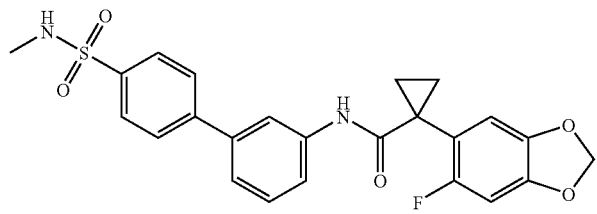
1182
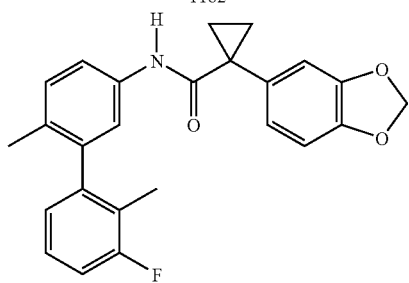
1183
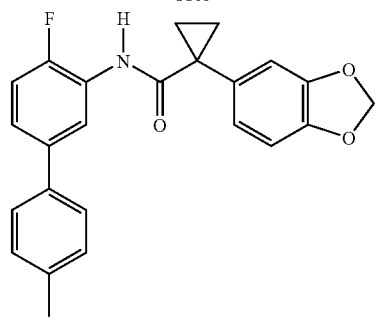

TABLE 1-continued
Examples of compounds of the present invention.
1184
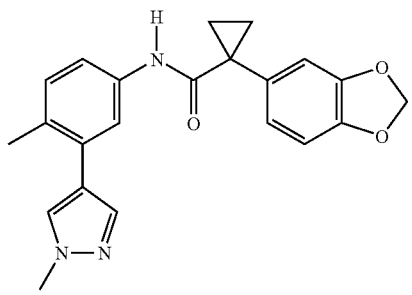
1185
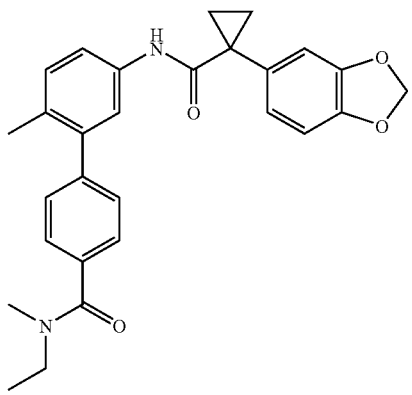
1186
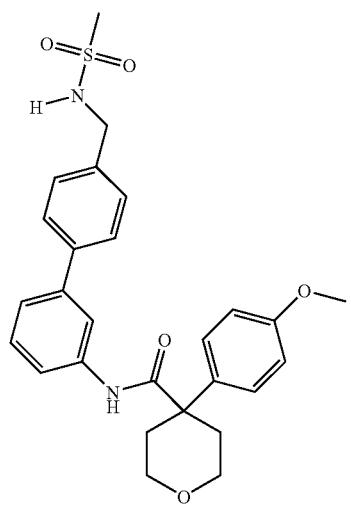

TABLE 1-continued
Examples of compounds of the present invention.
1187
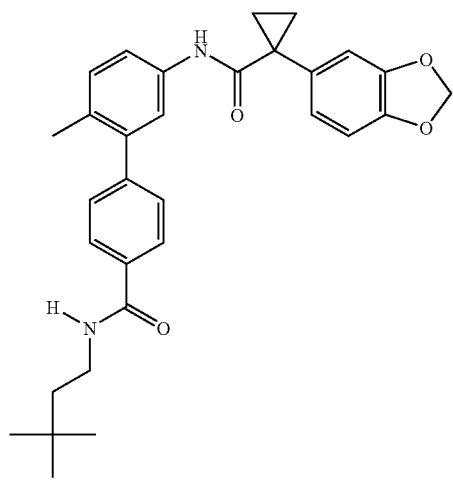
1188
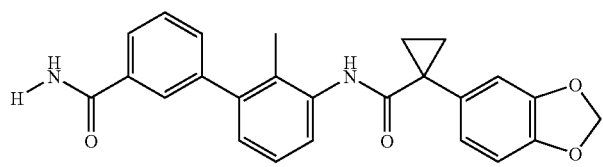
1189
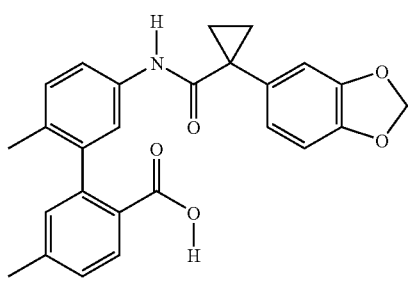
1190
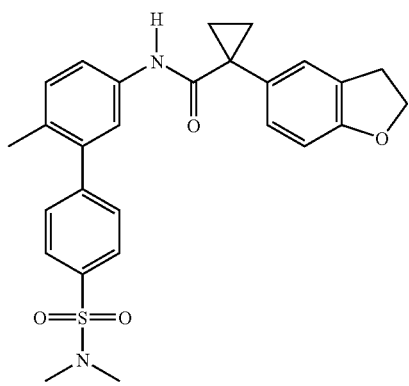

TABLE 1-continued
Examples of compounds of the present invention.
1191
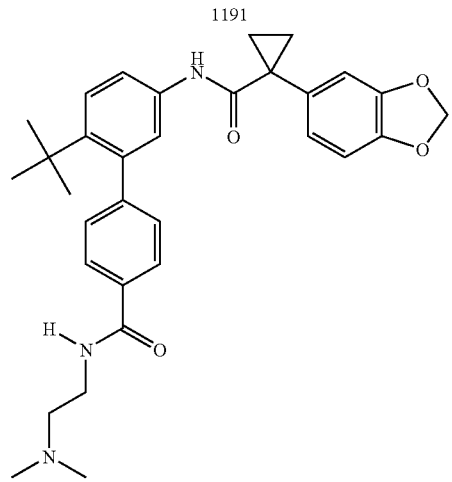
1192
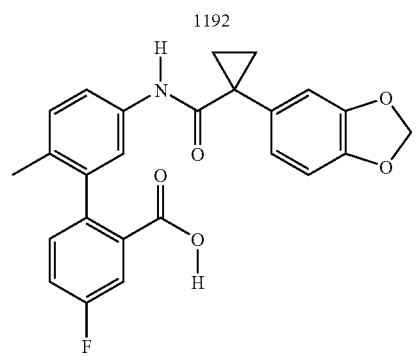
1193
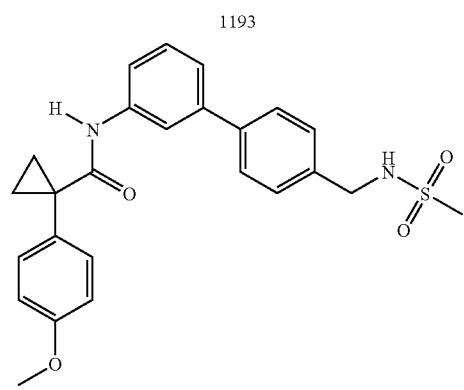
1194
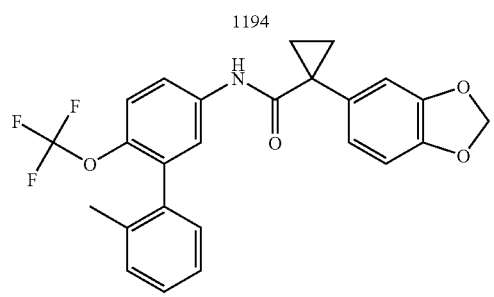

TABLE 1-continued
Examples of compounds of the present invention.
1195
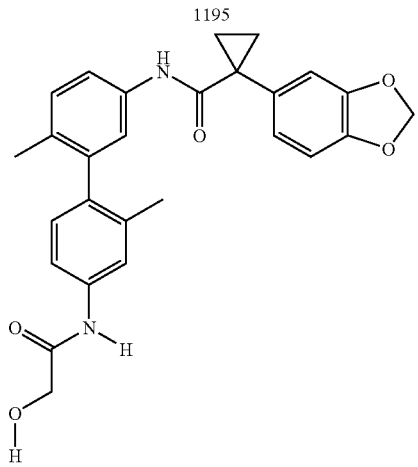
1196
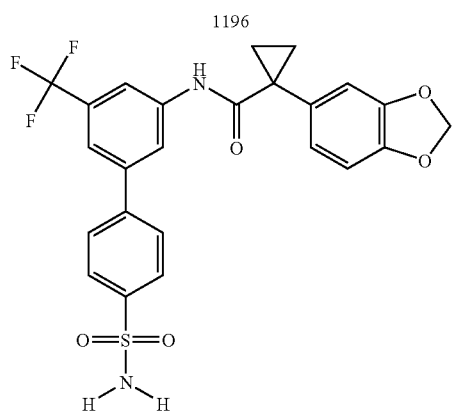
1197
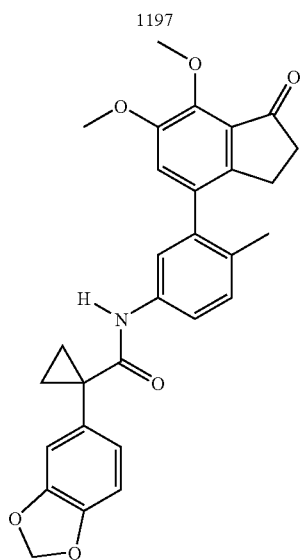

TABLE 1-continued
Examples of compounds of the present invention.
1198
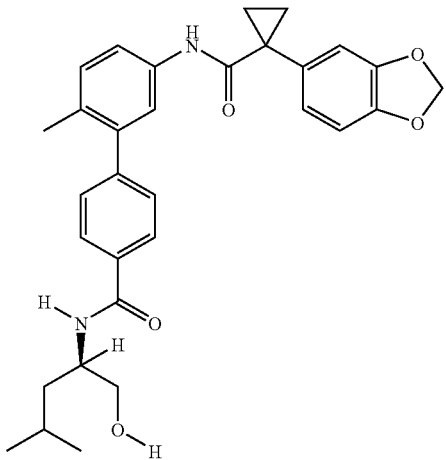
1199
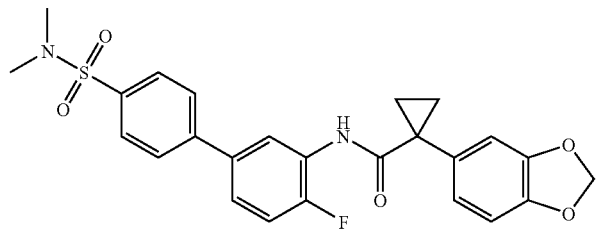
1200
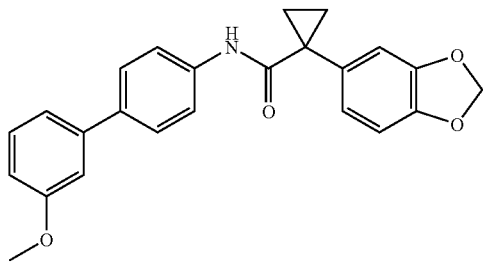
1201
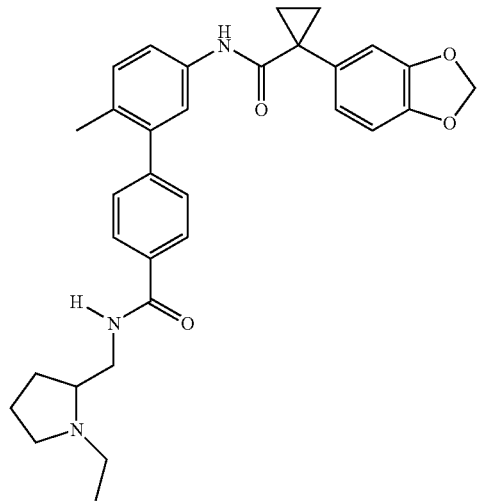

TABLE 1-continued
Examples of compounds of the present invention.
1202
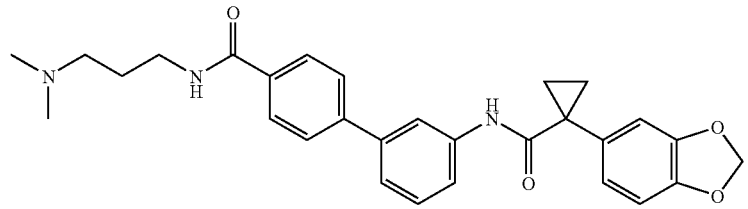
1203
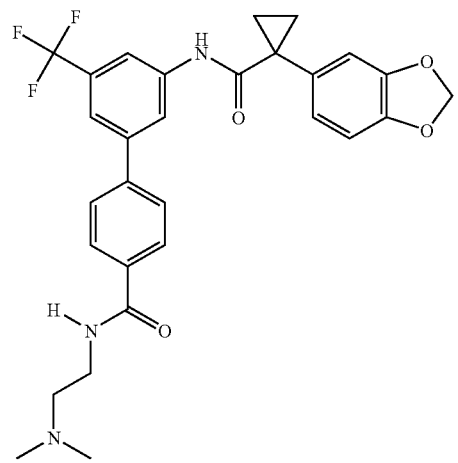
1204
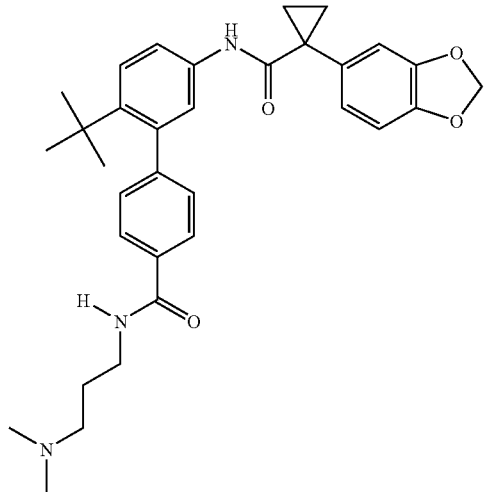
1205
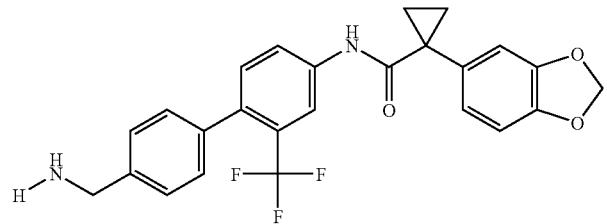

TABLE 1-continued
Examples of compounds of the present invention.
1206
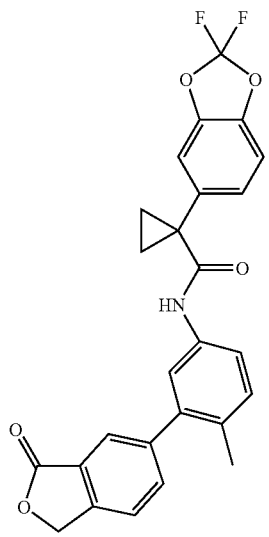
1207
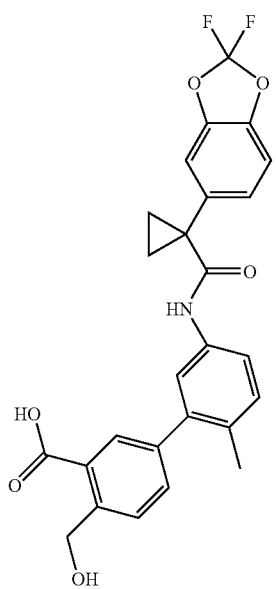

TABLE 1-continued
Examples of compounds of the present invention.
1208
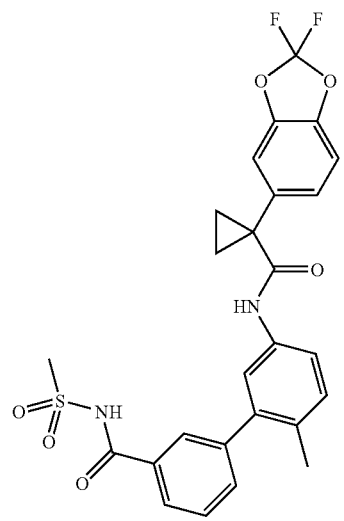
1209
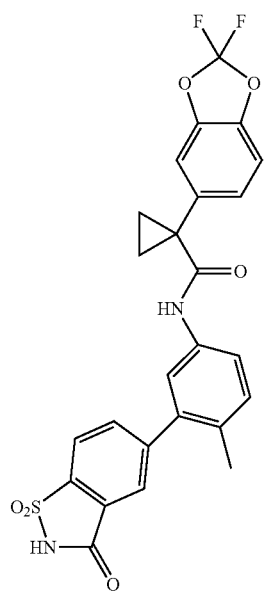

TABLE 1-continued
Examples of compounds of the present invention.
1210
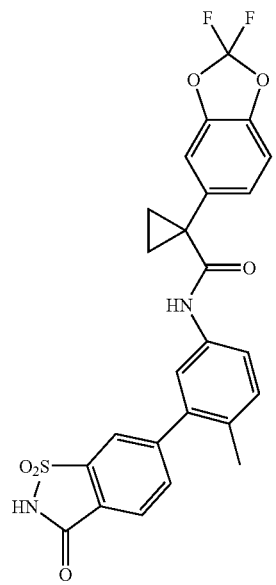
1211
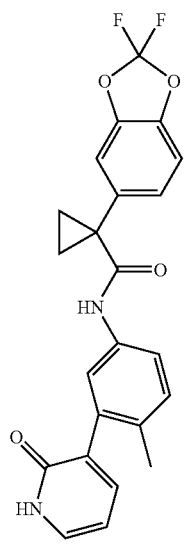

TABLE 1-continued
Examples of compounds of the present invention.
1212
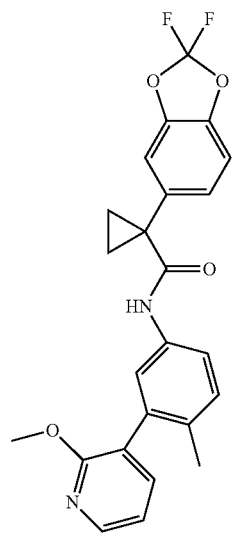
1213
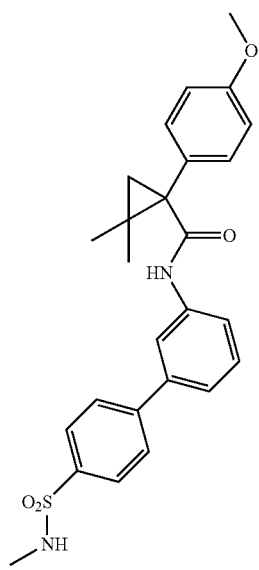

TABLE 1-continued
Examples of compounds of the present invention.
1214
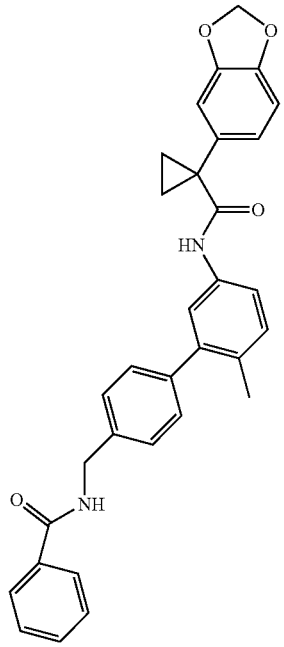
1215
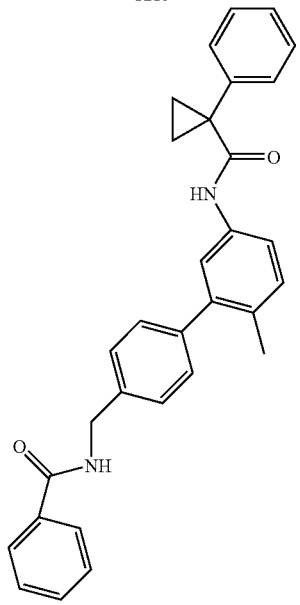

TABLE 1-continued

Examples of compounds of the present invention.

1216

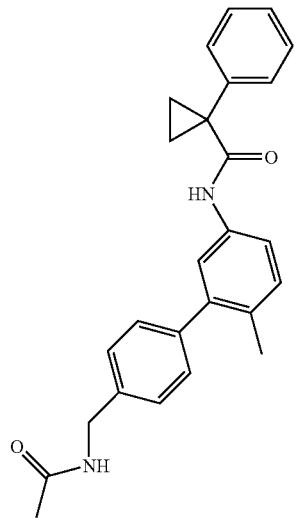

Synthetic Schemes

Compounds of the invention may be prepared by well-known methods in the art. Exemplary methods are illustrated below in Scheme I-Scheme IV.

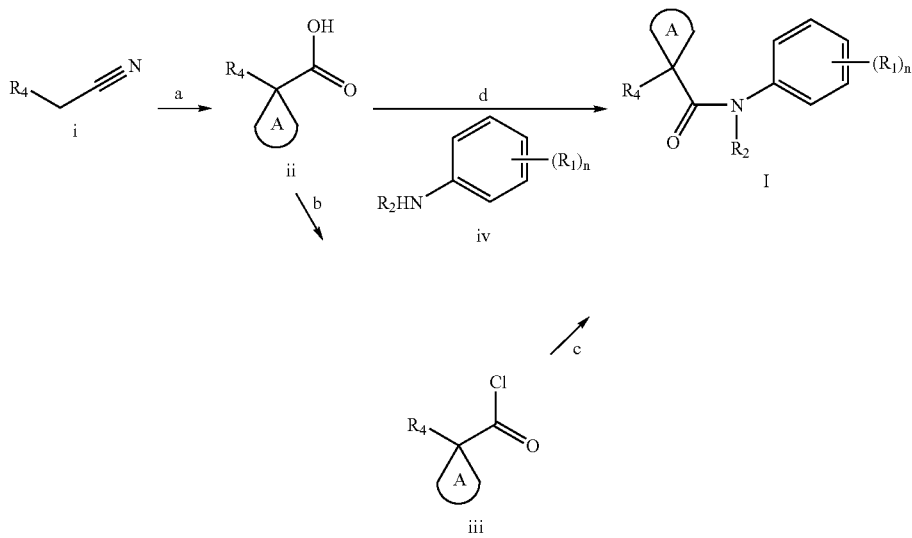

Scheme I

Referring to Scheme I, a nitrile of formula i is alkylated (step a) with a dihalo-aliphatic in the presence of a base such as, for example, 50% sodium hydroxide and, optionally, a phase transfer reagent such as, for example, benzyltriethylammonium chloride (BTEAC), to produce the corresponding alkylated nitrile (not shown) which on hydrolysis in situ produces the acid ii. Compounds of formula ii may be converted to the acid chloride iii (step b) with a suitable reagent such as, for example, thionyl chloride/DMF. Reaction of the acid chloride iii with an aniline of formula iv under known conditions, (step c) produces the amide compounds of the invention formula I. Alternatively, the acid ii may be reacted directly with the aniline iv (step d) in the presence of a coupling reagent such as, for example, HATU, under known conditions to give the amides I.

In some instances, when one of $R_1$ is a halogen, compounds of formula I may be further modified as shown below in Scheme II.

Scheme II

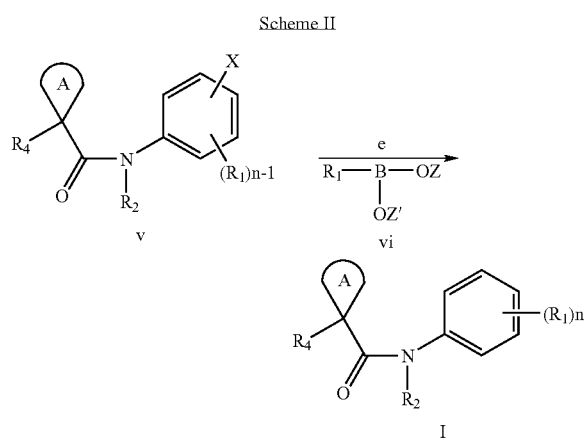

Referring to Scheme II, reaction of the amide v, wherein X is halogen, with a boronic acid derivative vi (step e) wherein Z and Z' are independently H, alkyl or Z and Z' together with the atoms to which they are bound form a five or six membered optionally substituted cycloaliphatic ring, in the presence of a catalyst such as, for example, palladium acetate or dichloro-[1,1-bis(diphenylphosphino) ferrocene]palladium (II) (Pd(dppf)Cl$_2$), provides compounds of the invention wherein one of R$_1$ is aryl or heteroaryl.

The phenylacetonitriles of formula i are commercially available or may be prepared as shown in Scheme III.

Scheme III

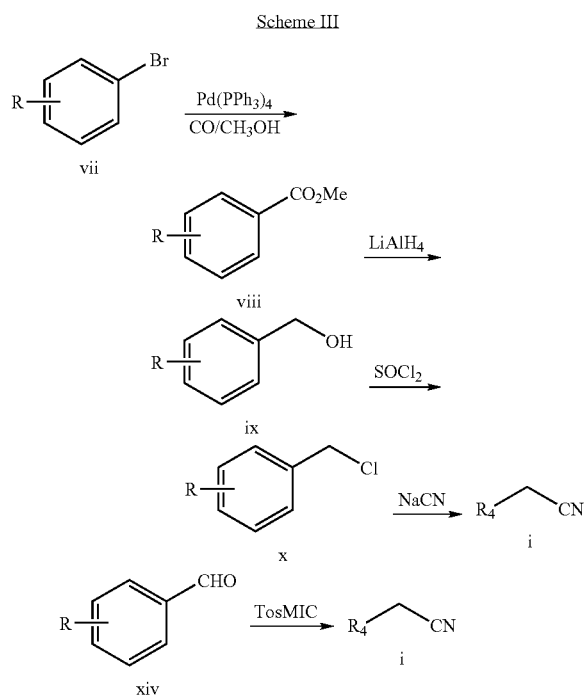

Referring to Scheme III, wherein R represents substituents as described for R$_4$, the aryl bromide vii is converted to the ester viii with carbon monoxide and methanol in the presence of tetrakis(triphenylphosphine)palladium (0). The ester viii is reduced to the alcohol ix with a reducing reagent such as lithium aluminum hydride. The benzyl alcohol ix is converted to the corresponding benzylchloride with, for example, thionyl chloride. Reaction of the benzylchloride x with a cyanide, for example sodium cyanide, provides the starting nitrites i. Or the aldehyde xiv can also be converted into the corresponding nitrile i by reaction with TosMIC reagent.

The aryl bromides vii are commercially available or may be prepared by known methods.

In some instances, the anilines iv (Scheme I) wherein one of R$_1$ is aryl or heteroaryl may be prepared as shown in Scheme IV.

Scheme IV

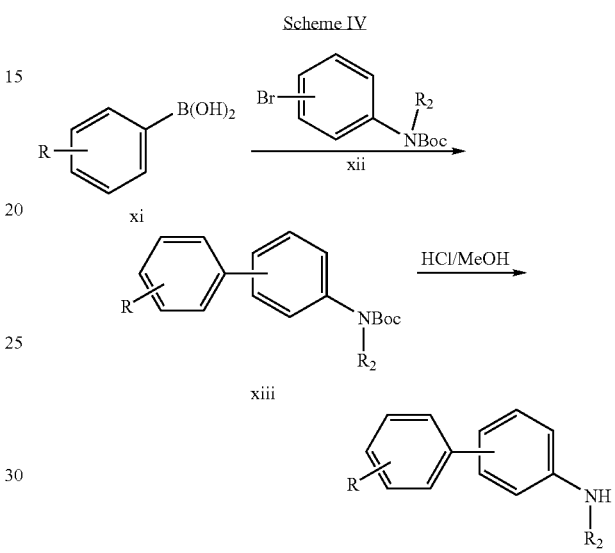

Referring to Scheme IV, an aryl boronic acid xi is coupled with an aniline xii protected as, for example, a tert-butoxycarbonyl derivative (BOC), in the presence of a palladium reagent as previously described for Scheme II to give xiii. Removal of the protecting group under known conditions such as aqueous HCl provides the desired substituted aniline.

Boronic acids are commercially available or may be prepared by known methods.

In some instances, R$_1$ and R$_4$ may contain functionality such as, for example, a carboxylate, a nitrile or an amine, which may be further modified using known methods. For example, carboxylates may be converted to amides or carbamates; amines may be converted to amides, sulfonamides or carbamates; nitrites may be reduced to amino methyl compounds which in turn may be further converted to amine derivatives.

Formulations, Administrations, and Uses

Pharmaceutically Acceptable Compositions

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component (s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by ABC transporter activity. In certain embodiments, the present invention provides a method of treating a condition, disease, or disorder implicated by a deficiency of ABC transporter activity, the method comprising administering a composition comprising a compound of formula (I) to a subject, preferably a mammal, in need thereof.

In certain preferred embodiments, the present invention provides a method of treating Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease, Straussler-Scheinker disease, secretory diarrhea, polycystic kidney disease, chronic obstructive pulmonary disease (COPD), dry eye disease, and Sjögren's Syndrome, comprising the step of administering to said mammal an effective amount of a composition comprising a compound of formula (I), or a preferred embodiment thereof as set forth above.

According to an alternative preferred embodiment, the present invention provides a method of treating cystic fibrosis comprising the step of administering to said mammal a composition comprising the step of administering to said mammal an effective amount of a composition comprising a compound of formula (I), or a preferred embodiment thereof as set forth above.

According to the invention an "effective amount" of the compound or pharmaceutically acceptable composition is that amount effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, polycystic kidney disease, chronic obstructive pulmonary disease (COPD), dry eye disease, and Sjögren's Syndrome.

The compounds and compositions, according to the method of the present invention, may be administered using any amount and any route of administration effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, polycystic kidney disease, chronic obstructive pulmonary disease (COPD), dry eye disease, and Sjögren's Syndrome.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracistemally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of ABC transporters. Thus, without wishing to be bound by any particular theory, the compounds and compositions are particularly useful for treating or lessening the severity of a disease, condition, or disorder where hyperactivity or inactivity of ABC transporters is implicated in the disease, condition, or disorder. When hyperactivity or inactivity of an ABC transporter is implicated in a particular disease, condition, or disorder, the disease, condition, or disorder may also be referred to as a "ABC transporter-mediated disease, condition or disorder". Accordingly, in another aspect, the present invention provides a method for treating or lessening the severity of a disease, condition, or disorder where hyperactivity or inactivity of an ABC transporter is implicated in the disease state.

The activity of a compound utilized in this invention as a modulator of an ABC transporter may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating ABC transporter activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of ABC transporter activity in a biological sample is useful for a variety of purposes that are known to one of skill in the art. Examples of such purposes include, but are not limited to, the study of ABC transporters in biological and pathological phenomena; and the comparative evaluation of new modulators of ABC transporters.

In yet another embodiment, a method of modulating activity of an anion channel in vitro or in vivo, is provided comprising the step of contacting said channel with a compound of formula (I). In preferred embodiments, the anion channel is a chloride channel or a bicarbonate channel. In other preferred embodiments, the anion channel is a chloride channel.

According to an alternative embodiment, the present invention provides a method of increasing the number of functional ABC transporters in a membrane of a cell, comprising the step of contacting said cell with a compound of formula (I). The term "functional ABC transporter" as used herein means an ABC transporter that is capable of transport activity. In preferred embodiments, said functional ABC transporter is CFTR.

According to another preferred embodiment, the activity of the ABC transporter is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells" Biophys J 69(4): 1272-80, and Gonzalez, J. E. and R. Y. Tsien (1997) "Improved indicators of cell membrane potential that use fluorescence resonance energy transfer" Chem Biol 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" Drug Discov Today 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a ABC transporter or a fragment thereof in a biological sample in vitro or in vivo comprising (i) a composition comprising a compound of formula (I) or any of the above embodiments; and (ii) instructions for a.) contacting the composition with the biological sample and b.) measuring activity of said ABC transporter or a fragment thereof. In one embodiment, the kit further comprises instructions for a.) contacting an additional composition with the biological sample; b.) measuring the activity of said ABC transporter or a fragment thereof in the presence of said additional compound, and c.) comparing the activity of the ABC transporter in the presence of the additional compound with the density of the ABC transporter in the presence of a composition of formula (I). In preferred embodiments, the kit is used to measure the density of CFTR.

PREPARATIONS AND EXAMPLES

General Procedure 1

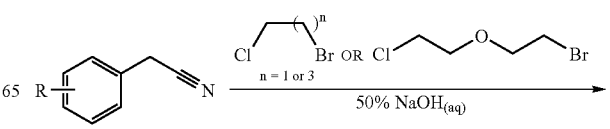

Preparation 1

1-Benzo[1,3]dioxol-5-yl-cyclopropanecarboxylic acid (A-8)

A mixture of benzo[1,3]dioxole-5-acetonitrile (5.10 g 31.7 mmol), 1-bromo-2-chloro-ethane (9.00 mL 109 mmol), and benzyltriethylammonium chloride (0.181 g, 0.795 mmol) was heated at 70° C. and then 50% (wt./wt.) aqueous sodium hydroxide (26 mL) was slowly added to the mixture. The reaction was stirred at 70° C. for 24 hours and was then heated at 130° C. for 48 hours. The dark brown reaction mixture was diluted with water (400 mL) and extracted once with an equal volume of ethyl acetate and once with an equal volume of dichloromethane. The basic aqueous solution was acidified with concentrated hydrochloric acid to pH less than one and the precipitate was filtered and washed with 1 M hydrochloric acid. The solid material was dissolved in dichloromethane (400 mL) and extracted twice with equal volumes of 1 M hydrochloric acid and once with a saturated aqueous solution of sodium chloride. The organic solution was dried over sodium sulfate and evaporated to dryness to give a white to slightly off-white solid (5.23 g, 80%) ESI-MS m/z calc. 206.1, found 207.1 (M+1)$^+$. Retention time 2.37 minutes. $^1$H NMR (400 MHz, DMSO-$d_6$) δ 1.07-1.11 (m, 2H), 1.38-1.42 (m, 2H), 5.98 (s, 2H), 6.79 (m, 2H), 6.88 (m, 1H), 12.26 (s, 1H).

Preparation 2

1-(2,2-Difluoro-benzo[1,3]dioxol-5-yl)-cyclopropanecarboxylic acid (A-9)

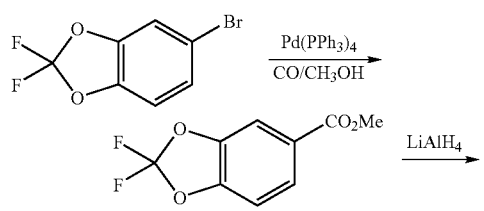

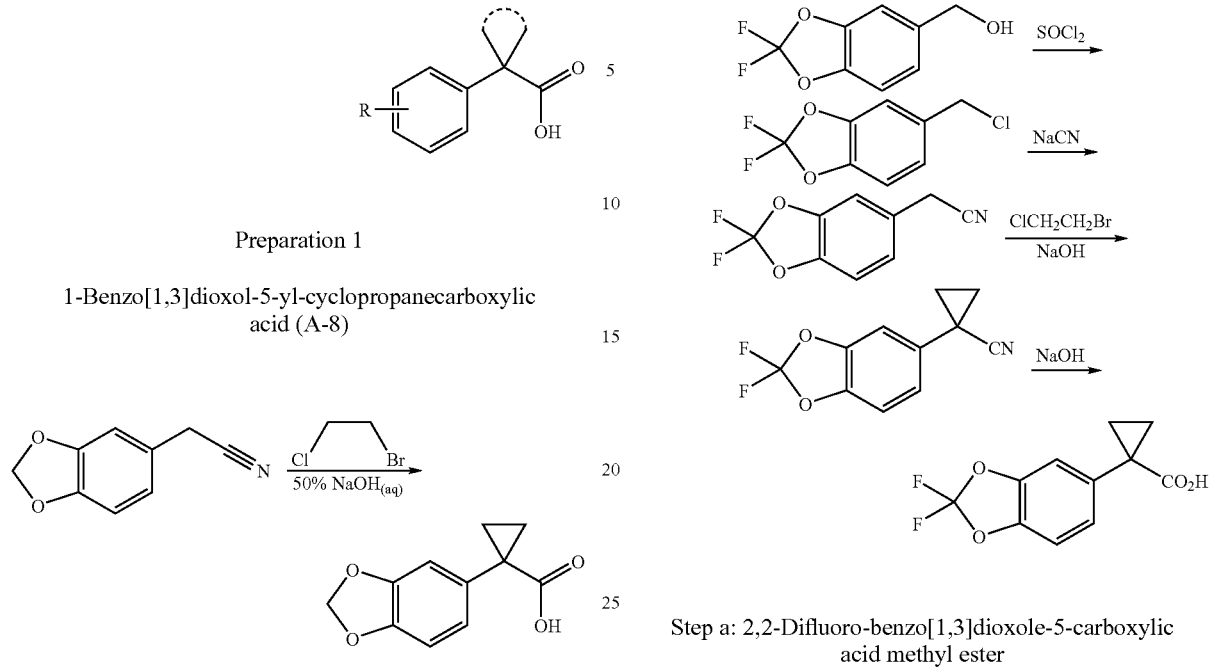

Step a: 2,2-Difluoro-benzo[1,3]dioxole-5-carboxylic acid methyl ester

A solution of 5-bromo-2,2-difluoro-benzo[1,3]dioxole (11.8 g, 50.0 mmol) and tetrakis(triphenylphosphine)palladium (0) [Pd(PPh$_3$)$_4$, 5.78 g, 5.00 mmol] in methanol (20 mL) containing acetonitrile (30 mL) and triethylamine (10 mL) was stirred under a carbon monoxide atmosphere (55 PSI) at 75° C. (oil bath temperature) for 15 hours. The cooled reaction mixture was filtered and the filtrate was evaporated to dryness. The residue was purified by silica gel column chromatography to give crude 2,2-difluoro-benzo[1,3]dioxole-5-carboxylic acid methyl ester (11.5 g), which was used directly in the next step.

Step b: (2,2-Difluoro-benzo[1,3]dioxol-5-yl)-methanol

Crude 2,2-difluoro-benzo[1,3]dioxole-5-carboxylic acid methyl ester (11.5 g) dissolved in 20 mL of anhydrous tetrahydrofuran (THF) was slowly added to a suspension of lithium aluminum hydride (4.10 g, 106 mmol) in anhydrous THF (100 mL) at 0° C. The mixture was then warmed to room temperature. After being stirred at room temperature for 1 hour, the reaction mixture was cooled to 0° C. and treated with water (4.1 g), followed by sodium hydroxide (10% aqueous solution, 4.1 mL). The resulting slurry was filtered and washed with THF. The combined filtrate was evaporated to dryness and the residue was purified by silica gel column chromatography to give (2,2-difluoro-benzo[1,3]dioxol-5-yl)-methanol (7.2 g, 76% over two steps) as a colorless oil.

Step c: 5-Chloromethyl-2,2-difluoro-benzo[1,3]dioxole

Thionyl chloride (45 g, 38 mmol) was slowly added to a solution of (2,2-difluoro-benzo[1,3]dioxol-5-yl)-methanol (7.2 g, 38 mmol) in dichloromethane (200 mL) at 0° C. The resulting mixture was stirred overnight at room temperature and then evaporated to dryness. The residue was partitioned between an aqueous solution of saturated sodium bicarbonate (100 mL) and dichloromethane (100 mL). The separated aqueous layer was extracted with dichloromethane (150 mL) and the organic layer was dried over sodium sulfate, filtrated, and evaporated to dryness to give crude 5-chloromethyl-2,2-difluoro-benzo[1,3]dioxole (4.4 g) which was used directly in the next step.

Step d: (2,2-Difluoro-benzo[1,3]dioxol-5-yl)-acetonitrile

A mixture of crude 5-chloromethyl-2,2-difluoro-benzo[1,3]dioxole (4.4 g) and sodium cyanide (1.36 g, 27.8 mmol) in dimethylsulfoxide (50 mL) was stirred at room temperature overnight. The reaction mixture was poured into ice and extracted with ethyl acetate (300 mL). The organic layer was dried over sodium sulfate and evaporated to dryness to give crude (2,2-difluoro-benzo[1,3]dioxol-5-yl)-acetonitrile (3.3 g) which was used directly in the next step.

Step e: 1-(2,2-Difluoro-benzo[1,3]dioxol-5-yl)-cyclopropanecarbonitrile

Sodium hydroxide (50% aqueous solution, 10 mL) was slowly added to a mixture of crude (2,2-difluoro-benzo[1,3]dioxol-5-yl)-acetonitrile, benzyltriethylammonium chloride (3.00 g, 15.3 mmol), and 1-bromo-2-chloroethane (4.9 g, 38 mmol) at 70° C. The mixture was stirred overnight at 70° C. before the reaction mixture was diluted with water (30 mL) and extracted with ethyl acetate. The combined organic layers were dried over sodium sulfate and evaporated to dryness to give crude 1-(2,2-difluoro-benzo[1,3]dioxol-5-yl)-cyclopropanecarbonitrile, which was used directly in the next step.

Step f: 1-(2,2-Difluoro-benzo[1,3]dioxol-5-yl)-cyclopropanecarboxylic acid (A-9)

To 1-(2,2-difluoro-benzo[1,3]dioxol-5-yl)-cyclopropanecarbonitrile (crude from the last step) was added 10% aqueous sodium hydroxide (50 mL) and the mixture was heated at reflux for 2.5 hours. The cooled reaction mixture was washed with ether (100 mL) and the aqueous phase was acidified to pH 2 with 2M hydrochloric acid. The precipitated solid was filtered to give 1-(2,2-difluoro-benzo[1,3]dioxol-5-yl)-cyclopropanecarboxylic acid as a white solid (0.15 g, 2% over four steps). ESI-MS m/z calc. 242.2, found 243.3; $^1$H NMR (CDCl$_3$) δ 7.14-7.04 (m, 2H), 6.98-6.96 (m, 1H), 1.74-1.64 (m, 2H), 1.26-1.08 (m, 2H).

Preparation 3

2-(4-(Benzyloxy)-3-chlorophenyl)acetonitrile

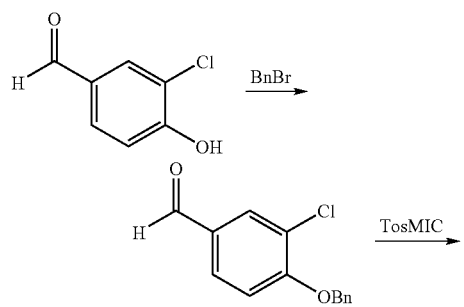

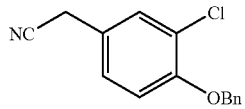

Step a: 4-Benzyloxy-3-chloro-benzaldehyde

To a solution of 3-chloro-4-hydroxy-benzaldehyde (5.0 g, 32 mmol) and BnBr (6.6 g, 38 mmol) in CH$_3$CN (100 mL) was added K$_2$CO$_3$ (8.8 g, 64 mmol). The mixture was heated at reflux for 2 hours. The resulting mixture was poured into water (100 mL), and extracted with EtOAc (100 mL×3). The combined organic layers were washed with brine, dried over anhydrous Na$_2$SO$_4$ and evaporated under vacuum to give crude product, which was purified by column (petroleum ether/EtOAc 15:1) to give 4-benzyloxy-3-chloro-benzaldehyde (7.5 g, 95%). $^1$H NMR (CDCl$_3$, 400 MHz) δ 9.85 (s, 1H), 7.93 (d, J=2.0 Hz, 1H), 7.73 (dd, J=2.0, 8.4 Hz, 1H), 7.47-7.34 (m, 5H), 7.08 (d, J=8.8 Hz, 1H), 4.26 (s, 2H).

Step b: 2-(4-(Benzyloxy)-3-chlorophenyl)acetonitrile

To a suspension of t-BuOK (11.7 g, 96 mmol) in THF (200 mL) was added a solution of TosMIC (9.4 g, 48 mmol) in THF (100 mL) at −78° C. The mixture was stirred for 15 minutes, treated with a solution of 4-benzyloxy-3-chloro-benzaldehyde (7.5 g, 30 mmol) in THF (50 mL) dropwise, and continued to stir for 1.5 hours at −78° C. To the cooled reaction mixture was added methanol (30 mL). The mixture was heated at reflux for 30 minutes. Solvent of the reaction mixture was removed to give a crude product, which was dissolved in water (300 mL). The aqueous phase was extracted with EtOAc (3×100 mL). The combined organic layers were dried and evaporated under reduced pressure to give crude product, which was purified by column chromatography (petroleum ether/EtOAc 10:1) to afford 2-(4-(benzyloxy)-3-chlorophenyl)acetonitrile (2.7 g, 34%). $^1$H NMR (400 MHz, CDCl$_3$) δ 7.52-7.32 (m, 6H), 7.15 (dd, J=2.4, 8.4 Hz, 1H), 6.95 (d, J=8.4 Hz, 1H), 5.26 (s, 2H), 3.73 (s, 2H). $^{13}$C NMR (100 MHz, CDCl$_3$) δ 154.0, 136.1, 129.9, 128.7, 128.7, 128.1, 127.2, 127.1, 127.1, 124.0, 123.0, 117.5, 114.4, 70.9, 22.5.

Preparation 4

1-(2-Oxo-2,3-dihydrobenzo[d]oxazol-5-yl)cyclopropane-carboxylic acid (A-19)

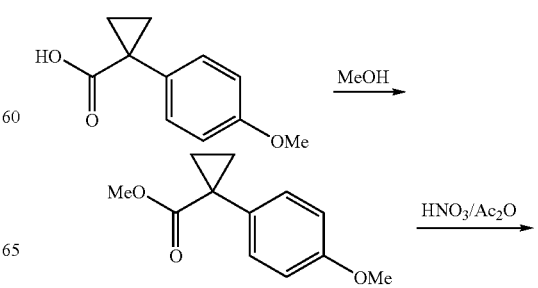

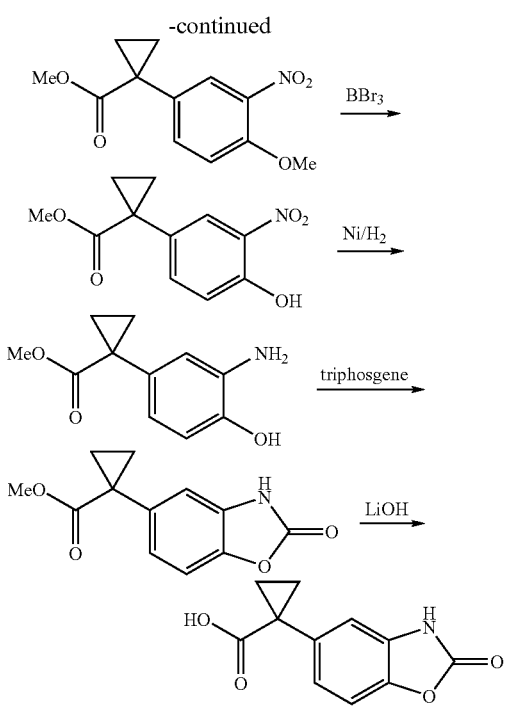

Step a:
1-(4-Methoxy-phenyl)-cyclopropanecarboxylic acid methyl ester

To a solution of 1-(4-methoxy-phenyl)-cyclopropanecarboxylic acid (50.0 g, 0.26 mol) in MeOH (500 mL) was added toluene-4-sulfonic acid monohydrate (2.5 g, 13.1 mmol) at room temperature. The reaction mixture was heated at reflux for 20 hours. MeOH was removed by evaporation under vacuum and EtOAc (200 mL) was added. The organic layer was washed with sat. aq. NaHCO$_3$ (100 mL) and brine, dried over anhydrous Na$_2$SO$_4$ and evaporated under vacuum to give 1-(4-methoxy-phenyl)-cyclopropanecarboxylic acid methyl ester (53.5 g, 99%). $^1$H NMR (CDCl$_3$, 400 MHz) δ 7.25-7.27 (m, 2H), 6.85 (d, J=8.8 Hz, 2H), 3.80 (s, 3H), 3.62 (s, 3H), 1.58 (q, J=3.6 Hz, 2H), 1.15 (q, J=3.6 Hz, 2H).

Step b: 1-(4-Methoxy-3-nitro-phenyl)-cyclopropanecarboxylic acid methyl ester

To a solution of 1-(4-methoxy-phenyl)-cyclopropanecarboxylic acid methyl ester (30.0 g, 146 mmol) in Ac$_2$O (300 mL) was added a solution of HNO$_3$ (14.1 g, 146 mmol, 65%) in AcOH (75 mL) at 0° C. The reaction mixture was stirred at 0~5° C. for 3 h before aq. HCl (20%) was added dropwise at 0° C. The resulting mixture was extracted with EtOAc (200 mL×3). The organic layer was washed with sat. aq. NaHCO$_3$ then brine, dried over anhydrous Na$_2$SO$_4$ and evaporated under vacuum to give 1-(4-methoxy-3-nitro-phenyl)-cyclopropanecarboxylic acid methyl ester (36.0 g, 98%), which was directly used in the next step. $^1$H NMR (CDCl$_3$, 300 MHz) δ 7.84 (d, J=2.1 Hz, 1H), 7.54 (dd, J=2.1, 8.7 Hz, 1H), 7.05 (d, J=8.7 Hz, 1H), 3.97 (s, 3H), 3.65 (s, 3H), 1.68-1.64 (m, 2H), 1.22-1.18 (m, 2H).

Step c: 1-(4-Hydroxy-3-nitro-phenyl)-cyclopropanecarboxylic acid methyl ester

To a solution of 1-(4-methoxy-3-nitro-phenyl)-cyclopropane-carboxylic acid methyl ester (10.0 g, 39.8 mmol) in CH$_2$Cl$_2$ (100 mL) was added BBr$_3$ (12.0 g, 47.8 mmol) at −70° C. The mixture was stirred at −70° C. for 1 hour, then allowed to warm to −30° C. and stirred at this temperature for 3 hours. Water (50 mL) was added dropwise at −20° C., and the resulting mixture was allowed to warm room temperature before it was extracted with EtOAc (200 mL×3). The combined organic layers were dried over anhydrous Na$_2$SO$_4$ and evaporated under vacuum to give the crude product, which was purified by column chromatography on silica gel (petroleum ether/EtOAc 15:1) to afford 1-(4-hydroxy-3-nitro-phenyl)-cyclopropanecarboxylic acid methyl ester (8.3 g, 78%). $^1$H NMR (CDCl$_3$, 400 MHz) δ 10.5 (s, 1H), 8.05 (d, J=2.4 Hz, 1H), 7.59 (dd, J=2.0, 8.8 Hz, 1H), 7.11 (d, J=8.4 Hz, 1H), 3.64 (s, 3H), 1.68-1.64 (m, 2H), 1.20-1.15 (m, 2H).

Step d: 1-(3-Amino-4-hydroxy-phenyl)-cyclopropanecarboxylic acid methyl ester

To a solution of 1-(4-hydroxy-3-nitro-phenyl)-cyclopropanecarboxylic acid methyl ester (8.3 g, 35.0 mmol) in MeOH (100 mL) was added Raney Ni (0.8 g) under nitrogen atmosphere. The mixture was stirred under hydrogen atmosphere (1 atm) at 35° C. for 8 hours. The catalyst was filtered off through a Celite pad and the filtrate was evaporated under vacuum to give crude product, which was purified by column chromatography on silica gel (P.E./EtOAc 1:1) to give 1-(3-amino-4-hydroxy-phenyl)-cyclopropanecarboxylic acid methyl ester (5.3 g, 74%). $^1$H NMR (CDCl$_3$, 400 MHz) δ 6.77 (s, 1H), 6.64 (d, J=2.0 Hz, 2H), 3.64 (s, 3H), 1.55-1.52 (m, 2H), 1.15-1.12 (m, 2H).

Step e: 1-(2-Oxo-2,3-dihydro-benzooxazol-5-yl)-cyclopropanecarboxylic acid methyl ester To a solution of 1-(3-amino-4-hydroxy-phenyl)-cyclopropanecarboxylic acid methyl ester (2.0 g, 9.6 mmol) in THF (40 mL) was added triphosgene (4.2 g, 14 mmol) at room temperature. The mixture was stirred for 20 minutes at this temperature before water (20 mL) was added dropwise at 0° C. The resulting mixture was extracted with EtOAc (100 mL×3). The combined organic layers were dried over anhydrous Na$_2$SO$_4$ and evaporated under vacuum to give 1-(2-oxo-2,3-dihydro-benzooxazol-5-yl)-cyclopropanecarboxylic acid methyl ester (2.0 g, 91%), which was directly used in the next step. $^1$H NMR (CDCl$_3$, 300 MHz) δ 8.66 (s, 1H), 7.13-7.12 (m, 2H), 7.07 (s, 1H), 3.66 (s, 3H), 1.68-1.65 (m, 2H), 1.24-1.20 (m, 2H).

Step f: 1-(2-Oxo-2,3-dihydrobenzo[d]oxazol-5-yl) cyclopropanecarboxylic acid

To a solution of 1-(2-oxo-2,3-dihydro-benzooxazol-5-yl)-cyclopropanecarboxylic acid methyl ester (1.9 g, 8.1 mmol) in MeOH (20 mL) and water (2 mL) was added LiOH.H$_2$O (1.7 g, 41 mmol) in portions at room temperature. The reaction mixture was stirred for 20 hours at 50° C. MeOH was removed by evaporation under vacuum before water (100 mL) and EtOAc (50 mL) were added. The aqueous layer was separated, acidified with HCl (3 mol/L) and extracted with EtOAc (100 mL×3). The combined organic layers were dried over anhydrous Na$_2$SO$_4$ and evaporated under vacuum to give 1-(2-oxo-2,3-dihydrobenzo[d]oxazol-5-yl)cyclopropanecarboxylic acid (1.5 g, 84%). $^1$H NMR (DMSO 400 MHz) δ

12.32 (brs, 1H), 11.59 (brs, 1H), 7.16 (d, J=8.4 Hz, 1H), 7.00 (d, J=8.0 Hz, 1H), 1.44-1.41 (m, 2H), 1.13-1.10 (m, 2H). MS (ESI) m/e (M+H⁺) 218.1.

Preparation 5

1-(Benzo[d]oxazol-5-yl)cyclopropanecarboxylic acid (A-20)

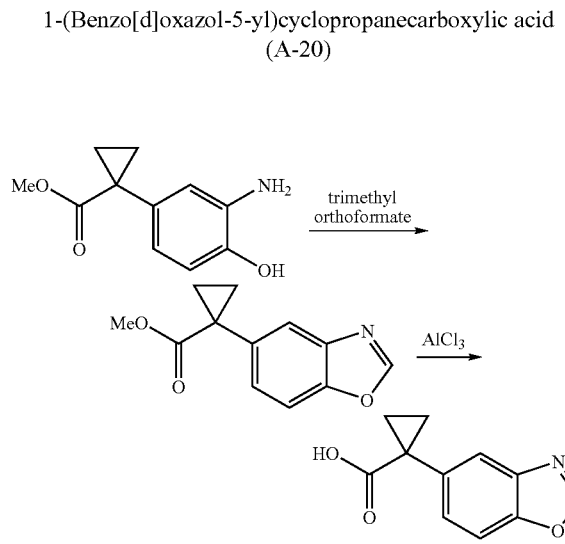

Step a: 1-Benzooxazol-5-yl-cyclopropanecarboxylic acid methyl ester

To a solution of 1-(3-amino-4-hydroxy-phenyl)-cyclopropanecarboxylic acid methyl ester (3.00 g, 14.5 mmol) in DMF were added trimethyl orthoformate (5.30 g, 14.5 mmol) and a catalytic amount of p-tolueneslufonic acid monohydrate (0.3 g) at room temperature. The mixture was stirred for 3 hours at room temperature. The mixture was diluted with water and extracted with EtOAc (100 mL×3). The combined organic layers were dried over anhydrous $Na_2SO_4$ and evaporated under vacuum to give crude 1-benzooxazol-5-yl-cyclopropanecarboxylic acid methyl ester (3.1 g), which was directly used in the next step. ¹H NMR (CDCl₃, 400 MHz) δ 8.09 (s, 1), 7.75 (d, J=1.2 Hz, 1H), 7.53-7.51 (m, 1H), 7.42-7.40 (m, 1H), 3.66 (s, 3H), 1.69-1.67 (m, 2H), 1.27-1.24 (m, 2H).

Step b:
1-(Benzo[d]oxazol-5-yl)cyclopropanecarboxylic acid

To a solution of crude 1-benzooxazol-5-yl-cyclopropanecarboxylic acid methyl ester (2.9 g) in EtSH (30 mL) was added AlCl₃ (5.3 g, 40.1 mmol) in portions at 0° C. The reaction mixture was stirred for 18 hours at room temperature. Water (20 mL) was added dropwise at 0° C. The resulting mixture was extracted with EtOAc (100 mL×3). The combined organic layers were dried over anhydrous $Na_2SO_4$ and evaporated under vacuum to give the crude product, which was purified by column chromatography on silica gel (petroleum ether/EtOAc 1:2) to give 1-(benzo[d]oxazol-5-yl) cyclopropanecarboxylic acid (280 mg, two steps: 11%). ¹H NMR (DMSO 400 MHz) δ 12.25 (brs, 1H), 8.71 (s, 1H), 7.70-7.64 (m, 2H), 7.40 (dd, J=1.6, 8.4 Hz, 1H), 1.49-1.46 (m, 2H), 1.21-1.18 (m, 2H). MS (ESI) m/e (M+H⁺) 204.4.

Preparation 6

2-(7-Chlorobenzo[d][1,3]dioxol-5-yl)acetonitrile

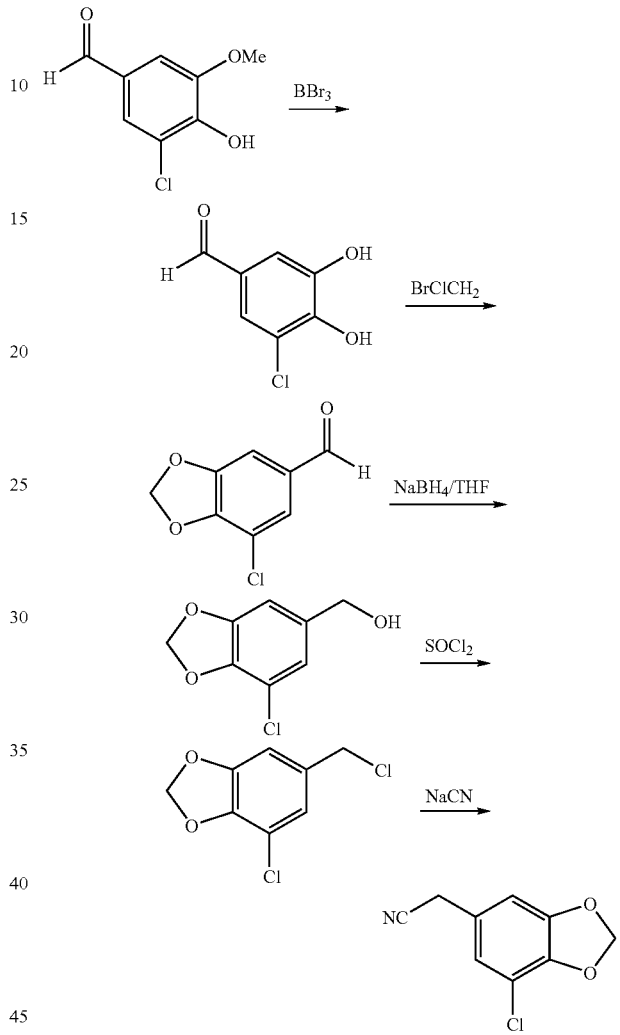

Step a: 3-Chloro-4,5-dihydroxybenzaldehyde

To a suspension of 3-chloro-4-hydroxy-5-methoxy-benzaldehyde (10 g, 54 mmol) in dichloromethane (300 mL) was added BBr₃ (26.7 g, 107 mmol) dropwise at −40° C. under N₂. After addition, the mixture was stirred at this temperature for 5 h and then was poured into ice water. The precipitated solid was filtered and washed with petroleum ether. The filtrate was evaporated under reduced pressure to afford 3-chloro-4,5-dihydroxybenzaldehyde (9.8 g, 89%), which was directly used in the next step.

Step b:
7-Chlorobenzo[d][1,3]dioxole-5-carbaldehyde

To a solution of 3-chloro-4,5-dihydroxybenzaldehyde (8.0 g, 46 mmol) and BrClCH₂ (23.9 g, 185 mmol) in dry DMF (100 mL) was added Cs$_2$CO$_3$ (25 g, 190 mmol). The mixture was stirred at 60° C. overnight and was then poured into water. The resulting mixture was extracted with EtOAc (50 mL×3). The combined extracts were washed with brine (100 mL), dried over Na$_2$SO$_4$ and concentrated under reduced pressure to afford 7-chlorobenzo[d][1,3]dioxole-5-carbaldehyde (6.0 g, 70%). $^1$H NMR (400 MHz, CDCl$_3$) δ 9.74 (s, 1H), 7.42 (d, J=0.4 Hz, 1H), 7.26 (d, J=3.6 Hz, 1H), 6.15 (s, 2H)

Step c: (7-Chlorobenzo[d][1,3]dioxol-5-yl)methanol

To a solution of 7-chlorobenzo[d][1,3]dioxole-5-carbaldehyde (6.0 g, 33 mmol) in THF (50 mL) was added NaBH$_4$ (2.5 g, 64 mmol)) in portion at 0° C. The mixture was stirred at this temperature for 30 min and then poured into aqueous NH$_4$Cl solution. The organic layer was separated, and the aqueous phase was extracted with EtOAc (50 mL×3). The combined extracts were dried over Na$_2$SO$_4$ and evaporated under reduced pressure to afford (7-chlorobenzo[d][1,3]dioxol-5-yl)methanol, which was directly used in the next step.

Step d:
4-Chloro-6-(chloromethyl)benzo[d][1,3]dioxole

A mixture of (7-chlorobenzo[d][1,3]dioxol-5-yl)methanol (5.5 g, 30 mmol) and SOCl$_2$ (5.0 mL, 67 mmol) in dichloromethane (20 mL) was stirred at room temperature for 1 h and was then poured into ice water. The organic layer was separated and the aqueous phase was extracted with dichloromethane (50 mL×3). The combined extracts were washed with water and aqueous NaHCO$_3$ solution, dried over Na$_2$SO$_4$ and evaporated under reduced pressure to afford 4-chloro-6-(chloromethyl)benzo[d][1,3]dioxole, which was directly used in the next step.

Step e:
2-(7-Chlorobenzo[d][1,3]dioxol-5-yl)acetonitrile

A mixture of 4-chloro-6-(chloromethyl)benzo[d][1,3]dioxole (6.0 g, 29 mmol) and NaCN (1.6 g, 32 mmol) in DMSO (20 mL) was stirred at 40° C. for 1 h and was then poured into water. The mixture was extracted with EtOAc (30 mL×3). The combined organic layers were washed with water and brine, dried over Na$_2$SO$_4$ and evaporated under reduced pressure to afford 2-(7-chlorobenzo[d][1,3]dioxol-5-yl)acetonitrile (3.4 g, 58%). $^1$H NMR 67 6.81 (s, 1H), 6.71 (s, 1H), 6.07 (s, 2H), 3.64 (s, 2H). $^{13}$C-NMR δ149.2, 144.3, 124.4, 122.0, 117.4, 114.3, 107.0, 102.3, 23.1.

Preparation 7

2-(7-Fluorobenzo[d][1,3]dioxol-5-yl)acetonitrile

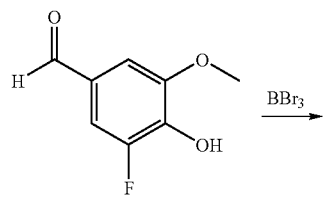

-continued

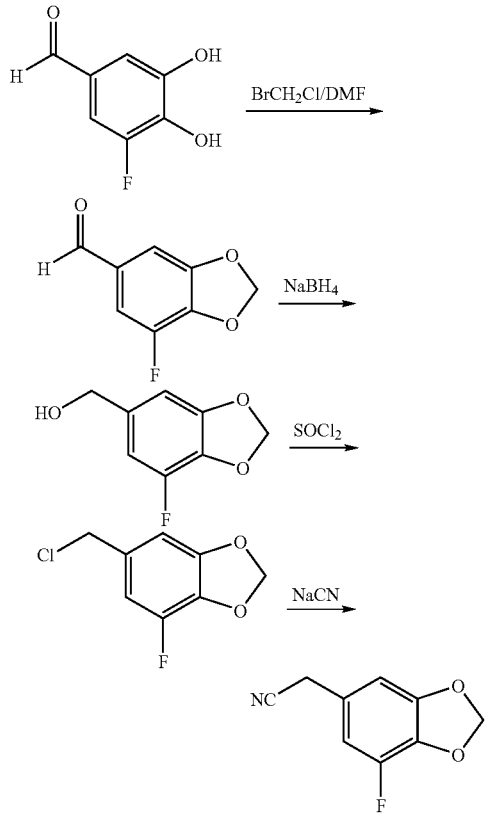

Step a: 3-Fluoro-4,5-dihydroxy-benzaldehyde

To a suspension of 3-fluoro-4-hydroxy-5-methoxy-benzaldehyde (1.35 g, 7.94 mmol) in dichloromethane (100 mL) was added BBr$_3$ (1.5 mL, 16 mmol) dropwise at −78° C. under N$_2$. After addition, the mixture was warmed to −30° C. and it was stirred at this temperature for 5 h. The reaction mixture was poured into ice water. The precipitated solid was collected by filtration and washed with dichloromethane to afford 3-fluoro-4,5-dihydroxy-benzaldehyde (1.1 g, 89%), which was directly used in the next step.

Step b: 7-Fluoro-benzo[1,3]dioxole-5-carbaldehyde

To a solution of 3-fluoro-4,5-dihydroxy-benzaldehyde (1.5 g, 9.6 mmol) and BrClCH$_2$ (4.9 g, 38.5 mmol) in dry DMF (50 mL) was added Cs$_2$CO$_3$ (12.6 g, 39 mmol). The mixture was stirred at 60° C. overnight and was then poured into water. The resulting mixture was extracted with EtOAc (50 mL×3). The combined organic layers were washed with brine (100 mL), dried over Na$_2$SO$_4$ and evaporated under reduced pressure to give the crude product, which was purified by column chromatography on silica gel (petroleum ether/E.A.=10/1) to afford 7-fluoro-benzo[1,3]dioxole-5-carbaldehyde (0.80 g, 49%). $^1$H NMR (300 MHz, CDCl$_3$) δ 9.78 (d, J=0.9 Hz, 1H), 7.26 (dd, J=1.5, 9.3 Hz, 1H), 7.19 (d, J=1.2 Hz, 1H), 6.16 (s, 2H).

Step c: (7-Fluoro-benzo[1,3]dioxol-5-yl)-methanol

To a solution of 7-fluoro-benzo[1,3]dioxole-5-carbaldehyde (0.80 g, 4.7 mmol) in MeOH (50 mL) was added NaBH$_4$ (0.36 g, 9.4 mmol) in portions at 0° C. The mixture was stirred at this temperature for 30 min and was then concentrated to dryness. The residue was dissolved in EtOAc. The EtOAc layer was washed with water, dried over $Na_2SO_4$ and concentrated to dryness to afford (7-fluoro-benzo[1,3]dioxol-5-yl)-methanol (0.80 g, 98%), which was directly used in the next step.

Step d: 6-Chloromethyl-4-fluoro-benzo[1,3]dioxole

To $SOCl_2$ (20 mL) was added (7-fluoro-benzo[1,3]dioxol-5-yl)-methanol (0.80 g, 4.7 mmol) in portions at 0° C. The mixture was warmed to room temperature over 1 h and then was heated at reflux for 1 h. The excess $SOCl_2$ was evaporated under reduced pressure to give the crude product, which was basified with saturated aqueous $NaHCO_3$ to pH ~7. The aqueous phase was extracted with EtOAc (50 mL×3). The combined organic layers were dried over $Na_2SO_4$ and evaporated under reduced pressure to give 6-chloromethyl-4-fluoro-benzo[1,3]dioxole (0.80 g, 92%), which was directly used in the next step.

Step e: 2-(7-Fluorobenzo[d][1,3]dioxol-5-yl)acetonitrile

A mixture of 6-chloromethyl-4-fluoro-benzo[1,3]dioxole (0.80 g, 4.3 mmol) and NaCN (417 mg, 8.51 mmol) in DMSO (20 mL) was stirred at 30° C. for 1 h and was then poured into water. The mixture was extracted with EtOAc (50 mL×3). The combined organic layers were washed with water (50 mL) and brine (50 mL), dried over $Na_2SO_4$ and evaporated under reduced pressure to give the crude product, which was purified by column chromatography on silica gel (petroleum ether/E.A.=10/1) to afford 2-(7-fluorobenzo[d][1,3]dioxol-5-yl)acetonitrile (530 mg, 70%). $^1$H NMR (300 MHz, $CDCl_3$) δ 6.68-6.64 (m, 2H), 6.05 (s, 2H), 3.65 (s, 2H). $^{13}$C-NMR δ151.1, 146.2, 134.1, 124.2, 117.5, 110.4, 104.8, 102.8, 23.3.

Additional acids given in Table 2 were either commercially available or synthesized using appropriate starting materials and the procedures of preparations 1-7.

TABLE 2

| Acids | Carboxylic Acids. Name |
|---|---|
| A-1 | 1-Phenylcyclopropanecarboxylic acid |
| A-2 | 1-(2-Methoxyphenyl)cyclopropanecarboxylic acid |
| A-3 | 1-(3-Methoxyphenyl)cyclopropanecarboxylic acid |
| A-4 | 1-(4-Methoxyphenyl)cyclopropanecarboxylic acid |
| A-5 | 1-(4-(Trifluoromethoxy)phenyl)cyclopropanecarboxylic acid |
| A-6 | 1-(4-Chlorophenyl)cyclopropanecarboxylic acid |
| A-7 | 1-(3,4-Dimethoxyphenyl)cyclopropanecarboxylic acid |
| A-8 | 1-Benzo[1,3]dioxol-5-yl-cyclopropanecarboxylic acid |
| A-9 | 1-(2,2-Difluoro-benzo[1,3]dioxol-5-yl)-cyclopropanecarboxylic acid |
| A-10 | 1-Phenylcyclopentanecarboxylic acid |
| A-11 | 1-(4-Chlorophenyl)cyclopentanecarboxylic acid |
| A-12 | 1-(4-Methoxyphenyl)cyclopentanecarboxylic acid |
| A-13 | 1-(Benzo[d][1,3]dioxol-5-yl)cyclopentanecarboxylic acid |
| A-14 | 1-Phenylcyclohexanecarboxylic acid |
| A-15 | 1-(4-Chlorophenyl)cyclohexanecarboxylic acid |
| A-16 | 1-(4-Methoxyphenyl)cyclohexanecarboxylic acid |
| A-17 | 4-(4-Methoxyphenyl)tetrahydro-2H-pyran-4-carboxylic acid |
| A-18 | 1-(3-Chloro-4-hydroxyphenyl)cyclopropanecarboxylic acid |
| A-19 | 1-(2-Oxo-2,3-dihydrobenzo[d]oxazol-5-yl)cyclopropanecarboxylic acid |
| A-20 | 1-(Benzo[d]oxazol-5-yl)cyclopropanecarboxylic acid |
| A-21 | 1-(7-Chlorobenzo[d][1,3]dioxol-5-yl)cyclopropanecarboxylic acid |

TABLE 2-continued

| Acids | Carboxylic Acids. Name |
|---|---|
| A-22 | 1-(7-Fluorobenzo[d][1,3]dioxol-5-yl)cyclopropanecarboxylic acid |
| A-23 | 1-(3,4-Difluorophenyl)cyclopropanecarboxylic acid |
| A-24 | 1-(1H-Indol-5-yl)cyclopropanecarboxylic acid |
| A-25 | 1-(2,3-Dihydrobenzo[b][1,4]dioxin-6-yl)cyclopropanecarboxylic acid |
| A-26 | 1-(2,3-Dihydrobenzofuran-5-yl)cyclopropanecarboxylic acid |
| A-27 | 1-(3,4-Dichlorophenyl)cyclopropanecarboxylic acid |
| A-28 | 1-(2-Methyl-1H-benzo[d]imidazol-5-yl)cyclopropanecarboxylic acid |
| A-29 | 1-(4-Hydroxy-4-methoxychroman-6-yl)cyclopropanecarboxylic acid |
| A-30 | 1-(Benzofuran-6-yl)cyclopropanecarboxylic acid |
| A-31 | 1-(1-Methyl-1H-benzo[d][1,2,3]triazol-5-yl)cyclopropanecarboxylic acid |
| A-32 | 1-(2,3-Dihydrobenzofuran-6-yl)cyclopropanecarboxylic acid |
| A-33 | 1-(3-Methylbenzo[d]isoxazol-5-yl)cyclopropanecarboxylic acid |
| A-34 | 1-(4-Oxochroman-6-yl)cyclopropanecarboxylic acid |
| A-35 | 1-(Spiro[benzo[d][1,3]dioxole-2,1'-cyclobutane]-5-yl)cyclopropanecarboxylic acid |
| A-36 | 1-(1,3-Dihydroisobenzofuaran-5-yl)cyclopropanecarboxylic acid |
| A-37 | 1-(6-Fluorobenzo[d][1,3]dioxol-5-yl)cyclopropanecarboxylic acid |
| A-38 | 1-(Chroman-6-yl)cyclopropanecarboxylic acid |

Preparation 8

3-Bromo-4-methoxybenzenamine

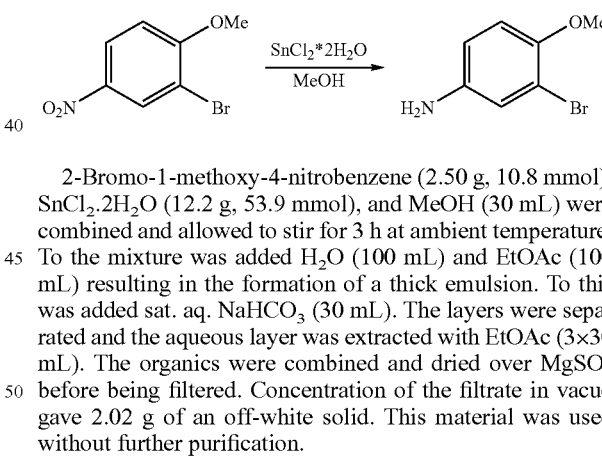

2-Bromo-1-methoxy-4-nitrobenzene (2.50 g, 10.8 mmol), $SnCl_2.2H_2O$ (12.2 g, 53.9 mmol), and MeOH (30 mL) were combined and allowed to stir for 3 h at ambient temperature. To the mixture was added $H_2O$ (100 mL) and EtOAc (100 mL) resulting in the formation of a thick emulsion. To this was added sat. aq. $NaHCO_3$ (30 mL). The layers were separated and the aqueous layer was extracted with EtOAc (3×30 mL). The organics were combined and dried over $MgSO_4$ before being filtered. Concentration of the filtrate in vacuo gave 2.02 g of an off-white solid. This material was used without further purification.

In addition to bromo-anilines prepared according to preparation 8, non-limiting examples of commercially available bromo anilines and bromo nitrobenzenes are given in Table 3.

TABLE 3

| Non-limiting examples of commercially available anilines. |
|---|
| Name |
| 4-Bromoaniline |
| 4-Bromo-3-methylaniline |
| 4-Bromo-3-(trifluoromethyl)aniline |
| 3-Bromoaniline |
| 5-Bromo-2-methylaniline |
| 5-Bromo-2-fluoroaniline |

TABLE 3-continued

Non-limiting examples of commercially available anilines.

Name

5-Bromo-2-(trifluoromethoxy)aniline
3-Bromo-4-methylaniline
3-Bromo-4-fluoroaniline
2-Bromo-1-methoxy-4-nitrobenzene
2-Bromo-1-chloro-4-nitrobenzene
4-Bromo-3-methylaniline
3-Bromo-4-methylaniline
3-Bromo-4-(trifluoromethoxy)aniline
3-Bromo-5-(trifluoromethyl)aniline
3-Bromo-2-methylaniline

Preparation 9

1-(Benzo[d][1,3]dioxol-5-yl)-N-(3-bromo-4-methoxyphenyl)cyclopropane-carboxamide (B-10)

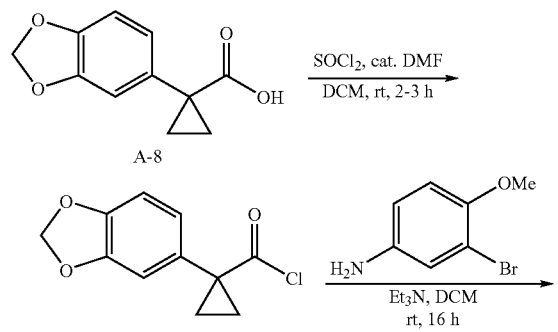

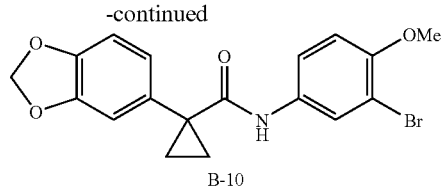

Step a:
1-Benzo[1,3]dioxol-5-yl-cyclopropanecarbonyl chloride

To an oven-dried round bottom flask containing 1-(benzo[d][1,3]dioxol-5-yl)-cyclopropanecarboxylic acid (A-8) (618 mg, 3.0 mmol) and $CH_2Cl_2$ (3 mL) was added thionyl chloride (1.07 g, 9.0 mmol) and N,N-dimethylformamide (0.1 mL). The reaction mixture was stirred at ambient temperature under an Ar atmosphere until the gas evolution ceased (2-3 h). The excess thionyl chloride was removed under vacuum and the resulting residue dissolved in $CH_2Cl_2$ (3 mL). The mixture was used without further manipulation.

Step b: 1-(Benzo[d][1,3]dioxol-5-yl)-N-(3-bromo-4-methoxyphenyl)-cyclopropane-carboxamide (B-10)

To a Solution of the Crude 1-Benzo[1,3]Dioxol-5-yl-Cyclopropanecarbonyl Chloride (3.0 mmol) in $CH_2Cl_2$ (30 mL) at ambient temperature was added a solution of 3-bromo-4-methoxybenzenamine (3.3 mmol), $Et_3N$ (15 mmol), and $CH_2Cl_2$ (90 mL) dropwise. The mixture was allowed to stir for 16 h before it was diluted with $CH_2Cl_2$ (500 mL). The solution was washed with 1N HCl (2×250 mL), sat. aq. $NaHCO_3$ (2×250 mL), then brine (250 mL). The organics were dried over $Na_2SO_4$, filtered, and concentrated in vacuo to provide 1-(benzo[d][1,3]dioxol-5-yl)-N-(3-bromo-4-methoxyphenyl)cyclopropanecarboxamide (B-10) with suitable purity to be used without further purification.

Table 4 lists additional N-bromophenyl amides prepared according to preparation 9 and using appropriate starting materials.

TABLE 4

N-bromophenyl amides prepared according to preparation 9 and using appropriate starting materials.

| Aryl bromides | Name | Anilines |
|---|---|---|
| B-1 | 1-(Benzo[d][1,3]dioxol-5-yl)-N-(4-bromophenyl)cyclopropanecarboxamide | 4-Bromoaniline |
| B-2 | 1-(Benzo[d][1,3]dioxol-5-yl)-N-(4-bromo-3-methylphenyl)cyclopropanecarboxamide | 4-Bromo-3-methylaniline |
| B-3 | 1-(Benzo[d][1,3]dioxol-5-yl)-N-(4-bromo-3-(trifluoromethyl)phenyl)cyclopropanecarboxamide | 4-Bromo-3-(trifluoromethyl)aniline |
| B-4 | 1-(Benzo[d][1,3]dioxol-5-yl)-N-(3-bromophenyl)cyclopropanecarboxamide | 3-Bromoaniline |
| B-5 | 1-(Benzo[d][1,3]dioxol-5-yl)-N-(5-bromo-2-methylphenyl)cyclopropanecarboxamide | 5-Bromo-2-methylaniline |
| B-6 | 1-(Benzo[d][1,3]dioxol-5-yl)-N-(5-bromo-2-fluorophenyl)cyclopropanecarboxamide | 5-Bromo-2-fluoroaniline |
| B-7 | 1-(Benzo[d][1,3]dioxol-5-yl)-N-(5-bromo-2-(trifluoromethoxy)phenyl)cyclopropanecarboxamide | 5-Bromo-2-(trifluoromethoxy)aniline |
| B-8 | 1-(Benzo[d][1,3]dioxol-5-yl)-N-(3-bromo-4-methylphenyl)cyclopropanecarboxamide | 3-Bromo-4-methylaniline |
| B-9 | 1-(Benzo[d][1,3]dioxol-5-yl)-N-(3-bromo-4-fluorophenyl)cyclopropanecarboxamide | 3-Bromo-4-fluoroaniline |
| B-10 | 1-(Benzo[d][1,3]dioxol-5-yl)-N-(3-bromo-4-methoxyphenyl)cyclopropanecarboxamide | 3-Bromo-4-methoxybenzenamine |

TABLE 4-continued

N-bromophenyl amides prepared according to preparation 9 and using appropriate starting materials.

| Aryl bromides | Name | Anilines |
|---|---|---|
| B-11 | 1-(Benzo[d][1,3]dioxol-5-yl)-N-(3-bromo-4-chlorophenyl)cyclopropanecarboxamide | 3-Bromo-4-chloroaniline |
| B-13 | 1-(Benzo[d][1,3]dioxol-5-yl)-N-(3-bromo-4-isopropylphenyl)cyclopropanecarboxamide | 3-Bromo-4-isopropylaniline |
| B-14 | N-(4-Bromo-3-methylphenyl)-1-(2,2-difluorobenzo[d][1,3]dioxol-5-yl)cyclopropanecarboxamide | 4-Bromo-3-methylaniline |
| B-15 | N-(3-Bromo-4-methylphenyl)-1-(2,2-difluorobenzo[d][1,3]dioxol-5-yl)cyclopropanecarboxamide | 3-Bromo-4-methylaniline |
| B-16 | 1-(Benzo[d][1,3]dioxol-5-yl)-N-(3-bromo-4-tert-butylphenyl)cyclopropanecarboxamide | 3-Bromo-4-tert-butylaniline |
| B-18 | 1-(Benzo[d][1,3]dioxol-5-yl)-N-(3-bromo-4-ethylphenyl)cyclopropanecarboxamide | 3-Bromo-4-ethylaniline |
| B-19 | 1-(Benzo[d][1,3]dioxol-5-yl)-N-(3-bromo-4-(trifluoromethoxy)phenyl)cyclopropanecarboxamide | 3-Bromo-4-(trifluoromethoxy)aniline |
| B-20 | 1-(Benzo[d][1,3]dioxol-5-yl)-N-(5-bromo-2-fluoro-4-methylphenyl)cyclopropanecarboxamide | 5-Bromo-2-fluoro-4-methylaniline |
| B-21 | 1-(Benzo[d][1,3]dioxol-5-yl)-N-(3-bromo-5-(trifluoromethyl)phenyl)cyclopropanecarboxamide | 3-Bromo-5-(trifluoromethyl)aniline |
| B-22 | 1-(Benzo[d][1,3]dioxol-5-yl)-N-(3-bromo-2-methylphenyl)cyclopropanecarboxamide | 3-Bromo-2-methylaniline |
| B-23 | N-(3-Bromo-4-(3-methyloxetan-3-yl)phenyl)-1-(2,2-difluorobenzo[d][1,3]dioxol-5-yl)cyclopropanecarboxamide | 3-Bromo-4-(3-methyloxetan-3-yl)aniline |
| B-24 | N-(3-Bromo-4-methylphenyl)-1-(4-methoxyphenyl)cyclopropanecarboxamide | 3-Bromo-4-methylaniline |

Preparation 10

((3'-Aminobiphenyl-4-yl)methyl)-methanesulfonamide (C-1)

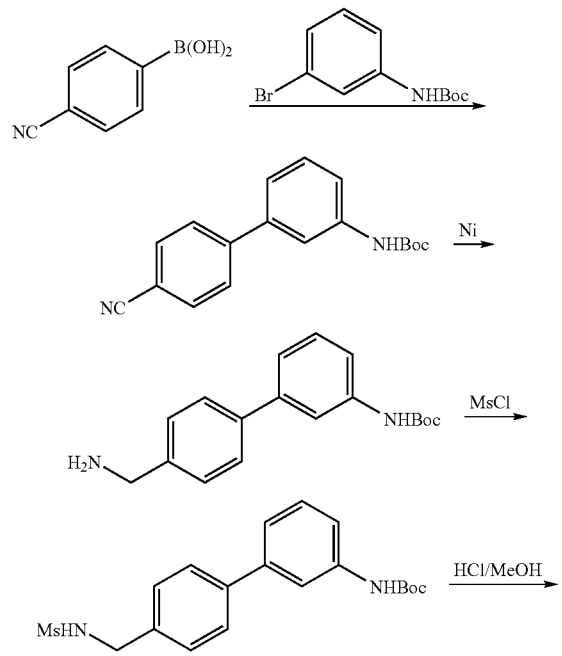

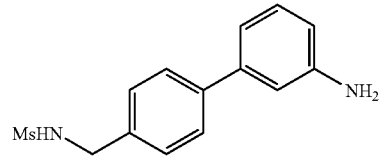

Step a: (4'-Cyano-biphenyl-3-yl)-carbamic acid tert-butyl ester

A mixture of 4-cyanobenzeneboronic acid (14.7 g, 0.10 mol), 3-bromo-phenyl-carbamic acid tert-butyl ester (27.2 g, 0.10 mol), Pd(Ph$_3$P)$_4$ (11.6 g, 0.01 mol) and K$_2$CO$_3$ (21 g, 0.15 mol) in DMF/H$_2$O (1:1, 350 mL) was stirred under argon at 80° C. overnight. The DMF was evaporated under reduced pressure, and the residue was dissolved in EtOAc (200 mL). The mixture was washed with water and brine, dried over Na$_2$SO$_4$, and concentrated to dryness. The residue was purified by column chromatography (petroleum ether/EtOAc 50:1) on silica gel to give (4'-cyano-biphenyl-3-yl)-carbamic acid tert-butyl ester (17 g, 59%). $^1$H NMR (300 MHz, DMSO-d$_6$) δ 9.48 (s, 1H), 7.91 (d, J=8.4 Hz, 2H), 7.85 (s, 1H), 7.76 (d, J=8.4 Hz, 2H), 7.32-7.48 (m, 3H), 1.47 (s, 9H).

Step b: (4'-Aminomethyl-biphenyl-3-yl)-carbamic acid tert-butyl ester

A suspension of (4'-cyano-biphenyl-3-yl)-carbamic acid tert-butyl ester (7.6 g, 26 mmol) and Raney Ni (1 g) in EtOH (500 mL) and NH$_3$.H$_2$O (10 mL) was hydrogenated under 50 psi of H$_2$ at 50° C. for 6 h. The catalyst was filtered off and the filtrate was concentrated to dryness to give (4'-aminomethyl-biphenyl-3-yl)-carbamic acid tert-butyl ester, which was used directly in next step.

Step c: [4'-(Methanesulfonylamino-methyl)-biphenyl-3-yl]-carbamic acid tert-butyl ester To a solution of crude (4'-aminomethyl-biphenyl-3-yl)-carbamic acid tert-butyl ester (8.2 g 27 mmol) and Et$_3$N (4.2 g, 40 mmol) in dichloromethane (250 mL) was added dropwise MsCl (3.2 g, 27 mmol) at 0° C. The reaction mixture was stirred at this temperature for 30 min and was then washed with water and saturated aqueous NaCl solution, dried over Na$_2$SO$_4$, and concentrated to dryness. The residue was recrystallized with DCM/pet ether (1:3) to give [4'-(methanesulfonylamino-methyl)-biphenyl-3-yl]-carbamic acid tert-butyl ester (7.5 g, yield 73%). $^1$H NMR (300 MHz, CDCl$_3$) δ 7.67 (s, 1H), 7.58 (d, J=8.1 Hz, 2H), 7.23-7.41 (m, 5H), 6.57 (s, 1H), 4.65-4.77 (m, 1H), 4.35 (d, J=6 Hz, 2H), 2.90 (s, 3H), 1.53 (s, 9H).

Step d: N-((3'-Aminobiphenyl-4-yl)methyl)methanesulfonamide

A solution of [4'-(methanesulfonylamino-methyl)-biphenyl-3-yl]-carbamic acid tert-butyl ester (5 g, 13 mmol) in HCl/MeOH (4M, 150 mL) was stirred at room temperature overnight. The mixture was concentrated to dryness and the residue was washed with ether to give the target compound N-((3'-aminobiphenyl-4-yl)methyl)methanesulfonamide as its HCl salt (3.0 g, 71%). $^1$H NMR (300 MHz, DMSO-d$_6$) δ 7.54-7.71 (m, 6H), 7.46 (d, J=7.8 Hz, 2H), 7.36 (d, J=7.5 Hz, 1H), 4.19 (s, 2H), 2.87 (s, 3H). MS (ESI) m/e (M+H$^+$): 277.0.

Preparation 11

(R)-(1-(3'-Aminobiphenyl-4-ylsulfonyl)pyrrolidin-2-yl)methanol (C-2)

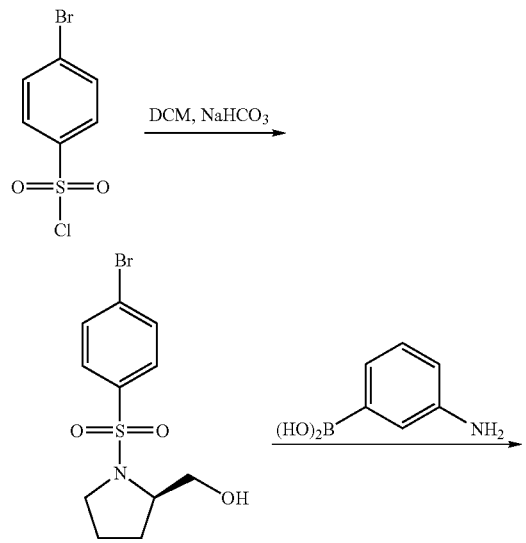

Step a: (R)-Bromo-benzenesulfonyl)-pyrrolidin-2-yl]-methanol

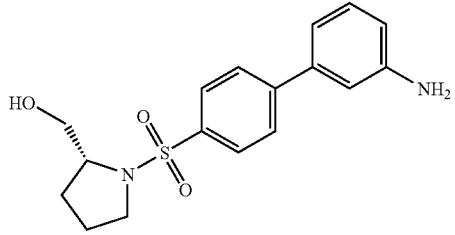

To a mixture of sat aq. NaHCO$_3$ (44 g, 0.53 mol), CH$_2$Cl$_2$ (400 mL) and (R)-pyrrolidin-2-yl-methanol (53 g, 0.53 mol) was added 4-bromo-benzenesulfonyl chloride (130 g, 0.50 mol) in CH$_2$Cl$_2$ (100 mL). The reaction was stirred at 20° C. overnight. The organic phase was separated and dried over Na$_2$SO$_4$. Evaporation of the solvent under reduced pressure provided (R)-[1-(4-bromo-benzenesulfonyl)-pyrrolidin-2-yl]-methanol (145 g, crude), which was used in the next step without further purification. $^1$H NMR (CDCl$_3$, 300 MHz) δ 7.66-7.73 (m, 4H), 3.59-3.71 (m, 3H), 3.43-3.51 (m, 1H), 3.18-3.26 (m, 1H), 1.680-1.88 (m, 3H), 1.45-1.53 (m, 1H).

Step b: (R)-(1-(3'-Aminobiphenyl-4-ylsulfonyl)pyrrolidin-2-yl)methanol (C-2)

To a solution of (R)-[1-(4-bromo-benzenesulfonyl)-pyrrolidin-2-yl]-methanol (1.6 g, 5.0 mmol) in DMF (10 mL) was added 3-amino-phenyl boronic acid (0.75 g, 5.5 mmol), Pd(PPh$_3$)$_4$ (45 mg, 0.15 mmol), potassium carbonate (0.75 g, 5.5 mmol) and water (5 mL). The resulting mixture was degassed by gently bubbling argon through the solution for 5 minutes at 20° C. The reaction mixture was then heated at 80° C. overnight. The reaction was filtered through a pad of silica gel, which was washed with CH$_2$Cl$_2$ (25 mL×3). The combined organics were concentrated under reduced pressure to give the crude product, which was washed with EtOAc to give pure (R)-(1-(3'-aminobiphenyl-4-ylsulfonyl)pyrrolidin-2-yl) methanol (C-2) (810 mg, 49%). $^1$H NMR (300 MHz, CDCl$_3$) δ 7.88 (d, J=8.7 Hz, 2H), 7.70 (d, J=8.7 Hz, 2H), 7.23-7.28 (m, 1H), 6.98 (d, J=7.8 Hz, 1H), 6.91 (d, J=1.8 Hz, 1H), 6.74 (dd, J=7.8, 1.2 Hz, 1H), 3.66-3.77 (m, 3H), 3.45-3.53 (m, 1H), 3.26-3.34 (m, 1H), 1.68-1.88 (m, 3H), 1.45-1.55 (m, 1H). MS (ESI) m/e (M+H$^+$) 333.0.

Preparation 12

3'-Amino-N-methylbiphenyl-4-sulfonamide (C-3)

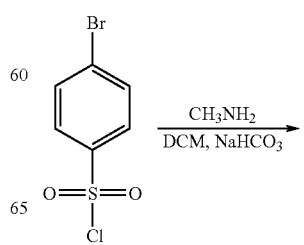

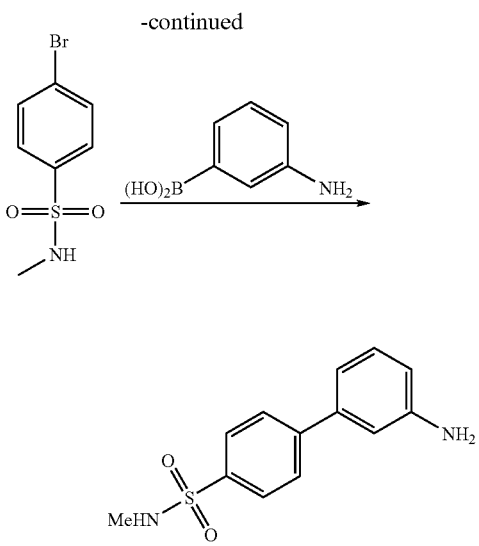

Step a: 4-Bromo-N-methyl-benzenesulfonamide

To a mixture of sat aq. NaHCO₃ (42 g, 0.50 mol), CH₂Cl₂ (400 mL) and methylamine (51.7 g, 0.50 mol, 30% in methanol) was added a solution of 4-bromo-benzenesulfonyl chloride (130 g, 0.50 mol) in CH₂Cl₂ (100 mL). The reaction was stirred at 20° C. overnight. The organic phase was separated and dried over Na₂SO₄. Evaporation of the solvent under reduced pressure provided 4-bromo-N-methyl-benzenesulfonamide (121 g, crude), which was used in the next step without further purification. $^1$H NMR (CDCl₃, 300 MHz) δ 7.65-7.74 (m, 4H), 4.40 (br, 1H), 2.67 (d, J=5.4 Hz, 3H).

Step b: 3'-Amino-N-methylbiphenyl-4-sulfonamide (C-3)

To a solution of 4-bromo-N-methyl-benzene sulfonamide (2.49 g, 10 mmol) in DMF (20 mL) was added 3-aminophenyl boronic acid (1.51 g, 11 mmol), Pd(PPh₃)₄ (90 mg, 0.30 mmol), potassium carbonate (1.52 g, 11 mmol) and water (5 mL). The resulting mixture was degassed by gently bubbling argon through the solution for 5 minutes at 20° C. The reaction mixture was then heated at 80° C. overnight. The reaction was filtered through a pad of silica gel, which was washed with CH₂Cl₂ (50 mL×3). The combined organics were concentrated under reduced pressure to give crude product, which was washed with EtOAc to give pure 3'-amino-N-methylbiphenyl-4-sulfonamide (C-3) (1.3 g, 50%). $^1$H NMR (300 MHz, CDCl₃) δ 7.85 (d, J=8.7 Hz, 2H), 7.75 (d, J=8.7 Hz, 2H), 7.19 (t, J=7.8 Hz, 1H), 6.95-7.01 (m, 2H), 6.73-6.77 (m, 1H), 2.54 (s, 3H). MS (ESI) m/e (M+H⁺) 263.0.

Preparation 13

5'-(1-(Benzo[d][1,3]dioxol-5-yl)cyclopropanecarboxamido)-2'-(hydroxymethyl)-N,N-dimethylbiphenyl-4-carboxamide

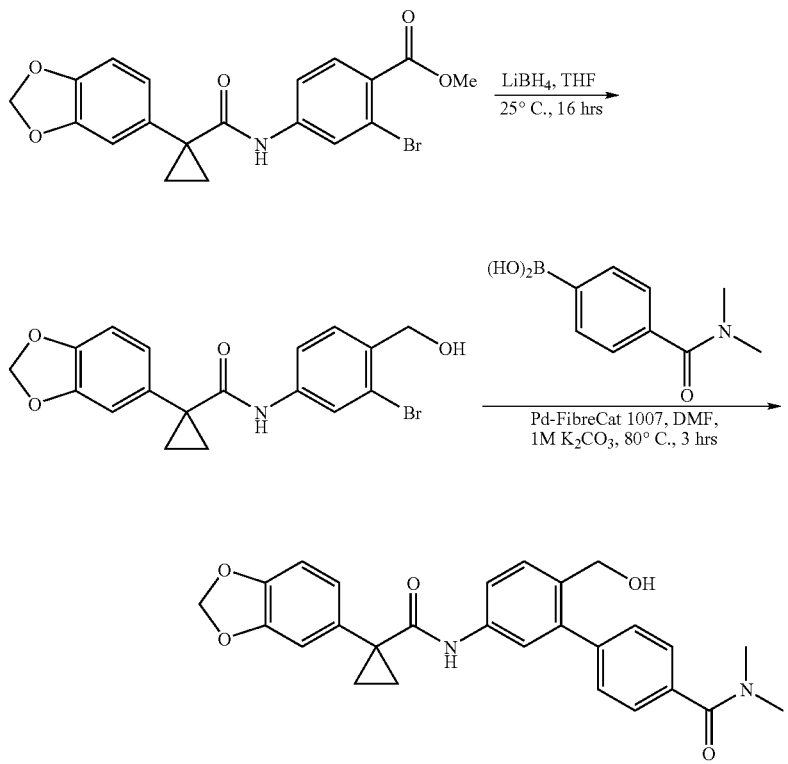

Step a: 1-(Benzo[d][1,3]dioxol-5-yl)-N-(3-bromo-4-(hydroxymethyl)phenyl)cyclopropanecarboxamide Methyl 4-(1-(benzo[d][1,3]dioxol-5-yl)cyclopropanecarboxamido)-2-bromobenzoate (4.12 g, 9.9 mmol) was added to a solution of LiBH$_4$ (429 mg, 19.8 mmol) in THF/ether/H$_2$O (20/20/1 mL) and was allowed to stir at 25° C. After 16 hours, the reaction was quenched with H$_2$O (10 mL). The reaction mixture was diluted with dichloromethane (25 mL) and was extracted with 1N HCl (30 mL×3) and brine (30 mL). The organic extracts were dried over Na$_2$SO$_4$ and evaporated. The crude product was purified by chromatography on silica gel (eluting with 0-100% ethyl acetate in hexanes) to afford 1-(benzo[d][1,3]dioxol-5-yl)-N-(3-bromo-4-(hydroxymethyl)phenyl)cyclopropanecarboxamide (2.84 g, 74%). ESI-MS m/z calc. 389.0, found 390.1 (M+1)$^+$; retention time 2.91 minutes.

Step b: 5'-(1-(Benzo[d][1,3]dioxol-5-yl)cyclopropanecarboxamido)-2'-(hydroxymethyl)-N,N-dimethylbiphenyl-4-carboxamide 1-(Benzo[d][1,3]dioxol-5-yl)-N-(3-bromo-4-(hydroxymethyl)-phenyl)cyclopropanecarboxamide (39 mg, 0.10 mmol), 4-(dimethylcarbamoyl)-phenylboronic acid (29 mg, 0.15 mmol), 1 M K$_2$CO$_3$ (0.3 mL, 0.3 mmol), Pd-FibreCat 1007 (8 mg, 0.1 mmol), and N,N-dimethylformamide (1 mL) were combined. The mixture was heated at 80° C. for 3 h. After cooling, the mixture was filtered and purified by reverse phase HPLC to yield 5'-(1-(benzo[d][1,3]dioxol-5-yl)cyclopropanecarboxamido)-2'-(hydroxymethyl)-N,N-dimethylbiphenyl-4-carboxamide (16 mg, 34%). ESI-MS m/z calc. 458.5, found 459.5 (M+1)$^+$; Retention time 2.71 minutes.

Preparation 14

5'-(1-(Benzo[d][1,3]dioxol-5-yl)cyclopropanecarboxamido)-2'-(ethoxymethyl)-N,N-dimethylbiphenyl-4-carboxamide

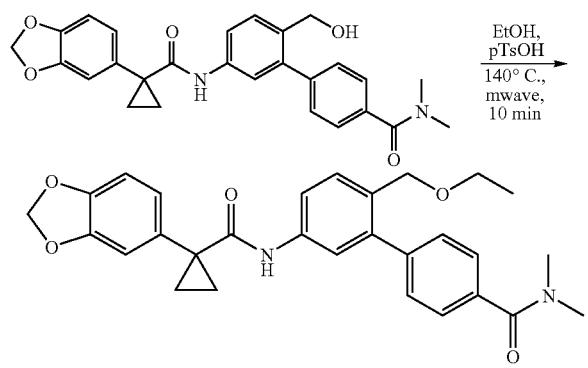

5'-(1-(Benzo[d][1,3]dioxol-5-yl)cyclopropanecarboxamido)-2'-(hydroxymethyl)-N,N-dimethylbiphenyl-4-carboxamide (49 mg, 0.10 mmol) and para-toluenesulfonic acid (38 mg, 0.2 mmol) were dissolved in ethanol (1.0 mL) and irradiated in the microwave at 140° C. for 10 minutes. Volatiles were removed in vacuo and crude product was purified by reverse phase HPLC to afford the pure product (6.4 mg, 13%). ESI-MS m/z calc. 486.2, found 487.5 (M+1)$^+$; retention time 3.17 minutes.

Preparation 15

5'-(1-(Benzo[d][1,3]dioxol-5-yl)cyclopropane-carboxamido)-2'-(isopropoxymethyl)-N,N-dimethylbiphenyl-4-carboxamide

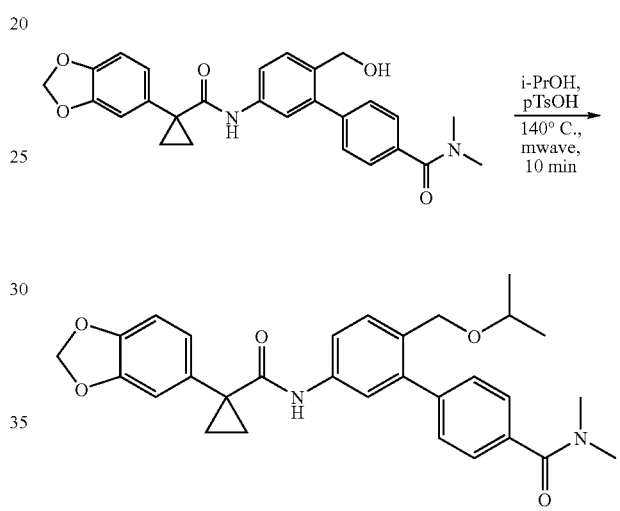

5'-(1-(Benzo[d][1,3]dioxol-5-yl)cyclopropanecarboxamido)-2'-(hydroxymethyl)-N,N-dimethylbiphenyl-4-carboxamide (46 mg, 0.10 mmol) and para-toluenesulfonic acid (38 mg, 0.2 mmol) were dissolved in isopropanol (1.0 mL) and irradiated in the microwave at 140° C. for 10 minutes. Volatiles were removed in vacuo and crude product was purified by reverse phase HPLC to afford the pure product (22 mg, 44%). ESI-MS m/z calc. 500.2, found 501.3 (M+1)$^+$; retention time 3.30 minutes.

Preparation 16

5'-(1-(Benzo[d][1,3]dioxol-5-yl)cyclopropanecarboxamido)-2'-(cyanomethyl)-N,N-dimethylbiphenyl-4-carboxamide

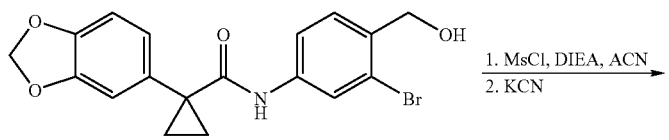

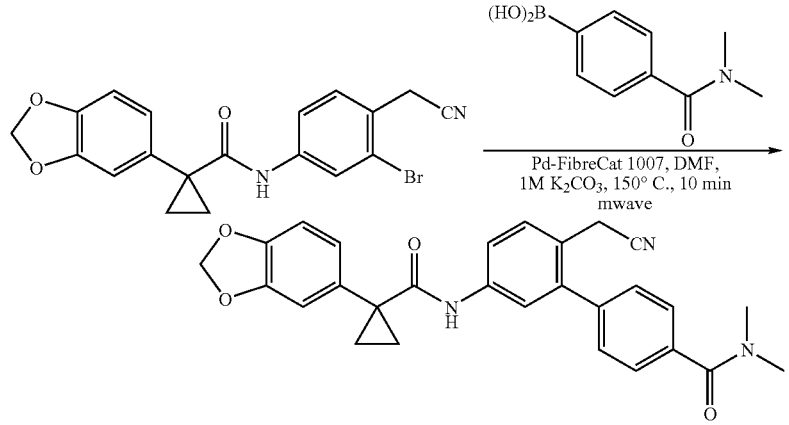

Step a: 1-(Benzo[d][1,3]dioxol-5-yl)-N-(3-bromo-4-(cyanomethyl)phenyl)cyclo-propane carboxamide 1-(Benzo[d][1,3]dioxol-5-yl)-N-(3-bromo-4-(hydroxymethyl)phenyl)cyclopropane-carboxamide (1.08 g, 2.78 mmol), methanesulfonyl chloride (0.24 mL, 3.1 mmol), and N,N-diisopropylethylamine (0.72 mL, 4.1 mmol) were dissolved in acetonitrile (27 mL) at 25° C. After complete dissolution, KCN (450 mg, 6.95 mmol) was added and the reaction was stirred for 14 d. The reaction was diluted with dichloromethane (25 mL) and washed with water (25 mL). The organic extracts were dried over $Na_2SO_4$ and evaporated. The crude product was purified by chromatography on silica gel (eluting with 0-100% ethyl acetate in hexanes) to afford 1-(benzo[d][1,3]dioxol-5-yl)-N-(3-bromo-4-(cyanomethyl)phenyl)cyclo-propane carboxamide (514 mg, 46%). ESI-MS m/z calc. 398.0, found 399.1 $(M+1)^+$; retention time 3.24 minutes.

Step b: 5'-(1-(Benzo[d][1,3]dioxol-5-yl)cyclopropanecarboxamido)-2'-(cyanomethyl)-N,N-dimethylbiphenyl-4-carboxamide 1-(Benzo[d][1,3]dioxol-5-yl)-N-(3-bromo-4-(cyanomethyl)phenyl)cyclopropane-carboxamide (40 mg, 0.10 mmol), 4-(dimethylcarbamoyl)phenylboronic acid (29 mg, 0.15 mmol), 1 M $K_2CO_3$ (0.2 mL, 0.2 mmol), Pd-FibreCat 1007 (8 mg, 0.1 mmol), and N,N-dimethylformamide (1 mL) were combined. The mixture was irradiated in the microwave at 150° C. for 10 minutes. Volatiles were removed in vacuo and crude product was purified by chromatography on silica gel (eluting with 0-100% ethyl acetate in hexanes) to afford 5'-(1-(benzo[d][1,3]dioxol-5-yl)cyclopropanecarboxamido)-2'-(cyanomethyl)-N,N-dimethylbiphenyl-4-carboxamide (9.1 mg, 20%). ESI-MS m/z calc. 467.2, found 468.5 $(M+1)^+$; retention time 2.96 minutes.

Preparation 17

2'-((1H-Tetrazol-5-yl)methyl)-5'-(1-(benzo[d][1,3]dioxol-5-yl)cyclopropanecarboxamido)-N,N-dimethylbiphenyl-4-carboxamide

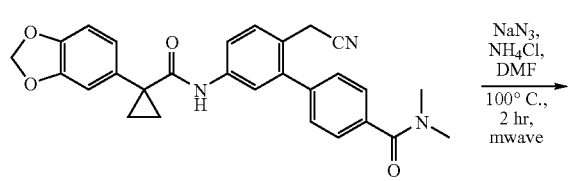

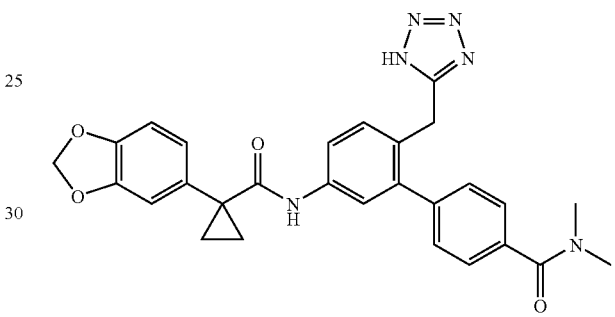

5'-(1-(Benzo[d][1,3]dioxol-5-yl)cyclopropanecarboxamido)-2'-(cyanomethyl)-N,N-dimethylbiphenyl-4-carboxamide (32 mg, 0.070 mmol), sodium azide (55 mg, 0.84 mmol), and ammonium chloride (45 mg, 0.84 mmol) were dissolved in N,N-dimethylformamide (1.5 mL) and irradiated in the microwave at 100° C. for 2 hours. After cooling, the mixture was filtered and purified by reverse phase HPLC to yield 2'-((1H-tetrazol-5-yl)methyl)-5'-(1-(benzo[d][1,3]dioxol-5-yl)cyclopropane carboxamido)-N,N-dimethylbiphenyl-4-carboxamide (9.2 mg, 26%). ESI-MS m/z calc. 510.2, found 511.5 $(M+1)^+$; Retention time 2.68 minutes.

Preparation 18

2'-(2-Amino-2-oxoethyl)-5'-(1-(benzo[d][1,3]dioxol-5-yl)cyclopropanecarboxamido)-N,N-dimethylbiphenyl-4-carboxamide

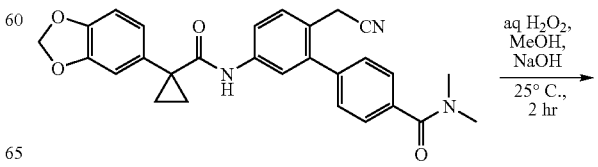

-continued

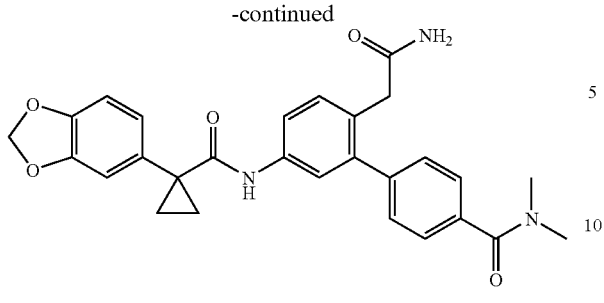

5'-(1-(Benzo[d][1,3]dioxol-5-yl)cyclopropanecarboxamido)-2'-(cyanomethyl)-N,N-dimethylbiphenyl-4-carboxamide (58 mg, 0.12 mmol), H$_2$O$_2$ (30 wt % solution in water, 36 μL, 1.2 mmol), and NaOH (10 wt % in water, 0.15 mL, 0.42 mmol) were dissolved in MeOH (1.2 mL) and stirred at 25° C. for 2 hours. The reaction was filtered and purified by reverse phase HPLC to yield 2'-(2-amino-2-oxoethyl)-5'-(1-(benzo[d][1,3]dioxol-5-yl)cyclopropanecarboxamido)-N,N-dimethylbiphenyl-4-carboxamide (14 mg, 23%). ESI-MS m/z calc. 485.2, found 486.5 (M+1)$^+$; Retention time 2.54 minutes.

Preparation 19

N-(4'-(Aminomethyl)-6-methylbiphenyl-3-yl)-1-(benzo[d][1,3]dioxol-5-yl)cyclopropanecarboxamide

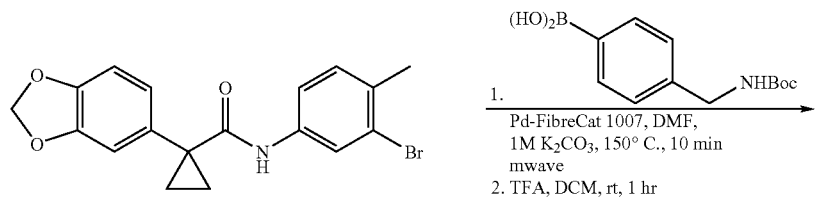

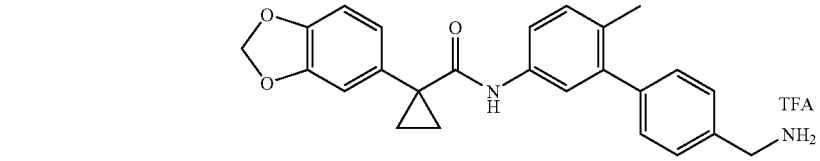

1-(Benzo[d][1,3]dioxol-5-yl)-N-(3-bromo-4-methylphenyl)cyclopropanecarboxamide (37 mg, 0.10 mmol), 4-((tert-butoxycarbonylamino)methyl)phenylboronic acid (37 mg, 0.15 mmol), 1 M K$_2$CO$_3$ (0.2 mL, 0.2 mmol), Pd-FibreCat 1007 (8 mg, 0.1 mmol), and N,N-dimethylformamide (1 mL) were combined. The mixture was irradiated in the microwave at 150° C. for 10 minutes. The reaction was filtered and purified by reverse phase HPLC. The obtained material was dissolved in dichloromethane (2 mL) containing trifluoroacetic acid (2 mL) and stirred at 25° C. for 1 hour. The reaction was filtered and purified by reverse phase HPLC to yield N-(4'-(aminomethyl)-6-methylbiphenyl-3-yl)-1-(benzo[d][1,3]dioxol-5-yl)cyclopropanecarboxamide as the TFA salt (8.1 mg, 20%). ESI-MS m/z calc. 400.2, found 401.5 (M+1)$^+$; retention time 2.55 minutes.

Preparation 20

1-(Benzo[d][1,3]dioxol-5-yl)-N-(6-methyl-4'-(propionamidomethyl)biphenyl-3-yl)cyclopropanecarboxamide

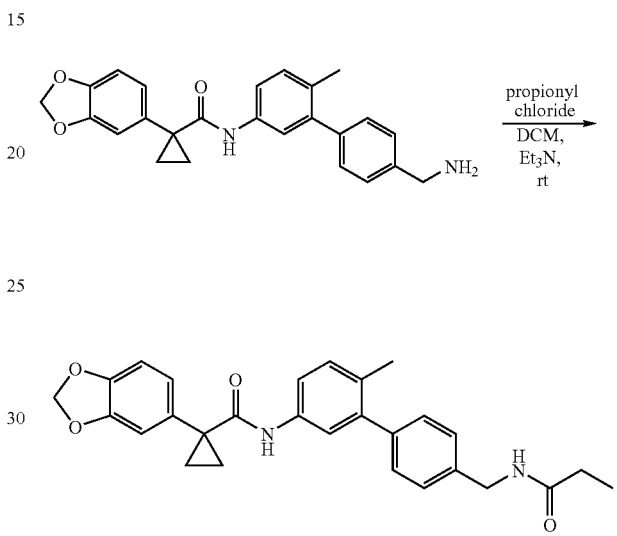

N-(4'-(Aminomethyl)-6-methylbiphenyl-3-yl)-1-(benzo[d][1,3]dioxol-5-yl)cyclopropanecarboxamide (40 mg, 0.10 mmol), propionyl chloride (8.7 μL, 0.10 mmol) and Et$_3$N (28 μL, 0.20 mmol) were dissolved in dichloromethane (1.0 mL) and allowed to stir at 25° C. for 3 hours. Volatiles were removed in vacuo and crude product was purified by reverse phase HPLC to afford 1-(benzo[d][1,3]dioxol-5-yl)-N-(6-methyl-4'-(propionamidomethyl)biphenyl-3-yl)cyclopropanecarboxamide (13 mg, 28%). ESI-MS m/z calc. 456.5, found 457.5 (M+1)$^+$; retention time 3.22 minutes.

Preparation 21

1-(Benzo[d][1,3]dioxol-5-yl)-N-(6-methyl-4'-(propylsulfonamidomethyl)biphenyl-3-yl)cyclopropanecarboxamide

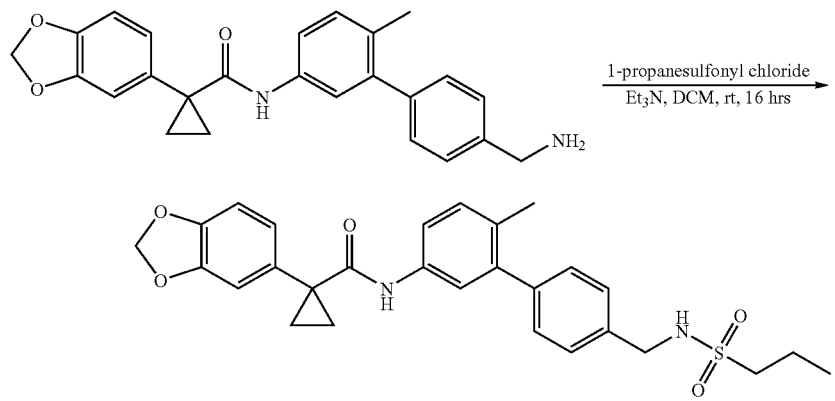

N-(4'-(Aminomethyl)-6-methylbiphenyl-3-yl)-1-(benzo[d][1,3]dioxol-5-yl)cyclopropanecarboxamide (40 mg, 0.10 mmol), 1-propanesulfonyl chloride (11 μL, 0.10 mmol) and Et$_3$N (28 μL, 0.20 mmol) were dissolved in dichloromethane (1.0 mL) and allowed to stir at 25° C. for 16 hours. Volatiles were removed in vacuo and crude product was purified by reverse phase HPLC to afford 1-(benzo[d][1,3]dioxol-5-yl)-N-(6-methyl-4'-(propylsulfonamidomethyl)biphenyl-3-yl)cyclopropanecarboxamide (5.3 mg, 10%). ESI-MS m/z calc. 506.6, found 507.3 (M+1)$^+$; retention time 3.48 minutes.

Preparation 22

1-(Benzo[d][1,3]dioxol-5-yl)-N-(6-methyl-4'-((propylamino)methyl)biphenyl-3-yl)cyclopropanecarboxamide

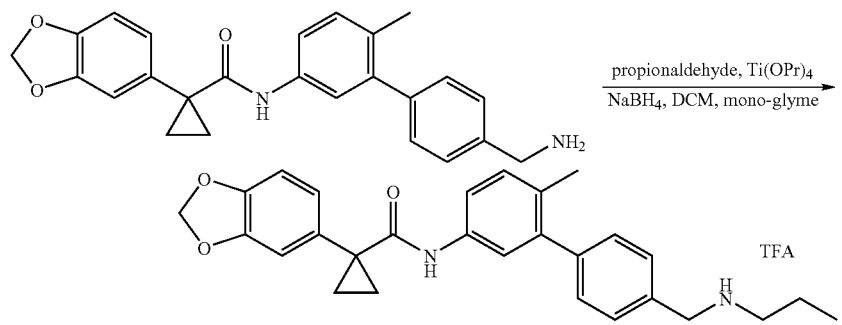

N-(4'-(Aminomethyl)-6-methylbiphenyl-3-yl)-1-(benzo[d][1,3]dioxol-5-yl)cyclopropanecarboxamide (40 mg, 0.10 mmol), propionaldehyde (5.1 μL, 0.10 mmol) and Ti(OPr)$_4$ (82 μL, 0.30 mmol) were dissolved in dichloromethane (1.0 mL) and mono-glyme (1.0 mL). The mixture was allowed to stir at 25° C. for 16 hours. NaBH$_4$ (5.7 mg, 0.15 mmol) was added and the reaction was stirred for an additional 1 h. The reaction was diluted to 5 mL with dichloromethane before water (5 mL) was added. The reaction was filtered through celite to remove the titanium salts and the layers separated. The organic extracts were dried over Na$_2$SO$_4$ and evaporated. The crude product was purified by reverse phase HPLC to afford 1-(benzo[d][1,3]dioxol-5-yl)-N-(6-methyl-4'-((propylamino)methyl)biphenyl-3-yl)cyclopropanecarboxamide (7.8 mg, 14%). ESI-MS m/z calc. 442.6, found 443.5 (M+1)$^+$; retention time 2.54 minutes.

Preparation 23

1-(Benzo[d][1,3]dioxol-5-yl)-N-(4'-((isopentylamino)methyl)-6-methylbiphenyl-3-yl)cyclopropanecarboxamide

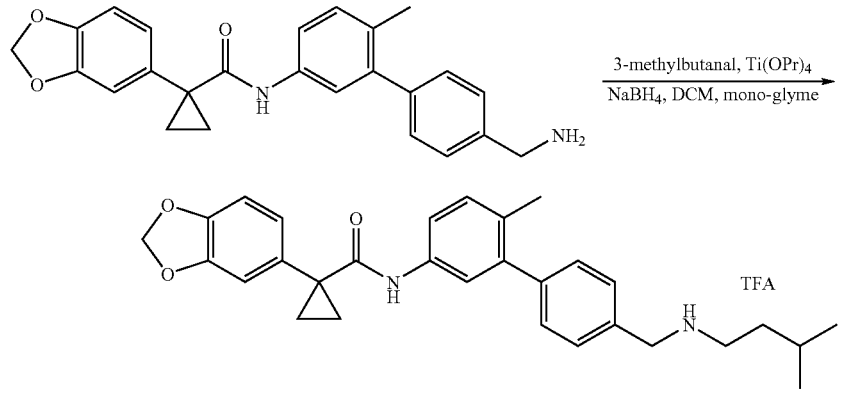

N-(4'-(Aminomethyl)-6-methylbiphenyl-3-yl)-1-(benzo[d][1,3]dioxol-5-yl)cyclopropanecarboxamide (40 mg, 0.10 mmol), 3-methylbutanal (8.6 mg, 0.10 mmol) and Ti(OPr)$_4$ (82 µL, 0.30 mmol) were dissolved in dichloromethane (1.0 mL) and mono-glyme (1.0 mL) and allowed to stir at 25° C. for 16 hours. NaBH$_4$ (5.7 mg, 0.15 mmol) was added and the reaction was stirred for an additional 1 h. The reaction was diluted to 5 mL with dichloromethane before water (5 mL) was added. The reaction was filtered through celite to remove the titanium salts and the layers separated. The organic extracts were dried over Na$_2$SO$_4$ and evaporated. The crude product was purified by reverse phase HPLC to afford 1-(benzo[d][1,3]dioxol-5-yl)-N-(4'-((isopentylamino)methyl)-6-methylbiphenyl-3-yl)cyclopropanecarboxamide (5.7 mg, 10%). ESI-MS m/z calc. 470.3, found 471.5 (M+1)$^+$; retention time 2.76 minutes.

Preparation 24

1-(Benzo[d][1,3]dioxol-5-yl)-N-(4'-(hydroxymethyl)-6-methylbiphenyl-3-yl)cyclopropanecarboxamide

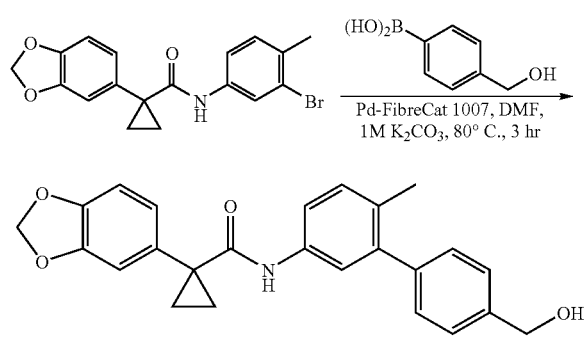

1-(Benzo[d][1,3]dioxol-5-yl)-N-(3-bromo-4-methylphenyl)cyclopropanecarboxamide (3.0 g, 8.1 mmol), 4-(hydroxymethyl)phenylboronic acid (1.5 g, 9.7 mmol), 1 M K$_2$CO$_3$ (16 mL, 16 mmol), Pd-FibreCat 1007 (640 mg), and N,N-dimethylformamide (80 mL) were combined. The mixture was heated at 80° C. for 3 h. The volatiles were removed in vacuo and residue was redissolved in dichloromethane (100 mL). The organics were washed with 1N HCl (100 mL×2), then dried over Na$_2$SO$_4$ and evaporated. The crude product was purified by chromatography on silica gel to afford 1-(benzo[d][1,3]dioxol-5-yl)-N-(4'-(hydroxymethyl)-6-methylbiphenyl-3-yl)cyclopropanecarboxamide (1.9 g, 59%). ESI-MS m/z calc. 401.5, found 402.5 (M+1)$^+$; retention time 3.18 minutes.

Preparation 25

1-(Benzo[d][1,3]dioxol-5-yl)-N-(4'-(methoxymethyl)-6-methylbiphenyl-3-yl)cyclopropanecarboxamide

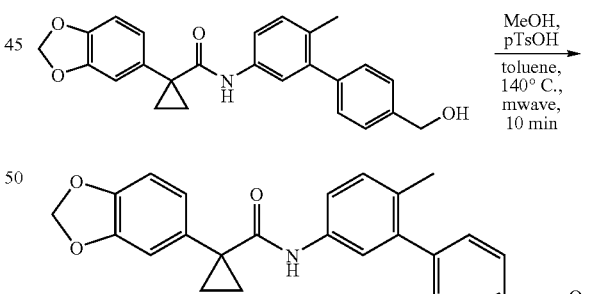

1-(Benzo[d][1,3]dioxol-5-yl)-N-(4'-(hydroxymethyl)-6-methylbiphenyl-3-yl)cyclopropanecarboxamide (40 mg, 0.10 mmol), para-toluenesulfonic acid (24 mg, 0.13 mmol) and MeOH (53 µL, 1.3 mmol) were dissolved in toluene (2.0 mL) and irradiated in the microwave at 140° C. for 10 minutes. Volatiles were removed in vacuo and crude product was purified by reverse phase HPLC to afford 1-(benzo[d][1,3]dioxol-5-yl)-N-(4'-(methoxymethyl)-6-methylbiphenyl-3-yl)cyclopropanecarboxamide (9.6 mg, 23%). ESI-MS m/z calc. 415.5, found 416.5 (M+1)$^+$; retention time 3.68 minutes.

Preparation 26

1-(Benzo[d][1,3]dioxol-5-yl)-N-(6-methyl-4'-((methylamino)methyl)biphenyl-3-yl)cyclopropanecarboxamide

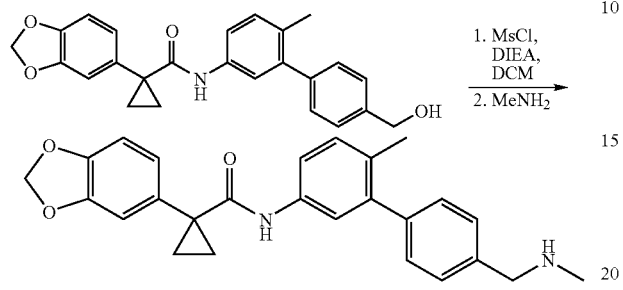

1-(Benzo[d][1,3]dioxol-5-yl)-N-(4'-(hydroxymethyl)-6-methylbiphenyl-3-yl)cyclopropanecarboxamide (610 mg, 1.52 mmol), methanesulfonyl chloride (0.13 mL, 1.7 mmol), and N,N-diisopropylethylamine (0.79 mL, 4.6 mmol) were dissolved in dichloromethane (10 mL) at 25° C. The reaction was stirred for 10 minutes before a 2.0 M solution of MeNH$_2$ in THF (15 mL, 30 mmol) was added. The mixture was stirred for 30 minutes at ambient temperature before it was extracted with 1N HCl (20 mL×2) and saturated NaHCO$_3$ (20 mL×2). The organic extracts were dried over Na$_2$SO$_4$ and evaporated. The crude product was purified by chromatography on silica gel (eluting with 0-20% methanol in dichloromethane) to afford 1-(Benzo[d][1,3]dioxol-5-yl)-N-(6-methyl-4'-((methylamino)methyl)biphenyl-3-yl)cyclopropanecarboxamide (379 mg, 60%). ESI-MS m/z calc. 414.5, found 415.5 (M+1)$^+$; retention time 2.44 minutes.

Preparation 27

1-(Benzo[d][1,3]dioxol-5-yl)-N-(6-methyl-4'-((N-methylpivalamido)methyl)biphenyl-3-yl)cyclopropanecarboxamide

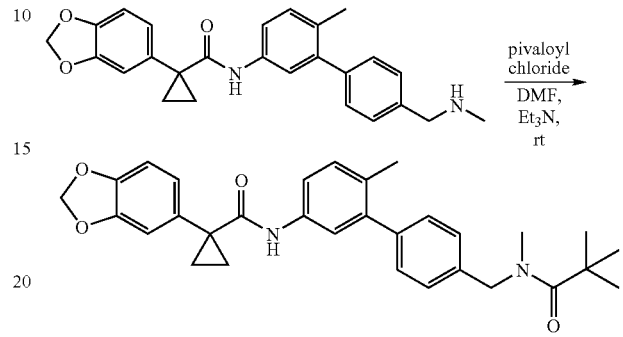

1-(Benzo[d][1,3]dioxol-5-yl)-N-(6-methyl-4'-((methylamino)methyl)biphenyl-3-yl)cyclopropanecarboxamide (30 mg, 0.070 mmol), pivaloyl chloride (12.3 µL, 0.090 mmol) and Et$_3$N (20 µL, 0.14 mmol) were dissolved in N,N-dimethylformamide (1.0 mL) and allowed to stir at 25° C. for 3 hours. The crude reaction was purified by reverse phase HPLC to afford 1-(benzo[d][1,3]dioxol-5-yl)-N-(6-methyl-4'-((N-methylpivalamido)methyl)biphenyl-3-yl)cyclopropanecarboxamide (15 mg, 30%). ESI-MS m/z calc. 498.3, found 499.3 (M+1)$^+$; retention time 3.75 minutes.

Preparation 28

1-(Benzo[d][1,3]dioxol-5-yl)-N-(6-methyl-4'-((N-methylmethylsulfonamido)methyl)biphenyl-3-yl)cyclopropanecarboxamide

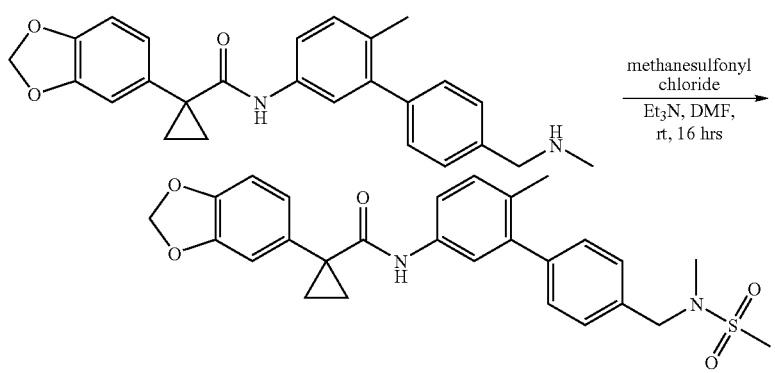

1-(Benzo[d][1,3]dioxol-5-yl)-N-(6-methyl-4'-((methylamino)-methyl)biphenyl-3-yl)cyclopropane carboxamide (30 mg, 0.070 mmol), methanesulfonyl chloride (7.8 µL, 0.14 mmol) and Et$_3$N (30 µL, 0.22 mmol) were dissolved in N,N-dimethylformamide (1.0 mL) and allowed to stir at 25° C. for 16 hours. The crude reaction was purified by reverse phase HPLC to afford 1-(benzo[d][1,3]dioxol-5-yl)-N-(6-methyl-4'-((N-methylmethylsulfonamido)methyl)biphenyl-3-yl)cyclopropanecarboxamide (22 mg, 64%). ESI-MS m/z calc. 492.2, found 493.3 (M+1)$^+$; retention time 3.45 minutes.

Preparation 29

1-(Benzo[d][1,3]dioxol-5-yl)-N-(4'-((isobutyl(methyl)amino)-methyl)-6-methylbiphenyl-3-yl)cyclopropanecarboxamide

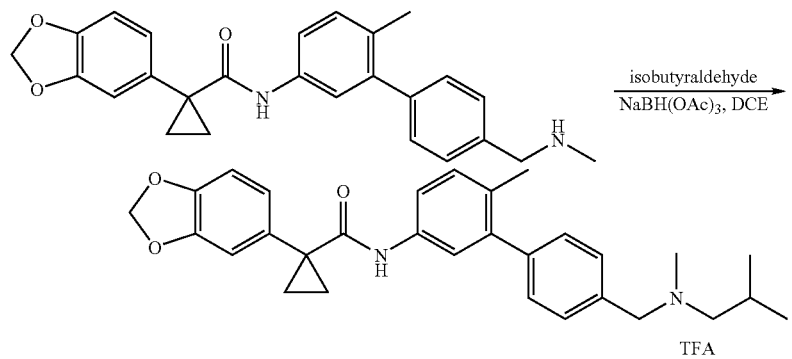

1-(Benzo[d][1,3]dioxol-5-yl)-N-(6-methyl-4'-((methylamino)methyl)biphenyl-3-yl)cyclopropanecarboxamide (49 mg, 0.12 mmol), isobutyraldehyde (11 μL, 0.12 mmol) and NaBH(OAc)$_3$ (76 mg, 0.36 mmol) were dissolved in dichloroethane (2.0 mL) and heated at 70° C. for 16 hours. The reaction was quenched with MeOH (0.5 mL) and 1 N HCl (0.5 mL). The volatiles were removed in vacuo and the crude product was purified by reverse phase HPLC to afford 1-(benzo[d][1,3]dioxol-5-yl)-N-(4'-((isobutyl(methyl)amino)-methyl)-6-methylbiphenyl-3-yl)cyclopropanecarboxamide as the TFA salt (5.0 mg, 9%). ESI-MS m/z calc. 470.3, found 471.3 (M+1)$^+$; retention time 2.64 minutes.

The following compounds were prepared using procedures 20-23 and 27-29 above: 6, 14, 24, 26, 70, 79, 84, 96, 114, 122, 159, 200, 206, 214, 223, 248, 284-5, 348, 355, 382, 389, 391, 447, 471, 505, 511, 524, 529-30, 534, 551, 562, 661, 682, 709, 783, 786, 801, 809, 828, 844, 846, 877, 937, 947, 1012, 1049, 1089.

Preparation 30

1-(Benzo[d][1,3]dioxol-5-yl)-N-(4-(2-methylthiazol-4-yl)phenyl)cyclopropane-carboxamide

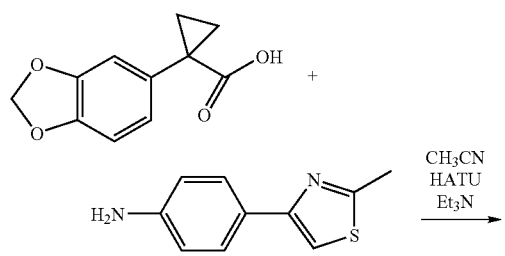

-continued

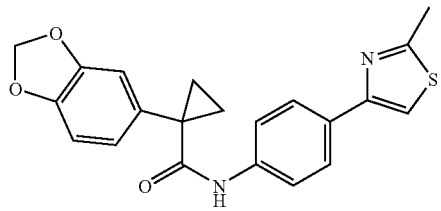

4-(2-Methylthiazol-4-yl)aniline (19 mg, 0.10 mmol) and 1-(benzo[d][1,3]dioxol-5-yl)cyclopropanecarboxylic acid (20.6 mg, 0.100 mmol) were dissolved in acetonitrile (1.0 mL) containing triethylamine (42 μL, 0.30 mmol). O-(7-Azabenzotriazol-1-yl)-N,N,N',N'-tetramethyluronium hexafluorophosphate (42 mg, 0.11 mmol) was added to the mixture and the resulting solution was allowed to stir for 16 hours. The crude product was purified by reverse-phase preparative liquid chromatography to yield 1-(benzo[d][1,3]dioxol-5-yl)-N-(4-(2-methylthiazol-4-yl)phenyl)cyclopropane-carboxamide. ESI-MS m/z calc. 378.1, found; 379.1 (M+1)$^+$; Retention time 2.72 minutes. $^1$H NMR (400 MHz, DMSO-d$_6$) δ 1.04-1.10 (m, 2H), 1.40-1.44 (m, 2H), 2.70 (s, 3H), 6.03 (s, 2H), 6.88-6.96 (m, 2H), 7.01 (d, J=1.4 Hz, 1H), 7.57-7.61 (m, 2H), 7.81-7.84 (m, 3H), 8.87 (s, 1H).

Preparation 31

1-Benzo[1,3]dioxol-5-yl-N-[3-[4-(methylsulfamoyl)phenyl]phenyl]-cyclopropane-1-carboxamide

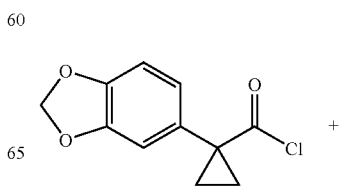

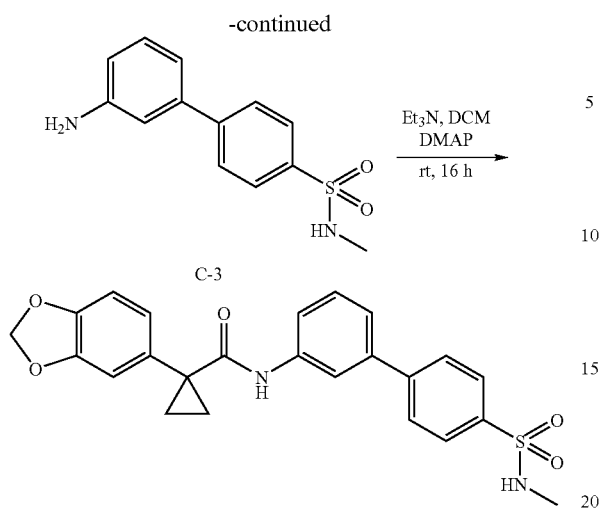

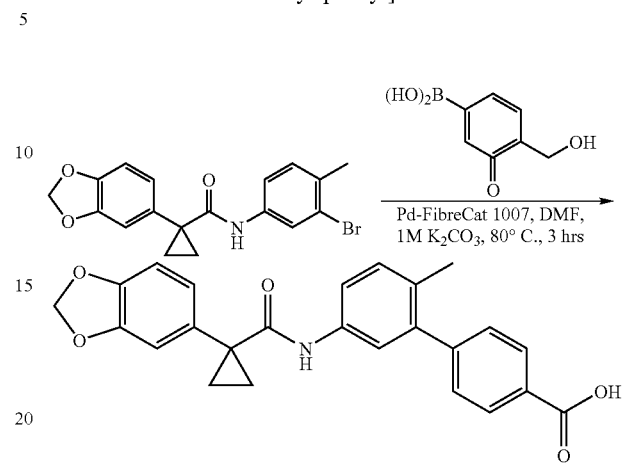

Preparation 32

4-[5-(1-Benzo[1,3]dioxol-5-ylcyclopropyl)carbonylamino-2-methyl-phenyl]benzoic acid To a solution of 1-benzo[1,3]dioxol-5-yl-cyclopropanecarbonyl chloride (0.97 mmol) in CH₂Cl₂ (3 mL) at ambient temperature was added a solution of 3'-amino-N-methylbiphenyl-4-sulfonamide (0.25 g, 0.97 mmol), Et₃N (0.68 mL, 4.9 mmol), DMAP (0.050 g, 0.058 mmol), and CH₂Cl₂ (1 mL) dropwise. The mixture was allowed to stir for 16 h before it was diluted with CH₂Cl₂ (50 mL). The solution was washed with 1N HCl (2×25 mL), sat. aq. NaHCO₃ (2×25 mL), then brine (25 mL). The organics were dried over Na₂SO₄, filtered, and concentrated in vacuo. The residue was purified by column chromatography (5-25% EtOAc/hexanes) to provide 1-benzo[1,3]dioxol-5-yl-N-[3-[4-(methylsulfamoyl)phenyl]phenyl]-cyclopropane-1-carboxamide as a white solid. ESI-MS m/z calc. 450.5, found 451.3 (M+1)⁺. Retention time of 3.13 minutes.

The following compounds were prepared using procedures 30 and 31 above: 4-5, 27, 35, 39, 51, 55, 75, 81, 90, 97-8, 101, 110, 132, 146, 155, 166, 186, 208, 211, 218, 230, 239, 245, 247, 258, 261, 283, 292, 308, 334, 339, 352, 356, 379, 405, 411, 433, 462, 477, 504, 514, 526, 536, 554, 563, 573, 590-2, 612, 619, 623, 627, 637, 648, 653, 660, 668-9, 692, 728, 740, 747, 748, 782, 814, 826-7, 834-6, 845, 916, 931-2, 938, 944, 950, 969, 975, 996, 1004, 1007, 1009, 1033, 1064, 1084-5, 1088, 1097, 1102, 1127, 1151, 1157, 1159, 1162, 1186, 1193.

1-(Benzo[d][1,3]dioxol-5-yl)-N-(3-bromo-4-methylphenyl)cyclopropanecarbox-amide (B-8) (5.1 g, 14 mmol), 4-boronobenzoic acid (3.4 g, 20 mmol), 1 M K₂CO₃ (54 mL, 54 mmol), Pd-FibreCat 1007 (810 mg, 1.35 mmol), and DMF (135 mL) were combined. The mixture was heated at 80° C. for 3 h. After cooling, the mixture was filtered and DMF was removed in vacuo. The residue was partitioned between dichloromethane (250 mL) and 1N HCl (250 mL). The organics were separated, washed with saturated NaCl solution (250 mL), and dried over Na₂SO₄. Evaporation of organics yielded 4-[5-(1-benzo[1,3]dioxol-5-ylcyclopropyl)carbonylamino-2-methyl-phenyl]benzoic acid (5.5 g, 98%). ESI-MS m/z calc. 415.1, found 416.5 (M+1)⁺; Retention time 3.19 minutes. ¹H NMR (400 MHz, DMSO-d6) δ 13.06 (s, 1H), 8.83 (s, 1H), 8.06-8.04 (m, 2H), 7.58-7.56 (m, 1H), 7.50-7.48 (m, 3H), 7.27-7.24 (m, 1H), 7.05-7.04 (m, 1H), 6.98-6.94 (m, 2H), 6.07 (s, 2H), 2.22 (s, 3H), 1.46-1.44 (m, 2H), 1.12-1.09 (m, 2H).

Preparation 33

5'-(1-(Benzo[d][1,3]dioxol-5-yl)cyclopropanecarboxamido)-2'-methyl-N-(2-(pyridin-2-yl)ethyl)biphenyl-4-carboxamide

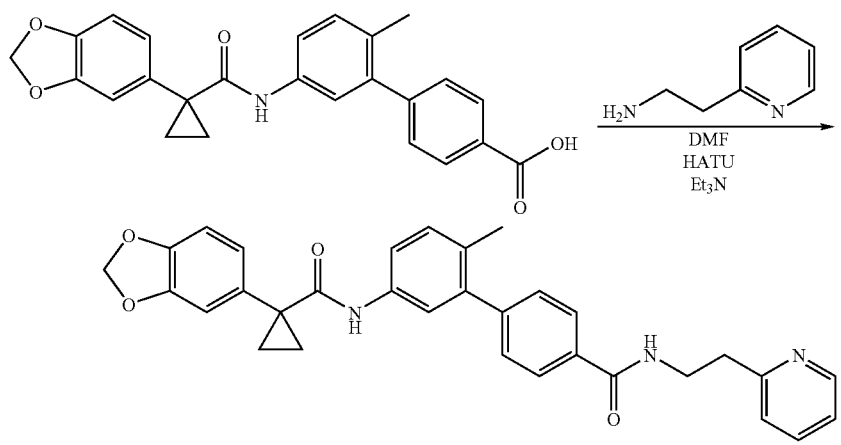

2-(Pyridin-2-yl)ethanamine (12 mg, 0.10 mmol) and 5'-(1-(benzo[d][1,3]dioxol-5-yl)cyclopropanecarboxamido)-2'-methylbiphenyl-4-carboxylic acid (42 mg, 0.10 mmol) were dissolved in N,N-dimethylformamide (1.0 mL) containing triethylamine (28 μL, 0.20 mmol). O-(7-Azabenzotriazol-1-yl)-N,N,N',N'-tetramethyluronium hexafluorophosphate (42 mg, 0.11 mmol) was added to the mixture and the resulting solution was allowed to stir for 1 hour at ambient temperature. The crude product was purified by reverse-phase preparative liquid chromatography to yield 5'-(1-(benzo[d][1,3]dioxol-5-yl)cyclopropanecarboxamido)-2'-methyl-N-(2-(pyridin-2-yl)ethyl)biphenyl-4-carboxamide as the trifluoroacetic acid salt (43 mg, 67%). ESI-MS m/z calc. 519.2, found 520.5 (M+1)$^+$; Retention time 2.41 minutes. $^1$H NMR (400 MHz, DMSO-d6) δ 8.77 (s, 1H), 8.75-8.74 (m, 1H), 8.68-8.65 (m, 1H), 8.23 (m, 1H), 7.83-7.82 (m, 2H), 7.75-7.68 (m, 2H), 7.48-7.37 (m, 4H), 7.20-7.18 (m, 1H), 6.99-6.98 (m, 1H), 6.90-6.89 (m, 2H), 6.01 (s, 2H), 3.72-3.67 (m, 2H), 3.20-3.17 (m, 2H), 2.15 (s, 3H), 1.40-1.37 (m, 2H), 1.06-1.03 (m, 2H).

The following compounds were prepared using procedure 33 above: 32, 78, 118, 134, 156, 171, 188, 237, 279, 291, 297, 309, 319, 338, 341, 362, 373, 376, 393, 406-7, 410, 448, 452-3, 474, 482, 494, 508, 577, 580, 593-4, 622, 629, 638, 651, 663-4, 681, 698, 704, 707, 710, 736-7, 739, 775, 806, 810, 825, 842, 853, 866, 871, 900, 905-7, 926, 935, 941, 966, 971, 973, 978-9, 1046, 1048, 1066, 1077, 1079, 1083, 1141, 1150, 1155-6, 1163, 1180, 1185, 1187, 1198, 1201.

Preparation 34

4-[5-(1-Benzo[1,3]dioxol-5-ylcyclopropyl)carbonylamino-2-methylphenyl]-N,N-dimethyl-benzamide 3H), 6.01 (s, 2H), 6.87-6.93 (m, 2H), 6.98 (d, J=1.3 Hz, 1H), 7.19 (d, J=8.4 Hz, 1H), 7.34-7.37 (m, 2H), 7.40-7.52 (m, 4H), 8.75 (s, 1H).

Preparation 35

5'-(1-(Benzo[d][1,3]dioxol-5-yl)cyclopropanecarboxamido)-2'-(isopropoxymethyl)-N,N-dimethylbiphenyl-4-carboxamide

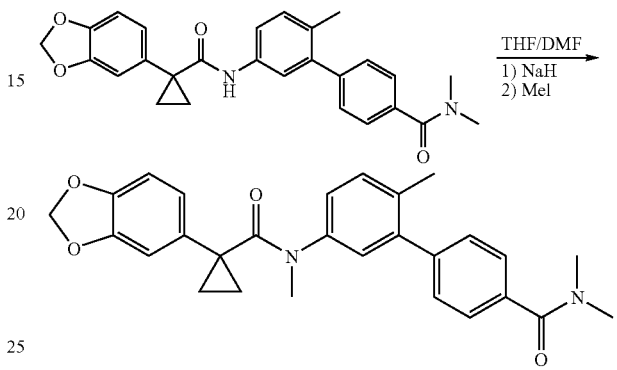

Sodium hydride (2.2 mg, 0.055 mmol, 60% by weight dispersion in oil) was slowly added to a stirred solution of 5'-(1-(benzo[d][1,3]dioxol-5-yl)cyclopropanecarboxamido)-N,N,2'-trimethylbiphenyl-4-carboxamide (21 mg, 0.048 mmol) in a mixture of 0.90 mL of anhydrous tetrahydrofuran (THF) and 0.10 mL of anhydrous N,N-dimethylfor-

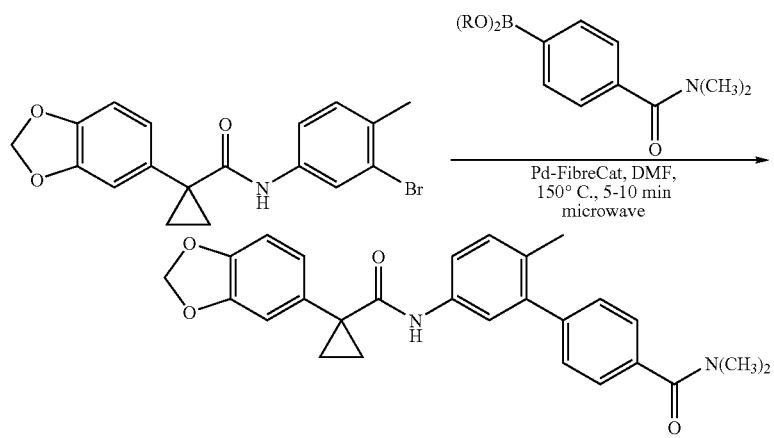

1-(Benzo[d][1,3]dioxol-5-yl)-N-(3-bromo-4-methylphenyl)cyclopropanecarbox-amide (0.10 mmol), N,N-dimethyl-4-(4,4,5,5-tetramethyl-1,3,2-dioxaborolan-2-yl)benzamide (0.11 mmol), K$_2$CO$_3$ (240 μL, 1 M), Pd-FibreCat (7 mg), and DMF (1 mL) were combined. The mixture was heated at 150° C. for 5 min (5 min ramp time) in a microwave reactor. After cooling, the mixture was filtered and purified by prep-HPLC to provide 4-[5-(1-benzo[1,3]dioxol-5-ylcyclopropyl)carbonylamino-2-methyl-phenyl]-N,N-dimethyl-benzamide. ESI-MS m/z calc. 442.2, found 443.5 (M+1)$^+$; Retention time 3.12 minutes. $^1$H NMR (400 MHz, DMSO-d$_6$) δ 1.02-1.08 (m, 2H), 1.37-1.44 (m, 2H), 2.17 (s, 3H), 2.96 (s, 3H), 3.00 (s, mamide (DMF). The resulting suspension was allowed to stir for 3 minutes before iodomethane (0.0048 mL, 0.072 mmol) was added to the reaction mixture. An additional aliquot of sodium hydride and iodomethane were required to consume all of the starting material which was monitored by LCMS. The crude reaction product was evaporated to dryness, redissolved in a minimum of DMF and purified by preparative LCMS chromatography to yield 5'-(1-(benzo[d][1,3]dioxol-5-yl)cyclopropanecarboxamido)-2'-(isopropoxymethyl)-N,N-dimethylbiphenyl-4-carboxamide (9.1 mg, 42%) ESI-MS m/z calc. 456.2, found 457.5 (M+1)$^+$. Retention time of 2.94 minutes. $^1$H NMR (400 MHz, CD$_3$CN) δ 0.91-0.93 (m, 2H), 1.41-1.45 (m, 2H), 2.23 (s, 3H), 3.00 (s, 3H), 3.07 (s, 3H), 3.20 (s, 3H), 5.81 (s, 2H), 6.29-6.36 (m, 2H), 6.56 (d, J=8.0 Hz, 1H), 6.69 (s, 1H), 6.92 (dd, J=1.6, 7.9 Hz, 1H), 7.17 (d, J=8.1 Hz, 1H), 7.28 (d, J=8.1 Hz, 2H), 7.46 (dd, J=1.8, 6.4 Hz, 2H).

Preparation 36

(S)-1-(5'-(1-(Benzo[d][1,3]dioxol-5-yl)cyclopropan-ecarboxamido)-2'-methylbiphenyl-4-ylsulfonyl)pyrrolidine-2-carboxylic acid

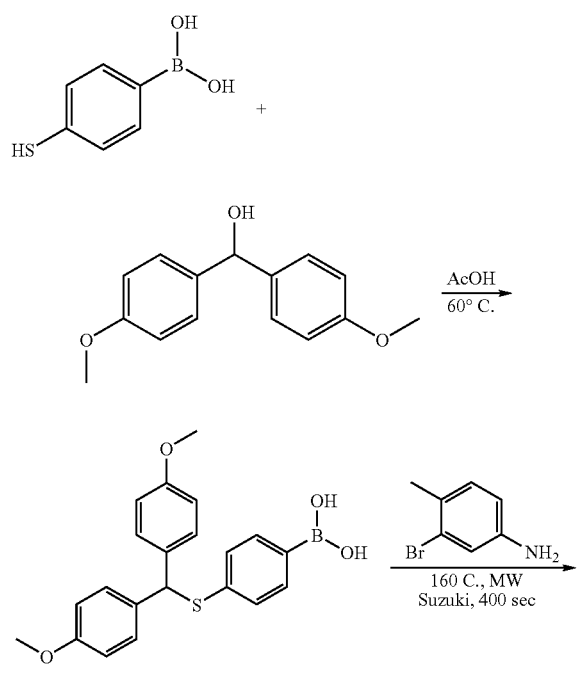

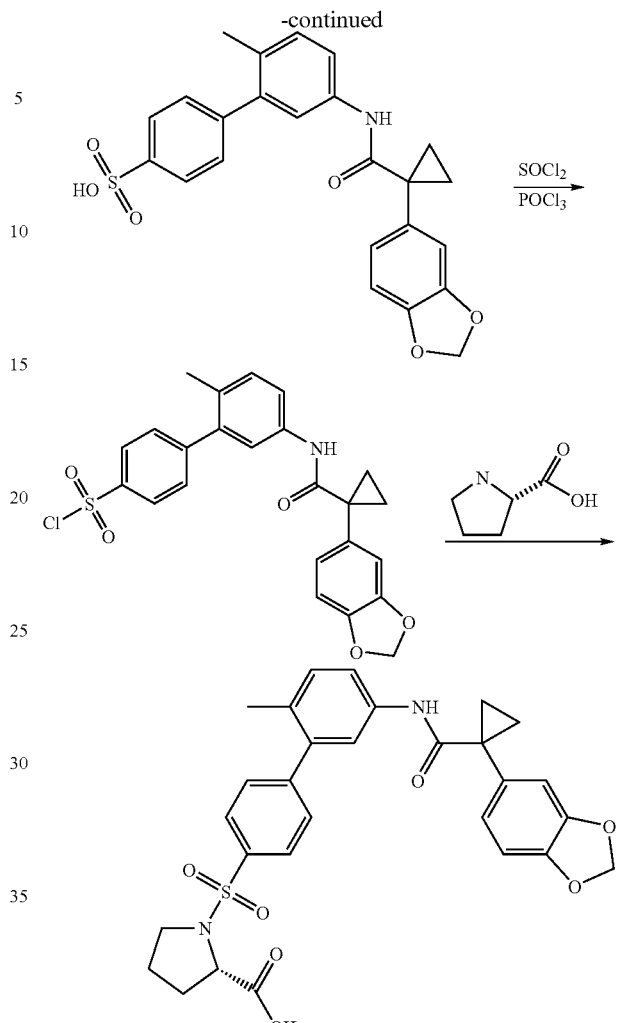

Step a: 4-(4,4'-Dimethoxybenzhydryl)-thiophenyl boronic acid 4,4'-Dimethoxybenzhydrol (2.7 g, 11 mmol) and 4-mercaptophenylboronic acid (1.54 g, 10 mmol) were dissolved in AcOH (20 mL) and heated at 60° C. for 1h. Solvent was evaporated and the residue was dried under high vacuum. This material was used without further purification.

Step b: 4'-[Bis-(4-methoxyphenyl)-methylsulfanyl]-6-methylbiphenyl-3-ylamine 4-(4,4'-Dimethoxybenzhydryl)-thiophenyl boronic acid (10 mmol) and 3-bromo-4-methylaniline (1.86 g, 10 mmol) were dissolved in MeCN (40 mL). Pd (PPh$_3$)$_4$ (~50 mg) and aqueous solution K$_2$CO$_3$ (1 M, 22 mL) were added before the reaction mixture was heated portion-wise in a microwave oven (160° C., 400 sec). Products were distributed between ethyl acetate and water. The organic layer was washed with water, brine and dried over MgSO$_4$. Evaporation yielded an oil that was used without purification in the next step. ESI-MS m/z calc. 441.0, found 442.1 (M+1).

Step c: 1-Benzo[1,3]dioxol-5-yl-cyclopropanecarboxylic acid 4'-[bis-(4-methoxyphenyl)-methylsulfanyl]-6-methylbiphenyl-3-ylamide 4'-[Bis-(4-methoxyphenyl)-methylsulfanyl]-6-methylbiphenyl-3-ylamine (~10 mmol) and 1-benzo[1,3]dioxol-5-yl-cyclopropanecarboxylic acid (2.28 g, 11 mmol) were dissolved in chloroform (25 mL) followed by addition of TCPH (4.1 g, 12 mmol) and DIEA (5.0 mL, 30 mmol). The reaction mixture was heated at 65° C. for 48 h. The volatiles were removed under reduced pressure. The residue was distributed between water (200 mL) and ethyl acetate (150 mL). The organic layer was washed with 5% NaHCO$_3$ (2×150 mL), water (1×150 mL), brine (1×150 mL) and dried over MgSO$_4$. Evaporation of the solvent yielded crude 1-benzo[1,3]dioxol-5-yl-cyclopropanecarboxylic acid 4'-[bis-(4-methoxyphenyl)-methylsulfanyl]-6-methylbiphenyl-3-ylamide as a pale oil, which was used without further purification. ESI-MS m/z calc. 629.0, found 630.0 (M+1) (HPLC purity ~85-90%, UV254 nm).

Step d: 5'-[(1-Benzo[1,3]dioxol-5-yl-cyclopropanecarbonyl)-amino]-2'-methylbiphenyl-4-sulfonic acid 1'-Benzo[1,3]dioxol-5-yl-cyclopropanecarboxylic acid 4'-[bis-(4-methoxyphenyl)-methylsulfanyl]-6-methylbiphenyl-3-ylamide (~8.5 mmol) was dissolved in acetic acid (75 mL) followed by addition of 30% H$_2$O$_2$ (10 mL). Additional hydrogen peroxide (10 mL) was added 2 h later. The reaction mixture was stirred at 35-45° C. overnight (~90% conversion, HPLC). The volume of reaction mixture was reduced to a third by evaporation (bath temperature below 40° C.). The reaction mixture was loaded directly onto a prep RP HPLC column (C-18) and purified. The appropriate fractions with were collected and evaporated to provide 5'-[(1-benzo[1,3]dioxol-5-yl-cyclopropanecarbonyl)-amino]-2'-methylbiphenyl-4-sulfonic acid (2.1 g, 46%, cal. based on 4-mercaptophenylboronic acid). ESI-MS m/z calc. 451.0, found 452.2 (M+1).

Step e: 5'-[(1-Benzo[1,3]dioxol-5-yl-cyclopropanecarbonyl)-amino]-2'-methylbiphenyl-4-sulfonyl chloride 5'-[(1-Benzo[1,3]dioxol-5-yl-cyclopropanecarbonyl)-amino]-2'-methylbiphenyl-4-sulfonic acid (1.9 g, 4.3 mmol) was dissolved in POCl$_3$ (30 mL) followed by the addition of SOCl$_2$ (3 mL) and DMF (100 µl). The reaction mixture was heated at 70-80° C. for 15 min. The reagents were evaporated and re-evaporated with chloroform-toluene. The residual brown oil was diluted with chloroform (22 mL) and immediately used for sulfonylation. ESI-MS m/z calc. 469.0, found 470.1 (M+1).

Step f: (S)-1-{5'-[(1-Benzo[1,3]dioxol-5-yl-cyclopropane-carbonyl)-amino]-2'-methyl-biphenyl-4-sulfonyl}-pyrrolidine-2-carboxylic acid L-Proline (57 mg, 0.50 mmol) was treated with N,O-bis(trimethylsilyl)acetamide (250 µl, 1.0 mmol) in 1 mL dioxane overnight at 50° C. To this mixture was added 5'-(1-(benzo[d][1,3]dioxol-5-yl)cyclopropanecarboxamido)-2'-methyl-biphenyl-4-sulfonyl chloride (~35 µmol, 400 µl solution in chloroform) followed by DIEA (100 µL). The reaction mixture was kept at room temperature for 1 h, evaporated, and diluted with DMSO (400 µl). The resulting solution was subjected to preparative HPLC purification. Fractions containing the desired material were combined and concentrated in vacuum centrifuge at 40° C. to provide the trifluoroacetic salt of (S)-1-{5'-[(1-Benzo[1,3]dioxol-5-yl-cyclopropanecarbonyl)-amino]-2'-methyl-biphenyl-4-sulfonyl}-pyrrolidine-2-carboxylic acid. ESI-MS m/z calc. 548.1, found 549.1 (M+1), retention time 3.40 min; $^1$H NMR (250 MHz, DMSO-d$_6$) δ 1.04 (m, 2H), δ 1.38 (m, 2H), δ 1.60 (m, 1H), δ 1.80-1.97 (m, 3H) δ 2.16 (s, 3H), δ 3.21 (m, 1H), 3.39 (m, 1H), 4.15 (dd, 1H, J=4.1 Hz, J=7.8 Hz), δ 6.01 (s, 2H), δ 6.89 (s, 2H), δ 6.98 (s, 1H), δ 7.21 (d, 1H, J=8.3 Hz), δ 7.45 (d, 1H, J=2 Hz), δ 7.52 (dd, 1H, J=2 Hz, J=8.3 Hz), δ 7.55 (d, 2H, J=8.3 Hz), δ 7.88 (d, 2H, J=8.3 Hz), δ 8.80 (s, 1H).

The following compounds were prepared using procedure 36 above: 9, 17, 30, 37, 41, 62, 88, 104, 130, 136, 169, 173, 184, 191, 216, 219, 259-60, 265, 275, 278, 281, 302, 306, 342, 350, 366, 371, 380, 387, 396, 404, 412, 430, 438, 449, 460, 478, 486, 496, 499-500, 503, 512, 517, 579, 581-2, 603, 610, 611, 615, 652, 676, 688, 701, 706, 712, 725, 727, 732, 734, 751, 764, 770, 778, 780, 790, 802, 829, 841, 854, 885, 889, 897, 902, 930, 951-2, 970, 986, 992, 994, 997, 1040, 1050-1, 1054, 1056, 1065, 1082, 1090, 1093, 1107, 1114, 1130, 1143, 1147, 1158, 1160, 1164, 1170, 1174-5.

Preparation 37

5'-(1-(Benzo[d][1,3]dioxol-5-yl)cyclopropanecarboxamido)-2-fluoro-2'-methylbiphenyl-4-carboxamide

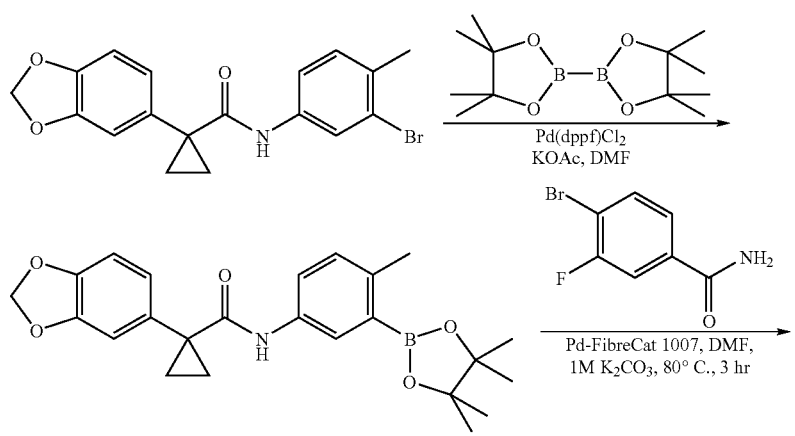

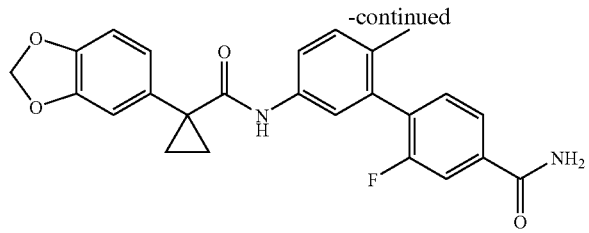

Step a: 1-(Benzo[d][1,3]dioxol-5-yl)-N-(4-methyl-3-(4,4,5,5-tetramethyl-1,3,2-dioxaborolan-2-yl)phenyl)cyclopropanecarboxamide 1-(Benzo[d][1,3]dioxol-5-yl)-N-(3-bromo-4-methylphenyl)cyclopropanecarboxamide (5.0 g, 13 mmol), 4,4,4',4',5,5,5',5'-octamethyl-2,2'-bi(1,3,2-dioxaborolane) (4.1 g, 16 mmol), Pd(dppf)Cl$_2$ (0.66 g, 0.81 mmol), and DMF (100 mL) were added to a flask containing oven-dried KOAc (3.9 g, 40 mmol). The mixture was heated at 80° C. for 2 h (~40% conversion). The mixture was cooled to ambient temperature and the volatiles were removed under vacuum. The residue was taken up in CH$_2$Cl$_2$, filtered, and loaded onto a SiO$_2$ column (750 g of SiO$_2$). The product was eluted with EtOAc/Hexanes (0-25%, 70 min, 250 mL/min) to provide 1-(benzo[d][1,3]dioxol-5-yl)-N-(4-methyl-3-(4,4,5,5-tetramethyl-1,3,2-dioxaborolan-2-yl)phenyl)cyclopropanecarboxamide (1.5 g, 27%) and unreacted starting material: 1-(benzo[d][1,3]dioxol-5-yl)-N-(3-bromo-4-methylphenyl)cyclopropanecarboxamide (3.0 g).

Step b: 5'-(1-(Benzo[d][1,3]dioxol-5-yl)cyclopropanecarboxamido)-2-fluoro-2'-methylbiphenyl-4-carboxamide 1-(Benzo[d][1,3]dioxol-5-yl)-N-(4-methyl-3-(4,4,5,5-tetramethyl-1,3,2-dioxaborolan-2-yl)phenyl)cyclopropanecarboxamide (42 mg, 0.10 mmol), 4-bromo-3-fluorobenzamide (24 mg, 0.11 mmol), Pd-FibreCat 1007 (10 mg), K$_2$CO$_3$ (1M, 240 mL), and DMF (1 mL) were combined in a scintillation vial and heated at 80° C. for 3 hr. The mixture was filtered and purified using reverse-phase preparative HPLC to provide 5'-(1-(benzo[d][1,3]dioxol-5-yl)cyclopropanecarboxamido)-2-fluoro-2'-methylbiphenyl-4-carboxamide (ESI-MS m/z calc. 428.5, found 429.5 (M+1); retention time 3.30 min).

Preparation 38

1-(Benzo[d][1,3]dioxol-5-yl)-N-(6-methyl-3'-(2H-tetrazol-5-yl)biphenyl-3-yl)cyclopropanecarboxamide

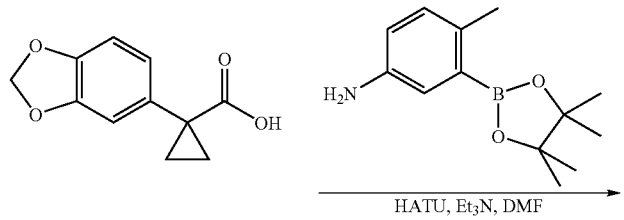

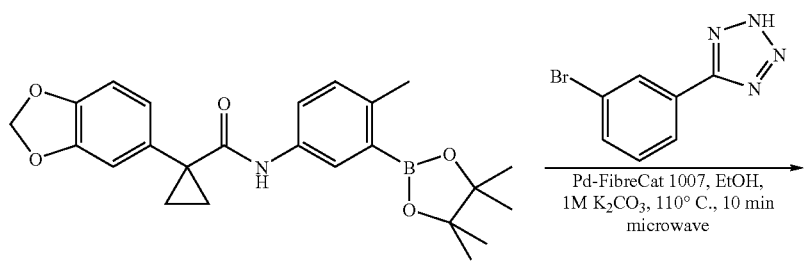

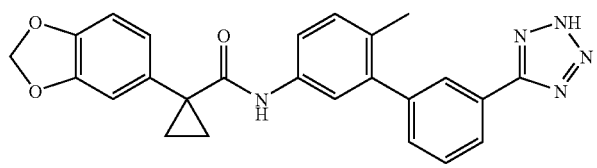

Step a: 1-(Benzo[d][1,3]dioxol-5-yl)-N-(4-methyl-3-(4,4,5,5-tetramethyl-1,3,2-dioxaborolan-2-yl)phenyl)cyclopropanecarboxamide To a solution of 1-(benzo[d][1,3]dioxol-5-yl)cyclopropanecarboxylic acid (1.74 g, 8.57 mmol) in DMF (10 mL) was added HATU (3.59 g, 9.45 mmol), $Et_3N$ (3.60 mL, 25.8 mmol), then 4-methyl-3-(4,4,5,5-tetramethyl-1,3,2-dioxaborolan-2-yl)aniline (2.19 g, 9.40 mmol) at ambient temperature. The mixture was heated at 70° C. for 18 h. The mixture was cooled, then concentrated under reduced pressure. The residue was taken up in EtOAc before it was washed with $H_2O$, then brine (2×). The organics were dried ($Na_2SO_4$) and concentrated under reduced pressure to provide an orange-tan foam/semi-solid. Column chromatography on the residue (5-15% EtOAc/hexanes) provided a white foam. MeOH was added to the material and the slurry was concentrated under reduced pressure to yield 3.10 g of 1-(benzo[d][1,3]dioxol-5-yl)-N-(4-methyl-3-(4,4,5,5-tetramethyl-1,3,2-dioxaborolan-2-yl)phenyl)cyclopropanecarboxamide as a white, granular solid, (85%).

Step b: 1-(Benzo[d][1,3]dioxol-5-yl)-N-(6-methyl-3'-(2H-tetrazol-5-yl)-biphenyl-3-yl)cyclopropanecarboxamide 1-(Benzo[d][1,3]dioxol-5-yl)-N-(4-methyl-3-(4,4,5,5-tetramethyl-1,3,2-dioxaborolan-2-yl)phenyl)cyclopropanecarboxamide (42.1 mg, 0.100 mmol), 5-(3-bromophenyl)-tetrazole (22.5 mg, 0.100 mmol), a 1 M aqueous solution of potassium carbonate (0.50 mL), Pd-FibreCat 1007 (6 mg), and ethanol (0.50 mL) were combined. The mixture was heated at 110° C. for 5 min (5 min ramp time) in a microwave reactor. After cooling, the mixture was filtered and purified by prep-HPLC to provide 1-(benzo[d][1,3]dioxol-5-yl)-N-(6-methyl-3'-(2H-tetrazol-5-yl)-biphenyl-3-yl)cyclopropanecarboxamide. ESI-MS m/z calc. 439.2, found 440.2 (M+1)$^+$; Retention time 2.59 minutes.

The following compounds were prepared using procedures 13, 24, 32, 34, 37 and 38 above: 1-3, 7-8, 10-13, 15-6, 18-23, 25, 28-9, 31, 33-4, 36, 38, 40, 42-50, 52-54, 56-61, 63-9, 71, 72 (1), 73-4, 76-7, 80, 82-3, 85-7, 89, 91-5, 99-100, 102-3, 105-9, 111-113, 115 (1), 116-7, 119-21, 123-4, 125 (2), 126-9, 131, 133, 135, 137-45, 147-54, 157-8, 160-5, 167-8, 170, 172, 174-5, 176 (1), 177-83, 185, 187, 189-90, 193-4, 195 (1), 196, 197 (1), 198-9, 201-5, 207, 209-10, 212-3, 215, 217, 220-2, 224-9, 231, 232 (2), 233-6, 238, 240-4, 246, 249-52, 253 (1), 254-7, 262-74, 276-7, 280, 282, 286-8, 290, 293-6, 298-301, 303-5, 307, 310, 312-8, 320-31, 332 (2), 333, 335-7, 340, 340, 343-7, 349, 351, 353-4, 357-61, 363-4, 367-70, 372, 374, 375 (2), 377 (2), 378, 381, 383-6, 388, 390, 394-5, 397-403, 408, 409 (2), 413, 414 (1), 415-29, 431-2, 434-7, 439-46, 450-1, 454-8, 461, 463-4, 466-8, 469 (2), 470, 472-3, 475-6, 479, 480-1, 483-5, 487-93, 497-8, 501-2, 506-7, 509-510, 513, 515-6, 518-21, 523, 525, 527-8, 531-3, 535, 537-8, 539 (1), 540-50, 552-3, 555-561, 564-72, 574-6, 578, 583-89, 595-602, 604-5, 606 (1), 607-9, 613-4, 616-8, 620, 624-6, 630, 631 (1), 632-6, 639-42, 644-7, 649-50, 654-9, 662, 665-7, 670-1, 673-5, 677-80, 683-5, 686 (1), 687, 689-91, 693-97, 699-700, 702-3, 705, 708, 711, 713-24, 726, 729 (2), 730, 733, 735 (1), 738, 741-6, 752-4, 756-63, 765-9, 771-4, 776-7, 779, 781, 784-5, 787-9, 791-6, 798-799, 800 (1), 803-5, 807-8, 811, 813, 815-21, 822 (1), 823-4, 830-3, 837-40, 847-52, 855-65, 867-70, 872-76, 878-84, 886-8, 890-6, 898-9, 901, 903-4, 908, 910-4, 915 (1), 917-25, 927-8, 933-4, 936, 939-40, 942-3, 945-6, 948-9, 953-64, 967-8, 972, 974, 976-7, 980-5, 987-91, 993, 995, 998-1001, 1003, 1005-6, 1008, 1010-11, 1013-32, 1034-6, 1038-9, 1041-5, 1047, 1052-3, 1055, 1057-60, 1062-3, 1067-9, 1071-6, 1078, 1081, 1086-7, 1091-2, 1094-6, 1098-1101, 1103-6, 1108-13, 1115, 1116 (2), 1117-26, 1128-9, 1131-40, 1142, 1144-6, 1148-9, 1152-4, 1161, 1165, 1167-9, 1171-3, 1176, 1177 (1), 1178-9, 1181-4, 1188-92, 1194, 1197, 1199-1200, 1202-4, 1205 (2).

Following the coupling with 2-(3-(4,4,5,5-tetramethyl-1,3,2-dioxaborolan-2-yl)benzyl)isoindoline-1,3-dione and 2-(2-(4,4,5,5-tetramethyl-1,3,2-dioxaborolan-2-yl)benzyl)isoindoline-1,3-dione, examples were obtained after removal of the phthalimide group with hydrazine using known deprotecting procedures.

Following the coupling with 4-((tert-butoxycarbonylamino)methyl)phenylboronic acid, examples were obtained after removal of the Boc-group with TFA using known deprotecting procedures.

Preparation 39

5-(1-(Benzo[d][1,3]dioxol-5-yl)cyclopropanecarboxamido)-N2,N4',N4'-trimethylbiphenyl-2,4'-dicarboxamide

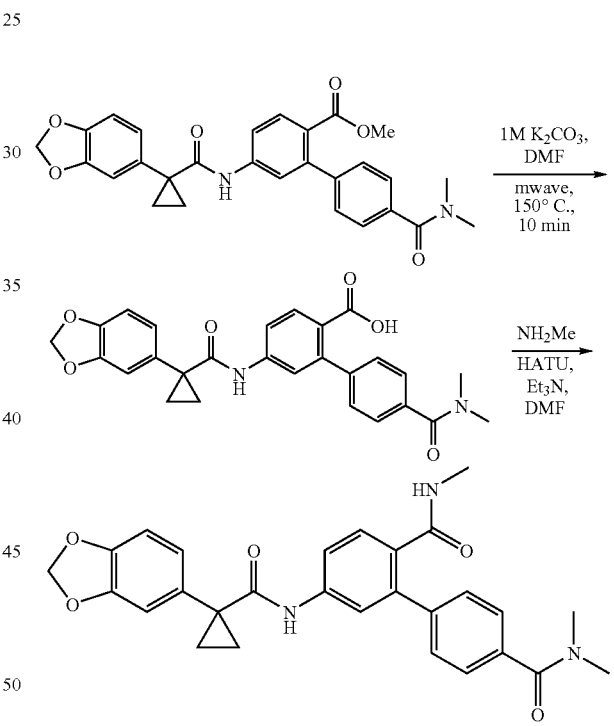

Step a: 5-(1-(Benzo[d][1,3]dioxol-5-yl)cyclopropanecarboxamido)-4'-(dimethylcarbamoyl)biphenyl-2-carboxylic acid Methyl 5-(1-(benzo[d][1,3]dioxol-5-yl)cyclopropanecarboxamido)-4'-(dimethylcarbamoyl)biphenyl-2-carboxylate (84 mg, 0.20 mmol) was dissolved in DMF (2.0 mL) with 1 M $K_2CO_3$ (1.0 mL) and irradiated in the microwave at 150° C. for 10 minutes. Purification by reverse phase HPLC yielded 5-(1-(benzo[d][1,3]dioxol-5-yl)cyclopropanecarboxamido)-4'-(dimethylcarbamoyl)-biphenyl-2-carboxylic acid (7.3 mg, 8%). ESI-MS m/z calc. 472.5, found 473.3 (M+1)$^+$; retention time 2.79 minutes.

Step b: 5-(1-(Benzo[d][1,3]dioxol-5-yl)cyclopropanecarboxamido)-N2,N4',N4'-trimethylbiphenyl-2,4'-dicarboxamide 5-(1-(Benzo[d][1,3]dioxol-5-yl)cyclopropanecarboxamido)-4'-(dimethylcarbamoyl)biphenyl-2-carboxylic acid (47 mg, 0.10 mmol) and 75 µL of a 2.0 M solution of methylamine in tetrahydrofuran (0.15 mmol) were dissolved in DMF (1.0 mL) containing $Et_3N$ (28 µL, 0.20 mmol). O-(7-Azabenzotriazol-1-yl)-N,N,N',N'-tetramethyluronium hexafluorophosphate (42 mg, 0.11 mmol) was added to the mixture and the resulting solution was allowed to stir for 3 hours. The mixture was filtered and purified by reverse phase HPLC to yield 5-(1-(benzo[d][1,3]dioxol-5-yl)cyclopropane-carboxamido)-N2,N4',N4'-trimethylbiphenyl-2,4'-dicarboxamide (5.0 mg, 10%). ESI-MS m/z calc. 485.5, found 486.5 $(M+1)^+$; retention time 2.54 minutes.

The following compounds were prepared using procedure 39 above: 311, 495, 755, 812, 1070.

Preparation 40

5'-(1-(Benzo[d][1,3]dioxol-5-yl)cyclopropanecarboxamido)-2'-((2-hydroxyethylamino)methyl)-N,N-dimethylbiphenyl-4-carboxamide

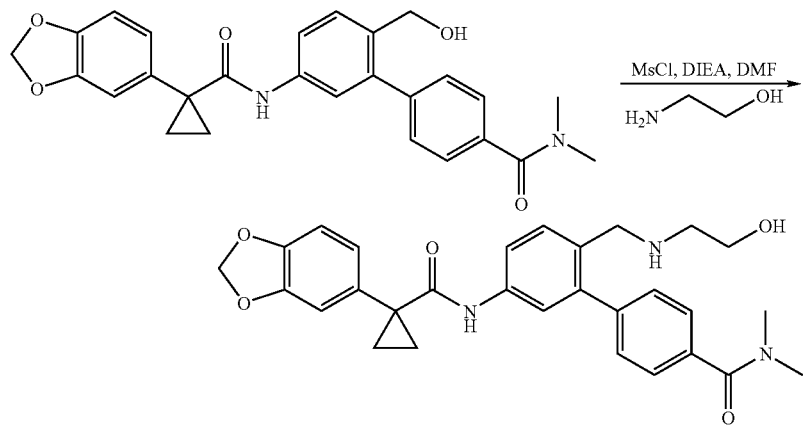

To a solution of 5'-(1-(benzo[d][1,3]dioxol-5-yl)cyclopropanecarboxamido)-2'-(hydroxymethyl)-N,N-dimethylbiphenyl-4-carboxamide (46 mg, 0.10 mmol) and diisopropylethylamine (30 µL, 0.20 mmol) in DMF (1.0 mL) was added methanesulfonyl chloride (8.5 µL, 0.11 mmol). After stirring at 25° C. for 15 minutes, ethanolamine (13 µL, 0.30 mmol) was added and the mixture was stirring for an additional 1 hour. The mixture was filtered and purified by reverse phase HPLC to yield 5'-(1-(benzo[d][1,3]dioxol-5-yl)cyclopropanecarboxamido)-2'-((2-hydroxyethyl-amino)methyl)-N,N-dimethylbiphenyl-4-carboxamide as the trifluoroacetic acid salt (5.0 mg, 8%). ESI-MS m/z calc. 501.2, found 502.5 $(M+1)^+$; retention time 2.28 minutes.

The following compounds were prepared using procedure 40 above: 843, 909, 1080.

Preparation 41

5'-(1-(Benzo[d][1,3]dioxol-5-yl)cyclopropanecarboxamido)-2'-((2-hydroxyethylamino)methyl)-N,N-dimethylbiphenyl-4-carboxamide

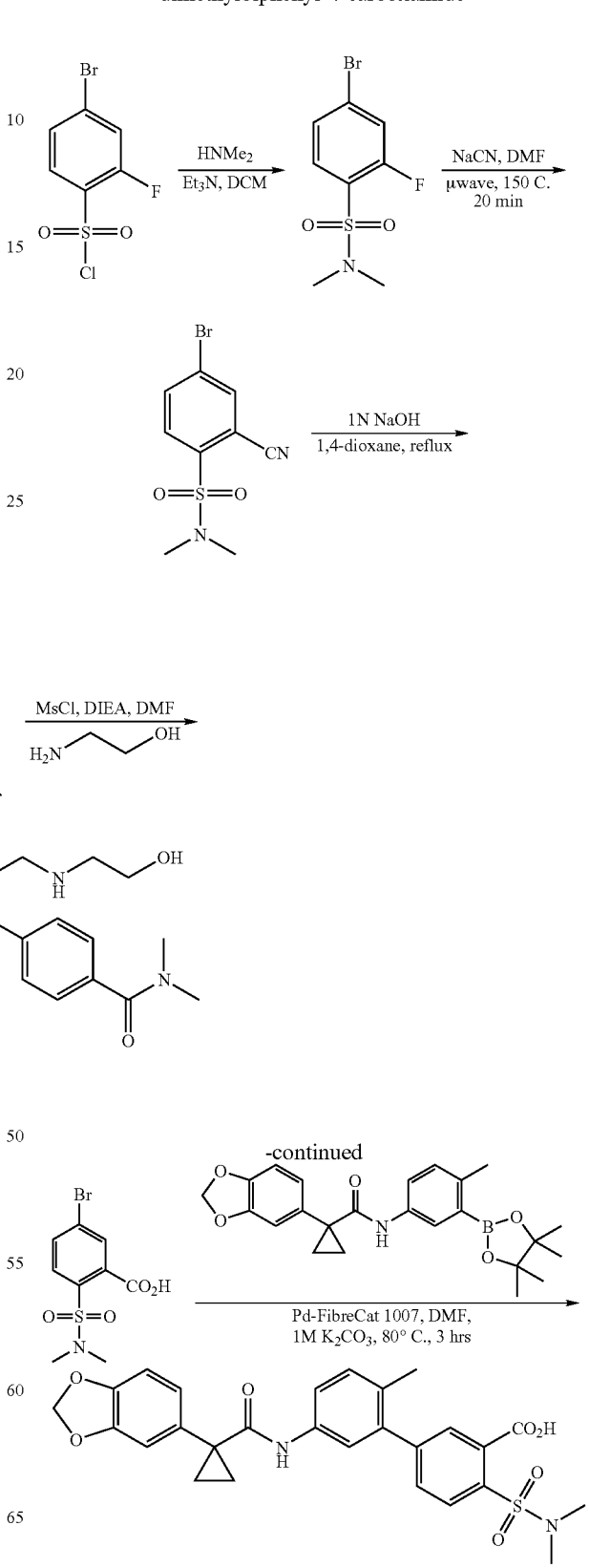

Step a: 4-Bromo-2-fluoro-N,N-dimethylbenzenesulfonamide

To 4-bromo-2-fluorobenzene-1-sulfonyl chloride (1.0 g, 3.7 mmol) and Et₃N (1.5 mL, 11 mmol) in dichloromethane (10 mL) was added a solution of dimethylamine 2.0 M in THF (2.2 mL, 4.4 mmol). The reaction was stirred at ambient temperature for 30 minutes. The reaction was washed with 10 mL of 1N aqueous HCl and 10 mL of brine. Organics were dried over Na₂SO₄ and evaporated to dryness. Crude product was purified by chromatography on silica gel (eluting with 0-25% ethyl acetate in hexanes) to afford 4-bromo-2-fluoro-N,N-dimethylbenzenesulfonamide (780 mg, 75%).

Step b: 4-Bromo-2-cyano-N,N-dimethylbenzenesulfonamide

4-Bromo-2-fluoro-N,N-dimethylbenzenesulfonamide (1.0 g, 3.5 mmol) and sodium cyanide (350 mg, 7.1 mmol) were dissolved in DMF (3 mL) and irradiated in the microwave at 150° C. for 20 minutes. DMF was removed in vacuo and the residue was redissolved in dichloromethane (5 mL). The organics were washed with 5 mL of each 1N aqueous HCl, saturated aqueous NaHCO₃, and brine. Organics were dried over Na₂SO₄ and evaporated to dryness. Crude product was purified by chromatography on silica gel (eluting with 0-50% ethyl acetate in hexanes) to afford 4-bromo-2-cyano-N,N-dimethylbenzenesulfonamide (72 mg, 7%). ESI-MS m/z calc. 288.0, found 288.9 (M+1)$^+$; retention time 1.44 minutes.

Step c: 5-Bromo-2-(N,N-dimethylsulfamoyl)benzoic acid

A mixture of 4-bromo-2-cyano-N,N-dimethylbenzenesulfonamide (110 mg, 0.38 mmol) and 1N aqueous NaOH (2.0 mL, 2.0 mmol) in 1,4-dioxane (2 mL) was heated at reflux. The cooled reaction mixture was washed with dichloromethane (5 mL). The aqueous layer was acidified by the addition of 1N aqueous HCl. The acidified aqueous layer was extracted with dichloromethane (2×5 mL). The combined organics were dried over Na₂SO₄ and evaporated to dryness to yield 5-bromo-2-(N,N-dimethylsulfamoyl)benzoic acid in 34% yield (40 mg, 0.13 mmol). ESI-MS m/z calc. 307.0, found 308.1 (M+1)$^+$; retention time 1.13 minutes.

Step d: 5'-(1-(Benzo[d][1,3]dioxol-5-yl)cyclopropanecarboxamido)-4-(N,N-dimethylsulfamoyl)-2'-methylbiphenyl-3-carboxylic acid 1-(Benzo[d][1,3]dioxol-5-yl)-N-(4-methyl-3-(4,4,5,5-tetramethyl-1,3,2-dioxaborolan-2-yl)phenyl)cyclopropanecarboxamide (42 mg, 0.10 mmol), 5-bromo-2-(N,N-dimethylsulfamoyl)benzoic acid (31 mg, 0.10 mmol), 1 M K₂CO₃ (0.30 mL, 0.30 mmol), and Pd-FibreCat 1007 (8 mg, 0.004 mmol) were dissolved in DMF (1 mL) and heated at 80° C. for 3 hr in an oil bath. The mixture was filtered and purified by reverse phase HPLC to yield 5'-(1-(benzo[d][1,3]dioxol-5-yl)cyclopropanecarboxamido)-4-(N,N-dimethylsulfamoyl)-2'-methylbiphenyl-3-carboxylic acid. ESI-MS m/z calc. 522.6, found 523.5 (M+1)$^+$; retention time 1.79 minutes.

Preparation 42

3-Bromo-4-(3-methyloxetan-3-yl)aniline

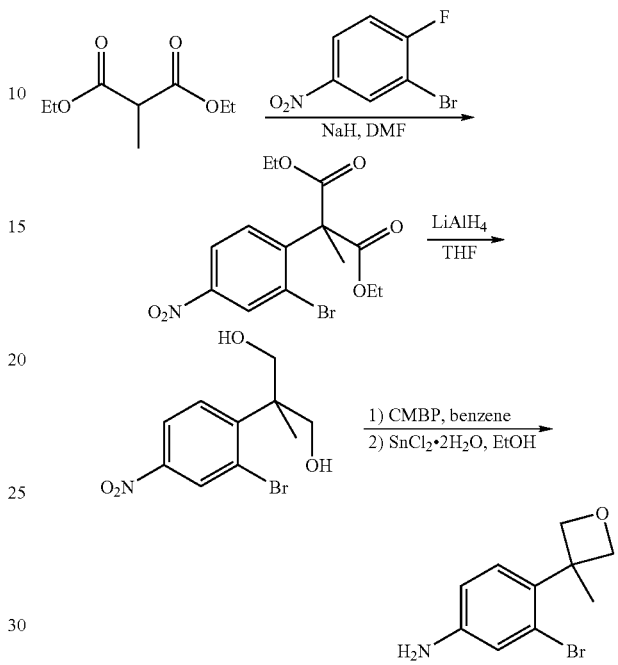

Step a: Diethyl 2-(2-bromo-4-nitrophenyl)-2-methylmalonate

Diethyl 2-methylmalonate (4.31 mL, 25.0 mmol) was dissolved in 25 mL of anhydrous DMF. This solution was cooled to 0° C. under an atmosphere of nitrogen. Sodium hydride (1.04 g, 26 mmol, 60% by weight in mineral oil) was slowly added to the solution. The resulting mixture was allowed to stir for 3 minutes at 0° C., and then at room temperature for 10 minutes. 2-Bromo-1-fluoro-4-nitrobenzene (5.00 g, 22.7 mmol) was quickly added and the mixture turned bright red. After stirring for 10 minutes at room temperature, the crude mixture was evaporated to dryness and then partitioned between dichloromethane and a saturated aqueous solution of sodium chloride. The layers were separated and the organic phase was washed twice with a saturated aqueous solution of sodium chloride. The organics were concentrated to yield diethyl 2-(2-bromo-4-nitrophenyl)-2-methylmalonate (8.4 g, 99%) as a pale yellow oil which was used without further purification. Retention time 1.86 min.

Step b: 2-(2-Bromo-4-nitrophenyl)-2-methylpropane-1,3-diol

Diethyl 2-(2-bromo-4-nitrophenyl)-2-methylmalonate (8.12 g, 21.7 mmol) was dissolved in 80 mL of anhydrous tetrahydrofuran (THF) under an atmosphere of nitrogen. The solution was then cooled to 0° C. before a solution of lithium aluminum hydride (23 mL, 23 mmol, 1.0 M in THF) was added slowly. The pale yellow solution immediately turned bright red upon the addition of the lithium aluminum hydride.

After 5 min, the mixture was quenched by the slow addition of methanol while maintaining the temperature at 0° C. The reaction mixture was then partitioned between dichloromethane and 1 N hydrochloric acid. The layers were separated and the aqueous layer was extracted three times with dichloromethane. The combined organics were evaporated to dryness and then purified by column chromatography (SiO$_2$, 120 g) utilizing a gradient of 0-100% ethyl acetate in hexanes over 45 minutes. 2-(2-Bromo-4-nitrophenyl)-2-methylpropane-1,3-diol was isolated as a red solid (2.0 g, 31%). $^1$H NMR (400 MHz, d$_6$-DMSO) δ 8.34 (d, J=2.6 Hz, 1H), 8.16 (dd, J=2.6, 8.9 Hz, 1H), 7.77 (d, J=8.9 Hz, 1H), 4.78 (t, J=5.2 Hz, 2H), 3.98-3.93 (m, 2H), 3.84-3.79 (m, 2H), 1.42 (s, 3H). Retention time 0.89 min.

Step c: 3-Bromo-4-(3-methyloxetan-3-yl)aniline 2-(2-Bromo-4-nitrophenyl)-2-methylpropane-1,3-diol (0.145 g, 0.500 mmol) was dissolved in 2.5 mL of anhydrous benzene. Cyanomethylenetributylphosphorane (CMBP) (0.181 g, 0.750 mmol) was then added and the solution was allowed to stir at room temperature for 72 hours. The mixture was evaporated to dryness and then re-dissolved in 4 mL of EtOH. Tin(II) chloride dihydrate (0.564 g, 2.50 mmol) was then added and the resulting solution was heated at 70° C. for 1 hour. The mixture was cooled to room temperature and then quenched with a saturated aqueous solution of sodium bicarbonate. The mixture was then extracted three times with ethyl acetate. The combined ethyl acetate extracts were evaporated to dryness and purified by preparative LC/MS to yield 3-bromo-4-(3-methyloxetan-3-yl)aniline as a pale yellow oil (0.032 g, 32%) $^1$H NMR (400 MHz, CD$_3$CN) δ 7.13 (dd, J=0.7, 1.8 Hz, 1H), 6.94-6.88 (m, 2H), 6.75 (br s, 2H), 4.98 (d, J=5.6 Hz, 2H), 4.51 (d, J=6.1 Hz, 2H), 1.74 (s, 3H). ESI-MS m/z calc. 241.0, found; 242.1 (M+1)$^+$ Retention time 0.53 minutes.

Preparation 43

3-Bromo-4-ethylaniline

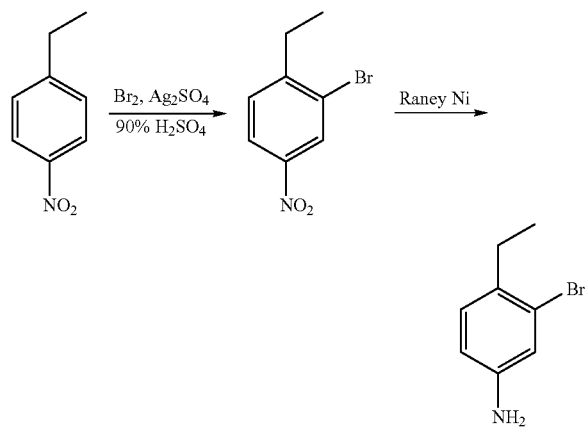

Step a: 2-Bromo-1-ethyl-4-nitrobenzene

To a mixture of 1-ethyl-4-nitro-benzene (30 g, 0.20 mol), silver sulfate (62 g, 0.20 mol), concentrated sulfuric acid (180 mL) and water (20 g) was added bromine (20 mL, 0.40 mol) dropwise at ambient temperature. After addition, the mixture was stirred for 2 hours at ambient temperature, and then was poured into dilute sodium hydrogen sulfite solution (1 L, 10%). The mixture was extracted with diethylether. The combined organics were dried over Na$_2$SO$_4$ and then concentrated under vacuum to provide a mixture of 2-bromo-1-ethyl-4-nitrobenzene and 1,3-dibromo-2-ethyl-5-nitro-benzene. The mixture was purified by column chromatography (petroleum ether/EtOAc 100:1) to yield 2-bromo-1-ethyl-4-nitrobenzene (25 g) as a yellow oil with a purity of 87%. $^1$H NMR (300 MHz, CDCl$_3$) δ 8.39 (d, J=2.4 Hz, 1H), 8.09 (dd, J=2.4, 8.4 Hz, 1H), 7.39 (d, J=8.4 Hz, 1H), 2.83 (q, J=7.5 Hz, 2H), 1.26 (t, J=7.5 Hz, 3H).

Step b: 3-Bromo-4-ethylaniline

To a solution of 2-bromo-1-ethyl-4-nitro-benzene (25 g, 0.019 mol) in MeOH (100 mL) was added Raney-Ni (2.5 g). The reaction mixture was hydrogenated under hydrogen (1 atm) at room temperature. After stirring for 3 hours, the mixture was filtered and concentrated under reduced pressure. The crude material was purified by preparative HPLC to give 3-bromo-4-ethylaniline (8.0 g, 48%). $^1$H NMR (400 MHz, CDCl$_3$) δ 6.92 (d, J=8.4 Hz, 1H), 6.83 (d, J=2.4 Hz, 1H), 6.52 (dd, J=2.4, 8.4 Hz, 1H), 2.57 (q, J=7.6 Hz, 2H), 1.10 (t, J=7.6 Hz, 3H). MS (ESI) m/e (M+H$^+$) 200.

3-Bromo-4-iso-propylaniline and 3-bromo-4-tert-butylaniline were synthesized following preparation 43 above.

Preparation 44

5-Bromo-2-fluoro-4-methylaniline

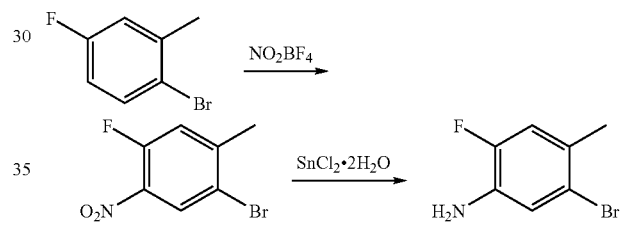

Step a: 1-Bromo-4-fluoro-2-methyl-5-nitrobenzene

To a stirred solution of 1-bromo-4-fluoro-2-methyl-benzene (15.0 g, 79.8 mmol) in dichloromethane (300 mL) was added nitronium tetrafluoroborate (11.7 g, 87.8 mmol) in portions at 0° C. The mixture was heated at reflux for 5 h and was then poured into ice water. The organic layer was separated and the aqueous phase was extracted with dichloromethane (100 mL×3). The combined organic layers were dried over anhydrous Na$_2$SO$_4$ and evaporated under reduced pressure to give crude 1-bromo-4-fluoro-2-methyl-5-nitrobenzene (18.0 g), which was used directly in the next step.

Step b: 5-Bromo-2-fluoro-4-methylaniline

To a stirred solution of 1-bromo-4-fluoro-2-methyl-5-nitrobenzene (18.0 g) in ethanol (300 mL) was added SnCl$_2$.2H$_2$O (51.8 g, 0.230 mol) at room temperature. The mixture was heated at reflux for 3 h. The solvent was evaporated under reduced pressure to give a residue, which was poured into ice water. The aqueous phase was basified with sat. NaHCO$_3$ to pH 7. The solid was filtered off and the filtrate was extracted with dichloromethane (200 mL×3). The combined organics were dried over anhydrous Na$_2$SO$_4$ and evaporated under reduced pressure. The residue was purified by column chromatography (petroleum ether/EtOAc=10/1) to afford 5-bromo-2-fluoro-4-methylaniline (5.0 g, 30% yield for two steps). $^1$H NMR (400 MHz, CDCl$_3$) δ 6.96 (d, J=8.8 Hz, 1H), 6.86 (d, J=11.6 Hz, 1H), 3.64 (br, 2H), 2.26 (s, 3H). MS (ESI) m/z (M+H$^+$) 204.0.

Preparation 45

1-(Benzo[d][1,3]dioxol-5-yl)-N-(3'-chloro-6-methyl-4'-(2H-tetrazol-5-yl)biphenyl-3-yl)cyclopropanecarboxamide

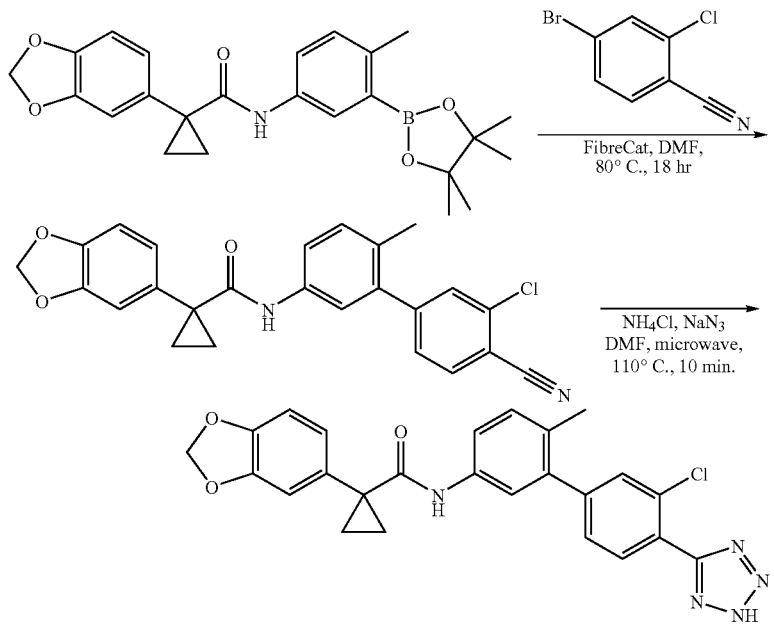

Step a: 1-(Benzo[d][1,3]dioxol-5-yl)-N-(3'-chloro-6-methyl-4'-(2H-tetrazol-5-yl)biphenyl-3-yl)cyclopropanecarboxamide 1-(Benzo[d][1,3]dioxol-5-yl)-N-(4-methyl-3-(4,4,5,5-tetramethyl-1,3,2-dioxaborolan-2-yl)phenyl)cyclopropanecarboxamide (0.084 g, 0.20 mmol), 4-bromo-2-chlorobenzonitrile (0.043 g, 0.20 mmol), aqueous potassium carbonate (520 µL, 1 M), FibreCat 1007 (7 mg), and DMF (1 mL) were combined. The mixture was heated at 80° C. for 18 hours. After cooling, the mixture was filtered and purified by preparative HPLC to provide 1-(benzo[d][1,3]dioxol-5-yl)-N-(3'-chloro-4'-cyano-6-methylbiphenyl-3-yl)cyclopropanecarboxamide.

Step b: 1-(Benzo[d][1,3]dioxol-5-yl)-N-(3'-chloro-6-methyl-4'-(2H-tetrazol-5-yl)biphenyl-3-yl)cyclopropanecarboxamide To 1-(benzo[d][1,3]dioxol-5-yl)-N-(3'-chloro-4'-cyano-6-methylbiphenyl-3-yl)-cyclopropanecarboxamide was added ammonium chloride (0.13 g, 2.4 mmol), sodium azide (0.156 g, 2.40 mmol) and 1 mL of DMF. The mixture was heated at 110° C. in a microwave reactor for 10 minutes. After cooling, the mixture was filtered and purified by preparative HPLC to provide 1-(benzo[d][1,3]dioxol-5-yl)-N-(3'-chloro-6-methyl-4'-(2H-tetrazol-5-yl)biphenyl-3-yl)cyclopropanecarboxamide (8.6 mg, 9%). ESI-MS m/z calc. 473.1, found 474.3 (M+1)$^+$; retention time 1.86 minutes.

Preparation 46

3-Bromo-4-(3-methyloxetan-3-yl)aniline

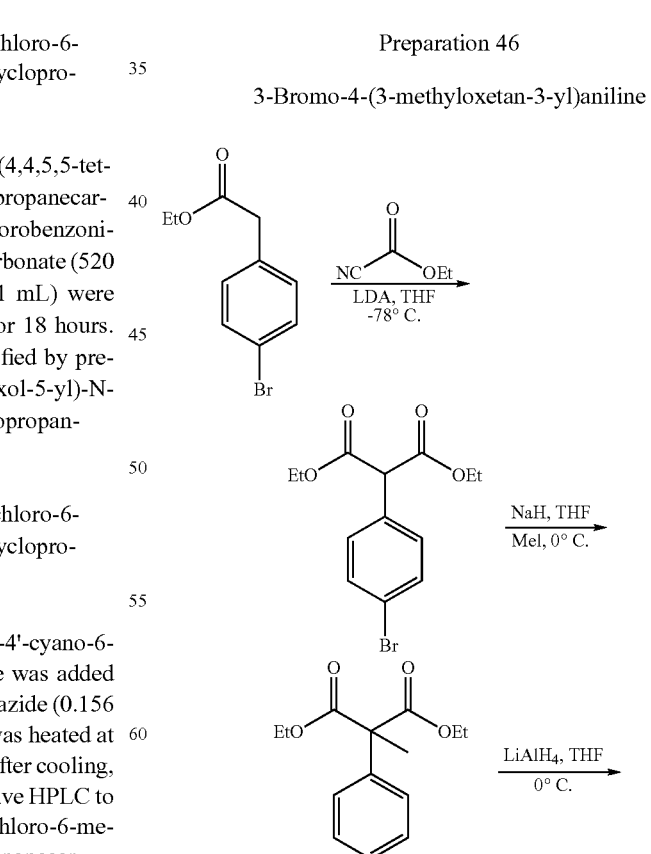

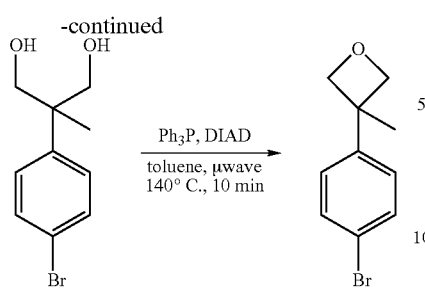

Step a: Diethyl 2-(4-bromophenyl)malonate

To a solution of ethyl 2-(4-bromophenyl)acetate (5.0 g, 21 mmol) in dry THF (40 mL) at −78° C. was added a 2.0M solution of lithium diisopropylamide in THF (11 mL, 22 mmol). After stirring for 30 minutes at −78° C., ethyl cyanoformate (2.0 mL, 21 mmol) was added and the mixture was allowed to warm to room temperature. After stirring for 48 h at room temperature, the mixture was quenched with water (10 mL). The reaction was partitioned between 1 N HCl (50 mL) and dichloromethane (50 mL), and the organic layer was separated. The organic layer was washed with 1 N HCl (50 mL), dried over Na$_2$SO$_4$ and evaporated. The crude material was purified by silica gel chromatography, eluting with 0-20% ethyl acetate in hexanes to give diethyl 2-(4-bromophenyl)malonate (2.6 g, 41%) $^1$H NMR (400 MHz, DMSO-d6) δ 7.60-7.58 (m, 2H), 7.36-7.34 (m, 2H), 5.03 (s, 1H), 4.21-4.09 (m, 4H), 1.20-1.16 (m, 6H).

Step b: Diethyl 2-(4-bromophenyl)-2-methylmalonate

To a solution of diethyl 2-(4-bromophenyl)malonate (1.5 g, 4.8 mmol) in dry THF (5 mL) at 0° C. was added sodium hydride (380 mg, 9.5 mmol). After stirring for 30 minutes at 0° C., iodomethane (600 µL, 9.5 mmol) was added and the reaction was allowed to warm to room temperature. After stirring for 12 h at room temperature, the reaction was quenched with water (3 mL). The mixture was partitioned between 1 N HCl (10 mL) and dichloromethane (10 mL), and the organic layer was separated. The organic layer was washed with 1 N HCl (10 mL), dried over Na$_2$SO$_4$ and evaporated. The crude material was purified by silica gel chromatography, eluting with 0-20% ethyl acetate in hexanes, to give diethyl 2-(4-bromophenyl)-2-methylmalonate (850 mg, 55%) $^1$H NMR (400 MHz, DMSO-d6) δ7.59-7.55 (m, 2H), 7.31-7.27 (m, 2H), 4.21-4.14 (m, 4H), 1.75 (s, 3H), 1.19-1.16 (m, 6H).

Step c: 2-(4-Bromophenyl)-2-methylpropane-1,3-diol

To a solution of diethyl 2-(4-bromophenyl)-2-methylmalonate (850 mg, 2.6 mmol) in dry THF (5 mL) at 0° C. was added a 1.0M solution of lithium aluminum hydride in THF (2.6 mL, 2.6 mmol). After stirring for 2 h at 0° C., the mixture was quenched by slow addition of water (5 mL). The mixture was made acidic by addition of 1N HCl and was then extracted with dichloromethane (2×20 mL). The organics were combined, dried over Na$_2$SO$_4$ and evaporated to give 2-(4-bromophenyl)-2-methylpropane-1,3-diol (500 mg, 79%) $^1$H NMR (400 MHz, DMSO-d6) δ 7.47-7.43 (m, 2H), 7.35-7.32 (m, 2H), 4.59-4.55 (m, 2H), 3.56-3.51 (m, 4H), 1.17 (s, 3H).

Step d: 3-(4-Bromophenyl)-3-methyloxetane 2-(4-Bromophenyl)-2-methylpropane-1,3-diol (100 mg, 0.41 mmol), triphenyl phosphine (210 mg, 0.82 mmol), and diisopropyl azodicarboxylate (160 µL, 0.82 mmol) were combined in toluene (2 mL) and irradiated in the microwave at 140° C. for 10 minutes. The mixture was directly purified by silica gel chromatography eluting with 0-20% ethyl acetate in hexanes to give 3-(4-bromophenyl)-3-methyloxetane (39 mg, 42%) $^1$H NMR (400 MHz, DMSO-d6) δ 7.38-7.34 (m, 2H), 7.26-7.22 (m, 2H), 4.82-4.80 (m, 2H), 4.55-4.54 (m, 2H), 1.62 (s, 3H).

Preparation 47

N-(4-bromophenylsulfonyl)acetamide

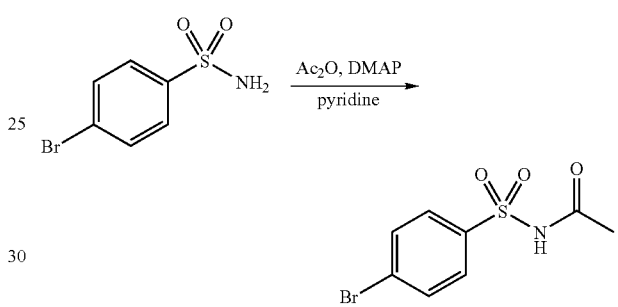

3-Bromobenzenesulfonamide (470 mg, 2.0 mmol) was dissolved in pyridine (1 mL). To this solution was added DMAP (7.3 mg, 0.060 mmol) and then acetic anhydride (570 µL, 6.0 mmol). The reaction was stirred for 3 h at room temperature during which time the reaction changed from a yellow solution to a clear solution. The solution was diluted with ethyl acetate, and then washed with aqueous NH$_4$Cl solution (×3) and water. The organic layer was dried over MgSO$_4$ and concentrated. The resulting oil was triturated with hexanes and the precipitate was collected by filtration to obtain N-(3-bromophenylsulfonyl)-acetamide as a shiny white solid (280 mg, 51%). $^1$H NMR (400 MHz, DMSO-d6) δ 12.43 (s, 1H), 8.01 (t, J=1.8 Hz, 1H), 7.96-7.90 (m, 2H), 7.61 (t, J=8.0 Hz, 1H), 1.95 (s, 3H); HPLC ret. time 1.06 min; ESI-MS 278.1 m/z (MH$^+$).

Preparation 48

6-Bromoisobenzofuran-1(3H)-one

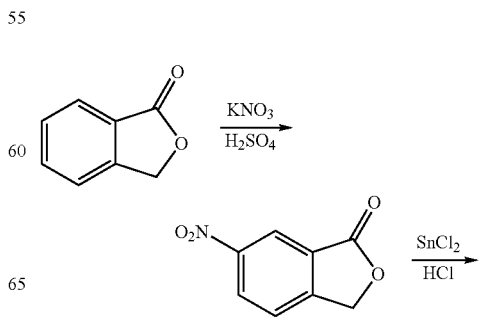

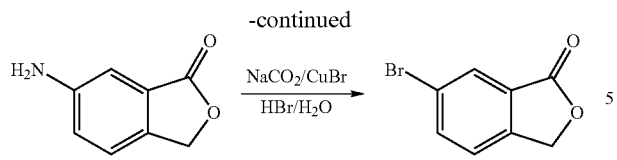

Step a: 6-Nitroisobenzofuran-1(3H)-one

To a stirred solution of 3H-isobenzofuran-1-one (30.0 g, 0.220 mol) in $H_2SO_4$ (38 mL) was added $KNO_3$ (28.0 g, 0.290 mol) in $H_2SO_4$ (60 mL) at 0° C. The mixture was stirred at 20° C. for 1 h. The reaction mixture was poured into ice and the resulting precipitate was filtered off. The solid was recrystallized from ethanol to give 6-nitroisobenzofuran-1(3H)-one (32.0 g, 80%). $^1$H NMR (300 MHz, $CDCl_3$) δ 8.76 (d, J=2.1, 1H), 8.57 (dd, J=8.4, 2.1, 1H), 7.72 (d, J=8.4, 1H), 5.45 (s, 2H).

Step b: 6-Aminoisobenzofuran-1(3H)-one

To a solution of 6-nitroisobenzofuran-1(3H)-one (15 g, 0.080 mol) in $HCl/H_2O$ (375 mL/125 mL) was added $SnCl_2 \cdot 2H_2O$ (75 g, 0.33 mol). The reaction mixture was heated at reflux for 4 h before it was quenched with water and extracted with EtOAc (300 mL×3). The organics were dried over $Na_2SO_4$ and evaporated in vacuo to give 6-aminoisobenzofuran-1(3H)-one (10 g, 78%). $^1$H NMR (300 MHz, $CDCl_3$) δ 7.23 (d, J=8.1, 1H), 7.13 (d, J=2.1, 1H), 6.98 (dd, J=8.1, 2.1, 1H), 5.21 (s, 2H), 3.99 (br s, 2H).

Step c: 6-Bromoisobenzofuran-1(3H)-one

A solution of $NaNO_2$ (2.2 g, 0.040 mol) in $H_2O$ (22 mL) was added to a mixture of 6-aminoisobenzofuran-1(3H)-one (5.0 g, 0.030 mol) in HBr (70 mL, 48%) over 5 min at 0° C. The mixture was stirred for 20 minutes before it was pipetted into an ice cold solution of CuBr (22 g, 0.21 mol) in HBr (48%, 23 mL). The resulting dark brown mixture was stirred for 20 min and was then diluted with $H_2O$ (200 mL) to produce an orange precipitate. The precipitate was filtered off, treated with sat. $NaHCO_3$ solution, and extracted with EtOAc (20 mL×3). The organics were dried over $Na_2SO_4$ and evaporated in vacuo to give 6-bromoisobenzofuran-1(3H)-one (5.4 g, 84%). $^1$H NMR (300 MHz, $CDCl_3$) δ 8.05 (d, J=1.8, 1H), 7.80 (dd, J=8.1, 1.8, 1H), 7.39 (d, J=8.1, 1H), 5.28 (s, 2H).

Preparation 49

6-Bromo-1,1-dioxo-1,2-dihydro-1λ$^6$-benzo[d]isothiazol-3-one

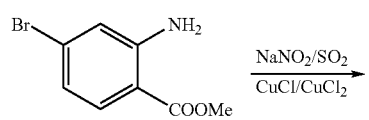

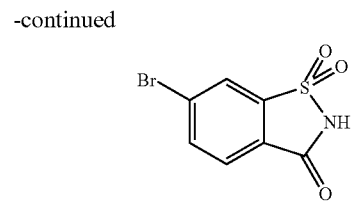

A solution of methyl 2-amino-4-bromobenzoate (4.5 g, 20 mmol) in 20% hydrochloric acid (30 mL) was stirred until all solids were dissolved. The solution was cooled to 0° C. and a solution of sodium nitrite (1.4 g, 0.020 mol) in water (20 mL) was added dropwise at such a rate that the internal reaction temperature did not exceed 5° C. The mixture was stirred at 0° C. for 45 minutes. Sulfur dioxide was bubbled into a mixture of acetic acid (50 mL) and water (5 mL) at 0° C. until the solution was saturated. Copper (I) chloride (2.0 g, 0.020 mol) was then added to the saturated sulfur dioxide solution. The mixture was cooled to 0° C. To this mixture was added the diazonium salt solution dropwise with vigorous stirring over a period of 30 minutes. The reaction mixture was stirred at 0° C. for 1 hour and then the mixture was allowed to warm to room temperature. The mixture was stirred at room temperature for 2 h before it was poured into ice water (250 mL) and extracted with EtOAc (3×50 mL). The organics were washed with sat. $NaHCO_3$ solution and dried over anhydrous $Na_2SO_4$. The solvent was removed in vacuo to afford an oily residue which was dissolved in tetrahydrofuran (40 mL) and cooled to 0° C. To this mixture was added a cold (0° C.) solution of ammonium hydroxide (28%, 40 mL) portion-wise at such a rate that the internal reaction temperature was maintained below 10° C. The mixture was allowed to warm to room temperature and was then stirred at room temperature for 1 h. The solvent was removed in vacuo and the residue was dissolved in saturated aqueous sodium bicarbonate (40 mL) and washed with diethyl ether (50 mL). The aqueous layer was acidified with concentrated hydrochloric acid to pH 1. The resulting precipitate was collected by filtration and was dried under vacuum to produce of 6-Bromo-1,1-dioxo-1,2-dihydro-1λ$^6$-benzo[d]isothiazol-3-one (500 mg, 10% yield). $^1$H NMR (400 MHz, DMSO) δ 8.44 (d, J=1.5, 1H), 8.04 (dd, J=8.1, 1.5, 1H), 7.81 (d, J=8.0, 1H).

Preparation 50

5-Bromo-1,1-dioxo-1,2-dihydro-1λ$^6$-benzo[d]isothiazol-3-one

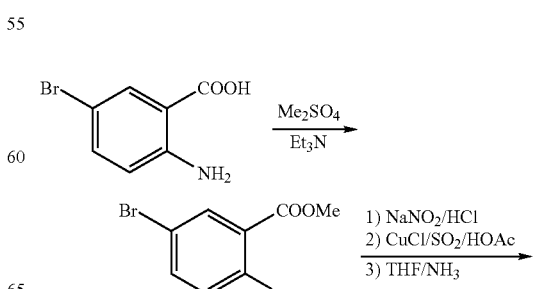

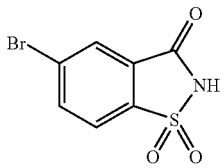

Step a: Methyl 2-amino-5-bromobenzoate

MeSO$_4$ (26.3 mL, 0.280 mol) was added to a solution of 2-amino-5-bromobenzoic acid (50.0 g, 0.230 mol) in DMF and Et$_3$N (40 mL, 0.28 mol). The reaction mixture was stirred at rt for 48 h. The mixture was quenched with water, extracted with EtOAc and dried over MgSO$_4$. The solvent was evaporated in vacuo and the residue was purified by chromatography on silica gel (5% EtOAc in petroleum ether) to afford methyl 2-amino-5-bromobenzoate (30 g, 56% yield). $^1$H NMR (300 MHz, DMSO) δ 7.74 (d, J=2.7, 1H), 7.35 (dd, J=9.0, 2.1, 1H), 6.78-6.73 (m, 3H), 3.77 (s, 3H).

Step b: 6-Bromo-1,1-dioxo-1,2-dihydro-1λ$^6$-benzo[d]isothiazol-3-one

A solution of the methyl 2-amino-5-bromobenzoate (20.0 g, 86.9 mol) in 20% hydrochloric acid (60 mL) was warmed until all solids were dissolved. The solution was cooled to 0° C. with stirring to precipitate the hydrochloride salt. To this suspension was added a solution of sodium nitrite (6.10 g, 8.84 mol) in water (20 mL) dropwise at such a rate that the internal reaction temperature did not exceed 5° C. The mixture was stirred at 0° C. for 45 minutes to afford a clear solution. Sulfur dioxide was bubbled into a mixture of acetic acid (100 mL) and water (10 mL) at 0° C., Copper (I) chloride (8.6 g, 0.088 mol) was then added to the sulfur dioxide solution. The mixture was then cooled to 0° C. To this mixture was added the diazonium salt solution portion-wise with vigorous stirring over a period of 30 minutes. The reaction mixture was stirred at 0° C. for 1 h and then the mixture was allowed to warm to room temperature. The mixture was stirred at room temperature for 2 h before it was quenched with ice water (500 mL). The mixture was extracted with EtOAc (3×) and the extracts were washed with sat. NaHCO$_3$ and dried over anhydrous Na$_2$SO$_4$. The solvent was removed in vacuo to afford an oily residue. The residue was dissolved in THF (60 mL) and the solution was cooled to 0° C. To this mixture was added a cold (0° C.) solution of sat. NH$_3$ (50 mL) in MeOH portion-wise at such a rate that the internal reaction temperature was maintained below 10° C. After the addition was complete, the mixture was allowed to warm to room temperature and was stirred for 1 h. The solvent was removed in vacuo and the residue was dissolved in saturated aqueous sodium bicarbonate (60 mL) and washed with diethyl ether (80 mL). The aqueous layer was acidified with concentrated HCl to pH to 1. The resulting precipitate was collected by filtration and was dried in vacuo to afford 6-bromo-1,1-dioxo-1,2-dihydro-1λ$^6$-benzo[d]isothiazol-3-one (2.1 g, 9% yield). $^1$H NMR (300 MHz, CDCl$_3$) δ 8.18 (d, J=1.8, 1H), 8.03 (dd, J=8.1, 1.8, 1H), 7.79 (d, J=8.1, 1H).

Preparation 51

1-(2,2-Difluorobenzo[d][1,3]dioxol-5-yl)-N-(4-methyl-3-(3-oxo-1,3-dihydroisobenzofuran-5-yl)phenyl)cyclopropanecarboxamide and 5'-(1-(2,2-difluorobenzo[d][1,3]dioxol-5-yl)cyclopropanecarboxamido)-4-(hydroxymethyl)-2'-methylbiphenyl-3-carboxylic acid

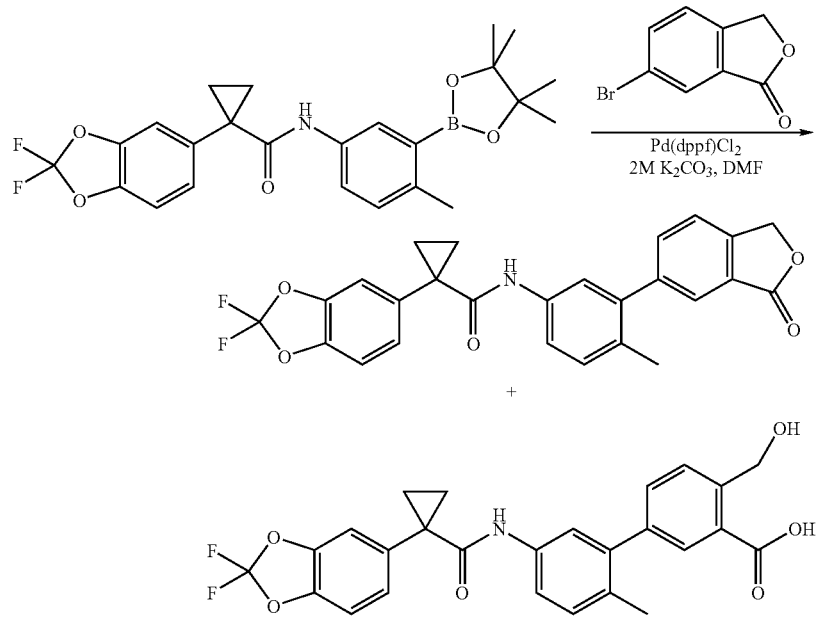

1-(2,2-Difluorobenzo[d][1,3]dioxol-5-yl)-N-(4-methyl-3-(4,4,5,5-tetramethyl-1,3,2-dioxaborolan-2-yl)phenyl)cyclopropanecarboxamide (45 mg, 0.10 mmol), 6-bromoisobenzofuran-1(3H)-one (42 mg, 0.20 mmol), and Pd(dppf)Cl$_2$ (5 mg, 0.006 mmol) were combined in a reaction tube. DMF (1 mL) and 2M K$_2$CO$_3$ aqueous solution (250 µL) were added and the mixture was stirred under N$_2$. atmosphere at 80° C. overnight. The mixture was filtered and purified by reverse-phase HPLC (10-99% CH$_3$CN—H$_2$O without TFA modifier) to yield two products: 1-(2,2-difluorobenzo[d][1,3]dioxol-5-yl)-N-(4-methyl-3-(3-oxo-1,3-dihydroisobenzofuran-5-yl)phenyl)cyclopropanecarboxamide: ESI-MS m/z calc. 463.1, found 464.3 (M+1)$^+$. Retention time 2.07 minutes. $^1$H NMR (400 MHz, DMSO-d6) δ 8.85 (s, 1H), 7.76-7.69 (m, 3H), 7.53-7.48 (m, 2H), 7.42 (d, J=2.2 Hz, 1H), 7.37 (d, J=8.3 Hz, 1H), 7.27 (dd, J=1.7, 8.3 Hz, 1H), 7.22 (d, J=8.4 Hz, 1H), 5.47 (s, 2H), 2.17 (s, 3H), 1.48-1.45 (m, 2H), 1.14-1.11 (m, 2H); and 5'-(1-(2,2-difluorobenzo[d][1,3]dioxol-5-yl)cyclopropanecarboxamido)-4-(hydroxymethyl)-2'-methylbiphenyl-3-carboxylic acid: ESI-MS m/z calc. 481.1, found 482.3 (M+1)$^+$. Retention time 1.84 minutes. $^1$H NMR (400 MHz, DMSO-d6) δ 8.84 (s, 1H), 8.21 (t, J=6.4 Hz, 1H), 7.67 (d, J=1.9 Hz, 1H), 7.49 (d, J=1.6 Hz, 1H), 7.45 (dd, J=2.2, 8.3 Hz, 1H), 7.37-7.33 (m, 2H), 7.27 (dd, J=1.7, 8.3 Hz, 1H), 7.16-7.10 (m, 3H), 4.44 (d, J=6.2 Hz, 2H), 2.16 (s, 3H), 1.48-1.45 (m, 2H), 1.12-1.09 (m, 2H).

Preparation 52

5'-(1-(2,2-Difluorobenzo[d][1,3]dioxol-5-yl)cyclopropanecarboxamido)-2'-methyl-N-(methylsulfonyl)biphenyl-3-carboxamide

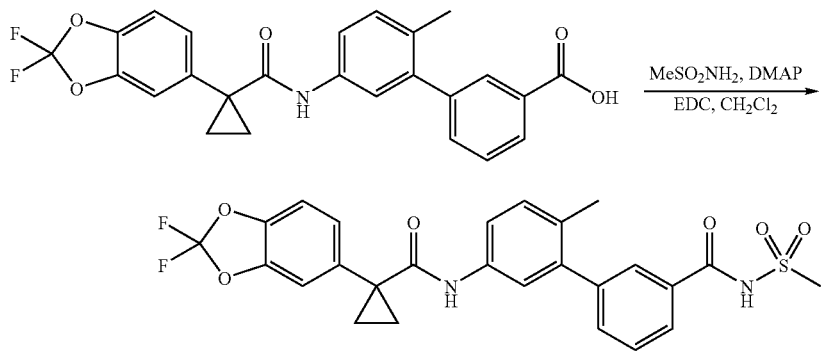

To a mixture of 5'-(1-(2,2-difluorobenzo[d][1,3]dioxol-5-yl)cyclopropanecarboxamido)-2'-methylbiphenyl-3-carboxylic acid (50 mg, 0.11 mmol), methansulfonamide (7.0 mg, 0.074 mmol), DMAP (13 mg, 0.11 mmol), and CH$_2$Cl$_2$ (1 mL) was added EDC (28 mg, 0.15 mmol) at ambient temperature. The mixture was allowed to stir for 18 h before it was concentrated. The residue was taken up in DMF (1 mL) and was purified by reverse phase preparatory HPLC to provide 5'-(1-(2,2-difluorobenzo[d][1,3]dioxol-5-yl)cyclopropanecarboxamido)-2'-methyl-N-(methylsulfonyl)biphenyl-3-carboxamide as a white solid. ESI-MS m/z calc. 528.5, found 529.2 (M+1)$^+$. Retention time 1.97 minutes.

Preparation 53

1-(2,2-Difluoro-2H-1,3-benzodioxol-5-yl)-N-[4-methyl-3-(1,1,3-trioxo-2,3-dihydro-1λ$^6$,2-benzothiazol-5-yl)phenyl]cyclopropane-1-carboxamide

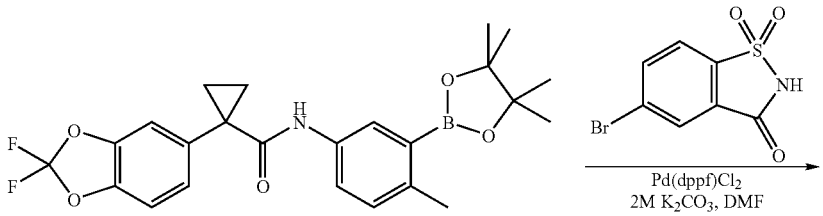

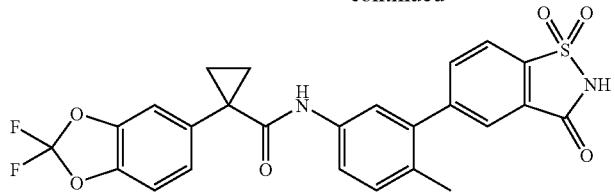

1-(2,2-Difluorobenzo[d][1,3]dioxol-5-yl)-N-(4-methyl-3-(4,4,5,5-tetramethyl-1,3,2-dioxaborolan-2-yl)phenyl)cyclopropanecarboxamide (46 mg, 0.10 mmol), 5-bromo-1,1-dioxo-1,2-dihydro-1$\lambda^6$-benzo[d]isothiazol-3-one (26 mg, 0.10 mmol), Pd(dppf)Cl$_2$ (4.0 mg, 0.0050 mmol), 2M Na$_2$CO$_3$ (150 μL, 0.30 mmol), and DMF (1 mL) were combined and heated at 120° C. in the microwave for 10 min. The mixture was filtered and purified by reverse phase preparatory HPLC to give 1-(2,2-difluoro-2H-1,3-benzodioxol-5-yl)-N-[4-methyl-3-(1,1,3-trioxo-2,3-dihydro-1$\lambda^6$,2-benzothiazol-5-yl)phenyl]cyclopropane-1-carboxamide. ESI-MS m/z calc. 512.5, found 513.1 (M+1)$^+$. Retention time 1.94 minutes.

Preparation 54

1-(2,2-Difluoro-2H-1,3-benzodioxol-5-yl)-N-[4-methyl-3-(1,1,3-trioxo-2,3-dihydro-1$\lambda^6$,2-benzothiazol-6-yl)phenyl]cyclopropane-1-carboxamide

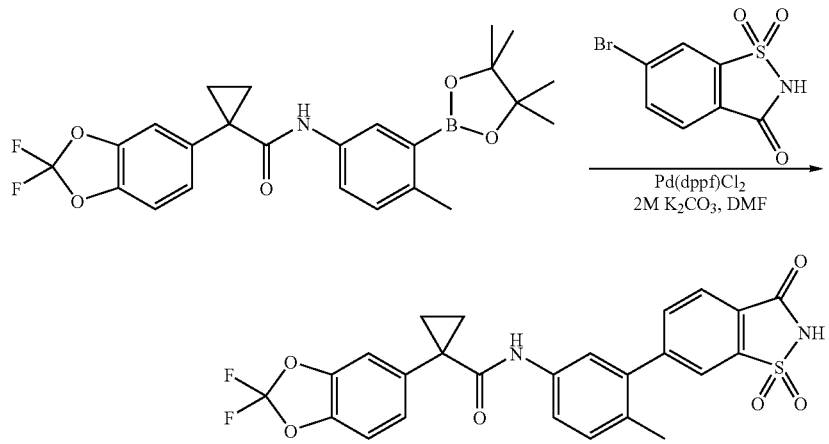

1-(2,2-Difluorobenzo[d][1,3]dioxol-5-yl)-N-(4-methyl-3-(4,4,5,5-tetramethyl-1,3,2-dioxaborolan-2-yl)phenyl)cyclopropanecarboxamide (46 mg, 0.10 mmol), 6-bromo-1,1-dioxo-1,2-dihydro-1$\lambda^6$-benzo[d]isothiazol-3-one (26 mg, 0.10 mmol), Pd(dppf)Cl$_2$ (4.0 mg, 0.0050 mmol), 2M Na$_2$CO$_3$ (150 μL, 0.30 mmol), and DMF (1 mL) were combined and heated at 120° C. in the microwave for 10 min. The mixture was filtered and purified by reverse phase preparatory HPLC to give 1-(2,2-difluoro-2H-1,3-benzodioxol-5-yl)-N-[4-methyl-3-(1,1,3-trioxo-2,3-dihydro-1$\lambda^6$,2-benzothiazol-6-yl)phenyl]cyclopropane-1-carboxamide. ESI-MS m/z calc. 512.5, found 513.5 (M+1)$^+$. Retention time 1.93 minutes.

Assays

Assays for Detecting and Measuring ΔF508-CFTR Correction Properties of Compounds A. Membrane Potential Optical Methods for Assaying ΔF508-CFTR Modulation Properties of Compounds The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" Biophys J 69(4): 1272-80, and Gonzalez, J. E. and R. Y. Tsien (1997) "Improved indicators of cell membrane potential that use fluorescence resonance energy transfer" Chem Biol 4(4): 269-77) in combination with instrumentation for measuring fluorescence changes such as the Voltage/Ion Probe Reader (VIPR) (See. Gonzalez, J. E., K. Oades, et al. (1999) "Cell-based assays and instrumentation for screening ion-channel targets" Drug Discov Today 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential (V$_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

1. Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with Cl$^-$-free medium to each well. The addition of Cl$^-$-free medium promoted Cl$^-$ efflux in response to ΔF508-CFTR activation and the resulting membrane depolarization was optically monitored using the FRET-based voltage-sensor dyes.

2. Identification of Potentiator Compounds

To identify potentiators of ΔF508-CFTR, a double-addition HTS assay format was developed. During the first addition, a Cl$^-$-free medium with or without test compound was added to each well. After 22 sec, a second addition of Cl$^-$-free medium containing 2-10 μM forskolin was added to activate ΔF508-CFTR. The extracellular Cl$^-$ concentration following both additions was 28 mM, which promoted Cl$^-$ efflux in response to ΔF508-CFTR activation and the resulting membrane depolarization was optically monitored using the FRET-based voltage-sensor dyes. 3. Solutions Bath Solution #1: (in mM) NaCl 160, KCl 4.5, CaCl$_2$ 2, MgCl$_2$ 1, HEPES 10, pH 7.4 with NaOH.

Chloride-free bath solution: Chloride salts in Bath Solution #1 are substituted with gluconate salts.

CC2-DMPE: Prepared as a 10 mM stock solution in DMSO and stored at −20° C.

DiSBAC$_2$(3): Prepared as a 10 mM stock in DMSO and stored at −20° C.

4. Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours B. Electrophysiological Assays for assaying ΔF508-CFTR modulation properties of compounds

1. Using Chamber Assay

Using chamber experiments were performed on polarized epithelial cells expressing ΔF508-CFTR to further characterize the ΔF508-CFTR modulators identified in the optical assays. FRT$^{ΔF508-CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, IA, and, Physiologic Instruments, Inc., San Diego, Calif.). Transepithelial resistance was measured by applying a 2-mV pulse. Under these conditions, the FRT epithelia demonstrated resistances of 4 KΩ/cm$^2$ or more. The solutions were maintained at 27° C. and bubbled with air. The electrode offset potential and fluid resistance were corrected using a cell-free insert. Under these conditions, the current reflects the flow of Cl$^-$ through ΔF508-CFTR expressed in the apical membrane. The I$_{SC}$ was digitally acquired using an MP100A-CE interface and AcqKnowledge software (v3.2.6; BIOPAC Systems, Santa Barbara, Calif.).

2. Identification of Correction Compounds

Typical protocol utilized a basolateral to apical membrane Cl$^-$ concentration gradient. To set up this gradient, normal ringer was used on the basolateral membrane, whereas apical NaCl was replaced by equimolar sodium gluconate (titrated to pH 7.4 with NaOH) to give a large Cl$^-$ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated I$_{SC}$ in compound-treated cells was normalized to the 27° C. and 37° C. controls and expressed as percentage activity. Preincubation of the cells with the correction compound significantly increased the cAMP- and genistein-mediated I$_{SC}$ compared to the 37° C. controls.

3. Identification of Potentiator Compounds

Typical protocol utilized a basolateral to apical membrane Cl$^-$ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl$^-$ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

4. Solutions

Basolateral solution (in mM): NaCl (135), CaCl$_2$ (1.2), MgCl$_2$ (1.2), K$_2$HPO$_4$ (2.4), KHPO$_4$ (0.6), N-2-hydroxyethylpiperazine-N'-2-ethanesulfonic acid (HEPES) (10), and dextrose (10). The solution was titrated to pH 7.4 with NaOH. Apical solution (in mM): Same as basolateral solution with NaCl replaced with Na Gluconate (135).

5. Cell Culture

Fisher rat epithelial (FRT) cells expressing ΔF508-CFTR (FRT$^{ΔF508-CFTR}$) were used for Ussing chamber experiments for the putative ΔF508-CFTR modulators identified from our optical assays. The cells were cultured on Costar Snapwell cell culture inserts and cultured for five days at 37° C. and 5% CO$_2$ in Coon's modified Ham's F-12 medium supplemented with 5% fetal calf serum, 100 U/ml penicillin, and 100 µg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

6. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance<15 MΩ. Pulse generation, data acquisition, and analysis were performed using a PC equipped with a Digidata 1320 A/D interface in conjunction with Clampex 8 (Axon Instruments Inc.). The bath contained <250 µl of saline and was continuously perifused at a rate of 2 ml/min using a gravity-driven perfusion system.

7. Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 µM forskolin and 20 µM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 µM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 µM of correction compounds significantly increased the cAMP- and genistein-dependent current compared to the 37° C. controls.

8. Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

9. Solutions

Intracellular solution (in mM): Cs-aspartate (90), CsCl (50), MgCl$_2$ (1), HEPES (10), and 240 µg/ml amphotericin-B (pH adjusted to 7.35 with CsOH).

Extracellular solution (in mM): N-methyl-D-glucamine (NMDG)-Cl (150), MgCl$_2$ (2), CaCl$_2$ (2), HEPES (10) (pH adjusted to 7.35 with HCl).

10. Cell Culture

NIH3T3 mouse fibroblasts stably expressing ΔF508-CFTR are used for whole-cell recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

11. Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the non-specific phosphatase inhibitor F⁻ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≦2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o = I/i(N)$, where I=mean current, i=single-channel current amplitude, and N=number of active channels in patch.

12. Solutions

Extracellular solution (in mM): NMDG (150), aspartic acid (150), $CaCl_2$ (5), $MgCl_2$ (2), and HEPES (10) (pH adjusted to 7.35 with Tris base).
Intracellular solution (in mM): NMDG-Cl (150), $MgCl_2$ (2), EGTA (5), TES (10), and Tris base (14) (pH adjusted to 7.35 with HCl).

13. Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

The exemplified compounds of Table 1 have an activity of less than 20 mM as measured using the assays described hereinabove.

VIII. OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound selected from

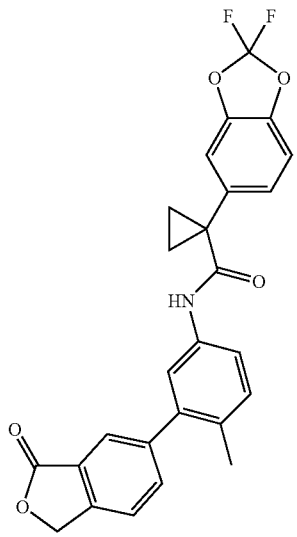

1206

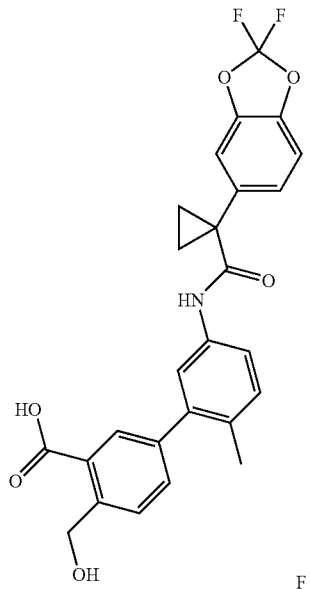

1207

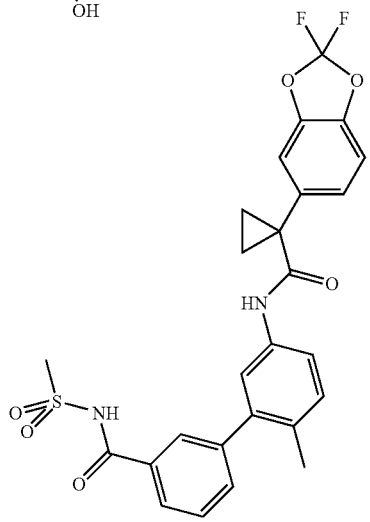

1208

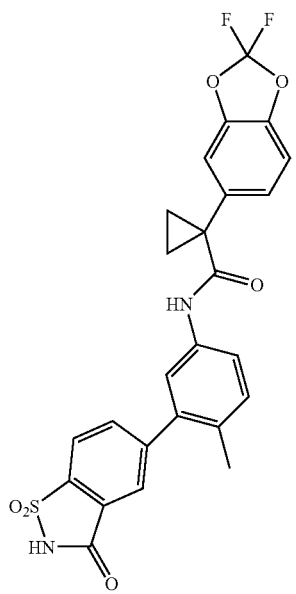

1209

-continued
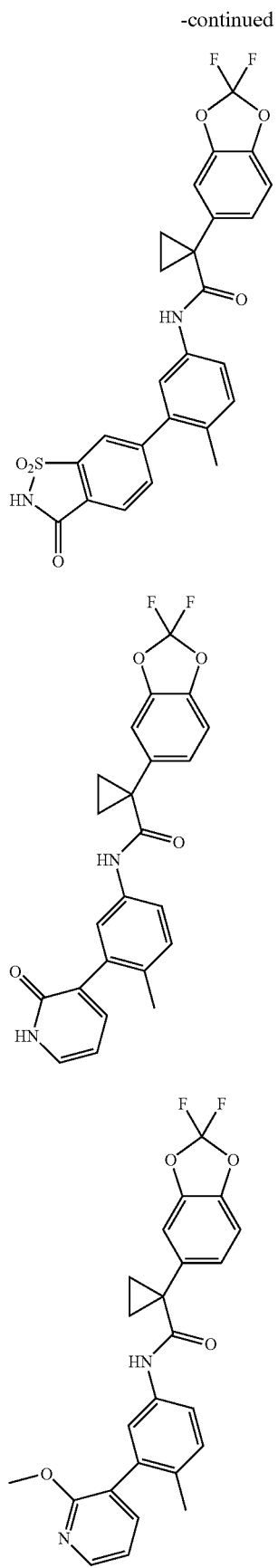
-continued
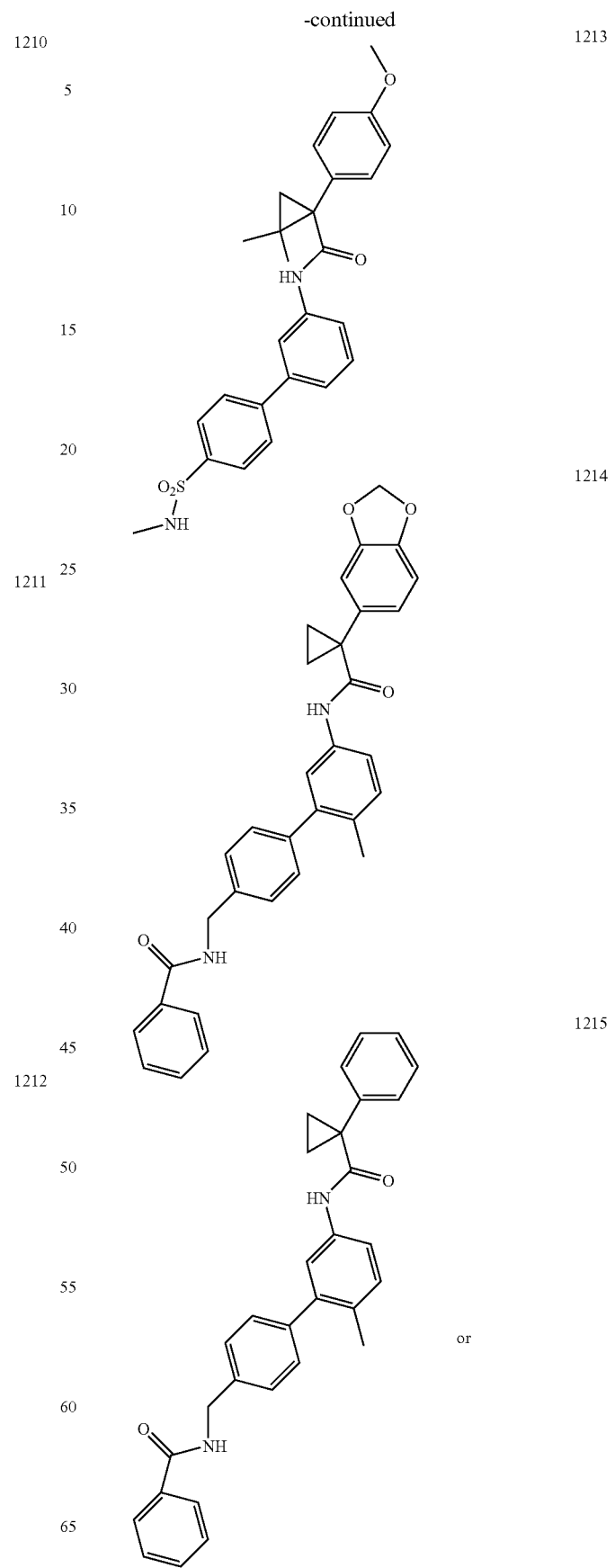

-continued
1216
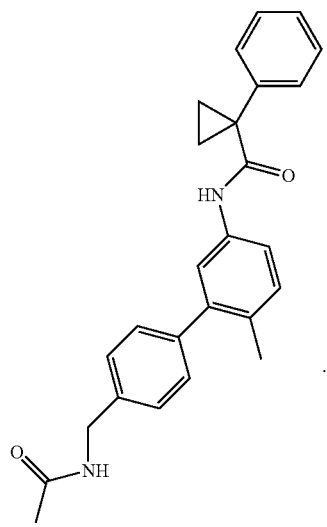
2. A pharmaceutical composition comprising a compound according to claim 1 and a pharmaceutical carrier.
3. A method of increasing CFTR transporter activity comprising the step of contacting said CFTR transporter with a compound selected from
1206
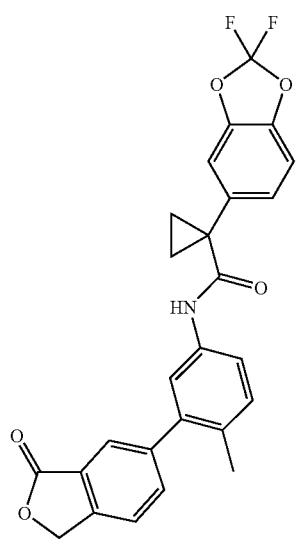
-continued
1207
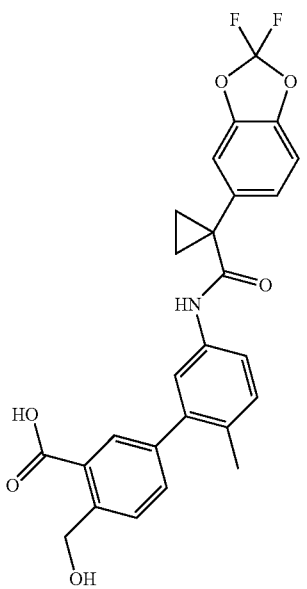
1208
1209

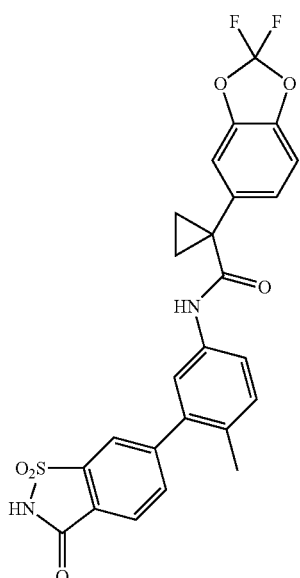
1210
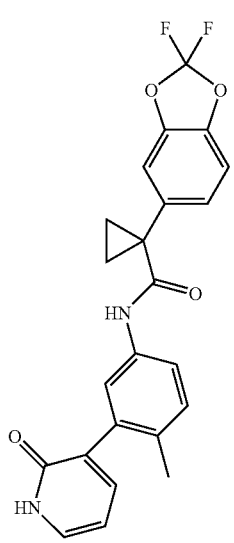
1211
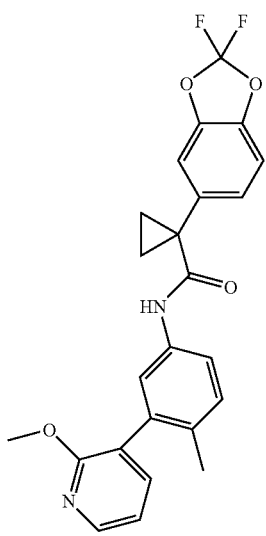
1212
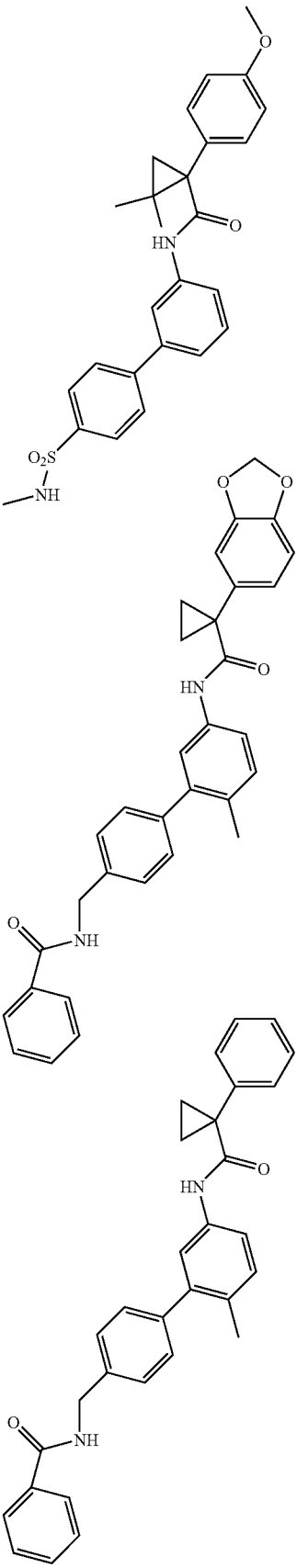
1213
1214
1215
or

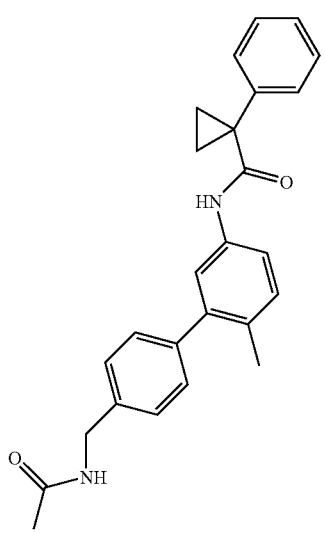

1216

4. A method of treating or lessening the severity of cystic fibrosis comprising the step of administering to said patient an effective amount of a compound according to claim 1.

5. A kit for use in measuring the activity of a CFTR transporter or a fragment thereof in a biological sample in vitro or in vivo, combining:
   (i) a composition comprising a compound according to claim 1; and
   (ii) instructions for:
      a) contacting the composition with the biological sample; and
      b) measuring activity of said CFTR transporter or a fragment thereof.

6. The kit of claim 5, further comprising instructions for
   a) contacting an additional composition with the biological sample;
   b) measuring the activity of said CFTR transporter or a fragment thereof in the presence of said additional compound; and
   c) comparing the activity of the CFTR transporter in the presence of the additional compound with the density of the CFTR transporter in the presence of a compound selected from.

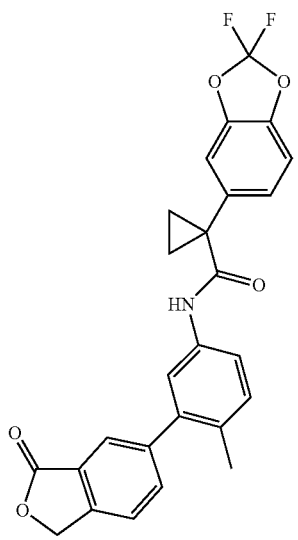

1206

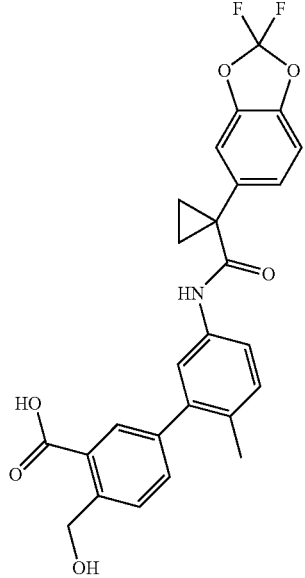

1207

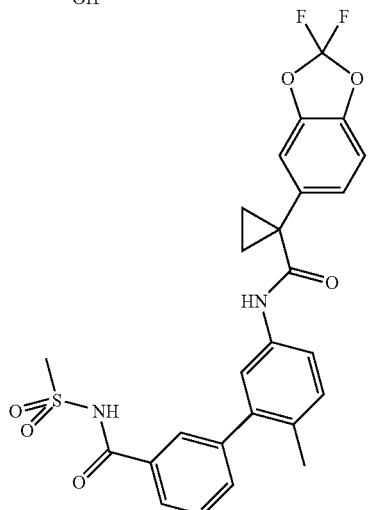

1208

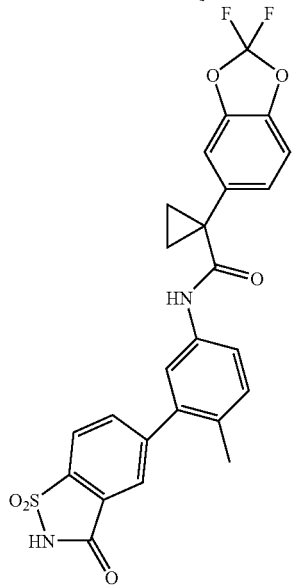

1209

789
-continued
1210
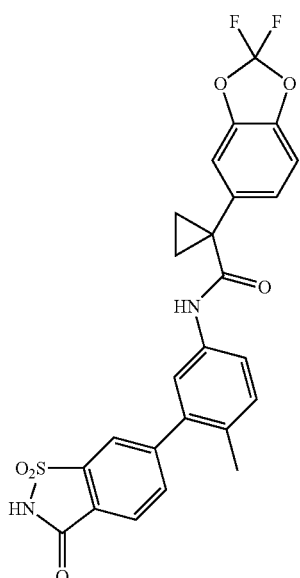
1211
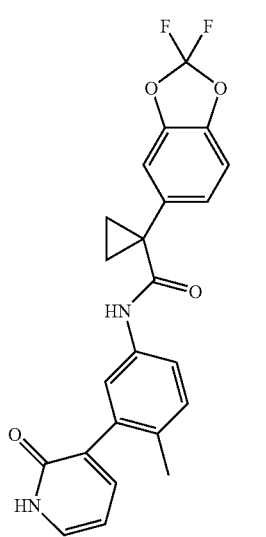
1212
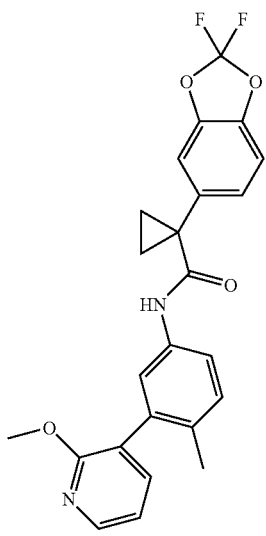
790
-continued
1213
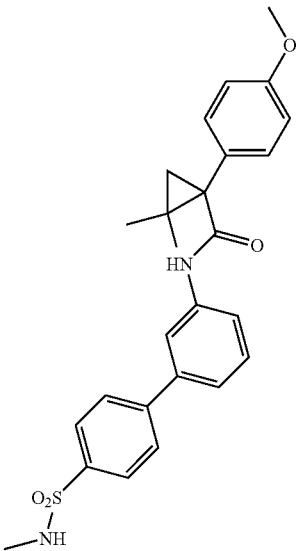
1214
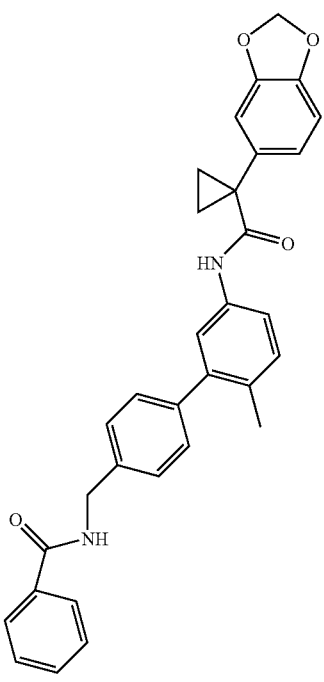

791
-continued
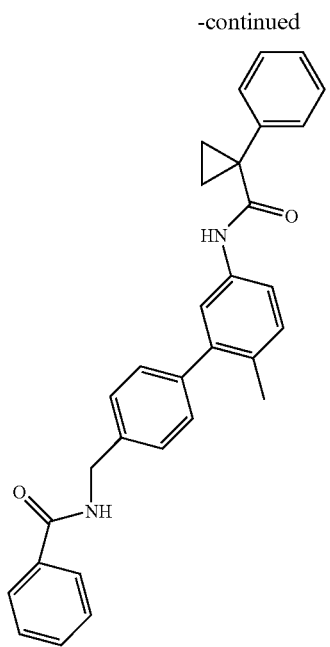
1215
or
792
-continued
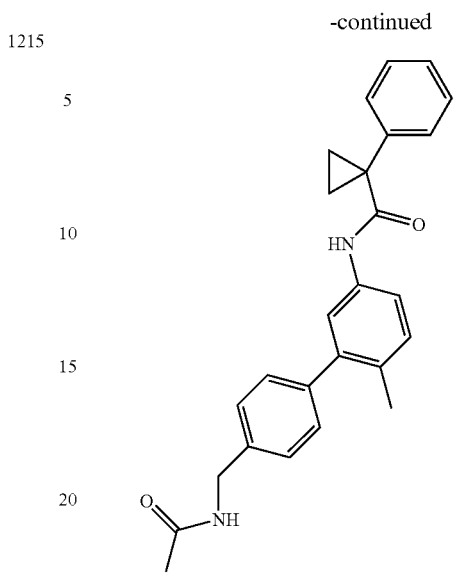
1216
* * * * *